US008039597B2

(12) United States Patent
Raitano et al.

(10) Patent No.: US 8,039,597 B2
(45) Date of Patent: Oct. 18, 2011

(54) ANTIBODIES AND RELATED MOLECULES THAT BIND TO 24P4C12 PROTEINS

(75) Inventors: Arthur B. Raitano, Los Angeles, CA (US); Robert Kendall Morrison, Santa Monica, CA (US); Karen Jane Meyrick Morrison, Santa Monica, CA (US); Steven B. Kanner, Santa Monica, CA (US); Pia M. Challita-Eid, Encino, CA (US); Xiao-chi Jia, Los Angeles, CA (US); Jean Gudas, Los Angeles, CA (US); Aya Jakobovits, Beverly Hills, CA (US)

(73) Assignee: Agensys, Inc., Santa Monica, CA (US)

( * ) Notice: Subject to any disclaimer, the term of this patent is extended or adjusted under 35 U.S.C. 154(b) by 331 days.

(21) Appl. No.: 12/205,560

(22) Filed: Sep. 5, 2008

(65) Prior Publication Data

US 2009/0175796 A1    Jul. 9, 2009

Related U.S. Application Data

(60) Provisional application No. 61/190,034, filed on Sep. 7, 2007.

(51) Int. Cl.
| | |
|---|---|
| C07K 16/00 | (2006.01) |
| C07K 17/00 | (2006.01) |
| C07K 17/14 | (2006.01) |
| C12P 21/08 | (2006.01) |
| A61K 39/395 | (2006.01) |
| A61K 39/00 | (2006.01) |

(52) U.S. Cl. ............. 530/388.15; 530/387.1; 530/391.1; 530/391.3; 424/130.1; 424/133.1; 424/134.1; 424/178.1

(58) Field of Classification Search .......... None
See application file for complete search history.

(56) References Cited

U.S. PATENT DOCUMENTS

| | | | |
|---|---|---|---|
| 4,742,000 A | 5/1988 | Greene | |
| 5,693,762 A | 12/1997 | Queen et al. | |
| 6,312,922 B1 | 11/2001 | Edwards et al. | |
| 6,551,795 B1 | 4/2003 | Rubenfield et al. | |
| 6,682,736 B1 * | 1/2004 | Hanson et al. | 424/144.1 |
| 6,747,137 B1 | 6/2004 | Weinstock et al. | |
| 6,913,919 B2 | 7/2005 | Botstein et al. | |
| 6,930,170 B2 | 8/2005 | Desnoyers et al. | |
| 6,943,235 B1 | 9/2005 | Afar et al. | |
| 6,953,836 B2 | 10/2005 | Desnoyers et al. | |
| 6,956,108 B2 | 10/2005 | Desnoyers et al. | |
| 6,972,185 B2 | 12/2005 | Desnoyers et al. | |
| 7,018,811 B2 | 3/2006 | Botstein et al. | |
| 7,019,116 B2 | 3/2006 | Desnoyers et al. | |
| 7,029,873 B2 | 4/2006 | Desnoyers et al. | |
| 7,034,106 B2 | 4/2006 | Desnoyers et al. | |
| 7,034,122 B2 | 4/2006 | Desnoyers et al. | |
| 7,034,136 B2 | 4/2006 | Goddard et al. | |
| 7,244,827 B2 | 7/2007 | Raitano et al. | |
| 7,288,251 B2 * | 10/2007 | Bedian et al. | 424/153.1 |
| 7,303,895 B1 | 12/2007 | O'Regan et al. | |
| 7,378,492 B2 | 5/2008 | Chawla et al. | |
| 2002/0022248 A1 | 2/2002 | Xu et al. | |
| 2002/0103125 A1 | 8/2002 | Ashkenazi et al. | |
| 2002/0119130 A1 | 8/2002 | Eaton et al. | |
| 2002/0123463 A1 | 9/2002 | Ashkenazi et al. | |
| 2002/0127576 A1 | 9/2002 | Ashkenazi et al. | |
| 2002/0132252 A1 | 9/2002 | Ashkenazi et al. | |
| 2002/0142961 A1 | 10/2002 | Ashkenazi et al. | |
| 2002/0160384 A1 | 10/2002 | Ashkenazi et al. | |
| 2002/0177164 A1 | 11/2002 | Ashkenazi et al. | |
| 2002/0182638 A1 | 12/2002 | Eaton et al. | |
| 2002/0183493 A1 | 12/2002 | Eaton et al. | |
| 2002/0183494 A1 | 12/2002 | Eaton et al. | |
| 2002/0192763 A1 | 12/2002 | Xu et al. | |
| 2002/0193299 A1 | 12/2002 | Ashkenazi et al. | |
| 2002/0193300 A1 | 12/2002 | Ashkenazi et al. | |
| 2002/0194148 A1 | 12/2002 | Ashkenazi et al. | |
| 2002/0197615 A1 | 12/2002 | Ashkenazi et al. | |
| 2003/0003531 A1 | 1/2003 | Ashkenazi et al. | |
| 2003/0008297 A1 | 1/2003 | Ashkenazi et al. | |
| 2003/0009012 A1 | 1/2003 | Eaton et al. | |
| 2003/0009013 A1 | 1/2003 | Eaton et al. | |
| 2003/0013855 A1 | 1/2003 | Eaton et al. | |
| 2003/0017476 A1 | 1/2003 | Ashkenazi et al. | |
| 2003/0017981 A1 | 1/2003 | Ashkenazi et al. | |

(Continued)

FOREIGN PATENT DOCUMENTS

CA    CA-2369413    10/2000

(Continued)

OTHER PUBLICATIONS

International Search Report for PCT/US08/75488, mailed on Feb. 13, 2009, 5 pages.
Non-Final Office Action for U.S. Appl. No. 11/842,016, mailed Dec. 30, 2008, 9 pages.
Written Opinion of the International Searching Authority for PCT/US0875488, mailed on Feb. 13, 2009, 7 pages.
Casset et al., Biochem. Biophys. Res. Commun. (2003) 307:198-205.
Pascalis et al., Journal of Immunology (2002) 169:3076-3084.
Rudikoff et al., PNAS USA (1982) 79:1979-1983.
Dictionary Definition of "coupled to" from Merriam-Webster online, visited Jan. 16, 2010.

(Continued)

*Primary Examiner* — Anne M. Gussow
(74) *Attorney, Agent, or Firm* — Morrison & Foerster LLP

(57) ABSTRACT

Antibodies and molecules derived therefrom that bind to 24P4C12 protein and variants thereof, are described wherein 24P4C12 exhibits tissue specific expression in normal adult tissue, and is aberrantly expressed in the cancers listed in Table I. Consequently, 24P4C12 provides a diagnostic, prognostic, prophylactic and/or therapeutic target for cancer. The 24P4C12 gene or fragment thereof, or its encoded protein, or variants thereof, or a fragment thereof, can be used to elicit a humoral or cellular immune response; antibodies or T cells reactive with 24P4C12 can be used in active or passive immunization.

24 Claims, 113 Drawing Sheets

U.S. PATENT DOCUMENTS

| | | |
|---|---|---|
| 2003/0017982 A1 | 1/2003 | Ashkenazi et al. |
| 2003/0018168 A1 | 1/2003 | Eaton et al. |
| 2003/0018172 A1 | 1/2003 | Eaton et al. |
| 2003/0018173 A1 | 1/2003 | Eaton et al. |
| 2003/0018183 A1 | 1/2003 | Eaton et al. |
| 2003/0022187 A1 | 1/2003 | Ashkenazi et al. |
| 2003/0023042 A1 | 1/2003 | Eaton et al. |
| 2003/0027162 A1 | 2/2003 | Ashkenazi et al. |
| 2003/0027163 A1 | 2/2003 | Ashkenazi et al. |
| 2003/0027212 A1 | 2/2003 | Eaton et al. |
| 2003/0027754 A1 | 2/2003 | Ashkenazi et al. |
| 2003/0027985 A1 | 2/2003 | Ashkenazi et al. |
| 2003/0027986 A1 | 2/2003 | Eaton et al. |
| 2003/0027992 A1 | 2/2003 | Eaton et al. |
| 2003/0027993 A1 | 2/2003 | Eaton et al. |
| 2003/0032023 A1 | 2/2003 | Ashkenazi et al. |
| 2003/0036634 A1 | 2/2003 | Eaton et al. |
| 2003/0040473 A1 | 2/2003 | Ashkenazi et al. |
| 2003/0044806 A1 | 3/2003 | Ashkenazi et al. |
| 2003/0045463 A1 | 3/2003 | Ashkenazi et al. |
| 2003/0045684 A1 | 3/2003 | Eaton et al. |
| 2003/0049638 A1 | 3/2003 | Ashkenazi et al. |
| 2003/0049681 A1 | 3/2003 | Ashkenazi et al. |
| 2003/0049682 A1 | 3/2003 | Ashkenazi et al. |
| 2003/0049735 A1 | 3/2003 | Eaton et al. |
| 2003/0050462 A1 | 3/2003 | Eaton et al. |
| 2003/0050465 A1 | 3/2003 | Eaton et al. |
| 2003/0054359 A1 | 3/2003 | Ashkenazi et al. |
| 2003/0054403 A1 | 3/2003 | Ashkenazi et al. |
| 2003/0054404 A1 | 3/2003 | Ashkenazi et al. |
| 2003/0054987 A1 | 3/2003 | Ashkenazi et al. |
| 2003/0059780 A1 | 3/2003 | Ashkenazi et al. |
| 2003/0059782 A1 | 3/2003 | Ashkenazi et al. |
| 2003/0059783 A1 | 3/2003 | Ashkenazi et al. |
| 2003/0059831 A1 | 3/2003 | Ashkenazi et al. |
| 2003/0059832 A1 | 3/2003 | Ashkenazi et al. |
| 2003/0059833 A1 | 3/2003 | Ashkenazi et al. |
| 2003/0060407 A1 | 3/2003 | Ashkenazi et al. |
| 2003/0060600 A1 | 3/2003 | Eaton et al. |
| 2003/0060601 A1 | 3/2003 | Eaton et al. |
| 2003/0060602 A1 | 3/2003 | Eaton et al. |
| 2003/0064375 A1 | 4/2003 | Ashkenazi et al. |
| 2003/0065143 A1 | 4/2003 | Eaton et al. |
| 2003/0065161 A1 | 4/2003 | Eaton et al. |
| 2003/0068623 A1 | 4/2003 | Ashkenazi et al. |
| 2003/0068647 A1 | 4/2003 | Ashkenazi et al. |
| 2003/0069394 A1 | 4/2003 | Eaton et al. |
| 2003/0069403 A1 | 4/2003 | Ashkenazi et al. |
| 2003/0073090 A1 | 4/2003 | Ashkenazi et al. |
| 2003/0073623 A1 | 4/2003 | Drmanac et al. |
| 2003/0078387 A1 | 4/2003 | Eaton et al. |
| 2003/0082546 A1 | 5/2003 | Ashkenazi et al. |
| 2003/0083461 A1 | 5/2003 | Ashkenazi et al. |
| 2003/0083473 A1 | 5/2003 | Eaton et al. |
| 2003/0087304 A1 | 5/2003 | Ashkenazi et al. |
| 2003/0087305 A1 | 5/2003 | Ashkenazi et al. |
| 2003/0099974 A1 | 5/2003 | Lillie et al. |
| 2003/0147904 A1 | 8/2003 | Afar et al. |
| 2003/0211100 A1 | 11/2003 | Bedian et al. |
| 2004/0228858 A1 | 11/2004 | Hanson et al. |
| 2005/0019870 A1 | 1/2005 | Afar et al. |
| 2007/0004910 A1 | 1/2007 | Sexton et al. |
| 2007/0027308 A1 | 2/2007 | Edwards et al. |
| 2007/0160617 A1 | 7/2007 | Ma et al. |
| 2008/0311107 A1 | 12/2008 | Bollinger et al. |

FOREIGN PATENT DOCUMENTS

| | | |
|---|---|---|
| EP | 1 033 401 | 9/2000 |
| EP | 1 074 617 | 2/2001 |
| WO | WO-99/06548 | 2/1999 |
| WO | WO-99/06549 | 2/1999 |
| WO | WO-99/06550 | 2/1999 |
| WO | WO-99/40189 | 8/1999 |
| WO | WO-99/63088 | 12/1999 |
| WO | WO-00/04149 | 1/2000 |
| WO | WO-00/61746 | 10/2000 |
| WO | WO-00/73454 | 12/2000 |
| WO | WO-00/77021 | 12/2000 |
| WO | WO-01/16318 | 3/2001 |
| WO | WO-01/25272 | 4/2001 |
| WO | WO-01/34802 | 5/2001 |
| WO | WO-01/46258 | 6/2001 |
| WO | WO-01/51628 | 7/2001 |
| WO | WO-01/51633 | 7/2001 |
| WO | WO-01/53836 | 7/2001 |
| WO | WO-01/57270 | 8/2001 |
| WO | WO-01/57271 | 8/2001 |
| WO | WO-01/57272 | 8/2001 |
| WO | WO-01/57273 | 8/2001 |
| WO | WO-01/57274 | 8/2001 |
| WO | WO-01/57275 | 8/2001 |
| WO | WO-01/57276 | 8/2001 |
| WO | WO-01/57277 | 8/2001 |
| WO | WO-01/57278 | 8/2001 |
| WO | WO-01/60860 | 8/2001 |
| WO | WO-01/73027 | 10/2001 |
| WO | WO-01/73032 | 10/2001 |
| WO | WO-01/75067 | 10/2001 |
| WO | WO-01/86003 | 11/2001 |
| WO | WO-01/90304 | 11/2001 |
| WO | WO-01/96388 | 12/2001 |
| WO | WO-01/96390 | 12/2001 |
| WO | WO-02/12328 | 2/2002 |
| WO | WO-02/058534 | 8/2002 |
| WO | WO-02/074961 | 9/2002 |
| WO | WO-02/083876 | 10/2002 |
| WO | WO-02/089747 | 11/2002 |
| WO | WO-02/097031 | 12/2002 |
| WO | WO-2009/033094 | 3/2009 |

OTHER PUBLICATIONS

Sequence Search Result (enablement), searched Jan. 24, 2010.
Sequence Search Result (ODP-'827), searched Jan. 18, 2010.
Sequence Search Result (ODP-'823), searched Jan. 24, 2010.
Sequence Search Result (ODP-138), searched Feb. 2, 2010.
Sequence Search Result (Ashkenazi), searched Jan. 11, 2010.
Stites et al., Basic and Clinical Immunology, Seventh Edition (1991), Appleton and Lange, East Norwalk, CT, p. 102.
Supplementary European Search Report for 02789937.6, mailed May 25, 2009, 7 pages.
International Search Report for PCT/US10/26429, mailed on Jun. 10, 2010, 3 pages.
Written Opinion of the International Searching Authority for PCT/US10/26429, mailed on Jun. 10, 2010, 3 pages.
Alberts et al., Molecular Biology of the Cell, 3rd. ed. (1994) p. 465.
Alzari et al., Annual Rev Immunol (1988) 6:555-580.
Benedict et al., J. Exp. Medicine (2001) 193(1):89-99.
Boehringer Mannheim Biochemicals, 1994 Catalog, p. 93.
Bowie et al., Science (1990) 247:1306-1310.
Brennan et al., Journal of Autoimmunity (1989) 2(suppl.):177-186.
Bruggemann et al., PNAS USA (1989) 86:6709-6713.
Busken et al., Digestive Disease Week Abstracts and Itinerary Planner (2003) Abstract No. 850.
Chang et al., The Journal of Histochemistry and Cytochemistry (1991) 39(9):1281-1287.
Craft et al., Cancer Res. (1999) 59:5030-5036.
Dermer, Bio/Technology (1994) 12:320.
Drexler et al., Leukemia and Lymphoma (1993) 9:1-25.
Dulcert et al., Accession No. AAY12282, 1999.
Ericksson et al., Diabetologia (1992) 35:143-147.
Ezzell, Journal of NIH Research (1995) 7:46-49.
Freshney, Culture of Animal Cells, A Manual of Basic Technique, Alan R. Liss, Inc., New York (1983) p. 4.
Fu et al., EMBO Journal (1996) 15:4392-4401.
Greenbaum et al., Genome Biology (2003) 4(9):117.1-117.8.
Gura, Science (1997) 278:1041-1042.
Gussow and Seemann, Methods in Enzymology (1991) 203:99-121.
Harlow and Lane (eds.), Antibodies: A Laboratory Manual, Cold Spring Harbor (1988) pp. 591-598.
Hirashima et al., Int. Arch. Allergy Immunol. (2000) Suppl.1:6-9.
Hsu, in Tissue Culture Methods and Applications, Kruse and Patterson, eds. (1973) Academic Press, Abstract p. 764.

Huang, G.M. et al., "Prostate cancer expression profiling by cDNA sequencing analysis," EMBL Database entry AI557659, Accession No. AI557659, Mar. 25, 1999, EP002144281, & Huang, G.M. et al., Genomics, vol. 59, No. 2, Jul. 1999, pp. 178-186.

Huang, Guyang Matthew, Aug. 9, 1999, dbEST Id 2373824, GenBank Acc. AI557660.

Hubert et al., PNAS USA (1999) 96(25):14523-14528.

Huston et al., PNAS USA (1988) 85:5879-5883.

Inoko, Hidetoshi, Mar. 30, 2000, NCBI Accession No. AP000502.

International Search Report for PCT/US02/38264, mailed on Oct. 20, 2004, 3 pages.

Jakobovits, Expert Opinion on Investigational Drugs (1998) 7(4):607-614.

Jiang et al., JBC (2003) 278(7):4763-4769.

Johnstone and Thorpe, Immunochemistry in Practice, 2nd edition, Blackwell Scientific Publications, Oxford (1987) pp. 113-130.

Kerlavage, A. R, Apr. 21, 1997, dbEST Id 1008183, GenBank Acc. AA 366876.

Kilty and Amara, Curr. Opin. Biotechnology (1992) 3:675-682.

Klein, Immunology: the Science of Self-Nonself Discrimination, John Wiley & Sons, New York, (1982) p. 355.

Klein et al., Nature Med. (1997) 3:402-408.

Kohler and Milstein, Nature (1975) 256:495-497.

Lewin et al., Genes VI, Oxford University Press, Inc., New York, (1997) Chapter 29.

Mallampalli et al., Biochem. J. (1996) 318:333-341.

Mcclean and Hill, Eur. J. Cancer (1993) 29A:2243-2248.

Morrison et al., PNAS USA (1984) 81:6851-6855.

Morton and Myszka, Methods in Enzymology (1998) 295:268.

Muller et al., MCB (1991) 11:1785.

NCI-CGAP, "National Cancer Institute, Cancer Genome Anatomy Project (CGAP)", Oct. 7, 1997, EMBL Database Entry AA612666, Accession No. AA612666, XP002144282.

Paul, W.E., ed. Fundamental Immunology, Raven Press (1984) pp. 614-619.

Pemberton et al., J. of Histochemistry and Cytochemistry (1997) 45:1697-1706.

Pinto et al., Clin Cancer Res (1996) 2(9):1445-1451.

Reiter, Robert E. et al., Prostate stem cell antigen: A cell surface marker overexpressed in prostate cancer:, Proc. Natl. Acad. Sci., Feb. 1998, vol. 95, pp. 1735-1740, XP-002078363.

Rowen, L. et al., "Sequence of the human major histocompatibility complex class III region", Mar. 29, 1999, EMBL Database Entry AF134726, Accession No. AF134726, XP002144283.

Rowen, L., Mar. 24, 1999, NCBI Accession No. AAD21813.

Simpson, A.J.G., Mar. 16, 2000, dbEST Id 4011587, GenBank Acc. AW579065.

Simpson, A. J. G., Mar. 23, 2000, dbEST Id 4036649, GenBank Acc. AW603383.

Simpson, A. J. G., Mar. 23, 2000, dbEST Id 4035408, GenBank Acc. AW602142.

Simpson, A.J.G., Feb. 4, 2000, dbEST Id 3787048, GenBank Acc. AW393065.

Slootstra et al., Molecular Diversity (1996) 2:156-164.

Spitler, Cancer Biotherapy (1995) 10:1-3.

Storrie et al., Methods Enzymol. (1990) 182:203-225.

Strausberg, Robert, Sep. 6, 1999, dbEST Id 3075200, GenBank Acc. AI951815.

Strausberg, Robert, Mar. 9, 2000, dbEST Id 3079479, GenBank Acc. AI956094.

Strausberg, Robert, Jun. 21, 1999, dbEST Id 2655196, GenBank Acc. AI745450.

Strausberg, Robert, Mar. 7, 2000, dbEST Id 2893738, GenBank Acc. AI813886.

Strausberg, Robert, Aug. 14, 1997, dbEST Id 1112901, GenBank Acc. AA468365.

Strausberg, Robert, Aug. 21, 1997, dbEST Id 1178186, GenBank Acc. AA533783.

Strausberg, Robert, Feb. 16, 1999, dbEST Id 2101871, GenBank Acc. AI318311.

Strausberg, Robert, Oct. 30, 1999, dbEST Id 3291479, GenBank Acc. AW139432.

Strausberg, Robert, Feb. 24, 2000, dbEST Id 3880006, GenBank Acc. AW469133.

Strausberg, Robert, Mar. 7, 2000, dbEST Id 2947457, GenBank Acc. AI858987.

Strausberg, Robert, May 13, 1999, dbEST Id 2376359, GenBank Acc. AI560195.

Strausberg, Robert, Mar. 7, 2000, dbEST Id 2946846, GenBank Acc. AI858299.

Strausberg, Robert, May 14, 1999, dbEST Id 2390443, GenBank Acc. AI572115.

Strausberg, Robert, May 14, 1999, dbEST Id 2381301, GenBank Acc. AI565097.

Strausberg, Robert, Dec. 14, 1999, dbEST Id 2443929, GenBank Acc. AI625125.

Strausberg, Robert, Mar. 8, 2000, dbEST Id 3055029, GenBank Acc. AI932443.

Su et al., PNAS USA (1996) 93:7252-7257.

Takeda, Jun, Sep. 9, 1997, dbEST Id 1241269, GenBank Acc. C75094.

Tockman et al., Cancer Res (1992) 52:2711s-2718s.

Welch et al., Int. J. Cancer (1989) 43:449-457.

Welford, Opt. Quant. Elect. (1991) 23:1.

White et al., Ann. Rev. Med. (2001) 52:125-145.

Wilson, R. K., Jun. 10, 1999, dbEST Id 2629269, GenBank Acc. AI721101.

Wilson, R. K., Jul. 7, 1995, dbEST Id 285541, GenBank Acc. H25030.

Wilson, R. K., Apr. 20, 1995, dbEST Id 194186, GenBank Acc. R24141.

Zellner et al., Clin. Can. Res. (1998) 4:1797-1802.

Zimmer, Cell Motility and the Cytoskeleton (1991) 20:325 337.

Correale et al., J. Natl. Cancer Inst. (1997) 89(4):293-300.

Mcneel et al., Cancer Res (2001) 61(13):5161-5167.

Office Action for Canadian Patent Application 2,503,346, mailed Mar. 28, 2011, 3 pages.

* cited by examiner

Figure 1:

Figure 1A-1. The cDNA (SEQ ID NO:1) and amino acid sequence (SEQ ID NO:2) of 24P4C12 variant 1. The open reading frame extends from nucleic acid 6-2138 including the stop codon. The start methionine is underlined.

```
  1      M   G   G   K   Q   R   D   E   D   D   E   A   Y   G   K   P   V   K   Y
  1    gagccATGGGGGGAAAGCAGCGGGACGAGGATGACGAGGCCTACGGGAAGCCAGTCAAAT
 20      D   P   S   F   R   G   P   I   K   N   R   S   C   T   D   V   I   C   C   V
 61    ACGACCCCTCCTTTCGAGGCCCCATCAAGAACAGAAGCTGCACAGATGTCATCTGCTGCG
 40      L   F   L   L   F   I   L   G   Y   I   V   V   G   I   V   A   W   L   Y   G
121    TCCTCTTCCTGCTCTTCATTCTAGGTTACATCGTGGTGGGGATTGTGGCCTGGTTGTATG
 60      D   P   R   Q   V   L   Y   P   R   N   S   T   G   A   Y   C   G   M   G   E
181    GAGACCCCCGGCAAGTCCTCTACCCCAGGAACTCTACTGGGGCCTACTGTGGCATGGGGG
 80      N   K   D   K   P   Y   L   L   Y   F   N   I   F   S   C   I   L   S   S   N
241    AGAACAAAGATAAGCCGTATCTCCTGTACTTCAACATCTTCAGCTGCATCCTGTCCAGCA
100      I   I   S   V   A   E   N   G   L   Q   C   P   T   P   Q   V   C   V   S   S
301    ACATCATCTCAGTTGCTGAGAACGGCCTACAGTGCCCCACACCCCAGGTGTGTGTGTCCT
120      C   P   E   D   P   W   T   V   G   K   N   E   F   S   Q   T   V   G   E   V
361    CCTGCCCGGAGGACCCATGGACTGTGGGAAAAAACGAGTTCTCACAGACTGTTGGGGAAG
140      F   Y   T   K   N   R   N   F   C   L   P   G   V   P   W   N   M   T   V   I
421    TCTTCTATACAAAAAACAGGAACTTTTGTCTGCCAGGGGTACCCTGGAATATGACGGTGA
160      T   S   L   Q   Q   E   L   C   P   S   F   L   L   P   S   A   P   A   L   G
481    TCACAAGCCTGCAACAGGAACTCTGCCCCAGTTTCCTCCTCCCCTCTGCTCCAGCTCTGG
180      R   C   F   P   W   T   N   V   T   P   P   A   L   P   G   I   T   N   D   T
541    GGCGCTGCTTTCCATGGACCAACGTTACTCCACCGGCGCTCCCAGGGATCACCAATGACA
200      T   I   Q   Q   G   I   S   G   L   I   D   S   L   N   A   R   D   I   S   V
601    CCACCATACAGCAGGGGATCAGCGGTCTTATTGACAGCCTCAATGCCCGAGACATCAGTG
220      K   I   F   E   D   F   A   Q   S   W   Y   W   I   L   V   A   L   G   V   A
661    TTAAGATCTTTGAAGATTTTGCCCAGTCCTGGTATTGGATTCTTGTTGCCCTGGGGGTGG
240      L   V   L   S   L   L   F   I   L   L   L   R   L   V   A   G   P   L   V   L
721    CTCTGGTCTTGAGCCTACTGTTTATCTTGCTTCTGCGCCTGGTGGCTGGGCCCCTGGTGC
260      V   L   I   L   G   V   L   G   V   L   A   Y   G   I   Y   Y   C   W   E   E
781    TGGTGCTGATCCTGGGAGTGCTGGGCGTGCTGGCATACGGCATCTACTACTGCTGGGAGG
280      Y   R   V   L   R   D   K   G   A   S   I   S   Q   L   G   F   T   T   N   L
841    AGTACCGAGTGCTGCGGGACAAGGGCGCCTCCATCTCCCAGCTGGGTTTCACCACCAACC
300      S   A   Y   Q   S   V   Q   E   T   W   L   A   A   L   I   V   L   A   V   L
901    TCAGTGCCTACCAGAGCGTGCAGGAGACCTGGCTGGCCGCCCTGATCGTGTTGGCGGTGC
320      E   A   I   L   L   M   L   I   F   L   R   Q   R   I   R   I   A   I   A
961    TTGAAGCCATCCTGCTGCTGATGCTCATCTTCCTGCGGCAGCGGATTCGTATTGCCATCG
340      L   L   K   E   A   S   K   A   V   G   Q   M   M   S   T   M   F   Y   P   L
1021   CCCTCCTGAAGGAGGCCAGCAAGGCTGTGGGACAGATGATGTCTACCATGTTCTACCCAC
360      V   T   F   V   L   L   L   I   C   I   A   Y   W   A   M   T   A   L   Y   L
1081   TGGTCACCTTTGTCCTCCTCCTCATCTGCATTGCCTACTGGGCCATGACTGCTCTGTACC
```

Figure 1A-2

```
 380    A  T  S  G  Q  P  Q  Y  V  L  W  A  S  N  I  S  S  P  G  C
1141 TGGCTACATCGGGGCAACCCCAGTATGTGCTCTGGGCATCCAACATCAGCTCCCCCGGCT
 400    E  K  V  P  I  N  T  S  C  N  P  T  A  H  L  V  N  S  S  C
1201 GTGAGAAAGTGCCAATAAATACATCATGCAACCCCACGGCCCACCTTGTGAACTCCTCGT
 420    P  G  L  M  C  V  F  Q  G  Y  S  S  K  G  L  I  Q  R  S  V
1261 GCCCAGGGCTGATGTGCGTCTTCCAGGGCTACTCATCCAAAGGCCTAATCCAACGTTCTG
 440    F  N  L  Q  I  Y  G  V  L  G  L  F  W  T  L  N  W  V  L  A
1321 TCTTCAATCTGCAAATCTATGGGGTCCTGGGGCTCTTCTGGACCCTTAACTGGGTACTGG
 460    L  G  Q  C  V  L  A  G  A  F  A  S  F  Y  W  A  F  H  K  P
1381 CCCTGGGCCAATGCGTCCTCGCTGGAGCCTTTGCCTCCTTCTACTGGGCCTTCCACAAGC
 480    Q  D  I  P  T  F  P  L  I  S  A  F  I  R  T  L  R  Y  H  T
1441 CCCAGGACATCCCTACCTTCCCCTTAATCTCTGCCTTCATCCGCACACTCCGTTACCACA
 500    G  S  L  A  F  G  A  L  I  L  T  L  V  Q  I  A  R  V  I  L
1501 CTGGGTCATTGGCATTTGGAGCCCTCATCCTGACCCTTGTGCAGATAGCCCGGGTCATCT
 520    E  Y  I  D  H  K  L  R  G  V  Q  N  P  V  A  R  C  I  M  C
1561 TGGAGTATATTGACCACAAGCTCAGAGGAGTGCAGAACCCTGTAGCCCGCTGCATCATGT
 540    C  F  K  C  C  L  W  C  L  E  K  F  I  K  F  L  N  R  N  A
1621 GCTGTTTCAAGTGCTGCCTCTGGTGTCTGGAAAAATTTATCAAGTTCCTAAACCGCAATG
 560    Y  I  M  I  A  I  Y  G  K  N  F  C  V  S  A  K  N  A  F  M
1681 CATACATCATGATCGCCATCTACGGGAAGAATTTCTGTGTCTCAGCCAAAAATGCGTTCA
 580    L  L  M  R  N  I  V  R  V  V  V  L  D  K  V  T  D  L  L  L
1741 TGCTACTCATGCGAAACATTGTCAGGGTGGTCGTCCTGGACAAAGTCACAGACCTGCTGC
 600    F  F  G  K  L  L  V  V  G  G  V  G  V  L  S  F  F  F  F  S
1801 TGTTCTTTGGGAAGCTGCTGGTGGTCGGAGGCGTGGGGGTCCTGTCCTTCTTTTTTTTCT
 620    G  R  I  P  G  L  G  K  D  F  K  S  P  H  L  N  Y  Y  W  L
1861 CCGGTCGCATCCCGGGGCTGGGTAAAGACTTTAAGAGCCCCCACCTCAACTATTACTGGC
 640    P  I  M  T  S  I  L  G  A  Y  V  I  A  S  G  F  F  S  V  F
1921 TGCCCATCATGACCTCCATCCTGGGGGCCTATGTCATCGCCAGCGGCTTCTTCAGCGTTT
 660    G  M  C  V  D  T  L  F  L  C  F  L  E  D  L  E  R  N  N  G
1981 TCGGCATGTGTGTGGACACGCTCTTCCTCTGCTTCCTGGAAGACCTGGAGCGGAACAACG
 680    S  L  D  R  P  Y  Y  M  S  K  S  L  L  K  I  L  G  K  K  N
2041 GCTCCCTGGACCGGCCCTACTACATGTCCAAGAGCCTTCTAAAGATTCTGGGCAAGAAGA
 700    E  A  P  P  D  N  K  K  R  K  K  *
2101 ACGAGGCGCCCCCGGACAACAAGAAGAGGAAGAAGTGAcagctccggccctgatccagga
2161 ctgcaccccaccccaccgtccagccatccaacctcacttcgccttacaggtctccattt
2221 tgtggtaaaaaaaggttttaggccaggcgccgtggctcacgcctgtaatccaacactttg
2281 agaggctgaggcgggcggatcacctgagtcaggagttcgagaccagcctggccaacatgg
2341 tgaaaccteegtctctattaaaaatacaaaaattagccgagagtggtggcatgcacctgt
2401 catcccagctactcgggaggctgaggcaggagaatcgcttgaacccgggaggcagaggtt
2461 gcagtgagccgagatcgcgccactgcactccaacctgggtgacagactctgtctccaaaa
2521 caaacaaacaaacaaaaagatttttattaaagatattttgttaactcagtaaaaaaaaaa
2581 aaaaaaa
```

Figure 1B-1: The cDNA (SEQ ID NO:3) and amino acid sequence (SEQ ID NO:4) of 24P4C12 variant 2. The open reading frame extends from nucleic acid 6-2138 including the stop codon. The start methionine is underlined.

```
  1       M   G   G   K   Q   R   D   E   D   D   E   A   Y   G   K   P   V   K   Y
  1    gagccATGGGGGGAAAGCAGCGGGACGAGGATGACGAGGCCTACGGGAAGCCAGTCAAAT
 20       D   P   S   F   R   G   P   I   K   N   R   S   C   T   D   V   I   C   C   V
 61    ACGACCCCTCCTTTCGAGGCCCCATCAAGAACAGAAGCTGCACAGATGTCATCTGCTGCG
 40       L   F   L   L   F   I   L   G   Y   I   V   V   G   I   V   A   W   L   Y   G
121    TCCTCTTCCTGCTCTTCATTCTAGGTTACATCGTGGTGGGGATTGTGGCCTGGTTGTATG
 60       D   P   R   Q   V   L   Y   P   R   N   S   T   G   A   Y   C   G   M   G   E
181    GAGACCCCCGGCAAGTCCTCTACCCCAGGAACTCTACTGGGGCCTACTGTGGCATGGGGG
 80       N   K   D   K   P   Y   L   L   Y   F   N   I   F   S   C   I   L   S   S   N
241    AGAACAAAGATAAGCCGTATCTCCTGTACTTCAACATCTTCAGCTGCATCCTGTCCAGCA
100       I   I   S   V   A   E   N   G   L   Q   C   P   T   P   Q   V   C   V   S   S
301    ACATCATCTCAGTTGCTGAGAACGGCCTACAGTGCCCCACACCCCAGGTGTGTGTGTCCT
120       C   P   E   D   P   W   T   V   G   K   N   E   F   S   Q   T   V   G   E   V
361    CCTGCCCGGAGGACCCATGGACTGTGGGAAAAAACGAGTTCTCACAGACTGTTGGGGAAG
140       F   Y   T   K   N   R   N   F   C   L   P   G   V   P   W   N   M   T   V   I
421    TCTTCTATACAAAAAACAGGAACTTTTGTCTGCCAGGGGTACCCTGGAATATGACGGTGA
160       T   S   L   Q   Q   E   L   C   P   S   F   L   L   P   S   A   P   A   L   G
481    TCACAAGCCTGCAACAGGAACTCTGCCCCAGTTTCCTCCTCCCCTCTGCTCCAGCTCTGG
180       R   C   F   P   W   T   N   V   T   P   P   A   L   P   G   I   T   N   D   T
541    GACGCTGCTTTCCATGGACCAACGTTACTCCACCGGCGCTCCCAGGGATCACCAATGACA
200       T   I   Q   Q   G   I   S   G   L   I   D   S   L   N   A   R   D   I   S   V
601    CCACCATACAGCAGGGGATCAGCGGTCTTATTGACAGCCTCAATGCCCGAGACATCAGTG
220       K   I   F   E   D   F   A   Q   S   W   Y   W   I   L   V   A   L   G   V   A
661    TTAAGATCTTTGAAGATTTTGCCCAGTCCTGGTATTGGATTCTTGTTGCCCTGGGGGTGG
240       L   V   L   S   L   L   F   I   L   L   R   L   V   A   G   P   L   V   L
721    CTCTGGTCTTGAGCCTACTGTTTATCTTGCTTCTGCGCCTGGTGGCTGGGCCCCTGGTGC
260       V   L   I   L   G   V   L   G   V   L   A   Y   G   I   Y   Y   C   W   E   E
781    TGGTGCTGATCCTGGGAGTGCTGGGCGTGCTGGCATACGGCATCTACTACTGCTGGGAGG
280       Y   R   V   L   R   D   K   G   A   S   I   S   Q   L   G   F   T   T   N   L
841    AGTACCGAGTGCTGCGGGACAAGGGCGCCTCCATCTCCCAGCTGGGTTTCACCACCAACC
300       S   A   Y   Q   S   V   Q   E   T   W   L   A   A   L   I   V   L   A   V   L
901    TCAGTGCCTACCAGAGCGTGCAGGAGACCTGGCTGGCCGCCCTGATCGTGTTGGCGGTGC
320       E   A   I   L   L   L   M   L   I   F   L   R   Q   R   I   R   I   A   I   A
961    TTGAAGCCATCCTGCTGCTGATGCTCATCTTCCTGCGGCAGCGGATTCGTATTGCCATCG
340       L   L   K   E   A   S   K   A   V   G   Q   M   M   S   T   M   F   Y   P   L
1021   CCCTCCTGAAGGAGGCCAGCAAGGCTGTGGGACAGATGATGTCTACCATGTTCTACCCAC
360       V   T   F   V   L   L   I   C   I   A   Y   W   A   M   T   A   L   Y   L
1081   TGGTCACCTTTGTCCTCCTCCTCATCTGCATTGCCTACTGGGCCATGACTGCTCTGTACC
380       A   T   S   G   Q   P   Q   Y   V   L   W   A   S   N   I   S   S   P   G   C
```

Figure 1B-2

```
1141 TGGCTACATCGGGGCAACCCCAGTATGTGCTCTGGGCATCCAACATCAGCTCCCCCGGCT
 400   E  K  V  P  I  N  T  S  C  N  P  T  A  H  L  V  N  S  S  C
1201 GTGAGAAAGTGCCAATAAATACATCATGCAACCCCACGGCCCACCTTGTGAACTCCTCGT
 420   P  G  L  M  C  V  F  Q  G  Y  S  S  K  G  L  I  Q  R  S  V
1261 GCCCAGGGCTGATGTGCGTCTTCCAGGGCTACTCATCCAAAGGCCTAATCCAACGTTCTG
 440   F  N  L  Q  I  Y  G  V  L  G  L  F  W  T  L  N  W  V  L  A
1321 TCTTCAATCTGCAAATCTATGGGGTCCTGGGGCTCTTCTGGACCCTTAACTGGGTACTGG
 460   L  G  Q  C  V  L  A  G  A  F  A  S  F  Y  W  A  F  H  K  P
1381 CCCTGGGCCAATGCGTCCTCGCTGGAGCCTTTGCCTCCTTCTACTGGGCCTTCCACAAGC
 480   Q  D  I  P  T  F  P  L  I  S  A  F  I  R  T  L  R  Y  H  T
1441 CCCAGGACATCCCTACCTTCCCCTTAATCTCTGCCTTCATCCGCACACTCCGTTACCACA
 500   G  S  L  A  F  G  A  L  I  L  T  L  V  Q  I  A  R  V  I  L
1501 CTGGGTCATTGGCATTTGGAGCCCTCATCCTGACCCTTGTGCAGATAGCCCGGGTCATCT
 520   E  Y  I  D  H  K  L  R  G  V  Q  N  P  V  A  R  C  I  M  C
1561 TGGAGTATATTGACCACAAGCTCAGAGGAGTGCAGAACCCTGTAGCCCGCTGCATCATGT
 540   C  F  K  C  C  L  W  C  L  E  K  F  I  K  F  L  N  R  N  A
1621 GCTGTTTCAAGTGCTGCCTCTGGTGTCTGGAAAAATTTATCAAGTTCCTAAACCGCAATG
 560   Y  I  M  I  A  I  Y  G  K  N  F  C  V  S  A  K  N  A  F  M
1681 CATACATCATGATCGCCATCTACGGGAAGAATTTCTGTGTCTCAGCCAAAAATGCGTTCA
 580   L  L  M  R  N  I  V  R  V  V  V  L  D  K  V  T  D  L  L  L
1741 TGCTACTCATGCGAAACATTGTCAGGGTGGTCGTCCTGGACAAAGTCACAGACCTGCTGC
 600   F  F  G  K  L  L  V  V  G  G  V  G  V  L  S  F  F  F  F  S
1801 TGTTCTTTGGGAAGCTGCTGGTGGTCGGAGGCGTGGGGGTCCTGTCCTTCTTTTTTTTCT
 620   G  R  I  P  G  L  G  K  D  F  K  S  P  H  L  N  Y  Y  W  L
1861 CCGGTCGCATCCCGGGGCTGGGTAAAGACTTTAAGAGCCCCCACCTCAACTATTACTGGC
 640   P  I  M  T  S  I  L  G  A  Y  V  I  A  S  G  F  F  S  V  F
1921 TGCCCATCATGACCTCCATCCTGGGGGCCTATGTCATCGCCAGCGGCTTCTTCAGCGTTT
 660   G  M  C  V  D  T  L  F  L  C  F  L  E  D  L  E  R  N  N  G
1981 TCGGCATGTGTGTGGACACGCTCTTCCTCTGCTTCCTGGAAGACCTGGAGCGGAACAACG
 680   S  L  D  R  P  Y  Y  M  S  K  S  L  L  K  I  L  G  K  K  N
2041 GCTCCCTGGACCGGCCCTACTACATGTCCAAGAGCCTTCTAAAGATTCTGGGCAAGAAGA
 700   E  A  P  P  D  N  K  K  R  K  K  *
2101 ACGAGGCGCCCCCGGACAACAAGAAGAGGAAGAAGTGAcagctccggccctgatccagga
2161 ctgcacccaccccacgtccagccatccaacctcacttcgccttacaggtctccattt
2221 tgtggtaaaaaaaggttttaggccaggcgccgtggctcacgcctgtaatccaacactttg
2281 agaggctgaggcgggcggatcacctgagtcaggagttcgagaccagcctggccaacatgg
2341 tgaaacctccgtctctattaaaaatacaaaaattagccgagagtggtggcatgcacctgt
2401 catcccagctactcgggaggctgaggcaggagaatcgcttgaacccgggaggcagaggtt
2461 gcagtgagccgagatcgcgccactgcactccaacctgggtgacagactctgtctccaaaa
2521 caaaacaaacaaacaaaaagatttttattaaagatattttgttaactcagtaaaaaaaaaa
2581 aaaaaaa
```

Figure 1C-1: The cDNA (SEQ ID NO:5) and amino acid sequence (SEQ ID NO:6) of 24P4C12 variant 3. The open reading frame extends from nucleic acid 6-2138 including the stop codon. The start methionine is underlined.

```
  1     M   G   G   K   Q   R   D   E   D   D   E   A   Y   G   K   P   V   K   Y
  1   gagccATGGGGGGAAAGCAGCGGGACGAGGATGACGAGGCCTACGGGAAGCCAGTCAAAT
 20     D   P   S   F   R   G   P   I   K   N   R   S   C   T   D   V   I   C   C   V
 61   ACGACCCCTCCTTTCGAGGCCCCATCAAGAACAGAAGCTGCACAGATGTCATCTGCTGCG
 40     L   F   L   L   F   I   L   G   Y   I   V   V   G   I   V   A   W   L   Y   G
121   TCCTCTTCCTGCTCTTCATTCTAGGTTACATCGTGGTGGGGATTGTGGCCTGGTTGTATG
 60     D   P   R   Q   V   L   Y   P   R   N   S   T   G   A   Y   C   G   M   G   E
181   GAGACCCCCGGCAAGTCCTCTACCCCAGGAACTCTACTGGGGCCTACTGTGGCATGGGGG
 80     N   K   D   K   P   Y   L   L   Y   F   N   I   F   S   C   I   L   S   S   N
241   AGAACAAAGATAAGCCGTATCTCCTGTACTTCAACATCTTCAGCTGCATCCTGTCCAGCA
100     I   I   S   V   A   E   N   G   L   Q   C   P   T   P   Q   V   C   V   S   S
301   ACATCATCTCAGTTGCTGAGAACGGCCTACAGTGCCCCACACCCCAGGTGTGTGTGTCCT
120     C   P   E   D   P   W   T   V   G   K   N   E   F   S   Q   T   V   G   E   V
361   CCTGCCCGGAGGACCCATGGACTGTGGGAAAAAACGAGTTCTCACAGACTGTTGGGGAAG
140     F   Y   T   K   N   R   N   F   C   L   P   G   V   P   W   N   M   T   V   I
421   TCTTCTATACAAAAAACAGGAACTTTTGTCTGCCAGGGGTACCCTGGAATATGACGGTGA
160     T   S   L   Q   Q   E   L   C   P   S   F   L   L   P   S   A   P   A   L   G
481   TCACAAGCCTGCAACAGGAACTCTGCCCCAGTTTCCTCCTCCCCTCTGCTCCAGCTCTGG
180     R   C   F   P   W   T   N   I   T   P   P   A   L   P   G   I   T   N   D   T
541   GGCGCTGCTTTCCATGGACCAACATTACTCCACCGGCGCTCCCAGGGATCACCAATGACA
200     T   I   Q   Q   G   I   S   G   L   I   D   S   L   N   A   R   D   I   S   V
601   CCACCATACAGCAGGGGATCAGCGGTCTTATTGACAGCCTCAATGCCCGAGACATCAGTG
220     K   I   F   E   D   F   A   Q   S   W   Y   W   I   L   V   A   L   G   V   A
661   TTAAGATCTTTGAAGATTTTGCCCAGTCCTGGTATTGGATTCTTGTTGCCCTGGGGGTGG
240     L   V   L   S   L   L   F   I   L   L   L   R   L   V   A   G   P   L   V   L
721   CTCTGGTCTTGAGCCTACTGTTTATCTTGCTTCTGCGCCTGGTGGCTGGGCCCCTGGTGC
260     V   L   I   L   G   V   L   G   V   L   A   Y   G   I   Y   Y   C   W   E   E
781   TGGTGCTGATCCTGGGAGTGCTGGGCGTGCTGGCATACGGCATCTACTACTGCTGGGAGG
280     Y   R   V   L   R   D   K   G   A   S   I   S   Q   L   G   F   T   T   N   L
841   AGTACCGAGTGCTGCGGGACAAGGGCGCCTCCATCTCCCAGCTGGGTTTCACCACCAACC
300     S   A   Y   Q   S   V   Q   E   T   W   L   A   A   L   I   V   L   A   V   L
901   TCAGTGCCTACCAGAGCGTGCAGGAGACCTGGCTGGCCGCCCTGATCGTGTTGGCGGTGC
320     E   A   I   L   L   M   L   I   F   L   R   Q   R   I   R   I   A   I   A
961   TTGAAGCCATCCTGCTGCTGATGCTCATCTTCCTGCGGCAGCGGATTCGTATTGCCATCG
340     L   L   K   E   A   S   K   A   V   G   Q   M   M   S   T   M   F   Y   P   L
1021  CCCTCCTGAAGGAGGCCAGCAAGGCTGTGGGACAGATGATGTCTACCATGTTCTACCCAC
360     V   T   F   V   L   L   I   C   I   A   Y   W   A   M   T   A   L   Y   L
1081  TGGTCACCTTTGTCCTCCTCCTCATCTGCATTGCCTACTGGGCCATGACTGCTCTGTACC
380     A   T   S   G   Q   P   Q   Y   V   L   W   A   S   N   I   S   S   P   G   C
```

Figure 1C-2

```
1141 TGGCTACATCGGGGCAACCCCAGTATGTGCTCTGGGCATCCAACATCAGCTCCCCCGGCT
 400    E  K  V  P  I  N  T  S  C  N  P  T  A  H  L  V  N  S  S  C
1201 GTGAGAAAGTGCCAATAAATACATCATGCAACCCCACGGCCCACCTTGTGAACTCCTCGT
 420    P  G  L  M  C  V  F  Q  G  Y  S  S  K  G  L  I  Q  R  S  V
1261 GCCCAGGGCTGATGTGCGTCTTCCAGGGCTACTCATCCAAAGGCCTAATCCAACGTTCTG
 440    F  N  L  Q  I  Y  G  V  L  G  L  F  W  T  L  N  W  V  L  A
1321 TCTTCAATCTGCAAATCTATGGGGTCCTGGGGCTCTTCTGGACCCTTAACTGGGTACTGG
 460    L  G  Q  C  V  L  A  G  A  F  A  S  F  Y  W  A  F  H  K  P
1381 CCCTGGGCCAATGCGTCCTCGCTGGAGCCTTTGCCTCCTTCTACTGGGCCTTCCACAAGC
 480    Q  D  I  P  T  F  P  L  I  S  A  F  I  R  T  L  R  Y  H  T
1441 CCCAGGACATCCCTACCTTCCCCTTAATCTCTGCCTTCATCCGCACACTCCGTTACCACA
 500    G  S  L  A  F  G  A  L  I  L  T  L  V  Q  I  A  R  V  I  L
1501 CTGGGTCATTGGCATTTGGAGCCCTCATCCTGACCCTTGTGCAGATAGCCCGGGTCATCT
 520    E  Y  I  D  H  K  L  R  G  V  Q  N  P  V  A  R  C  I  M  C
1561 TGGAGTATATTGACCACAAGCTCAGAGGAGTGCAGAACCCTGTAGCCCGCTGCATCATGT
 540    C  F  K  C  C  L  W  C  L  E  K  F  I  K  F  L  N  R  N  A
1621 GCTGTTTCAAGTGCTGCCTCTGGTGTCTGGAAAAATTTATCAAGTTCCTAAACCGCAATG
 560    Y  I  M  I  A  I  Y  G  K  N  F  C  V  S  A  K  N  A  F  M
1681 CATACATCATGATCGCCATCTACGGGAAGAATTTCTGTGTCTCAGCCAAAAATGCGTTCA
 580    L  L  M  R  N  I  V  R  V  V  V  L  D  K  V  T  D  L  L  L
1741 TGCTACTCATGCGAAACATTGTCAGGGTGGTCGTCCTGGACAAAGTCACAGACCTGCTGC
 600    F  F  G  K  L  L  V  V  G  G  V  G  V  L  S  F  F  F  F  S
1801 TGTTCTTTGGGAAGCTGCTGGTGGTCGGAGGCGTGGGGGTCCTGTCCTTCTTTTTTTTCT
 620    G  R  I  P  G  L  G  K  D  F  K  S  P  H  L  N  Y  Y  W  L
1861 CCGGTCGCATCCCGGGGCTGGGTAAAGACTTTAAGAGCCCCCACCTCAACTATTACTGGC
 640    P  I  M  T  S  I  L  G  A  Y  V  I  A  S  G  F  F  S  V  F
1921 TGCCCATCATGACCTCCATCCTGGGGGCCTATGTCATCGCCAGCGGCTTCTTCAGCGTTT
 660    G  M  C  V  D  T  L  F  L  C  F  L  E  D  L  E  R  N  N  G
1981 TCGGCATGTGTGTGGACACGCTCTTCCTCTGCTTCCTGGAAGACCTGGAGCGGAACAACG
 680    S  L  D  R  P  Y  Y  M  S  K  S  L  L  K  I  L  G  K  K  N
2041 GCTCCCTGGACCGGCCCTACTACATGTCCAAGAGCCTTCTAAAGATTCTGGGCAAGAAGA
 700    E  A  P  P  D  N  K  K  R  K  K  *
2101 ACGAGGCGCCCCCGGACAACAAGAAGAGGAAGAAGTGAcagctccggccctgatccagga
2161 ctgcaccccaccccaccgtccagccatccaacctcacttcgccttacaggtctccattt
2221 tgtggtaaaaaaaggttttaggccaggcgccgtggctcacgcctgtaatccaacactttg
2281 agaggctgaggcgggcggatcacctgagtcaggagttcgagaccagcctggccaacatgg
2341 tgaaacctccgtctctattaaaaatacaaaaattagccgagagtggtggcatgcacctgt
2401 catcccagctactcgggaggctgaggcaggagaatcgcttgaacccgggaggcagaggtt
2461 gcagtgagccgagatcgcgccactgcactccaacctgggtgacagactctgtctccaaaa
2521 caaacaaacaaacaaaagatttattaaagatattttgttaactcagtaaaaaaaaa
2581 aaaaaaa
```

Figure 1D-1: The cDNA (SEQ ID NO:7) and amino acid sequence (SEQ ID NO:8) of 24P4C12 variant 4. The open reading frame extends from nucleic acid 6-2138 including the stop codon. The start methionine is underlined.

```
  1     M  G  G  K  Q  R  D  E  D  D  E  A  Y  G  K  P  V  K  Y
  1   gagccATGGGGGGAAAGCAGCGGGACGAGGATGACGAGGCCTACGGGAAGCCAGTCAAAT
 20     D  P  S  F  R  G  P  I  K  N  R  S  C  T  D  V  I  C  C  V
 61   ACGACCCCTCCTTTCGAGGCCCCATCAAGAACAGAAGCTGCACAGATGTCATCTGCTGCG
 40     L  F  L  L  F  I  L  G  Y  I  V  V  G  I  V  A  W  L  Y  G
121   TCCTCTTCCTGCTCTTCATTCTAGGTTACATCGTGGTGGGGATTGTGGCCTGGTTGTATG
 60     D  P  R  Q  V  L  Y  P  R  N  S  T  G  A  Y  C  G  M  G  E
181   GAGACCCCCGGCAAGTCCTCTACCCCAGGAACTCTACTGGGGCCTACTGTGGCATGGGGG
 80     N  K  D  K  P  Y  L  L  Y  F  N  I  F  S  C  I  L  S  S  N
241   AGAACAAAGATAAGCCGTATCTCCTGTACTTCAACATCTTCAGCTGCATCCTGTCCAGCA
100     I  I  S  V  A  E  N  G  L  Q  C  P  T  P  Q  V  C  V  S  S
301   ACATCATCTCAGTTGCTGAGAACGGCCTACAGTGCCCCACACCCCAGGTGTGTGTGTCCT
120     C  P  E  D  P  W  T  V  G  K  N  E  F  S  Q  T  V  G  E  V
361   CCTGCCCGGAGGACCCATGGACTGTGGGAAAAAACGAGTTCTCACAGACTGTTGGGGAAG
140     F  Y  T  K  N  R  N  F  C  L  P  G  V  P  W  N  M  T  V  I
421   TCTTCTATACAAAAAACAGGAACTTTTGTCTGCCAGGGGTACCCTGGAATATGACGGTGA
160     T  S  L  Q  Q  E  L  C  P  S  F  L  L  P  S  A  P  A  L  G
481   TCACAAGCCTGCAACAGGAACTCTGCCCCAGTTTCCTCCTCCCTCTGCTCCAGCTCTGG
180     R  C  F  P  W  T  N  V  T  P  P  A  L  P  G  I  T  N  D  T
541   GGCGCTGCTTTCCATGGACCAACGTTACTCCACCGGCGCTCCCAGGGATCACCAATGACA
200     T  I  Q  Q  G  I  S  G  L  I  D  S  L  N  A  R  D  I  S  V
601   CCACCATACAGCAGGGGATCAGCGGTCTTATTGACAGCCTCAATGCCCGAGACATCAGTG
220     K  I  F  E  D  F  A  Q  S  W  Y  W  I  L  V  A  L  G  V  A
661   TTAAGATCTTTGAAGATTTTGCCCAGTCCTGGTATTGGATTCTTGTTGCCCTGGGGGTGG
240     L  V  L  S  L  L  F  I  L  L  R  L  V  A  G  P  L  V  L
721   CTCTGGTCTTGAGCCTACTGTTTATCTTGCTTCTGCGCCTGGTGGCTGGGCCCCTGGTGC
260     V  L  I  L  G  V  L  G  V  L  A  Y  G  I  Y  Y  C  W  E  E
781   TGGTGCTGATCCTGGGAGTGCTGGGCGTGCTGGCATATGGCATCTACTACTGCTGGGAGG
280     Y  R  V  L  R  D  K  G  A  S  I  S  Q  L  G  F  T  T  N  L
841   AGTACCGAGTGCTGCGGGACAAGGGCGCCTCCATCTCCCAGCTGGGTTTCACCACCAACC
300     S  A  Y  Q  S  V  Q  E  T  W  L  A  A  L  I  V  L  A  V  L
901   TCAGTGCCTACCAGAGCGTGCAGGAGACCTGGCTGGCCGCCCTGATCGTGTTGGCGGTGC
320     E  A  I  L  L  M  L  I  F  L  R  Q  R  I  R  I  A  I  A
961   TTGAAGCCATCCTGCTGCTGATGCTCATCTTCCTGCGGCAGCGGATTCGTATTGCCATCG
340     L  L  K  E  A  S  K  A  V  G  Q  M  M  S  T  M  F  Y  P  L
1021  CCCTCCTGAAGGAGGCCAGCAAGGCTGTGGGACAGATGATGTCTACCATGTTCTACCCAC
360     V  T  F  V  L  L  I  C  I  A  Y  W  A  M  T  A  L  Y  L
1081  TGGTCACCTTTGTCCTCCTCCTCATCTGCATTGCCTACTGGGCCATGACTGCTCTGTACC
380     A  T  S  G  Q  P  Q  Y  V  L  W  A  S  N  I  S  S  P  G  C
```

Figure 1D-2

```
1141 TGGCTACATCGGGGCAACCCCAGTATGTGCTCTGGGCATCCAACATCAGCTCCCCGGCT
 400   E   K   V   P   I   N   T   S   C   N   P   T   A   H   L   V   N   S   S   C
1201 GTGAGAAAGTGCCAATAAATACATCATGCAACCCCACGGCCCACCTTGTGAACTCCTCGT
 420   P   G   L   M   C   V   F   Q   G   Y   S   S   K   G   L   I   Q   R   S   V
1261 GCCCAGGGCTGATGTGCGTCTTCCAGGGCTACTCATCCAAAGGCCTAATCCAACGTTCTG
 440   F   N   L   Q   I   Y   G   V   L   G   L   F   W   T   L   N   W   V   L   A
1321 TCTTCAATCTGCAAATCTATGGGGTCCTGGGGCTCTTCTGGACCCTTAACTGGGTACTGG
 460   L   G   Q   C   V   L   A   G   A   F   A   S   F   Y   W   A   F   H   K   P
1381 CCCTGGGCCAATGCGTCCTCGCTGGAGCCTTTGCCTCCTTCTACTGGGCCTTCCACAAGC
 480   Q   D   I   P   T   F   P   L   I   S   A   F   I   R   T   L   R   Y   H   T
1441 CCCAGGACATCCCTACCTTCCCCTTAATCTCTGCCTTCATCCGCACACTCCGTTACCACA
 500   G   S   L   A   F   G   A   L   I   L   T   L   V   Q   I   A   R   V   I   L
1501 CTGGGTCATTGGCATTTGGAGCCCTCATCCTGACCCTTGTGCAGATAGCCCGGGTCATCT
 520   E   Y   I   D   H   K   L   R   G   V   Q   N   P   V   A   R   C   I   M   C
1561 TGGAGTATATTGACCACAAGCTCAGAGGAGTGCAGAACCCTGTAGCCCGCTGCATCATGT
 540   C   F   K   C   C   L   W   C   L   E   K   F   I   K   F   L   N   R   N   A
1621 GCTGTTTCAAGTGCTGCCTCTGGTGTCTGGAAAAATTTATCAAGTTCCTAAACCGCAATG
 560   Y   I   M   I   A   I   Y   G   K   N   F   C   V   S   A   K   N   A   F   M
1681 CATACATCATGATCGCCATCTACGGGAAGAATTTCTGTGTCTCAGCCAAAAATGCGTTCA
 580   L   L   M   R   N   I   V   R   V   V   L   D   K   V   T   D   L   L   L
1741 TGCTACTCATGCGAAACATTGTCAGGGTGGTCGTCCTGGACAAAGTCACAGACCTGCTGC
 600   F   F   G   K   L   L   V   V   G   G   V   G   V   L   S   F   F   F   F   S
1801 TGTTCTTTGGGAAGCTGCTGGTGGTCGGAGGCGTGGGGGTCCTGTCCTTCTTTTTTTTCT
 620   G   R   I   P   G   L   G   K   D   F   K   S   P   H   L   N   Y   Y   W   L
1861 CCGGTCGCATCCCGGGGCTGGGTAAAGACTTTAAGAGCCCCCACCTCAACTATTACTGGC
 640   P   I   M   T   S   I   L   G   A   Y   V   I   A   S   G   F   F   S   V   F
1921 TGCCCATCATGACCTCCATCCTGGGGGCCTATGTCATCGCCAGCGGCTTCTTCAGCGTTT
 660   G   M   C   V   D   T   L   F   L   C   F   L   E   D   L   E   R   N   N   G
1981 TCGGCATGTGTGTGGACACGCTCTTCCTCTGCTTCCTGGAAGACCTGGAGCGGAACAACG
 680   S   L   D   R   P   Y   Y   M   S   K   S   L   L   K   I   L   G   K   K   N
2041 GCTCCCTGGACCGGCCCTACTACATGTCCAAGAGCCTTCTAAAGATTCTGGGCAAGAAGA
 700   E   A   P   P   D   N   K   K   R   K   K   *
2101 ACGAGGCGCCCCCGGACAACAAGAAGAGGAAGAAGTGAcagctccggccctgatccagga
2161 ctgcaccccaccccaccgtccagccatccaacctcacttcgccttacaggtctccattt
2221 tgtggtaaaaaaggttttaggccaggcgccgtggctcacgcctgtaatccaacactttg
2281 agaggctgaggcgggcggatcacctgagtcaggagttcgagaccagcctggccaacatgg
2341 tgaaacctccgtctctattaaaaatacaaaaattagccgagagtggtggcatgcacctgt
2401 catcccagctactcgggaggctgaggcaggagaatcgcttgaacccgggaggcagaggtt
2461 gcagtgagccgagatcgcgccactgcactccaacctgggtgacagactctgtctccaaaa
2521 caaaacaaacaaacaaaaagatttattaaagatattttgttaactcagtaaaaaaaaaa
2581 aaaaaaa
```

Figure 1E-1: The cDNA (SEQ ID NO:9) and amino acid sequence (SEQ ID NO:10) of 24P4C12 variant 5. The open reading frame extends from nucleic acid 6-2138 including the stop codon.

```
   1     M  G  G  K  Q  R  D  E  D  D  E  A  Y  G  K  P  V  K  Y
   1   gagccATGGGGGGAAAGCAGCGGGACGAGGATGACGAGGCCTACGGGAAGCCAGTCAAAT
  20     D  P  S  F  R  G  P  I  K  N  R  S  C  T  D  V  I  C  C  V
  61   ACGACCCCTCCTTTCGAGGCCCCATCAAGAACAGAAGCTGCACAGATGTCATCTGCTGCG
  40     L  F  L  L  F  I  L  G  Y  I  V  V  G  I  V  A  W  L  Y  G
 121   TCCTCTTCCTGCTCTTCATTCTAGGTTACATCGTGGTGGGGATTGTGGCCTGGTTGTATG
  60     D  P  R  Q  V  L  Y  P  R  N  S  T  G  A  Y  C  G  M  G  E
 181   GAGACCCCCGGCAAGTCCTCTACCCAGGAACTCTACTGGGGCCTACTGTGGCATGGGGG
  80     N  K  D  K  P  Y  L  L  Y  F  N  I  F  S  C  I  L  S  S  N
 241   AGAACAAAGATAAGCCGTATCTCCTGTACTTCAACATCTTCAGCTGCATCCTGTCCAGCA
 100     I  I  S  V  A  E  N  G  L  Q  C  P  T  P  Q  V  C  V  S  S
 301   ACATCATCTCAGTTGCTGAGAACGGCCTACAGTGCCCCACACCCCAGGTGTGTGTGTCCT
 120     C  P  E  D  P  W  T  V  G  K  N  E  F  S  Q  T  V  G  E  V
 361   CCTGCCCGGAGGACCCATGGACTGTGGGAAAAAACGAGTTCTCACAGACTGTTGGGGAAG
 140     F  Y  T  K  R  N  F  C  L  P  G  V  P  W  N  M  T  V  I
 421   TCTTCTATACAAAAAACAGGAACTTTTGTCTGCCAGGGGTACCCTGGAATATGACGGTGA
 160     T  S  L  Q  Q  E  L  C  P  S  F  L  L  P  S  A  P  A  L  G
 481   TCACAAGCCTGCAACAGGAACTCTGCCCCAGTTTCCTCCTCCCCTCTGCTCCAGCTCTGG
 180     R  C  F  P  W  T  N  V  T  P  P  A  L  P  G  I  T  N  D  T
 541   GGCGCTGCTTTCCATGGACCAACGTTACTCCACCGGCGCTCCCAGGGATCACCAATGACA
 200     T  I  Q  Q  G  I  S  G  L  I  D  S  L  N  A  R  D  I  S  V
 601   CCACCATACAGCAGGGGATCAGCGGTCTTATTGACAGCCTCAATGCCCGAGACATCAGTG
 220     K  I  F  E  D  F  A  Q  S  W  Y  W  I  L  V  A  L  G  V  A
 661   TTAAGATCTTTGAAGATTTTGCCCAGTCCTGGTATTGGATTCTTGTTGCCCTGGGGGTGG
 240     L  V  L  S  L  L  F  I  L  L  R  L  V  A  G  P  L  V  L
 721   CTCTGGTCTTGAGCCTACTGTTTATCTTGCTTCTGCGCCTGGTGGCTGGGCCCCTGGTGC
 260     V  L  I  L  G  V  L  G  V  L  A  Y  G  I  Y  Y  C  W  E  E
 781   TGGTGCTGATCCTGGGAGTGCTGGGCGTGCTGGCATACGGCATCTACTACTGCTGGGAGG
 280     Y  R  V  L  R  D  K  G  A  S  I  S  Q  L  G  F  T  T  N  L
 841   AGTACCGAGTGCTGCGGGACAAGGGCGCCTCCATCTCCCAGCTGGGTTTCACCACCAACC
 300     S  A  Y  Q  S  V  Q  E  T  W  L  A  A  L  I  V  L  A  V  L
 901   TCAGTGCCTACCAGAGCGTGCAGGAGACCTGGCTGGCCGCCCTGATCGTGTTGGCGGTGC
 320     E  A  I  L  L  L  V  L  I  F  L  R  Q  R  I  R  I  A  I  A
 961   TTGAAGCCATCCTGCTGCTGGTGCTCATCTTCCTGCGGCAGCGGATTCGTATTGCCATCG
 340     L  L  K  E  A  S  K  A  V  G  Q  M  M  S  T  M  F  Y  P  L
1021   CCCTCCTGAAGGAGGCCAGCAAGGCTGTGGGACAGATGATGTCTACCATGTTCTACCCAC
 360     V  T  F  V  L  L  L  I  C  I  A  Y  W  A  M  T  A  L  Y  L
1081   TGGTCACCTTTGTCCTCCTCCTCATCTGCATTGCCTACTGGGCCATGACTGCTCTGTACC
 380     A  T  S  G  Q  P  Q  Y  V  L  W  A  S  N  I  S  S  P  G  C
1141   TGGCTACATCGGGGCAACCCCAGTATGTGCTCTGGGCATCCAACATCAGCTCCCCCGGCT
```

Figure 1E-2

```
 400       E  K  V  P  I  N  T  S  C  N  P  T  A  H  L  V  N  S  S  C
1201 GTGAGAAAGTGCCAATAAATACATCATGCAACCCCACGGCCCACCTTGTGAACTCCTCGT
 420       P  G  L  M  C  V  F  Q  G  Y  S  S  K  G  L  I  Q  R  S  V
1261 GCCCAGGGCTGATGTGCGTCTTCCAGGGCTACTCATCCAAAGGCCTAATCCAACGTTCTG
 440       F  N  L  Q  I  Y  G  V  L  G  L  F  W  T  L  N  W  V  L  A
1321 TCTTCAATCTGCAAATCTATGGGGTCCTGGGGCTCTTCTGGACCCTTAACTGGGTACTGG
 460       L  G  Q  C  V  L  A  G  A  F  A  S  F  Y  W  A  F  H  K  P
1381 CCCTGGGCCAATGCGTCCTCGCTGGAGCCTTTGCCTCCTTCTACTGGGCCTTCCACAAGC
 480       Q  D  I  P  T  F  P  L  I  S  A  F  I  R  T  L  R  Y  H  T
1441 CCCAGGACATCCCTACCTTCCCCTTAATCTCTGCCTTCATCCGCACACTCCGTTACCACA
 500       G  S  L  A  F  G  A  L  I  L  T  L  V  Q  I  A  R  V  I  L
1501 CTGGGTCATTGGCATTTGGAGCCCTCATCCTGACCCTTGTGCAGATAGCCCGGGTCATCT
 520       E  Y  I  D  H  K  L  R  G  V  Q  N  P  V  A  R  C  I  M  C
1561 TGGAGTATATTGACCACAAGCTCAGAGGAGTGCAGAACCCTGTAGCCCGCTGCATCATGT
 540       C  F  K  C  C  L  W  C  L  E  K  F  I  K  F  L  N  R  N  A
1621 GCTGTTTCAAGTGCTGCCTCTGGTGTCTGGAAAAATTTATCAAGTTCCTAAACCGCAATG
 560       Y  I  M  I  A  I  Y  G  K  N  F  C  V  S  A  K  N  A  F  M
1681 CATACATCATGATCGCCATCTACGGGAAGAATTTCTGTGTCTCAGCCAAAAATGCGTTCA
 580       L  L  M  R  N  I  V  R  V  V  L  D  K  V  T  D  L  L  L
1741 TGCTACTCATGCGAAACATTGTCAGGGTGGTCGTCCTGGACAAAGTCACAGACCTGCTGC
 600       F  F  G  K  L  L  V  V  G  G  V  G  V  L  S  F  F  F  S
1801 TGTTCTTTGGGAAGCTGCTGGTGGTCGGAGGCGTGGGGGTCCTGTCCTTCTTTTTTTTCT
 620       G  R  I  P  G  L  G  K  D  F  K  S  P  H  L  N  Y  Y  W  L
1861 CCGGTCGCATCCCGGGGCTGGGTAAAGACTTTAAGAGCCCCCACCTCAACTATTACTGGC
 640       P  I  M  T  S  I  L  G  A  Y  V  I  A  S  G  F  F  S  V  F
1921 TGCCCATCATGACCTCCATCCTGGGGGCCTATGTCATCGCCAGCGGCTTCTTCAGCGTTT
 660       G  M  C  V  D  T  L  F  L  C  F  L  E  D  L  E  R  N  N  G
1981 TCGGCATGTGTGTGGACACGCTCTTCCTCTGCTTCCTGGAAGACCTGGAGCGGAACAACG
 680       S  L  D  R  P  Y  Y  M  S  K  S  L  L  K  I  L  G  K  K  N
2041 GCTCCCTGGACCGGCCCTACTACATGTCCAAGAGCCTTCTAAAGATTCTGGGCAAGAAGA
 700       E  A  P  P  D  N  K  K  R  K  K  *
2101 ACGAGGCGCCCCCGGACAACAAGAAGAGGAAGAAGTGAcagctccggccctgatccagga
2161 ctgcaccccaccccaccgtccagccatccaacctcacttcgccttacaggtctccatt
2221 tgtggtaaaaaaaggttttaggccaggcgccgtggctcacgcctgtaatccaacactttg
2281 agaggctgaggcgggcggatcacctgagtcaggagttcgagaccagcctggccaacatgg
2341 tgaaacctccgtctctattaaaaatacaaaaattagccgagagtggtggcatgcacctgt
2401 catcccagctactcgggaggctgaggcaggagaatcgcttgaacccgggaggcagaggtt
2461 gcagtgagccgagatcgcgccactgcactccaacctgggtgacagactctgtctccaaaa
2521 caaaacaaacaaacaaaagatttattaaagatattttgttaactcagtaaaaaaaaaa
2581 aaaaaaa
```

Figure 1F-1: The cDNA (SEQ ID NO:11) and amino acid sequence (SEQ ID NO:12) of 24P4C12 variant 6. The open reading frame extends from nucleic acid 6-2138 including the stop codon.

```
   1      M   G   G   K   Q   R   D   E   D   D   E   A   Y   G   K   P   V   K   Y
   1    gagccATGGGGGGAAAGCAGCGGGACGAGGATGACGAGGCCTACGGGAAGCCAGTCAAAT
  20      D   P   S   F   R   G   P   I   K   N   R   S   C   T   D   V   I   C   C   V
  61    ACGACCCCTCCTTTCGAGGCCCCATCAAGAACAGAAGCTGCACAGATGTCATCTGCTGCG
  40      L   F   L   L   F   I   L   G   Y   I   V   V   G   I   V   A   W   L   Y   G
 121    TCCTCTTCCTGCTCTTCATTCTAGGTTACATCGTGGTGGGGATTGTGGCCTGGTTGTATG
  60      D   P   R   Q   V   L   Y   P   R   N   S   T   G   A   Y   C   G   M   G   E
 181    GAGACCCCCGGCAAGTCCTCTACCCCAGGAACTCTACTGGGGCCTACTGTGGCATGGGGG
  80      N   K   D   K   P   Y   L   L   Y   F   N   I   F   S   C   I   L   S   S   N
 241    AGAACAAAGATAAGCCGTATCTCCTGTACTTCAACATCTTCAGCTGCATCCTGTCCAGCA
 100      I   I   S   V   A   E   N   G   L   Q   C   P   T   P   Q   V   C   V   S   S
 301    ACATCATCTCAGTTGCTGAGAACGGCCTACAGTGCCCCACACCCCAGGTGTGTGTGTCCT
 120      C   P   E   D   P   W   T   V   G   K   N   E   F   S   Q   T   V   G   E   V
 361    CCTGCCCGGAGGACCCATGGACTGTGGGAAAAAACGAGTTCTCACAGACTGTTGGGGAAG
 140      F   Y   T   K   R   N   F   C   L   P   G   V   P   W   N   M   T   V   I
 421    TCTTCTATACAAAAAACAGGAACTTTTGTCTGCCAGGGGTACCCTGGAATATGACGGTGA
 160      T   S   L   Q   Q   E   L   C   P   S   F   L   L   P   S   A   P   A   L   G
 481    TCACAAGCCTGCAACAGGAACTCTGCCCCAGTTTCCTCCTCCCCTCTGCTCCAGCTCTGG
 180      R   C   F   P   W   T   N   V   T   P   P   A   L   P   G   I   T   N   D   T
 541    GGCGCTGCTTTCCATGGACCAACGTTACTCCACCGGCGCTCCCAGGGATCACCAATGACA
 200      T   I   Q   Q   G   I   S   G   L   I   D   S   L   N   A   R   D   I   S   V
 601    CCACCATACAGCAGGGGATCAGCGGTCTTATTGACAGCCTCAATGCCCGAGACATCAGTG
 220      K   I   F   E   D   F   A   Q   S   W   Y   W   I   L   V   A   L   G   V   A
 661    TTAAGATCTTTGAAGATTTTGCCCAGTCCTGGTATTGGATTCTTGTTGCCCTGGGGGTGG
 240      L   V   L   S   L   L   F   I   L   L   R   L   V   A   G   P   L   V   L
 721    CTCTGGTCTTGAGCCTACTGTTTATCTTGCTTCTGCGCCTGGTGGCTGGGCCCCTGGTGC
 260      V   L   I   L   G   V   L   G   V   L   A   Y   G   I   Y   Y   C   W   E   E
 781    TGGTGCTGATCCTGGGAGTGCTGGGCGTGCTGGCATACGGCATCTACTACTGCTGGGAGG
 280      Y   R   V   L   R   D   K   G   A   S   I   S   Q   L   G   F   T   T   N   L
 841    AGTACCGAGTGCTGCGGGACAAGGGCGCCTCCATCTCCCAGCTGGGTTTCACCACCAACC
 300      S   A   Y   Q   S   V   Q   E   T   W   L   A   A   L   I   V   L   A   V   L
 901    TCAGTGCCTACCAGAGCGTGCAGGAGACCTGGCTGGCCGCCCTGATCGTGTTGGCGGTGC
 320      E   A   I   L   L   M   L   I   F   L   R   Q   R   I   R   I   A   I   A
 961    TTGAAGCCATCCTGCTGCTGATGCTCATCTTCCTGCGGCAGCGGATTCGTATTGCCATCG
 340      L   L   K   E   A   S   K   A   V   G   Q   M   M   S   T   M   F   Y   P   L
1021    CCCTCCTGAAGGAGGCCAGCAAGGCTGTGGGACAGATGATGTCTACCATGTTCTACCCAC
 360      V   T   F   V   L   L   I   C   I   A   Y   W   A   M   T   A   L   Y   L
1081    TGGTCACCTTTGTCCTCCTCCTCATCTGCATTGCCTACTGGGCCATGACTGCTCTGTACC
 380      A   T   S   G   Q   P   Q   Y   V   L   W   A   S   N   I   S   S   P   G   C
1141    TGGCTACATCGGGGCAACCCCAGTATGTGCTCTGGGCATCCAACATCAGCTCCCCCGGCT
```

Figure 1F-2

```
 400        E   K   V   P   I   N   T   S   C   N   P   T   A   H   L   V   N   S   S   C
1201 GTGAGAAAGTGCCAATAAATACATCATGCAACCCCACGGCCCACCTTGTGAACTCCTCGT
 420        P   G   L   M   C   V   F   Q   G   Y   S   S   K   G   L   I   P   R   S   V
1261 GCCCAGGGCTGATGTGCGTCTTCCAGGGCTACTCATCCAAAGGCCTAATCCCACGTTCTG
 440        F   N   L   Q   I   Y   G   V   L   G   L   F   W   T   L   N   W   V   L   A
1321 TCTTCAATCTGCAAATCTATGGGGTCCTGGGGCTCTTCTGGACCCTTAACTGGGTACTGG
 460        L   G   Q   C   V   L   A   G   A   F   A   S   F   Y   W   A   F   H   K   P
1381 CCCTGGGCCAATGCGTCCTCGCTGGAGCCTTTGCCTCCTTCTACTGGGCCTTCCACAAGC
 480        Q   D   I   P   T   F   P   L   I   S   A   F   I   R   T   L   R   Y   H   T
1441 CCCAGGACATCCCTACCTTCCCCTTAATCTCTGCCTTCATCCGCACACTCCGTTACCACA
 500        G   S   L   A   F   G   A   L   I   L   T   L   V   Q   I   A   R   V   I   L
1501 CTGGGTCATTGGCATTTGGAGCCCTCATCCTGACCCTTGTGCAGATAGCCCGGGTCATCT
 520        E   Y   I   D   H   K   L   R   G   V   Q   N   P   V   A   R   C   I   M   C
1561 TGGAGTATATTGACCACAAGCTCAGAGGAGTGCAGAACCCTGTAGCCCGCTGCATCATGT
 540        C   F   K   C   C   L   W   C   L   E   K   F   I   K   F   L   N   R   N   A
1621 GCTGTTTCAAGTGCTGCCTCTGGTGTCTGGAAAAATTTATCAAGTTCCTAAACCGCAATG
 560        Y   I   M   I   A   I   Y   G   K   N   F   C   V   S   A   K   N   A   F   M
1681 CATACATCATGATCGCCATCTACGGAAGAATTTCTGTGTCTCAGCCAAAAATGCGTTCA
 580        L   L   M   R   N   I   V   R   V   V   V   L   D   K   V   T   D   L   L   L
1741 TGCTACTCATGCGAAACATTGTCAGGGTGGTCGTCCTGGACAAAGTCACAGACCTGCTGC
 600        F   F   G   K   L   L   V   V   G   G   V   G   V   L   S   F   F   F   F   S
1801 TGTTCTTTGGGAAGCTGCTGGTGGTCGGAGGCGTGGGGGTCCTGTCCTTCTTTTTTTTCT
 620        G   R   I   P   G   L   G   K   D   F   K   S   P   H   L   N   Y   Y   W   L
1861 CCGGTCGCATCCCGGGGCTGGGTAAAGACTTTAAGAGCCCCCACCTCAACTATTACTGGC
 640        P   I   M   T   S   I   L   G   A   Y   V   I   A   S   G   F   F   S   V   F
1921 TGCCCATCATGACCTCCATCCTGGGGGCCTATGTCATCGCCAGCGGCTTCTTCAGCGTTT
 660        G   M   C   V   D   T   L   F   L   C   F   L   E   D   L   E   R   N   N   G
1981 TCGGCATGTGTGTGGACACGCTCTTCCTCTGCTTCCTGGAAGACCTGGAGCGGAACAACG
 680        S   L   D   R   P   Y   Y   M   S   K   S   L   L   K   I   L   G   K   K   N
2041 GCTCCCTGGACCGGCCCTACTACATGTCCAAGAGCCTTCTAAAGATTCTGGGCAAGAAGA
 700        E   A   P   P   D   N   K   K   R   K   K   *
2101 ACGAGGCGCCCCCGGACAACAAGAAGAGGAAGAAGTGAcagctccggccctgatccagga
2161 ctgcacccaccccaccgtccagccatccaacctcacttcgccttacaggtctccattt
2221 tgtggtaaaaaaaggttttaggccaggcgccgtggctcacgcctgtaatccaacactttg
2281 agaggctgaggcgggcggatcacctgagtcaggagttcgagaccagcctggccaacatgg
2341 tgaaaccctccgtctctattaaaaatacaaaaattagccgagagtggtggcatgcacctgt
2401 catcccagctactcgggaggctgaggcaggagaatcgcttgaacccgggaggcagaggtt
2461 gcagtgagccgagatcgcgccactgcactccaacctgggtgacagactctgtctccaaaa
2521 caaaacaaacaaacaaaagatttattaaagatatttgttaactcagtaaaaaaaaaa
2581 aaaaaaa
```

Figure 1G-1: The cDNA (SEQ ID NO:13) and amino acid sequence (SEQ ID NO:14) of 24P4C12 variant 7. The open reading frame extends from nucleic acid 6-1802 including the stop codon.

```
  1      M  G  G  K  Q  R  D  E  D  D  E  A  Y  G  K  P  V  K  Y
  1    gagccATGGGGGGAAAGCAGCGGGACGAGGATGACGAGGCCTACGGGAAGCCAGTCAAAT
 20      D  P  S  F  R  G  P  I  K  N  R  S  C  T  D  V  I  C  C  V
 61    ACGACCCCTCCTTTCGAGGCCCCATCAAGAACAGAAGCTGCACAGATGTCATCTGCTGCG
 40      L  F  L  L  F  I  L  G  Y  I  V  V  G  I  V  A  W  L  Y  G
121    TCCTCTTCCTGCTCTTCATTCTAGGTTACATCGTGGTGGGGATTGTGGCCTGGTTGTATG
 60      D  P  R  Q  V  L  Y  P  R  N  S  T  G  A  Y  C  G  M  G  E
181    GAGACCCCCGGCAAGTCCTCTACCCCAGGAACTCTACTGGGGCCTACTGTGGCATGGGGG
 80      N  K  D  K  P  Y  L  L  Y  F  N  I  F  S  C  I  L  S  S  N
241    AGAACAAAGATAAGCCGTATCTCCTGTACTTCAACATCTTCAGCTGCATCCTGTCCAGCA
100      I  I  S  V  A  E  N  G  L  Q  C  P  T  P  Q  V  C  V  S  S
301    ACATCATCTCAGTTGCTGAGAACGGCCTACAGTGCCCCACACCCCAGGTGTGTGTGTCCT
120      C  P  E  D  P  W  T  V  G  K  N  E  F  S  Q  T  V  G  E  V
361    CCTGCCCGGAGGACCCATGGACTGTGGGAAAAAACGAGTTCTCACAGACTGTTGGGGAAG
140      F  Y  T  K  N  R  N  F  C  L  P  G  V  P  W  N  M  T  V  I
421    TCTTCTATACAAAAAACAGGAACTTTTGTCTGCCAGGGGTACCCTGGAATATGACGGTGA
160      T  S  L  Q  Q  E  L  C  P  S  F  L  L  P  S  A  P  A  L  G
481    TCACAAGCCTGCAACAGGAACTCTGCCCCAGTTTCCTCCTCCCCTCTGCTCCAGCTCTGG
180      R  C  F  P  W  T  N  V  T  P  P  A  L  P  G  I  T  N  D  T
541    GGCGCTGCTTTCCATGGACCAACGTTACTCCACCGGCGCTCCCAGGGATCACCAATGACA
200      T  I  Q  Q  G  I  S  G  L  I  D  S  L  N  A  R  D  I  S  V
601    CCACCATACAGCAGGGGATCAGCGGTCTTATTGACAGCCTCAATGCCCGAGACATCAGTG
220      K  I  F  E  D  F  A  Q  S  W  Y  W  I  L  V  A  V  G  Q  M
661    TTAAGATCTTTGAAGATTTTGCCCAGTCCTGGTATTGGATTCTTGTGGCTGTGGGACAGA
240      M  S  T  M  F  Y  P  L  V  T  F  V  L  L  L  I  C  I  A  Y
721    TGATGTCTACCATGTTCTACCCACTGGTCACCTTTGTCCTCCTCCTCATCTGCATTGCCT
260      W  A  M  T  A  L  Y  L  A  T  S  G  Q  P  Q  Y  V  L  W  A
781    ACTGGGCCATGACTGCTCTGTACCTGGCTACATCGGGGCAACCCCAGTATGTGCTCTGGG
280      S  N  I  S  S  P  G  C  E  K  V  P  I  N  T  S  C  N  P  T
841    CATCCAACATCAGCTCCCCCGGCTGTGAGAAAGTGCCAATAAATACATCATGCAACCCCA
300      A  H  L  V  N  S  S  C  P  G  L  M  C  V  F  Q  G  Y  S  S
901    CGGCCCACCTTGTGAACTCCTCGTGCCCAGGGCTGATGTGCGTCTTCCAGGGCTACTCAT
320      K  G  L  I  Q  R  S  V  F  N  L  Q  I  Y  G  V  L  G  L  F
961    CCAAAGGCCTAATCCAACGTTCTGTCTTCAATCTGCAAATCTATGGGGTCCTGGGGCTCT
340      W  T  L  N  W  V  L  A  L  G  Q  C  V  L  A  G  A  F  A  S
1021   TCTGGACCCTTAACTGGGTACTGGCCCTGGGCCAATGCGTCCTCGCTGGAGCCTTTGCCT
360      F  Y  W  A  F  H  K  P  Q  D  I  P  T  F  P  L  I  S  A  F
1081   CCTTCTACTGGGCCTTCCACAAGCCCCAGGACATCCCTACCTTCCCCTTAATCTCTGCCT
380      I  R  T  L  R  Y  H  T  G  S  L  A  F  G  A  L  I  L  T  L
1141   TCATCCGCACACTCCGTTACCACACTGGGTCATTGGCATTTGGAGCCCTCATCCTGACCC
```

Figure 1G-2

```
400       V  Q  I  A  R  V  I  L  E  Y  I  D  H  K  L  R  G  V  Q  N
1201  TTGTGCAGATAGCCCGGGTCATCTTGGAGTATATTGACCACAAGCTCAGAGGAGTGCAGA
420       P  V  A  R  C  I  M  C  C  F  K  C  C  L  W  C  L  E  K  F
1261  ACCCTGTAGCCCGCTGCATCATGTGCTGTTTCAAGTGCTGCCTCTGGTGTCTGGAAAAAT
440       I  K  F  L  N  R  N  A  Y  I  M  I  A  I  Y  G  K  N  F  C
1321  TTATCAAGTTCCTAAACCGCAATGCATACATCATGATCGCCATCTACGGGAAGAATTTCT
460       V  S  A  K  N  A  F  M  L  L  M  R  N  I  V  R  V  V  V  L
1381  GTGTCTCAGCCAAAAATGCGTTCATGCTACTCATGCGAAACATTGTCAGGGTGGTCGTCC
480       D  K  V  T  D  L  L  F  F  G  K  L  L  V  V  G  G  V  G
1441  TGGACAAAGTCACAGACCTGCTGCTGTTCTTTGGGAAGCTGCTGGTGGTCGGAGGCGTGG
500       V  L  S  F  F  F  F  S  G  R  I  P  G  L  G  K  D  F  K  S
1501  GGGTCCTGTCCTTCTTTTTTTTCTCCGGTCGCATCCCGGGGCTGGGTAAAGACTTTAAGA
520       P  H  L  N  Y  Y  W  L  P  I  M  T  S  I  L  G  A  Y  V  I
1561  GCCCCCACCTCAACTATTACTGGCTGCCCATCATGACCTCCATCCTGGGGGCCTATGTCA
540       A  S  G  F  F  S  V  F  G  M  C  V  D  T  L  F  L  C  F  L
1621  TCGCCAGCGGCTTCTTCAGCGTTTTCGGCATGTGTGTGGACACGCTCTTCCTCTGCTTCC
560       E  D  L  E  R  N  N  G  S  L  D  R  P  Y  Y  M  S  K  S  L
1681  TGGAAGACCTGGAGCGGAACAACGGCTCCCTGGACCGGCCCTACTACATGTCCAAGAGCC
580       L  K  I  L  G  K  K  N  E  A  P  P  D  N  K  K  R  K  K  *
1741  TTCTAAAGATTCTGGGCAAGAAGAACGAGGCGCCCCCGGACAACAAGAAGAGGAAGAAGT
1801  GAcagctccggccctgatccaggactgcaccccaccccaccgtccagccatccaacctc
1861  acttcgccttacaggtctccattttgtggtaaaaaaaggtttaggccaggcgccgtggc
1921  tcacgcctgtaatccaacactttgagaggctgaggcgggcggatcacctgagtcaggagt
1981  tcgagaccagcctggccaacatggtgaaacctccgtctctattaaaaatacaaaaattag
2041  ccgagagtggtggcatgcacctgtcatcccagctactcgggaggctgaggcaggagaatc
2101  gcttgaaccgggaggcagaggttgcagtgagccgagatcgcgccactgcactccaacct
2161  gggtgacagactctgtctccaaaacaaaacaaacaaacaaaagattttattaaagatat
2221  tttgttaactcagtaaaaaaaaaaaaaaaaa
```

Figure 1H-1 The cDNA (SEQ ID NO:15) and amino acid sequence (SEQ ID NO.:16) of 24P4C12v.8. The start methionine is underlined. The open reading frame extends from nucleic acid 6-2174 including the stop codon.

```
1         M  G  G  K  Q  R  D  E  D  D  E  A  Y  G  K  P  V  K  Y
1     gagccATGGGGGGAAAGCAGCGGGACGAGGATGACGAGGCCTACGGGAAGCCAGTCAAAT
20        D  P  S  F  R  G  P  I  K  N  R  S  C  T  D  V  I  C  C  V
61    ACGACCCCTCCTTTCGAGGCCCCATCAAGAACAGAAGCTGCACAGATGTCATCTGCTGCG
40        L  F  L  L  F  I  L  G  Y  I  V  V  G  I  V  A  W  L  Y  G
121   TCCTCTTCCTGCTCTTCATTCTAGGTTACATCGTGGTGGGGATTGTGGCCTGGTTGTATG
60        D  P  R  Q  V  L  Y  P  R  N  S  T  G  A  Y  C  G  M  G  E
181   GAGACCCCCGGCAAGTCCTCTACCCCAGGAACTCTACTGGGGCCTACTGTGGCATGGGGG
80        N  K  D  K  P  Y  L  L  Y  F  N  I  F  S  C  I  L  S  S  N
```

Figure 1H-2

```
241  AGAACAAAGATAAGCCGTATCTCCTGTACTTCAACATCTTCAGCTGCATCCTGTCCAGCA
100    I  I  S  V  A  E  N  G  L  Q  C  P  T  P  Q  V  C  V  S  S
301  ACATCATCTCAGTTGCTGAGAACGGCCTACAGTGCCCCACACCCCAGGTGTGTGTGTCCT
120    C  P  E  D  P  W  T  V  G  K  N  E  F  S  Q  T  V  G  E  V
361  CCTGCCCGGAGGACCCATGGACTGTGGGAAAAAACGAGTTCTCACAGACTGTTGGGGAAG
140    F  Y  T  K  R  N  F  C  L  P  G  V  P  W  N  M  T  V  I
421  TCTTCTATACAAAAAACAGGAACTTTTGTCTGCCAGGGGTACCCTGGAATATGACGGTGA
160    T  S  L  Q  Q  E  L  C  P  S  F  L  L  P  S  A  P  A  L  G
481  TCACAAGCCTGCAACAGGAACTCTGCCCCAGTTTCCTCCTCCCCTCTGCTCCAGCTCTGG
180    R  C  F  P  W  T  N  V  T  P  P  A  L  P  G  I  T  N  D  T
541  GGCGCTGCTTTCCATGGACCAACGTTACTCCACCGGCGCTCCCAGGGATCACCAATGACA
200    T  I  Q  Q  G  I  S  G  L  I  D  S  L  N  A  R  D  I  S  V
601  CCACCATACAGCAGGGGATCAGCGGTCTTATTGACAGCCTCAATGCCCGAGACATCAGTG
220    K  I  F  E  D  F  A  Q  S  W  Y  W  I  L  V  A  L  G  V  A
661  TTAAGATCTTTGAAGATTTTGCCCAGTCCTGGTATTGGATTCTTGTTGCCCTGGGGGTGG
240    L  V  L  S  L  L  F  I  L  L  L  R  L  V  A  G  P  L  V  L
721  CTCTGGTCTTGAGCCTACTGTTTATCTTGCTTCTGCGCCTGGTGGCTGGGCCCCTGGTGC
260    V  L  I  L  G  V  L  G  V  L  A  Y  G  I  Y  Y  C  W  E  E
781  TGGTGCTGATCCTGGGAGTGCTGGGCGTGCTGGCATACGGCATCTACTACTGCTGGGAGG
280    Y  R  V  L  R  D  K  G  A  S  I  S  Q  L  G  F  T  T  N  L
841  AGTACCGAGTGCTGCGGGACAAGGGCGCCTCCATCTCCCAGCTGGGTTTCACCACCAACC
300    S  A  Y  Q  S  V  Q  E  T  W  L  A  A  L  I  V  L  A  V  L
901  TCAGTGCCTACCAGAGCGTGCAGGAGACCTGGCTGGCCGCCCTGATCGTGTTGGCGGTGC
320    E  A  I  L  L  L  M  L  I  F  L  R  Q  R  I  R  I  A  I  A
961  TTGAAGCCATCCTGCTGCTGATGCTCATCTTCCTGCGGCAGCGGATTCGTATTGCCATCG
340    L  L  K  E  A  S  K  A  V  G  Q  M  M  S  T  M  F  Y  P  L
1021 CCCTCCTGAAGGAGGCCAGCAAGGCTGTGGGACAGATGATGTCTACCATGTTCTACCCAC
360    V  T  F  V  L  L  L  I  C  I  A  Y  W  A  M  T  A  L  Y  L
1081 TGGTCACCTTTGTCCTCCTCCTCATCTGCATTGCCTACTGGGCCATGACTGCTCTGTACC
380    A  T  S  G  Q  P  Q  Y  V  L  W  A  S  N  I  S  S  P  G  C
1141 TGGCTACATCGGGGCAACCCCAGTATGTGCTCTGGGCATCCAACATCAGCTCCCCCGGCT
400    E  K  V  P  I  N  T  S  C  N  P  T  A  H  L  V  N  S  S  C
1201 GTGAGAAAGTGCCAATAAATACATCATGCAACCCCACGGCCCACCTTGTGAACTCCTCGT
420    P  G  L  M  C  V  F  Q  G  Y  S  S  K  G  L  I  Q  R  S  V
1261 GCCCAGGGCTGATGTGCGTCTTCCAGGGCTACTCATCCAAAGGCCTAATCCAACGTTCTG
440    F  N  L  Q  I  Y  G  V  L  G  L  F  W  T  L  N  W  V  L  A
1321 TCTTCAATCTGCAAATCTATGGGGTCCTGGGGCTCTTCTGGACCCTTAACTGGGTACTGG
460    L  G  Q  C  V  L  A  G  A  F  A  S  F  Y  W  A  F  H  K  P
1381 CCCTGGGCCAATGCGTCCTCGCTGGAGCCTTTGCCTCCTTCTACTGGGCCTTCCACAAGC
480    Q  D  I  P  T  F  P  L  I  S  A  F  I  R  T  L  R  Y  H  T
1441 CCCAGGACATCCCTACCTTCCCCTTAATCTCTGCCTTCATCCGCACACTCCGTTACCACA
500    G  S  L  A  F  G  A  L  I  L  T  L  V  Q  I  A  R  V  I  L
```

Figure 1H-3

```
1501 CTGGGTCATTGGCATTTGGAGCCCTCATCCTGACCCTTGTGCAGATAGCCCGGGTCATCT
 520    E  Y  I  D  H  K  L  R  G  V  Q  N  P  V  A  R  C  I  M  C
1561 TGGAGTATATTGACCACAAGCTCAGAGGAGTGCAGAACCCTGTAGCCCGCTGCATCATGT
 540    C  F  K  C  C  L  W  C  L  E  K  F  I  K  F  L  N  R  N  A
1621 GCTGTTTCAAGTGCTGCCTCTGGTGTCTGGAAAAATTTATCAAGTTCCTAAACCGCAATG
 560    Y  I  M  I  A  I  Y  G  K  N  F  C  V  S  A  K  N  A  F  M
1681 CATACATCATGATCGCCATCTACGGGAAGAATTTCTGTGTCTCAGCCAAAAATGCGTTCA
 580    L  L  M  R  N  I  V  R  V  V  L  D  K  V  T  D  L  L  L
1741 TGCTACTCATGCGAAACATTGTCAGGGTGGTCGTCCTGGACAAAGTCACAGACCTGCTGC
 600    F  F  G  K  L  L  V  V  G  G  V  G  V  L  S  F  F  F  F  S
1801 TGTTCTTTGGGAAGCTGCTGGTGGTCGGAGGCGTGGGGGTCCTGTCCTTCTTTTTTTTCT
 620    G  R  I  P  G  L  G  K  D  F  K  S  P  H  L  N  Y  Y  W  L
1861 CCGGTCGCATCCCGGGGCTGGGTAAAGACTTTAAGAGCCCCCACCTCAACTATTACTGGC
 640    P  I  M  R  N  P  I  T  P  T  G  H  V  F  Q  T  S  I  L  G
1921 TGCCCATCATGAGGAACCCAATAACCCCAACGGGTCATGTCTTCCAGACCTCCATCCTGG
 660    A  Y  V  I  A  S  G  F  F  S  V  F  G  M  C  V  D  T  L  F
1981 GGGCCTATGTCATCGCCAGCGGCTTCTTCAGCGTTTTCGGCATGTGTGTGGACACGCTCT
 680    L  C  F  L  E  D  L  E  R  N  N  G  S  L  D  R  P  Y  Y  M
2041 TCCTCTGCTTCCTGGAAGACCTGGAGCGGAACAACGGCTCCCTGGACCGGCCCTACTACA
 700    S  K  S  L  L  K  I  L  G  K  K  N  E  A  P  P  D  N  K  K
2101 TGTCCAAGAGCCTTCTAAAGATTCTGGGCAAGAAGAACGAGGCGCCCCCGGACAACAAGA
 720    R  K  K  *
2161 AGAGGAAGAAGTGAcagctccggccctgatccaggactgcaccccaccccaccgtccag
2221 ccatccaacctcacttcgccttacaggtctccattttgtggtaaaaaaggttttaggcc
2281 aggcgccgtggctcacgcctgtaatccaacactttgagaggctgaggcgggcggatcacc
2341 tgagtcaggagttcgagaccagcctggccaacatggtgaaacctccgtctctattaaaaa
2401 tacaaaaattagccgagagtggtggcatgcacctgtcatcccagctactcgggaggctga
2461 ggcaggagaatcgcttgaacccgggaggcagaggttgcagtgagccgagatcgcgccact
2521 gcactccaacctgggtgacagactctgtctccaaaacaaaacaaacaaacaaaaagattt
2581 tattaaagatattttgttaactcagtaaaaaaaaaaaaaaaaa
```

Figure 1I-1. The cDNA (SEQ ID NO:17) and amino acid sequence (SEQ ID NO:18) of 24P4C12 v.9. The start methionine is underlined. The open reading frame extends from nucleic acid 6-2144 including the stop codon.

```
  1       M  G  G  K  Q  R  D  E  D  D  E  A  Y  G  K  P  V  K  Y
  1    gagccATGGGGGGAAAGCAGCGGGACGAGGATGACGAGGCCTACGGGAAGCCAGTCAAAT
 20       D  P  S  F  R  G  P  I  K  N  R  S  C  T  D  V  I  C  C  V
 61    ACGACCCCTCCTTTCGAGGCCCCATCAAGAACAGAAGCTGCACAGATGTCATCTGCTGCG
 40       L  F  L  L  F  I  L  G  Y  I  V  V  G  I  V  A  W  L  Y  G
121    TCCTCTTCCTGCTCTTCATTCTAGGTTACATCGTGGTGGGGATTGTGGCCTGGTTGTATG
 60       D  P  R  Q  V  L  Y  P  R  N  S  T  G  A  Y  C  G  M  G  E
```

Figure 1I-2

```
 181 GAGACCCCCGGCAAGTCCTCTACCCCAGGAACTCTACTGGGGCCTACTGTGGCATGGGGG
  80    N  K  D  K  P  Y  L  L  Y  F  N  I  F  S  C  I  L  S  S  N
 241 AGAACAAAGATAAGCCGTATCTCCTGTACTTCAACATCTTCAGCTGCATCCTGTCCAGCA
 100    I  I  S  V  A  E  N  G  L  Q  C  P  T  P  Q  V  C  V  S  S
 301 ACATCATCTCAGTTGCTGAGAACGGCCTACAGTGCCCCACACCCCAGGTGTGTGTGTCCT
 120    C  P  E  D  P  W  T  V  G  K  N  E  F  S  Q  T  V  G  E  V
 361 CCTGCCCGGAGGACCCATGGACTGTGGGAAAAAACGAGTTCTCACAGACTGTTGGGGAAG
 140    F  Y  T  K  N  R  N  F  C  L  P  G  V  P  W  N  M  T  V  I
 421 TCTTCTATACAAAAAACAGGAACTTTTGTCTGCCAGGGGTACCCTGGAATATGACGGTGA
 160    T  S  L  Q  Q  E  L  C  P  S  F  L  L  P  S  A  P  A  L  G
 481 TCACAAGCCTGCAACAGGAACTCTGCCCCAGTTTCCTCCTCCCCTCTGCTCCAGCTCTGG
 180    R  C  F  P  W  T  N  V  T  P  P  A  L  P  G  I  T  N  D  T
 541 GGCGCTGCTTTCCATGGACCAACGTTACTCCACCGGCGCTCCCAGGGATCACCAATGACA
 200    T  I  Q  G  I  S  G  L  I  D  S  L  N  A  R  D  I  S  V
 601 CCACCATACAGCAGGGGATCAGCGGTCTTATTGACAGCCTCAATGCCCGAGACATCAGTG
 220    K  I  F  E  D  F  A  Q  S  W  Y  W  I  L  V  A  L  G  V  A
 661 TTAAGATCTTTGAAGATTTTGCCCAGTCCTGGTATTGGATTCTTGTTGCCCTGGGGGTGG
 240    L  V  L  S  L  L  F  I  L  L  R  L  V  A  G  P  L  V  L
 721 CTCTGGTCTTGAGCCTACTGTTTATCTTGCTTCTGCGCCTGGTGGCTGGGCCCCTGGTGC
 260    V  L  I  L  G  V  L  G  V  L  A  Y  G  I  Y  Y  C  W  E  E
 781 TGGTGCTGATCCTGGGAGTGCTGGGCGTGCTGGCATACGGCATCTACTACTGCTGGGAGG
 280    Y  R  V  L  R  D  K  G  A  S  I  S  Q  L  G  F  T  T  N  L
 841 AGTACCGAGTGCTGCGGGACAAGGGCGCCTCCATCTCCCAGCTGGGTTTCACCACCAACC
 300    S  A  Y  Q  S  V  Q  E  T  W  L  A  A  L  I  V  L  A  V  L
 901 TCAGTGCCTACCAGAGCGTGCAGGAGACCTGGCTGGCCGCCCTGATCGTGTTGGCGGTGC
 320    E  A  I  L  L  L  M  L  I  F  L  R  Q  R  I  R  I  A  I  A
 961 TTGAAGCCATCCTGCTGCTGATGCTCATCTTCCTGCGGCAGCGGATTCGTATTGCCATCG
 340    L  L  K  E  A  S  K  A  V  G  Q  M  M  S  T  M  F  Y  P  L
1021 CCCTCCTGAAGGAGGCCAGCAAGGCTGTGGGACAGATGATGTCTACCATGTTCTACCCAC
 360    V  T  F  V  L  L  L  I  C  I  A  Y  W  A  M  T  A  L  Y  P
1081 TGGTCACCTTTGTCCTCCTCCTCATCTGCATTGCCTACTGGGCCATGACTGCTCTGTATC
 380    L  P  T  Q  P  A  T  L  G  Y  V  L  W  A  S  N  I  S  S  P
1141 CTCTGCCCACGCAGCCAGCCACTCTTGGATATGTGCTCTGGGCATCCAACATCAGCTCCC
 400    G  C  E  K  V  P  I  N  T  S  C  N  P  T  A  H  L  V  N  S
1201 CCGGCTGTGAGAAAGTGCCAATAAATACATCATGCAACCCCACGGCCCACCTTGTGAACT
 420    S  C  P  G  L  M  C  V  F  Q  G  Y  S  S  K  G  L  I  Q  R
1261 CCTCGTGCCCAGGGCTGATGTGCGTCTTCCAGGGCTACTCATCCAAAGGCCTAATCCAAC
 440    S  V  F  N  L  Q  I  Y  G  V  L  G  L  F  W  T  L  N  W  V
1321 GTTCTGTCTTCAATCTGCAAATCTATGGGGTCCTGGGGCTCTTCTGGACCCTTAACTGGG
 460    L  A  L  G  Q  C  V  L  A  G  A  F  A  S  F  Y  W  A  F  H
1381 TACTGGCCCTGGGCCAATGCGTCCTCGCTGGAGCCTTTGCCTCCTTCTACTGGGCCTTCC
 480    K  P  Q  D  I  P  T  F  P  L  I  S  A  F  I  R  T  L  R  Y
```

Figure 1I-3

```
1441 ACAAGCCCCAGGACATCCCTACCTTCCCCTTAATCTCTGCCTTCATCCGCACACTCCGTT
 500   H  T  G  S  L  A  F  G  A  L  I  L  T  L  V  Q  I  A  R  V
1501 ACCACACTGGGTCATTGGCATTTGGAGCCCTCATCCTGACCCTTGTGCAGATAGCCCGGG
 520   I  L  E  Y  I  D  H  K  L  R  G  V  Q  N  P  V  A  R  C  I
1561 TCATCTTGGAGTATATTGACCACAAGCTCAGAGGAGTGCAGAACCCTGTAGCCCGCTGCA
 540   M  C  C  F  K  C  C  L  W  C  L  E  K  F  I  K  F  L  N  R
1621 TCATGTGCTGTTTCAAGTGCTGCCTCTGGTGTCTGGAAAAATTTATCAAGTTCCTAAACC
 560   N  A  Y  I  M  I  A  I  Y  G  K  N  F  C  V  S  A  K  N  A
1681 GCAATGCATACATCATGATCGCCATCTACGGGAAGAATTTCTGTGTCTCAGCCAAAAATG
 580   F  M  L  L  M  R  N  I  V  R  V  V  V  L  D  K  V  T  D  L
1741 CGTTCATGCTACTCATGCGAAACATTGTCAGGGTGGTCGTCCTGGACAAAGTCACAGACC
 600   L  L  F  F  G  K  L  L  V  V  G  G  V  G  V  L  S  F  F  F
1801 TGCTGCTGTTCTTTGGGAAGCTGCTGGTGGTCGGAGGCGTGGGGGTCCTGTCCTTCTTTT
 620   F  S  G  R  I  P  G  L  G  K  D  F  K  S  P  H  L  N  Y  Y
1861 TTTTCTCCGGTCGCATCCCGGGGCTGGGTAAAGACTTTAAGAGCCCCCACCTCAACTATT
 640   W  L  P  I  M  T  S  I  L  G  A  Y  V  I  A  S  G  F  F  S
1921 ACTGGCTGCCCATCATGACCTCCATCCTGGGGGCCTATGTCATCGCCAGCGGCTTCTTCA
 660   V  F  G  M  C  V  D  T  L  F  L  C  F  L  E  D  L  E  R  N
1981 GCGTTTTCGGCATGTGTGTGGACACGCTCTTCCTCTGCTTCCTGGAAGACCTGGAGCGGA
 680   N  G  S  L  D  R  P  Y  Y  M  S  K  S  L  L  K  I  L  G  K
2041 ACAACGGCTCCCTGGACCGGCCCTACTACATGTCCAAGAGCCTTCTAAAGATTCTGGGCA
 700   K  N  E  A  P  P  D  N  K  K  R  K  K  *
2101 AGAAGAACGAGGCGCCCCCGGACAACAAGAAGAGGAAGAAGTGAcagctccggccctgat
2161 ccaggactgcaccccaccccaccgtccagccatccaacctcacttcgccttacaggtct
2221 ccattttgtggtaaaaaaggttttaggccaggcgccgtggctcacgcctgtaatccaac
2281 actttgagaggctgaggcgggcggatcacctgagtcaggagttcgagaccagcctggcca
2341 acatggtgaaaccccgtctctattaaaaatacaaaaattagccgagagtggtggcatgc
2401 acctgtcatcccagctactcgggaggctgaggcaggagaatcgcttgaaccgggaggca
2461 gaggttgcagtgagccgagatcgcgccactgcactccaacctgggtgacagactctgtct
2521 ccaaaacaaaacaaacaaacaaaaagattttattaaagatattttgttaactcagtaaaa
2581 aaaaaaaaaaaa
```

Figure 2:

Figure 2A The cDNA (SEQ ID NO:19) and amino acid sequence (SEQ ID NO:20) of Ha5-1(5)1 VH.

Underlined is a portion of the heavy chain constant region.

```
        Q   V   Q   L   V   E   S   G   G   G   V   V   Q   P   G   R   S   L   R   L   S   C   G   A   S
  1   CAGGTGCAGCTGGTGGAGTCTGGGGGAGGCGTGGTCCAGCCTGGGAGGTCCCTGAGACTCTCCTGTGGAGCCTCT
        G   F   T   F   S   S   Y   G   M   H   W   V   R   Q   A   P   G   K   G   L   E   W   V   A   V
 76   GGATTCACCTTCAGTAGTTATGGCATGCACTGGGTCCGCCAGGCTCCAGGCAAGGGGCTGGAGTGGGTGGCAGTT
        M   S   Y   D   G   S   K   K   Y   Y   T   D   S   V   K   G   R   F   T   I   S   R   D   N   S
151   ATGTCATATGATGGAAGTAAAAAATACTATACAGACTCCGTGAAGGGCCGATTCACCATCTCCAGAGACAATTCC
        K   N   T   L   Y   L   Q   M   N   S   L   R   V   E   D   T   A   V   Y   Y   C   A   R   D   G
226   AAGAACACGCTGTATCTGCAAATGAACAGCCTGAGAGTTGAGGACACGGCTGTGTATTACTGTGCGAGAGATGGG
        G   D   Y   V   R   Y   Y   Y   Y   G   M   D   V   W   G   Q   G   T   T   V   T   V   S   S   A
301   GGTGACTACGTCCGCTACTACTACTACGGTATGGACGTCTGGGGCCAAGGGACCACGGTCACCGTCTCCTCAGCC
        S   T   K   G   P   S   V   F   P   L   A   P   C   S   R   S   T   S   E   S   T   A   A   L   G
376   TCCACCAAGGGCCCATCGGTCTTCCCCCTGGCGCCCTGCTCCAGGAGCACCTCCGAGAGCACAGCGGCCCTGGGC
        C   L   V   K   D   Y   F   P   E   P   V   T   V   S   W   N   S   G   A   L   T   S   G   V   H
451   TGCCTGGTCAAGGACTACTTCCCCGAACCGGTGACGGTGTCGTGGAACTCAGGCGCTCTGACCAGCGGCGTGCAC
        T   F   P   A   V   L   Q   S   S   G   L   Y   S   L   S   S   V
526   ACCTTCCCAGCTGTCCTACAGTCCTCAGGACTCTACTCCCTCAGCAGCGTG
```

Figure 2B The cDNA (SEQ ID NO:21) and amino acid sequence (SEQ ID NO:22) of Ha5-1(5)1 VL.

Double underline is the leader sequence. Underlined is a portion of the light chain constant region.

```
              L   P   D   T   R   C   D   I   Q   M   T   Q   S   P   S   S   L   S   A   S   V   G   D   R   V
  1   CTCCCAGATACCAGATGTGACATCCAGATGACCCAGTCTCCATCCTCCCTGTCTGCATCTGTAGGAGACAGAGTC
        T   I   T   C   R   A   R   Q   G   I   T   Y   H   L   A   W   Y   Q   Q   R   P   G   K   V   P
 76   ACCATCACTTGCCGGGCGCGTCAGGGCATTACCTATCATTTAGCCTGGTATCAGCAGAGACCGGGGAAAGTTCCT
        K   L   L   I   Y   D   T   S   S   L   Q   S   G   V   P   S   R   F   S   G   S   G   S   G   T
151   AAACTCCTGATCTATGATACATCCTCTTTGCAATCAGGGGTCCCATCTCGGTTCAGTGGCAGTGGATCTGGGACA
        D   F   T   L   T   I   S   S   L   Q   P   E   D   V   A   T   Y   Y   C   Q   R   F   N   S   A
226   GATTTCACTCTCACCATCAGCAGCCTGCAGCCTGAAGATGTTGCAACTTATTACTGTCAAAGGTTTAACAGTGCC
        P   L   T   F   G   G   G   T   K   V   E   I   K   R   T   V   A   A   P   S   V   F   I   F   P
301   CCGCTCACTTTCGGCGGAGGGACCAAGGTGGAGATCAAACGAACTGTGGCTGCACCATCTGTCTTCATCTTCCCG
        P   S   D   E   Q   L   K   S   G   T   A   S   V   V   C   L   L   N   N   F   Y   P   R   E   A
376   CCATCTGATGAGCAGTTGAAATCTGGAACTGCCTCTGTTGTGTGCCTGCTGAATAACTTCTATCCCAGAGAGGCC
        K   V   Q   W   K   V   D   N   A   L   Q   S   G   N   S   Q   E   S   V   T   E   Q   D   S   K
451   AAAGTACAGTGGAAGGTGGATAACGCCCTCCAATCGGGTAACTCCCAGGAGAGTGTCACAGAGCAGGACAGCAAG
        D   S   T   Y   S   L   S   S   T   L   T   L   S   K   A   D   Y   E   K   H   K   V   Y   A   C
526   GACAGCACCTACAGCCTCAGCAGCACCCTGACGCTGAGCAAAGCAGACTACGAGAAACACAAAGTCTACGCCTGC
        E   V   T   H   Q   G   L   S
601   GAAGTCACCCATCAGGGCCTGAGCT
```

Figure 2C The cDNA (SEQ ID NO:23) and amino acid sequence (SEQ ID NO:24) of Ha5-1(5)2.1 VH.

Underlined is a portion of the heavy chain constant region.

```
            Q   V   Q   L   V   E   S   G   G   G   V   V   Q   P   G   R   S   L   R   L
  1   CAGGTGCAGCTGGTGGAGTCTGGGGGAGGCGTGGTCCAGCCTGGGAGGTCCCTGAGACTC
            S   C   A   A   S   G   F   T   F   S   S   Y   G   M   H   W   V   R   Q   A
 61   TCCTGTGCAGCCTCTGGATTCACCTTCAGTAGTTATGGCATGCACTGGGTCCGCCAGGCT
            P   G   K   G   L   E   W   V   A   V   M   S   Y   D   G   S   K   K   Y   Y
121   CCAGGCAAGGGGCTGGAGTGGGTGGCAGTTATGTCATATGATGGAAGTAAAAAATTCTAT
            T   D   S   V   K   G   R   F   T   I   S   R   D   N   S   K   N   T   L   Y
181   ACAGACTCCGTGAAGGGCCGATTCACCATCTCCAGAGACAATTCCAAGAACACGCTGTAT
            L   Q   M   N   S   L   R   A   E   D   T   A   V   Y   Y   C   A   R   D   G
241   CTGCAAATGAACAGCCTGAGAGCTGAGGACACGGCTGTGTATTACTGTGCGAGAGATGGG
            G   D   Y   V   R   Y   H   Y   Y   G   M   D   V   W   G   Q   G   T   T   V
301   GGTGACTATGTCCGCTACCACTACTACGGTATGGACGTCTGGGGCCAAGGGACCACGGTC
            T   V   S   S   A   S   T   K   G   P   S   V   F   P   L   A   P   C   S   R
361   ACCGTCTCCTCAGCCTCCACCAAGGGCCCATCGGTCTTCCCCCTGGCGCCCTGCTCCAGG
            S   T   S   E   S   T   A   A   L   G   C   L   V   K   D   Y   F   P   E   P
421   AGCACCTCCGAGAGCACAGCGGCCCTGGGCTGCCTGGTCAAGGACTACTTCCCCGAACCG
            V   T   V   S   W   N   S   G   A   L   T   S   G   V   H   T   F   P   A   V
481   GTGACGGTGTCGTGGAACTCAGGCGCTCTGACCAGCGGCGTGCACACCTTCCCAGCTGTC
            L   Q   S   S   G   L   Y   S   L   S
541   CTACAGTCCTCAGGACTCTACTCCCTCAGCA
```

Figure 2D The cDNA (SEQ ID NO:25) and amino acid sequence (SEQ ID NO:26) of Ha5-1(5)2.1 VL.
Double-underlined is the leader sequence, and underlined is a portion of the heavy chain constant region.

```
           L   L   G   L   L   L   W   L   P   D   T   R   C   D   I   Q   M   T   Q   S   P   S   T   L
  1  CTCCTGGGACTCCTGCTGCTCTGGCTCCCAGATACCAGATGTGACATCCAGATGACCCAGTCTCCATCCACCCTG
         S   A   S   I   G   D   R   V   T   I   T   C   R   A   S   Q   G   I   S   Y   Y   L   A   W   Y
 76  TCTGCATCTATAGGAGACAGAGTCACCATCACTTGCCGGGCGAGTCAGGGCATTAGCTATTATTTAGCCTGGTAT
         Q   Q   K   P   G   K   I   P   K   L   L   I   Y   D   T   S   S   L   Q   S   G   V   P   S   R
151  CAGCAGAAACCGGGGAAAATTCCTAAGCTCCTGATCTATGATACATCCTCTTTGCAATCAGGGGTCCCATCTCGA
         F   S   G   S   R   S   G   T   D   L   S   L   T   I   S   S   L   Q   P   E   D   V   A   T   Y
226  TTCAGTGGCAGTAGATCTGGGACAGATCTCTCTCTCACCATCAGCAGCCTGCAGCCTGAAGATGTTGCAACTTAT
         Y   C   Q   R   Y   D   S   A   P   L   T   F   G   G   G   T   K   V   E   I   K   R   T   V   A
301  TACTGTCAAAGGTATGACAGTGCCCCGCTCACTTTCGGCGGAGGGACCAAGGTGGAGATCAAACGAACTGTGGCT
         A   P   S   V   F   I   F   P   P   S   D   E   Q   L   K   S   G   T   A   S   V   V   C   L   L
376  GCACCATCTGTCTTCATCTTCCCGCCATCTGATGAGCAGTTGAAATCTGGAACTGCCTCTGTTGTGTGCCTGCTG
         N   N   F   Y   P   R   E   A   K   V   Q   W   K   V   D   N   A   L   Q   S   G   N   S   Q   E
451  AATAACTTCTATCCCAGAGAGGCCAAAGTACAGTGGAAGGTGGATAACGCCCTCCAATCGGGTAACTCCCAGGAG
         S   V   T   E   Q   D   S   K   D   S   T   Y   S   L   S   S   T   L   T   L   S   K   A   D   Y
526  AGTGTCACAGAGCAGGACAGCAAGGACAGCACCTACAGCCTCAGCAGCACCCTGACGCTGAGCAAAGCAGACTAC
         E   K   H   K   V   Y   A   C   E   V   T   H   Q   G   L   S   S   P   V   T   K   S   F   N   R
601  GAGAAACACAAAGTCTACGCCTGCGAAGTCACCCATCAGGGCCTGAGCTCGCCCGTCACAAAGAGCTTCAACAGG
         G
676  GGA
```

Figure 2E The cDNA (SEQ ID NO:27) and amino acid sequence (SEQ ID NO:28) of Ha5-3(1,4)2.1 VH.
Underlined is a portion of the heavy chain constant region.

```
          Q   V   Q   L   V   E   S   G   G   G   V   V   Q   P   G   R   S   L   R   L
  1  CAGGTGCAGCTGGTGGAGTCTGGGGGAGGCGTGGTCCAGCCTGGGAGGTCCCTGAGACTC
         S   C   A   A   S   G   F   T   F   S   S   Y   G   M   H   W   V   R   Q   A
 61  TCCTGTGCAGCGTCTGGATTCACCTTCAGTAGCTATGGCATGCACTGGGTCCGCCAGGCT
         P   G   K   G   L   E   W   V   A   V   I   W   Y   D   G   R   N   K   F   Y
121  CCAGGCAAGGGGCTGGAGTGGGTGGCAGTTATATGGTATGATGGAAGAAATAAATTCTAT
         A   D   S   V   K   G   R   F   T   V   S   R   D   N   S   K   N   T   L   Y
181  GCAGACTCCGTGAAGGGCCGATTCACCGTCTCCAGAGACAATTCCAAGAACACGCTGTAT
         L   Q   M   N   S   L   R   A   E   D   T   A   V   Y   Y   C   A   R   D   W
241  CTGCAAATGAACAGCCTGAGAGCCGAGGACACGGCTGTGTATTACTGTGCGAGAGATTGG
         G   A   T   M   A   F   D   I   W   G   Q   G   T   M   V   T   V   S   S   A
301  GGAGCTACTATGGCTTTTGATATCTGGGGCCAAGGGACAATGGTCACCGTCTCTTCAGCC
         S   T   K   G   P   S   V   F   P   L   A   P   S   S   K   S
361  TCCACCAAGGGCCCATCGGTCTTCCCCCTGGCACCCTCCTCCAAGAGCAC
```

Figure 2F The cDNA (SEQ ID NO:29) and amino acid sequence (SEQ ID NO:30) of Ha5-3(1,4)2.1 VL.
Double underlined is a portion of the leader sequence. Underlined is a portion of the light chain constant region.

```
           L   L   T   L   L   T   H   C   A   G   S   W   A   Q   S   V   L   T   Q   P   P   S   A   S   K
  1  CTCCTCACCCTCCTCACTCACTGTGCAGGGTCCTGGGCCCAGTCTGTGCTGACTCAGCCACCCTCAGCGTCTAAG
         T   P   G   Q   R   V   T   I   S   C   S   G   S   S   S   N   I   G   S   N   T   V   N   W   Y
 76  ACCCCCGGGCAGAGGGTCACCATCTCTTGTTCTGGAAGCAGCTCCAACATCGGAAGTAATACTGTCAACTGGTAC
         Q   Q   L   P   G   T   A   P   K   L   L   I   F   G   N   N   Q   R   P   S   G   V   P   D   R
151  CAACAGCTCCCAGGAACGGCCCCCAAACTCCTCATCTTTGGTAATAATCAGCGGCCCTCAGGGGTCCCTGACCGA
         F   S   G   S   K   S   G   T   S   A   S   L   A   I   S   G   L   Q   S   E   D   E   A   D   Y
226  TTCTCTGGCTCCAAGTCTGGCACCTCAGCCTCCCTGGCCATCAGTGGTCTCCAGTCTGAGGATGAGGCTGATTAT
         Y   C   A   A   W   D   D   S   L   N   Y   V   F   G   T   G   T   K   V   T   V   L   G   Q   P
301  TACTGTGCAGCATGGGATGACAGCCTGAATTATGTCTTCGGAACTGGGACCAAGGTCACCGTCCTAGGTCAGCCC
         K   A   N   P   T   V   T   L   F   P   P   S   S   E   E   L   Q   A   N   K   A   T   L   V   C
376  AAGGCCAACCCCACTGTCACTCTGTTCCCGCCCTCCTCTGAGGAGCTCCAAGCCAACAAGGCCACACTAGTGTGT
         L   I   S   D   F   Y   P   G   A   V   T   V   A   W   K   A   D   G   S   P   V   K   A   G   V
451  CTGATCAGTGACTTCTACCCGGGAGCTGTGACAGTGGCCTGGAAGGCAGATGGCAGCCCCGTCAAGGCGGGAGTG
         E   T   T   K   P   S   K   Q   S   N   N   K   Y   A   A   S   S   Y   L   S   L   T   P   E   Q
526  GAGACCACCAAACCCTCCAAACAGAGCAACAACAAGTACGCGGCCAGCAGCTACCTGAGCCTGACGCCCGAGCAG
         W   K   S   H   R   S   Y   S   C   Q   V   T   H   E   G
601  TGGAAGTCCCACAGAAGCTACAGCTGCCAGGTCACGCATGAAGGAG
```

Figure 2G The cDNA (SEQ ID NO:31) and amino acid sequence (SEQ ID NO:32) of Ha5-3(1,4)7.1 VH.
Underlined is a portion of the heavy chain constant region.

```
        Q   V   Q   L   V   E   S   G   G   G   V   V   Q   P   G   R   S   L   R   L   S   C   A   A   S
  1   CAGGTGCAGCTGGTGGAGTCTGGGGGAGGCGTGGTCCAGCCTGGGAGGTCCCTGAGACTCTCCTGTGCAGCGTCT
        G   F   T   F   S   S   Y   G   M   H   W   V   R   Q   A   P   G   K   G   L   E   W   V   A   V
 76   GGATTCACCTTCAGTAGCTATGGCATGCACTGGGTCCGCCAGGCTCCAGGCAAGGGGCTGGAGTGGGTGGCAGTT
        I   W   Y   D   G   S   N   K   Y   Y   A   D   S   V   K   G   R   F   T   I   S   R   D   N   S
151   ATATGGTATGATGGAAGTAATAAATACTATGCAGACTCCGTGAAGGGCCGATTCACCATCTCCAGAGACAATTCC
        K   N   T   L   Y   L   Q   M   N   S   L   R   A   E   D   T   A   V   Y   Y   C   A   R   D   R
226   AAGAACACGCTGTATCTGCAAATGAACAGCCTGAGAGCCGAAGACACGGCTGTCTATTACTGTGCGAGAGATCGA
        Y   S   G   Y   G   Y   Y   Y   Y   Y   G   M   D   V   W   G   Q   G   T   T   V   T   V   S   S
301   TATAGTGGCTACGGTTACTACTACTACTACGGTATGGACGTCTGGGGCCAAGGGACCACGGTCACCGTCTCCTCA
        A   S   T   K   G   P   S   V   F   P   L   A   P
376   GCCTCCACCAAGGGCCCATCGGTCTTCCCCCTGGCACCCTC
```

Figure 2H The cDNA (SEQ ID NO:33) and amino acid sequence (SEQ ID NO:34) of Ha5-3(1,4)7.1 VL.
Double underlined is a portion of the leader sequence. Underlined is a portion of the light chain constant region.

```
        G   A   R   C   D   I   Q   M   T   Q   S   P   S   S   L   S   A   S   V   G   D   R   V   T   I
  1   GGTGCCAGATGTGACATCCAGATGACCCAGTCTCCATCCTCACTGTCTGCATCTGTAGGAGACAGAGTCACCATC
        T   C   R   A   S   Q   D   I   S   N   Y   L   A   W   F   Q   Q   K   P   G   K   A   P   K   S
 76   ACTTGTCGGGCGAGTCAGGACATTAGCAATTATTTAGCCTGGTTTCAGCAGAAACCAGGGAAAGCCCCTAAGTCC
        L   I   Y   A   A   S   S   L   H   S   G   V   P   S   K   F   S   G   S   G   S   G   T   D   F
151   CTGATCTATGCTGCATCCAGTTTGCACAGTGGGGTCCCATCAAAGTTCAGCGGCAGTGGATCTGGGACAGATTTC
        T   L   T   I   S   S   L   Q   P   E   D   F   A   T   Y   Y   C   Q   Q   Y   T   I   Y   P   F
226   ACTCTCACCATCAGCAGCCTGCAGCCTGAAGATTTTGCAACTTATTACTGCCAACAGTATACTATTTACCCATTC
        T   F   G   P   G   T   K   V   D   I   K   R   T   V   A   A   P   S   V   F   I   F   P   P   S
301   ACTTTCGGCCCTGGGACCAAAGTGGATATCAAACGAACTGTGGCTGCACCATCTGTCTTCATCTTCCCGCCATCT
        D   E   Q   L   K   S   G   T   A   S   V   V   C   L   L   N   N   F   Y   P   R   E   A   K   V
376   GATGAGCAGTTGAAATCTGGAACTGCCTCTGTTGTCTGCCTGCTGAATAACTTCTATCCCAGAGAGGCCAAAGTA
        Q   W   K   V   D   N   A   L   Q   S   G   N   S   Q   E   S   V   T   E   Q   D   S   K   D   S
451   CAGTGGAAGGTGGATAACGCCCTCCAATCGGGTAACTCCCAGGAGAGTGTCACAGAGCAGGACAGCAAGGACAGC
        T   Y   S   L   S   S   T   L   T   L   S   K   A   D   Y   E   K   H   K   V   Y   A   C   E   V
526   ACCTACAGCCTCAGCAGCACCCTGACGCTGAGCAAAGCAGACTACGAGAAACACAAAGTCTACGCCTGCGAAGTC
        T   H   Q   G   L   S   S   P   V   T   K   S   F   N   R   G   E
601   ACCCATCAGGGCCTGAGCTCGCCCGTCACAAAGAGCTTCAACAGGGGAGAG
```

Figure 2I The cDNA (SEQ ID NO:35) and amino acid sequence (SEQ ID NO:36) of Ha5-3(3,5)37.1 VH.
Underlined is a portion of the heavy chain constant region.

```
        Q   V   Q   L   Q   E   S   G   P   G   L   V   K   P   S   E   T   L   S   L   T   C   T   V   S
  1   CAGGTGCAGCTGCAGGAGTCTGGCCCAGGACTGGTGAAGCCTTCGGAGACCCTGTCCCTCACCTGCACTGTCTCT
        G   G   S   I   S   S   Y   Y   W   S   W   I   R   Q   P   P   G   K   G   L   E   W   I   G   Y
 76   GGTGGCTCCATCAGTAGTTACTACTGGAGCTGGATCCGGCAGCCCCCAGGGAAGGGACTGGAGTGGATTGGGTAT
        I   Y   Y   S   G   S   T   N   Y   N   P   S   L   K   S   R   V   T   I   S   V   D   T   S   K
151   ATCTATTACAGTGGGAGCACCAACTACAACCCCTCCCTCAAGAGTCGAGTCACCATATCAGTAGACACGTCCAAG
        N   Q   F   S   L   K   L   N   S   V   T   A   A   D   T   A   V   Y   Y   C   A   R   G   Y   Y
226   AACCAGTTCTCCCTGAAGCTGAACTCTGTGACCGCTGCGGACACGGCCGTGTATTACTGTGCGAGAGGGTATTAC
        Y   G   S   E   S   P   Y   G   M   D   V   W   G   Q   G   T   T   V   T   V   S   S   A   S   T
301   TATGGTTCGGAGAGTCCATACGGTATGGACGTCTGGGGCCAAGGGACCACGGTCACCGTCTCCTCAGCCTCCACC
        K   G   P   S   V   F   P   L   A   P   S   S   K   S   T   S   G   G   T   A   A   L   G   C   L
376   AAGGGCCCATCGGTCTTCCCCCTGGCACCCTCCTCCAAGAGCACCTCTGGGGGCACAGCGGCCCTGGGCTGCCTG
        V   K   D   Y   F   P   E   P   V   T   V   S   W   N   S   G   A   L   T   S   G   V   H   T   F
451   GTCAAGGACTACTTCCCCGAACCGGTGACGGTGTCGTGGAACTCAGGCGCCCTGACCAGCGGCGTGCACACCTTC
        P   A
526   CCAGCTG
```

Figure 2J The cDNA (SEQ ID NO:37) and amino acid sequence (SEQ ID NO:38) of Ha5-3(3,5)37.1 VL.
Underlined is a portion of the light chain constant region.

```
      D   I   V   M   T   Q   S   P   L   S   L   P   V   T   P   G   E   P   A   S   I   S   C   R   S
  1 GATATTGTGATGACTCAGTCTCCACTCTCCCTGCCCGTCACCCCTGGAGAGCCGGCCTCCATCTCCTGCAGGTCT
      S   Q   S   L   L   H   S   N   G   H   N   Y   L   D   W   Y   L   Q   K   P   G   Q   S   P   H
 76 AGTCAGAGCCTCCTGCATAGTAATGGACACAACTATTTGGATTGGTACCTGCAGAAGCCAGGGCAGTCTCCACAC
      L   L   I   Y   L   G   S   N   R   D   S   G   V   P   D   R   F   S   G   S   G   S   G   T   D
151 CTCCTGATCTATTTGGGTTCTAATCGGGACTCCGGGGTCCCTGACAGGTTCAGTGGCAGTGGATCAGGCACAGAT
      F   T   L   K   I   S   R   V   E   A   E   D   V   G   V   Y   Y   C   M   Q   A   L   Q   I   P
226 TTTACACTGAAAATCAGCAGAGTGGAGGCTGAGGATGTTGGGGTTTATTACTGCATGCAAGCTCTACAAATTCCG
      C   S   F   G   Q   G   T   K   L   E   I   K   R   T   V   A   A   P   S   V   F   I   F   P   P
301 TGCAGTTTTGGCCAGGGGACCAAGCTGGAGATCAAACGAACTGTGGCTGCACCATCTGTCTTCATCTTCCCGCCA
      S   D   E   Q   L   K   S   G   T   A   S   V   V   C   L   L   N   N   F   Y   P   R   E   A   K
376 TCTGATGAGCAGTTGAAATCTGGAACTGCCTCTGTTGTGTGCCTGCTGAATAACTTCTATCCCAGAGAGGCCAAA
      V   Q   W   K   V   D   N   A   L   Q   S   G   N   S   Q   E   S   V   T   E   Q   D   S   K   D
451 GTACAGTGGAAGGTGGATAACGCCCTCCAATCGGGTAACTCCCAGGAGAGTGTCACAGAGCAGGACAGCAAGGAC
      S   T   Y   S   L   S   S   T   L   T   L   S   K   A   D   Y   E   K   H   K   V   Y   A   C   E
526 AGCACCTACAGCCTCAGCAGCACCCTGACGCTGAGCAAAGCAGACTACGAGAAACACAAAGTCTACGCCTGCGAA
      V   T   H   Q   G   L   S   S   P   V   T   K   S   F   N   R
601 GTCACCCATCAGGGCCTGAGCTCGCCCGTCACAAAGAGCTTCAACAGGG
```

Figure 2K The cDNA (SEQ ID NO:39) and amino acid sequence (SEQ ID NO:40) of Ha5-4(2,5)13.1 VH.

```
      Q   V   Q   L   V   E   F   G   G   G   V   V   Q   P   G   R   S   L   R   L   S   C   A   A   S
  1 CAGGTGCAGCTGGTGGAGTTTGGGGGAGGCGTGGTCCAGCCTGGGAGGTCCCTGAGACTCTCCTGTGCAGCGTCT
      G   F   T   F   R   S   Y   G   M   H   W   V   R   Q   A   P   G   K   G   L   E   W   V   A   V
 76 GGATTCACCTTCAGAAGCTATGGCATGCACTGGGTCCGCCAGGCTCCAGGCAAGGGGCTGGAGTGGGTGGCAGTT
      I   W   Y   D   G   S   N   K   Y   Y   A   D   S   V   K   G   R   S   T   I   S   R   D   N   S
151 ATATGGTATGATGGAAGTAATAAATACTATGCAGACTCCGTGAAGGGCCGATCCACCATCTCCAGAGACAACTCC
      K   N   T   L   Y   L   Q   M   N   S   L   R   A   E   D   T   A   V   Y   Y   C   A   R   D   G
226 AAGAACACGCTGTATCTGCAAATGAACAGCCTGAGAGCCGAGGACACGGCTGTGTATTACTGTGCGAGAGATGGG
      V   A   V   A   G   T   D   Y   F   D   Y   W   G   Q   G   T   L   V   T   V   S   S   A   S   T
301 GTAGCAGTGGCTGGTACAGACTACTTTGACTACTGGGGCCAGGGAACCCTGGTCACCGTCTCCTCAGCCTCCACC
      K   G   P   S   V   F   P   L   A   P   S   S   K   S   T   S   G   G   T   A   A   L   G   C   L
376 AAGGGCCCATCGGTCTTCCCCCTGGCACCCTCCTCCAAGAGCACCTCTGGGGGCACAGCCGCCCTGGGCTGCCTG
      V   K   D   Y   F   P   E   P   V   T   V   S   W   N   S   G   A   L   T   S   G   V   H   T
451 GTCAAGGACTACTTCCCCGAACCGGTGACGGTGTCGTGGAACTCAGGCGCCCTGACCAGCGGCGTGCACACCTT
```

Figure 2L The cDNA (SEQ ID NO:41) and amino acid sequence (SEQ ID NO:42) of Ha5-4(2,5)13.1 VL.

Double underline is a portion of the leader sequence. Underlined is the light chain constant region.

```
      W   L   R   G   A   R   C   D   I   Q   M   T   Q   S   P   S   S   L   S   A   S   V   G   D   ·
  1 TCTGGCTCCGAGGTGCCAGATGTGACATCCAGATGACCCAGTCTCCATCCTCCCTGTCTGCATCTGTAGGAGACA
      ·   V   T   I   T   C   R   A   S   Q   S   I   S   S   H   L   N   W   Y   Q   Q   K   P   G   K   A   ·
 76 GAGTCACCATCACTTGCCGGGCAAGTCAGAGCATTAGCAGCCATTTAAATTGGTATCAGCAGAAACCAGGGAAAG
      ·   P   K   L   L   I   Y   V   A   S   S   L   Q   S   G   V   P   S   R   F   S   G   S   G   S   G   ·
151 CCCCTAAGCTCCTGATCTATGTTGCATCCAGTTTGCAAAGTGGGGTCCCATCAAGGTTCAGTGGCAGTGGATCTG
      ·   T   D   F   T   L   T   I   S   S   L   Q   P   E   D   F   A   T   Y   Y   C   Q   Q   S   Y   S   ·
226 GGACAGATTTCACTCTCACCATCAGCAGTCTGCAACCTGAAGATTTTGCAACTTACTACTGTCAACAGAGTTACA
      ·   T   P   L   I   F   G   G   G   T   K   V   E   I   K   R   T   V   A   A   P   S   V   F   I   F   ·
301 GTACCCCGCTCATTTTCGGCGGAGGGACCAAGGTGGAGATCAAACGAACTGTGGCTGCACCATCTGTCTTCATCT
      ·   P   P   S   D   E   Q   L   K   S   G   T   A   S   V   V   C   L   L   N   N   F   Y   P   R   E   ·
376 TCCCGCCATCTGATGAGCAGTTGAAATCTGGAACTGCCTCTGTTGTGTGCCTGCTGAATAACTTCTATCCCAGAG
      ·   A   K   V   Q   W   K   V   D   N   A   L   Q   S   G   N   S   Q   E   S   V   T   E   Q   D   S   ·
451 AGGCCAAAGTACAGTGGAAGGTGGATAACGCCCTCCAATCGGGTAACTCCCAGGAGAGTGTCACAGAGCAGGACA
      ·   K   D   S   T   Y   S   L   S   S   T   L   T   L   S   K   A   D   Y   E   K   H   K   V   Y   A   ·
526 GCAAGGACAGCACCTACAGCCTCAGCAGCACCCTGACGCTGAGCAAAGCAGACTACGAGAAACACAAAGTCTACG
      ·   C   E   V   T   H   Q   G   L   S   S   P   V
601 CCTGCGAAGTCACCCATCAGGGCCTGAGCTCGCCCGTCA
```

Figure 2M The cDNA (SEQ ID NO :43) and amino acid sequence (SEQ ID NO:44) of Ha5-4(2,5)34.1 VH.
Underlined is a portion of the heavy chain constant region.

```
        E   V   Q   L   L   E   S   G   G   G   L   V   Q   P   G   G   S   L   R   L   S   C   A   A   S
   1  GAGGTGCAGCTGTTGGAGTCTGGGGGAGGCTTGGTACAGCCTGGGGGGTCCCTGAGACTCTCCTGTGCAGCCTCT
        T   F   T   F   S   S   Y   A   M   S   W   V   R   Q   A   P   G   K   G   L   E   W   V   S   A
  76  ACATTCACCTTTAGCAGCTATGCCATGAGCTGGGTCCGCCAGGCTCCAGGGAAGGGGCTGGAGTGGGTCTCAGCT
        F   S   G   R   G   G   S   T   Y   Y   A   D   S   V   K   G   R   F   T   I   S   R   D   N   S
 151  TTTAGTGGTCGTGGTGGTAGCACATACTACGCAGACTCCGTGAAGGGCCGGTTCACCATCTCCAGAGACAATTCC
        K   N   T   L   F   L   Q   M   N   S   L   R   A   E   D   T   A   V   Y   Y   C   A   K   D   S
 226  AAGAACACGCTGTTTCTGCAAATGAACAGCCTGAGAGCCGAGGACACGGCCGTATATTACTGTGCGAAAGATAGC
        S   G   P   L   L   G   Y   G   M   D   V   W   G   Q   G   T   T   V   T   V   S   S   A   S   T
 301  AGTGGCCCCCTGCTGGGCTACGGTATGGACGTCTGGGGCCAAGGGACCACGGTCACCGTCTCCTCAGCCTCCACC
        K   G   P   S   V   F   P   L   A   P   S   S   K   S   T   S   G   G   T   A   A   L   G   C   L
 376  AAGGGCCCATCGGTCTTCCCCCTGGCACCCTCCTCCAAGAGCACCTCTGGGGGCACAGCGGCCCTGGGCTGCCTG
        V   K   D   Y   F   P   E   P   V   T   V   S
 451  GTCAAGGACTACTTCCCCGAACCGGTGACGGTGTCGT
```

Figure 2N The cDNA (SEQ ID NO:45) and amino acid sequence (SEQ ID NO:46) of Ha5-4(2,5)34.1 VL.
Underlined is a portion of the light chain constant region.

```
        S   Y   E   L   T   Q   P   P   S   V   S   V   S   P   G   Q   T   A   S   I   T   C   S   G   D
   1  TCCTATGAGCTGACTCAGCCACCCTCAGTGTCCGTGTCCCCAGGACAGACAGCCAGCATCACCTGCTCTGGAGAT
        K   V   G   D   K   Y   A   C   W   Y   Q   Q   K   P   G   Q   S   P   V   L   V   I   Y   Q   D
  76  AAAGTGGGGGATAAATATGCTTGTTGGTATCAGCAGAAGCCAGGCCAGTCCCCTGTACTGGTCATCTATCAAGAT
        S   K   R   P   S   G   I   P   E   R   F   S   G   S   N   S   G   N   T   A   T   L   T   I   S
 151  AGCAAGCGGCCCTCAGGGATCCCTGAGCGATTCTCTGGCTCCAATTCTGGAAACACAGCCACTCTGACCATCAGC
        G   T   Q   A   M   D   E   A   D   Y   Y   C   Q   A   W   D   S   S   T   Y   V   V   F   G   G
 226  GGGACCCAGGCTATGGATGAGGCTGACTATTACTGTCAGGCGTGGGACAGCAGCACTTATGTGGTATTCGGCGGA
        G   T   K   L   T   V   L   G   Q   P   K   A   A   P   S   V   T   L   F   P   P   S   S   E   E
 301  GGGACCAAACTGACCGTCCTAGGTCAGCCCAAGGCTGCCCCCTCGGTCACTCTGTTCCCGCCCTCCTCTGAGGAG
        L   Q   A   N   K   A   T   L   V   C   L   I   S   D   F   Y   P   G   A   V   T   V   A   W   K
 376  CTTCAAGCCAACAAGGCCACACTGGTGTGTCTCATAAGTGACTTCTACCCGGGAGCCGTGACAGTGGCCTGGAAG
        A   D   S   S   P   V   K   A   G   V   E   T   T   T   P   S   K   Q   S   N   N   K   Y   A   A
 451  GCAGATAGCAGCCCCGTCAAGGCGGGAGTGGAGACCACCACACCCTCCAAACAAAGCAACAACAAGTACGCGGCC
        S   S   Y   L   S   L   T   P   E   Q   W   K   S   H   R   S   Y   S   C   Q   V   T   H   E   G
 526  AGCAGCTATCTGAGCCTGACGCCTGAGCAGTGGAAGTCCCACAGAAGCTACAGCTGCCAGGTCACGCATGAAGGG
        S   T   V   E   K   T
 601  AGCACCGTGGAGAAGACAGT
```

Figure 2O The cDNA (SEQ ID NO:47) and amino acid sequence (SEQ ID NO:48) of Ha5-7acd4.1 VH.
Underlined is a portion of the heavy chain constant region.

```
        Q   V   Q   L   V   E   S   G   G   G   V   V   Q   P   G   R   S   L   R   L   S   C   A   A   S
   1  CAGGTGCAGCTGGTGGAGTCTGGGGGAGGCGTGGTCCAGCCTGGGAGGTCCCTGAGACTCTCCTGTGCAGCGTCT
        G   F   T   F   S   S   Y   G   M   H   W   V   R   Q   A   P   G   K   G   L   E   W   V   A   V
  76  GGATTCACCTTCAGTAGCTATGGCATGCACTGGGTCCGCCAGGCTCCAGGCAAGGGGCTGGAGTGGGTGGCAGTT
        I   W   Y   D   G   S   N   K   Y   Y   A   D   S   V   K   G   R   F   T   I   S   R   D   N   S
 151  ATATGGTATGATGGAAGTAATAAATACTATGCAGACTCCGTGAAGGGCCGATTCACCATCTCCAGAGACAATTCC
        K   N   T   L   Y   L   Q   M   N   S   L   R   A   E   D   T   A   V   Y   Y   C   A   R   D   R
 226  AAGAACACGCTGTATCTGCAAATGAACAGCCTGAGAGCCGAGGACACGGCTGTGTATTACTGTGCGAGAGATCGA
        Y   S   G   Y   D   Y   Y   Y   Y   G   M   D   V   W   G   Q   G   T   T   V   T   V   S   S
 301  TATAGTGGCTACGATTACTACTACTACTACGGTATGGACGTCTGGGGCCAAGGGACCACGGTCACCGTCTCCTCA
        A   S   T   K   G   P   S   V   F   P   L   A   P   S
 376  GCCTCCACCAAGGGCCCATCGGTCTTCCCCCTGGCACCCTCC
```

Figure 2P The cDNA (SEQ ID NO:49) and amino acid sequence (SEQ ID NO:50) of Ha5-7acd4.1 VL.

Double underline is a portion of the leader sequence. Underlined is a portion of the light chain constant region.

```
        L   C   F   P   G   A   R   C   D   I   Q   M   T   Q   S   P   S   S   L   S   A   S   V   G   D
   1  CTCTGTTTCCCAGGTGCCAGATGTGACATCCAGATGACCCAGTCTCCATCCTCACTGTCTGCATCTGTGGGAGAC
        R   V   T   I   T   C   R   A   S   Q   V   I   Y   N   Y   L   A   W   F   Q   Q   K   P   G   K
  76  AGAGTCACCATCACTTGTCGGGCGAGTCAGGTCATTTACAATTATTTAGCCTGGTTTCAGCAGAAACCAGGGAAA
        A   P   K   S   L   I   Y   G   A   S   S   L   H   S   G   V   P   S   K   F   S   G   S   G   S
 151  GCCCCTAAGTCCCTGATCTATGGTGCATCCAGTTTGCACAGTGGGGTCCCATCAAAGTTCAGCGGCAGTGGATCT
        G   T   E   F   T   L   T   I   S   S   L   Q   P   E   D   F   A   T   Y   Y   C   Q   Q   Y   T
 226  GGGACAGAATTCACTCTCACCATCAGCAGCCTGCAGCCTGAAGATTTTGCAACTTATTACTGCCAACAATATACT
        I   Y   P   F   S   F   G   P   G   T   K   V   D   I   K   R   T   V   A   A   P   S   V   F   I
 301  ATTTACCCTTTCTCTTTCGGCCCTGGGACCAAAGTGGATATCAAACGAACTGTGGCTGCACCATCTGTCTTCATC
        F   P   P   S   D   E   Q   L   K   S   G   T   A   S   V   V   C   L   L   N   N   F   Y   P   R
 376  TTCCCGCCATCTGATGAGCAGTTGAAATCTGGAACTGCCTCTGTTGTGTGCCTGCTGAATAACTTCTATCCCAGA
        E   A   K   V   Q   W   K   V   D   N   A   L   Q   S   G   N   S   Q   E   S   V   T   E   Q   D
 451  GAGGCCAAAGTACAGTGGAAGGTGGATAACGCCCTCCAATCGGGTAACTCCCAGGAGAGTGTCACAGAGCAGGAC
        S   K   D   S   T   Y   S   L   S   S   T   L   T   L   S   K   A   D   Y   E   K   H   K   V   Y
 526  AGCAAGGACAGCACCTACAGCCTCAGCAGCACCCTGACGCTGAGCAAAGCAGACTACGAGAAACACAAAGTCTAC
        A   C   E   V   T   H   Q   G   L   S   S   P   V
 601  GCCTGCGAAGTCACCCATCAGGGCCTGAGCTCGCCCGTCA
```

Figure 2Q The cDNA (SEQ ID NO:51) and amino acid sequence (SEQ ID NO:52) of Ha5-7acd20.1.1 VH.

Underlined is a portion of the heavy chain constant region.

```
        Q   V   Q   L   V   E   S   G   G   G   V   V   Q   P   G   R   S   L   R   L   S   C   A   A   S
   1  CAGGTGCAGCTGGTGGAGTCTGGGGGAGGCGTGGTCCAGCCTGGGAGGTCCCTGAGACTCTCCTGTGCAGCGTCT
        G   F   T   F   S   S   Y   G   M   H   W   V   R   Q   A   P   G   K   G   L   E   W   V   A   V
  76  GGATTCACCTTCAGCAGCTATGGCATGCACTGGGTCCGCCAGGCTCCAGGCAAGGGGCTGGAGTGGGTGGCAGTT
        I   W   Y   D   G   R   N   K   Y   Y   V   D   S   V   K   G   R   F   T   I   S   R   D   N   S
 151  ATATGGTATGATGGAAGAAATAAATATTATGTAGACTCCGTGAAGGGCCGATTCACCATCTCCAGAGACAATTCC
        K   N   T   L   Y   L   Q   M   N   S   L   R   A   E   D   T   A   V   Y   Y   C   A   R   D   R
 226  AAGAATACGCTGTATCTGCAAATGAACAGCCTGAGAGCCGAGGACACGGCTGTGTATTACTGTGCGAGAGATCGG
        Y   S   G   S   D   Y   Y   Y   Y   Y   G   M   D   V   W   G   Q   G   T   T   V   T   V   S   S
 301  TATAGTGGCTCCGATTACTACTACTACTACGGTATGGACGTCTGGGGCCAAGGGACCACGGTCACCGTCTCCTCA
        A   S   T   K   G   P   S   V   F   P   L
 376  GCCTCCACCAAGGGCCCATCGGTCTTCCCCCTGGC
```

Figure 2R The cDNA (SEQ ID NO:53) and amino acid sequence (SEQ ID NO:54) of Ha5-7acd20.1.1 VL.

Double underline is a portion of the leader sequence. Underlined is a portion of the light chain constant region.

```
        L   C   F   P   G   A   R   C   D   I   Q   M   T   Q   S   P   S   S   L   S   A   S   V   G   D
   1  TCCTCTGTTTCCCAGGTGCCAGATGTGACATTCAGATGACCCAGTCTCCATCCTCACTGTCTGCATCTGTAGGAG
        R   V   T   I   T   C   R   A   S   Q   G   I   Y   N   Y   L   A   W   F   Q   Q   K   P   G   K
  76  ACAGAGTCACCATCACTTGTCGGGCGAGTCAGGGCATTTACAATTATTTAGCCTGGTTTCAGCAGAAACCAGGGA
        A   P   K   S   L   I   Y   A   A   S   S   L   Q   S   G   V   P   S   K   F   S   G   S   G   S
 151  AAGCCCCTAAGTCCCTGATCTATGCTGCATCCAGTTTGCAAAGTGGGGTCCCATCAAAGTTCAGCGGCAGTGGAT
        G   T   V   F   T   L   T   I   S   S   L   Q   P   E   D   F   A   T   Y   Y   C   Q   Q   Y   T
 226  CTGGGACAGTTTTCACTCTCACCATCAGCAGCCTGCAGCCTGAAGATTTTGCAACTTATTACTGCCAACAGTATA
        V   Y   P   F   T   F   G   P   G   T   K   V   D   F   K   R   T   V   A   A   P   S   V   F   I
 301  CTGTTTACCCATTCACTTTCGGCCCTGGGACCAAAGTGGATTTCAAACGAACTGTGGCTGCACCATCTGTCTTCA
        F   P   P   S   D   E   Q   L   K   S   G   T   A   S   V   V   C   L   L   N   N   F   Y   P   R
 376  TCTTCCCGCCATCTGATGAGCAGTTGAAATCTGGAACTGCCTCTGTTGTGTGCCTGCTGAATAACTTCTATCCCA
        E   A   K   V   Q   W   K   V   D   N   A   L   Q   S   G   N   S   Q   E   S   V   T   E   Q   D
 451  GAGAGGCCAAAGTACAGTGGAAGGTGGATAACGCCCTCCAATCGGGTAACTCCCAGGAGAGTGTCACAGAGCAGG
        S   K   D   S   T   Y   S   L   S   S   T   L   T   L   S   K   A   D   Y   E   K   H   K   V   Y
 526  ACAGCAAGGACAGCACCTACAGCCTCAGCAGCACCCTGACGCTGAGCAAAGCAGACTACGAGAAACACAAAGTCT
        A   C   E   V   T   H   Q   G   L   S   S   P   V   T   K   S   F   N   R
 601  ACGCCTGCGAAGTCACCCATCAGGGCCTGAGCTCGCCCGTCACAAAGAGCTTCAACAGG
```

Figure 2S The cDNA (SEQ ID NO:55) and amino acid sequence (SEQ ID NO:56) of Ha5-7be31.1 VH. Underlined is a portion of the heavy chain constant region.

```
        Q  V  Q  L  Q  E  S  G  P  G  L  V  K  P  S  E  T  L  S  L  T  C  T  V  S
  1   CAGGTGCAGCTGCAGGAGTCGGGCCCAGGACTGGTGAAGCCTTCGGAGACCCTGTCCCTCACCTGCACTGTCTCT
        G  G  S  I  S  S  Y  Y  W  S  W  I  R  Q  P  P  G  K  G  L  E  W  I  G  Y
 76   GGTGGCTCCATCAGTAGTTACTACTGGAGCTGGATCCGGCAGCCCCCAGGGAAGGGACTGGAGTGGATTGGGTAT
        I  Y  Y  S  G  S  T  N  Y  N  P  S  L  K  S  R  V  T  I  S  V  D  T  S  K
151   ATCTATTACAGTGGGAGCACCAACTACAACCCCTCCCTCAAGAGTCGAGTCACCATATCAGTAGACACGTCCAAG
        N  Q  F  S  L  K  L  S  S  V  T  A  A  D  T  A  V  Y  Y  C  A  R  G  Y  Y
226   AACCAGTTCTCCCTGAAGCTGAGCTCTGTGACCGCTGCGGACACGGCCGTGTATTACTGTGCGAGAGGCTATTAC
        Y  G  A  G  S  Y  G  M  D  V  W  G  Q  G  T  T  V  T  V  S  S  A  S  T  K
301   TATGGTGCGGGGAGTTACGGTATGGACGTCTGGGGCCAAGGGACCACGGTCACCGTCTCCTCAGCCTCCACCAAG
        G  P  S  V  F  P  L  A  P
376   GGCCCATCGGTCTTCCCCCTGGCACCC
```

Figure 2T The cDNA (SEQ ID NO:57) and amino acid sequence (SEQ ID NO:58) of Ha5-7be31.1 VL. Double underline is a portion of the leader sequence. Underlined is a portion of the light chain constant region.

```
        L  W  V  S  G  S  S  G  D  I  V  M  T  Q  S  P  L  S  L  P  V  T  P  G  E ·
  1   TTCTCTGGGTCTCTGGATCCAGTGGGGATATTGTGATGACTCAGTCTCCACTCTCCCTGCCCGTCACCCCTGGAG
      ·  P  A  S  I  S  C  R  S  S  Q  S  L  L  H  S  T  G  F  N  Y  L  D  W  Y  L ·
 76   AGCCGGCCTCCATCTCCTGCAGGTCTAGTCAGAGCCTCCTGCATAGTACTGGATTCAACTATTTGGATTGGTACC
      ·  Q  K  P  G  Q  S  P  Q  L  L  I  Y  L  G  S  I  R  A  S  G  V  P  D  R  F ·
151   TGCAGAAGCCAGGGCAGTCTCCACAGCTCCTGATCTATTTGGGTTCTATTCGGGCCTCCGGGGTCCCTGACAGGT
      ·  S  G  S  G  S  G  T  D  F  T  L  K  I  S  R  V  E  T  E  D  V  G  V  Y  Y ·
226   TCAGTGGCAGTGGTTCAGGCACAGATTTTACACTGAAAATCAGCAGAGTGGAGACTGAGGATGTTGGGGTTTATT
      ·  C  M  Q  T  L  Q  T  P  I  T  F  G  Q  G  T  R  L  E  I  K  R  T  V  A  A ·
301   ACTGCATGCAAACTCTACAAACTCCCATCACCTTCGGCCAAGGGACACGACTGGAGATTAAACGAACTGTGGCTG
      ·  P  S  V  F  I  F  P  P  S  D  E  Q  L  K  S  G  T  A  S  V  V  C  L  L  N ·
376   CACCATCTGTCTTCATCTTCCCGCCATCTGATGAGCAGTTGAAATCTGGAACTGCCTCTGTTGTGTGCCTGCTGA
      ·  N  F  Y  P  R  E  A  K  V  Q  W  K  V  D  N  A  L  Q  S  G  N  S  Q  E  S ·
451   ATAACTTCTATCCCAGAGAGGCCAAAGTACAGTGGAAGGTGGATAACGCCCTCCAATCGGGTAACTCCCAGGAGA
      ·  V  T  E  Q  D  S  K  D  S  T  Y  S  L  S  S  T  L  T  L  S  K  A  D  Y  E ·
526   GTGTCACAGAGCAGGACAGCAAGGACAGCACCTACAGCCTCAGCAGCACCCTGACGCTGAGCAAAGCAGACTACG
      ·  K  H  K  V  Y  A  C  E  V  T  H  Q  G  L  S  S  P  V  T  K  S  F  N  R  G ·
601   AGAAACACAAAGTCTACGCCTGCGAAGTCACCCATCAGGGCCTGAGCTCGCCCGTCACAAAGAGCTTCAACAGGG
      ·  G
676   GA
```

Figure 2U The cDNA (SEQ ID NO:59) and amino acid sequence (SEQ ID NO:60) of Ha5-7acd10.1 VH. Underlined is a portion of the heavy chain constant region.

```
        Q  V  Q  L  V  E  S  G  G  G  V  V  Q  P  G  R  S  L  R  L  S  C  A  A  S
  1   CAGGTGCAGCTGGTGGAGTCTGGGGGAGGCGTGGTCCAGCCTGGGAGGTCCCTGAGACTCTCCTGTGCAGCGTCT
        G  F  T  F  S  S  Y  G  M  H  W  V  R  Q  A  P  G  K  G  L  E  W  V  A  V
 76   GGATTCACCTTCAGTAGCTATGGCATGCACTGGGTCCGCCAGGCTCCAGGCAAGGGGCTGGAGTGGGTGGCAGTT
        I  W  Y  D  G  S  N  K  Y  Y  A  D  S  V  K  G  R  F  T  I  S  R  D  N  S
151   ATATGGTATGATGGAAGTAATAAATACTATGCAGACTCCGTGAAGGGCCGATTCACCATCTCCAGAGACAATTCC
        K  N  T  L  Y  L  Q  M  N  S  L  R  A  E  D  T  A  V  Y  Y  C  A  R  D  R
226   AAGAACACGCTGTATCTGCAAATGAACAGCCTGAGAGCCGAGGACACGGCTGTGTATTACTGTGCGAGAGATCGG
        Y  S  G  Y  D  Y  Y  Y  Y  Y  G  M  D  V  W  G  Q  G  T  T  V  T  V  S  S
301   TATAGTGGCTACGATTACTACTACTACTACGGTATGGACGTCTGGGGCCAAGGGACCACGGTCACCGTCTCCTCA
        A  S  T  K  G  P  S  V  F  P  L  A  P  S  S
376   GCCTCCACCAAGGGCCCATCGGTCTTCCCCCTGGCACCCTCCTCC
```

Figure 2V  The cDNA (SEQ ID NO:61) and amino acid sequence (SEQ ID NO:62) of Ha5-7acd10.1 VL.

Double underline is a portion of the leader sequence. Underlined is a portion of the light chain constant region.

```
         L  C  F  P  G  A  R  C  D  I  Q  M  T  Q  S  P  S  S  L  S  A  S  V  G  D  ·
    1  TGCTCTGTTTCCCAGGTGCCAGATGTGACATCCAGATGACCCAGTCTCCATCCTCACTGTCTGCATCTGTCGGAG
         ·  R  V  T  I  T  C  R  A  S  Q  G  I  Y  N  Y  L  A  W  F  Q  Q  K  P  G  K  ·
   76  ACAGAGTCACCATCACTTGTCGGGCGAGTCAGGGCATTTATAATTATTTGGCCTGGTTTCAGCAGAAACCAGGGA
         ·  A  P  K  S  L  I  Y  A  A  S  S  L  H  S  G  V  P  S  K  F  S  G  G  G  S  ·
  151  AAGCCCCTAAGTCCCTGATCTATGCTGCATCCAGTTTGCACAGTGGGGTCCCATCAAAGTTCAGCGGCGGTGGTT
         ·  G  T  D  F  T  L  T  I  S  S  L  Q  P  E  D  F  A  T  Y  Y  C  Q  Q  Y  T  ·
  226  CTGGGACAGATTTCACTCTCACCATCAGCAGCCTGCAGCCTGAAGATTTTGCAACTTATTACTGCCAACAGTATA
         ·  I  Y  P  F  T  F  G  P  G  T  K  V  D  I  K  R  T  V  A  A  P  S  V  F  I  ·
  301  CTATTTACCCATTCACTTTCGGCCCTGGGACCAAAGTGGATATCAAACGAACTGTGGCTGCACCATCTGTCTTCA
         ·  F  P  P  S  D  E  Q  L  K  S  G  T  A  S  V  V  C  L  L  N  N  F  Y  P  R  ·
  376  TCTTCCCGCCATCTGATGAGCAGTTGAAATCTGGAACTGCCTCTGTTGTGTGCCTGCTGAATAACTTCTATCCCA
         ·  E  A  K  V  Q  W  K  V  D  N  A  L  Q  S  G  N  S  Q  E  S  V  T  E  Q  D  ·
  451  GAGAGGCCAAAGTACAGTGGAAGGTGGATAACGCCCTCCAATCGGGTAACTCCCAGGAGAGTGTCACAGAGCAGG
         ·  S  K  D  S  T  Y  S  L  S  S  T  L  T  L  S  K  A  D  Y  E  K  H  K  V  Y  ·
  526  ACAGCAAGGACAGCACCTACAGCCTCAGCAGCACCCTGACGCTGAGCAAAGCAGACTACGAGAAACACAAAGTCT
         ·  A  C  E  V  T  H  Q  G  L  S  S  P  V  T  K  S  F  N  R
  601  ACGCCTGCGAAGTCACCCATCAGGGCCTGAGCTCGCCCGTCACAAAGAGCTTCAACAGGG
```

Figure 2W  The cDNA (SEQ ID NO:63) and amino acid sequence (SEQ ID NO:64) of Ha5-7acd13.1 VH.

Underlined is a portion of the heavy chain constant region.

```
         Q  V  Q  L  Q  E  S  G  P  G  L  V  K  P  S  E  T  L  S  L  T  C  T  V  S
    1  CAGGTGCAGCTGCAGGAGTCTGGCCCAGGACTGGTGAAGCCTTCGGAGACCCTGTCCCTCACCTGCACTGTCTCT
         G  G  S  I  S  S  Y  Y  W  S  W  I  R  Q  P  P  G  K  G  L  E  W  I  G  Y
   76  GGTGGCTCCATCAGTAGTTACTACTGGAGCTGGATCCGGCAGCCCCCAGGGAAGGGACTGGAGTGGATTGGGTAT
         I  Y  Y  S  G  S  T  N  Y  N  P  S  L  K  S  R  V  T  I  S  V  D  T  S  K
  151  ATCTATTACAGTGGGAGCACCAACTACAACCCCTCCCTCAAGAGTCGAGTCACCATATCAGTAGACACGTCCAAG
         N  Q  F  S  L  K  L  S  S  V  T  A  A  D  T  A  V  Y  Y  C  A  N  T  Y  Y
  226  AACCAGTTCTCCCTGAAGCTGAGCTCTGTGACCGCTGCGGACACGGCCGTGTATTACTGTGCGAACACGTATTAC
         Y  G  S  G  Y  G  M  D  V  W  G  Q  G  T  T  V  T  V  S  S  A  S  T  K  G
  301  TATGGTTCGGGGTACGGTATGGACGTCTGGGGCCAAGGGACCACGGTCACCGTCTCCTCAGCCTCCACCAAGGGC
         P  S  V  F  P  L  A  P
  376  CCATCGGTCTTCCCCCTGGCACCCT
```

Figure 2X  The cDNA (SEQ ID NO:65) and amino acid sequence (SEQ ID NO:66) of Ha5-7acd13.1 VL.

Double underline is a portion of the leader sequence. Underlined is a portion of the light chain constant region.

```
         L  W  V  S  G  S  S  G  D  I  V  M  T  Q  S  P  L  S  L  P  V  T  P  G  E  ·
    1  TGCTCTGGGTCTCTGGATCCAGTGGGGATATTGTGATGACTCAGTCTCCACTCTCCCTGCCCGTCACCCCTGGAG
         ·  P  A  S  I  S  C  R  S  S  Q  S  L  L  H  S  T  G  H  N  Y  L  D  W  Y  L  ·
   76  AGCCGGCCTCCATCTCCTGCAGGTCTAGTCAGAGCCTCCTGCATAGTACTGGACACAACTATTTGGATTGGTACC
         ·  Q  K  P  G  Q  S  P  Q  L  L  I  Y  L  G  S  I  R  A  S  G  V  P  D  R  F  ·
  151  TGCAGAAGCCAGGGCAGTCTCCACAGCTCCTGATCTATTTGGGTTCTATTCGGGCCTCCGGGGTCCCTGACAGGT
         ·  S  G  S  G  T  D  F  T  L  K  I  S  R  V  E  A  E  D  V  G  V  Y  Y  ·
  226  TCAGTGGCAGTGGATCAGGCACAGATTTTACACTGAAAATCAGCAGAGTGGAGGCTGAGGATGTTGGGGTTTATT
         ·  C  M  Q  A  L  Q  T  I  T  F  G  Q  G  T  R  L  E  I  K  R  T  V  A  A  P  ·
  301  ACTGCATGCAAGCTCTACAAACTATCACCTTCGGCCAAGGGACACGACTGGAGATTAAACGAACTGTGGCTGCAC
         ·  S  V  F  I  F  P  P  S  D  E  Q  L  K  S  G  T  A  S  V  V  C  L  L  N  N  ·
  376  CATCTGTCTTCATCTTCCCGCCATCTGATGAGCAGTTGAAATCTGGAACTGCCTCTGTTGTGTGCCTGCTGAATA
         ·  F  Y  P  R  E  A  K  V  Q  W  K  V  D  N  A  L  Q  S  G  N  S  Q  E  S  V  ·
  451  ACTTCTATCCCAGAGAGGCCAAAGTACAGTGGAAGGTGGATAACGCCCTCCAATCGGGTAACTCCCAGGAGAGTG
         ·  T  E  Q  D  S  K  D  S  T  Y  S  L  S  S  T  L  T  L  S  K  A  D  Y  E  K  ·
  526  TCACAGAGCAGGACAGCAAGGACAGCACCTACAGCCTCAGCAGCACCCTGACGCTGAGCAAAGCAGACTACGAGA
         ·  H  K  V  Y  A  C  E  V  T  H  Q  G  L  S  S  P  V  T
  601  AACACAAAGTCTACGCCTGCGAAGTCACCCATCAGGGCCTGAGCTCGCCCGTCACAAA
```

Figure 2Y The cDNA (SEQ ID NO:67) and amino acid sequence (SEQ ID NO:68) of Ha5-7acd19.1 VH. Underlined is a portion of the heavy chain constant region.

```
       Q  V  Q  L  Q  E  S  G  P  G  L  V  K  P  S  E  T  L  S  L  T  C  T  V  S
  1  CAGGTGCAGCTGCAGGAGTCTGGCCCCGGACTGGTGAAGCCTTCGGAGACCCTGTCCCTCACCTGCACTGTCTCT
       G  G  S  I  S  S  Y  Y  W  S  W  I  R  Q  P  P  G  K  G  L  E  W  I  G  F
 76  GGTGGCTCCATCAGTAGTTACTACTGGAGCTGGATCCGGCAGCCCCCAGGGAAGGGACTGGAGTGGATTGGATTT
       I  Y  Y  T  G  S  T  N  Y  N  P  S  L  K  S  R  V  T  I  S  V  D  T  S  K
151  ATCTATTACACTGGGAGCACCAACTACAACCCCTCCCTCAAGAGTCGAGTCACCATATCAGTAGACACGTCCAAG
       N  Q  F  S  L  K  L  S  S  V  T  A  A  D  T  A  V  Y  Y  C  A  N  T  Y  Y
226  AACCAGTTCTCCCTGAAGCTGAGCTCTGTGACCGCTGCGGACACGGCCGTGTATTACTGTGCGAACACGTATTAC
       Y  G  S  G  Y  G  M  D  V  W  G  Q  G  T  T  V  T  V  S  S  A  S  T  K  G
301  TATGGTTCGGGGTACGGTATGGACGTCTGGGGCCAAGGGACCACGGTCACCGTCTCCTCAGCCTCCACCAAGGGC
       P  S  V  F  P  L  A  P  S  S
376  CCATCGGTCTTCCCCCTGGCACCCTCCTCCAA
```

Figure 2Z The cDNA (SEQ ID NO:69) and amino acid sequence (SEQ ID NO:70) of Ha5-7acd19.1 VL. Double underline is a portion of the leader sequence. Underlined is a portion of the light chain constant region.

```
         L  L  G  L  L  M  L  W  V  S  G  S  S  G  D  I  V  M  T  Q  S  P  L  S  L  ·
  1  AGCTCCTGGGGCTGCTAATGCTCTGGGTCTCTGGATCCAGCGGGGATATTGTGATGACTCAGTCTCCACTCTCCC
       ·  P  V  T  P  G  E  P  A  S  I  S  C  R  S  S  Q  S  L  L  H  S  N  G  F  N  ·
 76  TGCCCGTCACCCCTGGAGAGCCGGCCTCCATCTCCTGCAGGTCTAGTCAGAGCCTCCTGCATAGTAATGGATTCA
       ·  Y  L  D  W  Y  L  Q  K  P  G  Q  S  P  Q  L  L  I  Y  L  G  S  R  R  A  S  ·
151  ACTATTTGGATTGGTACCTGCAGAAGCCAGGGCAGTCTCCACAGCTCCTGATCTATTTGGGTTCTAGACGGGCCT
       ·  G  V  P  D  R  F  S  G  S  G  S  G  T  D  F  T  L  K  I  S  R  V  E  A  E  ·
226  CCGGGGTCCCTGACAGGTTCAGTGGCAGTGGATCAGGCACAGATTTTACACTGAAAATCAGCAGAGTGGAGGCTG
       ·  D  V  G  V  Y  Y  C  M  Q  A  L  E  T  I  T  F  G  Q  G  T  R  L  E  I  K  ·
301  AGGATGTTGGGGTTTATTACTGCATGCAAGCTCTAGAAACTATCACCTTCGGCCAAGGGACACGACTGGAGATTA
       ·  R  T  V  A  A  P  S  V  F  I  F  P  P  S  D  E  Q  L  K  S  G  T  A  S  V  ·
376  AACGAACTGTGGCTGCACCATCTGTCTTCATCTTCCCGCCATCTGATGAGCAGTTGAAATCTGGAACTGCCTCTG
       ·  V  C  L  L  N  N  F  Y  P  R  E  A  K  V  Q  W  K  V  D  N  A  L  Q  S  G  ·
451  TTGTGTGCCTGCTGAATAACTTCTATCCCAGAGAGGCCAAAGTACAGTGGAAGGTGGATAACGCCCTCCAATCGG
       ·  N  S  Q  E  S  V  T  E  Q  D  S  K  D  S  T  Y  S  L  S  S  T  L  T  L  S  ·
526  GTAACTCCCAGGAGAGTGTCACAGAGCAGGACAGCAAGGACAGCACCTACAGCCTCAGCAGCACCCTGACGCTGA
       ·  K  A  D  Y  E  K  H  K  V  Y  A  C  E  V  T  H  Q  G  L  S  S  P  V  T  K  ·
601  GCAAAGCAGACTACGAGAAACACAAAGTCTACGCCTGCGAAGTCACCCATCAGGGCCTGAGCTCGCCCGTCACAA
       ·  S  F  N  R
676  AGAGCTTCAACAGGG
```

Figure 2AA The cDNA (SEQ ID NO:71) and amino acid sequence (SEQ ID NO:72) of Ha5-7be37.1 VH.

```
       Q  V  Q  L  Q  E  S  G  P  G  L  V  K  P  S  E  T  L  S  L  T  C  T  V  S
  1  CAGGTGCAGCTGCAGGAGTCTGGCCCAGGACTGGTGAAGCCTTCGGAGACCCTGTCCCTCACCTGCACTGTCTCT
       G  G  S  I  S  S  Y  Y  W  S  W  I  R  Q  P  P  G  K  G  L  E  W  I  G  Y
 76  GGTGGCTCCATCAGTAGTTACTACTGGAGCTGGATCCGGCAGCCCCCAGGGAAGGGACTGGAGTGGATTGGGTAT
       I  Y  Y  S  G  S  T  N  Y  N  P  S  L  K  S  R  V  T  I  S  V  D  T  S  K
151  ATCTATTACAGTGGGAGCACCAACTACAACCCCTCCCTCAAGAGTCGAGTCACCATATCAGTAGACACGTCCAAG
       N  Q  F  S  L  K  L  S  S  V  T  A  A  D  T  A  V  Y  Y  C  A  R  G  Y  Y
226  AACCAGTTCTCCCTGAAGCTGAGCTCTGTGACCGCTGCGGACACGGCCGTGTATTACTGTGCGAGAGGCTATTAC
       Y  G  S  G  S  Y  G  M  D  V  W  G  Q  G  T  T  V  T  V  S  S  A  S  T  K
301  TATGGTTCGGGGAGTTACGGTATGGACGTCTGGGGCCAAGGGACCACGGTCACCGTCTCCTCAGCCTCCACCAAG
       G  P  S  V  F  P  L  A  P  S  S
376  GGCCCATCGGTCTTCCCCCTGGCACCCTCCTCCAA
```

Figure 2AB  The cDNA (SEQ ID NO:73) and amino acid sequence (SEQ ID NO:74) of Ha5-7be37.1 VL.
Double underline is a portion of the leader sequence. Underlined is a portion of the light chain constant region.

```
        G  S  S  G  D  I  V  M  T  Q  S  P  L  S  L  P  V  T  P  G  E  P  A  S  I
  1   GGATCCAGTGGGGATATTGTGATGACTCAGTCTCCACTCTCCCTGCCCGTCACCCCTGGAGAGCCGGCCTCCATC
        S  C  R  S  S  Q  S  L  L  H  S  T  G  Y  N  Y  L  D  W  Y  L  Q  K  P  G
 76   TCCTGCAGGTCTAGTCAGAGCCTCCTGCATAGTACTGGATACAACTATTTGGATTGGTACCTGCAGAAGCCAGGG
        Q  S  P  Q  L  L  I  Y  L  G  S  N  R  A  S  G  V  P  D  R  F  S  G  S  G
151   CAGTCTCCACAGCTCCTGATCTATTTGGGTTCTAATCGGGCCTCCGGGGTCCCTGACAGGTTCAGTGGCAGTGGA
        S  G  T  D  F  T  L  K  I  S  R  V  E  A  E  D  V  G  V  C  Y  C  M  Q  A
226   TCAGGCACAGATTTTACACTGAAGATCAGCAGAGTGGAGGCTGAGGATGTTGGGGTTTGTTACTGCATGCAAGCT
        L  Q  T  P  I  T  F  G  Q  G  T  R  L  E  I  K  R  T  V  A  A  P  S  V  F
301   CTACAAACTCCCATCACCTTCGGCCAAGGGACACGACTGGAGATTAAACGAACTGTGGCTGCACCATCTGTCTTC
        I  F  P  P  S  D  E  Q  L  K  S  G  T  A  S  V  V  C  L  L  N  N  F  Y  P
376   ATCTTCCCGCCATCTGATGAGCAGTTGAAATCTGGAACTGCCTCTGTTGTGTGCCTGCTGAATAACTTCTATCCC
        R  E  A  K  V  Q  W  K  V  D  N  A  L  Q  S  G  N  S  Q  E  S  V  T  E  Q
451   AGAGAGGCCAAAGTACAGTGGAAGGTGGATAACGCCCTCCAATCGGGTAACTCCCAGGAGAGTGTCACAGAGCAG
        D  S  K  D  S  T  Y  S  L  S  S  T  L  T  L  S  K  A  D  Y  E  K  H  K  V
526   GACAGCAAGGACAGCACCTACAGCCTCAGCAGCACCCTGACGCTGAGCAAAGCAGACTACGAGAAACACAAAGTC
        Y  A  C  E  V  T  H  Q  G  L  S  S  P  V  T
601   TACGCCTGCGAAGTCACCCATCAGGGCCTGAGCTCGCCCGTCACAAA
```

Figure 2AC  The cDNA (SEQ ID NO:75) and amino acid sequence (SEQ ID NO:76) of Ha5-7acd16.1 VH.
Underlined is a portion of the heavy chain constant region.

```
        Q  V  Q  L  V  E  S  G  G  G  V  V  Q  P  G  R  S  L  R  L  S  C  A  A  S
  1   CAGGTGCAGCTGGTGGAGTCTGGGGGAGGCGTGGTCCAGCCTGGGAGGTCCCTGAGACTCTCCTGTGCAGCGTCT
        G  F  T  F  S  S  H  G  M  H  W  V  R  Q  A  P  G  K  G  L  E  W  V  A  V
 76   GGATTCACCTTCAGTAGCCATGGCATGCACTGGGTCCGCCAGGCTCCAGGCAAGGGGCTGGAGTGGGTGGCAGTT
        I  W  Y  D  G  S  N  K  Y  Y  A  D  S  V  K  G  R  F  T  I  S  R  D  N  S
151   ATATGGTATGATGGAAGTAATAAATACTATGCAGACTCCGTGAAGGGCCGATTCACCATCTCCAGAGACAATTCC
        K  N  T  L  Y  L  Q  M  N  S  L  R  A  E  D  T  A  V  Y  Y  C  A  R  D  A
226   AAGAACACGCTGTATCTGCAAATGAACAGCCTGAGAGCCGAGGACACGGCTGTGTATTACTGTGCGAGAGATGCA
        Y  S  G  Y  D  Y  Y  Y  Y  Y  G  M  D  V  W  G  Q  G  T  T  V  T  V  S  S
301   TATAGTGGCTACGATTACTACTACTACTACGGTATGGACGTCTGGGGCCAAGGGACCACGGTCACCGTCTCCTCA
        A  S  T  K  G  P  S  V  F  P  L
376   GCCTCCACCAAGGGCCCATCGGTCTTCCCCCTGGC
```

Figure 2AD  The cDNA (SEQ ID NO:77) and amino acid sequence (SEQ ID NO:78) of Ha5-7acd16.1 VL.
Underlined is a portion of the light chain constant region. Double underline is a portion of the leader sequence.

```
        G  L  L  L  L  C  F  P  G  A  R  C  D  I  Q  M  T  Q  S  P  S  S  L  S  A ·
  1   GGGGCTCCTGCTGCTCTGTTTCCCAGGTGCCAGATGTGACATCCAGATGACCCAGTCTCCATCCTCACTGTCTGC
      · S  V  G  D  R  V  T  I  T  C  R  A  S  Q  G  I  Y  T  Y  L  A  W  F  Q  Q ·
 76   ATCTGTAGGAGACAGAGTCACCATCACTTGTCGGGCGAGTCAGGGCATTTACACTTATTTAGCCTGGTTTCAGCA
      · K  P  G  K  A  P  K  S  L  I  Y  G  A  S  S  L  Q  S  G  V  P  S  K  F  S ·
151   GAAACCAGGGAAAGCCCCTAAGTCCCTGATCTATGGTGCATCCAGTCTGCAAAGTGGGGTCCCATCAAAGTTCAG
      · G  S  G  S  G  T  D  F  T  L  T  I  T  S  L  Q  P  E  D  F  A  T  Y  Y  C ·
226   CGGCAGTGGATCTGGGACAGATTTCACTCTCACCATCACCAGCCTGCAGCCTGAAGATTTTGCAACTTATTACTG
      · Q  Q  Y  T  I  Y  P  F  S  F  G  P  G  T  K  V  D  I  K  R  T  V  A  A  P ·
301   CCAACAGTATACTATTTACCCATTCAGTTTCGGCCCTGGGACCAAAGTGGATATCAAACGAACTGTGGCTGCACC
      · S  V  F  I  F  P  P  S  D  E  Q  L  K  S  G  T  A  S  V  V  C  L  L  N  N ·
376   ATCTGTCTTCATCTTCCCGCCATCTGATGAGCAGTTGAAATCTGGAACTGCCTCTGTTGTGTGCCTGCTGAATAA
      · F  Y  P  R  E  A  K  V  Q  W  K  V  D  N  A  L  Q  S  G  N  S  Q  E  S  V ·
451   CTTCTATCCCAGAGAGGCCAAAGTACAGTGGAAGGTGGATAACGCCCTCCAATCGGGTAACTCCCAGGAGAGTGT
      · T  E  Q  D  S  K  D  S  T  Y  S  L  S  S  T  L  T  L  S  K  A  D  Y  E  K ·
526   CACAGAGCAGGACAGCAAGGACAGCACCTACAGCCTCAGCAGCACCCTGACGCTGAGCAAAGCAGACTACGAGAA
      · H  K  V  Y  A  C  E  V  T  H  Q  G  L  S  S  P  V  T  K  S  F  N  R
601   ACACAAAGTCTACGCCTGCGAAGTCACCCATCAGGGCCTGAGCTCGCCCGTCACAAAGAGCTTCAACAGGG
```

Figure 2AE The cDNA (SEQ ID NO:79) and amino acid sequence (SEQ ID NO:80) of Ha5-7acd7.1.1 VH.
Underlined is a portion of the heavy chain constant region.

```
        Q   V   Q   L   Q   E   S   G   P   G   L   V   K   P   S   E   T   L   S   L   T   C   T   V   S
  1  CAGGTGCAGCTGCAGGAGTCTGGCCCAGGACTGGTGAAGCCTTCGGAGACCCTGTCCCTCACCTGCACTGTCTCT
        G   G   S   V   S   S   G   G   Y   Y   W   S   W   I   R   Q   P   P   G   K   G   L   E   W   I
 76  GGTGGCTCCGTCAGCAGTGGTGGTTACTACTGGAGCTGGATCCGGCAGCCCCCAGGGAAGGGACTGGAGTGGATT
        G   Y   I   Y   Y   S   G   G   T   N   Y   N   P   S   L   K   S   R   V   T   I   S   V   D   T
151  GGGTATATCTATTACAGTGGGGGCACCAACTACAACCCCTCCCTCAAGAGTCGAGTCACCATATCAGTAGACACG
        S   K   N   Q   F   S   L   K   L   T   S   V   T   A   A   D   T   A   V   Y   Y   C   A   R   E
226  TCCAAGAACCAGTTCTCCCTGAAGCTGACCTCTGTGACCGCTGCGGACACGGCCGTGTATTACTGTGCGAGAGAG
        S   G   Y   C   T   N   V   A   C   F   P   D   A   F   D   I   W   G   Q   G   T   M   V   T   V
301  TCGGGATATTGTACTAATGTTGCATGCTTCCCTGATGCTTTTGATATCTGGGGCCAAGGGACAATGGTCACCGTG
        S   S   A   S   T   K   G   P   S   V   F   P   L   A   P   S
376  TCTTCAGCCTCCACCAAGGGCCCATCGGTCTTCCCCCTGGCACCCTCCT
```

Figure 2AF The cDNA (SEQ ID NO:81) and amino acid sequence (SEQ ID NO:82) of Ha5-7acd7.1.1 VL.
Double-underlined is the leader sequence, and underlined is a portion of the light chain constant region.

```
        L   L   G   L   L   M   L   W   V   S   G   S   S   G   D   V   V   M   T   Q   S   P   F   S   L
  1  CTCCTGGGGCTGCTAATGCTCTGGGTCTCTGGATCCAGTGGGGATGTTGTGATGACTCAGTCTCCATTCTCCCTG
        P   V   T   P   G   E   P   A   S   I   S   C   R   S   S   Q   S   L   L   H   S   N   G   F   N
 76  CCCGTCACCCCTGGAGAGCCGGCCTCCATCTCCTGCAGGTCTAGTCAGAGCCTCCTGCATAGTAATGGATTCAAC
        F   L   D   W   Y   L   Q   K   P   G   Q   S   P   Q   L   L   I   Y   L   G   S   I   R   A   S
151  TTTTTGGATTGGTACCTGCAGAAGCCAGGGCAGTCTCCACAGCTCCTGATCTATTTGGGTTCTATTCGGGCCTCC
        G   V   P   D   R   F   S   G   S   G   S   G   T   D   F   T   L   K   I   S   R   V   E   A   E
226  GGGGTCCCTGACAGGTTCAGTGGCAGTGGATCAGGCACAGATTTTACACTGAAAATCAGCAGAGTGGAGGCTGAG
        D   V   G   V   Y   Y   C   M   Q   A   L   Q   T   P   L   T   F   G   G   G   T   R   V   E   I
301  GATGTTGGAGTTTATTACTGCATGCAAGCTCTACAAACTCCACTCACTTTCGGCGGCGGGACCAGGGTGGAGATC
        K   R   T   V   A   A   P   S   V   F   I   F   P   P   S   D   E   Q   L   K   S   G   T   A   S
376  AAACGAACTGTGGCTGCACCATCTGTCTTCATCTTCCCGCCATCTGATGAGCAGTTGAAATCTGGAACTGCCTCT
        V   V   C   L   L   N   N   F   Y   P   R   E   A   K   V   Q   W   K   V   D   N   A   L   Q   S
451  GTTGTGTGCCTGCTGAATAACTTCTATCCCAGAGAGGCCAAAGTACAGTGGAAGGTGGATAACGCCCTCCAATCG
        G   N   S   Q   E   S   V   T   E   Q   D   S   K   D   S   T   Y   S   L   S   S   T   L   T   L
526  GGTAACTCCCAGGAGAGTGTCACAGAGCAGGACAGCAAGGACAGCACCTACAGCCTCAGCAGCACCCTGACGCTG
        S   K   A   D   Y   E   K   H   K   V   Y   A   C   E   V   T   H   Q   G   L   S   S   P   V   T
601  AGCAAAGCAGACTACGAGAAACACAAAGTCTACGCCTGCGAAGTCACCCATCAGGGCCTGAGCTCGCCCGTCACA
676  AA
```

Figure 2AG The cDNA (SEQ ID NO:83) and amino acid sequence (SEQ ID NO:84) of Ha5-7be20.1 VH.
Double-underlined is the leader sequence, and underlined is a portion of the heavy chain constant region.

```
        Q   V   Q   L   Q   E   S   G   P   G   L   V   K   P   S   E   T   L   S   L   T   C   T   V   S
  1  CAGGTGCAGCTGCAGGAGTCTGGCCCAGGACTGGTGAAGCCTTCGGAGACCCTGTCCCTCACCTGCACTGTCTCT
        G   G   S   I   S   S   Y   Y   W   S   W   I   R   Q   P   P   G   K   G   L   E   W   I   G   Y
 76  GGTGGCTCCATCAGTAGTTACTACTGGAGCTGGATCCGGCAGCCCCCAGGGAAGGGACTGGAGTGGATTGGGTAT
        I   Y   Y   S   G   S   T   N   Y   N   P   S   L   K   S   R   V   T   I   S   V   D   T   S   K
151  ATCTATTACAGTGGGAGCACCAACTACAATCCCTCCCTCAAGAGTCGAGTCACCATATCAGTAGACACGTCCAAG
        N   Q   F   S   L   K   L   S   S   V   T   A   A   D   T   A   V   Y   Y   C   A   R   G   Y   Y
226  AACCAGTTCTCCCTGAAGCTGAGCTCTGTGACCGCTGCGGACACGGCCGTGTATTATTGTGCGAGAGGCTATTAC
        Y   G   S   G   S   Y   G   L   D   V   W   G   Q   G   T   T   V   T   V   S   S   A   S   T   K
301  TATGGTTCGGGGAGTTACGGCTTGGACGTCTGGGGCCAAGGGACCACGGTCACCGTCTCCTCAGCCTCCACCAAG
        G   P   S   V   F   P   L   A   P   S   S
376  GGCCCATCGGTCTTCCCCCTGGCACCCTCCTCCA
```

Figure 2AH The cDNA (SEQ ID NO:85) and amino acid sequence (SEQ ID NO:86) of Ha5-7be20.1 VL. Double-underlined is the leader sequence, and underlined is a portion of the light chain constant region.

```
        L  L  G  L  L  M  L  W  V  S  G  S  S  G  D  I  V  M  T  Q  S  P  L  S  L ·
  1 AGCTCCTGGGGCTGCTAATGCTCTGGGTCTCTGGATCCAGTGGGGATATTGTGATGACTCAGTCTCCACTCTCCC
      · P  V  T  P  G  E  P  A  S  I  S  C  R  S  S  Q  S  L  L  H  S  T  G  Y  N ·
 76 TGCCCGTCACCCCTGGAGAGCCGGCCTCCATCTCCTGCAGGTCTAGTCAGAGCCTCCTGCATAGTACTGGATACA
      · Y  L  D  W  Y  L  Q  K  P  G  Q  S  P  Q  L  L  I  Y  L  G  S  I  R  A  S ·
151 ACTATTTGGATTGGTACCTGCAGAAGCCAGGGCAGTCTCCACAACTCCTGATCTATTTGGGTTCTATTCGGGCCT
      · G  V  P  D  R  F  S  G  S  G  S  G  T  D  F  T  L  K  I  S  R  V  E  A  E ·
226 CCGGGGTCCCTGACAGGTTCAGTGGCAGTGGATCAGGCACAGATTTTACACTGAAAATCAGCAGAGTGGAGGCTG
      · D  V  G  V  Y  Y  C  M  Q  A  L  Q  T  P  I  T  F  G  Q  G  T  R  L  E  I ·
301 AGGATGTTGGGGTTTATTACTGCATGCAAGCTCTACAGACTCCCATCACCTTCGGCCAAGGGACACGACTGGAGA
      · K  R  T  V  A  A  P  S  V  F  I  F  P  P  S  D  E  Q  L  K  S  G  T  A  S ·
376 TTAAACGAACTGTGGCTGCACCATCTGTCTTCATCTTCCCGCCATCTGATGAGCAGTTGAAATCTGGAACTGCCT
      · V  V  C  L  L  N  N  F  Y  P  R  E  A  K  V  Q  W  K  V  D  N  A  L  Q  S ·
451 CTGTTGTGTGCCTGCTGAATAACTTCTATCCCAGAGAGGCAAAGTACAGTGGAAGGTGGATAACGCCCTCCAAT
      · G  N  S  Q  E  S  V  T  E  Q  D  S  K  D  S  T  Y  S  L  S  S  T  L  T  L ·
526 CGGGTAACTCCCAGGAGAGTGTCACAGAGCAGGACAGCAAGGACAGCACCTACAGCCTCAGCAGCACCCTGACGC
      · S  K  A  D  Y  E  K  H  K  V  Y  A  C  E  V  T  H  Q  G  L  S  S  P  V  T ·
601 TGAGCAAAGCAGACTACGAGAAACACAAAGTCTACGCCTGCGAAGTCACCCATCAGGGCCTGAGCTCGCCCGTCA
      · K  S  F  N  R
676 CAAAGAGCTTCAACAGGG
```

Figure 2AI The cDNA (SEQ ID NO:87) and amino acid sequence (SEQ ID NO:88) of Ha5-7acd5.1.1 VH. Underlined is a portion of the heavy chain constant region.

```
        Q  V  Q  L  Q  E  S  G  P  G  L  V  K  P  S  E  T  L  S  L  T  C  T  V  S
  1 CAGGTGCAGCTGCAGGAGTCGGGCCCAGGACTGGTGAAGCCTTCGGAGACCCTGTCCCTCACCTGCACTGTCTCT
       G  G  S  I  S  S  Y  Y  W  S  W  I  R  Q  P  P  G  K  G  L  E  W  I  G  Y
 76 GGTGGCTCCATCAGTAGTTACTACTGGAGCTGGATCCGGCAGCCCCCAGGGAAGGGACTGGAGTGGATTGGGTAT
       I  Y  Y  S  G  S  T  N  Y  N  P  S  L  K  S  R  V  T  I  S  V  D  T  S  K
151 ATCTATTACAGTGGGAGCACCAACTACAACCCCTCCCTCAAGAGTCGAGTCACCATATCAGTAGACACGTCCAAG
       N  Q  F  S  L  K  L  S  S  V  T  A  A  D  T  A  V  Y  Y  C  A  N  T  Y  Y
226 AACCAGTTCTCCCTGAAGCTGAGCTCTGTGACCGCTGCGGACACGGCCGTGTATTACTGTGCGAACACGTATTAC
       Y  G  S  G  Y  G  M  D  V  W  G  Q  G  T  T  V  T  V  S  S  A  S
301 TATGGTTCGGGGTACGGTATGGACGTCTGGGGCCAAGGGACCACGGTCACCGTCTCCTCAGCCTCC
```

Figure 2AJ The cDNA (SEQ ID NO:89) and amino acid sequence (SEQ ID NO:90) of Ha5-7acd7.1.1 VL. Underlined is a portion of the light chain constant region. Double underline is a portion of the leader sequence.

```
        S  G  S  S  G  D  I  V  M  T  Q  S  P  L  S  L  P  V  T  P  G  E  P  A  S
  1 TCTGGATCCAGTGGGGATATTGTGATGACTCAGTCTCCACTCTCCCTGCCCGTCACCCCTGGAGAGCCGGCCTCC
       I  S  C  R  S  S  Q  S  L  L  H  S  T  G  H  N  Y  L  D  W  Y  L  Q  K  P
 76 ATCTCCTGCAGGTCTAGTCAGAGCCTCCTGCATAGTACTGGACACAACTATTTGGATTGGTACCTGCAGAAGCCA
       G  Q  S  P  Q  L  L  I  Y  L  G  S  I  R  A  S  G  V  P  D  R  F  S  G  S
151 GGGCAGTCTCCACAGCTCCTGATCTATTTGGGTTCTATTCGGGCCTCCGGGGTCCCTGACAGGTTCAGTGGCAGT
       G  S  G  T  D  F  T  L  K  I  S  R  V  E  A  E  D  V  G  V  Y  Y  C  M  Q
226 CGATCAGGCACAGATTTTACACTGAAAATCAGCAGAGTGGAGGCTGAGGATGTTGGGGTTTATTACTGCATGCAA
       A  L  Q  T  I  T  F  G  Q  G  T  R  L  E  I  K  R  T  V  A  A  P  S  V  F
301 GCTCTACAAACTATCACCTTCGGCCAAGGGACACGACTGGAGATTAAACGAACTGTGGCTGCACCATCTGTCTTC
       I  F  P  P  S  D  E  Q  L  K  S  G  T  A  S  V  V  C  L  L  N  N  F  Y  P
376 ATCTTCCCGCCATCTGATGAGCAGTTGAAATCTGGAACTGCCTCTGTTGTGTGCCTGCTGAATAACTTCTATCCC
       R  E  A  K  V  Q  W  K  V  D  N  A  L  Q  S  G  N  S  Q  E  S  V  T  E  Q
451 AGAGAGGCCAAAGTACAGTGGAAGGTGGATAACGCCCTCCAATCGGGTAACTCCCAGGAGAGTGTCACAGAGCAG
       D  S  K  D  S  T  Y  S  L  S  S  T  L  T  L  S  K  A  D  Y  E  K  H  K  V
526 GACAGCAAGGACAGCACCTACAGCCTCAGCAGCACCCTGACGCTGAGCAAAGCAGACTACGAGAAACACAAAGTC
       Y  A  C  E  V  T  H  Q  G  L  S  S  P  V  T  K  S  F  N  R
601 TACGCCTGCGAAGTCACCCATCAGGGCCTGAGCTCGCCCGTCACAAAGAGCTTCAACAGGG
```

Figure 2AK The cDNA (SEQ ID NO:91) and amino acid sequence (SEQ ID NO:92) of Ha5-7be34.1 VH. Underlined is a portion of the heavy chain constant region.

```
        Q  V  Q  L  Q  E  S  G  P  G  L  V  K  P  S  E  T  L  S  L  T  C  T  V  S
  1   CAGGTGCAGCTGCAGGAGTCTGGGCCCAGGACTGGTGAAGCCTTCGGAGACCCTGTCCCTCACCTGCACTGTCTCT
        G  G  S  I  S  S  Y  Y  W  S  W  I  R  Q  P  P  G  K  G  L  E  W  I  G  Y
 76   GGTGGCTCCATCAGTAGTTACTACTGGAGCTGGATCCGGCAGCCCCCAGGGAAGGGACTGGAGTGGATTGGGTAT
        I  Y  Y  S  G  S  T  N  Y  K  P  S  L  K  S  R  V  T  I  S  V  D  T  S  K
151   ATCTATTACAGTGGCAGCACCAACTACAAACCCTCCCTCAAGAGTCGAGTCACCATATCAGTAGACACGTCCAAG
        N  Q  F  S  L  K  L  S  S  V  T  A  A  D  T  A  V  Y  Y  C  A  R  G  Y  Y
226   AACCAGTTCTCCCTGAAGCTGAGCTCTGTGACCGCTGCGGACACGGCCGTGTATTACTGTGCGAGAGGCTATTAC
        Y  G  S  G  S  Y  G  M  D  V  W  G  Q  G  T  T  V  T  V  S  S  A  S  T  K
301   TATGGTTCGGGGAGTTACGGTATGGACGTCTGGGGCCAAGGGACCACGGTCACCGTCTCCTCAGCCTCCACCAAG
        G  P  S  V  F  P  L  A  P  S  S
376   GGCCCATCGGTCTTCCCCCTGGCACCCTCCTCCA
```

Figure 2AL The cDNA (SEQ ID NO:93) and amino acid sequence (SEQ ID NO:94) of Ha5-7be34.1 VL. Underlined is a portion of the light chain constant region. Double underline is a portion of the leader sequence.

```
        L  L  G  L  L  M  L  W  V  S  G  S  S  G  D  I  V  M  T  Q  S  P  L  S  L  ·
  1   GCTCCTGGGGCTGCTAATGCTCTGGGTCTCTGGATCCAGTGGGGATATTGTGATGACTCAGTCTCCACTCTCCCT
      ·  P  V  T  P  G  E  P  A  S  I  S  C  R  S  S  Q  S  L  L  H  S  T  G  Y  N  ·
 76   GCCCGTCACCCCTGGAGAGCCGGCCTCCATCTCCTGCAGGTCTAGTCAGAGCCTCCTGCATAGTACTGGATACAA
      ·  Y  L  D  W  Y  L  Q  K  P  G  Q  S  P  Q  L  L  I  Y  L  G  S  I  R  A  S  ·
151   CTATTTGGATTGGTACCTGCAGAAGCCAGGGCAGTCTCCACAGCTCCTCATCTATTTGGGTTCTATTCGGGCCTC
      ·  G  V  P  D  R  F  S  G  S  G  S  G  T  D  F  T  L  K  I  S  R  V  E  A  E  ·
226   CGGGGTCCCTGACAGGTTCAGTGGCAGTGGATCAGGCACAGATTTTACACTGAAAATCAGCAGAGTGGAGGCTGA
      ·  D  V  G  I  Y  Y  C  M  Q  A  L  Q  T  P  I  T  F  G  Q  G  T  R  L  E  I  ·
301   GGATGTTGGAATTTATTACTGCATGCAAGCTCTACAAACTCCCATCACCTTCGGCCAAGGGACACGACTGGAGAT
      ·  K  R  T  V  A  A  P  S  V  F  I  F  P  P  S  D  E  Q  L  K  S  G  T  A  S  ·
376   TAAACGAACTGTGGCTGCACCATCTGTCTTCATCTTCCCGCCATCTGATGAGCAGTTGAAATCTGGAACTGCCTC
      ·  V  V  C  L  L  N  N  F  Y  P  R  E  A  K  V  Q  W  K  V  D  N  A  L  Q  S  ·
451   TGTTGTGTGCCTGCTGAATAACTTCTATCCCAGAGAGGCCAAAGTACAGTGGAAGGTGGATAACGCCCTCCAATC
      ·  G  N  S  Q  E  S  V  T  E  Q  D  S  K  D  S  T  Y  S  L  S  S  T  L  T  L  ·
526   GGGTAACTCCCAGGAGAGTGTCACAGAGCAGGACAGCAAGGACAGCACCTACAGCCTCAGCAGCACCCTGACGCT
      ·  S  K  A  D  Y  E  K  H  K  V  Y  A  C  E  V  T  H  Q  G  L  S  S  P  V  T  ·
601   GAGCAAAGCAGACTACGAGAAACACAAAGTCTACGCCTGCGAAGTCACCCATCAGGGCCTGAGCTCGCCCGTCAC
      ·  K  S  F  N  R  G
676   AAAGAGCTTCAACAGGGGA
```

Figure 2AM The cDNA (SEQ ID NO:95) and amino acid sequence (SEQ ID NO:96) of Ha5-7acd3.1 VH. Double-underlined is the leader sequence, and underlined is a portion of the heavy chain constant region.

```
        Q  V  Q  L  V  E  S  G  G  G  V  V  Q  P  G  R  S  L  R  L  S  C  A  A  S
  1   CAGGTGCAGCTGGTGGAGTCTGGGGGAGGCGTGGTCCAGCCTGGGAGGTCCCTGAGACTCTCCTGTGCAGCGTCT
        G  F  T  F  S  S  Y  G  M  H  W  V  R  Q  A  P  G  K  G  L  E  W  V  A  V
 76   GGATTCACCTTCAGTAGCTATGGCATGCACTGGGTCCGCCAGGCTCCAGGCAAGGGGCTGGAGTGGGTGGCAGTT
        I  W  Y  D  G  S  N  K  Y  Y  T  D  S  V  K  G  R  F  T  I  S  R  D  N  S
151   ATTTGGTATGATGGAAGTAATAAATACTATACAGACTCCGTGAAGGGCCGATTCACCATCTCCAGAGACAATTCC
        K  N  T  L  Y  L  Q  M  N  S  L  R  A  E  D  T  A  V  Y  Y  C  A  R  D  R
226   AAGAACACGCTGTATCTGCAAATGAACAGCCTGAGAGCCGAGGACACGGCTGTGTATTACTGTGCGCGAGATCGG
        Y  S  G  Y  D  Y  F  Y  Y  Y  G  M  D  V  W  G  Q  G  T  T  V  T  V  S  S
301   TATAGTGGCTACGATTACTTCTACTACTACGGTATGGACGTCTGGGGCCAAGGGACCACGGTCACCGTCTCCTCA
        A  S  T  K  G  P  S  V  F  P  L  A  P
376   GCCTCCACCAAGGGCCCATCGGTCTTCCCCCTGGCACCCT
```

Figure 2AN The cDNA (SEQ ID NO:97) and amino acid sequence (SEQ ID NO:98) of Ha5-7acd3.1 VL.
Double-underlined is part of the leader sequence, and underlined is a portion of the light chain constant region.

```
          C   F   P   G   A   R   C   D   I   Q   M   T   Q   S   P   S   S   L   S   A   S   V   G   D   R
  1   TGTTTCCCAGGTGCCAGATGTGACATCCAGATGACCCAGTCTCCATCCTCACTGTCTGCATCTGTAGGAGACAGA
          V   T   I   T   C   R   A   S   Q   G   I   Y   N   Y   L   A   W   F   Q   Q   K   P   G   K   A
 76   GTCACCATCACTTGTCGGGCGAGTCAGGGCATTTACAATTATTTAGCCTGGTTTCAGCAGAAACCCGGGAAAGCC
          P   R   S   L   I   Y   A   A   S   S   L   H   S   G   V   P   S   K   F   S   G   S   G   S   G
151   CCTAGGTCCCTGATCTATGCTGCATCCAGTTTGCACAGTGGGGTCCCATCTAAGTTCAGCGGCAGTGGATCTGGG
          T   D   F   T   L   T   I   S   S   L   Q   P   E   D   F   A   T   Y   Y   C   Q   Q   Y   T   I
226   ACAGATTTCACTCTCACCATCAGCAGCCTGCAGCCTGAAGATTTTGCAACTTATTACTGCCAACAATATACTATT
          Y   P   F   T   F   G   P   G   T   K   V   D   I   K   R   T   V   A   A   P   S   V   F   I   F
301   TACCCATTCACTTTCGGCCCTGGGACCAAAGTGGATATCAAACGAACTGTGGCTGCACCATCTGTCTTCATCTTC
          P   P   S   D   E   Q   L   K   S   G   T   A   S   V   V   C   L   L   N   N   F   Y   P   R   E
376   CCGCCATCTGATGAGCAGTTGAAATCTGGAACTGCCTCTGTTGTGCCTGCTGAATAACTTCTATCCCAGAGAG
          A   K   V   Q   W   K   V   D   N   A   L   Q   S   G   N   S   Q   E   S   V   T   E   Q   D   S
451   GCCAAAGTACAGTGGAAGGTGGATAACGCCCTCCAATCGGGTAACTCCCAGGAGAGTGTCACAGAGCAGGACAGC
          K   D   S   T   Y   S   L   S   S   T   L   T   L   S   K   A   D   Y   E   K   H   K   V   Y   A
526   AAGGACAGCACCTACAGCCTCAGCAGCACCCTGACGCTGAGCAAAGCAGACTACGAGAAACACAAAGTCTACGCC
          C   E   V   T   H   Q   G   L   S   S   P   V
601   TGCGAAGTCACCCATCAGGGCCTGAGCTCGCCCGTC
```

Figure 2AO The cDNA (SEQ ID NO:99) and amino acid sequence (SEQ ID NO:100) of Ha5-7acd2.1 VH.
Double-underlined is the leader sequence, and underlined is a portion of the heavy chain constant region.

```
          Q   V   Q   L   Q   E   S   G   P   G   L   V   K   P   S   E   T   L   S   L   T   C   T   V   S
  1   CAGGTGCAGCTGCAGGAGTCTGGCCCAGGACTGGTGAAGCCTTCGGAGACCCTGTCCCTCACCTGCACTGTCTCT
          G   G   S   I   S   S   Y   Y   W   S   W   I   R   Q   P   P   G   K   G   L   E   W   I   G   Y
 76   GGTGGCTCCATCAGTAGTTACTACTGGAGCTGGATCCGGCAGCCCCCAGGGAAGGGACTGGAGTGGATTGGGTAT
          I   Y   Y   S   G   S   T   N   Y   N   P   S   L   K   S   R   V   T   I   S   V   D   T   S   K
151   ATCTATTACAGTGGGAGCACCAACTACAACCCCTCCCTCAAGAGTCGAGTCACCATATCAGTAGACACGTCCAAG
          N   Q   F   S   L   K   L   S   S   V   T   A   A   D   T   A   V   Y   Y   C   A   N   T   Y   Y
226   AACCAGTTCTCCCTGAAGCTGAGCTCTGTGACCGCTGCGGACACGGCCGTGTATTACTGTGCGAACACGTATTAC
          Y   G   S   G   M   D   V   W   G   Q   G   T   T   V   T   V   S   S   A   S   T   K   G
301   TATGGTTCGGGGTACGGTATGGACGTCTGGGGCCAAGGGACCACGGTCACCGTCTCCTCAGCCTCCACCAAGGGC
          P   S   V   F   P   L   A   P
376   CCATCGGTCTTCCCCCTGGCACCC
```

Figure 2AP The cDNA (SEQ ID NO:101) and amino acid sequence (SEQ ID NO:102) of Ha5-7acd2.1 VL.
Double-underlined is part of the leader sequence, and underlined is a portion of the light chain constant region.

```
          L   W   V   S   G   S   S   G   D   I   V   M   T   Q   S   P   L   S   L   P   V   T   P   G   E
  1   CTCTGGGTCTCTGGATCCAGTGGGGATATTGTGATGACTCAGTCTCCACTCTCCCTGCCCGTCACCCCTGGAGAG
          P   A   S   I   S   C   R   S   S   Q   S   L   L   H   S   T   G   H   N   Y   L   D   W   Y   L
 76   CCGGCCTCCATCTCCTGCAGGTCTAGTCAGAGCCTCCTGCATAGTACTGGACACAACTATTTGGATTGGTACCTG
          Q   K   P   G   Q   S   P   Q   L   L   I   Y   L   G   S   I   R   A   S   G   V   P   D   R   F
151   CAGAAGCCAGGGCAGTCTCCACAGCTCCTGATCTATTTGGGTTCTATTCGGGCCTCCGGGGTCCCTGACAGGTTC
          S   G   S   G   T   D   F   T   L   K   I   S   R   V   E   A   E   D   V   G   V   Y   Y
226   AGTGGCAGTGGATCAGGCACAGATTTTACACTGAAAATCAGCAGAGTGGAGGCTGAGGATGTTGGGGTTTATTAC
          C   M   Q   A   L   Q   T   I   T   F   G   Q   G   T   R   L   E   I   K   R   T   V   A   A   P
301   TGCATGCAAGCTCTACAAACTATCACCTTCGGCCAAGGGACACGACTGGAGATTAAACGAACTGTGGCTGCACCA
          S   V   F   I   F   P   P   S   D   E   Q   L   K   S   G   T   A   S   V   V   C   L   L   N   N
376   TCTGTCTTCATCTTCCCGCCATCTGATGAGCAGTTGAAATCTGGAACTGCCTCTGTTGTGCCTGCTGAATAAC
          F   Y   P   R   E   A   K   V   Q   W   K   V   D   N   A   L   Q   S   G   N   S   Q   E   S   V
451   TTCTATCCCAGAGAGGCCAAAGTACAGTGGAAGGTGGATAACGCCCTCCAATCGGGTAACTCCCAGGAGAGTGTC
          T   E   Q   D   S   K   D   S   T   Y   S   L   S   S   T   L   T   L   S   K   A   D   Y   E   K
526   ACAGAGCAGGACAGCAAGGACAGCACCTACAGCCTCAGCAGCACCCTGACGCTGAGCAAAGCAGACTACGAGAAA
          H   K   V   Y   A   C   E   V   T   H   Q   G   L   S   S   P   V   T   K   S   F   N   R   G
601   CACAAAGTCTACGCCTGCGAAGTCACCCATCAGGGCCTGAGCTCGCCCGTCACAAAGAGCTTCAACAGGGGA
```

Figure 2AQ The cDNA (SEQ ID NO:103) and amino acid sequence (SEQ ID NO:104) of Ha5-8ac4.1 VH. Double-underlined is the leader sequence, and underlined is a portion of the heavy chain constant region

```
        Q  V  Q  L  Q  E  S  G  P  G  L  V  K  P  S  E  T  L  S  L  T  C  T  V  S
  1   CAGGTGCAGCTGCAGGAGTCTGGCCCAGGACTGGTGAAGCCTTCGGAGACCCTGTCCCTCACCTGCACTGTCTCT
        G  G  S  I  S  R  Y  Y  W  S  W  I  R  Q  P  A  G  K  G  L  E  R  I  G  R
 76   GGTGGCTCCATCAGTCGTTACTACTGGAGCTGGATCCGGCAGCCCGCCGGGAAGGGACTGGAGAGGATTGGGCGG
        I  Y  T  S  G  S  T  D  Y  N  P  S  L  K  S  R  V  T  M  S  V  D  T  S  K
151   ATCTATACCAGTGGGAGCACCGACTACAACCCCTCTCTCAAGAGTCGAGTCACCATGTCAGTAGACACGTCCAAG
        N  Q  F  S  L  K  L  R  S  V  T  A  A  D  T  A  V  Y  Y  C  A  R  D  L  Y
226   AACCAGTTCTCCCTGAAGCTGAGGTCTGTGACCGCCGCGGACACGGCCGTGTATTACTGTGCGAGAGATTTGTAT
        S  N  G  Y  W  Y  F  D  L  W  G  R  G  T  L  V  T  V  S  S  A  S  T  K  G
301   AGCAATGGCTACTGGTACTTCGATCTCTGGGGCCGTGGCACCCTGGTCACTGTCTCCTCAGCCTCCACCAAGGGC
        P  S  V  F  P  L  A
376   CCATCGGTCTTCCCCCTGGCACC
```

Figure 2AR The cDNA (SEQ ID NO:105) and amino acid sequence (SEQ ID NO:106) of Ha5-8ac4.1 VL. Double-underlined is part of the leader sequence, and underlined is a portion of the light chain constant region.

```
          Q  S  V  L  T  Q  P  P  S  V  S  G  A  P  G  Q  R  V  T  I  S  C  T  G  ·
  1     TGCCCAGTCTGTGCTGACGCAGCCGCCCTCAGTGTCTGGGGCCCCAGGGCAGAGGGTCACCATCTCCTGCACTGG
        ·  S  S  N  I  G  A  G  Y  D  V  H  W  Y  Q  Q  L  P  G  T  A  P  K  L  L  ·
 76     GAGCAGCTCCAACATCGGGGCAGGTTATGATGTACACTGGTACCAGCAGCTTCCAGGAACAGCCCCCAAACTCCT
        ·  I  Y  G  N  S  N  R  P  S  G  V  P  D  R  F  S  G  S  K  S  G  T  S  A  S  ·
151     CATCTATGGTAACAGCAATCGGCCCTCAGGGGTCCCTGACCGATTCTCTGGCTCCAAGTCTGGCACCTCAGCCTC
        ·  L  A  I  T  G  L  Q  A  E  D  E  A  D  Y  Y  C  Q  S  Y  D  S  S  L  S  G  ·
226     CCTGGCCATCACTGGGCTCCAGGCTGAGGATGAGGCTGATTATTACTGCCAGTCCTATGACAGCAGCCTGAGTGG
        ·  V  V  F  G  G  G  T  K  L  T  V  L  G  Q  P  K  A  A  P  S  V  T  L  F  P  ·
301     TGTGGTATTCGGCGGAGGGACCAAGCTGACCGTCCTAGGTCAGCCCAAGGCTGCCCCCTCGGTCACTCTGTTCCC
        ·  P  S  S  E  E  L  Q  A  N  K  A  T  L  V  C  L  I  S  D  F  Y  P  G  A  V  ·
376     GCCCTCCTCTGAGGAGCTTCAAGCCAACAAGGCCACACTGGTGTGTCTCATAAGTGACTTCTACCCGGGAGCCGT
        ·  T  V  A  W  K  A  D  S  S  P  V  K  A  G  V  E  T  T  T  P  S  K  Q  S  N  ·
451     GACAGTGGCCTGGAAGGCAGATAGCAGCCCCGTCAAGGCGGGAGTGGAGACCACCACACCCTCCAAACAAAGCAA
        ·  N  K  Y  A  A  S  S  Y  L  S  L  T  P  E  Q  W  K  S  H  R  S  Y  S  C  Q  ·
526     CAACAAGTACGCGGCCAGCAGCTATCTGAGCCTGACGCCTGAGCAGTGGAAGTCCCACAGAAGCTACAGCTGCCA
        ·  V  T  H  E  G  S  T  V  E  K  T  V  A  P  T  E  C  S  *
601     GGTCACGCATGAAGGGAGCACCGTGGAGAAGACAGTGGCCCCTACAGAATGTTCATAGA
```

Figure 2AS The cDNA (SEQ ID NO:107) and amino acid sequence (SEQ ID NO:108) of Ha5-4(2,5)31.1 VH. Double-underlined is the leader sequence, and underlined is a portion of the heavy chain constant region.

```
        Q  V  Q  L  V  E  S  G  G  G  V  V  Q  P  G  R  S  L  R  L  S  C  A  A  S
  1   CAGGTGCAGCTGGTGGAGTCTGGGGGAGGCGTGGTCCAGCCTGGGAGGTCCCTGAGACTCTCCTGTGCAGCGTCT
        G  F  T  F  R  S  Y  G  M  H  W  V  R  Q  A  P  G  K  G  L  E  W  V  A  V
 76   GGATTCACCTTCAGAAGCTATGGCATGCACTGGGTCCGCCAGGCTCCAGGCAAGGGGCTGGAGTGGGTGGCAGTT
        I  W  Y  D  G  S  N  K  Y  Y  A  D  S  V  K  G  R  S  T  I  S  R  D  N  S
151   ATATGGTATGATGGAAGTAATAAATACTATGCAGACTCCGTGAAGGGCCGATCCACCATCTCCAGAGACAACTCC
        K  N  T  L  Y  L  Q  M  N  S  L  R  A  E  D  T  A  V  Y  Y  C  A  R  D  G
226   AAGAACACGCTGTATCTGCAAATGAACAGCCTGAGAGCCGAGGACACGGCTGTGTATTACTGTGCGAGAGATGGG
        V  A  V  A  G  T  D  Y  F  D  Y  W  G  Q  G  T  L  V  T  V  S  S  A  S  T
301   GTAGCAGTGGCTGGTACAGACTACTTTGACTACTGGGGCCAGGGAACCCTGGTCACCGTCTCCTCAGCCTCCACC
        K  G  P  S  V  F  P  L  A  P
376   AAGGGCCCATCGGTCTTCCCCCTGGCACCCT
```

Figure 2AT The cDNA (SEQ ID NO:109) and amino acid sequence (SEQ ID NO:110) of Ha5-4(2,5)31.1 VL.
Double-underlined is part of the leader sequence, and underlined is a portion of the light chain constant region.

```
         W   L   R   G   A   R   C   D   I   Q   M   T   Q   S   P   S   S   L   S   T   S   V   G   D   R ·
  1   CTGGCTCCGAGGTGCCAGATGTGACATCCAGATGACCCAGTCTCCATCCTCCCTGTCTACATCTGTAGGAGACAG
       · V   T   I   T   C   R   A   T   Q   S   I   S   S   H   L   N   W   Y   Q   Q   K   P   G   K   A ·
 76   AGTCACCATCACTTGCCGGGCAACTCAGAGCATTAGCAGCCATTTAAATTGGTATCAGCAGAAACCAGGGAAAGC
       · P   K   L   L   I   Y   V   A   S   S   L   Q   S   G   V   P   S   R   F   S   G   S   G   S   G ·
151   CCCTAAGCTCCTGATCTATGTTGCATCCAGTTTGCAAAGTGGGGTCCCATCAAGGTTCAGTGGCAGTGGATCTGG
       · T   D   F   T   L   T   I   S   S   L   Q   P   E   D   F   A   T   Y   Y   C   Q   Q   S   Y   S ·
226   GACAGATTTCACTCTCACCATCAGCAGTCTGCAACCTGAAGATTTTGCAACTTACTACTGTCAACAGAGTTACAG
       · T   P   L   T   F   G   G   G   T   K   V   E   I   K   R   T   V   A   A   P   S   V   F   I   F ·
301   TACCCCGCTCACTTTCGGCGGAGGGACCAAGGTGGAGATCAAACGAACTGTGGCTGCACCATCTGTCTTCATCTT
       · P   P   S   D   E   Q   L   K   S   G   T   A   S   V   V   C   L   L   N   N   F   Y   P   R   E ·
376   CCCGCCATCTGATGAGCAGTTGAAATCTGGAACTGCCTCTGTTGTGTGCCTGCTGAATAACTTCTATCCCAGAGA
       · A   K   V   Q   W   K   V   D   N   A   L   Q   S   G   N   S   Q   E   S   V   T   E   Q   D   S ·
451   GGCCAAAGTACAGTGGAAGGTGGATAACGCCCTCCAATCGGGTAACTCCCAGGAGAGTGTCACAGAGCAGGACAG
       · K   D   S   T   Y   S   L   S   S   T   L   T   L   S   K   A   D   Y   E   K   H   K   V   Y   A ·
526   CAAGGACAGCACCTACGCCTCAGCAGCACCCTGACGCTGAGCAAAGCAGACTACGAGAAACACAAAGTCTACGC
       · C   E   V   T   H   Q   G   L   S   S   P   V
601   CTGCGAAGTCACCCATCAGGGCCTGAGCTCGCCCGTCA
```

Figure 2AU The cDNA (SEQ ID NO:111) and amino acid sequence (SEQ ID NO:112) of Ha5-11a1.1.1 VH.
Underlined is a portion of the heavy chain constant region.

```
         Q   V   Q   L   Q   E   S   G   P   G   L   V   K   P   S   Q   T   L   S   L   T   S   T   V   S
  1   CAGGTGCAGCTGCAGGAGTCTGGCCCAGGACTGGTGAAGCCTTCACAGACCCTGTCCCTCACCAGCACTGTCTCT
         G   G   S   I   S   S   G   G   Y   Y   W   S   W   I   R   Q   L   P   G   K   G   L   E   W   V
 76   GGTGGCTCCATCAGCAGTGGTGGTTACTACTGGAGCTGGATCCGCCAGCTCCCAGGGAAGGGCCTGGAGTGGGTT
         G   Y   I   H   N   S   G   S   T   Y   Y   N   P   S   L   K   S   R   V   T   I   S   V   D   T
151   GGGTACATCCATAACAGTGGGAGCACCTACTACAACCCGTCCCTCAAGAGTCGAGTTACCATATCAGTAGACACG
         S   K   N   Q   F   S   L   K   L   R   S   V   T   A   A   D   T   A   V   Y   Y   C   A   R   G
226   TCTAAGAACCAGTTCTCCCTGAAGCTGAGATCTGTGACTGCCGCGGACACGGCCGTGTATTACTGTGCGAGAGGG
         Y   Y   Y   G   S   G   S   P   Y   G   M   D   V   W   G   Q   G   T   T   V   T   V   S   S   A
301   TATTACTATGGTTCGGGGAGCCCCTACGGTATGGACGTCTGGGGCCAAGGGACCACGGTCACCGTCTCCTCAGCC
         S   T   K   G   P   S   V   F   P   L   A   P
376   TCCACCAAGGGCCCATCGGTCTTCCCCCTGGCACCC
```

Figure 2AV The cDNA (SEQ ID NO:113) and amino acid sequence (SEQ ID NO:114) of Ha5-11a1.1.1 VL.
Underlined is a portion of the heavy chain constant region. Double underline is a portion of the leader sequence.

```
         L   W   V   S   G   S   S   G   D   I   V   M   T   Q   S   P   L   S   L   P   V   T   P   G   E ·
  1   GCTCTGGGTCTCTGGATCCAGTGGGATATTGTGATGACTCAGTCTCCACTCTCCCTGCCCGTCACCCCTGGAGA
       · T   A   S   I   S   C   R   S   S   Q   S   L   L   Q   S   N   G   H   N   Y   L   D   W   Y   L ·
 76   GACGGCCTCCATCTCCTGCAGGTCTAGTCAGAGCCTCCTGCAAAGTAATGGACACAACTATTTGGATTGGTACCT
       · Q   K   P   G   Q   S   P   Q   L   L   I   Y   L   G   S   Y   R   D   S   G   V   P   D   R   F ·
151   GCAGAAGCCAGGGCAGTCCCCACAGCTCCTGATCTATTTGGGTTCTTATCGGGACTCCGGGGTCCCTGACAGGTT
       · S   G   S   G   S   G   T   D   F   T   L   K   I   S   R   V   E   A   E   D   V   G   V   Y   Y ·
226   CAGTGGCAGTGGATCAGGCACGGATTTTACCCTGAAAATCAGCAGAGTGGAGGCTGAGGATGTTGGGGTCTATTA
       · C   M   Q   A   L   Q   T   P   P   T   F   G   G   G   T   K   L   E   I   K   R   T   V   A   A ·
301   CTGCATGCAAGCTCTTCAAACTCCTCCTACTTTCGGCGGAGGGACCAAGTTGGAGATCAAACGAACTGTGGCTGC
       · P   S   V   F   I   F   P   P   S   D   E   Q   L   K   S   G   T   A   S   V   V   C   L   L   N ·
376   ACCATCTGTCTTCATCTTCCCGCCATCTGATGAGCAGTTGAAATCTGGAACTGCCTCTGTTGTGTGCCTGCTGAA
       · N   F   Y   P   R   E   A   K   V   Q   W   K   V   D   N   A   L   Q   S   G   N   S   Q   E   S ·
451   TAACTTCTATCCCAGAGAGGCCAAAGTACAGTGGAAGGTGGATAACGCCCTCCAATCGGGTAACTCCCAGGAGAG
       · V   T   E   Q   D   S   K   D   S   T   Y   S   L   S   S   T   L   T   L   S   K   A   D   Y   E ·
526   TGTCACAGAGCAGGACAGCAAGGACAGCACCTACGCCTCAGCAGCACCCTGACGCTGAGCAAAGCAGACTACGA
       · K   H   K   V   Y   A   C   E   V   T   H   Q   G   L   S   S   P   V   T
601   GAAACACAAAGTCTACGCCTGCGAAGTCACCCATCAGGGCCTGAGCTCGCCCGTCACAAA
```

Figure 2AW The cDNA (SEQ ID NO:115) and amino acid sequence (SEQ ID NO:116) of Ha5-11b1.1 VH. Underlined is a portion of the heavy chain constant region.

```
          Q   V   Q   L   V   E   S   G   G   G   V   V   Q   P   G   R   S   L   R   L   S   C   A   A   S
    1   CAGGTGCAGCTGGTGGAGTCTGGGGGAGGCGTGGTCCAGCCTGGGAGGTCCCTGAGACTCTCCTGTGCAGCGTCT
          G   F   T   F   S   S   H   G   M   H   W   V   R   Q   A   P   G   K   G   L   E   W   V   A   V
   76   GGATTCACCTTCAGTAGTCATGGCATGCACTGGGTCCGCCAGGCTCCAGGCAAGGGGCTGGAGTGGGTGGCAGTT
          I   W   Y   D   G   S   N   K   Y   Y   A   D   S   V   K   G   R   F   T   I   S   R   D   N   S
  151   ATATGGTATGATGGAAGTAATAAATACTATGCAGACTCCGTGAAGGGCCGATTCACCATCTCCAGAGACAATTCC
          K   N   T   L   Y   L   Q   M   N   S   L   R   A   E   D   T   A   V   Y   Y   C   A   R   D   Q
  226   AAGAACACGCTGTATCTGCAAATGAACAGCCTGAGAGCCGAGGACACGGCTGTGTATTACTGTGCGAGAGATCAA
          Y   S   G   Y   D   L   Y   Y   Y   Y   G   M   D   V   W   G   Q   G   T   T   V   T   V   S   S
  301   TATAGTGGCTACGATCTCTACTACTACTACGGTATGGACGTCTGGGGCCAAGGGACCACGGTCACCGTCTCCTCA
          A   S   T   K   G   P   S   V   F   P   L   A   P
  376   GCCTCCACCAAGGGCCCATCGGTCTTCCCCCTGGCACCCTC
```

Figure 2AX The cDNA (SEQ ID NO:117) and amino acid sequence (SEQ ID NO:118) of Ha5-11b1.1 VL. Double-underlined is part of the leader sequence, and underlined is a portion of the light chain constant region.

```
          L   L   L   W   I   S   G   A   Y   G   D   I   V   M   T   Q   S   P   D   S   L   A   V   S   L ·
    1   TCTGTTGCTCTGGATCTCTGGTGCCTACGGGGACATCGTGATGACCCAGTCTCCAGACTCCCTGGCTGTGTCTCT
        · G   E   R   A   T   I   N   C   K   S   S   Q   S   V   L   Y   S   S   N   N   K   N   Y   L   A ·
   76   GGGCGAGAGGGCCACCATCAACTGCAAGTCCAGCCAGAGTGTTTTATACAGCTCCAACAATAAGAACTACTTAGC
        · W   Y   Q   Q   K   P   G   Q   P   P   K   L   L   I   Y   W   A   S   T   R   E   S   G   V   P ·
  151   TTGGTACCAGCAGAAACCAGGACAGCCTCCTAAGCTGCTCATTTACTGGGCATCTACCCGGGAATCCGGGGTCCC
        · D   R   F   S   G   S   G   S   G   T   D   F   T   L   T   I   S   S   L   Q   A   E   D   V   A ·
  226   TGACCGATTCAGTGGCAGCGGGTCTGGGACAGATTTCACTCTCACCATCAGCAGCCTGCAGGCTGAAGATGTGGC
        · V   Y   Y   C   Q   Q   Y   Y   S   T   P   R   T   F   G   Q   G   T   K   V   E   I   K   R   T ·
  301   AGTTTATTACTGTCAGCAATATTATAGTACTCCTCGGACGTTCGGCCAAGGGACCAAGGTGGAAATCAAACGAAC
        · V   A   A   P   S   V   F   I   F   P   P   S   D   E   Q   L   K   S   G   T   A   S   V   V   C ·
  376   TGTGGCTGCACCATCTGTCTTCATCTTCCCGCCATCTGATGAGCAGTTGAAATCTGGAACTGCCTCTGTTGTGTG
        · L   L   N   N   F   Y   P   R   E   A   K   V   Q   W   K   V   D   N   A   L   Q   S   G   N   S ·
  451   CCTGCTGAATAACTTCTATCCCAGAGAGGCCAAAGTACAGTGGAAGGTGGATAACGCCCTCCAATCGGGTAACTC
        · Q   E   S   V   T   E   Q   D   S   K   D   S   T   Y   S   L   S   S   T   L   T   L   S   K   A ·
  526   CCAGGAGAGTGTCACAGAGCAGGACAGCAAGGACAGCACCTACAGCCTCAGCAGCACCCTGACGCTGAGCAAAGC
        · D   Y   E   K   H   K   V   Y   A   C   E   V   T   H   Q   G   L   S   S   P   V   T   K   S   F ·
  601   AGACTACGAGAAACACAAAGTCTACGCCTGCGAAGTCACCCATCAGGGCCTGAGCTCGCCCGTCACAAAGAGCTT
        · N   R   G   E
  676   CAACAGGGGAGAGTG
```

Figure 2AY The cDNA (SEQ ID NO:119) and amino acid sequence (SEQ ID NO:120) of Ha5-7be7.1 VH. Double-underlined is part of the leader sequence, and underlined is a portion of the light chain constant region.

```
          E   V   Q   L   L   E   S   G   G   G   L   V   Q   P   G   G   S   L   R   L   S   C   A   A   S
    1   GAGGTGCAGCTGTTGGAGTCTGGGGGAGGCTTGGTACAGCCTGGGGGGTCCCTGAGACTCTCCTGTGCAGCCTCT
          G   F   T   F   S   S   N   A   M   N   W   V   R   Q   A   P   G   K   G   L   E   W   V   S   A
   76   GGATTCACCTTTAGCAGCAATGCCATGAACTGGGTCCGCCAGGCTCCAGGGAAGGGGCTGGAGTGGGTCTCAGCT
          I   S   G   S   G   G   S   T   C   Y   A   D   S   V   K   G   R   F   T   I   S   R   D   N   S
  151   ATTAGTGGTAGTGGTGGTAGCACATGCTACGCAGACTCCGTGAAGGGCCGGTTCACCATCTCCAGAGACAATTCC
          K   N   T   L   Y   L   Q   M   N   S   L   R   A   E   D   T   A   V   Y   Y   C   A   K   A   P
  226   AAGAACACGCTGTATCTGCAAATGAACAGCCTGAGAGCCGAGGACACGGCCGTATATTACTGTGCGAAAGCCCCG
          Y   Q   L   L   P   Y   Y   F   D   Y   W   G   Q   G   T   L   V   T   V   S   S   A   S   T   K
  301   TACCAGCTGCTGCCATACTATTTTGACTACTGGGGCCAGGGAACCCTGGTCACCGTCTCCTCAGCCTCCACCAAG
          G   P   S   V   F   P   L   A
  376   GGCCCATCGGTCTTCCCCCTGGCA
```

Figure 3:

Figure 3A  The amino acid sequence (SEQ ID NO:121) of Ha5-1(5)1 VH. Underlined is a portion of the heavy chain constant region.

```
  1 QVQLVESGGG VVQPGRSLRL SCGASGFTFS SYGMHWVRQA PGKGLEWVAV MSYDGSKKYY
 61 TDSVKGRFTI SRDNSKNTLY LQMNSLRVED TAVYYCARDG GDYVRYYYYG MDVWGQGTTV
121 TVSSASTKGP SVFPLAPCSR STSESTAALG CLVKDYFPEP VTVSWNSGAL TSGVHTFPAV
181 LQSSGLYSLS SV
```

Figure 3B  The amino acid sequence (SEQ ID NO:122) of Ha5-1(5)1 VL. Underlined is a portion of the light chain constant region. Double underline is the leader sequence.

```
  1 LPDTRCDIQM TQSPSSLSAS VGDRVTITCR ARQGITYHLA WYQQRPGKVP KLLIYDTSSL
 61 QSGVPSRFSG SGSGTDFTLT ISSLQPEDVA TYYCQRFNSA PLTFGGGTKV EIKRTVAAPS
121 VFIFPPSDEQ LKSGTASVVC LLNNFYPREA KVQWKVDNAL QSGNSQESVT EQDSKDSTYS
181 LSSTLTLSKA DYEKHKVYAC EVTHQGLS
```

Figure 3C  The amino acid sequence (SEQ ID NO:123) of Ha5-1(5)2.1 VH. Underlined is a portion of the heavy chain constant region.

```
  1 QVQLVESGGG VVQPGRSLRL SCAASGFTFS SYGMHWVRQA PGKGLEWVAV MSYDGSKKFY
 61 TDSVKGRFTI SRDNSKNTLY LQMNSLRAED TAVYYCARDG GDYVRYHYYG MDVWGQGTTV
121 TVSSASTKGP SVFPLAPCSR STSESTAALG CLVKDYFPEP VTVSWNSGAL TSGVHTFPAV
181 LQSSGLYSLS
```

Figure 3D  The amino acid sequence (SEQ ID NO:124) of Ha5-1(5)2.1 VL. Underlined is a portion of the light chain constant region. Double underline is the leader sequence.

```
  1 LLGLLLLWLP DTRCDIQMTQ SPSTLSASIG DRVTITCRAS QGISYYLAWY QQKPGKIPKL
 61 LIYDTSSLQS GVPSRFSGSR SGTDLSLTIS SLQPEDVATY YCQRYDSAPL TFGGGTKVEI
121 KRTVAAPSVF IFPPSDEQLK SGTASVVCLL NNFYPREAKV QWKVDNALQS GNSQESVTEQ
181 DSKDSTYSLS STLTLSKADY EKHKVYACEV THQGLSSPVT KSFNRG
```

Figure 3E  The amino acid sequence (SEQ ID NO:125) of Ha5-3(1,4)2.1 VH. Underlined is a portion of the heavy chain constant region.

```
  1 QVQLVESGGG VVQPGRSLRL SCAASGFTFS SYGMHWVRQA PGKGLEWVAV IWYDGRNKFY
 61 ADSVKGRFTV SRDNSKNTLY LQMNSLRAED TAVYYCARDW GATMAFDIWG QGTMVTVSSA
121 STKGPSVFPL APSSKS
```

Figure 3F  The amino acid sequence (SEQ ID NO:126) of Ha5-3(1,4)2.1 VL. Underlined is a portion of the light chain constant region. Double underline is the leader sequence.

```
  1 LLTLLTHCAG SWAQSVLTQP PSASKTPGQR VTISCSGSSS NIGSNTVNWY QQLPGTAPKL
 61 LIFGNNQRPS GVPDRFSGSK SGTSASLAIS GLQSEDEADY YCAAWDDSLN YVFGTGTKVT
121 VLGQPKANPT VTLFPPSSEE LQANKATLVC LISDFYPGAV TVAWKADGSP VKAGVETTKP
181 SKQSNNKYAA SSYLSLTPEQ WKSHRSYSCQ VTHEG
```

Figure 3G  The amino acid sequence (SEQ ID NO:127) of Ha5-3(1,4)7.1 VH. Underlined is a portion of the heavy chain constant region.

```
  1 QVQLVESGGG VVQPGRSLRL SCAASGFTFS SYGMHWVRQA PGKGLEWVAV IWYDGSNKYY
 61 ADSVKGRFTI SRDNSKNTLY LQMNSLRAED TAVYYCARDR YSGYGYYYYY GMDVWGQGTT
121 VTVSSASTKG PSVFPLAP
```

Figure 3H The amino acid sequence (SEQ ID NO:128) of Ha5-3(1,4)7.1 VL. Underlined is a portion of the light chain constant region. Double underline is the leader sequence.

```
  1 GARCDIQMTQ SPSSLSASVG DRVTITCRAS QDISNYLAWF QQKPGKAPKS LIYAASSLHS
 61 GVPSKFSGSG SGTDFTLTIS SLQPEDFATY YCQQYTIYPF TFGPGTKVDI KRTVAAPSVF
121 IFPPSDEQLK SGTASVVCLL NNFYPREAKV QWKVDNALQS GNSQESVTEQ DSKDSTYSLS
181 STLTLSKADY EKHKVYACEV THQGLSSPVT KSFNRGE
```

Figure 3I The amino acid sequence (SEQ ID NO:129) of Ha5-3(3,5)37.1 VH. Underlined is a portion of the heavy chain constant region.

```
  1 QVQLQESGPG LVKPSETLSL TCTVSGGSIS SYYWSWIRQP PGKGLEWIGY IYYSGSTNYN
 61 PSLKSRVTIS VDTSKNQFSL KLNSVTAADT AVYYCARGYY YGSESPYGMD VWGQGTTVTV
121 SSASTKGPSV FPLAPSSKST SGGTAALGCL VKDYFPEPVT VSWNSGALTS GVHTFPA
```

Figure 3J The amino acid sequence (SEQ ID NO. 130) of Ha5-3(3,5)37.1 VL. Underlined is a portion of the light chain constant region.

```
  1 DIVMTQSPLS LPVTPGEPAS ISCRSSQSLL HSNGHNYLDW YLQKPGQSPH LLIYLGSNRD
 61 SGVPDRFSGS GSGTDFTLKI SRVEAEDVGV YYCMQALQIP CSFGQGTKLE IKRTVAAPSV
121 FIFPPSDEQL KSGTASVVCL LNNFYPREAK VQWKVDNALQ SGNSQESVTE QDSKDSTYSL
181 SSTLTLSKAD YEKHKVYACE VTHQGLSSPV TKSFNR
```

Figure 3K The amino acid sequence (SEQ ID NO:131) of Ha5-4(2,5)13.1 VH. Underlined is a portion of the heavy chain constant region.

```
  1 QVQLVEFGGG VVQPGRSLRL SCAASGFTFR SYGMHWVRQA PGKGLEWVAV IWYDGSNKYY
 61 ADSVKGRSTI SRDNSKNTLY LQMNSLRAED TAVYYCARDG VAVAGTDYFD YWGQGTLVTV
121 SSASTKGPSV FPLAPSSKST SGGTAALGCL VKDYFPEPVT VSWNSGALTS GVHT
```

Figure 3L The amino acid sequence (SEQ ID NO:132) of Ha5-4(2,5)13.1 VL. Underlined is the light chain constant region. Double underline is the leader sequence.

```
  1 WLRGARCDIQ MTQSPSSLSA SVGDRVTITC RASQSISSHL NWYQQKPGKA PKLLIYVASS
 61 LQSGVPSRFS GSGSGTDFTL TISSLQPEDF ATYYCQQSYS TPLIFGGGTK VEIKRTVAAP
121 SVFIFPPSDE QLKSGTASVV CLLNNFYPRE AKVQWKVDNA LQSGNSQESV TEQDSKDSTY
181 SLSSTLTLSK ADYEKHKVYA CEVTHQGLSS PV
```

Figure 3M The amino acid sequence (SEQ ID NO:133) of Ha5-4(2,5)34.1 VH. Underlined is a portion of the heavy chain constant region.

```
  1 EVQLLESGGG LVQPGGSLRL SCAASTFTFS SYAMSWVRQA PGKGLEWVSA FSGRGGSTYY
 61 ADSVKGRFTI SRDNSKNTLF LQMNSLRAED TAVYYCAKDS SGPLLGYGMD VWGQGTTVTV
121 SSASTKGPSV FPLAPSSKST SGGTAALGCL VKDYFPEPVT VS
```

Figure 3N The amino acid sequence (SEQ ID NO:134) of Ha5-4(2,5)34.1 VL. Underlined is a portion of the light chain constant region.

```
  1 SYELTQPPSV SVSPGQTASI TCSGDKVGDK YACWYQQKPG QSPVLVIYQD SKRPSGIPER
 61 FSGSNSGNTA TLTISGTQAM DEADYYCQAW DSSTYVVFGG GTKLTVLGQP KAAPSVTLFP
121 PSSEELQANK ATLVCLISDF YPGAVTVAWK ADSSPVKAGV ETTTPSKQSN NKYAASSYLS
181 LTPEQWKSHR SYSCQVTHEG STVEKT
```

Figure 3O The amino acid sequence (SEQ ID NO:135) of Ha5-7acd4.1 VH. Underlined is a portion of the heavy chain constant region.

```
  1 QVQLVESGGG VVQPGRSLRL SCAASGFTFS SYGMHWVRQA PGKGLEWVAV IWYDGSNKYY
 61 ADSVKGRFTI SRDNSKNTLY LQMNSLRAED TAVYYCARDR YSGYDYYYY GMDVWGQGTT
121 VTVSSASTKG PSVFPLAPS
```

Figure 3P The amino acid sequence (SEQ ID NO:136) of Ha5-7acd4.1 VL. Underlined is a portion of the light chain constant region. Double underline is the leader sequence.

```
  1 LCFPGARCDI QMTQSPSSLS ASVGDRVTIT CRASQVIYNY LAWFQQKPGK APKSLIYGAS
 61 SLHSGVPSKF SGSGSGTEFT LTISSLQPED FATYYCQQYT IYPFSFGPGT KVDIKRTVAA
121 PSVFIFPPSD EQLKSGTASV VCLLNNFYPR EAKVQWKVDN ALQSGNSQES VTEQDSKDST
181 YSLSSTLTLS KADYEKHKVY ACEVTHQGLS SPV
```

Figure 3Q The amino acid sequence (SEQ ID NO:137) of Ha5-7acd20.1.1 VH. Underlined is a portion of the heavy chain constant region.

```
  1 QVQLVESGGG VVQPGRSLRL SCAASGFTFS SYGMHWVRQA PGKGLEWVAV
 51 IWYDGRNKYY VDSVKGRFTI SRDNSKNTLY LQMNSLRAED TAVYYCARDR
101 YSGSDYYYYY GMDVWGQGTT VTVSSASTKG PSVFPL
```

Figure 3R The amino acid sequence (SEQ ID NO:138) of Ha5-7acd20.1.1 VL. Underlined is a portion of the light chain constant region. Double underline is the leader sequence.

```
  1 LCFPGARCDI QMTQSPSSLS ASVGDRVTIT CRASQGIYNY LAWFQQKPGK APKSLIYAAS
 61 SLQSGVPSKF SGSGSGTVFT LTISSLQPED FATYYCQQYT VYPFTFGPGT KVDFKRTVAA
121 PSVFIFPPSD EQLKSGTASV VCLLNNFYPR EAKVQWKVDN ALQSGNSQES VTEQDSKDST
181 YSLSSTLTLS KADYEKHKVY ACEVTHQGLS SPVTKSFNR
```

Figure 3S The amino acid sequence (SEQ ID NO:139) of Ha5-7be31.1 VH. Underlined is a portion of the heavy chain constant region.

```
  1 QVQLQESGPG LVKPSETLSL TCTVSGGSIS SYYWSWIRQP PGKGLEWIGY
 51 IYYSGSTNYN PSLKSRVTIS VDTSKNQFSL KLSSVTAADT AVYYCARGYY
101 YGAGSYGMDV WGQGTTVTVS SASTKGPSVF PLAP
```

Figure 3T The amino acid sequence (SEQ ID NO:140) of Ha5-7be31.1 VL. Underlined is a portion of the light chain constant region. Double underline is the leader sequence.

```
  1 LWVSGSSGDI VMTQSPLSLP VTPGEPASIS CRSSQSLLHS TGFNYLDWYL QKPGQSPQLL
 61 IYLGSIRASG VPDRFSGSGS GTDFTLKISR VETEDVGVYY CMQTLQTPIT FGQGTRLEIK
121 RTVAAPSVFI FPPSDEQLKS GTASVVCLLN NFYPREAKVQ WKVDNALQSG NSQESVTEQD
181 SKDSTYSLSS TLTLSKADYE KHKVYACEVT HQGLSSPVTK SFNRG
```

Figure 3U The amino acid sequence (SEQ ID NO:141) of Ha5-7acd10.1 VH. Underlined is a portion of the heavy chain constant region.

```
  1 QVQLVESGGG VVQPGRSLRL SCAASGFTFS SYGMHWVRQA PGKGLEWVAV
 51 IWYDGSNKYY ADSVKGRFTI SRDNSKNTLY LQMNSLRAED TAVYYCARDR
101 YSGYDYYYYY GMDVWGQGTT VTVSSASTKG PSVFPLAPSS
```

Figure 3V The amino acid sequence (SEQ ID NO:142) of Ha5-7acd10.1 VL. Underlined is a portion of the light chain constant region. Double underline is the leader sequence.

```
  1 LCFPGARCDI QMTQSPSSLS ASVGDRVTIT CRASQGIYNY LAWFQQKPGK APKSLIYAAS
 61 SLHSGVPSKF SGGGSGTDFT LTISSLQPED FATYYCQQYT IYPFTFGPGT KVDIKRTVAA
121 PSVFIFPPSD EQLKSGTASV VCLLNNFYPR EAKVQWKVDN ALQSGNSQES VTEQDSKDST
181 YSLSSTLTLS KADYEKHKVY ACEVTHQGLS SPVTKSFNR
```

Figure 3W The amino acid sequence (SEQ ID NO:143) of Ha5-7acd31.1 VH. Underlined is a portion of the heavy chain constant region.

```
  1 QVQLQESGPG LVKPSETLSL TCTVSGGSIS SYYWSWIRQP PGKGLEWIGY
 51 IYYSGSTNYN PSLKSRVTIS VDTSKNQFSL KLSSVTAADT AVYYCANTYY
101 YGSGYGMDVW GQGTTVTVSS ASTKGPSVFP LAP
```

Figure 3X The amino acid sequence (SEQ ID NO:144) of Ha5-7acd13.1 VL. Underlined is a portion of the light chain constant region. Double underline is the leader sequence.

```
  1  LWVSGSSGDI VMTQSPLSLP VTPGEPASIS CRSSQSLLHS TGHNYLDWYL
 51  QKPGQSPQLL IYLGSIRASG VPDRFSGSGS GTDFTLKISR VEAEDVGVYY
101  CMQALQTITF GQGTRLEIKR TVAAPSVFIF PPSDEQLKSG TASVVCLLNN
151  FYPREAKVQW KVDNALQSGN SQESVTEQDS KDSTYSLSST LTLSKADYEK
201  HKVYACEVTH QGLSSPVT
```

Figure 3Y The amino acid sequence (SEQ ID NO:145) of Ha5-7acd19.1 VH. Underlined is a portion of the heavy chain constant region.

```
  1  QVQLQESGPG LVKPSETLSL TCTVSGGSIS SYYWSWIRQP PGKGLEWIGF
 51  IYYTGSTNYN PSLKSRVTIS VDTSKNQFSL KLSSVTAADT AVYYCANTYY
101  YGSGYGMDVW GQGTTVTVSS ASTKGPSVFP LAPSS
```

Figure 3Z The amino acid sequence (SEQ ID NO:146) of Ha5-7acd19.1 VL. Underlined is a portion of the light chain constant region. Double underline is the leader sequence.

```
  1  LLGLLMLWVS GSSGDIVMTQ SPLSLPVTPG EPASISCRSS QSLLHSNGFN
 51  YLDWYLQKPG QSPQLLIYLG SRRASGVPDR FSGSGSGTDF TLKISRVEAE
101  DVGVYYCMQA LETITFGQGT RLEIKRTVAA PSVFIFPPSD EQLKSGTASV
151  VCLLNNFYPR EAKVQWKVDN ALQSGNSQES VTEQDSKDST YSLSSTLTLS
201  KADYEKHKVY ACEVTHQGLS SPVTKSFNR
```

Figure 3AA The amino acid sequence (SEQ ID NO:147) of Ha5-7be37.1 VH.

```
  1  QVQLQESGPG LVKPSETLSL TCTVSGGSIS SYYWSWIRQP PGKGLEWIGY
 51  IYYSGSTNYN PSLKSRVTIS VDTSKNQFSL KLSSVTAADT AVYYCARGYY
101  YGSGSYGMDV WGQGTTVTVS SASTKGPSVF PLAPSS
```

Figure 3AB The amino acid sequence (SEQ ID NO:148) of Ha5-7be37.1 VL. Underlined is a portion of the light chain constant region. Double underline is the leader sequence.

```
  1  GSSGDIVMTQ SPLSLPVTPG EPASISCRSS QSLLHSTGYN YLDWYLQKPG
 51  QSPQLLIYLG SNRASGVPDR FSGSGSGTDF TLKISRVEAE DVGVCYCMQA
101  LQTPITFGQG TRLEIKRTVA APSVFIFPPS DEQLKSGTAS VVCLLNNFYP
151  REAKVQWKVD NALQSGNSQE SVTEQDSKDS TYSLSSTLTL SKADYEKHKV
201  YACEVTHQGL SSPVT
```

Figure 3AC The amino acid sequence (SEQ ID. NO. : 149) of Ha5-7acd16.1 VH.

```
  1  QVQLVESGGG VVQPGRSLRL SCAASGFTFS SHGMHWVRQA PGKGLEWVAV
 51  IWYDGSNKYY ADSVKGRFTI SRDNSKNTLY LQMNSLRAED TAVYYCARDA
101  YSGYDYYYYY GMDVWGQGTT VTVSSASTKG PSVFPL
```

Figure 3AD The amino acid sequence (SEQ ID. NO. : 150) of Ha5-7acd16.1 VL. Underlined is a portion of the light chain constant region. Double underline is the leader sequence.

```
  1  GLLLLCFPGA RCDIQMTQSP SSLSASVGDR VTITCRASQG IYTYLAWFQQ
 51  KPGKAPKSLI YGASSLQSGV PSKFSGSGSG TDFTLTITSL QPEDFATYYC
101  QQYTIYPFSF GPGTKVDIKR TVAAPSVFIF PPSDEQLKSG TASVVCLLNN
151  FYPREAKVQW KVDNALQSGN SQESVTEQDS KDSTYSLSST LTLSKADYEK
201  HKVYACEVTH QGLSSPVTKS FNR
```

Figure 3AE The amino acid sequence (SEQ ID NO:151) of Ha5-7acd7.1.1 VH. Underlined is a portion of the light chain constant region.

```
  1 QVQLQESGPG LVKPSETLSL TCTVSGGSVS SGGYYWSWIR QPPGKGLEWI GYIYYSGGTN
 61 YNPSLKSRVT ISVDTSKNQF SLKLTSVTAA DTAVYYCARE SGYCTNVACF PDAFDIWGQG
121 TMVTVSSAST KGPSVFPLAP S
```

Figure 3AF The amino acid sequence (SEQ ID NO:152) of Ha5-7acd7.1.1 VL. Double-underlined is the leader sequence. Underlined is a portion of the light chain constant region.

```
  1 LLGLLMLWVS GSSGDVVMTQ SPFSLPVTPG EPASISCRSS QSLLHSNGFN
 51 FLDWYLQKPG QSPQLLIYLG SIRASGVPDR FSGSGSGTDF TLKISRVEAE
101 DVGVYYCMQA LQTPLTFGGG TRVEIKRTVA APSVFIFPPS DEQLKSGTAS
151 VVCLLNNFYP REAKVQWKVD NALQSGNSQE SVTEQDSKDS TYSLSSTLTL
201 SKADYEKHKV YACEVTHQGL SSPVT
```

Figure 3AG The amino acid sequence (SEQ ID NO:153) of Ha5-7be20.1 VH. Double-underlined is the leader sequence. Underlined is a portion of the light chain constant region.

```
  1 QVQLQESGPG LVKPSETLSL TCTVSGGSIS SYYWSWIRQP PGKGLEWIGY
 51 IYYSGSTNYN PSLKSRVTIS VDTSKNQFSL KLSSVTAADT AVYYCARGYY
101 YGSGSYGLDV WGQGTTVTVS SASTKGPSVF PLAPSS
```

Figure 3AH The amino acid sequence (SEQ ID NO:154) of Ha5-7be20.1 VL. Double-underlined is part of the leader sequence. Underlined is a portion of the light chain constant region.

```
  1 LLGLLMLWVS GSSGDIVMTQ SPLSLPVTPG EPASISCRSS QSLLHSTGYN
 51 YLDWYLQKPG QSPQLLIYLG SIRASGVPDR FSGSGSGTDF TLKISRVEAE
101 DVGVYYCMQA LQTPITFGQG TRLEIKRTVA APSVFIFPPS DEQLKSGTAS
151 VVCLLNNFYP REAKVQWKVD NALQSGNSQE SVTEQDSKDS TYSLSSTLTL
201 SKADYEKHKV YACEVTHQGL SSPVTKSFNR
```

Figure 3AI The amino acid sequence (SEQ ID NO:155) of Ha5-7acd5.1.1 VH. Underlined is a portion of the heavy chain constant region.

```
  1 QVQLQESGPG LVKPSETLSL TCTVSGGSIS SYYWSWIRQP PGKGLEWIGY
 51 IYYSGSTNYN PSLKSRVTIS VDTSKNQFSL KLSSVTAADT AVYYCANTYY
101 YGSGYGMDVW GQGTTVTVSS AS
```

Figure 3AJ The amino acid sequence (SEQ ID NO:156) of Ha5-7acd5.1.1 VL. Underlined is a portion of the light chain constant region. Double underline is the leader sequence.

```
  1 SGSSGDIVMT QSPLSLPVTP GEPASISCRS SQSLLHSTGH NYLDWYLQKP
 51 GQSPQLLIYL GSIRASGVPD RFSGSGSGTD FTLKISRVEA EDVGVYYCMQ
101 ALQTITFGQG TRLEIKRTVA APSVFIFPPS DEQLKSGTAS VVCLLNNFYP
151 REAKVQWKVD NALQSGNSQE SVTEQDSKDS TYSLSSTLTL SKADYEKHKV
201 YACEVTHQGL SSPVTKSFNR
```

Figure 3AK The amino acid sequence (SEQ ID NO:157) of Ha5-7be34.1 VH. Underlined is a portion of the heavy chain constant region.

```
  1 QVQLQESGPG LVKPSETLSL TCTVSGGSIS SYYWSWIRQP PGKGLEWIGY
 51 IYYSGSTNYK PSLKSRVTIS VDTSKNQFSL KLSSVTAADT AVYYCARGYY
101 YGSGSYGMDV WGQGTTVTVS SASTKGPSVF PLAPSS
```

Figure 3AL The amino acid sequence (SEQ ID NO:158) of Ha5-7bc34.1 VL. Underlined is a portion of the light chain constant region. Double underline is the leader sequence.

```
  1 LLGLLMLWVS GSSGDIVMTQ SPLSLPVTPG EPASISCRSS QSLLHSTGYN YLDWYLQKPG
 61 QSPQLLIYLG SIRASGVPDR FSGSGSGTDF TLKISRVEAE DVGIYYCMQA LQTPITFGQG
121 TRLEIKRTVA APSVFIFPPS DEQLKSGTAS VVCLLNNFYP REAKVQWKVD NALQSGNSQE
181 SVTEQDSKDS TYSLSSTLTL SKADYEKHKV YACEVTHQGL SSPVTKSFNR G
```

Figure 3AM The amino acid sequence (SEQ ID NO:159) of Ha5-7acd3.1 VH. Underlined is a portion of the heavy chain constant region.

```
  1 QVQLVESGGG VVQPGRSLRL SCAASGFTFS SYGMHWVRQA PGKGLEWVAV IWYDGSNKYY
 61 TDSVKGRFTI SRDNSKNTLY LQMNSLRAED TAVYYCARDR YSGYDYFYYY GMDVWGQGTT
121 VTVSSASTKG PSVFPLAP
```

Figure 3AN The amino acid sequence (SEQ ID NO:160) of Ha5-7acd3.1 VL. Double-underlined is part of the leader sequence, and underlined is a portion of the light chain constant region.

```
  1 CFPGARCDIQ MTQSPSSLSA SVGDRVTITC RASQGIYNYL AWFQQKPGKA PRSLIYAASS
 61 LHSGVPSKFS GSGSGTDFTL TISSLQPEDF ATYYCQQYTI YPFTFGPGTK VDIKRTVAAP
121 SVFIFPPSDE QLKSGTASVV CLLNNFYPRE AKVQWKVDNA LQSGNSQESV TEQDSKDSTY
181 SLSSTLTLSK ADYEKHKVYA CEVTHQGLSS PV
```

Figure 3AO The amino acid sequence (SEQ ID NO:161) of Ha5-7acd2.1 VH. Underlined is a portion of the heavy chain constant region.

```
  1 QVQLQESGPG LVKPSETLSL TCTVSGGSIS SYYWSWIRQP PGKGLEWIGY IYYSGSTNYN
 61 PSLKSRVTIS VDTSKNQFSL KLSSVTAADT AVYYCANTYY YGSGYGMDVW GQGTTVTVSS
121 ASTKGPSVFP LAP
```

Figure 3AP The amino acid sequence (SEQ ID NO:162) of Ha5-7acd2.1 VL. Double-underlined is part of the leader sequence, and underlined is a portion of the light chain constant region.

```
  1 LWVSGSSGDI VMTQSPLSLP VTPGEPASIS CRSSQSLLHS TGHNYLDWYL QKPGQSPQLL
 61 IYLGSIRASG VPDRFSGSGS GTDFTLKISR VEAEDVGVYY CMQALQTITF GQGTRLEIKR
121 TVAAPSVFIF PPSDEQLKSG TASVVCLLNN FYPREAKVQW KVDNALQSGN SQESVTEQDS
181 KDSTYSLSST LTLSKADYEK HKVYACEVTH QGLSSPVTKS FNRG
```

Figure 3AQ The amino acid sequence (SEQ ID NO:163) of Ha5-8ac4.1 VH. Underlined is a portion of the heavy chain constant region.

```
  1 QVQLQESGPG LVKPSETLSL TCTVSGGSIS RYYWSWIRQP AGKGLERIGR IYTSGSTDYN
 61 PSLKSRVTMS VDTSKNQFSL KLRSVTAADT AVYYCARDLY SNGYWYFDLW GRGTLVTVSS
121 ASTKGPSVFP LA
```

Figure 3AR The amino acid sequence (SEQ ID NO:164) of Ha5-8ac4.1 VL. Underlined is a portion of the light chain constant region.

```
  1 QSVLTQPPSV SGAPGQRVTI SCTGSSSNIG AGYDVHWYQQ LPGTAPKLLI YGNSNRPSGV
 61 PDRFSGSKSG TSASLAITGL QAEDEADYYC QSYDSSLSGV VFGGGTKLTV LGQPKAAPSV
121 TLFPPSSEEL QANKATLVCL ISDFYPGAVT VAWKADSSPV KAGVETTTPS KQSNNKYAAS
181 SYLSLTPEQW KSHRSYSCQV THEGSTVEKT VAPTECS
```

Figure 3AS  The amino acid sequence (SEQ ID NO:165) of Ha5-4(2,5)31.1 VH. Underlined is a portion of the heavy chain constant region.

```
  1 QVQLVESGGG VVQPGRSLRL SCAASGFTFR SYGMHWVRQA PGKGLEWVAV IWYDGSNKYY
 61 ADSVKGRSTI SRDNSKNTLY LQMNSLRAED TAVYYCARDG VAVAGTDYFD YWGQGTLVTV
121 SSASTKGPSV FPLAP
```

Figure 3AT  The amino acid sequence (SEQ ID NO:166) of Ha5-4(2,5)31.1 VL. Double-underlined is part of the leader sequence, and underlined is a portion of the light chain constant region.

```
  1 WLRGARCDIQ MTQSPSSLST SVGDRVTITC RATQSISSHL NWYQQKPGKA PKLLIYVASS
 61 LQSGVPSRFS GSGSGTDFTL TISSLQPEDF ATYYCQQSYS TPLTFGGGTK VEIKRTVAAP
121 SVFIFPPSDE QLKSGTASVV CLLNNFYPRE AKVQWKVDNA LQSGNSQESV TEQDSKDSTY
181 SLSSTLTLSK ADYEKHKVYA CEVTHQGLSS PV
```

Figure 3AU  The amino acid sequence (SEQ ID NO:167) of Ha5-11a1.1.1 VH. Underlined is a portion of the heavy chain constant region.

```
  1 QVQLQESGPG LVKPSQTLSL TSTVSGGSIS SGGYYWSWIR QLPGKGLEWV GYIHNSGSTY
 61 YNPSLKSRVT ISVDTSKNQF SLKLRSVTAA DTAVYYCARG YYYGSGSPYG MDVWGQGTTV
121 TVSSASTKGP SVFPLAP
```

Figure 3AV  The amino acid sequence (SEQ IDNO:168) of Ha5-11a1.1.1 VH. Underlined is a portion of the heavy chain constant region. Double underline is the leader sequence.

```
  1 LWVSGSSGDI VMTQSPLSLP VTPGETASIS CRSSQSLLQS NGHNYLDWYL QKPGQSPQLL
 61 IYLGSYRDSG VPDRFSGSGS GTDFTLKISR VEAEDVGVYY CMQALQTPPT FGGGTKLEIK
121 RTVAAPSVFI FPPSDEQLKS GTASVVCLLN NFYPREAKVQ WKVDNALQSG NSQESVTEQD
181 SKDSTYSLSS TLTLSKADYE KHKVYACEVT HQGLSSPVT
```

Figure 3AW  The amino acid sequence (SEQ ID NO:169) of Ha5-11b1.1 VH. Underlined is a portion of the heavy chain constant region.

```
  1 QVQLVESGGG VVQPGRSLRL SCAASGFTFS SHGMHWVRQA PGKGLEWVAV IWYDGSNKYY
 61 ADSVKGRFTI SRDNSKNTLY LQMNSLRAED TAVYYCARDQ YSGYDLYYYY GMDVWGQGTT
121 VTVSSASTKG PSVFPLAP
```

Figure 3AX  The amino acid sequence (SEQ ID NO:170) of Ha5-11b1.1 VL. Double-underlined is part of the leader sequence, and underlined is a portion of the light chain constant region.

```
  1 LLLWISGAYG DIVMTQSPDS LAVSLGERAT INCKSSQSVL YSSNNKNYLA WYQQKPGQPP
 61 KLLIYWASTR ESGVPDRFSG SGSGTDFTLT ISSLQAEDVA VYYCQQYYST PRTFGQGTKV
121 EIKRTVAAPS VFIFPPSDEQ LKSGTASVVC LLNNFYPREA KVQWKVDNAL QSGNSQESVT
181 EQDSKDSTYS LSSTLTLSKA DYEKHKVYAC EVTHQGLSSP VTKSFNRGE
```

Figure 3AY  The amino acid sequence (SEQ ID NO:171) of Ha5-7be7.1 VH. Underlined is a portion of the light chain constant region.

```
  1 EVQLLESGGG LVQPGGSLRL SCAASGFTFS SNAMNWVRQA PGKGLEWVSA ISGSGGSTCY
 61 ADSVKGRFTI SRDNSKNTLY LQMNSLRAED TAVYYCAKAP YQLLPYYFDY WGQGTLVTVS
121 SASTKGPSVF PLA
```

Figure 4

Figure 4A-1 Alignment of Ha5-1(5)1 VH to human Ig germline.

```
                                <------------------------------FWR1--------------------------->
                                Q  V  Q  L  V  E  S  G  G  G  V  V  Q  P  G  R  S  L  R  L  S  C  G
Ha5-1(5)1    1                  CAGGTGCAGCTGGTGGAGTCTGGGGGAGGCGTGGTCCAGCCTGGGAGGTCCCTGAGACTCTCCTGTGAG   70
VH3-30            98.0(290/296) ..................................................................    70
D4-17             100(9/9)
JH6               98.3(58/59)                                                                    C..
                                                          <------CDR1----->                   <----FWR2--
                                A  S  G  F  T  F  S      S  Y  G  M  H    W  V  R  Q  A  P  G  K  G  L  E  W
Ha5-1(5)1   71                  CCTCTGGATTCACCTTCAGT  AGTTATGGCATGCAC  TGGGTCCGCCAGGCTCCAGGCAAGGGGCTGGAGTG  140
VH3-30            98.0(290/296) ........................C.........................................................  140
D4-17             100(9/9)
JH6               98.3(58/59)
                                                <---------CDR2--------->
                                V  A    V  M  S  Y  D  G  S  K  K  Y  Y  T  D  S  V  K  G    R  F  T  I
Ha5-1(5)1  141                  GGTGGCA GTTATGTCATATGATGGAAGTAAAAAATACTATACAGACTCCGTGAAGGGC CGATTCACCATC  210
VH3-30            98.0(290/296) ........A..........T............................G........................  210
D4-17             100(9/9)
JH6               98.3(58/59)
                                -----------------------FWR3-----------------------
                                S  R  D  N  S  K  N  T  L  Y  L  Q  M  N  S  L  R  V  E  D  T  A  V
Ha5-1(5)1  211                  TCCAGAGACAATTCCAAGAACACGCTGTATCTGCAAATGAACAGCCTGAGAGTTGAGGACACGGCTGTGT  280
VH3-30            98.0(290/296) ............................................................C........  280
D4-17             100(9/9)
JH6               98.3(58/59)
                                                  <---->
                                Y  Y  C  A  R    D  G  G  D  Y  V  R  Y  Y  Y  Y  M  D  V  W  G  Q  G
Ha5-1(5)1  281                  ATTACTGTGCGAGA  GATGGGGGTGACTACGTCCGCTACTACTACTACGGTATGGACGTCTGGGGCCAAGG  350
VH3-30            98.0(290/296) .............                                                             296
D4-17             100(9/9)                                                                                  16
JH6               98.3(58/59)     8
```

Figure 4A-2

```
                                                                                                G......  40
98.3(58/59)     JH6        5    ----------------------------
ID%
                                     T  T  V  T  V  S  S
                Ha5-1(5)1  351  GACCACGGTCACCGTCTCCTCAG          373

98.0(290/296)   VH3-30     ----------------------------
100(9/9)        D4-17      ----------------------------
98.3(58/59)     JH6        41   ..........................    63
ID%
```

Figure 4B-1 Alignment of Ha5-1(5)1 VL to human Ig germline

```
                                 <-------------------------------------FWR1------------------------------------->  <
                                 D  I  Q  M  T  Q  S  P  S  S  L  S  A  S  V  G  D  R  V  T  I  T  C
                Ha5-1(5)1  45    GACATCCAGATGACCCAGTCTCCATCCTCCCTGTCTGCATCTGTAGGAGACAGAGTCACCATCACTTGC            114
ID%
                A20        1    ..........................................................................      70
                JK4
                                 D  I  Q  M  T  Q  S  P  S  S  L  S  A  S  V  G  D  R  V  T  I  T  C

R  A  R  Q  G  I  T  Y  H  L  A      W  Y  Q  Q  R  P  G  K  V  P  K  L  L
                Ha5-1(5)1  115   GGGCGCGTCAGGCAGGCATTACCTATCATTTAGCC TGGTATCAGCAGAGACCGGGGAAAGTTCCTAAACTCCT        184
95.8(272/284)   A20        71    .....A...................G.A..T....      ...........A..A..........G..........  140
100(38/38)      JK4
ID%                              R  A  S  Q  G  I  S  N  Y  L  A      W  Y  Q  Q  K  P  G  K  V  P  K  L  L

<---------CDR2--------->                 <------------FWR2------------
                                 I  Y     D  T  S  S  L  Q  S                G  V  P  S  R  F  S  G  S  G  S  G  T  D
                Ha5-1(5)1  185   GATCTAT GATACATCCTCTTGCAATCA            -GGGGTCCCATCTCGTTCAGTGGCAGTGGATCTGGGACAGA  253
95.8(272/284)   A20        141   .........A..A.T..........A............      -..................................  209
100(38/38)      JK4
ID%                              I  Y     A  A  S  T  L  Q  S                G  V  P  S  R  F  S  G  S  G  S  G  T  D

---FWR3--------------->
                                 F  T  L  T  I  S  S  L  Q  P  E  D  V  A  T  Y  Y  C      Q  R  F  N  S
                Ha5-1(5)1  254   TTTCACTCTCACCATCAGCAGCCTGCAGCCTGAAGATGTTGCAACTTATTACTGT CAAAGGTTTAACAGT         323
95.8(272/284)   A20        210   ...........................................................     ...A..A..........  279
100(38/38)      JK4
ID%                              F  T  L  T  I  S  S  L  Q  P  E  D  V  A  T  Y  Y  C      Q  K  Y  N  S
```

Figure 4B-2

```
                    A  P  L  T  F  G  G  G  T  K  V  E  I  K
Ha5-1(5)1    324   GCCCCGCTCACTTCGGCGGAGGGACCAAGGTGGAGATCAAAC   366
                    A  P
95.8(272/284)  A20   280   ..........................................   284
100(38/38)     JK4     1   ------------------------------------------    38
```

Figure 4C-1 Alignment of Ha5-1(5)2.1 VH to human Ig germline

```
ID%                  <----------------------------FWR1---------------------------->
              Ha5-1(5)2.1   1   Q  V  Q  L  V  E  S  G  G  G  V  V  Q  P  G  R  S  L  R  L  S  C  A
                                CAGGTGCAGCTGGTGGAGTCTGGGGGAGGCGTGGTCCAGCCTGGGAGGTCCCTGAGACTCTCCTGTGCAG  70
98.3(291/296)  VH3-30    1      Q  V  Q  L  V  E  S  G  G  G  V  V  Q  P  G  R  S  L  R  L  S  C  A
90.9(10/11)    D2-21
96.6(57/59)    JH6              ..................................................................  70

ID%                              <----CDR1---->                    <-----
              Ha5-1(5)2.1  71   A  S  G  F  T  F  S     S  Y  G  M  H     W  V  R  Q  A  P  G  K  G  L  E  W
                                CCCTCTGATTCACCTTCAGT   AGTTATGGCATGCAC   TGGGTCCGCCAGGCTCCAGGCAAGGGGCTGGAGTG  140
98.3(291/296)  VH3-30   71      A  S  G  F  T  F  S     S  Y  G  M  H     W  V  R  Q  A  P  G  K  G  L  E  W
90.9(10/11)    D2-21             ..C.
96.6(57/59)    JH6              ..................................................................  140

ID%                              -------->     <----------CDR2---------->
              Ha5-1(5)2.1 141   V  A     V  M  S  Y  D  G  S  K  K  F  Y  T  D  S  V  K  G     R  F  T  I
                                GGTGGCA   GTTATGTCATATGATGGAAGTAAAAAATTCTATACAGACTCCGTGAAGGGC   CGATTCACCATC  210
98.3(291/296)  VH3-30  141      V  A     V  I  S  Y  D  G  S  N  K  Y  Y  A  D  S  V  K  G     R  F  T  I
90.9(10/11)    D2-21             .......    ....A..........T..A..G.........................   ...........
96.6(57/59)    JH6
88.5(261/295)  VH3-21           ..................................................................  210

ID%                              <-----------------------FWR3-----------------------
              Ha5-1(5)2.1 211   S  R  D  N  S  K  N  T  L  Y  L  Q  M  N  S  L  R  A  E  D  T  A  V
                                TCCAGAGACAATTCCAAGAACACGCTGTATCTGCAAATGAACAGCCTGAGAGCTGAGGACACGGCTGTGT  280
98.3(291/296)  VH3-30  211      S  R  D  N  S  K  N  T  L  Y  L  Q  M  N  S  L  R  A  E  D  T  A  V
90.9(10/11)    D2-21            ..................................................................  280
```

Figure 4C-2

```
                    JH6       ------------------------------------------------
96.6(57/59)                        Y Y C A R    D G G D Y V R Y H Y Y G M D V W G Q G
ID%
                    Ha5-1(5)2.1  281 ATTACTGTGCCAGA GATGGGGGTGACTATGTCCGCTACCACTACTACGGTATGGACGTCTGGGGCCAAGG  350
98.3(291/296)       VH3-30       281 ..............                                                          296
90.9(10/11)         D2-21        10  --------------  ...........T..............................             20
96.6(57/59)         JH6          5   --------------  ....................................T...........G...... 40
ID%
                    Ha5-1(5)2.1  351 GACCACGGTCACCGTCTCCTCAG  373
                                     T T V T V S S
98.3(291/296)       VH3-30
90.9(10/11)         D2-21        41  .......................  63
96.6(57/59)         JH6
```

Figure 4D-1 Alignment of Ha5-1(5)2.1 VL to human Ig germline

```
                                  <----------------------FWR1----------------------->   <
                                   D I Q M T Q S P S T L S A S I G D R V T I T C
                    Ha5-1(5)2.1  43  GACATCCAGATGACCCAGTCTCCATCCTCTCTGTCTGCATCTATAGGAGACAGAGTCACCATCACTTGC  112
                                   D I Q M T Q S P S T L S A S V G D R V T I T C
95.1(270/284)       A20          1   ....................................G..........................  70
100(38/38)          JK4                                                                                  -
ID%
                                    <--------CDR1----------->                      <--------FWR2--------
                                     R A S Q G I S Y Y L A     W Y Q Q K P G K I P K L L
                    Ha5-1(5)2.1  113 GGGCGAGTCAGGGCATTAGCTATTATTTAGCC TGGTATCAGCAGAAACCGGGGAAAATTCCTAAGCTCCT  182
                                     R A S Q G I S N Y L A     W Y Q Q K P G K V P K L L
95.1(270/284)       A20          71  ......................A.........  ....................A......G........  140
100(38/38)          JK4
ID%
                                    -->  <--------CDR2-------->            <
                                       I Y   D T S S L Q S            G V P S R F S G S R S G T D
                    Ha5-1(5)2.1  183 GATCTAT GATACATCCTCTTTGCAATCA -GGGGTCCCATCTCGATTCAGTGGCAGTAGATCTGGGACAGA  251
                                       I Y   A A S T L Q S            G V P S R F S G S G S G T D
95.1(270/284)       A20          141 ....... ..C.G....A...........  ...................................G....
```

Figure 4D-2

```
                                                                                                                              209
ID%                                                                L  S  L  T  I  S  S  L  Q  P  E  D  V  A  T  Y  Y  C   Q  R  Y  D  S
100(38/38)      JK4                                                ----------------FWR3------------------------------>
Ha5-1(5)2.1    252 TCTCTCTCCACCATCAGCAGCCTGCAGCCTGAGGCTGAAGATGTTGCAACTTATTACTGT CAAAGGTATGACAGT              321
                                                                   F  T  L  T  I  S  S  L  Q  P  P  E  D  D  V  A  T  Y  Y  C   Q  K  Y  N  S
95.1(270/284)  A20  210  .T.A........                                                                    ...A....A......         279
100(38/38)     JK4
ID%

A  P  L  T  F  G  G  G  T  K  V  E  I  K
Ha5-1(5)2.1    322 GCCCCGCTCACTTCCGGCGGAGGGACCAAGGTGGAGATCAAAC                 364
95.1(270/284)  A20  280  ------A--P--------------------------                        284
100(38/38)     JK4    1                                                              38
ID%
```

Figure 4E-1 Alignment of Ha5-3(1,4)2.1 VH to human Ig germline

```
                                                                                                                              ----FWR1----------------------------->
ID%                                                                Q  V  Q  L  V  E  S  G  G  G  V  V  Q  P  G  R  S  L  R  L  S  C  A
Ha5-3(1,4)2.1    1  CAGGTGCAGCTGGTGGAGTCTGGGGGAGGCGTGGTCCAGCCTGGGAGGTCCCTGAGACTCTCCTGTGCAG                                        59
VH3-33           1  Q  V  Q  L  V  E  S  G  G  G  V  V  Q  P  G  R  S  L  R  L  S  C  A
98.9(282/285)    VH3-33  .......................................................................     70
100(11/11)       D1-26
97.8(45/46)      JH3
ID%
                                                                   <---CDR1---->      <------------              ----FWR2---------
                                                                   A  S  G  F  T  F  S   S  Y  G  M  H   W  V  R  Q  A  P  G  K  G  L  E  W
Ha5-3(1,4)2.1   60  CGTCTGGATTCACCTTCAGT AGCTATGGCATGCAC TGGGTCCGCCAGGCTCCAGGCAAGGGGCTGGAGTG                129
                    A  S  G  F  T  F  S   S  Y  G  M  H   W  V  R  Q  A  P  G  K  G  L  E  W
VH3-33          71  ........................                                                            140
D1-26
JH3
                                                                   <------------CDR2------------>                   <-----
                                                                   V  A   V  I  W  Y  D  G  R  N  K  F  Y  A  D  S  V  K  G   R  F  T  V
Ha5-3(1,4)2.1  130  GGTGGCA GTTATATGGTATGATGGAAGAAATAAATTCTATGCAGACTCCGTGAAGGGC CGATTCACCGTC         199
                    V  A   V  I  W  Y  D  G  S  N  K  Y  Y  A  D  S  V  K  G   R  F  T  I
```

S  R  D  N  S  K  N  T  L  Y  L  Q  M  N  S  L  R  A  E  D  T  A  V
Ha5-3(1,4)2.1       200  TCCAGAGACAATTCCAAGAACACGCTGTATCTGCAAATGAACAGCCTGAGAGCCGAGGACACGGCTGTGT  269
                              S  R  D  N  S  K  N  T  L  Y  L  Q  M  N  S  L  R  A  E  D  T  A  V 98.9(282/285)  VH3-33    211  ............................................................... 280
100(11/11)     D1-26          -----------------------------------------------------------------
97.8(45/46)    JH3            -----------------------------------------------------------------
ID%
                                                       ---->
                              Y  Y  C  A  R     D  W  G  A  T  M  A  F  D  I  W  G  Q  G  T  M  V  T  V
Ha5-3(1,4)2.1       270  ATTACTGTGCCAGA GATTGGGGAGCTACTATGGCTTTTGATATCTGGGGCCAAGGGACAAATGGTCACCGT  339
                              Y  Y  C  A  R 98.9(282/285)  VH3-33    281  ...............                                                  296
100(11/11)     D1-26     9    ---                                                              19
97.8(45/46)    JH3       4    ...........G...........                                          41
ID%
                              S  S
Ha5-3(1,4)2.1       340  CTCTTCAG  347
98.9(282/285)  VH3-33         --------
100(11/11)     D1-26          --------
97.8(45/46)    JH3       42   ........ 49
ID%
```

Figure 4F-1 Alignment of Ha5-3(1,4)2.1 VL to human Ig germline.

```
ID%
                          <-----------------------FWR1---------------------------> <----
                         Q  S  V  L  T  Q  P  P  S  A  S  K  T  P  G  Q  R  V  T  I  S  C    S
Ha5-3(1,4)2.1    42  CAGTCTGTGCTGACTCAGCCACCCTCAGCCTCTAAGACCCCCGGCCAGAGGGTCACCATCTCTTGT TCTG  111
                         Q  S  V  L  T  Q  P  P  S  A  S  G  T  P  G  Q  R  V  T  I  S  C    S 97.6(284/291)  V1-16  1  ..............................GG..........................  .....  70
100(38/38)     JL1       --------------------------------------------                 -FWR2--
ID%
                         ------CDR1----------->  <---------
                         G  S  S  N  I  G        S  N  T  V  N     W  Y  Q  Q  L  P  G  T  A  P
```

Figure 4F-2

```
Ha5-3(1,4)2.1  112  GAAGCAGCTCCAACATCGG---AA---GTAATACTGTCAAC TGGTACCACAGTCCCAGGAACGGCCCC  175
                    G  S  S  S  N  I  G     S  N  T  V  N    W  Y  Q  Q  L  P  G  T  A  P
97.6(284/291)  V1-16  71  ..................................A...                        .G....                                134
100(38/38)     JL1
ID%                       <-------->  <-----CDR2----->
                          K  L  L  I  F  G  N  N  Q  R  P  S   G  V  P  D  R  F  S  G  S  K  S
Ha5-3(1,4)2.1  176  CAAACTCCTCCATCTTT GGTAATAATCAGCGGCCTCA GGGGTCCCTGACCGATTCTCTGGCTCCAAGTCT  245
                    K  L  L  I  Y  S  N  N  Q  R  P  S   G  V  P  D  R  F  S  G  S  K  S
97.6(284/291)  V1-16  135  ...............A..A.....                                              204
100(38/38)     JL1
ID%                                     <-----FWR3----->
                          G  T  S  A  S  L  A  I  S  G  L  Q  S  E  D  E  A  D  Y  Y  C    A  A
Ha5-3(1,4)2.1  246  GGCCACCTCAGCCTCCCTGGCCATCAGTGGTCTCCAGTCTGAGGATGAGGCTGATTATTACTGT GCAGCAT  315
                    G  T  S  A  S  L  A  I  S  G  L  Q  S  E  D  E  A  D  Y  Y  C    A  A
97.6(284/291)  V1-16  205  ........................G..........                                   274
100(38/38)     JL1
ID%                                          <----------->
                          W  D  D  S  L  N  Y  V  F  G  T  G  T  K  V  T  V  L
Ha5-3(1,4)2.1  316  GGGATGACAGCCTGAATTATGTCTTCGGAACTGGGACCAAGGTCACCGTCCTAG  369
                    W  D  D  S  L  N
97.6(284/291)  V1-16  275  .....                                                           291
100(38/38)     JL1  1  ......                                                          38
ID%
```

Figure 4G-1 Alignment of Ha5-3(1,4)7.1 VH to human Ig germline.

```
                          <-----------FWR1----------->
                          Q  V  Q  L  V  E  S  G  G  G  V  V  Q  P  G  R  S  L  R  L  S  C  A
Ha5-3(1,4)7.1  1    CAGGTGCAGCTGGTGGAGTCTGGGGGAGGCGTGGTCCAGCCTGGGAGGTCCCTGAGACTCTCCTGTGCAG  70
                    Q  V  Q  L  V  E  S  G  G  G  V  V  Q  P  G  R  S  L  R  L  S  C  A
99.3(283/285)  VH3-33  1   ...................................                                   70
95.0(19/20)    D5-12
98.4(61/62)    JH6
ID%                                       <----CDR1---->                    <-----FWR2----->
                          A  S  G  F  T  F  S  S  Y  G  M  H   W  V  R  Q  A  P  G  K  G  L  E  W
Ha5-3(1,4)7.1  71   CGTCTGGATTCACCTTCAGT AGCTATGGCATGCAC TGGGTCCGCCAGGCTCCAGGCAAGGGGCTGGAGTG  129
                    A  S  G  F  T  F  S  S  Y  G  M  H   W  V  R  Q  A  P  G  K  G  L  E  W
99.3(283/285)  VH3-33  71  ......................                                                 140
```

Figure 4G-2

```
                                                                                                                                210
95.0(19/20)    D5-12        ---------------------------|---------------------------|---------------------------|
98.4(61/62)    JH6                                                                                              210
ID%                                     <----------CDR2----------->                              <--  R  F  T  I
                                 V  A   V  I  W  Y  D  G  S  N  K  Y  Y  A  D  S  V  K  G   R  F  T  I
               Ha5-3(1,4)7.1 141 GGTGGCA GTTATATGGTATGATGGAAGTAATAAATACTATGCAGACTCCGTGAAGGGC CGATTCACCATC
99.3(283/285)  VH3-33        141 ..........................................................  ............
95.0(19/20)    D5-12             ---------------------------|---------------------------|  ------------
98.4(61/62)    JH6               ---------------------------|---------------------------|  ------------
                                                                                                                280
                                                                      <----------FWR3---------
                                 S  R  D  N  S  K  N  T  L  Y  L  Q  M  N  S  L  R  A  E  D  T  A  V
               Ha5-3(1,4)7.1 211 TCCAGAGAGACAATTCCAAGAACACCGCTGTATCTGCAAATGAACAGCCTGAGAGCCGAAGACACGGCTGTCT  280
99.3(283/285)  VH3-33        211 ...................................................................G...
95.0(19/20)    D5-12             -----------------------------------------------------------------------
98.4(61/62)    JH6                                              S  R  D  N  S  K  N  T  L  Y  L  Q  M  N  S  L  R  A  E  D  T  A  V
ID%
                                 ----->                                                                                          350
                                    Y  Y  C  A  R   D  R  Y  S  G  Y  G  Y  Y  Y  Y  Y  Y  G  M  D  V  W  G  Q
               Ha5-3(1,4)7.1 281 ATTACTGTGCCAGAGA GATCGATATAGTGGCTACGGTTACTACTACTACTACGGTATGGACGTCTGGGGCCA  296
99.3(283/285)  VH3-33        281 ................                                                           23
95.0(19/20)    D5-12         4                    ............A....                                           37
98.4(61/62)    JH6           2                                     ..................................G...
                                    Y  Y  C  A  R
ID%

G  T  T  V  T  V  S  S
               Ha5-3(1,4)7.1 351 AGGGACCACGGTCACCGTCTCCTCAG 376
99.3(283/285)  VH3-33        
95.0(19/20)    D5-12         
98.4(61/62)    JH6           38  ..........................  63
ID%
```

Figure 4H Alignment of Ha5-3(1,4)7.1 VL to human Ig germline.

```
                         <------------------------FWR1------------------------>  <
                          D  I  Q  M  T  Q  S  P  S  S  L  S  A  S  V  G  D  R  V  T  I  T  C
         Ha5-3(1,4)7.1 13 GACATCCAGATGACCCAGTCTCCATCCTCACTGTCTGCATCTGTAGGAGACAGAGTCACCATCACTTGT    82
ID%                       D  I  Q  M  T  Q  S  P  S  S  L  S  A  S  V  G  D  R  V  T  I  T  C
98.2(279/284) L1        1 ....................................................................    70
100(38/38)    JK3         -------------------------------------------------------------------

<---------------CDR1--------------->  <-----------------FWR2-----------
                          R  A  S  Q  D  I  S  N  Y  L  A     W  F  Q  Q  K  P  G  K  A  P  K  S  L
         Ha5-3(1,4)7.1 83 GGGCGAGTCAGGACATTAGCAATTATTTAGCC TGGTTTCAGCAGAAACCAGGGAAAGCCCCTAAGTCCCT   152
ID%                       R  A  S  Q  G  I  S  N  Y  L  A     W  F  Q  Q  K  P  G  K  A  P  K  S  L
98.2(279/284) L1       71 .....................G..............................................   140
100(38/38)    JK3         ------------------------------------

<-------CDR2-------->  <-----------------------------
                           I  Y  A  A  S  S  L  H  S     G  V  P  S  K  F  S  G  S  G  S  G  T  D
        Ha5-3(1,4)7.1 153 GATCTAT GCTGCATCCAGTTTGCACAGT GGGGTCCCATCAAGGTTCAGCGGCAGTGGATCTGGGACAGAT   222
ID%                        I  Y  A  A  S  S  L  Q  S     G  V  P  S  R  F  S  G  S  G  S  G  T  D
98.2(279/284) L1      141 ........................A...........................G...............   210

--------FWR3-------------------------------------------------->
                           F  T  L  T  I  S  S  L  Q  P  E  D  F  A  T  Y  Y  C     Q  Q  Y  T  I
        Ha5-3(1,4)7.1 223 TTCACTCTCACCATCAGCAGCCTGCAGCCTGAAGATTTTGCAACTTATTACTGC CAACAGTATACTATTT   292
ID%                        F  T  L  T  I  S  S  L  Q  P  E  D  F  A  T  Y  Y  C     Q  Q  Y  N  S
98.2(279/284) L1      211 ...................................................................A..G..   280

Y  P  F  T  F  G  P  G  T  K  V  D  I  K
        Ha5-3(1,4)7.1 293 ACCCATTCACTTTCGGCCCTGGGACCAAAGTGGATATCAAAC   334
ID%                        Y  P
98.2(279/284) L1      281 ..........                                   284
100(38/38)    JK3       1 ----------                                    38
```

Figure 4I-1 Alignment of Ha5-3(3,5)37.1 VH to human Ig germline.

Figure 4I-2

| | | |
|---|---|---|
| | Ha5-3(3,5)37.1 | 339 QCAAGGGACCACGGTCACCGTCTCCTCAG 367 |
| ID% | | |
| 99.3(290/292) | VH4-59 | ------------------------------- |
| 95.5(21/22) | D3-10 | ------------------------------- |
| 98.0(48/49) | JH6 | 35 G............................ 63 |

Figure 4J-1 Alignment of Ha5-3(3,5)37.1 VL to human Ig germline.

```
ID%                         <---------------------------FWR1-------------------------->
                            D   I   V   M   T   Q   S   P   L   S   L   P   V   T   P   G   E   P   A   S   I   S   C
              Ha5-3(3,5)37.1  1 GATATTGTGATGACTCAGTCTCCACTCTCCCTGCCCGTCACCCCTGGAGAGCCGGCCTCCATCTCCTGC   70
                            D   I   V   M   T   Q   S   P   L   S   L   P   V   T   P   G   E   P   A   S   I   S   C
98.7(295/299) A19           1 ............................................................A         70
94.7(36/38)   JK2
ID%                         <----------CDR1---------->
                            R   S   S   Q   S   L   L   H   S   N       G   H   N   Y   L   D       W   Y   L   Q   K   P   G
              Ha5-3(3,5)37.1 71 GGTCTAGTCAGAGCCTCCTGCATAGTAATG---GACACAACTATTTGGAT TGGTACCTGCAGAAGCCAGG 137
                            R   S   S   Q   S   L   L   H   S   N       G   Y   N   Y   L   D       W   Y   L   Q   K   P   G
98.7(295/299) A19          71 ..........................T.........                                  137
94.7(36/38)   JK2
ID%                         <--FWR2--------------->   <-------CDR2-------->
                            Q   S   P   H   L   L   I   Y       L   G   S   N   R   D   S           G   V   P   D   R   F   S   G
              Ha5-3(3,5)37.1 138 GCAGTCTCCACACTCCTGATCTAT TTGGGTTCTAATCGGGACTCC    GGGGTCCCTGACAGGTTCAGTGGC 207
                            Q   S   P   Q   L   L   I   Y       L   G   S   N   R   A   S           G   V   P   D   R   F   S   G
98.7(295/299) A19         138 ........Q.G..........................C..                              207
94.7(36/38)   JK2
ID%                         <---------FWR3
                            S   G   S   G   T   D   F   T   L   K   I   S   R   V   E   A   E   D   V   G   V   Y   Y
              Ha5-3(3,5)37.1 208 AGTGGATCAGGCACAGATTTTACACTGAAAATCAGCAGAGAGGCTGAGGATGTGGGGTTTATTACT 277
                            S   G   S   G   T   D   F   T   L   K   I   S   R   V   E   A   E   D   V   G   V   Y   Y
98.7(295/299) A19         208 .................................................                    277
94.7(36/38)   JK2
ID%                         ---->
                            C   M   Q   A   L   Q   T   P   C   S   F   G   Q   G   T   K   L   E   I   K
```

Figure 4J-2

```
                    Ha5-3(3,5)37.1   278  GC ATGCAAGCTCTACAAATTCCTGTCAGTTTTGGCCAGGGGACCAAGCTGGAGATCAAAC  337
                                          C  M  Q  A  L  Q  T  P
98.7(295/299)       A19              278  .. ...........................C........                        299
94.7(36/38)         JK2              2    -- .........................,A.C........                        39
```

Figure 4K-1 Alignment of Ha5-4(2,5)13.1 VH to human Ig germline.

```
                                              <------------------------FWR1-------------------------->
                    Ha5-4(2,5)13.1  1    CAGGTGCAGCTGGTGGAGTTTGGGGGAGGCGTGGTCCAGCCTGGGAGGTCCCTGAGACTCTCCTGTGCAG  70
                                         Q  V  Q  L  V  E  F  G  G  G  V  V  Q  P  G  R  S  L  R  L  S  C  A
98.6(292/296)       VH3-33           1   ............C........................................................  70
100(16/16)          D6-19
97.9(47/48)         JH4
ID%                                                                    <----CDR1------>
                                         A  S  G  F  T  F  R    S  Y  G  M  H    W  V  R  Q  A  P  G  K  G  L  E  W
                    Ha5-4(2,5)13.1  71   CGTCTGGATTCACCTTCAGA AGCTATGGCATGCAC TGGGTCCGCCAGGCTCCAGGCAAGGGGCTGGAGTG  140
                                         A  S  G  F  T  F  S    S  Y  G  M  H    W  V  R  Q  A  P  G  K  G  L  E  W
98.6(292/296)       VH3-33           71  ..................T..  .............  ...................................  140
100(16/16)          D6-19
97.9(47/48)         JH4
ID%                                               <--------------------------CDR2----------------------->
                                         V  A    V  I  W  Y  D  G  S  N  K  Y  Y  Y  A  D  S  V  K  G    R  S  T  I
                    Ha5-4(2,5)13.1  141  GGTGGCA GTTATATGGTATGATGGAAGTAATAAATACTATGCAGACTCCGTGAAGGGC CGATCCACCATC  210
                                         V  A    V  I  W  Y  D  G  S  N  K  Y  Y  Y  A  D  S  V  K  G    R  F  T  I
98.6(292/296)       VH3-33          141  .......  ..........................................................  ....T.......  210
100(16/16)          D6-19
97.9(47/48)         JH4
ID%                                      <--------------------------FWR3--------------------------->
                                         S  R  D  N  S  K  N  T  L  Y  L  Q  M  N  S  L  R  A  E  D  T  A  V
                    Ha5-4(2,5)13.1  211  TCCAGAGACAACTCCAAGAACACCCTGTATCTGCAAATGAACAGCCTGAGAGCCGAGGACACGGCTGTGT  280
                                         S  R  D  N  S  K  N  T  L  Y  L  Q  M  N  S  L  R  A  E  D  T  A  V
98.6(292/296)       VH3-33          211  .........T...........................................................  280
100(16/16)          D6-19
97.9(47/48)         JH4
ID%                                      ------>
```

Figure 4K-2

```
              Ha5-4(2,5)13.1   281  Y Y C A R   D G V A V A G T D Y F D Y W G Q G T L
                                    ATTACTGTCGAGA GATGGGGTAGCAGTGGCTGGTGTACAGACTTACTTTGACTACTGGGGCCAGGGAACCCT  350

98.6(292/296)  VH3-33          281                Y Y C A R                                                  296
100(16/16)     D6-19             6  -------------                                                             21
97.9(47/48)    JH4               1  -------------                                                    .A.....  31
ID%

V T V S S
              Ha5-4(2,5)13.1   351  GGTCACCGTCCTCAG  367

98.6(292/296)  VH3-33
100(16/16)     D6-19
97.9(47/48)    JH4              32  ...............   48
ID%
```

Figure 4L-1 Alignment of Ha5-4(2,5)13.1 VL to human Ig germline.

```
                                    <------------------------FWR1------------------------>  <
              Ha5-4(2,5)13.1   24   D I Q M T Q S P S S L S A S V G D R V T I T C
                                    GACATCCAGATGACCCAGTCTCCATCCTCCCTGTCTGCATCTGTAGGAGACAGAGTCACCATCACTTGC  93

99.3(282/284)  O12              1   D I Q M T Q S P S S L S A S V G D R V T I T C          .
97.4(37/38)    JK4                                                                         -
ID%

<--------------CDR1------------>  <--------FWR2-------->
              Ha5-4(2,5)13.1   94   R A S Q S I S S H L N             W Y Q Q K P G K A P K L L
                                    GGGCAAGTCAGAGCATTAGCAGCCATTTAAAT TGGTATCAGCAGAAACCAGGGAAAGCCCCTAAGCTCCT  163

99.3(282/284)  O12             71   R A S Q S I S S Y L N ......T..   W Y Q Q K P G K A P K L L  140
97.4(37/38)    JK4
ID%

<---->  <---CDR2---->  <                   FWR3
              Ha5-4(2,5)13.1  164   I Y     V A S S L Q S    G V P S R F S G S G S G T D
                                    GATCTAT GTTGCATCCAGTTTGCAAAGT GGGGTCCCATCCAAGGTTCAGTGGCAGTGGATCTGGGACAGAT  233

99.3(282/284)  O12            141   I Y .C. A A S S L Q S    G V P S R F S G S G S G.T D    210
97.4(37/38)    JK4
ID%

-----FWR3----->
              Ha5-4(2,5)13.1       F T L T I S S L Q P E D F A T Y Y C   Q Q S Y S
```

Figure 4L-2

```
Ha5-4(2,5)13.1   234  TTCACTCTCACCATCAGCAGTCTGCAACCTGAAGATTTTGCAACTTACTACTGT CAACAGAGTTACAGTA  303
                      F  T  L  T  I  S  S  L  Q  P  E  D  F  A  T  Y  Y  C  Q  Q  S  Y  S
99.3(282/284)    O12   211  ............................................................... ................  280
97.4(37/38)      JK4        ---------------------------------------------------------------  ----------------

T  P  L  I  F  G  G  G  T  K  V  E  I  K
Ha5-4(2,5)13.1   304  CCCCCCTCATTTTCGGCGGAGGGACCAAGGTGGAGATCAAAC  345
                      T  P
99.3(282/284)    O12   281  ....C..................................... 284
97.4(37/38)      JK4     1  ------..................................... 38
ID%
```

Figure 4M-1 Alignment of Ha5-4(2,5)34.1 VH to human Ig germline.

```
                      <---------------------------FWR1---------------------------->
                      E  V  Q  L  L  E  S  G  G  G  L  V  Q  P  G  G  S  L  R  L  S  C  A
Ha5-4(2,5)34.1     1  GAGGTGCAGCTGTTGGAGTCTGGGGGAGGCTTGGTACAGCCTGGGGGGTCCCTGAGACTCTCCTGTGCAG  70
                      E  V  Q  L  L  E  S  G  G  G  L  V  Q  P  G  G  S  L  R  L  S  C  A
VH3-23             1  ............................................................... 70
D6-19
JH6
                      A  S  T  F  T  F  S         S  Y  A  M  S    W  V  R  Q  A  P  G  K  G  L  E  W
Ha5-4(2,5)34.1    71  CCTCTACATTCACCTTTAGC AGCTATGCCATGAGC TGGGTCCGCCAGGCTCCAGGGAAGGGGCTGGAGTG  140
                      A  S  G  F  T  F  S         S  Y  A  M  S    W  V  R  Q  A  P  G  K  G  L  E  W
VH3-23            71  .....GG.............    ............    ............................. 140
D6-19
JH6
                      <---CDR1--->         <---FWR2--->
98.3(291/296)
100(11/11)
98.0(49/50)
ID%
                      V  S    A  F  S  G  R  G  G  S  T  Y  Y  A  D  S  V  K  G    R  F  T  I
Ha5-4(2,5)34.1   141  GGTCTCA GCTTTTAGTGGTCGTGGTGGTAGCACATACTACGCAGACTCCGTGAAGGGC CGGTTCACCATC  210
                      V  S    A  I  S  G  S  G  G  S  T  Y  Y  A  D  S  V  K  G    R  F  T  I
VH3-23           141  ........ ..A...........A................................. ............  210
D6-19
JH6
                      <---CDR2--->                    <---FWR3
98.3(291/296)
100(11/11)
98.0(49/50)
ID%
                      S  R  D  N  S  K  N  T  L  F  L  Q  M  N  S  L  R  A  E  D  T  A  V
Ha5-4(2,5)34.1   211  TCCAGAGACAATTCCAAGAACACGCTGTTTCTGCAAATGAACAGCCTGAGAGCCGAGGACACGGCCGTAT  280
98.3(291/296)   VH3-23
100(11/11)      D6-19
98.0(49/50)     JH6
ID%
```

Figure 4M-2

```
                                    S  R  D  N  S  K  N  T  L  Y  L  Q  M  N  S  L  R  A  E  D  T  A  V
98.3(291/296)  VH3-23         211  ............................................................A.....................  280
100(11/11)     D6-19
98.0(49/50)    JH6
ID%
                                    Y  Y  C  A  K       D  S  S  G  P  L  L  G  Y  G  M  D  V  W  G  Q  G  T  T
Ha5-4(2,5)34.1                281  ATTACTGTGCGAAA GATAGCAGTGGCCCCCTGCTTGGGCTACGGTATGGACGTCTGGGGCCAAGGGACCAC  350
                                    Y  Y  C  A  K
98.3(291/296)  VH3-23         281  ..............   ..................................................   296
100(11/11)     D6-19            5  ..............                                                       15
98.0(49/50)    JH6             14                 ...................................G..............   46
ID%

V  T  V  S  S
Ha5-4(2,5)34.1                351  GGTCACCGTCTCCTCAG  367
98.3(291/296)  VH3-23
100(11/11)     D6-19
98.0(49/50)    JH6             47  ................   63
ID%
```

Figure 4N-1 Alignment of Ha5-4(2,5)34.1 VL to human Ig germline.

```
                                 <----------FWR1----------------------------------------->  <---
                                  S  Y  E  L  T  Q  P  P  S  V  S  V  S  P  G  Q  T  A  S  I  T  C     S
Ha5-4(2,5)34.1              1   TCCTATGAGCTGACTCAGCCACCCTCAGTGTCCGTGTCCCCAGGACACAGCCAGCATCACCTGC  TCTG  70
ID%
                                  S  Y  E  L  T  Q  P  P  S  V  S  V  S  P  G  Q  T  A  S  I  T  C     S
98.2(277/282)  V2-1         1   ................................................................  ....  70
97.4(37/38)    JL2
ID%
                                 -----CDR1--------->    <---------------FWR2-------->         <---
                                  G  D  K  V  G  D  K  Y  A  C     W  Y  Q  Q  K  P  G  Q  S  P  V  L  V  I
Ha5-4(2,5)34.1             71   GAGATAAAGTGGGGGATAAATATGCTTGT TGGTATCAGCAGAAGCCAGGCCAGTCCCCTGTACTGGTCAT  140
                                  G  D  K  L  G  D  K  Y  A  C     W  Y  Q  Q  K  P  G  Q  S  P  V  L  V  I
98.2(277/282)  V2-1        71   ........T.................C. ..................................G.......  140
97.4(37/38)    JL2
ID%
                                 ---CDR2------>    <----------------------------------------
                                  Y  Q  D  S  K  R  P  S     G  I  P  E  R  F  S  G  S  N  S  G  N  T  A
Ha5-4(2,5)34.1            141   CTAT CAAGATAGCAAGCGGCCCCTCA  GGGATCCCTGAGCGATTCTCTGGCTCCAATTCTGGAAACACAGCC  210
                                  Y  Q  D  S  K  R  P  S     G  I  P  E  R  F  S  G  S  N  S  G  N  T  A
```

Figure 4N-2

```
                                                                                                         210
98.2(277/282)  V2-1                141  ....                     ........................C.....G........
97.4(37/38)    JL2                      ----                     ---------------------------------------
ID%                                      ----FWR3----------------------->
                                         T  L  T  I  S  G  T  Q  A  M  D  E  A  D  Y  Y  C    Q  A  W  D  S  S
Ha5-4(2,5)34.1                     211  ACTCTGACCATCAGCGGGACCCAGGCTATGGATGAGGCTGACTATTACTGT CAGGCGTGGGACAGCAGCA  280
                                         T  L  T  I  S  G  T  Q  A  M  D  E  A  D  Y  Y  C    Q  A  W  D  S  S
98.2(277/282)  V2-1                211  ----------------------------------------------------- --------------------  280
97.4(37/38)    JL2                      ----------------------------------------------------- --------------------
ID%
                                         T  Y  V  V  F  G  G  G  T  K  L  T  V  L
Ha5-4(2,5)34.1                     281  CTTATGTGGTATTCGGCGGAGGGACCAAACTGACCGTCCTAG                           322
                                         T
98.2(277/282)  V2-1                281  .........................................                          282
97.4(37/38)    JL2                   1  ............G.............                                          38
ID%
```

Figure 4O-1 Alignment of Ha5-7acd4.1 VH to human Ig germline.

```
                                         <-----------------------------------FWR1-------------------------->
                                         Q  V  Q  L  V  E  S  G  G  G  V  V  Q  P  G  R  S  L  R  L  S  C  A
Ha5-7acd4.1                          1  CAGGTGCAGCTGGTGGAGTCTGGGGGAGGCGTGGTCCAGCCTGGGAGGTCCCTGAGACTCTCCTGTGCAG   70
                                         Q  V  Q  L  V  E  S  G  G  G  V  V  Q  P  G  R  S  L  R  L  S  C  A
ID%
100(296/296)   VH3-33                1  ---------------------------------------------------------------------   70
100(20/20)     D5-12
98.4(62/63)    JH6
                                         <----------->  <-----CDR1------>                      <----FWR2----
                                         A  S  G  F  T  F  S    S  Y  G  M  H    W  V  R  Q  A  P  G  K  G  L  E  W
Ha5-7acd4.1                         71  CGTCTGGATTCACCTTCAGT  AGCTATGGCATGCAC  TGGGTCCGCCAGGCTCCAGGCAAGGGGCTGGAGTG  140
                                         A  S  G  F  T  F  S    S  Y  G  M  H    W  V  R  Q  A  P  G  K  G  L  E  W
ID%
100(296/296)   VH3-33               71  ------------------------------------------------------------------------  140
100(20/20)     D5-12
98.4(62/63)    JH6
                                                                   <------CDR2------->                <-----
                                         V  A    V  I  W  Y  D  G  S  N  K  Y  Y  A  D  S  V  K  G    R  F  T  I
Ha5-7acd4.1                        141  GGTGGCA GTTATATGGTATGATGGAAGTAATAAATACTATGCAGACTCCGTGAAGGGC CGATTCACCATC  210
                                         V  A    V  I  W  Y  D  G  S  N  K  Y  Y  A  D  S  V  K  G    R  F  T  I
ID%
100(296/296)   VH3-33              141  ------- ----------------------------------------------------- ............  210
100(20/20)     D5-12
```

Figure 4O-2

```
                                                             -----------------FWR3-----------------
98.4(62/63)     JH6          ---------------------------  ---------------------------------------------
ID%
                             S  R  D  N  S  K  N  T  L  Y  L  Q  M  N  S  L  R  A  E  D  T  A  V
                Ha5-7acd4.1 211 TCCAGAGACAATTCCAAGAACACGCTGTATCTGCAAATGAACAGCCTGAGAGCCGAGGACACGGCTGTGT 280
                             S  R  D  N  S  K  N  T  L  Y  L  Q  M  N  S  L  R  A  E  D  T  A  V
100(296/296)    VH3-33   211 ..............................................................  280
100(20/20)      D5-12
98.4(62/63)     JH6
ID%
                                  ------>
                             Y  Y  C  A  R      D  R  Y  S  G  Y  D  Y  Y  Y  Y  Y  G  M  D  V  W  G  Q
                Ha5-7acd4.1 281 ATTACTGTGCGAGA GATCCGATATAGTGGCTACGATTACTACTACTACTACGGTATGGACGTCTGGGGCCA 350
                             Y  Y  C  A  R
100(296/296)    VH3-33   281 ..............
100(20/20)      D5-12    4   ...............
98.4(62/63)     JH6      1                   ..........................................G...  37
ID%
                             G  T  T  V  T  V  S  S
                Ha5-7acd4.1 351 AGGGACCACGGTCACCGTCTCCTCAG 376
100(296/296)    VH3-33
100(20/20)      D5-12
98.4(62/63)     JH6      38  ........................... 63
```

Figure 4P-1 Alignment of Ha5-7acd4.1 VL to human Ig germline.

```
                                    <-------------------------FWR1------------------------->  <-
ID%                                 D  I  Q  M  T  Q  S  P  S  S  L  S  A  S  V  G  D  R  V  T  I  T  C
               Ha5-7acd4.1 25 GACATCCAGATGACCCAGTCTCCATCCTCACTGTCTGCATCTGTAGGAGACAGAGTCACCATCACTTGT 94
                                    D  I  Q  M  T  Q  S  P  S  S  L  S  A  S  V  G  D  R  V  T  I  T  C
96.1(274/285)  L1         1  ...................................................A............. 70
97.3(36/37)    JK3
ID%
                                    --CDR1---------------->    <---------FWR2--------->
                                    R  A  S  Q  V  I  Y  N  Y  L  A      W  F  Q  Q  K  P  G  K  A  P  K  S  L
               Ha5-7acd4.1 95 GGGCGAGTCAGGTCATTTACAATTATTTAGCC TGGTTTCAGCAGAAACCAGGAAAGGCCCCTAAGTCCCT 164
                                    R  A  S  Q  G  I  S  N  Y  L  A      W  F  Q  Q  K  P  G  K  A  P  K  S  L
96.1(274/285)  L1         71 .........G....AG...............  ....................................... 140
97.3(36/37)    JK3
```

Figure 4P-2

```
ID%                                    ------>  <-----CDR2----->  <----------
              Ha5-7acd4.1  165  GATCTAT  GGTGCATCCAGTTGCCACAGT  GGGGTCCCATCAAAGTTCAGCGGGCAGTGGATCTGGGACAGAA  234
                                  I  Y     G  A  S  S  L  E  S    G  V  P  S  K  F  S  G  S  G  S  G  T  E
96.1(274/285)  L1          141           ........C............  ............A...........................T  210
97.3(36/37)    JK3                I  Y     A  A  S  S  L  Q  S    G  V  P  S  R  F  S  G  S  G  S  G  T  D ID%                              -----FWR3------>
              Ha5-7acd4.1  235  TTCACTCTCACCATCAGCAGCCTGCAGCCTGAAGATTTTGCAACTTATTACTGC  CAACAATATACTATTT  304
                                  F  T  L  T  I  S  S  L  Q  P  E  D  F  A  T  Y  Y  C    Q  Q  Y  T  I
96.1(274/285)  L1          211  ......................................................  .....G....A.G..  280
97.3(36/37)    JK3                F  T  L  T  I  S  S  L  Q  P  E  D  F  A  T  Y  Y  C    Q  Q  Y  N  S ID%
              Ha5-7acd4.1  305  ACCCTTTCTTCTTCGGCCCTGGGACCAAAGTGGATATCAAAC  346
                                  Y  P  F  S  F  G  P  G  T  K  V  D  I  K
96.1(274/285)  L1          281  ......A...................................  285
97.3(36/37)    JK3            2    Y  P                                        38
```

Figure 4Q-1 Alignment of Ha5-7acd20.1.1 VH to human Ig germline.

```
ID%                                     <----------------------FWR1-----------------------
              Ha5-7acd20.1.1  1   CAGGTCCAGCTGGTGGAGTCTGGGGGAGGCGTGGTCCAGCCTGGGAGGTCCCTGAGACTCTCCTGTGCAG  70
                                   Q  V  Q  L  V  E  S  G  G  G  V  V  Q  P  G  R  S  L  R  L  S  C  A
98.3(291/296)  VH3-33       1     .....................................................................  70
94.4(17/18)    D5-12               Q  V  Q  L  V  E  S  G  G  G  V  V  Q  P  G  R  S  L  R  L  S  C  A
98.4(62/63)    JH6

ID%                                -------->  <----CDR1---->            <----FWR2----
              Ha5-7acd20.1.1  71  CGTCTGGATTCACCTTCAGC  AGCTATGGCATGCAC  TGGGTCCGCCAGGCTCCAGGCAAGGGGCTGGAGTG  140
                                    A  S  G  F  T  F  S    S  Y  G  M  H    W  V  R  Q  A  P  G  K  G  L  E  W
98.3(291/296)  VH3-33       71  ...............T.....  ................  ...................................  140
94.4(17/18)    D5-12                A  S  G  F  T  F  S    S  Y  G  M  H    W  V  R  Q  A  P  G  K  G  L  E  W
```

Figure 4Q-2

```
98.4(62/63)   JH6                                                                                                         <--
ID%                                          V  A   V  I  W  Y  D  G  R  N  K  Y  Y  V  D  S  V  K  G   R  F  T  I
              Ha5-7acd20.1.1  141  GGTGGCA  GTTATATGGTATGATGGAAGAAATAAATATTATGTAGACTCCGTGAAGGGC  CGATTCACCATC  210
98.3(291/296) VH3-33          141           ................................T....C.................  ............  210
94.4(17/18)   D5-12
98.4(62/63)   JH6                            V  A   V  I  W  Y  D  G  S  N  K  Y  Y  A  D  S  V  K  G   R  F  T  I
ID%                                                                      -------CDR2-------->
                                                                                                    -------FWR3-------

S  R  D  N  S  K  N  T  L  Y  L  Q  M  N  S  L  R  A  E  D  T  A  V
              Ha5-7acd20.1.1  211  TCCAGAGACAATTCCAAGAATACGCTGTATCTGCAAATGAACAGCCTGAGAGCCGAGGACACGGCTGTGT  280
98.3(291/296) VH3-33          211  .............................C.......................................  280
94.4(17/18)   D5-12
98.4(62/63)   JH6                            S  R  D  N  S  K  N  T  L  Y  L  Q  M  N  S  L  R  A  E  D  T  A  V
ID%
                                                     ------->
                                             Y  Y  C  A  R   D  R  Y  S  G  S  D  Y  Y  Y  Y  G  M  D  V  W  G  Q
              Ha5-7acd20.1.1  281  ATTACTGTGCGAGA  GATCGTATAGTGGCTCCGATTACTACTACTACGGTATGGACGTCTGGGGCCA  350
98.3(291/296) VH3-33          281  ..............                                                         296
94.4(17/18)   D5-12            6                   .......................A..........................       23
98.4(62/63)   JH6              1                   ...........................................G...          37
ID%                                          Y  Y  C  A  R G  T  T  V  T  V  S  S
              Ha5-7acd20.1.1  351  AGGGACCACGGTCACCGTCTCCTCAG  376
98.3(291/296) VH3-33
94.4(17/18)   D5-12
98.4(62/63)   JH6              38  ..........................   63
```

Figure 4R Alignment of Ha5-7acd20.1.1 VL to human Ig germline.

```
ID%                            <------------------------------FWR1----------------------------------->  <--
                               D  I  Q  M  T  Q  S  P  S  S  L  S  A  S  V  G  D  R  V  T  I  T  C     
              Ha5-7acd20.1.1 27 GACATTCAGATGACCCAGTCTCCATCCTCACTGTCTGCATCTGTAGGAGACAGAGTCACCATCACTTGT C  96
                               D  I  Q  M  T  Q  S  P  S  S  L  S  A  S  V  G  D  R  V  T  I  T  C
97.2(276/284) L1             1  .....C..........................................................  .   70
97.4(37/38)   JK3               ----------------------------------------------------------------  --
ID%                              <-------CDR1-------->                  <-------FWR2-------
                                 R  A  S  Q  G  I  Y  N  Y  L  A        W  F  Q  Q  K  P  G  K  A  P  K  S  L
              Ha5-7acd20.1.1 97 GGGCGAGTCAGGGCATTTACAATTATTTAGCC TGGTTTCAGCAGAAACCAGGGAAAGCCCCTAAGTCCCT 166
                                 R  A  S  Q  G  I  S  N  Y  L  A        W  F  Q  Q  K  P  G  K  A  P  K  S  L
97.2(276/284) L1            71  ...............AG...............  ...................................  140
97.4(37/38)   JK3               --------------------------------  -----------------------------------

ID%                            ------>  <-------CDR2------->              
                                I  Y    A  A  S  S  L  Q  S             G  V  P  S  K  F  S  G  S  G  S  G  T  V
              Ha5-7acd20.1.1 167 GATCTAT GCTGCATCCAGTTTGCAAAGT GGGGTCCCATCAAAGTTCAGCGGCAGTGGATCTGGGACAGTT 236
                                I  Y    A  A  S  S  L  Q  S             G  V  P  S  R  F  S  G  S  G  S  G  T  D
97.2(276/284) L1            141 .......  .....................  .................G................................A. 210
97.4(37/38)   JK3               -------  ---------------------  --------------------------------------------------

ID%                            ------FWR3----------->
                                F  T  L  T  I  S  S  L  Q  P  E  D  F  A  T  Y  Y  C        Q  Q  Y  T  V
              Ha5-7acd20.1.1 237 TTCACTCTCACCATCAGCAGCCTGCAGCCTGAAGATTTCGCAACTTATTACTGC CAACAGTATACTGTTT 306
                                F  T  L  T  I  S  S  L  Q  P  E  D  F  A  T  Y  Y  C        Q  Q  Y  N  S
97.2(276/284) L1            211 .....................................................  .........A.AG.. 280
97.4(37/38)   JK3               -----------------------------------------------------  ---------------

ID%                             Y  P  F  T  F  G  P  G  T  K  V  D  F  K
              Ha5-7acd20.1.1 307 ACCCATTCACTTTCGGCCCTGGGACCAAAGTGGATTTCAAAC 348
                                 Y  P
97.2(276/284) L1            281 ....  284
97.4(37/38)   JK3             1 ......A........  38
```

Figure 4S-1 Alignment of Ha5-7be31.1 VH to human Ig germline.

```
                    <------------------------------------FWR1----------------------------------->
                    Q  V  Q  L  Q  E  S  G  P  G  L  V  K  P  S  E  T  L  S  L  T  C  T
Ha5-7be31.1    1    CAGGTGCAGCTGCAGGAGTCGGGCCCAGGACTGGTGAAGCCTTCGGAGACCCTGTCCTCACTGCACTG   70
                    Q  V  Q  L  Q  E  S  G  P  G  L  V  K  P  S  E  T  L  S  L  T  C  T
VH4-59         1    ................................................................   70
D3-10
JH6
ID%
100(292/292)
95.7(22/23)
98.0(48/49)

<----------CDR1------>   <----------FWR
                    V  S  G  G  S  I  S     S     Y  Y  W  S     W  I  R  Q  P  P  P  G  K
Ha5-7be31.1   71    TCTCTGGTGGCTCCATCAG------AGT------TACTACTGGAGC  TGGATCCGGCAGCCCCCAGGGAA  128
                    V  S  G  G  S  I  S     S     Y  Y  W  S     W  I  R  Q  P  P  P  G  K
VH4-59        71    ..................................................................  128
D3-10
JH6
ID%
100(292/292)
95.7(22/23)
98.0(48/49)

------>   <--------------------CDR2--------------------->
                    G  L  E  W  I  G     Y  I  Y  Y  S  G  S  T  N  Y  Y  N  P  S  L  K  S
Ha5-7be31.1  129    GGGACTGGAGTGGATTGGG  TATATCTATTACAGTGGGAGCACCAACTACTACAACCCCTCCCTCAAGAGT  198
                    G  L  E  W  I  G     Y  I  Y  Y  S  G  S  T  N  Y  Y  N  P  S  L  K  S
VH4-59       129    ..................................................................  198
D3-10                                                                                     CGA   R
JH6
ID%
100(292/292)
95.7(22/23)
98.0(48/49)

<------------------FWR3------------------>
                    V  T  I  S  V  D  T  S  K  N  Q  F  S  L  K  L  S  S  V  T  A  A  D
Ha5-7be31.1  199    GTCACCATATCAGTAGACACCAGTAAGAACCAGTTCTCCCTGAAGCTGAGCTCTGTGACCGCTGCGGACA  268
                    V  T  I  S  V  D  T  S  K  N  Q  F  S  L  K  L  S  S  V  T  A  A  D
VH4-59       199    ..................................................................  268
D3-10
JH6
ID%
100(292/292)
95.7(22/23)
98.0(48/49)

---->
                    T  A  V  Y  Y  C  A  R     G  Y  Y  Y  G  A  G  S  Y  G  M  D  V  W  G  Q
Ha5-7be31.1  269    CGGCCGTGTATTACTGTGCGAGA  GGCTATTACTATGGTGCGGGGAGTTACGGTATGGACGTCTGGGGCCA  338
                    T  A  V  Y  Y  C  A  R
VH4-59       269    .......................                                                 292
D3-10          2    .........T.............                                                  24
JH6           15    .....................................G..                                 37
ID%
100(292/292)
95.7(22/23)
98.0(48/49)

| | | | ID% |
|---|---|---|---|
| Ha5-7be31.1 | 339 | AGGGACCACGGTCACCGTCCTCCTCAG | 364 |
| VH4-59 | | ------------------------- | | 100(292/292) |
| JH6 | 38 | ........................... | 63 | 98.0(48/49) |

Figure 4T Alignment of Ha5-7be31.1 VL to human Ig germline.

```
                  <-----------------------FWR1----------------------->
                   D  I  V  M  T  Q  S  P  L  S  L  P  V  T  P  G  E  P  P  A  S  I  S  C
Ha5-7be31.1  27  GATATTGTGATGACTCAGTCTCCACTCTCCCTGCCCGTCACCCCTGGAGAGCCGGCCTCCATCTCCTGC   96
A19           1  ...................................................................A   70
JK5                                                                                     ID%  98.0(293/299)
                                                                                             100(37/37)
                  <-------------CDR1------------->
                   R  S  S  Q  S  L  L  H  S  T     G  F  N  Y  L  D     W  Y  L  Q  K  P  G
Ha5-7be31.1  97  GGTCTAGTCAGAGCCTCCTGCATAGTACTG---GGATTCAACTATTTGGAT   TGGTACCTGCAGAAGCCAGG  163
A19          71  ..........................A.------..A...........   ....................  137
JK5                                                                                     ID%  98.0(293/299)
                                                                                             100(37/37)
                  -FWR2------------>  <---------CDR2---------->
                   Q  S  P  Q  L  L  I  Y     L  G  S  I  R  A  S     G  V  P  D  R  F  S  G
Ha5-7be31.1 164  GCAGTCTCCACAGCTCCTGATCTAT   TTGGGTTCTATTCGGGCCTCC   GGGGTCCCTGACAGGTTCAGTGGC  233
A19         138  ........................   ........A.............   .......................  207
JK5                                                                                     ID%  98.0(293/299)
                                                                                             100(37/37)
                  -------FWR3------------
                   S  G  S  G  T  D  F  T  L  K  I  S  R  V  E  T  E  D  V  G  V  Y  Y
Ha5-7be31.1 234  AGTGGCAGTGGTACAGATTTTACACTGAAAATCAGCAGAGTGGAGACTGAGGATGTTGGGGTTTATTACT  303
A19         208  .....A..............................................G...............  277
JK5                                                                                     ID%  98.0(293/299)
                                                                                             100(37/37)
                  ->
                   C     M  Q  T  L  Q  T  P  I  T  F  G  Q  G  T  R  L  E  I  K
Ha5-7be31.1 304  GC   ATGCAAACTCTACAAACTCCCATCACCTTCGGCCAAGGGACCACGACTGGAGAATTAAAC  363
A19         278  ..   ....................G..........................           299
JK5           3  --   ..                                ........................  39
                                                                                        ID%  98.0(293/299)
                                                                                             100(37/37)
```

Figure 4U-1 Alignment of Ha5-7acd10.1 VH to human Ig germline.

```
                                    <----------------------------FWR1---------------------------------
              Ha5-7acd10.1    1     Q  V  Q  L  V  E  S  G  G  G  V  V  Q  P  G  R  S  L  R  L  S  C  A
                                    CAGGTGCAGCTGGTGGAGTCTGGGGGAGGCGTGGTCCAGCCTGGGAGGTCCCTGAGACTCTCCTGTGCAG   70
100(296/296)  VH3-33          1     ....................................................................   70
100(18/18)    D5-12
98.4(62/63)   JH6                   Q  V  Q  L  V  E  S  G  G  G  V  V  Q  P  G  R  S  L  R  L  S  C  A
ID%
                                    ---------->   <----CDR1---->                       <------FWR2-----
              Ha5-7acd10.1   71     A  S  G  F  T  F  S     S  Y  G  M  H     W  V  R  Q  A  P  G  K  G  L  E  W
                                    CGTCTGGATTCACCTTCAGT AGCTATGGCATGCAC TGGGTCCGCCAGGCTCCAGGGCAAGGGGCTGGAGTG  140
100(296/296)  VH3-33         71     ...................................................................  140
100(18/18)    D5-12
98.4(62/63)   JH6                   A  S  G  F  T  F  S     S  Y  G  M  H     W  V  R  Q  A  P  G  K  G  L  E  W
ID%
                                      <---->    <--------------CDR2--------------->                <-------
              Ha5-7acd10.1  141     V  A     V  I  W  Y  D  G  S  N  K  Y  Y  A  D  S  V  K  G     R  F  T  I
                                    GGTGGCA GTTATATGGTATGATGGAAGTAATAAATACTATGCAGACTCCGTGAAGGGC CGATTCACCATC  210
100(296/296)  VH3-33        141     ........................................................................  210
100(18/18)    D5-12
98.4(62/63)   JH6                   V  A     V  I  W  Y  D  G  S  N  K  Y  Y  A  D  S  V  K  G     R  F  T  I
ID%
                                    ---FWR3------------------------------------------------>
              Ha5-7acd10.1  211     S  R  D  N  S  K  N  T  L  Y  L  Q  M  N  S  L  R  A  E  D  T  A  V
                                    TCCAGAGACAATTCCAAGAACACGCTGTATCTGCAAATGAACAGCCTGAGAGCCGAGGACACGGCTGTGT  280
100(296/296)  VH3-33        211     ....................................................................  280
100(18/18)    D5-12
98.4(62/63)   JH6                   S  R  D  N  S  K  N  T  L  Y  L  Q  M  N  S  L  R  A  E  D  T  A  V
ID%
                                                  <---->
              Ha5-7acd10.1  281     Y  Y  C  A  R     D  R  Y  S  G  Y  D  Y  Y  Y  Y  Y  G  M  D  V  W  G  Q
                                    ATTACTGTGCGAGA GATCGGTATAGTGGCTACGATTACTACTACTACTACGGTATGGACGTCTGGGGCCA  350
100(296/296)  VH3-33        281     ..............                                                          296
100(18/18)    D5-12           6                                                                             23
```

Figure 4U-2

```
                  JH6           1    ------------------------------------...G.. 37
98.4(62/63)
ID%
                                     G  T  T  V  T  V  S  S
                  Ha5-7acd10.1  351  AGGGACCACGTCACCGTCTCCTCAG  376

100(296/296)      VH3-33              ------------------------
100(18/18)        D5-12               ------------------------
98.4(62/63)       JH6                 ......................... 63
```

Figure 4V-1 Alignment of Ha5-7acd10.1 VL to human Ig germline.

```
                                <-------------------------FWR1-------------------------><
                                 D  I  Q  M  T  Q  S  P  S  S  L  S  A  S  V  G  D  R  V  T  I  T  C
              Ha5-7acd10.1  27  GACATCCAGATGACCCAGTCTCCATCCTCCACTCTGCTGTCTGCATCTGTCGGAGACAGAGTCACCATCACTTGT  96
                                 D  I  Q  M  T  Q  S  P  S  S  L  S  A  S  V  G  D  R  V  T  I  T  C
96.1(273/284)  L1           1   ......................................................A................  .
100(38/38)     JK3              ..........................................................................  -
ID%

<----------CDR1----------><
                                 R  A  S  Q  G  I  Y  N  Y  L  A     W  F  Q  Q  K  P  G  K  A  P  K  S  L
              Ha5-7acd10.1  97  GGGGAGTCAGGGCATTTATAATTATTTGGCC  TGGTTTCAGCAGAAACCAGGGAAAGCCCCTAAGTCCCT  166
                                 R  A  S  Q  G  I  S  N  Y  L  A     W  F  Q  Q  K  P  G  K  A  P  K  S  L
96.1(273/284)  L1           71  .........AGC......A............  ........................................  140
100(38/38)     JK3              ...............................  ........................................
ID%

<-----CDR2------>
                                 I  Y   A  A  S  S  L  H  S     G  V  P  S  K  F  S  G  G  G  S  G  T  D
              Ha5-7acd10.1  167  GATCTAT GCTGCATCCAGTTTGCACAGT  GGGGTCCCATCCAAAGTTCAGCGGCGGTGGTTCTGGGACAGAT  236
                                 I  Y   A  A  S  S  L  Q  S     G  V  P  S  R  F  S  G  S  G  S  G  T  D
96.1(273/284)  L1           141  .....  .........A...........  .........................A....A..........  210
100(38/38)     JK3              .....  .......................  ..........................................
ID%

<----FWR3---->
                                 F  T  L  T  I  S  S  L  Q  P  E  D  F  A  T  Y  Y  C     Q  Q  Y  T  I
              Ha5-7acd10.1  237  TTCACTCTCACCATCAGCAGCCTGCAGCCTGAAGATTTTGCAACTTATTACTGC  CAACAGTATACTATTT  306
                                 F  T  L  T  I  S  S  L  Q  P  E  D  F  A  T  Y  Y  C     Q  Q  Y  N  S
96.1(273/284)  L1           211  .....................................................  .........A..G..  260
100(38/38)     JK3              .....................................................  ................
ID%
```

Figure 4V-2

```
                              Y P F T F G P G T K V D I K
Ha5-7acd10.1  307  ACCCATTCACTTTCGGCCCTGGGACCAAAGTGGATATCAAAC  348
                     Y P
96.1(273/284)  L1   281  ................................................  284
100(38/38)     JK3    1  ................................................   38
```

Figure 4W-1 Alignment of Ha5-7acd13.1 VH to human Ig germline.

```
ID%                              <------------------------------FWR1-------------------------
                    Q V Q L Q E S G P G L V K P S E T L S L T C T
Ha5-7acd13.1   1   CAGGTGCAGCTGCAGGAGTCTGGCCCAGGACTGGTGAAGCCTTCGGAGACCCTGTCCCTCACCTGCACTG  70
                    Q V Q L Q E S G P G L V K P S E T L S L T C T
99.7(288/289) VH4-59  1  ...........................G...............................  70
100(19/19)    D3-10
98.0(48/49)   JH6
ID%                                            <---CDR1--->           <-------FWR
                    V S G G S I S         S   Y Y W S     W I R Q P P G K
Ha5-7acd13.1  71   TCTCTGGTGGCTCCATCAG------AGT------TACTACTGGAGC TGGATCCGGCAGCCCCCAGGGAA 128
                    V S G G S I S         S   Y Y W S     W I R Q P P G K
99.7(288/289) VH4-59 71  ..............................................................  128
100(19/19)    D3-10
98.0(48/49)   JH6
ID%                    2----------->   <----------CDR2---------->  <---
                    G L E W I G   Y I Y Y S G S T N Y N P S L K S  R
Ha5-7acd13.1 129   GGGACTGGAGTGGATTGGG TATATCTATTACAGTGGGAGCACCAACTACAACCCCTCCCTCAAGAGT CGA 198
                    G L E W I G   Y I Y Y S G S T N Y N P S L K S  R
99.7(288/289) VH4-59 129  ..............................................................  198
100(19/19)    D3-10
98.0(48/49)   JH6
ID%                           <-----------FWR3----------
                    V T I S V D T S K N Q F S L K L S S V T A A A D
Ha5-7acd13.1 199   GTCACCATATCAGTAGACACGTCCAAGAACCAGTTCTCCCTGAAGCTGAGCTCTGTGACCGCCTGCGGACA 268
                    V T I S V D T S K N Q F S L K L S S V T A A A D
99.7(288/289) VH4-59 199  ..............................................................  268
100(19/19)    D3-10
98.0(48/49)   JH6
ID%                                                              >
```

Figure 4W-2

```
                    T  A  V  Y  Y  C  A  N     T  Y  Y  Y  G  S  G  Y  G  M  D  V  W  G  Q  G
Ha5-7acd13.1  269   CGGCCGTGTATTACTGTGCGAAC   ACGTATTACTATGGTTCGGGTTACGGTATGGACGTCTGGGGCCAAGG   338
VH4-59        269   T  A  V  Y  Y  C  A                                                        289
D3-10           1   ---------------------                                                       19
JH6            15   ------------------...                                       G...            40
ID%
99.7(288/289)
100(19/19)
98.0(48/49)

T  T  V  T  V  S  S
Ha5-7acd13.1  339   GACCACGGTCACCGTCTCCTCAG    361
VH4-59
D3-10
JH6            41   ---------------------      63
ID%
99.7(288/289)
100(19/19)
98.0(48/49)
```

Figure 4X-1 Alignment of Ha5-7acd13.1 VL to human Ig germline.

```
                  <--------------------------FWR1--------------------------->  <
                    D  I  V  M  T  Q  S  P  L  S  L  P  V  T  P  G  E  P  A  S  I  S  C
Ha5-7acd13.1   27  GATATTGTGATGACTCAGTCTCCACTCTCCCTGCCCGTCACCCCTGGAGAGCCGGCCTCCATCTCCTGC  96
A19             1  ..................................................................  -
JK5                D  I  V  M  T  Q  S  P  L  S  L  P  V  T  P  G  E  P  A  S  I  S  C
ID%
99.0(294/297)
100(37/37)

<------------CDR1-------------->
                    R  S  S  Q  S  L  L  H  S  T     G  H  N  Y  L  D     W  Y  L  Q  K  P  G
Ha5-7acd13.1   97  GGTCTAGTCAGAGCCTCCTGCATAGTACTG---GACACAACTATTTGGAT  TGGTACCTGCAGAAGCCAGG  163
A19            71  ...........................A..---........T......  ....................
JK5                R  S  S  Q  S  L  L  H  S  N     G  Y  N  Y  L  D     W  Y  L  Q  K  P  G
ID%
99.0(294/297)
100(37/37)

--FWR2------->  <------------CDR2--------->  <
                    Q  S  P  Q  L  L  I  Y     L  G  S  I  R  A  S     G  V  P  D  R  F  S  G
Ha5-7acd13.1  164  CCAGTCTCCACAGCTCCTGATCTAT  TTGGGTTCTATTCGGGCCTCC  GGGGTCCCTGACAGGTTCAGTGGC  233
A19           138  .........................  ..........A..........  ........................
JK5                Q  S  P  Q  L  L  I  Y     L  G  S  N  R  A  S     G  V  P  D  R  F  S  G
ID%
99.0(294/297)
100(37/37)

FWR3
                    S  G  S  G  T  D  F  T  L  K  I  S  R  V  E  A  E  D  V  G  V  Y  Y
Ha5-7acd13.1  234  AGTGGATCAGGCACAGATTTTACACTGAAAATCAGCAGAGTGGAGGCTGAGGATGTTGGGGTTTATTACT  303
```

Figure 4X-2

```
99.0(294/297)  A19                   S  G  S  G  T  D  F  T  L  K  I  S  R  V  E  A  E  D  V  G  V  Y  Y
100(37/37)     JK5    208            ................................................................  277
ID%
                                     ->
                                     C  M  Q  A  L  Q  T  I  T  F  G  Q  G  T  R  L  E  I  K
               Ha5-7acd13.1  304  GC ATGCAAGCTCTACAAACTATCACCTTCGGCCAAGGGACACGACTGGAGATTAAAC  360

99.0(294/297)  A19    278            C  M  Q  A  L  Q  T                                              297
100(37/37)     JK5      3         -- ..                                                                 39
ID%
```

Figure 4Y-1 Alignment of Ha5-7acd19.1 VH to human Ig germline.

```
                                  <-----------------------------FWR1-------------------------------
               Ha5-7acd19.1  1    Q  V  Q  L  Q  E  S  G  P  G  L  V  K  P  S  E  T  L  S  L  T  C  T
                                  CAGGTGCAGCTGCAGGAGTCTGGGCCCGGACTGGTGAAGCCTTCGGAGACCCTGTCCCTCACCTGCACTG  70
ID%
98.3(284/289)  VH4-59  1          Q  V  Q  L  Q  E  S  G  P  G  L  V  K  P  S  E  T  L  S  L  T  C  T
100(19/19)     D3-10              .................G....A...........................................  70
98.0(48/49)    JH6
ID%
                                  <--------CDR1--------->  <-----------------------------FWR
               Ha5-7acd19.1  71   V  S  G  G  S  I  S      S     Y  Y  W  S     W  I  R  Q  P  P  G  K
                                  TCTCTGGTGGCTCCATCAG------AGT------TACTACTGGAGC TGGATCCGGCAGCCCCCAGGGAA  128
98.3(284/289)  VH4-59  71         V  S  G  G  S  I  S            Y  Y  W  S     W  I  R  Q  P  P  G  K
100(19/19)     D3-10              ..............................................................  128
98.0(48/49)    JH6
ID%
                                  2-------->  <---------------------CDR2----------------------> <----
               Ha5-7acd19.1  129  G  L  E  W  I  G   F  I  Y  Y  T  G  S  T  N  Y  N  P  S  L  K  S   R
                                  GGGACTGGAGTGGATTGGA TTTATCTATTACACTGGGAGCACCAACTACAACCCTCCCTCAAGAGT CGA  198
98.3(284/289)  VH4-59  129        G  L  E  W  I  G   Y  I  Y  Y  S  G  S  T  N  Y  N  P  S  L  K  S   R
100(19/19)     D3-10              ...................A............G.................................  198
98.0(48/49)    JH6
ID%
                                  FWR3----------------------------------------
               Ha5-7acd19.1  199  V  T  I  S  V  D  T  S  K  N  Q  F  S  L  K  L  S  S  V  T  A  A  D
                                  GTCACCATATCAGTAGACACGTCCAAGAACCAGTTCTCCCTGAAGCTGAGCTCTGTGACCGCTGCGGACA  268
                                  V  T  I  S  V  D  T  S  K  N  Q  F  S  L  K  L  S  S  V  T  A  A  D
```

Figure 4Y-2

```
98.3(284/289)  VH4-59                199
100(19/19)     D3-10
98.0(48/49)    JH6
ID%
                                         T  A  V  Y  Y  C  A  N     T  Y  Y  Y  G  S  G  Y  G  M  D  V  W  G  Q  G
               Ha5-7acd19.1  269  CGGCCGTGTATTACTGTGCGAAC ACGTATTACTATGGTTCGGGGTACGGTATGGACGTCTGGGGCCAAGG  338
                                         T  A  V  Y  Y  C  A
98.3(284/289)  VH4-59        269                                                                                289
100(19/19)     D3-10         1                                                                                   19
98.0(48/49)    JH6           15   .................................................G......                     40
ID%

T  T  V  T  V  S  S
               Ha5-7acd19.1  339  GACCACGGTCACCGTCTCCTCAG  361
98.3(284/289)  VH4-59
100(19/19)     D3-10
98.0(48/49)    JH6           41   .......................  63
ID%
```

Figure 4Z-1 Alignment of Ha5-7acd19.1 VL to human Ig germline.

```
                                 <-----------------------------FWR1-----------------------------><
                                    D  I  V  M  T  Q  S  P  L  S  L  P  V  T  P  G  E  P  A  S  I  S  C
ID%            Ha5-7acd19.1  45  GATATTGTGATGACTCAGTCTCCACTCTCCCTGCCCGTCACCCCTGGAGAGCCGGCCTCCATCTCTGC  A    114
                                    D  I  V  M  T  Q  S  P  L  S  L  P  V  T  P  G  E  P  A  S  I  S  C
98.7(293/297)  A19           1   ..................................................................  .     70
100(37/37)     JK5                                                                                    -      -
ID%
                                 <----------CDR1---------->
                                    R  S  S  Q  S  L  L  H  S  N     G  F  N  Y  L  D     W  Y  L  Q  K  P  G
               Ha5-7acd19.1  115 GGTCTAGTCAGAGCCTCCTGCATAGTAATG---GATTCAACTATTTGGAT TGGTACCTGCAGAAGCCAGG    181
                                    R  S  S  Q  S  L  L  H  S  N     G  Y  N  Y  L  D     W  Y  L  Q  K  P  G
98.7(293/297)  A19                  ...............................A..............   ....................   137
100(37/37)     JK5
ID%
                                 --FWR2---------><-----CDR2----->
                                    Q  S  P  Q  L  L  I  Y     L  G  S  R  R  A  S     G  V  P  D  R  F  S  G
               Ha5-7acd19.1  182 GCAGTCTCCACAGCTCCTGATCTAT TTGGGTTCTAGACGGGCCTCC GGGGTCCCTGACAGGTTCAGTGGC  251
                                    Q  S  P  Q  L  L  I  Y     L  G  S  N  R  A  S     G  V  P  D  R  F  S  G
```

Figure 4Z-2

```
98.7(293/297)    A19                  138   .................    AT........................................  207
100(37/37)       JK5                        ----------------------FWR3----------------------|
ID%                                         S G S G T D F T L K I S R V E A E D V G V Y Y
                 Ha5-7acd19.1          252  AGTGGATCAGGCACAGATTTTACACTGAAAATCAGCAGAGTGGAGGCTGAGGATGTTGGGGTTTATTACT  321
98.7(293/297)    A19                  208  ----------------------------------------------------------------------   277
100(37/37)       JK5                        S G S G T D F T L K I S R V E A E D V G V Y Y
ID%                                         ->
                                            C   M Q A L E T I T F G Q G T R L E I K
                 Ha5-7acd19.1          322  ATGCAAGCTCTAGAAACTATCACCTTCGGCCAAGGGACACGACTGGAGATTAAAC  378
98.7(293/297)    A19                  278  ..........C.....                                            297
100(37/37)       JK5                    3   --                                                           39
ID%                                         C   M Q A L Q T
                                            C   ....C..
```

Figure 4AA-1 Alignment of Ha5-7be37.1 VH to human Ig germline.

```
                                            <----------------------FWR1---------------------->
ID%                                         Q V Q L Q E S G P G L V K P S E T L S L T C T
                 Ha5-7be37.1           1    CAGGTGCAGCTGCAGGAGTCCAGGAGACTGGCCCAGGACTGGTGAAGCCTTCGGAGACCCTGTCCCTCACCTGCACTG  70
99.7(291/292)    VH4-59                1    ..............................G..............................   70
100(23/23)       D3-10
98.0(48/49)      JH6                        Q V Q L Q E S G P G L V K P S E T L S L T C T
ID%                                                            <-----CDR1-----> <------                    FWR
                                            V S G G S I S        S   Y Y W S    W I R Q P P G K
                 Ha5-7be37.1           71   TCTCTGGTGGCTCCATCAG---------AGT------TACTACTGGAGC TGGATCCGGCAGCCCCCAGGGAA   128
99.7(291/292)    VH4-59                71   ....................T.........................................   128
100(23/23)       D3-10
98.0(48/49)      JH6                        V S G G S I S        S   Y Y W S    W I R Q P P G K
ID%                                         2------>        <-----CDR2-----> <----               R
                                            G L E W I G      Y I Y Y S G S T N Y N P S L K S
                 Ha5-7be37.1           129  GGGACTGGAGTGGATTGGG TATATCTATTACAGTGGGAGCACCAACTACAACCCCTCCCTCAAGAGT CGA   198
99.7(291/292)    VH4-59                129  ...................                                              ...   198
                                            G L E W I G      Y I Y Y S G S T N Y N P S L K S    R
```

Figure 4AA-2

```
                                                       VTISVDTSKNQFSLKLSSVTAAD
100(23/23)     D3-10                                                                                                         ---
98.0(48/49)    JH6                                                                                                           ---
ID%                                                                             --------FWR3--------
               Ha5-7be37.1 199 GTCACCATATCAGTAGACACGTCCAAGAACCAGTTCTCCCTGAAGCTGAGCTGTGACCGCTGCGGACA 268
                                V T I S V D T S K N Q F S L K L S S V T A A D 99.7(291/292)  VH4-59       199 .................................................................. 268
100(23/23)     D3-10
98.0(48/49)    JH6
ID%                                                 ------>
                                T A V Y Y C A R       G Y Y Y G S G S Y G M D V W G Q
               Ha5-7be37.1 269 CGGCCCGTGTATTACTGTGCGAGA GGCTATTACTATGGTTCGGGGAGTTACGGTATGGACGTCTGGGGCCA 338
                                T A V Y Y C A R 99.7(291/292)  VH4-59       269 ........................                                                292
100(23/23)     D3-10         2 ........................ ---..                                          24
98.0(48/49)    JH6          15                          .........................G..                   37
ID%
                                 G   T T V T V S S
               Ha5-7be37.1 339 AGGGACCACGGTCACCGTCTCCTCAG 364

99.7(291/292)  VH4-59       269
100(23/23)     D3-10
98.0(48/49)    JH6          38 .........................  63
ID%
```

Figure 4AB-1 Alignment of Ha5-7be37.1 VL to human Ig germline.

```
                                <----------------FWR1---------------->   <
                                D I V M T Q S P L S L P V T P G E P A S I S C
               Ha5-7be37.1  13 GATATTGTGATGACTCAGTCTCCACTCTCCCTGCCCGTCACCCCTGGAGAGCCGGCCTCCATCTCCTGC  82
                                D I V M T Q S P L S L P V T P G E P A S I S C
99.0(296/299)  A19           1 ..................................................................  70
100(37/37)     JK5
ID%                                      ---------CDR1--------->             <------
                                R S S Q S L L H S T     G Y N Y L D    W Y L Q K P G
               Ha5-7be37.1  83 GGTCTAGTCAGAGCCTCCTGCATAGTACTG---GATACAACTATTTGGAT TGGTACCTGCAGAAGCCAGG 149
                                R S S Q S L L H S N     G Y N Y L D    W Y L Q K P G
99.0(296/299)  A19          71 .............................A...                 ................ 137
```

Figure 4AB-2

```
                                   <---FWR2------------->   <--------CDR2--------->
                                    Q  S  P  Q  L  L  I  Y   L  G  S  N  R  A  S    G  V  P  D  R  F  S  G
100(37/37)           JK5
ID%
              Ha5-7be37.1  150  GCAGTCTCCAAGCTCCTGATCTAT TTGGGTTCTAATCGGGCCTCC GGGGTCCCTGACAGGTTCAGTGGC  219
                                    Q  S  P  Q  L  L  I  Y   L  G  S  N  R  A  S    G  V  P  D  R  F  S  G
99.0(296/299) A19
100(37/37)    JK5
ID%
                                                                  <-----FWR3
                                    S  G  S  G  T  D  F  T  L  K  I  S  R  V  E  A  E  D  V  G  V  C  Y
              Ha5-7be37.1  220  AGTGGATCAGGCACAGATTTTACACTGAAGATCAGCAGAGTGGAGGCTGAGGATGTTGGGGTTTGTTACT  289
                                    S  G  S  G  T  D  F  T  L  K  K  I  S  R  V  E  A  E  D  V  G  V  Y  Y
99.0(296/299) A19
100(37/37)    JK5                                                                              .A.....    277
ID%
                                -->
                                    C  M  Q  A  L  Q  T  P  I  T  F  G  Q  G  T  R  L  E  I  K
              Ha5-7be37.1  290  GC ATGCAAGCTCTACAAACTCCCATCACCTTCGGCCAAGGGACACGACTGGAGATTAAAC  349
                                    C  M  Q  A  L  Q  T  P
99.0(296/299) A19                                              .....                              299
100(37/37)    JK5   3           ..                                                                 39
ID%
```

Figure 4AC-1 Alignment of Ha5-7acd16.1 VH to human Ig germline.

```
                                  <------FWR1------------------------------------------------------->
                                   Q  V  Q  L  V  E  S  G  G  G  V  V  Q  P  G  R  S  L  R  L  S  C  A
                   Ha5-7acd16.1 1  CAGGTGCAGCTGGTGGAGTCTGGGGGAGGCGTGGTCCAGCCTGGGAGGTCCCTGAGACTCTCCTGTGCAG  70
                                   Q  V  Q  L  V  E  S  G  G  G  V  V  Q  P  G  R  S  L  R  L  S  C  A
99.7(295/296) VH3-33
95.5(21/22)   D5-12
98.4(62/63)   JH6
ID%
                                                        <---CDR1--->         <------FWR2----------
                                    A  S  G  F  T  F  S  S  H  G  M  H  W  V  R  Q  A  P  G  K  G  L  E  W
                   Ha5-7acd16.1 71  CGTCTGGATTCACCTTCAGT AGCCATGGCATGCAC TGGGTCCGCCAGGCTCCAGGCAAGGGGCTGGAGTG  140
                                    A  S  G  F  T  F  S  S  Y  G  M  H  W  V  R  Q  A  P  G  K  G  L  E  W
99.7(295/296) VH3-33                                        .T..                                           140
95.5(21/22)   D5-12
98.4(62/63)   JH6
ID%                                                   <------>             <------CDR2-----
```

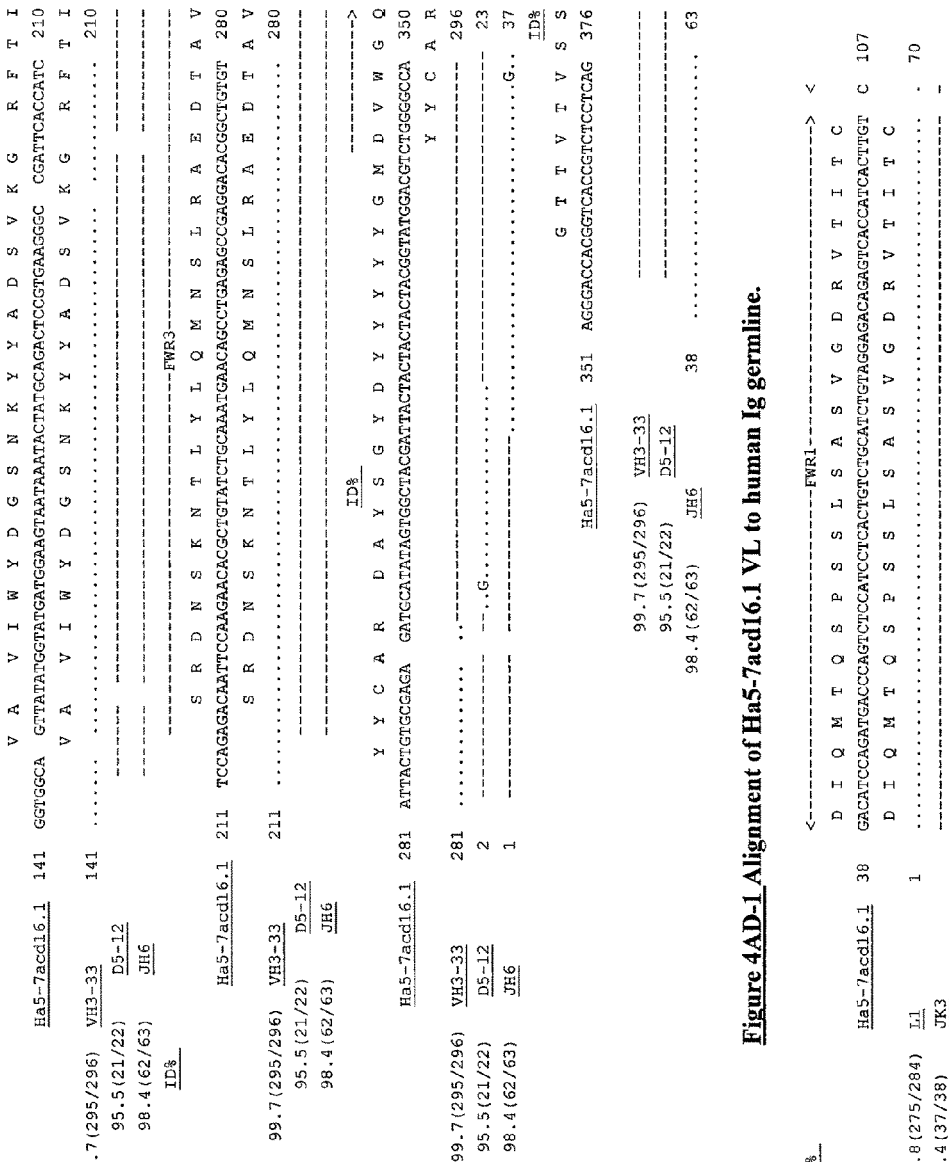

Figure 4AD-2

```
                                  <-------CDR1------->          <--------FWR2--------
                        R A S Q G I Y T Y L A    W F Q Q K P G K A P K S L
         Ha5-7acd16.1 108 GGGCGAGTCAGGGCATTTACACTTATTTAGCC  TGGTTTCAGCAGAAACAGGGAAAGCCCTAAGTCCCT 177
96.8(275/284) L1     71  R A S Q G I S N Y L A    W F Q Q K P G K A P K S L
97.4(37/38)   JK3        .............AG..A.............   ................................... 140
ID%
                        <-----> <-------CDR2------->
                        I Y    G A S S L Q S       G V P S K F S G S G S G T D
         Ha5-7acd16.1 178 GATCTAT GGTGCATCCAGTCTGCAAAGT   GGGGGTCCCATCAAAGTTCAGGGGCAGTGGATCTGGGACAGAT 247
96.8(275/284) L1     71  I Y    A A S S L Q S       G V P S R F S G S G S G T D
97.4(37/38)   JK3        ....... ..C.............T......   ...............G........................... 210
ID%
                        <---------FWR3--------------->
                        F T L T I T S L Q P E D F A T Y Y C    Q Q Y T I
         Ha5-7acd16.1 248 TTCACTCTCACCATCACCAGCCTGCAGCCTGAAGATTTTGCAACTTATTACTGC  CAACAGTATACTATTT 317
96.8(275/284) L1     71  F T L T I S S L Q P E D F A T Y Y C    Q Q Y N S
97.4(37/38)   JK3        ..........................................................  ........A..G..  280
ID%
                        Y P F S F G P G T K V D I K
         Ha5-7acd16.1 318 ACCCATTCAGTTCGGCCCTGGGACCAAAGTGGATATCAAAC 359
96.8(275/284) L1     71  Y P  ......................................... 284
97.4(37/38)   JK3    1   ...C. ........................................  38
ID%
```

Figure 4AE-1 Alignment of Ha5-7acd7.1.1 VH to human Ig germline.

```
                        <-------------------------------FWR1-------------------------------->
                        Q V Q L Q E S G P G L V K P S E T L S L T C T
         Ha5-7acd7.1.1 1 CAGGTCCAGCTGCAGGAGTCTGGCCCAGGACTGGTGAAGCCTTCGGAGACCCTGTCCCTCACCTGCACTG 70
99.0(296/299) VH4-61     Q V Q L Q E S G P G L V K P S E T L S L T C T
92.0(23/25)  D2-8        ...............G.....................................................  70
95.9(47/49)  JH3
ID%
                        <----CDR1---->      <------FWR2-------
                        V S G G S V S       S G G Y Y W S   W I R Q P P G K G L
         Ha5-7acd7.1.1 71 TCTCTGGTGGCTCCGTCAGC AGTGGTGGTTACTACTGGAGC TGGATCCGGCAGCCCCCAGGGAAGGGACT 140
```

Figure 4AE-2

```
                                            V  S  G  G  S  V  S     S  G  G  Y  Y  W  S     W  I  R  Q  P  P  G  K  G  L
99.0(296/299)   VH4-61     71               ........................................................................   140
92.0(23/25)     D2-8
95.9(47/49)     JH3
ID%
                                                                               <---------CDR2---------->
                                            E  W  I  G     Y  I  Y  Y  S  G  G  T  N  Y  N  P  S  L  K  S     R  V  T
Ha5-7acd7.1.1   141        GGAGTGGATTGGG TATATCTATTACAGTGGGGGCACCAACTACAACCCCTCCTCAAGAGT CGAGTCACC   210
99.0(296/299)   VH4-61     141              ------------- -------------------------------------------- ---------
92.0(23/25)     D2-8                        E  W  I  G     Y  I  Y  Y  S  G  S  T  N  Y  N  P  S  L  K  S     R  V  T
95.9(47/49)     JH3                         .............. ......A................................... .........   210
ID%
                                                                               <-------FWR3-------
                                            I  S  V  D  T  S  K  N  Q  F  S  L  K  L  T  S  V  T  A  A  D  T  A
Ha5-7acd7.1.1   211        ATATCAGTAGACACGTCCAAGAACCAGTTCTCCCTGAAGCTGACCTCTGTGACCGCTGCGGACACGGCCG   280
99.0(296/299)   VH4-61     211              ---------------------------------G--------------------------------   280
92.0(23/25)     D2-8                        I  S  V  D  T  S  K  N  Q  F  S  L  K  L  S  S  V  T  A  A  D  T  A
95.9(47/49)     JH3
ID%
                                                    ------->
                                            V  Y  Y  C  A  R     E  S  G  Y  C  T  N  V  A  C  F  P  D  A  F  D  I  W
Ha5-7acd7.1.1   281        TGTATTACTGTGCCGAGA GAGTCGGGATATTGTACTAATGTTGCATGCTTCCCTGATGCTTTTGATATCTG   350
99.0(296/299)   VH4-61     281              .................. ..............................................   299
92.0(23/25)     D2-8       2                ------------------ ..........................G..T..--------------   26
95.9(47/49)     JH3        1                ------------------ ...............................G........------   17
ID%                                         V  Y  Y  C  A  R G  Q  G  T  M  V  T  V  S  S
Ha5-7acd7.1.1   351        GGGCCAAGGGACAATGGTCACCGTGTCTTCAG   382
99.0(296/299)   VH4-61                      --------------------------------
92.0(23/25)     D2-8       18               ....................C...........   49
95.9(47/49)     JH3
ID%
```

Figure 4AF Alignment of Ha5-7acd7.1.1 VL to human Ig germline.

```
ID%                          <----------------------------FWR1--------------------------->  <
                              D  V  V  M  T  Q  S  P  F  S  L  P  V  T  P  G  E  P  A  S  I  S  C
              Ha5-7acd7.1.1  43 GATGTTGTGATGACTCAGTCTCCATTCTCCCTGCCCGTCACCCCTGGAGAGCCGGCCTCCATCTCCTGC  A  112
                              D  I  V  M  T  Q  S  P  L  S  L  P  V  T  P  G  E  P  A  S  I  S  C
98.0(293/299) A19            1  ....A.......................C......................................  .   70
94.6(35/37)   JK4                                                                                 --
ID%                          -----CDR1---------->
                              R  S  S  Q  S  L  L  H  S  N     G  F  N  F  L  D     W  Y  L  Q  K  P  G
              Ha5-7acd7.1.1  113 GGTCTAGTCAGAGCCTCCTGCATAGTAATG---GATTCAACTTTTTGGAT TGGTACCTGCAGAAGCCAGG  179
                              R  S  S  Q  S  L  L  H  S  N     G  Y  N  Y  L  D     W  Y  L  Q  K  P  G
98.0(293/299) A19            71 ........................................A....A...  ..................  137
94.6(35/37)   JK4                                                                                 --
ID%                          --FWR2---------->   <--------CDR2-------->                      <
                              Q  S  P  Q  L  L  I  Y     L  G  S  I  R  A  S        G  V  P  D  R  F  S  G
              Ha5-7acd7.1.1  180 GCAGTCTCCACAGCTCCTGATCTAT TTGGGTTCTATTCGGGCCTCC GGGGTCCCTGACAGGTTCAGTGGC  249
                              Q  S  P  Q  L  L  I  Y     L  G  S  N  R  A  S        G  V  P  D  R  F  S  G
98.0(293/299) A19            138 ........................ .........A...........  ........................  207
94.6(35/37)   JK4                                                                                 --
                              S  G  S  G  T  D  F  T  L  K  I  S  R  V  E  A  E  D  V  G  V  Y  Y
              Ha5-7acd7.1.1  250 AGTGGATCAGGCACAGATTTTACACTGAAAATCAGCAGAGTGGAGGCTGAGGATGTTGGAGTTTATTACT  319
                              S  G  S  G  T  D  F  T  L  K  I  S  R  V  E  A  E  D  V  G  V  Y  Y
98.0(293/299) A19            208 .....................................................................G.  277
94.6(35/37)   JK4                                                                                 --
ID%                          -->
                              C    M  Q  A  L  Q  T  P  L  T  F  G  G  G  T  R  V  E  I  K
              Ha5-7acd7.1.1  320 GC ATGCAAGCTCTACAAACTCCACTCACTTTCGGCGGCGGGACCAGGGTGGAGATCAAAC  379
                              C    M  Q  A  L  Q  T  P
98.0(293/299) A19            278 ..                                                           299
94.6(35/37)   JK4            2   --  .................A......A..                                 38
```

Figure 4AG-1 Alignment of Ha5-7be20.1 VH to human Ig germline.

```
ID%                        <----------------------------------FWR1---------------------------------
              Ha5-7be20.1  1    Q  V  Q  L  Q  E  S  G  P  G  L  V  K  P  S  E  T  L  S  L  T  C  T
                                CAGGTGCAGCTGCAGGAGTCTGGCCCAGGACTGGTGAAGCCTTCGGAGACCCTGTCCCTCACCTGCACTG  70
99.0(289/292) VH4-59       1    ........................G...........................................  70
100(23/23)    D3-10
93.9(46/49)   JH6
ID%                                                       <------CDR1---->  <-----                     FWR
                                                          S    Y  Y  W  S   W  I  R  Q  P  P  P  G  K
              Ha5-7be20.1  71   V  S  G  G  S  I  S       S    Y  Y  W  S   W  I  R  Q  P  P  P  G  K
                                TCTCTGTGGCTCCATCAG------T AGT----TACTACTGGAGC TGGATCCGGCAGCCCCCCAGGGAA  128
99.0(289/292) VH4-59       71   V  S  G  G  S  I  S       .    Y  Y  W  S   W  I  R  Q  P  P  P  G  K
                                ................---------  ...----..............................  128
100(23/23)    D3-10
93.9(46/49)   JH6
ID%                        2-------------->  <-----------------CDR2----------------->  <---           R
                           G  L  E  W  I  G  Y  I  Y  Y  S  G  S  T  N  Y  N  P  S  L  K  S          R
              Ha5-7be20.1  129 GGGACTGGAGTGGATTGGG TATATCTATTACAGTGGGAGCACCAACTACAATCCCTCCCTCAAGAGT  CGA  198
99.0(289/292) VH4-59       129 G  L  E  W  I  G  Y  I  Y  Y  S  G  S  T  N  Y  N  P  S  L  K  S     R
                               ................... ...................C................................   ...  198
100(23/23)    D3-10
93.9(46/49)   JH6
ID%                        <-------------------------------FWR3-------------------------------
                           V  T  I  S  V  D  T  S  K  N  Q  F  S  L  K  L  S  S  V  T  A  A  D
              Ha5-7be20.1  199 GTCACCATATCAGTAGACACGTCCAAGAACCAGTTCTCCCTGAAGCTGAGCTCTGTGACCGCTGCGGACA  268
99.0(289/292) VH4-59       199 V  T  I  S  V  D  T  S  K  N  Q  F  S  L  K  L  S  S  V  T  A  A  D
                               .....................................................................  268
100(23/23)    D3-10
93.9(46/49)   JH6
ID%                                                                                      <-----
                           T  A  V  Y  Y  C  A  R       G  Y  Y  Y  G  S  G  S  Y  G  L  D  V  W  G  Q
              Ha5-7be20.1  269 CGGCCGTGTATTATTGTGCGAGA GGCTATTACTATGGTTCGGGGAGTTACGGCCTTGGACGTCTGGGGCCA  338
99.0(289/292) VH4-59       269 T  A  V  Y  Y  C  A  R
                               ............C..........                                                  292
100(23/23)    D3-10        2                          ........................                          24
93.9(46/49)   JH6          15                                                 ..TA..............G..     37
ID%
```

Figure 4AG-2

```
              Ha5-7be20.1  339  AGGGACCACGGTCACCGTCTCCTCAG  364
                                 G  T  T  V  T  V  S  S
99.0(289/292) VH4-59              ------------------------
100(23/23)    D3-10               ------------------------
93.9(46/49)   JH6            38   ........................  63
```

Figure 4AH-1 Alignment of Ha5-7be20.1 VL to human Ig germline.

```
                                  <------------------------FWR1------------------------>  <
              Ha5-7be20.1  45   GATATTGTGATGACTCAGTCTCCACTCTCCCTGCCCGTCACCCCTGGAGAGCCGGCCTCCATCTCCTGC  114
                                 D  I  V  M  T  Q  S  P  L  S  L  P  V  T  P  G  E  P  P  A  S  I  S  C
ID%           A19           1    D  I  V  M  T  Q  S  P  L  S  L  P  V  T  P  G  E  P  P  A  S  I  S  C    70
98.7(295/299) JK5                                                                                          -
100(37/37)
ID%
                                   <--------CDR1---------->                         <
              Ha5-7be20.1  115  GGTCTAGTCAGAGCCCTCTGCATAGTACTG---GATACAACTATTTGGAT TGGTACCTGCAGAAGCCAGG  181
                                 R  S  S  Q  S  L  L  H  S  T     G  Y  N  Y  L  D   W  Y  L  Q  K  P  G
              A19          71    R  S  S  Q  S  L  L  H  S  N     G  Y  N  Y  L  D   W  Y  L  Q  K  P  G   137
              JK5                ..............A..--.............................................
ID%
                                  <----FWR2----> <-------CDR2------->   <
              Ha5-7be20.1  182  GCAGTCTCCACAACTCCTGATCTAT TTGGGTTCTATTCGGGCCTCC GGGGTCCCTGACAGGTTCAGTGGC  251
                                 Q  S  P  Q  L  L  I  Y  L  G  S  I  R  A  S   G  V  P  D  R  F  S  G
              A19         138    Q  S  P  Q  L  L  I  Y  L  G  S  N  R  A  S   G  V  P  D  R  F  S  G    207
              JK5                ......G.........................A.......................................
ID%
                                  <---------FWR3--------->
              Ha5-7be20.1  252  AGTGGATCAGGGACACAGATTTTACACTCTGAAAATCAGCAGAGTGGAGGCTGAGGATGTTGGGGTTTATTACT  321
                                 S  G  S  G  T  D  F  T  L  K  I  S  R  V  E  A  E  D  V  G  V  Y  Y
              A19         208    S  G  S  G  T  D  F  T  L  K  I  S  R  V  E  A  E  D  V  G  V  Y  Y    277
              JK5                ..............................................................
ID%
                                   <->
              Ha5-7be20.1  322  GC ATGCAAGCTCTACAGACTCCCATCACCTTCGGCCAAGGGACCACGCTGGAGACTGGAGATTAAAC  381
                                 C   M  Q  A  L  Q  T  P  I  T  F  G  Q  G  T  R  L  E  I  K
              A19                C   M  Q  A  L  Q  T  P
```

Figure 4AI-1 Alignment of Ha5-7acd5.1.1 VH to human Ig germline.

```
ID%
                           <------------------------------FWR1------------------------------
                           Q  V  Q  L  Q  E  S  G  P  G  L  V  K  P  S  E  T  L  S  L  T  C  T
              Ha5-7acd5.1.1   1  CAGGTGCAGCTGCAGGAGTCGGGCCCAGGACTGGTGAAGCCTTCGGAGACCCTGTCCCTCACCTGCACTG  70
100(289/289)  VH4-59         1  ..................................................................  70
100(19/19)    D3-10
98.0(48/49)   JH6
ID%                            <-----------------><    -----------CDR1----->  <--------FWR
                           V  S  G  G  S  I  S        S     Y  Y  Y  W  S       W  I  R  Q  P  P  G  K
              Ha5-7acd5.1.1  71  TCTCTGTGGCTCCATCAG-----T  AGT------TACTACTGGAGC  TGGATCCGGCAGCCCCCAGGGAA  128
100(289/289)  VH4-59        71  .................                 ..................  ......................  128
100(19/19)    D3-10                                               Y  Y  W  S        W  I  R  Q  P  P  G  K
98.0(48/49)   JH6
ID%                            <-----------------><    ---------CDR2---------->                         <--
                           G  L  E  W  I  G        Y  I  Y  Y  S  G  S  T  N  Y  N  P  S  L  K  S       R
              Ha5-7acd5.1.1 129  GGGACTGGAGTGGATTGGG  TATATCTATTACAGTGGGAGCACCAACTACAACCCCTCCCTCAAGAGT  CGA  198
100(289/289)  VH4-59       129  ...................                                                    ...  198
100(19/19)    D3-10                                 Y  I  Y  Y  S  G  S  T  N  Y  N  P  S  L  K  S       R
98.0(48/49)   JH6
ID%                            -------FWR3-------->
                           V  T  I  S  V  D  T  S  K  N  Q  F  S  L  K  L  S  S  V  T  A  A  D
              Ha5-7acd5.1.1 199  GTCACCATATCAGTAGACACGTCCAAGAACCAGTTCTCCCTGAAGCTGAGCTCTGTGACCGCTGCGGACA  268
100(289/289)  VH4-59       199  ..................................................................  268
100(19/19)    D3-10           V  T  I  S  V  D  T  S  K  N  Q  F  S  L  K  L  S  S  V  T  A  A  D
98.0(48/49)   JH6
ID%                                                            <------>
                           T  A  V  Y  Y  C  A  N        T  Y  Y  Y  G  S  G  Y  G  M  D  V  W  G  Q  G
              Ha5-7acd5.1.1 269  CGGCCGTGTATTACTGTGCGAAC  ACGTATTACTATGGTTCGGGGTTCGGGTACGGTATGGACGTCTGGGGCCAAGG  338
                           T  A  V  Y  Y  C  A
```

Ha5-7acd5.1.1  269  ........................................  289
                              1   ........................................  19
                              15  ........................................  40

Ha5-7acd5.1.1  339  GACCACGGTCACCGTCCTCAG  361
                                   T  T  V  T  V  S  S

100(289/289)  VH4-59
100(19/19)    D3-10
98.0(48/49)   JH6

Ha5-7acd5.1.1                                  63
                                                             41
```

Figure 4AJ-1 Alignment of Ha5-7acd5.1.1 VL to human Ig germline.

```
                          <-----------------------FWR1----------------------->  <
                           D  I  V  M  T  Q  S  P  L  S  L  P  V  T  P  G  E  P  A  S  I  S  C
ID%       Ha5-7acd5.1.1 16 GATATTGTGATGACTCAGTCTCCACTCTCCCTGCCCGTCACCCCTGGAGAGCCGGCCTCCATCTCCTGC 85
99.0(294/297) A19       1  D  I  V  M  T  Q  S  P  L  S  L  P  V  T  P  G  E  P  A  S  I  S  C   70
100(37/37)    JK5
ID%                                   <----------CDR1-------------->  <
                           R  S  S  Q  S  L  L  H  S  T  G  H  N  Y  L  D  W  Y  L  Q  K  P  G
          Ha5-7acd5.1.1 86 GGTCTAGTCAGAGCCTCCTGCATAGTACTG----GACACAACTATTTGGAT TGGTACCTGCAGAAGCCAGG 152
99.0(294/297) A19       71 R  S  S  Q  S  L  L  H  S  N    G  Y  N  Y  L  D  W  Y  L  Q  K  P  G  137
100(37/37)    JK5                       .....A......T..
ID%                        <-------FWR2------->  <-------CDR2------>
                           Q  S  P  Q  L  L  I  Y  L  G  S  I  R  A  S  G  V  P  D  R  F  S  G
          Ha5-7acd5.1.1 153 GCAGTCTCCACAGCTCCTGATCTAT TTGGGTTCTATTCGGGCCTCC GGGGTCCCTGACGGTTCAGTGGC 222
99.0(294/297) A19       138 Q  S  P  Q  L  L  I  Y  L  G  S  N  R  A  S  G  V  P  D  R  F  S  G  207
100(37/37)    JK5                                        ..........A..
ID%                                          <--------FWR3
                           S  G  S  G  T  D  F  T  L  K  I  S  R  V  E  A  E  D  V  G  V  Y  Y
          Ha5-7acd5.1.1 223 AGTGGATCAGGCACAGATTTTACACTGAAAATCAGCAGAGTGGAGGCTGAGGATGTTGGGGTTTATTACT 292
99.0(294/297) A19       208 S  G  S  G  T  D  F  T  L  K  I  S  R  V  E  A  E  D  V  G  V  Y  Y  277
100(37/37)    JK5
```

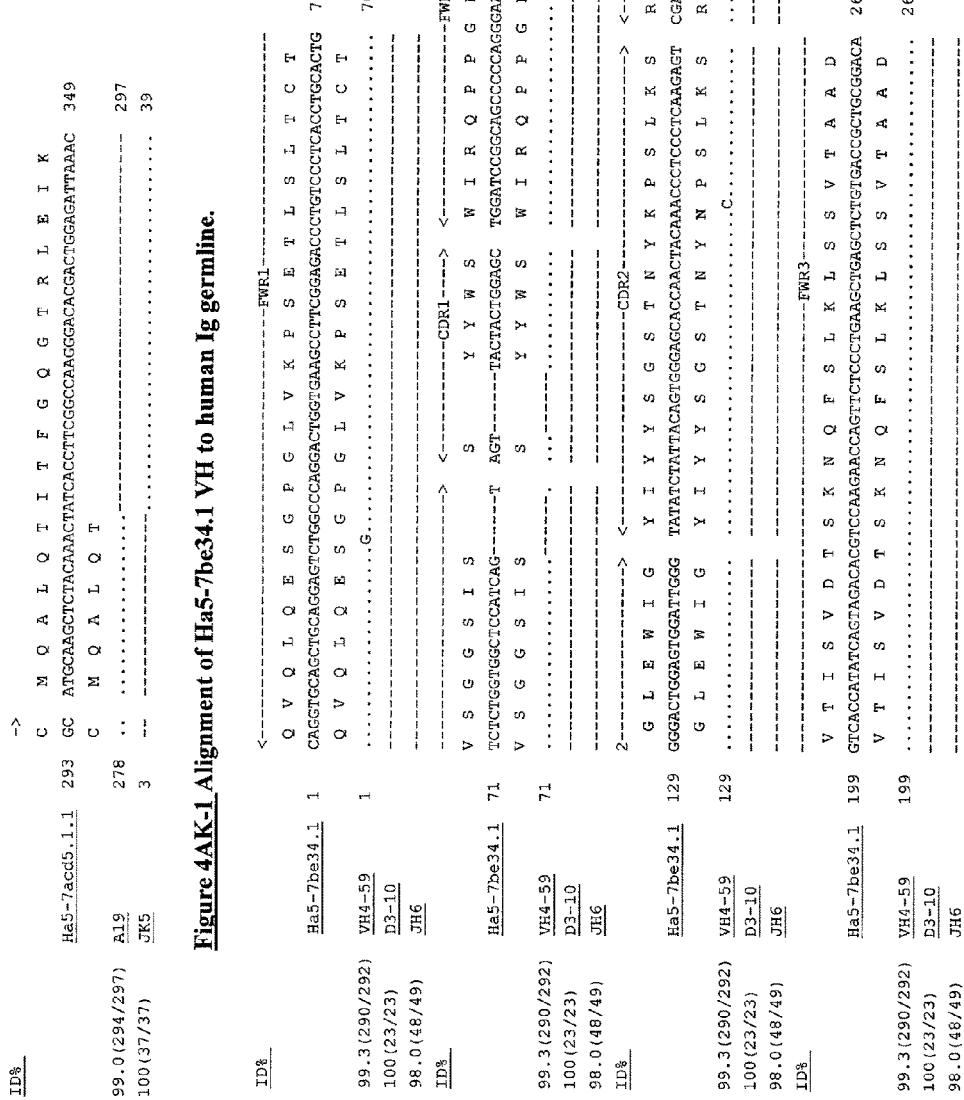

Figure 4AK-2

```
ID%                                    ---------------------->
                                       T  A  V  Y  Y  C  A  R     G  Y  Y  Y  G  S  G  S  Y  G  M  D  V  W  G  Q
              Ha5-7be34.1  269  CGGCCCGTGTATTACTGTGCGAGA GGCTATTACTATGGTTCGGGGAGTTACGGTTATGGACGTCTGGGGCCA  338
              VH4-59       269  T  A  V  Y  Y  C  A  R                                                           292
99.3(290/292)
100(23/23)    D3-10          2  .......................                                                            24
98.0(48/49)   JH6           15  ---------------------                                          ...G...             37

ID%
                                       G  T  T  V  T  V  S  S
              Ha5-7be34.1  339  AGGGACCACGGTCACCGTCTCCTCAG  364
99.3(290/292) VH4-59
100(23/23)    D3-10
98.0(48/49)   JH6           38  .........................   63
```

Figure 4AL-1 Alignment of Ha5-7be34.1 VL to human Ig germline.

```
ID%                  <--------------------------FWR1---------------------------->  <
                     D  I  V  M  T  Q  S  P  L  S  L  P  V  T  P  G  E  P  A  S  I  S  C
        Ha5-7be34.1  44   GATATTGTGATGACTCAGTCTCCACTCTCCCTGCCCGTCACCCCTGGAGAGCCGGCCTCCATCTCTGC  113
                     D  I  V  M  T  Q  S  P  L  S  L  P  V  T  P  G  E  P  A  S  I  S  C
98.3(294/299)  A19    1   ..................................................................   70
100(37/37)    JK5                                                                                .

ID%                  <--------CDR1--------->
                     R  S  S  Q  S  L  L  H  S  T     G  Y  N  Y  L  D     W  Y  L  Q  K  P  G
        Ha5-7be34.1  114  GGTCCTAGTCAGAGCCTCCTGCATAGTACTG---GATACAACTATTTGGAT TGGTACCTGCAGAAGCCAGG  180
                     R  S  S  Q  S  L  L  H  S  N     G  Y  N  Y  L  D     W  Y  L  Q  K  P  G
98.3(294/299)  A19   71   ..........................A...                    ....................  137
100(37/37)    JK5

ID%                  <----FWR2----> <------CDR2------>
                     Q  S  P  Q  L  L  I  Y     L  G  S  I  R  A  S      G  V  P  D  R  F  S  G
        Ha5-7be34.1  181  GCAGTCTCCACAGCTCCTCATCTAT TTGGGTTCTATTCGGGCCTCC  GGGGTCCCTGACAGGTTCAGTGGC  250
                     Q  S  P  Q  L  L  I  Y     L  G  S  N  R  A  S      G  V  P  D  R  F  S  G
98.3(294/299)  A19   138  ................G........  ............A.......   ........................  207
100(37/37)    JK5

<-----------FWR3------------
                     S  G  S  G  T  D  F  T  L  K  I  S  R  V  E  A  E  D  V  G  I  Y  Y
```

Figure 4AL-2

```
                Ha5-7be34.1  251  AGTGGATCAGGCACAGATTTACACTGAAAATCAGCAGAGTGAGGCTGAGGATGTTGGAATTATTACT  320
                                   S  G  S  G  T  D  F  T  L  K  I  S  R  V  E  A  E  D  V  G  V  Y  Y 98.3(294/299)   A19          208  .........................................................GG........  277
100(37/37)      JK5
ID%
                                  ->
                                   C  M  Q  A  L  Q  T  P  I  T  F  G  Q  G  T  R  L  E  I  K
                Ha5-7be34.1  321  ATGCAAGCTCTACAAACTCCCATCACCTTCGGCCAAGGGACACGACTGGAGATTAAAC  380
                                   C  M  Q  A  L  Q  T  P  P
98.3(294/299)   A19          278  ..                                                           299
100(37/37)      JK5             3  --                                                            39
ID%
```

Figure 4AM-1 Alignment of Ha5-7acd3.1 VH to human Ig germline.

```
                                 <-----------------------FWR1------------------------>  <-----CDR1---->
                                  Q  V  Q  L  V  E  S  G  G  G  V  V  Q  P  G  R  S  L  R  L  S  C  A    A  S  G  F  T  F  S    S  Y  G  M  H
ID%             Ha5-7acd3.1   1  CAGGTGCAGCTGGTGGAGTCTGGGGGAGGCGTGGTCCAGCCTGGGAGGTCCCTGAGACTCTCCTGTGCAG  70   CGTCTGGATTCACCTTCAGT  AGCTATGGCATGCAC
                                  Q  V  Q  L  V  E  S  G  G  G  V  V  Q  P  G  R  S  L  R  L  S  C  A    A  S  G  F  T  F  S    S  Y  G  M  H
99.0(293/296)   VH3-33        1  ....................................................................  70   ....................  ..............
100(18/18)      D5-12
96.8(61/63)     JH6
ID%

<------FWR2------>                                              <---
                                                      W  V  R  Q  A  P  G  K  G  L  E  W              V  A    V  I  W  Y  D  G  S  N  K  Y  Y  T  D  S  V  K  G
                Ha5-7acd3.1  71  TGGGTCCGCCAGGCTCCAGGCAAGGGCTGGAGTG  140                                GGTGGCA  GTTATTTGGTATGATGGAAGTAATAAATACTATACAGACTCCGTGAAGGGC
                                                      W  V  R  Q  A  P  G  K  G  L  E  W              V  A    V  I  W  Y  D  G  S  N  K  Y  Y  A  D  S  V  K  G
99.0(293/296)   VH3-33       71  ..................................  140                                .......  .....A..........................................
100(18/18)      D5-12
96.8(61/63)     JH6
ID%

<------
                                  R  F  T  I
                Ha5-7acd3.1  141  CGATTCACCATC  210
                                  R  F  T  I
99.0(293/296)   VH3-33       141  ............  210
100(18/18)      D5-12
96.8(61/63)     JH6
ID%

<-----------------------FWR3----------------------->
                                  S  R  D  N  S  K  N  T  L  Y  L  Q  M  N  S  L  R  A  E  D  T  A  V
                Ha5-7acd3.1  211  TCCAGAGACAATTCCAAGAACACCCTGTATCTGCAAATGAACAGCCTGAGAGCCGAGGACACGGCTGTGT  280
```

Figure 4AM-2

```
                                              S  R  D  N  S  K  N  T  L  Y  L  Q  M  N  S  L  R  A  E  D  T  A  V
99.0(293/296)   VH3-33      211               ............................................................  280
100(18/18)      D5-12
96.8(61/63)     JH6
ID%
                                              Y  Y  C  A  R      D  R  Y  S  G  Y  D  Y  F  Y  Y  Y  G  M  D  V  W  G  Q
                Ha5-7acd3.1 281               ATTACTGTGCGCGA GATCGGTATAGTGGCTACGATTACTTCTACTACTACGGTATGGACGTCTGGGGCCA 350
                                              Y  Y  C  A  R
99.0(293/296)   VH3-33      281               .........A...                                                              296
100(18/18)      D5-12       6                                                                                            23
96.8(61/63)     JH6         1                                ........................A.......................G..         37
ID%

G  T  T  V  T  V  S  S
                Ha5-7acd3.1 351               AGGGACCACGGTCACCGTCTCCTCAG 376
99.0(293/296)   VH3-33
100(18/18)      D5-12
96.8(61/63)     JH6         38                .........................  63
ID%
```

Figure 4AN-1 Alignment of Ha5-7acd3.1 VL to human Ig germline.

```
                                              <-----------------------FWR1------------------------>  <
                                              D  I  Q  M  T  Q  S  P  S  S  L  S  A  S  V  G  D  R  V  T  I  T  C
                Ha5-7acd3.1  22               GACATCCAGATGACCCAGTCTCCATCCTCCCTGTCTGCATCTGTAGGAGACAGAGTCACCATCACTTGT  91
                                              D  I  Q  M  T  Q  S  P  S  S  L  S  A  S  V  G  D  R  V  T  I  T  C
96.5(274/284)   L1           1                ..................................................................... 70
100(38/38)      JK3
ID%
                                              <---------CDR1---------->
                                              R  A  S  Q  G  I  Y  N  Y  L  A      W  F  Q  Q  K  P  G  K  A  P  R  S  L
                Ha5-7acd3.1  92               GGGCGAGTCAGGGCATTTACAATTATTTAGCC TGGTTTCAGCAGAAACCCGGGAAAGCCCCTAGGTCCT 161
                                              R  A  S  Q  G  I  S  N  Y  L  A      W  F  Q  Q  K  P  G  K  A  P  K  S  L
96.5(274/284)   L1          71                ..................AG.............   ......................A.......     140
100(38/38)      JK3
ID%
                                              <---------CDR2-------->
                                              I  Y  A  A  S  S  L  H  S      G  V  P  S  K  F  S  G  S  G  S  G  T  D
                Ha5-7acd3.1 162               GATCTAT GCTGCATCCAGTTTGCACAGT GGGGTCCCATCTAAGTTCAGCGGCAGTGGATCTGGGACAGAT 231
                                              I  Y  A  A  S  S  L  Q  S      G  V  P  S  R  F  S  G  S  G  S  G  T  D
```

Figure 4AN-2

```
                                                                                      210
96.5(274/284)   L1    141   ...........................A.G..........................
100(38/38)      JK3         -----FWR3----->
ID%
                            F  T  L  T  I  S  S  L  Q  P  E  D  F  A  T  Y  Y  C    Q  Q  Y  T  I
            Ha5-7acd3.1     TTCACTCCTCACCATCAGCAGCCTGCAGCCTGAAGATTTGCAACTTATTACTGC   CAACAATATACTATTT  301
96.5(274/284)   L1    211   F  T  L  T  I  S  S  L  Q  P  E  D  F  A  T  Y  Y  C    Q  Q  Y  N  S
100(38/38)      JK3         ...........................G....A..G..                                 280
ID%

Y  P  F  T  F  G  P  G  T  K  V  D  I  K
            Ha5-7acd3.1 302 ACCCATTCACTTCCGGCCCTGGGACCAAAGTGGATATCAAAC   343
96.5(274/284)   L1    281   Y  P
100(38/38)      JK3     1   ....                                         284
ID%                                                                       38
```

Figure 4AO-1 Alignment of Ha5-7acd2.1 VH to human Ig germline.

```
                                      <-------------------------FWR1-------------------------->
                                       Q  V  Q  L  Q  E  S  G  P  G  L  V  K  P  S  E  T  L  S  L  T  C  T
            Ha5-7acd2.1  1            CAGGTGCAGCTGCAGGAGTCTGGCCCAGGACTGGTGAAGCCTTCGGAGACCCTGTCCCTCACCTGCACTG  70
                                       Q  V  Q  L  Q  E  S  G  P  G  L  V  K  P  S  E  T  L  S  L  T  C  T
99.7(288/289)   VH4-59   1            ......G..............................................................  70
100(19/19)      D3-10
98.0(48/49)     JH6
ID%
                                      <----------------------->  <-----CDR1----->  <--------------FWR
                                       V  S  G  G  S  I  S           S     Y  Y  W  S        W  I  R  Q  P  P  G  K
            Ha5-7acd2.1  71           TCTCTGGTGGCTCCATCAG--------T   AGT---TACTACTGGAGC   TGGATCCGGCAGCCCCCAGGGAA  128
                                       V  S  G  G  S  I  S           S     Y  Y  W  S        W  I  R  Q  P  P  G  K
99.7(288/289)   VH4-59   71           ...............                ...   .............     ......................  128
100(19/19)      D3-10
98.0(48/49)     JH6
ID%
                                      2--------->  <------------CDR2------------>                        <--
                                       G  L  E  W  I  G     Y  I  Y  Y  S  G  S  T  N  Y  N  P  S  L  K  S     R
            Ha5-7acd2.1 129           GGGACTGGAGTGGGATTGGG TATATCTATTACAGTGGGAGCACCAACTACAACCCCTCCCTCAAGAGT   CGA  198
                                       G  L  E  W  I  G     Y  I  Y  Y  S  G  S  T  N  Y  N  P  S  L  K  S     R
99.7(288/289)   VH4-59  129           ....................  ..............................................   ...  198
100(19/19)      D3-10
```

Figure 4AO-2

```
                                                                                                        -------FWR3------------------------------------>
98.0(48/49)   JH6                V  T  I  S  V  D  T  S  K  N  Q  F  S  L  K  L  S  S  V  T  A  A  D
ID%                              GTCACCATATCAGTAGACACGTTCCAAGAACACCAGTTCTCCCTGAAGCTGAGCTCTGTGACCGCTGCGACA  268
              Ha5-7acd2.1  199
99.7(288/289) VH4-59             V  T  I  S  V  D  T  S  K  N  Q  F  S  L  K  L  S  S  V  T  A  A  D   268
100(19/19)    D3-10         199  ............................................................................
98.0(48/49)   JH6
ID%                                                    >
                                 T  A  V  Y  Y  C  A  N     T  Y  Y  Y  G  S  G  Y  G  M  D  V  W  G  Q  G
              Ha5-7acd2.1  269   CGGGCCGTGTATTACTGTGCGAAC  ACGTATTACTATGGTTCGGGGTACGGTATGGACGTCTGGGGCCAAGG  338
                                 T  A  V  Y  Y  C  A
99.7(288/289) VH4-59        269  ............................  ----------------------------------------     289
100(19/19)    D3-10         1    ------------------------      ..........................................    19
98.0(48/49)   JH6           15   ------------------------      ............G.............................    40
ID%
                                 T  T  V  T  V  S  S
              Ha5-7acd2.1  339   GACCACGGTCACCGTCTCCCTCAG  361
99.7(288/289) VH4-59        
100(19/19)    D3-10         
98.0(48/49)   JH6           41   ........................  63
ID%
```

Figure 4AP-1 Alignment of Ha5-7acd2.1 VL to human Ig germline.

```
                                <---------------------FWR1------------------------------------------->   <
                                 D  I  V  M  T  Q  S  P  L  S  L  P  V  T  P  G  E  P  A  S  I  S  C
              Ha5-7acd2.1  25    GATATTGTGATGACTCAGTCTCCACTCTCCCTGCCCGTCACCCCTGGAGAGCCGGCCTCCATCTCCTGC  94
99.0(294/297) A19           1    D  I  V  M  T  Q  S  P  L  S  L  P  V  T  P  G  E  P  A  S  I  S  C   .
100(37/37)    JK5                ............................................................................ 70
ID%                              
                                 <-----------CDR1------------->
                                 R  S  S  Q  S  L  L  H  S  T  G  H  N  Y  L  D     W  Y  L  Q  K  P  G
              Ha5-7acd2.1  95    GGTCTAGTAGTCAGAGCCTCCTGCATAGTACTG---GACACAACTATTTGGAT  TGGTACCTGCAGAAGCCAGG  161
99.0(294/297) A19           71   R  S  S  Q  S  L  L  H  S  N     G  Y  N  Y  L  D     W  Y  L  Q  K  P  G
100(37/37)    JK5                ....................................A.------..T..........  ..................... 137
```

Figure 4AP-2

```
                                --FWR2---------------->  <----CDR2----->
                       Q  S  P  Q  L  L  I  Y           L  G  S  I  R  A  S           G  V  P  D  R  F  S  G
Ha5-7acd2.1    162  GCAGTCTCCACAAGCTCCTGATCTAT          TTGGGTTCTATTCGGGCCTCC          GGGGTCCCTGACAGGTTCAGTGGC  231
A19            138  ...............................    ...........................     ........................  207
JK5
ID%
                       Q  S  P  Q  L  L  I  Y           L  G  S  N  R  A  S           G  V  P  D  R  F  S  G
99.0(294/297)
100(37/37)
ID%

S  G  S  G  T  D  F  T  L  K  I  S  R  V  E  A  E  D  V  G  V  Y  Y
Ha5-7acd2.1    232  AGTGGATCAGGCACAGATTTTACACTGAAAATCAGCAGAGTGGAGGCTGAGGATGTTGGGGTTATTACT  301
A19            208  ..........................................................          277
JK5                                                                        <-FWR3->
                       S  G  S  G  T  D  F  T  L  K  I  S  R  V  E  A  E  D  V  G  V  Y  Y
99.0(294/297)
100(37/37)
ID%
                    -->
                       C     M  Q  A  L  Q  T  I  T  F  G  Q  G  T  R  L  E  I  K
Ha5-7acd2.1    302  GC  ATGCAAGCTCTACAAACTATCACCTTCGGCCAAGGGACAGACTGGAGATTAAAC  358
A19            278  ..  ...........................................          297
JK5              3  ..  .......                                                39
                       C     M  Q  A  L  Q  T
99.0(294/297)
100(37/37)
ID%
```

Figure 4AQ-1 Alignment of Ha5-8ac4.1 VH to human Ig germline.

```
                       <---------------------------------------FWR1--------------------------------------->
                       Q  V  Q  L  Q  E  S  G  P  G  L  V  K  P  S  E  T  L  S  L  T  C  T
Ha5-8ac4.1      1  CAGGTGCAGCTGCAGGAGTCTGGCCCAGGACTGGTGAAGCCTTCGGAGACCCTGTCCCTCACCTGCACTG  70
VH4-4           1  ................G.................................................     70
D6-25
JH2
                       Q  V  Q  L  Q  E  S  G  P  G  L  V  K  P  S  E  T  L  S  L  T  C  T
97.6(286/293)
87.5(14/16)
100(53/53)
ID%

<-------CDR1------>          <--------FWR2---------->
                       V  S  G  G  S  I  S     R  Y  Y  Y  W  S     W  I  R  Q  P  A  G  K  G  L
Ha5-8ac4.1     71  TCTCTGGTGGCTCCATCAG------T  CGTTACTACTGGAGC    TGGATCCGGCAGCCCGCCGGGAAGGGACT  134
VH4-4              ...................          S.............A.    ..............................  134
D6-25
JH2
                       V  S  G  G  S  I  S     S  Y  Y  Y  W  S     W  I  R  Q  P  A  G  K  G  L
97.6(286/293)
87.5(14/16)
100(53/53)
ID%
                                                        <--------CDR2---------->
                       E  R  I  G     R  I  Y  T  S  G  S  T  D  Y  N  P  S  L  K  S     R  V  T
```

Figure 4AQ-2

```
                    Ha5-8ac4.1   135  GGAGAGGATTGGG  CGGATCTATACCAGTGGGAGCACCGACTACAACCCTCTCAAGAGT  CGAGTCACC  204
                                       E  W  I  G    R  I  Y  T  S  G  S  T  N  Y  N  P  S  L  K  S    R  V  T
97.6(286/293)       VH4-4        135  ....T........  ..T.........A................................  .........  204
87.5(14/16)         D6-25
100(53/53)          JH2
ID%
                                                                                              ---FWR3---
                    Ha5-8ac4.1   205  ATGTCAGTAGACACGTCCAAGAACCAGTTCTCCCTGAAGCTGAGCTCTGTGACCGCCGCGGACACGGCCG  274
                                       M  S  V  D  T  S  K  N  Q  F  S  L  K  L  R  S  V  T  A  A  D  T  A
97.6(286/293)       VH4-4        205  .....................................C...............................  274
87.5(14/16)         D6-25
100(53/53)          JH2
ID%                                    M  S  V  D  T  S  K  N  Q  F  S  L  K  L  S  S  V  T  A  A  D  T  A
                                                                                      ---->
                                       V  Y  Y  C  A  R         D  L  Y  S  N  G  Y  W  Y  F  D  L  W  G  R  G  T  L
                    Ha5-8ac4.1   275  TGTTATTACTGTGCGAGA  GATTTGTATAGCAATGGCTACTACTTCGATCTCTGGGGCCGTGGCACCCT  344
97.6(286/293)       VH4-4        275  ..................                                                          293
87.5(14/16)         D6-25        3    ------------------  ----------------GC--------------------------------           18
100(53/53)          JH2          1    ------------------  --------------------------------------------------           36
ID%                                    V  Y  Y  C  A  R

V  T  V  S  S
                    Ha5-8ac4.1   345  GGTCACTGTCTCCTCAG  361
97.6(286/293)       VH4-4
87.5(14/16)         D6-25
100(53/53)          JH2          37   ................  53
ID%
```

Figure 4AR-1 Alignment of Ha5-8ac4.1 VL to human Ig germline.

```
                                       <-----------------------FWR1----------------------->   <----
                                       Q  S  V  L  T  Q  P  P  S  V  S  G  A  P  G  Q  R  V  T  I  S  C           T
                    Ha5-8ac4.1   5    CAGTCTGTGCTGACGCAGCCGCCCTCAGTGTCTGGGGCCCCAGGGCAGAGGGTCACCATCTCCTGC  ACTG  74
100(297/297)        V1-13        1    .................................................................  ....  70
100(38/38)          JL2
ID%                                    Q  S  V  L  T  Q  P  P  S  V  S  G  A  P  G  Q  R  V  T  I  S  C           T
                                                                                                       ---FWR2---
                                       ----CDR1---->                                          <---FWR2------
                                       G  S  S  N  I  G  A  G  Y  D  V  H        W  Y  Q  Q  L  P  G  T  A  P  K
```

Figure 4AR-2

```
            Ha5-8ac4.1   75  GGAGCAGCTCCAACATCGGGGCAGGTTATGATGTACAC TGGTACCAGCAGCTTCCAGGAACAGCCCCAA 144
                                G  S  S  S   N  I  G  A  G  Y  D  V  H   W  Y  Q  Q  L  P  G  T  A  P  K
100(297/297) V1-13        71  .............................................................................  140
100(38/38)   JL2              .............................................................................
ID%                             L  L  I  Y   G  N  S  N  R  P  S   G  V  P  D  R  F  S  G  S  K  S  G

Ha5-8ac4.1  145  ACTCCTCCATCTAT GGTAACAGCAATCGGCCCTCA GGGGTCCCTGACCGATTCTCTGGCTCCAAGTCTGGC 214
                                L  L  I  Y   G  N  S  N  R  P  S   G  V  P  D  R  F  S  G  S  K  S  G
100(297/297) V1-13       141  .............................................................................  210
100(38/38)   JL2              .............................................................................
ID%                                        <-------FWR3-------
                              T  S  A  S  L  A  I  T  G  L  Q  A  E  D  E  A  D  Y  Y  C    Q  S  Y

Ha5-8ac4.1  215  ACCTCAGCCTCCCTGGCCATCACTGGGCTCCAGGCTGAGGATGAGGCTGATTATTACTGC CAGTCCTATG 284
                              T  S  A  S  L  A  I  T  G  L  Q  A  E  D  E  A  D  Y  Y  C    Q  S  Y
100(297/297) V1-13       211  .............................................................................  280
100(38/38)   JL2              .............................................................................
ID%
                              D  S  S  L  S  G  V  V  F  G  G  G  T  K  L  T  V  L

Ha5-8ac4.1  285  ACAGCAGCCTGAGTGGTGTGGTATTCGGCGGAGGGACCAAGCTGACCGTCCTAG 338
                              D  S  S  L  S  G
100(297/297) V1-13       281  ..............                                               297
100(38/38)   JL2           1  ..............                                                38
ID%
```

Figure 4AS-1 Alignment of Ha5-4(2,5)31.1 VH to human Ig germline.

```
                                    <-----------------------------FWR1-----------------------------
                                     Q  V  Q  L  V  E  S  G  G  G  V  V  Q  P  G  R  S  L  R  L  S  C  A
                Ha5-4(2,5)31.1  1   CAGGTGCAGCTGGTGGAGTCTGGGGGAGGCGTGGTCCAGCCTGGGAGGTCCCTGAGACTCTCCTGTGCAG 70
                                     Q  V  Q  L  V  E  S  G  G  G  V  V  Q  P  G  R  S  L  R  L  S  C  A
ID%
99.0(293/296)   VH3-33           1  ...........................................................................  70
100(16/16)      D6-19
97.9(47/48)     JH4
ID%                                                    <-----CDR1----->                 <------FWR2------
                                     A  S  G  F  T  F  R   S  Y  G  M  H   W  V  R  Q  A  P  G  K  G  L  E  W
                Ha5-4(2,5)31.1  71  CGTCTGGATTCACCTTCAGA AGCTATGGCATGCAC TGGGTCCGCCAGGCTCCAGGCAAGGGGCTGGAGTG 140
                                     A  S  G  F  T  F  S   S  Y  G  M  H   W  V  R  Q  A  P  G  K  G  L  E  W
99.0(293/296)   VH3-33          71  .............................T............................................. 140
```

Figure 4AS-2

```
                                                                                                                                              210
100(16/16)     D6-19      ------------------------------------------------------------
97.9(47/48)    JH4        ------------------------------------------------------------
ID%                       ------>  <----------------------CDR2----------------------------->  <---
                               V  A    V  I  W  Y  D  G  S  N  K  Y  Y  A  D  S  V  K  G    R  S  T  I
Ha5-4(2,5)31.1    141     GGTGGCA  GTTATATGGTATGATGGAAGTAATAAATACTATGCAGACTCCGTGAAGGGC  CGATCCACCATC   210
                               V  A    V  I  W  Y  D  G  S  N  K  Y  Y  A  D  S  V  K  G    R  F  T  I
VH3-33            141     ..........................................................   ...T........
D6-19                     ------------------------------------------------------------
JH4                       ------------------------------------------------------------
ID%                       ------------------------------------------------------------<----FWR3-----
                            S  R  D  N  S  K  N  T  L  Y  L  Q  M  N  S  L  R  A  E  D  T  A  V
Ha5-4(2,5)31.1    211     TCCAGAGACAACTCCAAGAACACGCTGTATCTGCAAATGAACAGCCTGAGAGCCGAGGACACGGCTGTGT   280
                            S  R  D  N  S  K  N  T  L  Y  L  Q  M  N  S  L  R  A  E  D  T  A  V
VH3-33            211     ...T..............................................................   280
D6-19                     ------------------------------------------------------------
JH4                       ------------------------------------------------------------
ID%                       ------------>
                            Y  Y  C  A  R      D  G  V  A  V  A  G  T  D  Y  F  D  Y  W  G  Q  G  T  L
Ha5-4(2,5)31.1    281     ATTACTGTGCGAGA  GATGGGGTAGCAGTGGCTGGTACAGACTACTTTGACTACTGGGGCCAGGGAACCCT   350
                            Y  Y  C  A  R
VH3-33            281     ..............                                                                296
D6-19               6                      ........................                                      21
JH4                 1                                             ...........................A........   31
ID%
                              V  T  V  S  S
Ha5-4(2,5)31.1    351     GGTCACCGTCTCCTCAG   367
VH3-33                    -----------------
D6-19                     -----------------
JH4                32     ................    48
ID%
99.0(293/296)
100(16/16)
97.9(47/48)
```

Figure 4AT Alignment of Ha5-4(2,5)31.1 VL to human Ig germline.

```
ID%                                 <----------------------FWR1----------------------------->  <
                                    D I Q M T Q S P S S L S T S V G D R V T I T C
              Ha5-4(2,5)31.1   22   GACATCCAGATGACCCAGTCTCCATCCTCCCTGTCTGCATCTGTAGGAGACAGAGTCACCATCACTTGC          91
98.6(280/284) O12               1   ...................................G........................          70
100(38/38)    JK4                   D I Q M T Q S P S S L S A S V G D R V T I T C
ID%                                 -----------CDR1-----------> <-----------------FWR2-----------
                                    R A T Q S I S S H L N   W Y Q Q K P G K A P K L L
              Ha5-4(2,5)31.1   92   GGGCAACTCAGAGACATTAGCAGCCATTTAAAT TGGTATCAGCAGAAACCAGGGAAAGCCCCTAAGCTCCT        161
98.6(280/284) O12              71   ......G..................T.....                                              140
100(38/38)    JK4                   R A S Q S I S S Y L N .  W Y Q Q K P G K A P K L L
ID%                                 -------> <----------CDR2-----------> <--------------------
                                    I Y V A S S L Q S   G V P S R F S G S G S G T D
              Ha5-4(2,5)31.1  162   GATCTAT GTTGCATCCAGTTTGCAAAGT GGGGTCCCATCAAGGTTCAGTGGCAGTCTGGGACAGAT          231
98.6(280/284) O12             141   ....... .C.....................                                              210
100(38/38)    JK4                   I Y A A S S L Q S   G V P S R F S G S G S G T D
ID%                                 ---------FWR3-------------------> <----------------------
                                    F T L T I S S L Q P E D F A T Y Y C   Q Q S Y S
              Ha5-4(2,5)31.1  232   TTCACTCTCACCATCAGCAGTCTGCAACTGGAAGATTTTGCAACTTACTACTGT CAACAGAGTTACAGTA       301
98.6(280/284) O12             211   ........................................................               .....  280
100(38/38)    JK4                   F T L T I S S L Q P E D F A T Y Y C   Q Q S Y S
ID%                                 T P L T F G G G T K V E I K
              Ha5-4(2,5)31.1  302   CCCCGCTCACTTTCGGCGGAGGGACCAAGGTGGAGATCAAAC                                    343
98.6(280/284) O12             281   ..........................................                                  284
100(38/38)    JK4               1   T P ---                                                                        38
```

Figure 4AU-1 Alignment of Ha5-11a1.1.1 VH to human Ig germline.

```
ID%                           <----------------------------------FWR1----------------------------------
                              Q   V   Q   L   Q   E   S   G   P   G   L   V   K   P   S   Q   T   L   S   L   T   S   T
              Ha5-11a1.1.1  1 CAGGTGCAGCTGCAGGAGTCTGGGCCCAGGACTGGTGAAGCCTTCACAGACCCTGTCCCTCACCAGCACTG  70
97.3(290/298) VH4-31        1 ..........................G......................................T.T....   70
100(21/21)    D3-10
98.0(49/50)   JH6
ID%
                                              <----CDR1---->                          <----FWR2------
                              V   S   G   G   S   I   S   S   G   G   Y   Y   W   S   W   I   R   Q   L   P   G   K   G   L
              Ha5-11a1.1.1 71 TCTCTGGTGGCTCCATCAGC AGTGGTGGTTACTACTGGAGC TGGATCCGCCAGCTCCCAGGAAGGGCCT 140
97.3(290/298) VH4-31       71 ....................  ...................  .........A................. 140
100(21/21)    D3-10
98.0(49/50)   JH6
ID%
                              <------------------------CDR2------------------------>                  <--
                              E   W   V   G   Y   I   H   N   S   G   S   T   Y   Y   N   P   S   L   K   S   R   V   T
              Ha5-11a1.1.1 141 GGAGTGGGTTGGG TACATCCATAACAGTGGGAGCACCTACTACTACAACCCGTCCCTCAAGAGT CGAGTTACC 210
97.3(290/298) VH4-31      141 .....A.......  .........T.T...................................  ......... 210
100(21/21)    D3-10
98.0(49/50)   JH6
ID%
                              --->
                              I   S   V   D   T   S   K   N   Q   F   S   L   K   L   R   S   V   T   A   A   D   T   A
              Ha5-11a1.1.1 211 ATATCAGTAGACACGTCTAAGAACCAGTTCTCCCTGAAGCTGAGATCTGTGACTGCCGCGGACACGGCCG 280
97.3(290/298) VH4-31      211 ..................................................C................ 280
100(21/21)    D3-10
98.0(49/50)   JH6
ID%
                                                  <------>
                              V   Y   Y   C   A   R   G   Y   Y   Y   G   S   G   S   P   Y   G   M   D   V   W   G   Q   G
              Ha5-11a1.1.1 281 TGTATTACTGTGCGAGA GGGTATTACTATGGTTCGGGGAGCCCCTACGGTATGGACGTCTGGGGCCAAGG 350
97.3(290/298) VH4-31      281 .................                                                      298
100(21/21)    D3-10         1                   .....................                                 21
98.0(49/50)   JH6          14                                        ..............G........          40
ID%
```

Figure 4AU-2

```
              Ha5-11a1.1.1  351 GACCACGGTCACCGTCTCCTCAG 373
                                 T  T  V  T  V  S  S
97.3(290/298) VH4-31
100(21/21)    D3-10          ...................... 
98.0(49/50)   JH6           41 ....................... 63
```

Figure 4AV-1 Alignment of Ha5-11a1.1.1 VL to human Ig germline.

```
ID%                           <------------------FWR1----------------->  <
              Ha5-11a1.1.1 26  D  I  V  M  T  Q  S  P  L  S  L  P  V  T  P  G  E  T  A  S  I  S  C
                               GATATTGTGATGACTCAGTCTCCACTCTCCCTGCCCGTCACCCCTGGAGAGACGGCCTCCATCTCCTGC  95
              A19              D  I  V  M  T  Q  S  P  L  S  L  P  V  T  P  G  E  P  A  S  I  S  C
              JK4           1  ..............................................C......................  70
ID%                            <-----------CDR1----------->                 <
              Ha5-11a1.1.1 96  R  S  S  Q  S  L  L  Q  S  N     G  H  N  Y  L  D     W  Y  L  Q  K  P  G
                               GGTCTAGTCAGAGCCTCCTGCAAAGTAATG---GACACAACTATTTGGAT  TGGTACCTGCAGAAGCCAGG  162
              A19              R  S  S  Q  S  L  L  H  S  N     G  Y  N  Y  L  D     W  Y  L  Q  K  P  G
              JK4           71 ...........................T....---------......T..  .....................  137
ID%                            <---FWR2------>  <----CDR2---->            <
              Ha5-11a1.1.1 163 Q  S  P  Q  L  L  I  Y     L  G  S  Y  R  D  S     G  V  P  D  R  F  S  G
                               GCAGTCCCCACAGCTCCTGATCTAT  TTGGGTTCTTATCGGGACTCC  GGGGTCCCTGACAGGTTCAGTGGC  232
              A19              Q  S  P  Q  L  L  I  Y     L  G  S  N  R  A  S     G  V  P  D  R  F  S  G
              JK4          138 .........................  ........A......C....  .......................  207
ID%                            <----------FWR3-------->
              Ha5-11a1.1.1 233 S  G  S  G  T  D  F  T  L  K  I  S  R  V  E  A  E  D  V  G  V  Y  Y
                               AGTGGATCAGGCACCGATTTTACCCTGAAAATCAGCAGGGTGGAGGCTGAGGATGTTGGGGTCTATTACT  302
              A19              S  G  S  G  T  D  F  T  L  K  I  S  R  V  E  A  E  D  V  G  V  Y  Y
              JK4          208 ....................A.................................................T.......  277
ID%                            -->
              Ha5-11a1.1.1 303 C  M  Q  A  L  Q  T  P  P  T  F  G  G  G  T  K  L  E  I  K
                               GC ATGCAAGCTCTCAAACTCCTCCTACTTTCGGCGGAGGGACCAAGTTGGAGATCAAAC  362
              A19              C  M  Q  A  L  Q  T  P  P  P
96.7(292/302) 
97.1(33/34)
ID%
```

Figure 4AW-1 Alignment of Ha5-11b1.1 VH to human Ig germline.

```
ID%
                                  <----------------------------------FWR1---------------------------------->
             Ha5-11b1.1    1      Q  V  Q  L  V  E  S  G  G  G  V  V  Q  P  G  R  S  L  R  L  S  C  A
                                  CAGGTGCAGCTGGTGGAGTCTGGGGGAGGCGTGGTCCAGCCTGGGAGGTCCCTGAGACTCTCCTGTGCAG   70
99.3(294/296) VH3-33   1          Q  V  Q  L  V  E  S  G  G  G  V  V  Q  P  G  R  S  L  R  L  S  C  A
100(16/16)    D5-12
98.3(58/59)   JH6
ID%
                                  <-------------> <-----CDR1-----> <---------------------------FWR2
             Ha5-11b1.1   71      A  S  G  F  T  F  S    S  H  G  M  H    W  V  R  Q  A  P  G  K  G  L  E  W
                                  CGTCTGGATTCACCTTCAGT   AGTCATGGCATGCAC   TGGGTCCGCCAGGCTCCAGGCAAGGGGCTGGAGTG  140
99.3(294/296) VH3-33   71         A  S  G  F  T  F  S    S  Y  G  M  H    W  V  R  Q  A  P  G  K  G  L  E  W
100(16/16)    D5-12                                       ..CT..
98.3(58/59)   JH6
ID%
                                  ------> <---------------------CDR2---------------------> <----
             Ha5-11b1.1  141      V  A    V  I  M  Y  D  G  S  N  K  Y  Y  Y  A  D  S  V  K  G    R  F  T  I
                                  GGTGGCA  GTTATATGGTATGATGGAAGTAATAAATACTATGCAGACTCCGTGAAGGGC   CGATTCACCATC   210
99.3(294/296) VH3-33  141         V  A    V  I  M  Y  D  G  S  N  K  Y  Y  Y  A  D  S  V  K  G    R  F  T  I
100(16/16)    D5-12
98.3(58/59)   JH6
ID%
                                  ----------------------FWR3----------------------------->
             Ha5-11b1.1  211      S  R  D  N  S  K  N  T  L  Y  L  Q  M  N  S  L  R  A  E  D  T  A  V
                                  TCCAGAGACAATTCCAAGAACACCCTGTATCTGCAAATGAACAGCCTGAGAGCCGAGGACACGGCTGTGT  280
99.3(294/296) VH3-33  211         S  R  D  N  S  K  N  T  L  Y  L  Q  M  N  S  L  R  A  E  D  T  A  V
100(16/16)    D5-12
98.3(58/59)   JH6
ID%
                                  ----->
             Ha5-11b1.1  281      Y  Y  C  A  R    D  Q  Y  S  G  Y  D  L  Y  Y  Y  Y  G  M  D  V  W  G  Q
                                  ATTACTGCGCGAGA   GATCAATATAGTGGCTACGATCTCTACTACTACTACGGTATGGACGTCTGGGGCCA  350
                                  Y  Y  C  A  R
```

G  T  T  V  S  S
            Ha5-11b1.1  351 AGGGACCACGGTCACCGTCCTCAG                            376

VH3-33      281 ------------------------                            296
            D5-12         5 --------------------                                 20
            JH6          38 .........                                           63
ID%
99.3(294/296)
100(16/16)
98.3(58/59)
```

Figure 4AX-1 Alignment of Ha5-11b1.1 VL to human Ig germline.

```
                     <-----------------------FWR1----------------------->  <
                      D  I  V  M  T  Q  S  P  D  S  L  A  V  S  L  G  E  R  A  T  I  N  C
         Ha5-11b1.1  32 GACATCGTGATGACCCAGTCTCCAGACTCCTGGCTGTGTCTCTGGGCGAGAGGGCCACCATCAACTGC  101
                      D  I  V  M  T  Q  S  P  D  S  L  A  V  S  L  G  E  R  A  T  I  N  C
ID%                B3  1 ..................................................................    70
100(304/304)       JK1   ----------------------------------------------------------------  -
100(36/36)
ID%
                     --------CDR1--------->                              <---------
                      K  S  S  Q  S  V  L  Y  S  S  N  N  K  N  Y  L  A  W  Y  Q  Q  K  P  G
         Ha5-11b1.1 102 AGTTCCAGCCAGAGTGTTTTATACAGCTCCAACAATAAGAACTACTTAGCT TGGTACCAGCAGAAACCAGG 171
                      K  S  S  Q  S  V  L  Y  S  S  N  N  K  N  Y  L  A  W  Y  Q  Q  K  P  G
100(304/304)       B3  71 ....................................................................   140
100(36/36)         JK1   ----------------------------------------------------                -

----FWR2----->     <--------CDR2-------->                  <-------
                      Q  P  P  K  L  L  I  Y  W  A  S  T  R  E  S  G  V  P  D  R  F  S  G
         Ha5-11b1.1 172 ACAGCCTCCTAAGCTCCTAATTTAC TGGGCATCTACCCGGGAATCC GGGGTCCCTGACCGATTCAGTGGC  241
                      Q  P  P  K  L  L  I  Y  W  A  S  T  R  E  S  G  V  P  D  R  F  S  G
100(304/304)       B3 141 ......................................................................   210
100(36/36)         JK1   ----------------------------------------------------------------------

-------FWR3------->
                      S  G  S  G  T  D  F  T  L  T  I  S  S  L  Q  A  E  D  V  A  V  Y  Y
         Ha5-11b1.1 242 AGCGGGTCTGGGACAGATTTCACTCTCACCATCAGCAGCCTGCAGGCTGAAGATGTGGCAGTTTATTACT  311
                      S  G  S  G  T  D  F  T  L  T  I  S  S  L  Q  A  E  D  V  A  V  Y  Y
100(304/304)       B3 211 ......................................................................   280
100(36/36)         JK1   ----------------------------------------------------------------------
```

Figure 4AX-2

| ID% | | | |
|---|---|---|---|
| | | -> | |
| | | C | Q Q Y Y S T P R T F G Q G T K V E I K |
| | Ha5-11b1.1 312 | GT | CAGCAATATATAGTACTCCTCGGACGTTCGGCCAAGGGACCAAGGTGGAAATCAAAC 371 |
| 100(304/304) | B3 281 | | ........................................................ 304 |
| 100(36/36) | JK1 3 | | ...................................... 38 |
|   | | C | Q Q Y Y S T P |

Figure 4AY-1 Alignment of Ha5-7be7.1 VH to human Ig germline.

| ID% | | | |
|---|---|---|---|
| | | <-------------------------------------FWR1--------------------------------> | |
| | | E V Q L L E S G G G L V Q P G G S L R L S C A | |
| | Ha5-7be7.1 1 | GAGGTGCAGCTGTTGGAGTCTGGGGGAGGCTTGGTACAGCCTGGGGGGTCCCTGAGACTCTCCTGTGCAG | 70 |
| 99.0(292/295) | VH3-23 1 | ...................................................................... | 70 |
| 100(12/12) | D2-2 | | |
| 95.8(46/48) | JH4 | | |
|   | | E V Q L L E S G G G L V Q P G G S L R L S C A | |

| ID% | | | |
|---|---|---|---|
| | | <---CDR1----> <-----------------------FWR2---------------> | |
| | | A S G F T F S S N A M N W V R Q A P G K G L E W | |
| | Ha5-7be7.1 71 | CCTCTGGATTCACCTTTAGC AGCAATGCCATGAAC TGGGTCCGCCAGGCTCCAGGGAAGGGCTGGAGTG | 140 |
| 99.0(292/295) | VH3-23 71 | .................. ...T...........G. .................................. | 140 |
| 100(12/12) | D2-2 | | |
| 95.8(46/48) | JH4 | | |
|   | | A S G F T F S S Y A M S W V R Q A P G K G L E W | |

| ID% | | | |
|---|---|---|---|
| | | <-------------------CDR2-----------------> <--- | |
| | | V S A I S G G G S T C Y A D S V K G R F T I | |
| | Ha5-7be7.1 141 | GGTCTCA GCTATTAGTGGTGGTAGTGGTAGCACATGCTACGCAGACTCCGTGAAGGGC CGGTTCACCATC | 210 |
| 99.0(292/295) | VH3-23 141 | ........ ...........................A............................. ........... | 210 |
| 100(12/12) | D2-2 | | |
| 95.8(46/48) | JH4 | | |
|   | | V S A I S G G G S T Y Y A D S V K G R F T I | |

| ID% | | | |
|---|---|---|---|
| | | <-----------------------FWR3-----------------------> | |
| | | S R D N S K N T L Y L Q M N S L R A E D T A V | |
| | Ha5-7be7.1 211 | TCCAGAGACAATTCCAAGAACACACTGTATCTGCAAATGAACAGCCTGAGAGCCGAGGACACGGCCGTAT | 280 |
| 99.0(292/295) | VH3-23 211 | .................................................................... | 280 |
| 100(12/12) | D2-2 | | |
| 95.8(46/48) | JH4 | | |
|   | | S R D N S K N T L Y L Q M N S L R A E D T A V | |

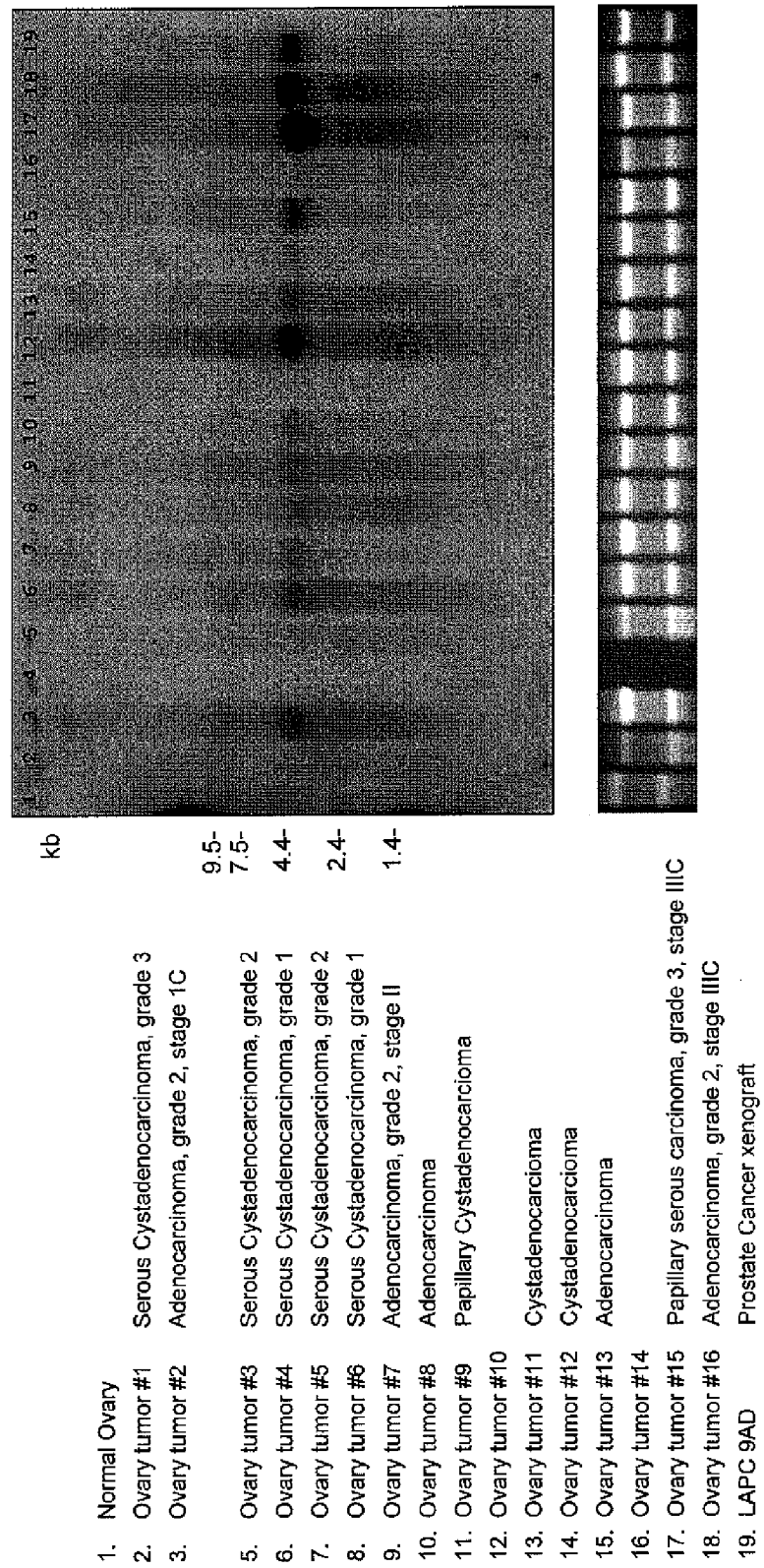

Figure 5A  24P4C12 Expression in Ovarian Cancer Patient Specimens

1. Normal Ovary
2. Ovary tumor #1   Serous Cystadenocarcinoma, grade 3
3. Ovary tumor #2   Adenocarcinoma, grade 2, stage 1C
5. Ovary tumor #3   Serous Cystadenocarcinoma, grade 2
6. Ovary tumor #4   Serous Cystadenocarcinoma, grade 1
7. Ovary tumor #5   Serous Cystadenocarcinoma, grade 2
8. Ovary tumor #6   Serous Cystadenocarcinoma, grade 1
9. Ovary tumor #7   Adenocarcinoma, grade 2, stage II
10. Ovary tumor #8  Adenocarcinoma
11. Ovary tumor #9  Papillary Cystadenocarcioma
12. Ovary tumor #10 Cystadenocarcioma
13. Ovary tumor #11 Cystadenocarcioma
14. Ovary tumor #12 Cystadenocarcioma
15. Ovary tumor #13 Adenocarcinoma
16. Ovary tumor #14
17. Ovary tumor #15 Papillary serous carcinoma, grade 3, stage IIIC
18. Ovary tumor #16 Adenocarcinoma, grade 2, stage IIIC
19. LAPC 9AD        Prostate Cancer xenograft

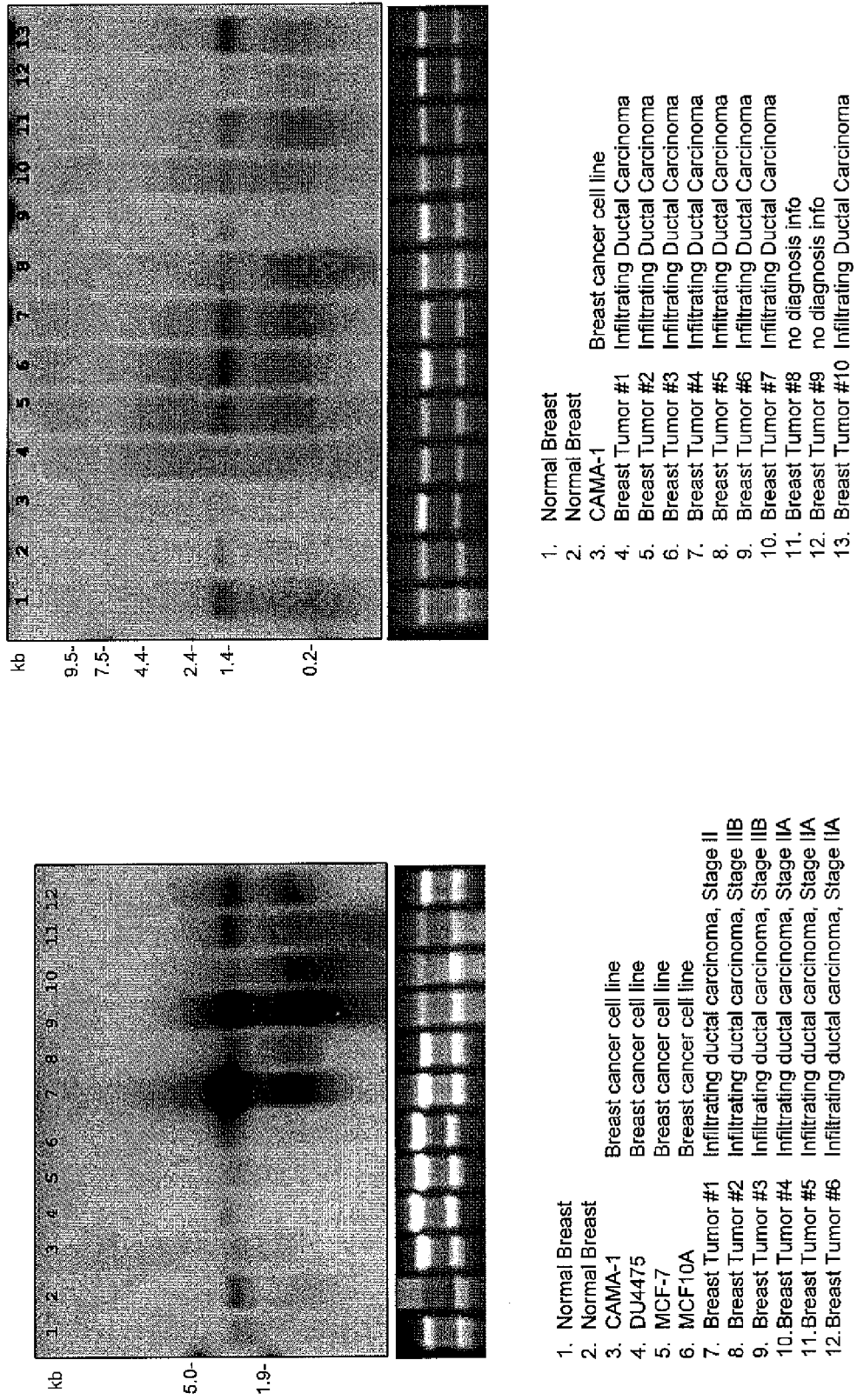

Figure 5C  24P4C12 Expression in Pancreas Patient Cancer Specimens, Xenografts and Cell Lines

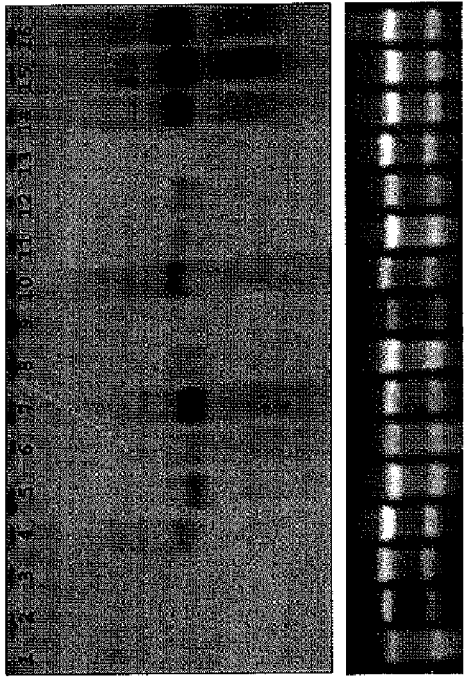

| # | Sample Name | Diagnosis |
|---|---|---|
| 1 | Normal | Normal pancreas |
| 2 | HPAC | Pancreatic Cancer Cell Line |
| 3 | CAPAN-1 | Pancreatic Cancer Cell Line |
| 4 | CFPAC-1 | Pancreatic Cancer Cell Line |
| 5 | Colon tumor | Adenocarcinoma; Stage II A; Grade: 2 |
| 6 | Pancreas tumor #1 | Adenocarcinoma; Grade: 1 |
| 7 | Pancreas tumor #2 | Adenocarcinoma; Stage I; Grade: 1 |
| 8 | Pancreas tumor #3 | Adenocarcinoma; Grade: 3 |
| 9 | Pancreas tumor #4 | Adenocarcinoma; Stage IIB; Grade: poorly differentiated |
| 10 | Pancreas tumor #5 | Adenocarcinoma; StageT3N1MX Stage IIB; Grade: moderate to poorly differentiated |
| 11 | Pancreas tumor #6 | Adenocarcinoma; Grade: II-III |
| 12 | Pancreas tumor #7 | Adenocarcinoma |
| 13 | AG-Panc1 xenograft | Xenograft from adenocarcinoma; Stage IIB; Grade: poorly differentiated |
| 14 | AG-Panc2 xenograft | Xenograft from adenocarcinoma; StageT3N1MX Stage IIB; Grade:mod to poor |
| 15 | AG-Panc3 xenograft | Xenograft from adenocarcinoma; Grade: moderately differentiated |
| 16 | AG-Panc4 xenograft | Xenograft from adenocarcinoma; Grade: moderately differentiated |

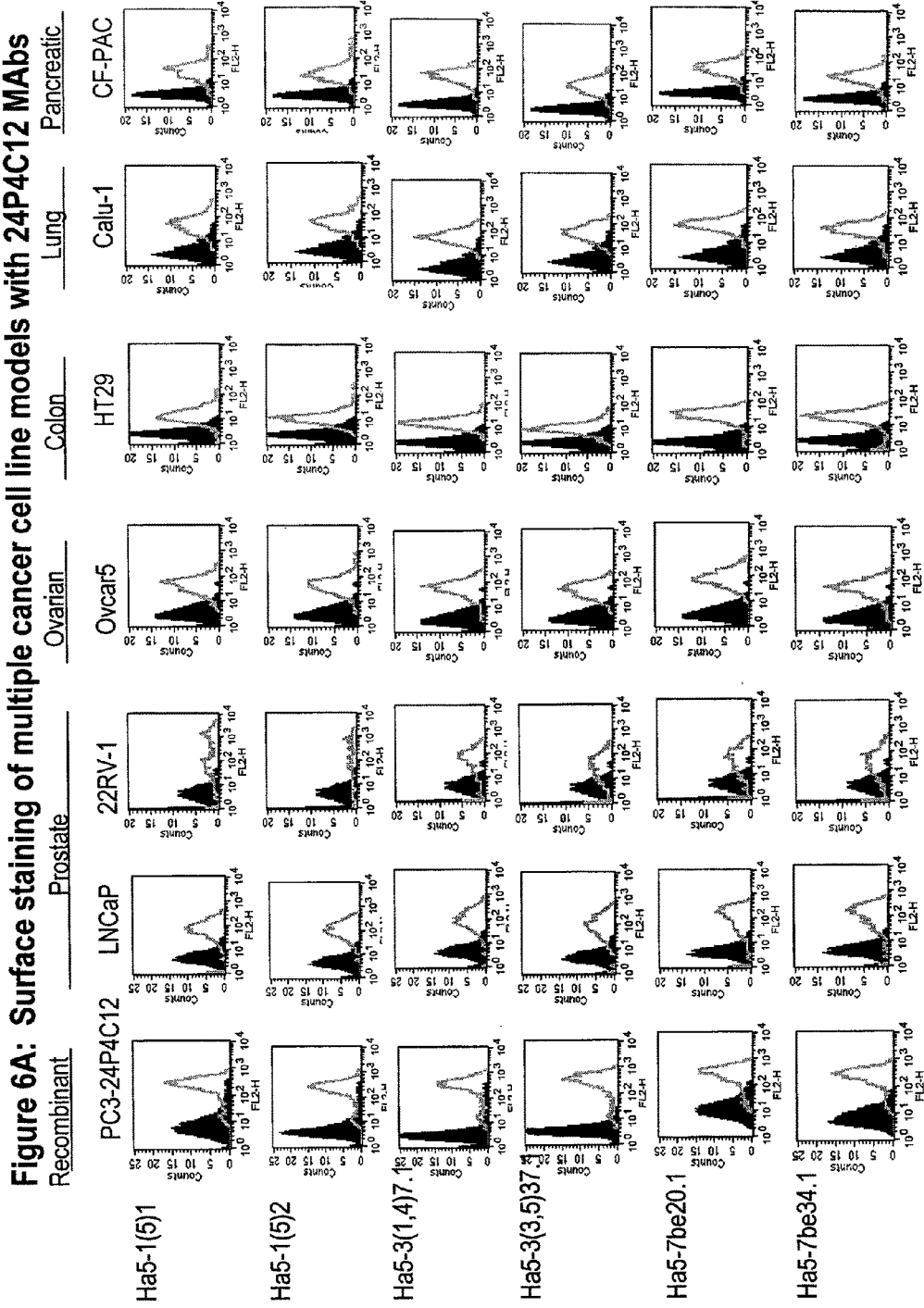
Figure 6A: Surface staining of multiple cancer cell line models with 24P4C12 MAbs

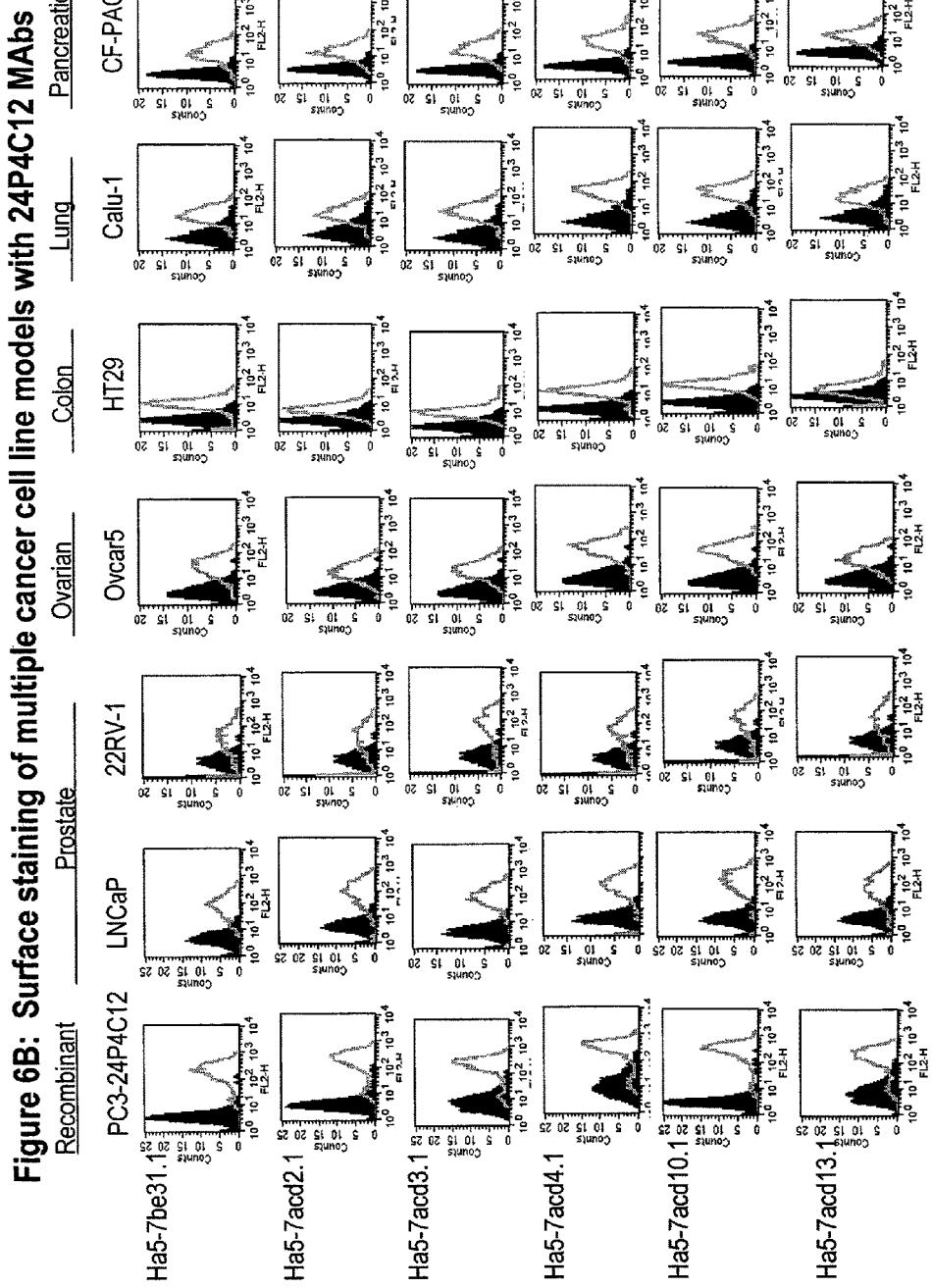
Figure 6B: Surface staining of multiple cancer cell line models with 24P4C12 MAbs

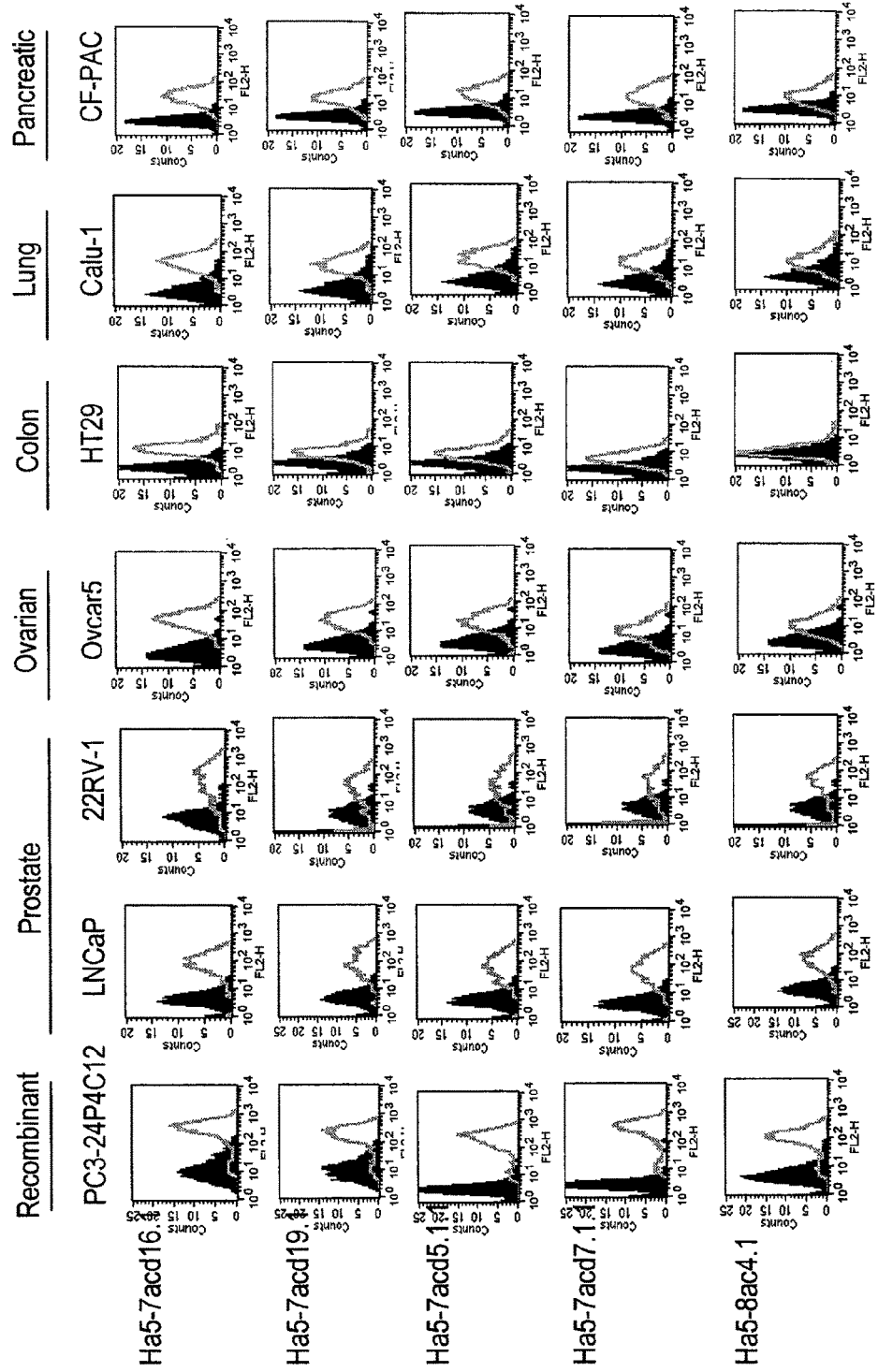
Figure 6C: Surface staining of multiple cancer cell line models with 24P4C12 MAbs

Figure 7: 24P4C12 Protein Sequence Alignment to Cynomolgus Monkey Ortholog
96.8% Identity

```
                                                                                                                    Section 1
           (1) 1              10          20          30          40          50          60          70        83
24P4C12    (1) MGGKQRDEDDEAYGKPVKYDPSFRGPIKNRSCTDVICCVLFLLFILGYIVVGIVAGLYGDPRQVLYPRNSTGAYCGMGENKDK
AGS-5 Cyno (1) MGGKQRDKDDEAYGKPVKYDPSFRGPIKNRSCTDVICCVLFLLFILGYIVVGIVAGLYGDPRQVLYPRNSTGAYCGMGENKDK
                                                                                                                    Section 2
           (84) 84            90         100         110         120         130         140         150       165
24P4C12    (84) PYLLYFNITFSCILSSNIISVAENGLQCPTPQVCVSSCPEDPWTVGKNEFSQTVGEVFYTKNRNFCLPGVPWNMTVITSLQQEL
AGS-5 Cyno (84) PYLLYFNIFSCILSSNIISVAENGLQCPTPQVCVSSCPEAPWTVGKNQFSQTVGEVFYTKNRNFCLPGVPWNMVITSLQQEL
                                                                                                                    Section 3
          (167) 167          180         190         200         210         220         230         249
24P4C12   (167) CPSFLLPSAPALGRCFPWTNVTPPALPGITNDTTIQQGISGLIDSLNARDISVKIFEDFAQSWYWILVALGVALLSLLFILL
AGS-5 Cyno(167) CPSFLLPSAPALGRCFPWTNVTLPELPGITNDTTIAQGISGLIDSLNARDISVKIFEDFAHSWYWILVALGVALLSLLFILL
                                                                                                                    Section 4
          (250) 250          260         270         280         290         300         310         320       332
24P4C12   (250) LRLVAGPLVLVLIILGVLGVLAYGIYYCWEEYRVLRDKGASISQLGFTTNLSAYQSVQETWLAALIVLAVLEAILLLLIFLRQ
AGS-5 Cyno(250) LRLVAGPLVLVLIILGVLGVLAYGIYYCWEEYRVLRDKGASISQLGFTTNLSAYQSVQETWLAALIVLAVLEAILLLLIFLRQ
                                                                                                                    Section 5
          (333) 333          350         360         370         380         390         400         415
24P4C12   (333) RIRIAIALLKEASKAVGQMMSTMFYPLVTFVLLLICIAYWANTALYLATSGQPQYVLWASNISSPGCEKVPINTSCNPTAHLV
AGS-5 Cyno(333) RIRIAIALLKEASKAVGQMMSTMFYPLVTFVLLLICIAYWANTALYLATSGQPQYVLWASNISSPGCEKVSINTSCNPMDQPV
                                                                                                                    Section 6
          (416) 416          430         440         450         460         470         480         498
24P4C12   (416) NSSCPGLMCVFQGYSSKGLWQRSWFNLQIYGVLGLFWTLNWVLALGQCVLAGAFASFYWAFHKPQDIPTFPLISAFIRTLRYH
AGS-5 Cyno(416) NSSCPGLMCVFQGYSSKGLWQRSWFNLQIYGVLGLFWTLNWVLALGQCVLAGAFASFYWAFHKPQDIPTFPLISAFIRTLRYH
                                                                                                                    Section 7
          (499) 499          510         520         530         540         550         560         581
24P4C12   (499) TGSLAFGALILTLVQIARVLIEYIDHKLRGVQNPVARCIMCCFKCCLWCLEKFIKFLNRNAYIMIAIYGKNFCVSAKNAFMLL
AGS-5 Cyno(499) TGSLAFGALILTLVQIARVLIEYIDHKLRGVQNPVARCIMCCFKCCLWCLEKFIKFLNRNAYIMIAIYGKNFCVSAKNAFTLL
                                                                                                                    Section 8
          (582) 582          590         600         610         620         630         640         650       664
24P4C12   (582) MRNIVRVVVLDKVTDLLLFFGKLLVVGGVGVLSFFFFSGRIPGLGEDFKSPHLNYYWLPINTSIWGAYVIASGFFSVFGMCVD
AGS-5 Cyno(582) MRNIVRVVVLDKVTDLLLFFGKLLVVGGVGVLSFFFFSGRIQGLGRDFKSPHLNYYWLPINTSIWGAYVIASGFFSVFGMCVD
                                                                                                                    Section 9
          (665) 665          680         690         700         710
24P4C12   (665) TLFLCFLEDLERNNGSLDRPYYMSKSLLKILGKKNEAPPDNKKRKK
AGS-5 Cyno(665) TLFLCFLEDLERNDGSLDRPYYMSKSLLKILGKKNEAPPDNKKRKK
```

▬▬▬ : extracellular domains

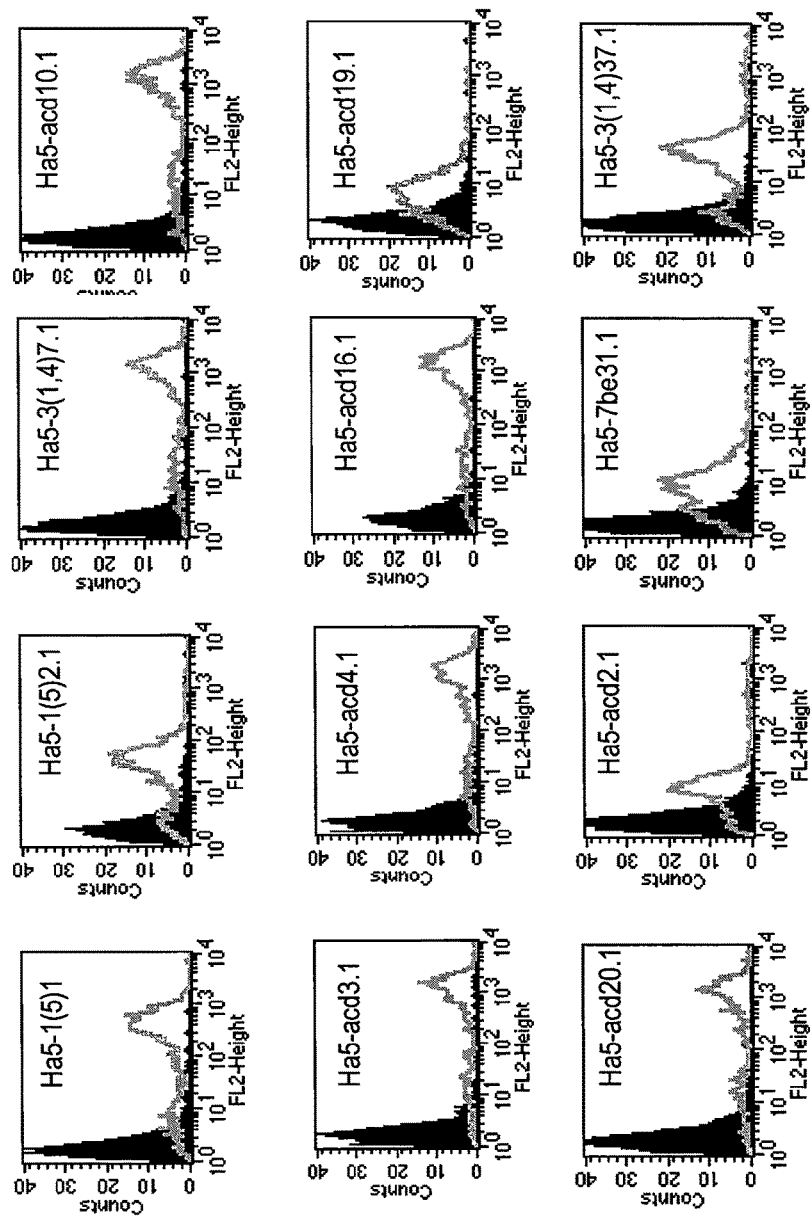
Figure 8: Surface binding of MAbs to the cynomolgus ortholog of 24P4C12 protein expressed in Rat1 cells

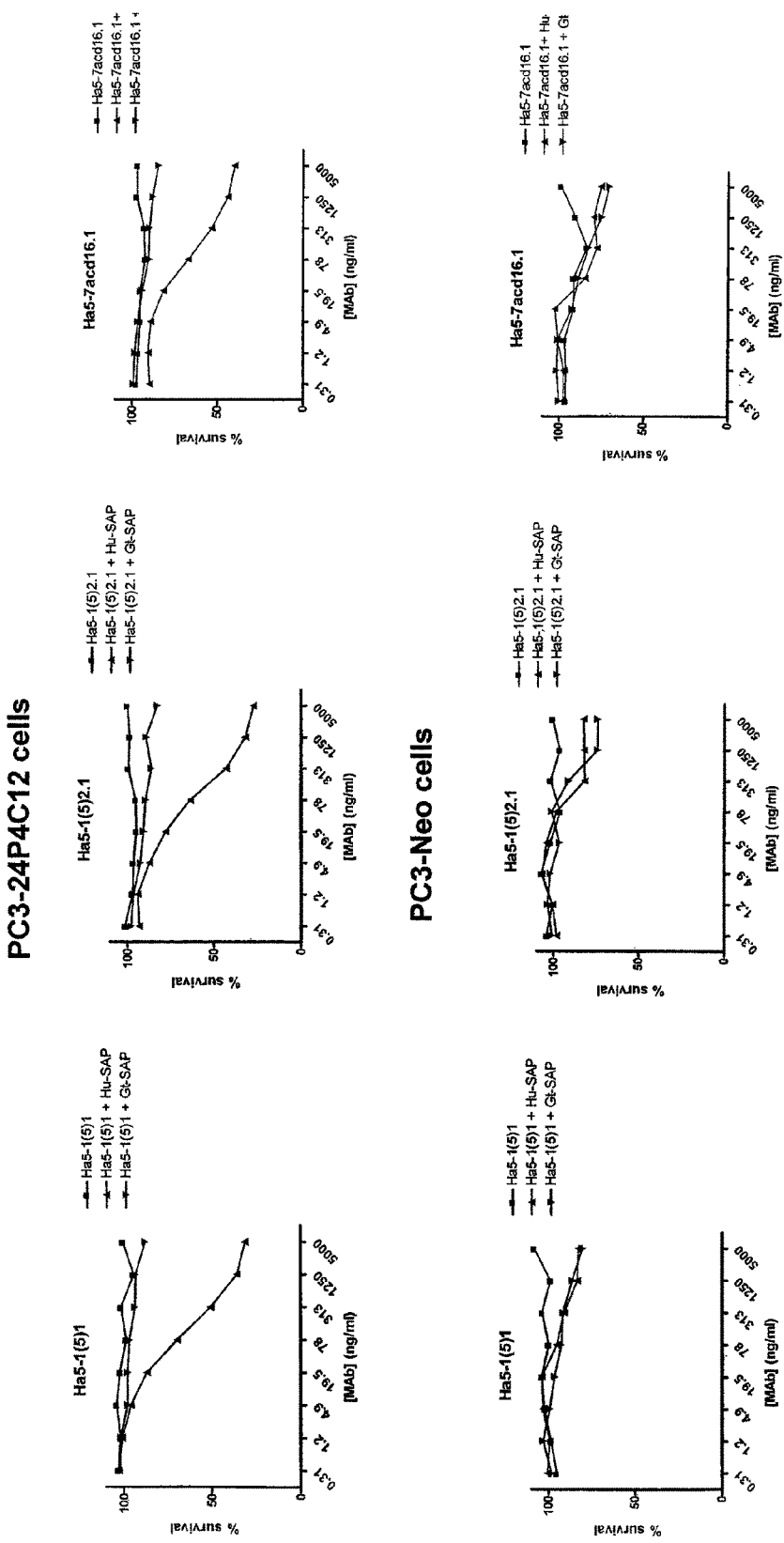
Figure 9: 24P4C12 MAbs mediate killing of PC3-24P4C12 cells via a secondary Ab-saporin toxin conjugate

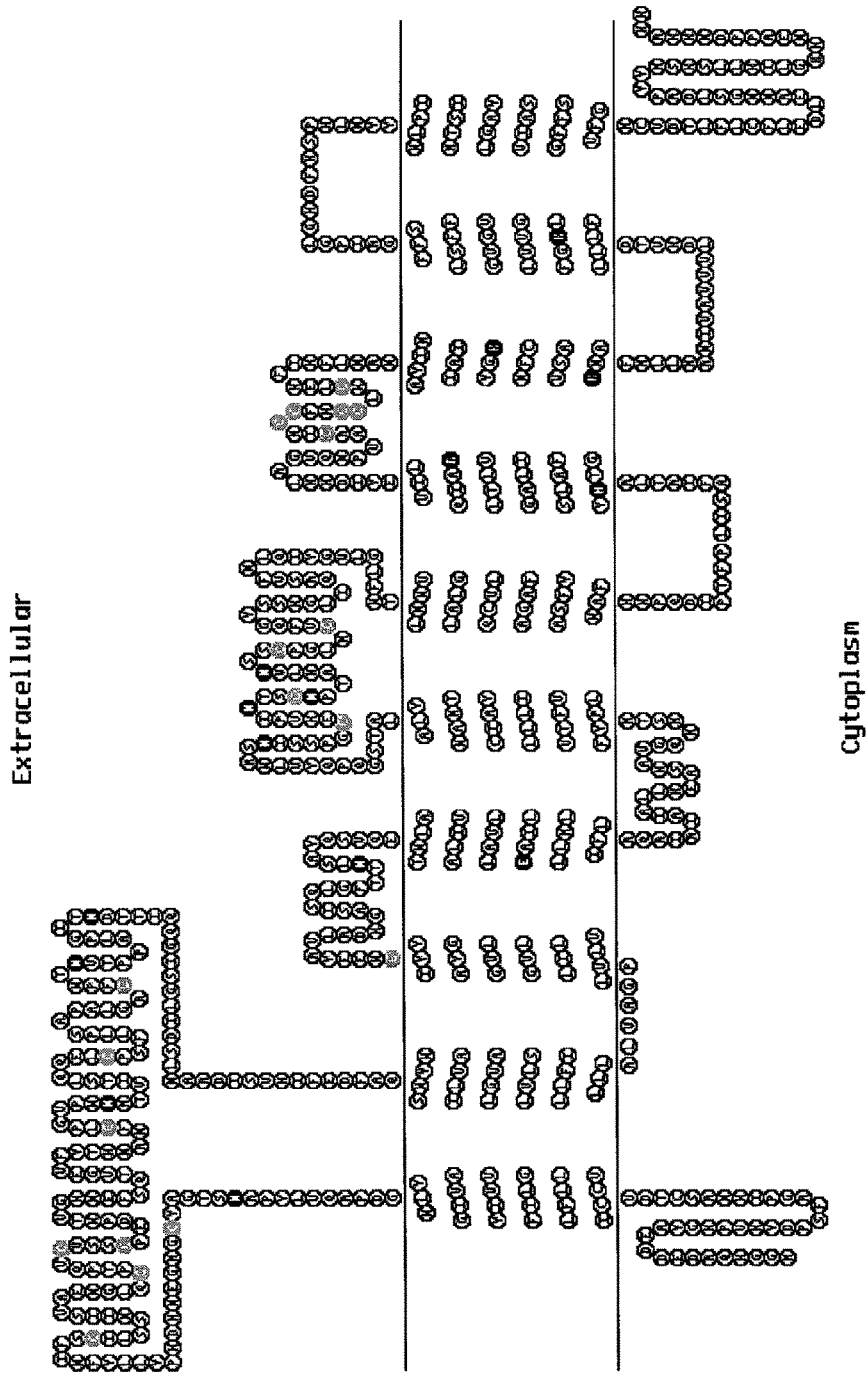
Figure 10: Membrane topology and amino acid sequence of 24P4C12

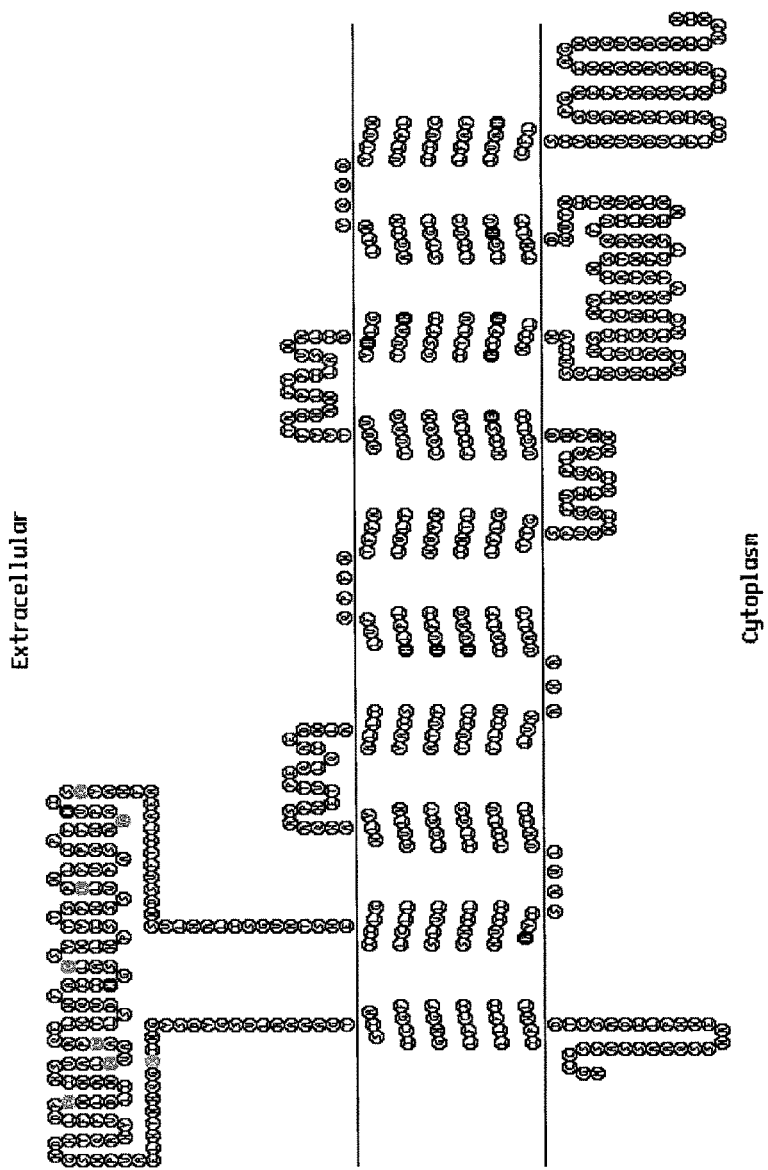
Figure 11: Membrane topology and amino acid sequence of CTL1

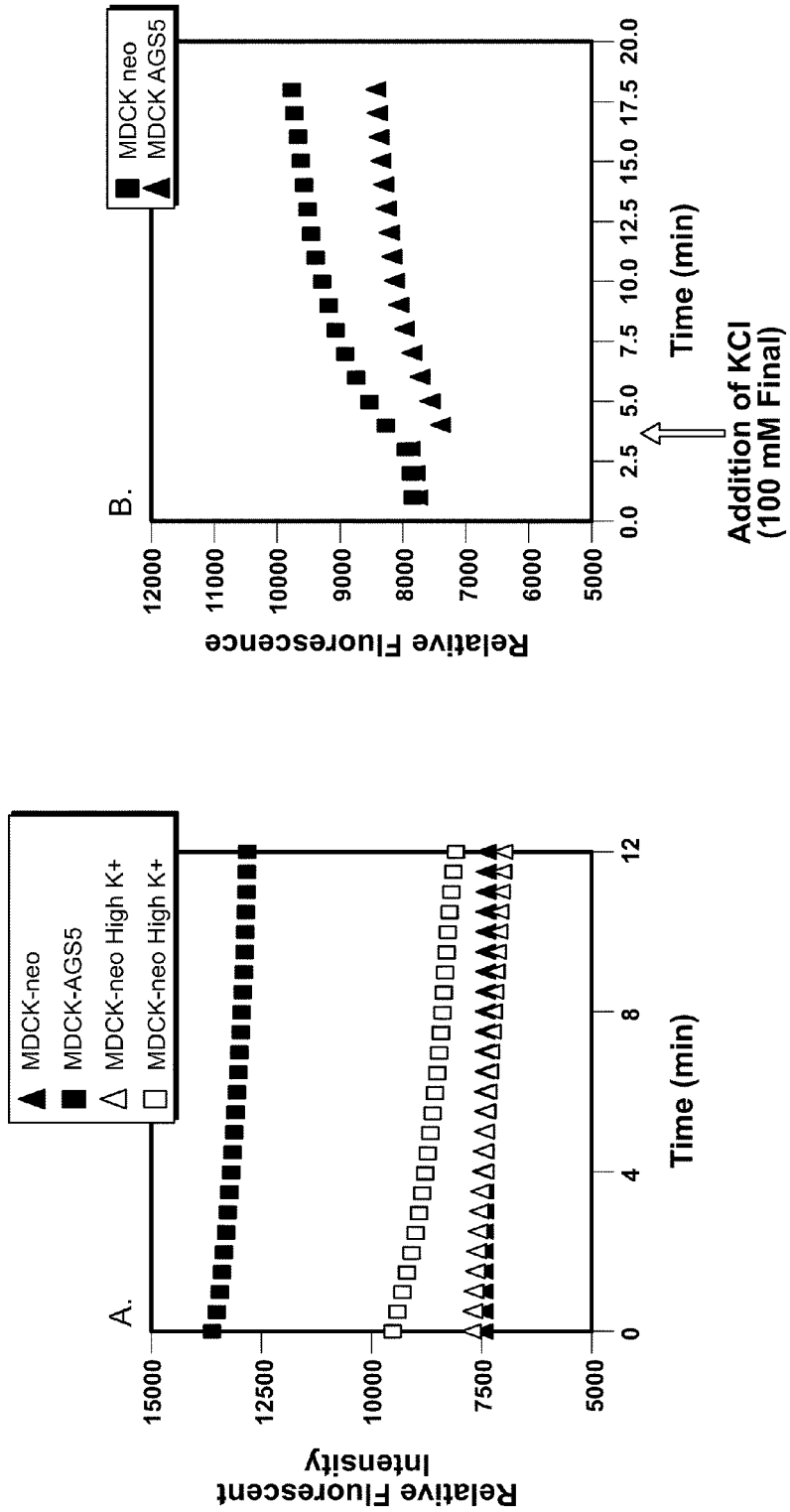
Figure 12: High extracellular K+ concentrations mediate a drop in CMFDA fluorescence in MDCK-AGS5 cells indicative of decreased intracellular pH

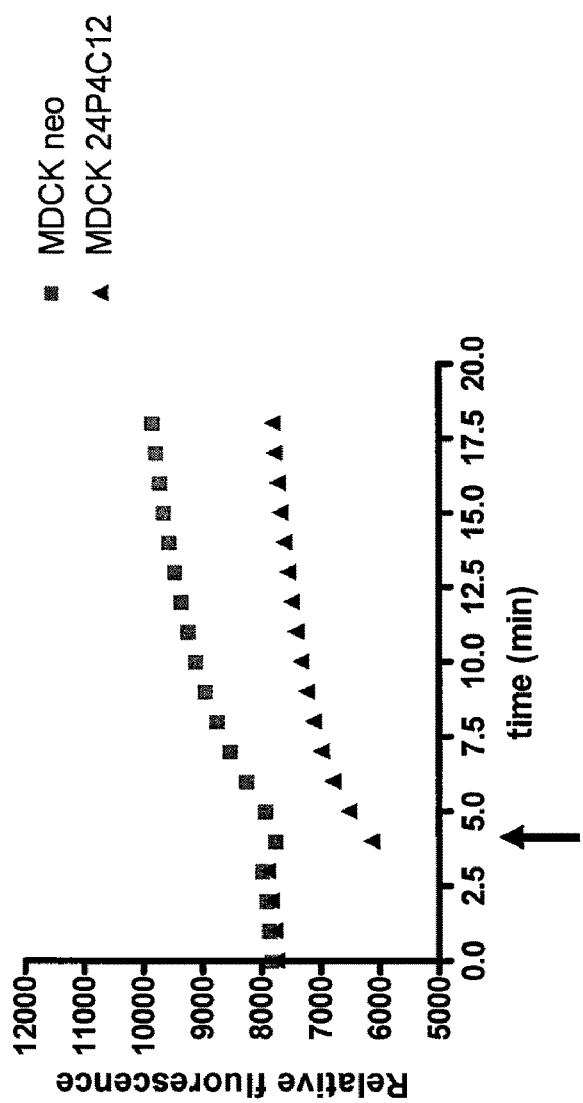
Figure 13: Acidification of media with Na+ propionate mediates decreased CMFDA fluorescence in MDCK-24P4C12 cells indicative of decreased intracellular pH.

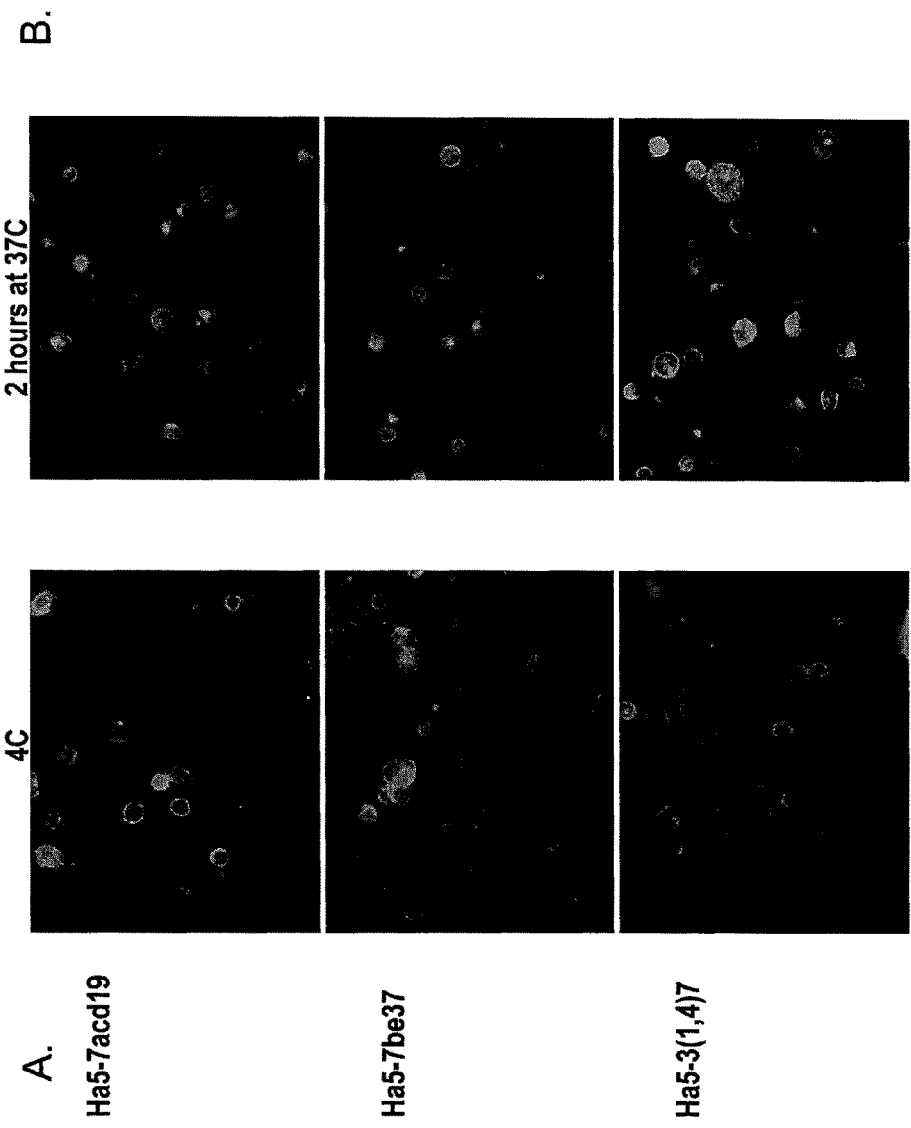
Figure 14: Capping and internalization of 24P4C12 protein by MAb engagement

Figure 15A: Ovarian Carcinoma Specimen
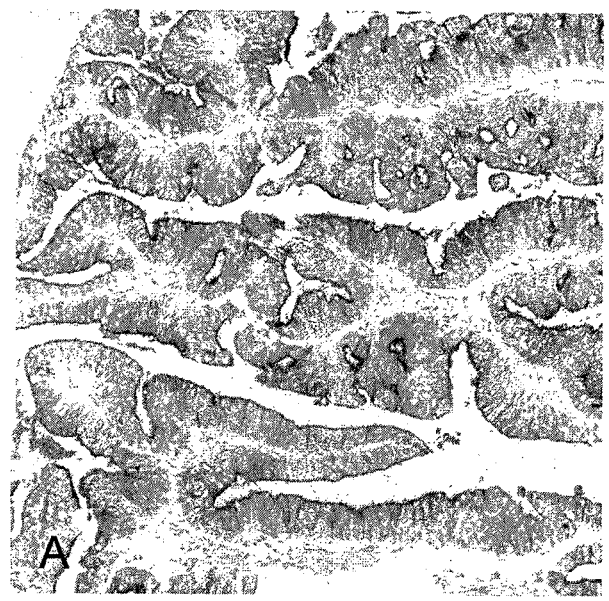
Figure 15B: Pancreatic Carcinoma Specimen
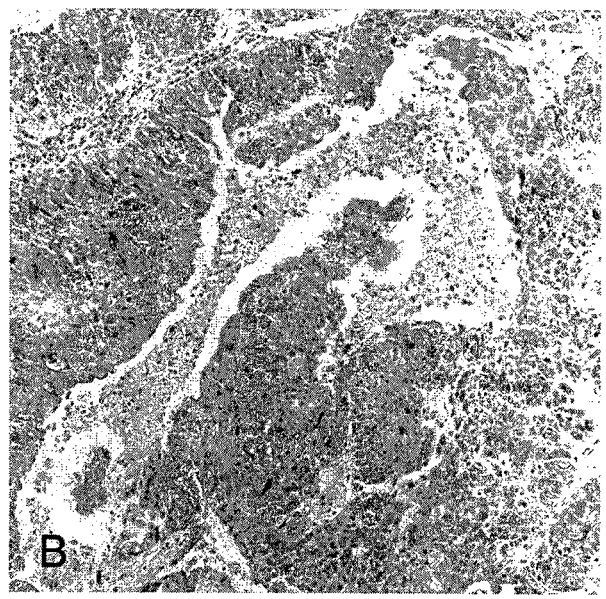

ANTIBODIES AND RELATED MOLECULES THAT BIND TO 24P4C12 PROTEINS

CROSS-REFERENCE TO RELATED APPLICATIONS

This application claims benefit of provisional application U.S. 61/190,034 filed 7 Sep. 2007. The contents of this application are incorporated herein by reference.

STATEMENT OF RIGHTS TO INVENTIONS MADE UNDER FEDERALLY SPONSORED RESEARCH

Not applicable.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 511582001131Seqlist.txt | Feb. 04, 2011 | 337,711 bytes |

FIELD OF THE INVENTION

The invention described herein relates to antibodies, as well as binding fragments thereof and molecules engineered therefrom, that bind proteins, termed 24P4C12. The invention further relates to diagnostic, prognostic, prophylactic and therapeutic methods and compositions useful in the treatment of cancers that express 24P4C12.

BACKGROUND OF THE INVENTION

Cancer is the second leading cause of human death next to coronary disease. Worldwide, millions of people die from cancer every year. In the United States alone, as reported by the American Cancer Society, cancer causes the death of well over a half-million people annually, with over 1.2 million new cases diagnosed per year. While deaths from heart disease have been declining significantly, those resulting from cancer generally are on the rise. In the early part of the next century, cancer is predicted to become the leading cause of death.

Worldwide, several cancers stand out as the leading killers. In particular, carcinomas of the lung, prostate, breast, colon, pancreas, ovary, and bladder represent the primary causes of cancer death. These and virtually all other carcinomas share a common lethal feature. With very few exceptions, metastatic disease from a carcinoma is fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients experience physical debilitations following treatment. Furthermore, many cancer patients experience a recurrence.

Worldwide, prostate cancer is the fourth most prevalent cancer in men. In North America and Northern Europe, it is by far the most common cancer in males and is the second leading cause of cancer death in men. In the United States alone, well over 30,000 men die annually of this disease—second only to lung cancer. Despite the magnitude of these figures, there is still no effective treatment for metastatic prostate cancer. Surgical prostatectomy, radiation therapy, hormone ablation therapy, surgical castration and chemotherapy continue to be the main treatment modalities. Unfortunately, these treatments are ineffective for many and are often associated with undesirable consequences.

On the diagnostic front, the lack of a prostate tumor marker that can accurately detect early-stage, localized tumors remains a significant limitation in the diagnosis and management of this disease. Although the serum prostate specific antigen (PSA) assay has been a very useful tool, however its specificity and general utility is widely regarded as lacking in several important respects.

Progress in identifying additional specific markers for prostate cancer has been improved by the generation of prostate cancer xenografts that can recapitulate different stages of the disease in mice. The LAPC (Los Angeles Prostate Cancer) xenografts are prostate cancer xenografts that have survived passage in severe combined immune deficient (SCID) mice and have exhibited the capacity to mimic the transition from androgen dependence to androgen independence (Klein et al., 1997, Nat. Med. 3:402). More recently identified prostate cancer markers include PCTA-1 (Su et al., 1996, Proc. Natl. Acad. Sci. USA 93: 7252), prostate-specific membrane antigen (PSMA) (Pinto et al., Clin Cancer Res 1996 September 2 (9): 1445-51), STEAP (Hubert, et al., Proc Natl Acad Sci USA. 1999 Dec. 7; 96(25): 14523-8) and prostate stem cell antigen (PSCA) (Reiter et al., 1998, Proc. Natl. Acad. Sci. USA 95: 1735).

While previously identified markers such as PSA, PSMA, PCTA and 24P4C12 have facilitated efforts to diagnose and treat prostate cancer, there is need for the identification of additional markers and therapeutic targets for prostate and related cancers in order to further improve diagnosis and therapy. An estimated 130,200 cases of colorectal cancer occurred in 2000 in the United States, including 93,800 cases of colon cancer and 36,400 of rectal cancer.

Colorectal cancers are the third most common cancers in men and women. Incidence rates declined significantly during 1992-1996 (−2.1% per year). Research suggests that these declines have been due to increased screening and polyp removal, preventing progression of polyps to invasive cancers. There were an estimated 56,300 deaths (47,700 from colon cancer, 8,600 from rectal cancer) in 2000, accounting for about 11% of all U.S. cancer deaths.

At present, surgery is the most common form of therapy for colorectal cancer, and for cancers that have not spread, it is frequently curative. Chemotherapy, or chemotherapy plus radiation, is given before or after surgery to most patients whose cancer has deeply perforated the bowel wall or has spread to the lymph nodes. A permanent colostomy (creation of an abdominal opening for elimination of body wastes) is occasionally needed for colon cancer and is infrequently required for rectal cancer. There continues to be a need for effective diagnostic and treatment modalities for colorectal cancer.

Of all new cases of cancer in the United States, bladder cancer represents approximately 5 percent in men (fifth most common neoplasm) and 3 percent in women (eighth most common neoplasm). The incidence is increasing slowly, concurrent with an increasing older population. In 1998, there was an estimated 54,500 cases, including 39,500 in men and 15,000 in women. The age-adjusted incidence in the United States is 32 per 100,000 for men and eight per 100,000 in women. The historic male/female ratio of 3:1 may be decreasing related to smoking patterns in women. There were an estimated 11,000 deaths from bladder cancer in 1998 (7,800 in men and 3,900 in women). Bladder cancer incidence and mortality strongly increase with age and will be an increasing problem as the population becomes more elderly.

Most bladder cancers recur in the bladder. Bladder cancer is managed with a combination of transurethral resection of the bladder (TUR) and intravesical chemotherapy or immunotherapy. The multifocal and recurrent nature of bladder cancer points out the limitations of TUR. Most muscle-invasive cancers are not cured by TUR alone. Radical cystectomy and urinary diversion is the most effective means to eliminate the cancer but carry an undeniable impact on urinary and sexual function. There continues to be a significant need for treatment modalities that are beneficial for bladder cancer patients.

There were an estimated 164,100 new cases of lung and bronchial cancer in 2000, accounting for 14% of all U.S. cancer diagnoses. The incidence rate of lung and bronchial cancer is declining significantly in men, from a high of 86.5 per 100,000 in 1984 to 70.0 in 1996. In the 1990s, the rate of increase among women began to slow. In 1996, the incidence rate in women was 42.3 per 100,000.

Lung and bronchial cancer caused an estimated 156,900 deaths in 2000, accounting for 28% of all cancer deaths. During 1992-1996, mortality from lung cancer declined significantly among men (−1.7% per year) while rates for women were still significantly increasing (0.9% per year). Since 1987, more women have died each year of lung cancer than breast cancer, which, for over 40 years, was the major cause of cancer death in women. Decreasing lung cancer incidence and mortality rates most likely resulted from decreased smoking rates over the previous 30 years; however, decreasing smoking patterns among women lag behind those of men. Of concern, although the declines in adult tobacco use have slowed, tobacco use in youth is increasing again.

Treatment options for lung and bronchial cancer are determined by the type and stage of the cancer and include surgery, radiation therapy, and chemotherapy. For many localized cancers, surgery is usually the treatment of choice. Because the disease has usually spread by the time it is discovered, radiation therapy and chemotherapy are often needed in combination with surgery. Chemotherapy alone or combined with radiation is the treatment of choice for small cell lung cancer; on this regimen, a large percentage of patients experience remission, which in some cases is long lasting. There is however, an ongoing need for effective treatment and diagnostic approaches for lung and bronchial cancers.

An estimated 182,800 new invasive cases of breast cancer were expected to occur among women in the United States during 2000. Additionally, about 1,400 new cases of breast cancer were expected to be diagnosed in men in 2000. After increasing about 4% per year in the 1980s, breast cancer incidence rates in women have leveled off in the 1990s to about 110.6 cases per 100,000.

In the U.S. alone, there were an estimated 41,200 deaths (40,800 women, 400 men) in 2000 due to breast cancer. Breast cancer ranks second among cancer deaths in women. According to the most recent data, mortality rates declined significantly during 1992-1996 with the largest decreases in younger women, both white and black. These decreases were probably the result of earlier detection and improved treatment.

Taking into account the medical circumstances and the patient's preferences, treatment of breast cancer may involve lumpectomy (local removal of the tumor) and removal of the lymph nodes under the arm; mastectomy (surgical removal of the breast) and removal of the lymph nodes under the arm; radiation therapy; chemotherapy; or hormone therapy. Often, two or more methods are used in combination. Numerous studies have shown that, for early stage disease, long-term survival rates after lumpectomy plus radiotherapy are similar to survival rates after modified radical mastectomy. Significant advances in reconstruction techniques provide several options for breast reconstruction after mastectomy. Recently, such reconstruction has been done at the same time as the mastectomy.

Local excision of ductal carcinoma in situ (DCIS) with adequate amounts of surrounding normal breast tissue may prevent the local recurrence of the DCIS. Radiation to the breast and/or tamoxifen may reduce the chance of DCIS occurring in the remaining breast tissue. This is important because DCIS, if left untreated, may develop into invasive breast cancer. Nevertheless, there are serious side effects or sequelae to these treatments. There is, therefore, a need for efficacious breast cancer treatments.

There were an estimated 23,100 new cases of ovarian cancer in the United States in 2000. It accounts for 4% of all cancers among women and ranks second among gynecologic cancers. During 1992-1996, ovarian cancer incidence rates were significantly declining. Consequent to ovarian cancer, there were an estimated 14,000 deaths in 2000. Ovarian cancer causes more deaths than any other cancer of the female reproductive system.

Surgery, radiation therapy, and chemotherapy are treatment options for ovarian cancer. Surgery usually includes the removal of one or both ovaries, the fallopian tubes (salpingo-oophorectomy), and the uterus (hysterectomy). In some very early tumors, only the involved ovary will be removed, especially in young women who wish to have children. In advanced disease, an attempt is made to remove all intra-abdominal disease to enhance the effect of chemotherapy. There continues to be an important need for effective treatment options for ovarian cancer.

There were an estimated 28,300 new cases of pancreatic cancer in the United States in 2000. Over the past 20 years, rates of pancreatic cancer have declined in men. Rates among women have remained approximately constant but may be beginning to decline. Pancreatic cancer caused an estimated 28,200 deaths in 2000 in the United States. Over the past 20 years, there has been a slight but significant decrease in mortality rates among men (about −0.9% per year) while rates have increased slightly among women.

Surgery, radiation therapy, and chemotherapy are treatment options for pancreatic cancer. These treatment options can extend survival and/or relieve symptoms in many patients but are not likely to produce a cure for most. There is a significant need for additional therapeutic and diagnostic options for cancers. These include the use of antibodies, vaccines, and small molecules as treatment modalities. Additionally, there is also a need to use these modilities as research tools to diagnose, detect, monitor, and further the state of the art in all areas of cancer treatment and studies.

The therapeutic utility of monoclonal antibodies (mAbs) (G. Kohler and C. Milstein, Nature 256:495-497 (1975)) is being realized. Monoclonal antibodies have now been approved as therapies in transplantation, cancer, infectious disease, cardiovascular disease and inflammation. Different isotypes have different effector functions. Such differences in function are reflected in distinct 3-dimensional structures for the various immunoglobulin isotypes (P. M. Alzari et al., Annual Rev. Immunol., 6:555-580 (1988)).

Because mice are convenient for immunization and recognize most human antigens as foreign, mAbs against human targets with therapeutic potential have typically been of murine origin. However, murine mAbs have inherent disadvantages as human therapeutics. They require more frequent dosing as mAbs have a shorter circulating half-life in humans than human antibodies. More critically, the repeated administration of murine antibodies to the human immune system causes the human immune system to respond by recognizing the mouse protein as a foreign and generating a human anti-mouse antibody (HAMA) response. Such a HAMA response may result in allergic reaction and the rapid clearing of the murine antibody from the system thereby rendering the treatment by murine antibody useless. To avoid such affects, attempts to create human immune systems within mice have been attempted.

Initial attempts hoped to create transgenic mice capable of responding to antigens with antibodies having human sequences (See Bruggemann et al., Proc. Nat'l. Acad. Sci. USA 86:6709-6713 (1989)), but were limited by the amount of DNA that could be stably maintained by available cloning vehicles. The use of yeast artificial chromosome (YAC) cloning vectors led the way to introducing large germline fragments of human Ig locus into transgenic mammals. Essentially a majority of the human V, D, and J region genes arranged with the same spacing found in the human genome and the human constant regions were introduced into mice using YACs. One such transgenic mouse strain is known as XenoMouse® mice and is commercially available from Amgen Fremont, Inc. (Fremont Calif.).

SUMMARY OF THE INVENTION

The invention provides antibodies as well as binding fragments thereof and molecules engineered therefrom, that bind to 24P4C12 proteins and polypeptide fragments of 24P4C12 proteins. The invention comprises polyclonal and monoclonal antibodies, murine and other mammalian antibodies, chimeric antibodies, humanized and fully human antibodies, and antibodies labeled with a detectable marker or therapeutic agent. In certain embodiments, there is a proviso that the entire nucleic acid sequence of FIG. 3 is not encoded and/or the entire amino acid sequence of FIG. 2 is not prepared. In certain embodiments, the entire nucleic acid sequence of FIG. 3 is encoded and/or the entire amino acid sequence of FIG. 2 is prepared, either of which are in respective human unit dose forms.

The invention further provides methods for detecting the presence and status of 24P4C12 polynucleotides and proteins in various biological samples, as well as methods for identifying cells that express 24P4C12. An embodiment of this invention provides methods for monitoring 24P4C12 gene products in a tissue or hematology sample having or suspected of having some form of growth dysregulation such as cancer.

The invention further provides various immunogenic or therapeutic compositions and strategies for treating cancers that express 24P4C12 such as cancers of tissues listed in Table I, including therapies aimed at inhibiting the transcription, translation, processing or function of 24P4C12 as well as cancer vaccines. In one aspect, the invention provides compositions, and methods comprising them, for treating a cancer that expresses 24P4C12 in a human subject wherein the composition comprises a carrier suitable for human use and a human unit dose of one or more than one agent that inhibits the production or function of 24P4C12. Preferably, the carrier is a uniquely human carrier. In another aspect of the invention, the agent is a moiety that is immunoreactive with 24P4C12 protein. Non-limiting examples of such moieties include, but are not limited to, antibodies (such as single chain, monoclonal, polyclonal, humanized, chimeric, or human antibodies), functional equivalents thereof (whether naturally occurring or synthetic), and combinations thereof. The antibodies can be conjugated to a diagnostic or therapeutic moiety. In another aspect, the agent is a small molecule as defined herein.

BRIEF DESCRIPTION OF THE FIGURES

FIG. 1. FIG. 1A. The cDNA and amino acid sequence of 24P4C12 variant 1 (also called "24P4C12 v.1" or "24P4C12 variant 1") is shown in FIG. 1A. The start methionine is underlined. The open reading frame extends from nucleic acid 44-2671 including the stop codon.

FIG. 1B. The cDNA and amino acid sequence of 24P4C12 variant 2 (also called "24P4C12 v.2") is shown in FIG. 1B. The codon for the start methionine is underlined. The open reading frame extends from nucleic acid 44-2671 including the stop codon.

FIG. 1C. The cDNA and amino acid sequence of 24P4C12 variant 3 (also called "24P4C12 v.3") is shown in FIG. 1C. The codon for the start methionine is underlined. The open reading frame extends from nucleic acid 44-2671 including the stop codon.

FIG. 1D. The cDNA and amino acid sequence of 24P4C12 variant 4 (also called "24P4C12 v.4") is shown in FIG. 1D. The codon for the start methionine is underlined. The open reading frame extends from nucleic acid 44-2671 including the stop codon.

FIG. 1E. The cDNA and amino acid sequence of 24P4C12 variant 5 (also called "24P4C12 v.5") is shown in FIG. 1E. The codon for the start methionine is underlined. The open reading frame extends from nucleic acid 44-2671 including the stop codon.

FIG. 1F. The cDNA and amino acid sequence of 24P4C12 variant 6 (also called "24P4C12 v.6") is shown in FIG. 1F. The codon for the start methionine is underlined. The open reading frame extends from nucleic acid 84-2711 including the stop codon.

FIG. 1G. The cDNA and amino acid sequence of 24P4C12 variant 7 (also called "24P4C12 v.7") is shown in FIG. 1G. The codon for the start methionine is underlined. The open reading frame extends from nucleic acid 276-2801 including the stop codon.

FIG. 1H. The cDNA and amino acid sequence of 24P4C12 variant 8 (also called "24P4C12 v.8") is shown in FIG. 1H. The start methionine is underlined. The open reading frame extends from nucleic acid 6-2174 including the stop codon.

FIG. 1I. The cDNA and amino acid sequence of 24P4C12 variant 9 (also called "24P4C12 v.9") is shown in FIG. 1I. The start methionine is underlined. The open reading frame extends from nucleic acid 6-2144 including the stop codon.

FIG. 2. Nucleic Acid and Amino Acid sequences of 24P4C12 antibodies. FIG. 2A The cDNA and amino acid sequence of Ha5-1(5)1 VH. Underlined is a portion of the heavy chain constant region.

FIG. 2B The cDNA and amino acid sequence of Ha5-1(5)1 VL. Underlined is a portion of the light chain constant region. Double underline is a portion of the leader sequence.

FIG. 2C The cDNA and amino acid sequence of Ha5-1(5) 2.1 VH. Underlined is a portion of the heavy chain constant region.

FIG. 2D The cDNA and amino acid sequence of Ha5-1(5) 2.1 VL. Double-underlined is the leader sequence, and underlined is a portion of the heavy chain constant region.

FIG. 2E The cDNA and amino acid sequence of Ha5-3(1,4)2.1 VH. Underlined is a portion of the heavy chain constant region.

FIG. 2F The cDNA and amino acid sequence of Ha5-3(1,4)2.1 VL. Underlined is a portion of the light chain constant region. Double underline is a portion of the leader sequence.

FIG. 2G The cDNA and amino acid sequence of Ha5-3(1,4)7.1 VH. Underlined is a portion of the heavy chain constant region.

FIG. 2H The cDNA and amino acid sequence of Ha5-3(1,4)7.1 VL. Underlined is a portion of the light chain constant region. Double underline is a portion of the leader sequence.

FIG. 2I The cDNA and amino acid sequence of Ha5-3(3,5)37.1 VH. Underlined is a portion of the heavy chain constant region.

FIG. 2J The cDNA and amino acid sequence of Ha5-3(3,5)37.1 VL. Underlined is a portion of the light chain constant region.

FIG. 2K The cDNA and amino acid sequence of Ha5-4(2,5)13.1 VH. Underlined is a portion of the heavy chain constant region.

FIG. 2L The cDNA and amino acid sequence of Ha5-4(2,5)13.1 VL. Underlined is the light chain constant region. Double underline is a portion of the leader sequence.

FIG. 2M The cDNA and amino acid sequence of Ha5-4(2,5)34.1 VH. Underlined is a portion of the heavy chain constant region.

FIG. 2N The cDNA and amino acid sequence of Ha5-4(2,5)34.1 VL. Underlined is a portion of the light chain constant region.

FIG. 2O The cDNA and amino acid sequence of Ha5-7acd4.1 VH. Underlined is a portion of the heavy chain constant region.

FIG. 2P The cDNA and amino acid sequence of Ha5-7acd4.1 VL. Underlined is a portion of the light chain constant region. Double underline is a leader sequence.

FIG. 2Q The cDNA and amino acid sequence of Ha5-7acd20.1.1 VH. Underlined is a portion of the heavy chain constant region.

FIG. 2R The cDNA and amino acid sequence of Ha5-7acd20.1.1 VL. Underlined is a portion of the light chain constant region. Double underline is the leader sequence.

FIG. 2S The cDNA and amino acid sequence of Ha5-7be31.1 VH. Underlined is a portion of the heavy chain constant region.

FIG. 2T The cDNA and amino acid sequence of Ha5-7be31.1 VL. Underlined is a portion of the light chain constant region. Double underline is the leader sequence.

FIG. 2U The cDNA and amino acid sequence of Ha5-7acd10.1 VH. Underlined is a portion of the heavy chain constant region.

FIG. 2V The cDNA and amino acid sequence of Ha5-7acd10.1 VL. Underlined is a portion of the light chain constant region. Double underline is the leader sequence.

FIG. 2W The cDNA and amino acid sequence of Ha5-7acd13.1 VH. Underlined is a portion of the heavy chain constant region.

FIG. 2X The cDNA and amino acid sequence of Ha5-7acd13.1 VL. Underlined is a portion of the light chain constant region. Double underline is the leader sequence.

FIG. 2Y The cDNA and amino acid sequence of Ha5-7acd19.1 VH. Underlined is a portion of the heavy chain constant region.

FIG. 2Z The cDNA and amino acid sequence of Ha5-7acd19.1 VL. Underlined is a portion of the light chain constant region. Double underline is the leader sequence.

FIG. 2AA The cDNA and amino acid sequence of Ha5-7be37.1 VH. Underlined is a portion of the light chain constant region.

FIG. 2AB The cDNA and amino acid sequence of Ha5-7be37.1 VL. Underlined is a portion of the light chain constant region. Double underline is the leader sequence.

FIG. 2AC The cDNA and amino acid sequence of Ha5-7acd16.1 VH. Underlined is a portion of the heavy chain constant region.

FIG. 2AD The cDNA and amino acid sequence of Ha5-7acd16.1 VL. Underlined is a portion of the light chain constant region. Double underline is the leader sequence.

FIG. 2AE The cDNA and amino acid sequence of Ha5-7acd7.1.1 VH. Underlined is a portion of the heavy chain constant region.

FIG. 2AF The cDNA and amino acid sequence of Ha5-7acd7.1.1 VL. Double-underlined is the leader sequence, and underlined is a portion of the light chain constant region.

FIG. 2AG The cDNA and amino acid sequence of Ha5-7be20.1 VH. Underlined is a portion of the heavy chain constant region.

FIG. 2AH The cDNA and amino acid sequence of Ha5-7be20.1 VL. Double-underlined is the leader sequence, and underlined is a portion of the light chain constant region.

FIG. 2AI The cDNA and amino acid sequence of Ha5-7acd5.1.1 VH. Underlined is a portion of the heavy chain constant region.

FIG. 2AJ The cDNA and amino acid sequence of Ha5-7acd5.1.1 VL. Underlined is a portion of the light chain constant region. Double underline is the leader sequence.

FIG. 2AK The cDNA and amino acid sequence of Ha5-7be34.1 VH. Underlined is a portion of the heavy chain constant region.

FIG. 2AL The cDNA and amino acid sequence of Ha5-7be34.1 VL. Underlined is a portion of the light chain constant region. Double underline is the leader sequence.

FIG. 2AM The cDNA and amino acid sequence of Ha5-7acd3.1 VH. Underlined is a portion of the heavy chain constant region.

FIG. 2AN The cDNA and amino acid sequence of Ha5-7acd3.1 VL. Double-underlined is part of the leader sequence, and underlined is a portion of the light chain constant region.

FIG. 2AO The cDNA and amino acid sequence of Ha5-7acd2.1 VH. Underlined is a portion of the heavy chain constant region.

FIG. 2AP The cDNA and amino acid sequence of Ha5-7acd2.1 VL. Double-underlined is part of the leader sequence, and underlined is a portion of the light chain constant region.

FIG. 2AQ The cDNA and amino acid sequence of Ha5-8ac4.1 VH. Underlined is a portion of the heavy chain constant region.

FIG. 2AR The cDNA and amino acid sequence of Ha5-8ac4.1 VL. Underlined is a portion of the light chain constant region.

FIG. 2AS The cDNA and amino acid sequence of Ha5-4(2,5)31.1 VH. Underlined is a portion of the heavy chain constant region.

FIG. 2AT The cDNA and amino acid sequence of Ha5-4(2,5)31.1 VL. Double-underlined is part of the leader sequence, and underlined is a portion of the light chain constant region.

FIG. 2AU The cDNA and amino acid sequence of Ha5-11a1.1.1 VH. Underlined is a portion of the heavy chain constant region.

FIG. 2AV The cDNA and amino acid sequence of Ha5-11a1.1.1 VL. Underlined is a portion of the heavy chain constant region. Double underline is the leader sequence.

FIG. 2AW The cDNA and amino acid sequence of Ha5-11b1.1 VH. Underlined is a portion of the heavy chain constant region.

FIG. 2AX The cDNA and amino acid sequence of Ha5-11b1.1 VL. Double-underlined is part of the leader sequence, and underlined is a portion of the light chain constant region.

FIG. 2AY The cDNA and amino acid sequence of Ha5-7be7.1 VH. Double-underlined is part of the leader sequence, and underlined is a portion of the light chain constant region.

FIG. 3. Amino Acid sequences of 24P4C12 antibodies.

FIG. 3A The amino acid sequence of Ha5-1(5)1 VH. Underlined is a portion of the heavy chain constant region.

FIG. 3B The amino acid sequence of Ha5-1(5)1 VL. Underlined is a portion of the light chain constant region.

FIG. 3C The amino acid sequence of Ha5-1(5)2.1 VH. Underlined is a portion of the heavy chain constant region.

FIG. 3D The amino acid sequence of Ha5-1(5)2.1 VL. Underlined is a portion of the light chain constant region.

FIG. 3E The amino acid sequence of Ha5-3(1,4)2.1 VH. Underlined is a portion of the heavy chain constant region.

FIG. 3F The amino acid sequence of Ha5-3(1,4)2.1 VL. Underlined is a portion of the light chain constant region.

FIG. 3G The amino acid sequence of Ha5-3(1,4)7.1 VH. Underlined is a portion of the heavy chain constant region.

FIG. 3H The amino acid sequence of Ha5-3(1,4)7.1 VL. Underlined is a portion of the light chain constant region.

FIG. 3I The amino acid sequence of Ha5-3(3,5)37.1 VH. Underlined is a portion of the heavy chain constant region.

FIG. 3J The amino acid sequence of Ha5-3(3,5)37.1 VL. Underlined is a portion of the light chain constant region.

FIG. 3K The amino acid sequence of Ha5-4(2,5)13.1 VH. Underlined is a portion of the heavy chain constant region.

FIG. 3L The amino acid sequence of Ha5-4(2,5)13.1 VL. Underlined is the light chain constant region.

FIG. 3M The amino acid sequence of Ha5-4(2,5)34.1 VH. Underlined is a portion of the heavy chain constant region.

FIG. 3N The amino acid sequence of Ha5-4(2,5)34.1 VL. Underlined is a portion of the light chain constant region.

FIG. 3O The amino acid sequence of Ha5-7acd4.1 VH. Underlined is a portion of the heavy chain constant region.

FIG. 3P The amino acid sequence of Ha5-7acd4.1 VL. Underlined is a portion of the light chain constant region.

FIG. 3Q The amino acid sequence of Ha5-7acd20.1.1 VH. Underlined is a portion of the heavy chain constant region.

FIG. 3R The amino acid sequence of Ha5-7acd20.1.1 VL. Underlined is a portion of the light chain constant region.

FIG. 3S The amino acid sequence of Ha5-7be31.1 VH. Underlined is a portion of the heavy chain constant region.

FIG. 3T The amino acid sequence of Ha5-7be31.1 VL. Underlined is a portion of the light chain constant region.

FIG. 3U The amino acid sequence of Ha5-7acd10.1 VH. Underlined is a portion of the heavy chain constant region.

FIG. 3V The amino acid sequence of Ha5-7acd10.1 VL. Underlined is a portion of the light chain constant region.

FIG. 3W The amino acid sequence of Ha5-7acd13.1 VH. Underlined is a portion of the heavy chain constant region.

FIG. 3X The amino acid sequence of Ha5-7acd13.1 VL. Underlined is a portion of the light chain constant region.

FIG. 3Y The amino acid sequence of Ha5-7acd19.1 VH. Underlined is a portion of the heavy chain constant region.

FIG. 3Z The amino acid sequence of Ha5-7acd19.1 VL. Underlined is a portion of the light chain constant region.

FIG. 3AA The amino acid sequence of Ha5-7be37.1 VH.

FIG. 3AB The amino acid sequence of Ha5-7be37.1 VL. Underlined is a portion of the light chain constant region.

FIG. 3AC The amino acid sequence of Ha5-7acd16.1 VH.

FIG. 3AD The amino acid sequence of Ha5-7acd16.1 VL. Underlined is a portion of the light chain constant region.

FIG. 3AE The amino acid sequence of Ha5-7acd7.1.1 VH. Double-underlined is the leader sequence. Underlined is a portion of the light chain constant region.

FIG. 3AF The amino acid sequence of Ha5-7acd7.1.1 VL. Double-underlined is the leader sequence. Underlined is a portion of the light chain constant region.

FIG. 3AG The amino acid sequence of Ha5-7be20.1 VH. Double-underlined is the leader sequence. Underlined is a portion of the light chain constant region.

FIG. 3AH The amino acid sequence of Ha5-7be20.1 VL. Double-underlined is part of the leader sequence. Underlined is a portion of the light chain constant region.

FIG. 3AI The amino acid sequence of Ha5-7acd5.1.1 VH. Double-underlined is part of the leader sequence, and underlined is a portion of the heavy chain constant region.

FIG. 3AJ The amino acid sequence of Ha5-7acd5.1.1 VL. Underlined is a portion of the light chain constant region.

FIG. 3AK The amino acid sequence of Ha5-7be34.1 VH. Underlined is a portion of the heavy chain constant region.

FIG. 3AL The amino acid sequence of Ha5-7be34.1 VL. Underlined is a portion of the light chain constant region.

FIG. 3AM The amino acid sequence of Ha5-7acd3.1 VH. Double-underlined is the leader sequence, and underlined is a portion of the heavy chain constant region.

FIG. 3AN The amino acid sequence of Ha5-7acd3.1 VL. Double-underlined is part of the leader sequence, and underlined is a portion of the light chain constant region.

FIG. 3AO The amino acid sequence of Ha5-7acd2.1 VH. Double-underlined is the leader sequence, and underlined is a portion of the heavy chain constant region.

FIG. 3AP The amino acid sequence of Ha5-7acd2.1 VL. Double-underlined is part of the leader sequence, and underlined is a portion of the light chain constant region.

FIG. 3AQ The amino acid sequence of Ha5-8ac4.1 VH. Double-underlined is the leader sequence, and underlined is a portion of the heavy chain constant region.

FIG. 3AR The amino acid sequence of Ha5-8ac4.1 VL. Double-underlined is part of the leader sequence, and underlined is a portion of the light chain constant region.

FIG. 3AS The amino acid sequence of Ha5-4(2,5)31.1 VH. Double-underlined is the leader sequence, and underlined is a portion of the heavy chain constant region.

FIG. 3AT The amino acid sequence of Ha5-4(2,5)31.1 VL. Double-underlined is part of the leader sequence, and underlined is a portion of the light chain constant region.

FIG. 3AU The amino acid sequence of Ha5-11a1.1.1 VH. Double-underlined is part of the leader sequence, and underlined is a portion of the heavy chain constant region.

FIG. 3AV The amino acid sequence of Ha5-11a1.1.1 VH. Underlined is a portion of the heavy chain constant region.

FIG. 3AW The amino acid sequence of Ha5-11b1.1 VH. Underlined is a portion of the heavy chain constant region.

FIG. 3AX The amino acid sequence of Ha5-11b1.1 VL. Double-underlined is part of the leader sequence, and underlined is a portion of the light chain constant region.

FIG. 3AY The amino acid sequence of Ha5-7be7.1 VH. Underlined is a portion of the light chain constant region.

FIG. 4. Alignment of 24P4C12 antibodies to human Ig germline.

FIG. 4B Alignment of Ha5-1(5)1 VL (a portion of SEQ ID NOS:21-22) to human Ig germline.

FIG. 4C Alignment of Ha5-1(5)2.1 VH (a portion of SEQ ID NOS:23-24) to human Ig germline.

FIG. 4D Alignment of Ha5-1(5)2.1 VL (a portion of SEQ ID NOS:25-26) to human Ig germline.

FIG. 4E Alignment of Ha5-3(1,4)2.1 VH (a portion of SEQ ID NOS:27-28) to human Ig germline.

FIG. 4F Alignment of Ha5-3(1,4)2.1 VL (a portion of SEQ ID NOS:29-30) to human Ig germline.

FIG. 4G Alignment of Ha5-3(1,4)7.1 VH (a portion of SEQ ID NOS:31-32) to human Ig germline.

Figures 1, 4I:
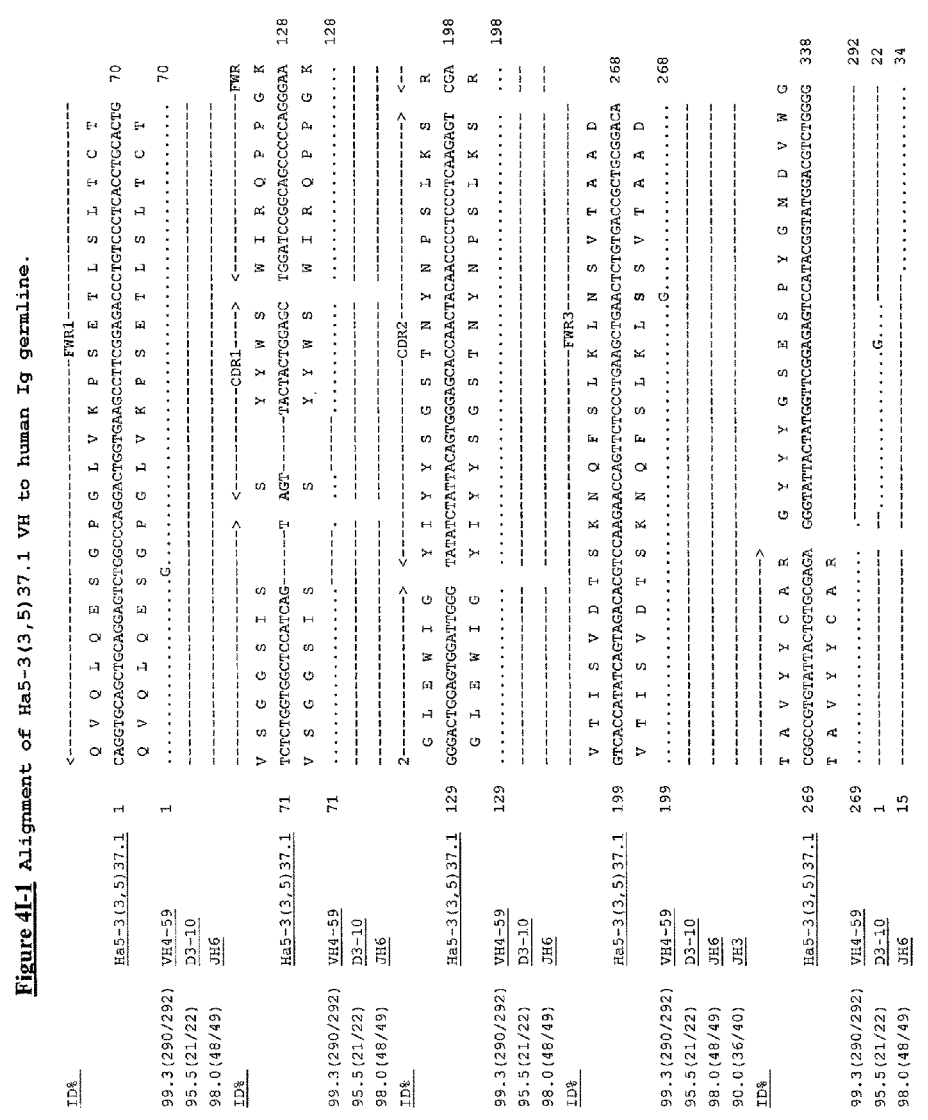
Figure 4A:
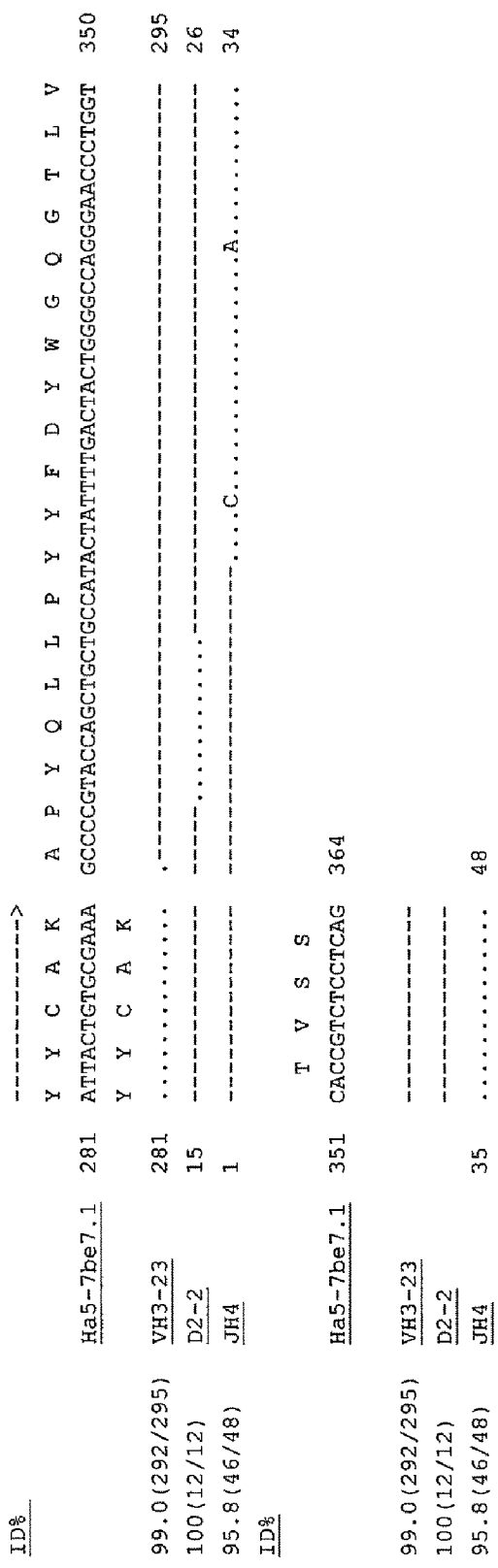
FIG. 4A Alignment of Ha5-1(5)1 VH (a portion of SEQ ID NOS:19-20) to human Ig germline.

FIG. 4H Alignment of Ha5-3(1,4)7.1 VL (a portion of SEQ ID NOS:33-34) to human Ig germline.

FIG. 4I Alignment of Ha5-3(3,5)37.1 VH (a portion of SEQ ID NOS:35-36) to human Ig germline.

FIG. 4J Alignment of Ha5-3(3,5)37.1 VL (a portion of SEQ ID NOS:37-38 to human Ig germline.

FIG. 4K Alignment of Ha5-4(2,5)13.1 VH (a portion of SEQ ID NOS:39-40) to human Ig germline.

FIG. 4L Alignment of Ha5-4(2,5)13.1 VL (a portion of SEQ ID NOS:41-42) to human Ig germline.

FIG. 4M Alignment of Ha5-4(2,5)34.1 VH (a portion of SEQ ID NOS:43-44) to human Ig germline.

FIG. 4N Alignment of Ha5-4(2,5)34.1 VL (a portion of SEQ ID NOS:45-46) to human Ig germline.

FIG. 4O Alignment of Ha5-7acd4.1 VH (a portion of SEQ ID NOS:47-48) to human Ig germline.

FIG. 4P Alignment of Ha5-7acd4.1 VL (a portion of SEQ ID NOS:49-50) to human Ig germline.

FIG. 4Q Alignment of Ha5-7acd20.1.1 VH (a portion of SEQ ID NOS:51-52) to human Ig germline.

FIG. 4R Alignment of Ha5-7acd20.1.1 VL (a portion of SEQ ID NOS:53-54) to human Ig germline.

FIG. 4S Alignment of Ha5-7be31.1 VH (a portion of SEQ ID NOS:55-56) to human Ig germline.

FIG. 4T Alignment of Ha5-7be31.1 VL (a portion of SEQ ID NOS:57-58) to human Ig germline.

FIG. 4U Alignment of Ha5-7acd10.1 VH (a portion of SEQ ID NOS:59-60) to human Ig germline.

FIG. 4V Alignment of Ha5-7acd10.1 VL (a portion of SEQ ID NOS:61-62) to human Ig germline.

FIG. 4W Alignment of Ha5-7acd13.1 VH (a portion of SEQ ID NOS:63-64) to human Ig germline.

FIG. 4X Alignment of Ha5-7acd13.1 VL (a portion of SEQ ID NOS:65-66) to human Ig germline.

FIG. 4Y Alignment of Ha5-7acd19.1 VH (a portion of SEQ ID NOS:67-68) to human Ig germline.

FIG. 4Z Alignment of Ha5-7acd19.1 VL (a portion of SEQ ID NOS:69-70) to human Ig germline.

FIG. 4AA Alignment of Ha5-7be37.1 VH (a portion of SEQ ID NOS:71-72) to human Ig germline.

FIG. 4AB Alignment of Ha5-7be37.1 VL (a portion of SEQ ID NOS:73-74) to human Ig germline.

FIG. 4AC Alignment of Ha5-7acd16.1 VH (a portion of SEQ ID NOS:75-76) to human Ig germline.

FIG. 4AD Alignment of Ha5-7acd16.1 VL (a portion of SEQ ID NOS:77-78) to human Ig germline.

FIG. 4AE Alignment of Ha5-7acd7.1.1 VH (a portion of SEQ ID NOS:79-80) to human Ig germline.

FIG. 4AF Alignment of Ha5-7acd7.1.1 VL (a portion of SEQ ID NOS:81-82) to human Ig germline.

FIG. 4AG Alignment of Ha5-7be20.1 VH (a portion of SEQ ID NOS:83-84) to human Ig germline.

FIG. 4AH Alignment of Ha5-7be20.1 VL (a portion of SEQ ID NOS:85-86) to human Ig germline.

FIG. 4AI Alignment of Ha5-7acd5.1.1 VH (a portion of SEQ ID NOS:87-88) to human Ig germline.

FIG. 4AJ Alignment of Ha5-7acd5.1.1 VL (a portion of SEQ ID NOS:89-90) to human Ig germline.

FIG. 4AK Alignment of Ha5-7be34.1 VH (a portion of SEQ ID NOS:91-92) to human Ig germline.

FIG. 4AL Alignment of Ha5-7be34.1 VL (a portion of SEQ ID NOS:93-94) to human Ig germline.

FIG. 4AM Alignment of Ha5-7acd3.1 VH (a portion of SEQ ID NOS:95-96) to human Ig germline.

FIG. 4AN Alignment of Ha5-7acd3.1 VL (a portion of SEQ ID NOS:97-98) to human Ig germline.

FIG. 4AO Alignment of Ha5-7acd2.1 VH (a portion of SEQ ID NOS:99-100) to human Ig germline.

FIG. 4AP Alignment of Ha5-7acd2.1 VL (a portion of SEQ ID NOS: 101-102) to human Ig germline.

FIG. 4AQ Alignment of Ha5-8acd4.1 VH (a portion of SEQ ID NOS:103-104) to human Ig germline.

FIG. 4AR Alignment of Ha5-8acd4.1 VL (a portion of SEQ ID NOS:105-106) to human Ig germline.

FIG. 4AS Alignment of Ha5-4(2,5)31.1 VH (a portion of SEQ ID NOS:107-108) to human Ig germline.

FIG. 4AT Alignment of Ha5-4(2,5)31.1 VL (a portion of SEQ ID NOS:109-110) to human Ig germline.

FIG. 4AU Alignment of Ha5-11a1.1.1 VH (a portion of SEQ ID NOS:111-112) to human Ig germline.

FIG. 4AV Alignment of Ha5-11a1.1.1 VL (a portion of SEQ ID NOS:113-114) to human Ig germline.

FIG. 4AW Alignment of Ha5-11b1.1 VH (a portion of SEQ ID NOS:115-116) to human Ig germline.

FIG. 4AX Alignment of Ha5-11b1.1 VL (a portion of SEQ ID NOS:117-118) to human Ig germline.

FIG. 4AY Alignment of Ha5-7be7.1 VH (a portion of SEQ ID NOS:119-120) to human Ig germline.

FIG. 5. Expression Analysis of 24P4C12 in Normal Tissues and Patient Specimens. FIG. 5A. 24P4C12 Expression in Ovarian Cancer Patient Specimens. FIG. 5B. Expression of 24P4C12 in Breast Cancer Patient Specimens. FIG. 5C. Expression of 24P4C12 in Pancreatic Cancer Patient Specimens.

FIG. 6. Surface staining of multiple cancer cell line models with 24P4C12 MAbs. FIGS. 6A, 6B, 6C. PC3-24P4C12, LNCaP, 22RV1, OVCaR-5, HT29, Calu-1, CF-PAC cancer cell lines (~1 million cells) representing multiple cancer indications, were incubated with 10 ug/ml of the indicated 24P4C12 MAb overnight at 4 C. Following washing, cells were incubated with anti-human IgG secondary Ab-PE conjugate, washed, fixed and subjected to FACS analysis. Shown are histograms of the staining profiles of cells incubated with 24P4C12 MAbs (open peak at the right of the histogram) overlayed on cells incubated with an irrelevant control MAb (solid peak at the left of the histogram). The higher fluorescent intensity of the 24P4C12 MAb peaks compared to the control indicates specific binding of the MAbs to 24P4C12 protein present on the surface of the cells. These data indicate expression and specific recognition of 24P4C12 protein by MAbs in cell lines derived from prostate, ovarian, colon, lung, and pancreatic cancer indications.

FIG. 7. 24P4C12 Protein Sequence Alignment to Cynomolgus Monkey Ortholog. Shown is the amino acid alignment of human 24P4C12 protein (SEQ ID NO:2) to cynomolgus sequence (SEQ ID NO:173). There is 98.6% identity. Amino acid differences between the species are at positions 8, 124, 132, 156, 189, 191, 202, 228, 411-414, 579, 624 and 679

(not conservative) and dark shaded regions (conservative). Extracellular sequences are underlined.

FIG. 8. Surface binding of 24P4C12 MAbs to the cynomolgus ortholog of 24P4C12 protein expressed in Rat1 cells. Rat1 cells were stably transduced with retrovirus encoding the cynomolgus homolog of 24P4C12. These cells were stained with 10 ug/ml of the indicated MAb for 2 hours at 4 C. Cells were washed and then incubated with PE-conjugated anti-human IgG secondary Ab, washed, fixed, and subjected to FACS analysis. Shown are histograms of the staining profiles of Rat1-cynomolgus 24P4C12 cells incubated with 24P4C12 MAbs (open line histogram) overlayed on control neo cells solid, dark histogram. The higher fluorescent intensity of the of Rat1-cynomolgus 24P4C12 cell histograms compared to the control neo cells indicates specific binding of the MAbs to cynomolgus 24P4C12 protein present on the surface of the cells.

FIG. 9. 24P4C12 MAbs mediate killing of PC3-24P4C12 cells via a secondary Ab-saporin toxin conjugate. Antibodies to 24P4C12 mediate saporin dependent killing in PC3-24P4C12 cells. PC3-24P4C12 or PC3-Neo cells (500 cells/well) were seeded into a 96 well plate on day 1. The following day an equal volume of medium containing 2x concentration of the indicated primary antibody together with a 2 fold excess of anti-human (Hu-Sap) or anti-goat (Gt-Sap) polyclonal antibody conjugated with saporin toxin (Advanced Targeting Systems, San Diego, Calif.) was added to each well. The cells were allowed to incubate for 5 days at 37 degrees C. At the end of the incubation period, Alamar Blue was added to each well and incubation continued for an additional 4 hours. The fluorescence of each well was determined in a plate reader using an excitation wavelength of 530 nm and an emission wavelength of 590 nm. The results show that 24P4C12 antibodies HA5-1(5)1.1, HA5-1(5)2.1 and HA5-acd16.1 mediated saporin dependent cytotoxicity in PC3 cells expressing 24P4C12 but not in PC3 cells infected with the Neo gene alone. To further demonstrate specificity, the same primary 24P4C12 antibodies were incubated with a 2 fold excess of saporin conjugated goat polyclonal antibody. These results indicate that drugs or cytotoxic proteins can selectively be delivered to cells expressing 24P4C12 using an appropriate anti-24P4C12 MAb.

FIG. 10. Membrane topology and amino acid sequence of 24P4C12. Shown is the membrane topologies and amino acid sequences of 24P4C12. 24P4C12 proteins and variants thereof exhibit predicted topologies of 10 transmembrane domains with 5 extracellular loops with the first being the largest. There are 9 potential asparagine-linked extracellular glycosylation sites and there are many potential extracellular cysteine residues that could be involved in disulfide bonding. Charged amino acids residing in the transmembrane domain are also shown—basic amino acids arginine (N), Histidine (H), and Lysine (K) and the acidic residue glutamic acid (E). There is no acidic aspartic acid (D) present in the transmembrane domains of either protein.

FIG. 11. Membrane topology and amino acid sequence of CTL1. CTL1 has been reported to transport choline in a Na+-independent manner, however, due to the differences in transmembrane topology and presence and spacing of the above charged amino acids in 24P4C12 compared to CTL1, it is probable that 24P4C12 may mediate the transport macromolecules or ions other than choline.

FIG. 12. High extracellular K+ concentrations mediate a drop in CMFDA fluorescence in MDCK-24P4C12 cells indicative of decreased intracellular pH. FIG. 12A: Confluent polarized MDCK-24P4C12 (squares) and control MDCK-neo cells were loaded for 1 hour at 37 C with the pH sensitive fluorescent dye 5-chloromethylfluorescein diacetate (CM-FDA). CMFDA fluorescence decreases with increased H+ concentration (decreasing pH). Following washing, cells were incubated in either standard Krebs-hepes buffer (130 mM NaCl, 4.7 mM KCl, 1.2 mM MgSO4, 1.2 mM KH 2PO4, 11.7 mM D-glucose, 1.3 mM CaCl2, 10 mM HEPES, pH 7.4, solid triangles and squares) or in high K+ Krebs-hepes buffer in which the NaCl and KCl concentrations are switched (130 mM KCl and 4.7 mM NaCl, open triangles and squares). Fluorescence was then measured in a fluorescent plate reader with an excitation wavelength of 485 nm and an emission wavelength of 530 nm with readings taken at 20 sec intervals. FIG. 12B: Confluent polarized MDCK-24P4C12 (triangles) and MDCK-neo cells (squares) were initially incubated in standard Krebs-hepes buffer and then concentrated KCl (1M) was added (arrow) to elevate the extracellular K+ to 100 mM.

FIG. 13. Acidification of media with Na+ propionate mediates decreased CMFDA fluorescence in MDCK-24P4C12 cells indicative of decreased intracellular pH. Confluent polarized MDCK-24P4C12 and neo cells were labeled with CMFDA as described in FIG. 12 and placed in standard Krebs-hepes buffer. Baseline fluorescence was obtained and then 100 uM sodium propionate was added to the cells at the time indicated (arrow) to acidify the extracellular medium. Fluorescence then continued to be monitored. MDCK-24P4C12 cells (triangles), but not neo cells (squares) exhibited a marked drop in fluorescence demonstrating a drop in intracellular pH.

FIG. 14. Capping and Internalization by 24P4C12 Mabs. MAbs Ha5-7acd19, Ha5-7be37, and Ha5-3(1,4)$_7$ were labeled with Alexa Fluor 488 fluorescent dye as per manufacturer's instructions (Invitrogen, Carlsbad Calif.). PC3-24P4C12 cells were incubated with the labeled MAbs for 2 hours at 4C. Following washing, the cells were either kept at 4 C or moved to 37 C for 2 hours. Cells were then fixed and examined by fluorescent microscopy. Shown on FIG. 14A are fluorescent pictures of cells incubated with MAb and kept at 4C demonstrating cell surface staining of 24P4C12 protein. FIG. 14B shows fluorescent pictures of cells stained with MAb and then incubated at 37 C for 2 hours. These cells exhibit a loss of the ring-like cell surface staining and the appearance of bright dots and punctate fluorescence demonstrating MAb-mediated capping and internalization of 24P4C12 protein.

FIG. 15A-B. Detection of 24P4C12 protein by immunohistochemistry in pancreatic and ovarian cancer patient specimens. Tissue was obtained from patients with pancreatic carcinoma and ovarian carcinoma. The results showed expression of 24P4C12 in the tumor cells of the cancer patients' tissue.

DETAILED DESCRIPTION OF THE INVENTION

Outline of Sections

I.) Definitions
II.) 24P4C12 Polynucleotides
   II.A.) Uses of 24P4C12 Polynucleotides
      II.A.1.) Monitoring of Genetic Abnormalities
      II.A.2.) Antisense Embodiments
      II.A.3.) Primers and Primer Pairs
      II.A.4.) Isolation of 24P4C12-Encoding Nucleic Acid Molecules
      II.A.5.) Recombinant Nucleic Acid Molecules and Host-Vector Systems III.) 24P4C12-related Proteins
   III.A.) Motif-bearing Protein Embodiments
   III.B.) Expression of 24P4C12-related Proteins
   III.C.) Modifications of 24P4C12-related Proteins
   III.D.) Uses of 24P4C12-related Proteins
IV.) 24P4C12 Antibodies
V.) 24P4C12 Cellular Immune Responses
VI.) 24P4C12 Transgenic Animals
VII.) Methods for the Detection of 24P4C12
VIII.) Methods for Monitoring the Status of 24P4C12-related Genes and Their Products
IX.) Identification of Molecules That Interact With 24P4C12
X.) Therapeutic Methods and Compositions
   X.A.) Anti-Cancer Vaccines
   X.B.) 24P4C12 as a Target for Antibody-Based Therapy
   X.C.) 24P4C12 as a Target for Cellular Immune Responses
   X.C.1. Minigene Vaccines
   X.C.2. Combinations of CTL Peptides with Helper Peptides
   X.C.3. Combinations of CTL Peptides with T Cell Priming Agents
   X.C.4. Vaccine Compositions Comprising DC Pulsed with CTL and/or HTL Peptides
   X.D.) Adoptive Immunotherapy
   X.E.) Administration of Vaccines for Therapeutic or Prophylactic Purposes
XI.) Diagnostic and Prognostic Embodiments of 24P4C12.
XII.) Inhibition of 24P4C12 Protein Function
   XII.A.) Inhibition of 24P4C12 With Intracellular Antibodies
   XII.B.) Inhibition of 24P4C12 with Recombinant Proteins
   XII.C.) Inhibition of 24P4C12 Transcription or Translation
   XII.D.) General Considerations for Therapeutic Strategies
XIII.) Identification, Characterization and Use of Modulators of 24P4C12
XIV.) RNAi and Therapeutic use of small interfering RNA (siRNAs)
XV.) KITS/Articles of Manufacture
I.) Definitions:

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

The terms "advanced cancer", "locally advanced cancer", "advanced disease" and "locally advanced disease" mean cancers that have extended through the relevant tissue capsule, and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease, and these patients have substantially less favorable outcomes compared to patients having clinically localized (organ-confined) cancer.

"Altering the native glycosylation pattern" is intended for purposes herein to mean deleting one or more carbohydrate moieties found in native sequence 24P4C12 (either by removing the underlying glycosylation site or by deleting the glycosylation by chemical and/or enzymatic means), and/or adding one or more glycosylation sites that are not present in the native sequence 24P4C12. In addition, the phrase includes qualitative changes in the glycosylation of the native proteins, involving a change in the nature and proportions of the various carbohydrate moieties present.

The term "analog" refers to a molecule which is structurally similar or shares similar or corresponding attributes with another molecule (e.g. a 24P4C12-related protein). For example, an analog of a 24P4C12 protein can be specifically bound by an antibody or T cell that specifically binds to 24P4C12.

The term "antibody" is used in the broadest sense unless clearly indicated otherwise. Therefore, an "antibody" can be naturally occurring or man-made such as monoclonal antibodies produced by conventional hybridoma technology. Anti-24P4C12 antibodies comprise monoclonal and polyclonal antibodies as well as fragments containing the antigen-binding domain and/or one or more complementarity determining regions of these antibodies. As used herein, the term "antibody" refers to any form of antibody or fragment thereof that specifically binds 24P4C12 and/or exhibits the desired biological activity and specifically covers monoclonal antibodies (including full length monoclonal antibodies), polyclonal antibodies, multispecific antibodies (e.g., bispecific antibodies), and antibody fragments so long as they specifically bind 24P4C12 and/or exhibit the desired biological activity. Any specific antibody can be used in the methods and compositions provided herein. Thus, in one embodiment the term "antibody" encompasses a molecule comprising at least one variable region from a light chain immunoglobulin molecule and at least one variable region from a heavy chain molecule that in combination form a specific binding site for the target antigen. In one embodiment, the antibody is an IgG antibody. For example, the antibody is a IgG1, IgG2, IgG3, or IgG4 antibody. The antibodies useful in the present methods and compositions can be generated in cell culture, in phage, or in various animals, including but not limited to cows, rabbits, goats, mice, rats, hamsters, guinea pigs, sheep, dogs, cats, monkeys, chimpanzees, apes. Therefore, in one embodiment, an antibody of the present invention is a mammalian antibody. Phage techniques can be used to isolate an initial antibody or to generate variants with altered specificity or avidity characteristics. Such techniques are routine and well known in the art. In one embodiment, the antibody is produced by recombinant means known in the art. For example, a recombinant antibody can be produced by transfecting a host cell with a vector comprising a DNA sequence encoding the antibody. One or more vectors can be used to transfect the DNA sequence expressing at least one VL and one VH region in the host cell. Exemplary descriptions of recombinant means of antibody generation and production include Delves, ANTIBODY PRODUCTION: ESSENTIAL TECHNIQUES (Wiley, 1997); Shephard, et al., MONOCLONAL ANTIBODIES (Oxford University Press, 2000); Goding, MONOCLONAL ANTIBODIES: PRINCIPLES AND PRACTICE (Academic Press, 1993); CURRENT PROTOCOLS IN IMMUNOLOGY (John Wiley & Sons, most recent edition). An antibody of the present invention can be modified by recombinant means to increase greater efficacy of the antibody in mediating the desired function. Thus, it is within the scope of the invention that antibodies can be modified by substitutions using recombinant means. Typically, the substitutions will be conservative substitutions. For example, at least one amino acid in the constant region of the antibody can be replaced with a different residue. See, e.g., U.S. Pat. No. 5,624,821, U.S. Pat. No. 6,194,551, Application No. WO 9958572; and Angal, et al., Mol. Immunol. 30: 105-08 (1993). The modification in amino acids includes deletions, additions, and substitutions of amino acids. In some cases, such changes are made to reduce undesired activities, e.g., complement-dependent cytotoxicity. Frequently, the antibodies are labeled by joining, either covalently or non-covalently, a substance which provides for a detectable signal. A wide variety of labels and conjugation techniques are known and are reported extensively in both the scientific and patent literature. These antibodies can be screened for binding to normal or defective 24P4C12. See e.g., ANTIBODY ENGINEERING: A PRACTICAL APPROACH (Oxford University Press, 1996). Suitable antibodies with the desired biologic activities can be identified the following in vitro assays including but not limited to: proliferation, migration, adhesion, soft agar growth, angiogenesis, cell-cell communication, apoptosis, transport, signal transduction, and the following in vivo assays such as the inhibition of tumor growth. The antibodies provided herein can also be useful in diagnostic applications. As capture or non-neutralizing antibodies, they can be screened for the ability to bind to the specific antigen without inhibiting the receptor-binding or biological activity of the antigen. As neutralizing antibodies, the antibodies can be useful in competitive binding assays. They can also be used to quantify the 24P4C12 or its receptor.

The term "antigen-binding portion" or "antibody fragment" of an antibody (or simply "antibody portion"), as used herein, refers to one or more fragments of a 24P4C12 antibody that retain the ability to specifically bind to an antigen (e.g., 24P4C12 and variants; FIG. 1). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a $F(ab')_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarily determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

As used herein, any form of the "antigen" can be used to generate an antibody that is specific for 24P4C12. Thus, the eliciting antigen may be a single epitope, multiple epitopes, or the entire protein alone or in combination with one or more immunogenicity enhancing agents known in the art. The eliciting antigen may be an isolated full-length protein, a cell surface protein (e.g., immunizing with cells transfected with at least a portion of the antigen), or a soluble protein (e.g., immunizing with only the extracellular domain portion of the protein). The antigen may be produced in a genetically modified cell. The DNA encoding the antigen may be genomic or non-genomic (e.g., cDNA) and encodes at least a portion of the extracellular domain. As used herein, the term "portion" refers to the minimal number of amino acids or nucleic acids, as appropriate, to constitute an immunogenic epitope of the antigen of interest. Any genetic vectors suitable for transformation of the cells of interest may be employed, including but not limited to adenoviral vectors, plasmids, and non-viral vectors, such as cationic lipids. In one embodiment, the antibody of the methods and compositions herein specifically bind at least a portion of the extracellular domain of the 24P4C12 of interest.

The antibodies or antigen binding fragments thereof provided herein may be conjugated to a "bioactive agent." As used herein, the term "bioactive agent" refers to any synthetic or naturally occurring compound that binds the antigen and/or enhances or mediates a desired biological effect to enhance cell-killing toxins.

In one embodiment, the binding fragments useful in the present invention are biologically active fragments. As used herein, the term "biologically active" refers to an antibody or antibody fragment that is capable of binding the desired antigenic epitope and directly or indirectly exerting a biologic effect. Direct effects include, but are not limited to the modulation, stimulation, and/or inhibition of a growth signal, the modulation, stimulation, and/or inhibition of an anti-apoptotic signal, the modulation, stimulation, and/or inhibition of an apoptotic or necrotic signal, modulation, stimulation, and/or inhibition the ADCC cascade, and modulation, stimulation, and/or inhibition the CDC cascade.

"Bispecific" antibodies are also useful in the present methods and compositions. As used herein, the term "bispecific antibody" refers to an antibody, typically a monoclonal antibody, having binding specificities for at least two different antigenic epitopes. In one embodiment, the epitopes are from the same antigen. In another embodiment, the epitopes are from two different antigens. Methods for making bispecific antibodies are known in the art. For example, bispecific antibodies can be produced recombinantly using the co-expression of two immunoglobulin heavy chain/light chain pairs. See, e.g., Milstein et al., Nature 305:537-39 (1983). Alternatively, bispecific antibodies can be prepared using chemical linkage. See, e.g., Brennan, et al., Science 229:81 (1985). Bispecific antibodies include bispecific antibody fragments. See, e.g., Hollinger, et al., Proc. Natl. Acad. Sci. U.S.A. 90:6444-48 (1993), Gruber, et al., J. Immunol. 152:5368 (1994).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they specifically bind the target antigen and/or exhibit the desired biological activity (U.S. Pat. No. 4,816,567; and Morrison et al., Proc. Natl. Acad. Sci. USA 81: 6851-6855 (1984)).

The term "Chemotherapeutic Agent" refers to all chemical compounds that are effective in inhibiting tumor growth. Non-limiting examples of chemotherapeutic agents include alkylating agents; for example, nitrogen mustards, ethyleneimine compounds and alkyl sulphonates; antimetabolites; for example, folic acid, purine or pyrimidine antagonists; mitotic inhibitors; for example, vinca alkaloids and derivatives of podophyllotoxin, cytotoxic antibiotics, compounds that damage or interfere with DNA expression, and growth factor receptor antagonists. In addition, chemotherapeutic agents include cytotoxic agents (as defined herein), antibodies, biological molecules and small molecules.

The term "codon optimized sequences" refers to nucleotide sequences that have been optimized for a particular host species by replacing any codons having a usage frequency of less than about 20%. Nucleotide sequences that have been optimized for expression in a given host species by elimination of spurious polyadenylation sequences, elimination of exon/intron splicing signals, elimination of transposon-like repeats and/or optimization of GC content in addition to codon optimization are referred to herein as an "expression enhanced sequences."

A "combinatorial library" is a collection of diverse chemical compounds generated by either chemical synthesis or biological synthesis by combining a number of chemical "building blocks" such as reagents. For example, a linear combinatorial chemical library, such as a polypeptide (e.g., mutein) library, is formed by combining a set of chemical building blocks called amino acids in every possible way for a given compound length (i.e., the number of amino acids in a polypeptide compound). Numerous chemical compounds are synthesized through such combinatorial mixing of chemical building blocks (Gallop et al., J. Med. Chem. 37(9): 1233-1251 (1994)).

Preparation and screening of combinatorial libraries is well known to those of skill in the art. Such combinatorial chemical libraries include, but are not limited to, peptide libraries (see, e.g., U.S. Pat. No. 5,010,175, Furka, Pept. Prot. Res. 37:487-493 (1991), Houghton et al., Nature, 354:84-88 (1991)), peptoids (PCT Publication No WO 91/19735), encoded peptides (PCT Publication WO 93/20242), random bio-oligomers (PCT Publication WO 92/00091), benzodiazepines (U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with a Beta-D-Glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho, et al., Science 261: 1303 (1993)), and/or peptidyl phosphonates (Campbell et al., J. Org. Chem. 59:658 (1994)). See, generally, Gordon et al., J. Med. Chem. 37:1385 (1994), nucleic acid libraries (see, e.g., Stratagene, Corp.), peptide nucleic acid libraries (see, e.g., U.S. Pat. No. 5,539,083), antibody libraries (see, e.g., Vaughn et al., Nature Biotechnology 14(3): 309-314 (1996), and PCT/US96/10287), carbohydrate libraries (see, e.g., Liang et al., Science 274:1520-1522 (1996), and U.S. Pat. No. 5,593,853), and small organic molecule libraries (see, e.g., benzodiazepines, Baum, C&EN, Jan. 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514; and the like).

Devices for the preparation of combinatorial libraries are commercially available (see, e.g., 357 NIPS, 390 NIPS, Advanced Chem Tech, Louisville Ky.; Symphony, Rainin, Woburn, Mass.; 433A, Applied Biosystems, Foster City, Calif.; 9050, Plus, Millipore, Bedford, NIA). A number of well-known robotic systems have also been developed for solution phase chemistries. These systems include automated workstations such as the automated synthesis apparatus developed by Takeda Chemical Industries, LTD. (Osaka, Japan) and many robotic systems utilizing robotic arms (Zymate H, Zymark Corporation, Hopkinton, Mass.; Orca, Hewlett-Packard, Palo Alto, Calif.), which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J.; Asinex, Moscow, RU; Tripos, Inc., St. Louis, Mo.; ChemStar, Ltd, Moscow, RU; 3D Pharmaceuticals, Exton, Pa.; Martek Biosciences, Columbia, Md.; etc.).

As used herein, the term "conservative substitution" refers to substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson, et al., MOLECULAR BIOLOGY OF THE GENE, The Benjamin/Cummings Pub. Co., p. 224 (4th Edition 1987)). Such exemplary substitutions are preferably made in accordance with those set forth in Table(s) III(a-b). For example, such changes include substituting any of isoleucine (I), valine (V), and leucine (L) for any other of these hydrophobic amino acids; aspartic acid (D) for glutamic acid (E) and vice versa; glutamine (O) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments (see, e.g. Table III(a) herein; pages 13-15 "Biochemistry" 2nd ED. Lubert Stryer ed (Stanford University); Henikoff et al., PNAS1992 Vol 89 10915-10919; Lei et al., J Biol Chem 1995 May 19; 270(20):11882-6). Other substitutions are also permissible and may be determined empirically or in accord with known conservative substitutions.

The term "cytotoxic agent" refers to a substance that inhibits or prevents the expression activity of cells, function of cells and/or causes destruction of cells. The term is intended to include radioactive isotopes, chemotherapeutic agents, and toxins such as small molecule toxins or enzymatically active toxins of bacterial, fungal, plant or animal origin, including fragments and/or variants thereof. Examples of cytotoxic agents include, but are not limited to auristatins, auristatin e, auristatin f, auromycins, maytansinoids, yttrium, bismuth, ricin, ricin A-chain, combrestatin, duocarmycins, dolostatins, doxorubicin, daunorubicin, taxol, cisplatin, cc1065, ethidium bromide, mitomycin, etoposide, tenoposide, vincristine, vinblastine, colchicine, dihydroxy anthracin dione, actinomycin, diphtheria toxin, *Pseudomonas* exotoxin (PE) A, PE40, abrin, abrin A chain, modeccin A chain, alpha-sarcin, gelonin, mitogellin, retstrictocin, phenomycin, enomycin, curicin, crotin, calicheamicin, Sapaonaria officinalis inhibitor, and glucocorticoid and other chemotherapeutic agents, as well as radioisotopes such as $At^{211}$, $I^{131}$, $I^{125}$, $Y^{90}$, $Re^{186}$, $Re^{188}$, $Sm^{153}$, $Bi^{212}$ or $^{213}$, P32 and radioactive isotopes of Lu including $Lu^{177}$. Antibodies may also be conjugated to an anti-cancer pro-drug activating enzyme capable of converting the pro-drug to its active form.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Hollinger et al., Proc. Natl. Acad. Sci. USA 90:6444-48 (1993).

The "gene product" is used herein to indicate a peptide/protein or mRNA. For example, a "gene product of the invention" is sometimes referred to herein as a "cancer amino acid sequence", "cancer protein", "protein of a cancer listed in Table I", a "cancer mRNA", "mRNA of a cancer listed in Table I", etc. In one embodiment, the cancer protein is encoded by a nucleic acid of FIG. 1. The cancer protein can be a fragment, or alternatively, be the full-length protein encoded by nucleic acids of FIG. 1. In one embodiment, a cancer amino acid sequence is used to determine sequence identity or similarity. In another embodiment, the sequences are naturally occurring allelic variants of a protein encoded by a nucleic acid of FIG. 1. In another embodiment, the sequences are sequence variants as further described herein.

"Heteroconjugate" antibodies are useful in the present methods and compositions. As used herein, the term "heteroconjugate antibody" refers to two covalently joined antibodies. Such antibodies can be prepared using known methods in synthetic protein chemistry, including using crosslinking agents. See, e.g., U.S. Pat. No. 4,676,980.

"High throughput screening" assays for the presence, absence, quantification, or other properties of particular nucleic acids or protein products are well known to those of skill in the art. Similarly, binding assays and reporter gene assays are similarly well known. Thus, e.g., U.S. Pat. No. 5,559,410 discloses high throughput screening methods for proteins; U.S. Pat. No. 5,585,639 discloses high throughput screening methods for nucleic acid binding (i.e., in arrays); while U.S. Pat. Nos. 5,576,220 and 5,541,061 disclose high throughput methods of screening for ligand/antibody binding.

In addition, high throughput screening systems are commercially available (see, e.g., Amersham Biosciences, Piscataway, N.J.; Zymark Corp., Hopkinton, Mass.; Air Technical Industries, Mentor, Ohio; Beckman Instruments, Inc. Fullerton, Calif.; Precision Systems, Inc., Natick, Mass.; etc.). These systems typically automate entire procedures, including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, e.g., Zymark Corp. provides technical bulletins describing screening systems for detecting the modulation of gene transcription, ligand binding, and the like.

The term "homolog" refers to a molecule which exhibits homology to another molecule, by for example, having sequences of chemical residues that are the same or similar at corresponding positions.

In one embodiment, the antibody provided herein is a "human antibody." As used herein, the term "human antibody" refers to an antibody in which essentially the entire sequences of the light chain and heavy chain sequences, including the complementary determining regions (CDRs), are from human genes. In one embodiment, human monoclonal antibodies are prepared by the trioma technique, the human B-cell technique (see, e.g., Kozbor, et al., Immunol. Today 4: 72 (1983), EBV transformation technique (see, e.g., Cole et al. MONOCLONAL ANTIBODIES AND CANCER THERAPY 77-96 (1985)), or using phage display (see, e.g., Marks et al., J. Mol. Biol. 222:581 (1991)). In a specific embodiment, the human antibody is generated in a transgenic mouse. Techniques for making such partially to fully human antibodies are known in the art and any such techniques can be used. According to one particularly preferred embodiment, fully human antibody sequences are made in a transgenic mouse engineered to express human heavy and light chain antibody genes. An exemplary description of preparing transgenic mice that produce human antibodies found in Application No. WO 02/43478 and U.S. Pat. No. 6,657,103 (Abgenix) and its progeny. B cells from transgenic mice that produce the desired antibody can then be fused to make hybridoma cell lines for continuous production of the antibody. See, e.g., U.S. Pat. Nos. 5,569,825; 5,625,126; 5,633,425; 5,661,016; and 5,545,806; and Jakobovits, Adv. Drug Del. Rev. 31:33-42 (1998); Green, et al., J. Exp. Med. 188: 483-95 (1998).

"Human Leukocyte Antigen" or "HLA" is a human class I or class II Major Histocompatibility Complex (MHC) protein (see, e.g., Stites, et al., IMMUNOLOGY, 8TH ED., Lange Publishing, Los Altos, Calif. (1994).

As used herein, the term "humanized antibody" refers to forms of antibodies that contain sequences from non-human (e.g., murine) antibodies as well as human antibodies. Such antibodies are chimeric antibodies which contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. See e.g., Cabilly U.S. Pat. No. 4,816,567; Queen et al. (1989) Proc. Nat'l Acad. Sci. USA 86:10029-10033; and ANTIBODY ENGINEERING: A PRACTICAL APPROACH (Oxford University Press 1996).

The terms "hybridize", "hybridizing", "hybridizes" and the like, used in the context of polynucleotides, are meant to refer to conventional hybridization conditions, preferably such as hybridization in 50% formamide/6×SSC/0.1% SDS/ 100 μg/ml ssDNA, in which temperatures for hybridization are above 37 degrees C. and temperatures for washing in 0.1×SSC/0.1% SDS are above 55 degrees C.

The phrases "isolated" or "biologically pure" refer to material which is substantially or essentially free from components which normally accompany the material as it is found in its native state. Thus, isolated peptides in accordance with the invention preferably do not contain materials normally associated with the peptides in their in situ environment. For example, a polynucleotide is said to be "isolated" when it is substantially separated from contaminant polynucleotides that correspond or are complementary to genes other than the 24P4C12 genes or that encode polypeptides other than 24P4C12 gene product or fragments thereof. A skilled artisan can readily employ nucleic acid isolation procedures to obtain an isolated 24P4C12 polynucleotide. A protein is said to be "isolated," for example, when physical, mechanical or chemical methods are employed to remove the 24P4C12 proteins from cellular constituents that are normally associated with the protein. A skilled artisan can readily employ standard purification methods to obtain an isolated 24P4C12 protein. Alternatively, an isolated protein can be prepared by chemical means.

Suitable "labels" include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. In addition, the antibodies provided herein can be useful as the antigen-binding component of fluorobodies. See e.g., Zeytun et al., Nat. Biotechnol. 21:1473-79 (2003).

The term "mammal" refers to any organism classified as a mammal, including mice, rats, rabbits, dogs, cats, cows, horses and humans. In one embodiment of the invention, the mammal is a mouse. In another embodiment of the invention, the mammal is a human.

The terms "metastatic cancer" and "metastatic disease" mean cancers that have spread to regional lymph nodes or to distant sites, and are meant to include stage D disease under the AUA system and stage T×N×M+under the TNM system.

The term "modulator" or "test compound" or "drug candidate" or grammatical equivalents as used herein describe any molecule, e.g., protein, oligopeptide, small organic molecule, polysaccharide, polynucleotide, etc., to be tested for the capacity to directly or indirectly alter the cancer phenotype or the expression of a cancer sequence, e.g., a nucleic acid or protein sequences, or effects of cancer sequences (e.g., signaling, gene expression, protein interaction, etc.) In one aspect, a modulator will neutralize the effect of a cancer protein of the invention. By "neutralize" is meant that an activity of a protein is inhibited or blocked, along with the consequent effect on the cell. In another aspect, a modulator will neutralize the effect of a gene, and its corresponding protein, of the invention by normalizing levels of said protein. In preferred embodiments, modulators alter expression profiles, or expression profile nucleic acids or proteins provided herein, or downstream effector pathways. In one embodiment, the modulator suppresses a cancer phenotype, e.g. to a normal tissue fingerprint. In another embodiment, a modulator induced a cancer phenotype. Generally, a plurality of assay mixtures is run in parallel with different agent concentrations to obtain a differential response to the various concentrations. Typically, one of these concentrations serves as a negative control, i.e., at zero concentration or below the level of detection.

Modulators, drug candidates or test compounds encompass numerous chemical classes, though typically they are organic molecules, preferably small organic compounds having a molecular weight of more than 100 and less than about 2,500 Daltons. Preferred small molecules are less than 2000, or less than 1500 or less than 1000 or less than 500 D. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Modulators also comprise biomolecules such as peptides, saccharides, fatty acids, steroids, purines, pyrimidines, derivatives, structural analogs or combinations thereof. Particularly preferred are peptides. One class of modulators are peptides, for example of from about five to about 35 amino acids, with from about five to about 20 amino acids being preferred, and from about 7 to about 15 being particularly preferred. Preferably, the cancer modulatory protein is soluble, includes a non-transmembrane region, and/or, has an N-terminal Cys to aid in solubility. In one embodiment, the C-terminus of the fragment is kept as a free acid and the N-terminus is a free amine to aid in coupling, i.e., to cysteine. In one embodiment, a cancer protein of the invention is conjugated to an immunogenic agent as discussed herein. In one embodiment, the cancer protein is conjugated to BSA. The peptides of the invention, e.g., of preferred lengths, can be linked to each other or to other amino acids to create a longer peptide/protein. The modulatory peptides can be digests of naturally occurring proteins as is outlined above, random peptides, or "biased" random peptides. In a preferred embodiment, peptide/protein-based modulators are antibodies, and fragments thereof, as defined herein.

Modulators of cancer can also be nucleic acids. Nucleic acid modulating agents can be naturally occurring nucleic acids, random nucleic acids, or "biased" random nucleic acids. For example, digests of prokaryotic or eukaryotic genomes can be used in an approach analogous to that outlined above for proteins.

The term "monoclonal antibody", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. In one embodiment, the polyclonal antibody contains a plurality of monoclonal antibodies with different epitope specificities, affinities, or avidities within a single antigen that contains multiple antigenic epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256: 495 (1975), or may be made by recombinant DNA methods (see, e.g., U.S. Pat. No. 4,816,567). The "monoclonal antibodies" may also be isolated from phage antibody libraries using the techniques described in Clackson et al., Nature 352: 624-628 (1991) and Marks et al., J. Mol. Biol. 222: 581-597 (1991), for example. These monoclonal antibodies will usually bind with at least a Kd of about 1 µM, more usually at least about 300 nM, typically at least about 30 nM, preferably at least about 10 nM, more preferably at least about 3 nM or better, usually determined by ELISA.

A "motif", as in biological motif of a 24P4C12-related protein, refers to any pattern of amino acids forming part of the primary sequence of a protein, that is associated with a particular function (e.g. protein-protein interaction, protein-DNA interaction, etc) or modification (e.g. that is phosphorylated, glycosylated or amidated), or localization (e.g. secretory sequence, nuclear localization sequence, etc.) or a sequence that is correlated with being immunogenic, either humorally or cellularly. A motif can be either contiguous or capable of being aligned to certain positions that are generally correlated with a certain function or property. In the context of HLA motifs, "motif" refers to the pattern of residues in a peptide of defined length, usually a peptide of from about 8 to about 13 amino acids for a class I HLA motif and from about 6 to about 25 amino acids for a class II HLA motif, which is recognized by a particular HLA molecule. Peptide motifs for HLA binding are typically different for each protein encoded by each human HLA allele and differ in the pattern of the primary and secondary anchor residues. Frequently occurring motifs are set forth in Table V.

A "pharmaceutical excipient" comprises a material such as an adjuvant, a carrier, pH-adjusting and buffering agents, tonicity adjusting agents, wetting agents, preservative, and the like.

"Pharmaceutically acceptable" refers to a non-toxic, inert, and/or composition that is physiologically compatible with humans or other mammals.

The term "polynucleotide" means a polymeric form of nucleotides of at least 10 bases or base pairs in length, either ribonucleotides or deoxynucleotides or a modified form of either type of nucleotide, and is meant to include single and double stranded forms of DNA and/or RNA. In the art, this term if often used interchangeably with "oligonucleotide". A polynucleotide can comprise a nucleotide sequence disclosed herein wherein thymidine (T), as shown for example in FIG. 1, can also be uracil (U); this definition pertains to the differences between the chemical structures of DNA and RNA, in particular the observation that one of the four major bases in RNA is uracil (U) instead of thymidine (T).

The term "polypeptide" means a polymer of at least about 4, 5, 6, 7, or 8 amino acids. Throughout the specification, standard three letter or single letter designations for amino acids are used. In the art, this term is often used interchangeably with "peptide" or "protein".

An HLA "primary anchor residue" is an amino acid at a specific position along a peptide sequence which is understood to provide a contact point between the immunogenic peptide and the HLA molecule. One to three, usually two, primary anchor residues within a peptide of defined length generally defines a "motif" for an immunogenic peptide. These residues are understood to fit in close contact with peptide binding groove of an HLA molecule, with their side chains buried in specific pockets of the binding groove. In one embodiment, for example, the primary anchor residues for an HLA class I molecule are located at position 2 (from the amino terminal position) and at the carboxyl terminal position of a 8, 9, 10, 11, or 12 residue peptide epitope in accordance with the invention. Alternatively, in another embodiment, the primary anchor residues of a peptide binds an HLA class II molecule are spaced relative to each other, rather than to the termini of a peptide, where the peptide is generally of at least 9 amino acids in length. The primary anchor positions for each motif and supermotif are set forth in Table IV(a). For example, analog peptides can be created by altering the presence or absence of particular residues in the primary and/or secondary anchor positions shown in Table IV. Such analogs are used to modulate the binding affinity and/or population coverage of a peptide comprising a particular HLA motif or supermotif.

"Radioisotopes" include, but are not limited to the following (non-limiting exemplary uses are also set forth in Table IV(I)).

By "randomized" or grammatical equivalents as herein applied to nucleic acids and proteins is meant that each nucleic acid and peptide consists of essentially random nucleotides and amino acids, respectively. These random peptides (or nucleic acids, discussed herein) can incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, a library is "fully randomized," with no sequence preferences or constants at any position. In another embodiment, the library is a "biased random" library. That is, some positions within the sequence either are held constant, or are selected from a limited number of possibilities. For example, the nucleotides or amino acid residues are randomized within a defined class, e.g., of hydrophobic amino acids, hydrophilic residues, sterically biased (either small or large) residues, towards the creation of nucleic acid binding domains, the creation of cysteines, for cross-linking, prolines for SH-3 domains, serines, threonines, tyrosines or histidines for phosphorylation sites, etc., or to purines, etc.

A "recombinant" DNA or RNA molecule is a DNA or RNA molecule that has been subjected to molecular manipulation in vitro.

As used herein, the term "single-chain Fv" or "scFv" or "single chain" antibody refers to antibody fragments comprising the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv, see Pluckthun, THE PHARMACOLOGY OF MONOCLONAL ANTIBODIES, vol. 113, Rosenburg and Moore eds. Springer-Verlag, New York, pp. 269-315 (1994).

Non-limiting examples of "small molecules" include compounds that bind or interact with 24P4C12, ligands including hormones, neuropeptides, chemokines, odorants, phospholipids, amino acids, polyamines, carbohydrates, steroids, minerals, vitamins, fatty acids, nucleotides, alcohols and functional equivalents or derivatives thereof that bind and preferably inhibit 24P4C12 protein function. Such non-limiting small molecules preferably have a molecular weight of less than about 10 kDa, more preferably below about 9, about 8, about 7, about 6, about 5 or about 4 kDa. In certain embodiments, small molecules physically associate with, or bind, 24P4C12 protein; are not found in naturally occurring metabolic pathways; and/or are more soluble in aqueous than non-aqueous solutions.

As used herein, the term "specific" refers to the selective binding of the antibody to the target antigen epitope. Antibodies can be tested for specificity of binding by comparing binding to appropriate antigen to binding to irrelevant antigen or antigen mixture under a given set of conditions. If the antibody binds to the appropriate antigen at least 2, 5, 7, and preferably 10 times more than to irrelevant antigen or antigen mixture then it is considered to be specific. In one embodiment, a specific antibody is one that only binds the 24P4C12 antigen, but does not bind to the irrelevent antigen. In another embodiment, a specific antibody is one that binds human 24P4C12 antigen but does not bind a non-human 24P4C12 antigen with 70%, 75%, 80%, 85%, 90%, 91%, 92%, 93%, 94%, 95%, 96%, 97%, 98%, 99% or greater amino acid homology with the 24P4C12 antigen. In another embodiment, a specific antibody is one that binds human 24P4C12 antigen and binds murine 24P4C12 antigen, but with a higher degree of binding the human antigen. In another embodiment, a specific antibody is one that binds human 24P4C12 antigen and binds primate 24P4C12 antigen, but with a higher degree of binding the human antigen. In another embodiment, the specific antibody binds to human 24P4C12 antigen and any non-human 24P4C12 antigen, but with a higher degree of binding the human antigen or any combination thereof.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured nucleic acid sequences to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, are identified by, but not limited to, those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. "Moderately stringent conditions" are described by, but not limited to, those in Sambrook et al., Molecular Cloning: A Laboratory Manual, New York: Cold Spring Harbor Press, 1989, and include the use of washing solution and hybridization conditions (e.g., temperature, ionic strength and % SDS) less stringent than those described above. An example of moderately stringent conditions is overnight incubation at 65° C. in a solution comprising: 1% bovine serum albumin, 0.5M sodium phosphate pH7.5, 1.25 mM EDTA, and 7% SDS 5×SSC (150 mM NaCl, 15 mM trisodium citrate), followed by washing the filters in 2×SSC/1% SDS at 50° C. and 0.2×SSC/0.1% SDS at 50° C. The skilled artisan will recognize how to adjust the temperature, ionic strength, etc. as necessary to accommodate factors such as probe length and the like.

An HLA "supermotif" is a peptide binding specificity shared by HLA molecules encoded by two or more HLA alleles. Overall phenotypic frequencies of HLA-supertypes in different ethnic populations are set forth in Table IV (f). The non-limiting constituents of various supertypes are as follows:

A2: A*0201, A*0202, A*0203, A*0204, A*0205, A*0206, A*6802, A*6901, A*0207

A3: A3, A11, A31, A*3301, A*6801, A*0301, A*1101, A*3101

B7: B7, B*3501-03, B*51, B*5301, B*5401, B*5501, B*5502, B*5601, B*6701, B*7801, B*0702, B*5101, B*5602

B44: B*3701, B*4402, B*4403, B*60 (B*4001), B61 (B*4006)

A1: A*0102, A*2604, A*3601, A*4301, A*8001

A24: A*24, A*30, A*2403, A*2404, A*3002, A*3003

B27: B*1401-02, B*1503, B*1509, B*1510, B*1518, B*3801-02, B*3901, B*3902, B*3903-04, B*4801-02, B*7301, B*2701-08

B58: B*1516, B*1517, B*5701, B*5702, B58

B62: B*4601, B52, B*1501 (B62), B*1502 (B75), B*1513 (B77)

Calculated population coverage afforded by different HLA-supertype combinations are set forth in Table IV(g).

As used herein "to treat" or "therapeutic" and grammatically related terms, refer to any improvement of any consequence of disease, such as prolonged survival, less morbidity, and/or a lessening of side effects which are the byproducts of an alternative therapeutic modality; as is readily appreciated in the art, full eradication of disease is a preferred out albeit not a requirement for a treatment act.

A "transgenic animal" (e.g., a mouse or rat) is an animal having cells that contain a transgene, which transgene was introduced into the animal or an ancestor of the animal at a prenatal, e.g., an embryonic stage. A "transgene" is a DNA that is integrated into the genome of a cell from which a transgenic animal develops.

As used herein, an HLA or cellular immune response "vaccine" is a composition that contains or encodes one or more peptides of the invention. There are numerous embodiments of such vaccines, such as a cocktail of one or more individual peptides; one or more peptides of the invention comprised by a polyepitopic peptide; or nucleic acids that encode such individual peptides or polypeptides, e.g., a minigene that encodes a polyepitopic peptide. The "one or more peptides" can include any whole unit integer from 1-150 or more, e.g., at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, or 150 or more peptides of the invention. The peptides or polypeptides can optionally be modified, such as by lipidation, addition of targeting or other sequences. HLA class I peptides of the invention can be admixed with, or linked to, HLA class II peptides, to facilitate activation of both cytotoxic T lymphocytes and helper T lymphocytes. HLA vaccines can also comprise peptide-pulsed antigen presenting cells, e.g., dendritic cells.

The term "variant" refers to a molecule that exhibits a variation from a described type or norm, such as a protein that has one or more different amino acid residues in the corresponding position(s) of a specifically described protein (e.g. the 24P4C12 protein shown in FIG. 1.) An analog is an example of a variant protein. Splice isoforms and single nucleotides polymorphisms (SNPs) are further examples of variants.

The "24P4C12-related proteins" of the invention include those specifically identified herein, as well as allelic variants, conservative substitution variants, analogs and homologs that can be isolated/generated and characterized without undue experimentation following the methods outlined herein or readily available in the art. Fusion proteins that combine parts of different 24P4C12 proteins or fragments thereof, as well as fusion proteins of a 24P4C12 protein and a heterologous polypeptide are also included. Such 24P4C12 proteins are collectively referred to as the 24P4C12-related proteins, the proteins of the invention, or 24P4C12. The term "24P4C12-related protein" refers to a polypeptide fragment or a 24P4C12 protein sequence of 4, 5, 6, 7, 8, 9, 10, 11, 12, 13, 14, 15, 16, 17, 18, 19, 20, 21, 22, 23, 24, 25, or more than 25 amino acids; or, at least 30, 35, 40, 45, 50, 55, 60, 65, 70, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 330, 335, 339 or more amino acids.

II.) 24P4C12 Polynucleotides

One aspect of the invention provides polynucleotides corresponding or complementary to all or part of a 24P4C12 gene, mRNA, and/or coding sequence, preferably in isolated form, including polynucleotides encoding a 24P4C12-related protein and fragments thereof, DNA, RNA, DNA/RNA hybrid, and related molecules, polynucleotides or oligonucleotides complementary to a 24P4C12 gene or mRNA sequence or a part thereof, and polynucleotides or oligonucleotides that hybridize to a 24P4C12 gene, mRNA, or to a 24P4C12 encoding polynucleotide (collectively, "24P4C12 polynucleotides"). In all instances when referred to in this section, T can also be U in FIG. 1.

Embodiments of a 24P4C12 polynucleotide include: a 24P4C12 polynucleotide having the sequence shown in FIG. 1, the nucleotide sequence of 24P4C12 as shown in FIG. 1 wherein T is U; at least 10 contiguous nucleotides of a polynucleotide having the sequence as shown in FIG. 1; or, at least 10 contiguous nucleotides of a polynucleotide having the sequence as shown in FIG. 1 where T is U.

Polynucleotides encoding relatively long portions of a 24P4C12 protein are also within the scope of the invention. For example, polynucleotides encoding from about amino acid 1 (or 20 or 30 or 40 etc.) to about amino acid 20, (or 30, or 40 or 50 etc.) of the 24P4C12 protein "or variant" shown in FIG. 1 or FIG. 3 can be generated by a variety of techniques well known in the art. These polynucleotide fragments can include any portion of the 24P4C12 sequence as shown in FIG. 1.

II.A.) Uses of 24P4C12 Polynucleotides

II.A.1. Monitoring of Genetic Abnormalities

The polynucleotides of the preceding paragraphs have a number of different specific uses. The human 24P4C12 gene maps to the chromosomal location set forth in the Example entitled "Chromosomal Mapping of 24P4C12." For example, because the 24P4C12 gene maps to this chromosome, polynucleotides that encode different regions of the 24P4C12 proteins are used to characterize cytogenetic abnormalities of this chromosomal locale, such as abnormalities that are identified as being associated with various cancers. In certain genes, a variety of chromosomal abnormalities including rearrangements have been identified as frequent cytogenetic abnormalities in a number of different cancers (see e.g. Krajinovic et al., Mutat. Res. 382(3-4): 81-83 (1998); Johansson et al., Blood 86(10): 3905-3914 (1995) and Finger et al., P.N.A.S. 85(23): 9158-9162 (1988)). Thus, polynucleotides encoding specific regions of the 24P4C12 proteins provide new tools that can be used to delineate, with greater precision than previously possible, cytogenetic abnormalities in the chromosomal region that encodes 24P4C12 that may contribute to the malignant phenotype. In this context, these polynucleotides satisfy a need in the art for expanding the sensitivity of chromosomal screening in order to identify more subtle and less common chromosomal abnormalities (see e.g. Evans et al., Am. J. Obstet. Gynecol 171(4): 1055-1057 (1994)).

Furthermore, as 24P4C12 was shown to be highly expressed in prostate and other cancers, 24P4C12 polynucleotides are used in methods assessing the status of 24P4C12 gene products in normal versus cancerous tissues. Typically, polynucleotides that encode specific regions of the 24P4C12 proteins are used to assess the presence of perturbations (such as deletions, insertions, point mutations, or alterations resulting in a loss of an antigen etc.) in specific regions of the 24P4C12 gene, such as regions containing one or more motifs. Exemplary assays include both RT-PCR assays as well as single-strand conformation polymorphism (SSCP) analysis (see, e.g., Marrogi et al., J. Cutan. Pathol. 26(8): 369-378 (1999), both of which utilize polynucleotides encoding specific regions of a protein to examine these regions within the protein.

II.A.2. Antisense Embodiments

Other specifically contemplated nucleic acid related embodiments of the invention disclosed herein are genomic DNA, cDNAs, ribozymes, and antisense molecules, as well as nucleic acid molecules based on an alternative backbone, or including alternative bases, whether derived from natural sources or synthesized, and include molecules capable of inhibiting the RNA or protein expression of 24P4C12. For example, antisense molecules can be RNAs or other molecules, including peptide nucleic acids (PNAs) or non-nucleic acid molecules such as phosphorothioate derivatives that specifically bind DNA or RNA in a base pair-dependent manner. A skilled artisan can readily obtain these classes of nucleic acid molecules using the 24P4C12 polynucleotides and polynucleotide sequences disclosed herein.

Antisense technology entails the administration of exogenous oligonucleotides that bind to a target polynucleotide located within the cells. The term "antisense" refers to the fact that such oligonucleotides are complementary to their intracellular targets, e.g., 24P4C12. See for example, Jack Cohen, Oligodeoxynucleotides, Antisense Inhibitors of Gene Expression, CRC Press, 1989; and Synthesis 1:1-5 (1988). The 24P4C12 antisense oligonucleotides of the present invention include derivatives such as S-oligonucleotides (phosphorothioate derivatives or S-oligos, see, Jack Cohen, supra), which exhibit enhanced cancer cell growth inhibitory action. S-oligos (nucleoside phosphorothioates) are isoelectronic analogs of an oligonucleotide (O-oligo) in which a nonbridging oxygen atom of the phosphate group is replaced by a sulfur atom. The S-oligos of the present invention can be prepared by treatment of the corresponding O-oligos with 3H-1,2-benzodithiol-3-one-1,1-dioxide, which is a sulfur transfer reagent. See, e.g., Iyer, R. P. et al., J. Org. Chem. 55:4693-4698 (1990); and Iyer, R. P. et al., J. Am. Chem. Soc. 112:1253-1254 (1990). Additional 24P4C12 antisense oligonucleotides of the present invention include morpholino antisense oligonucleotides known in the art (see, e.g., Partridge et al., 1996, Antisense & Nucleic Acid Drug Development 6: 169-175).

The 24P4C12 antisense oligonucleotides of the present invention typically can be RNA or DNA that is complementary to and stably hybridizes with the first 100 5' codons or last 100 3' codons of a 24P4C12 genomic sequence or the corresponding mRNA. Absolute complementarity is not required, although high degrees of complementarity are preferred. Use of an oligonucleotide complementary to this region allows for the selective hybridization to 24P4C12 mRNA and not to mRNA specifying other regulatory subunits of protein kinase. In one embodiment, 24P4C12 antisense oligonucleotides of the present invention are 15 to 30-mer fragments of the antisense DNA molecule that have a sequence that hybridizes to 24P4C12 mRNA. Optionally, 24P4C12 antisense oligonucleotide is a 30-mer oligonucleotide that is complementary to a region in the first 10 5' codons or last 10 3' codons of 24P4C12. Alternatively, the antisense molecules are modified to employ ribozymes in the inhibition of 24P4C12 expression, see, e.g., L. A. Couture & D. T. Stinchcomb; Trends Genet. 12: 510-515 (1996).

II.A.3. Primers and Primer Pairs

Further specific embodiments of these nucleotides of the invention include primers and primer pairs, which allow the specific amplification of polynucleotides of the invention or of any specific parts thereof, and probes that selectively or specifically hybridize to nucleic acid molecules of the invention or to any part thereof. Probes can be labeled with a detectable marker, such as, for example, a radioisotope, fluorescent compound, bioluminescent compound, a chemiluminescent compound, metal chelator or enzyme. Such probes and primers are used to detect the presence of a 24P4C12 polynucleotide in a sample and as a means for detecting a cell expressing a 24P4C12 protein.

Examples of such probes include polypeptides comprising all or part of the human 24P4C12 cDNA sequence shown in FIG. 1. Examples of primer pairs capable of specifically amplifying 24P4C12 mRNAs are also described in the Examples. As will be understood by the skilled artisan, a great many different primers and probes can be prepared based on the sequences provided herein and used effectively to amplify and/or detect a 24P4C12 mRNA.

The 24P4C12 polynucleotides of the invention are useful for a variety of purposes, including but not limited to their use as probes and primers for the amplification and/or detection of the 24P4C12 gene(s), mRNA(s), or fragments thereof; as reagents for the diagnosis and/or prognosis of prostate cancer and other cancers; as coding sequences capable of directing the expression of 24P4C12 polypeptides; as tools for modulating or inhibiting the expression of the 24P4C12 gene(s) and/or translation of the 24P4C12 transcript(s); and as therapeutic agents.

The present invention includes the use of any probe as described herein to identify and isolate a 24P4C12 or 24P4C12 related nucleic acid sequence from a naturally occurring source, such as humans or other mammals, as well as the isolated nucleic acid sequence per se, which would comprise all or most of the sequences found in the probe used.

II.A.4. Isolation of 24P4C12-Encoding Nucleic Acid Molecules

The 24P4C12 cDNA sequences described herein enable the isolation of other polynucleotides encoding 24P4C12 gene product(s), as well as the isolation of polynucleotides encoding 24P4C12 gene product homologs, alternatively spliced isoforms, allelic variants, and mutant forms of a 24P4C12 gene product as well as polynucleotides that encode analogs of 24P4C12-related proteins. Various molecular cloning methods that can be employed to isolate full length cDNAs encoding a 24P4C12 gene are well known (see, for example, Sambrook, J. et al., Molecular Cloning: A Laboratory Manual, 2d edition, Cold Spring Harbor Press, New York, 1989; Current Protocols in Molecular Biology. Ausubel et al., Eds., Wiley and Sons, 1995). For example, lambda phage cloning methodologies can be conveniently employed, using commercially available cloning systems (e.g., Lambda ZAP Express, Stratagene). Phage clones containing 24P4C12 gene cDNAs can be identified by probing with a labeled 24P4C12 cDNA or a fragment thereof. For example, in one embodiment, a 24P4C12 cDNA (e.g., FIG. 1) or a portion thereof can be synthesized and used as a probe to retrieve overlapping and full-length cDNAs corresponding to a 24P4C12 gene. A 24P4C12 gene itself can be isolated by screening genomic DNA libraries, bacterial artificial chromosome libraries (BACs), yeast artificial chromosome libraries (YACs), and the like, with 24P4C12 DNA probes or primers.

II.A.5. Recombinant Nucleic Acid Molecules and Host-Vector Systems

The invention also provides recombinant DNA or RNA molecules containing a 24P4C12 polynucleotide, a fragment, analog or homologue thereof, including but not limited to phages, plasmids, phagemids, cosmids, YACs, BACs, as well as various viral and non-viral vectors well known in the art, and cells transformed or transfected with such recombinant DNA or RNA molecules. Methods for generating such molecules are well known (see, for example, Sambrook et al., 1989, supra).

The invention further provides a host-vector system comprising a recombinant DNA molecule containing a 24P4C12 polynucleotide, fragment, analog or homologue thereof within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as an Sf9 or HighFive cell). Examples of suitable mammalian cells include various prostate cancer cell lines such as DU145 and TsuPr1, other transfectable or transducible prostate cancer cell lines, primary cells (PrEC), as well as a number of mammalian cells routinely used for the expression of recombinant proteins (e.g., COS, CHO, 293, 293T cells). More particularly, a polynucleotide comprising the coding sequence of 24P4C12 or a fragment, analog or homolog thereof can be used to generate 24P4C12 proteins or fragments thereof using any number of host-vector systems routinely used and widely known in the art.

A wide range of host-vector systems suitable for the expression of 24P4C12 proteins or fragments thereof are available, see for example, Sambrook et al., 1989, supra; Current Protocols in Molecular Biology, 1995, supra). Preferred vectors for mammalian expression include but are not limited to pcDNA 3.1 myc-His-tag (Invitrogen) and the retroviral vector pSR tkneo (Muller et al., 1991, MCB 11:1785). Using these expression vectors, 24P4C12 can be expressed in several prostate cancer and non-prostate cell lines, including for example 293, 293T, rat-1, PC3, NIH 3T3 and TsuPr1. The host-vector systems of the invention are useful for the production of a 24P4C12 protein or fragment thereof. Such host-vector systems can be employed to study the functional properties of 24P4C12 and 24P4C12 mutations or analogs.

Recombinant human 24P4C12 protein or an analog or homolog or fragment thereof can be produced by mammalian cells transfected with a construct encoding a 24P4C12-related nucleotide. For example, 293T cells can be transfected with an expression plasmid encoding 24P4C12 or fragment, analog or homolog thereof, a 24P4C12-related protein is expressed in the 293T cells, and the recombinant 24P4C12 protein is isolated using standard purification methods (e.g., affinity purification using anti-24P4C12 antibodies). In another embodiment, a 24P4C12 coding sequence is subcloned into the retroviral vector pSRαMSVtkneo and used to infect various mammalian cell lines, such as NIH 3T3, TsuPr1, PC3, 293 and rat-1 in order to establish 24P4C12 expressing cell lines. Various other expression systems well known in the art can also be employed. Expression constructs encoding a leader peptide joined in frame to a 24P4C12 coding sequence can be used for the generation of a secreted form of recombinant 24P4C12 protein.

As discussed herein, redundancy in the genetic code permits variation in 24P4C12 gene sequences. In particular, it is known in the art that specific host species often have specific codon preferences, and thus one can adapt the disclosed sequence as preferred for a desired host. For example, preferred analog codon sequences typically have rare codons (i.e., codons having a usage frequency of less than about 20% in known sequences of the desired host) replaced with higher frequency codons. Codon preferences for a specific species are calculated, for example, by utilizing codon usage tables available on the INTERNET.

Additional sequence modifications are known to enhance protein expression in a cellular host. These include elimination of sequences encoding spurious polyadenylation signals, exon/intron splice site signals, transposon-like repeats, and/or other such well-characterized sequences that are deleterious to gene expression. The GC content of the sequence is adjusted to levels average for a given cellular host, as calculated by reference to known genes expressed in the host cell. Where possible, the sequence is modified to avoid predicted hairpin secondary mRNA structures. Other useful modifications include the addition of a translational initiation consensus sequence at the start of the open reading frame, as described in Kozak, Mol. Cell. Biol., 9:5073-5080 (1989). Skilled artisans understand that the general rule that eukaryotic ribosomes initiate translation exclusively at the 5' proximal AUG codon is abrogated only under rare conditions (see, e.g., Kozak PNAS 92(7): 2662-2666, (1995) and Kozak NAR 15(20): 8125-8148 (1987)).

III.) 24P4C12-Related Proteins

Another aspect of the present invention provides 24P4C12-related proteins. Specific embodiments of 24P4C12 proteins comprise a polypeptide having all or part of the amino acid sequence of human 24P4C12 as shown in FIG. 1, preferably FIG. 1A. Alternatively, embodiments of 24P4C12 proteins comprise variant, homolog or analog polypeptides that have alterations in the amino acid sequence of 24P4C12 shown in FIG. 1.

Embodiments of a 24P4C12 polypeptide include: a 24P4C12 polypeptide having a sequence shown in FIG. 1, a peptide encoded by a polynucleotide sequence of a 24P4C12 as shown in FIG. 1 wherein T is U; at least 10 contiguous nucleotides encoding a polypeptide having the sequence as shown in FIG. 1; or, at least 10 contiguous peptides encoded by a polynucleotide having the sequence as shown in FIG. 1 where T is U.

Amino acid abbreviations are provided in Table II. Conservative amino acid substitutions can frequently be made in a protein without altering either the conformation or the function of the protein. Proteins of the invention can comprise 1, 2, 3, 4, 5, 6, 7, 8, 9, 10, 11, 12, 13, 14, 15 conservative substitutions.

Embodiments of the invention disclosed herein include a wide variety of art-accepted variants or analogs of 24P4C12 proteins such as polypeptides having amino acid insertions, deletions and substitutions. 24P4C12 variants can be made using methods known in the art such as site-directed mutagenesis, alanine scanning, and PCR mutagenesis. Site-directed mutagenesis (Carter et al., Nucl. Acids Res., 13:4331 (1986); Zoller et al., Nucl. Acids Res., 10:6487 (1987)), cassette mutagenesis (Wells et al., Gene, 34:315 (1985)), restriction selection mutagenesis (Wells et al., Philos. Trans. R. Soc. London SerA, 317:415 (1986)) or other known techniques can be performed on the cloned DNA to produce the 24P4C12 variant DNA.

Scanning amino acid analysis can also be employed to identify one or more amino acids along a contiguous sequence that is involved in a specific biological activity such as a protein-protein interaction. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions (Creighton, The Proteins, (W.H. Freeman & Co., N.Y.); Chothia, J. Mol. Biol., 150:1 (1976)). If alanine substitution does not yield adequate amounts of variant, an isosteric amino acid can be used.

As defined herein, 24P4C12 variants, analogs or homologs, have the distinguishing attribute of having at least one epitope that is "cross reactive" with a 24P4C12 protein having an amino acid sequence of FIG. 1. As used in this sentence, "cross reactive" means that an antibody or T cell that specifically binds to a 24P4C12 variant also specifically binds to a 24P4C12 protein having an amino acid sequence set forth in FIG. 1. A polypeptide ceases to be a variant of a protein shown in FIG. 1, when it no longer contains any epitope capable of being recognized by an antibody or T cell that specifically binds to the starting 24P4C12 protein. Those skilled in the art understand that antibodies that recognize proteins bind to epitopes of varying size, and a grouping of the order of about four or five amino acids, contiguous or not, is regarded as a typical number of amino acids in a minimal epitope. See, e.g., Nair et al., J. Immunol. 2000 165(12): 6949-6955; Hebbes et al., Mol Immunol (1989) 26(9):865-73; Schwartz et al., J Immunol (1985) 135(4):2598-608.

Other classes of 24P4C12-related protein variants share 70%, 75%, 80%, 85%, 90%, 95% or more similarity with an amino acid sequence of FIG. 1, or a fragment thereof. Another specific class of 24P4C12 protein variants or analogs comprises one or more of the 24P4C12 biological motifs described herein or presently known in the art. Thus, encompassed by the present invention are analogs of 24P4C12 fragments (nucleic or amino acid) that have altered functional (e.g. immunogenic) properties relative to the starting fragment. It is to be appreciated that motifs now or which become part of the art are to be applied to the nucleic or amino acid sequences of FIG. 1.

As discussed herein, embodiments of the claimed invention include polypeptides containing less than the full amino acid sequence of a 24P4C12 protein shown in FIG. 1. For example, representative embodiments of the invention comprise peptides/proteins having any 4, 5, 6, 7, 8, 9, 10, 11, 12, 13, 14, 15 or more contiguous amino acids of a 24P4C12 protein shown in FIG. 1.

24P4C12-related proteins are generated using standard peptide synthesis technology or using chemical cleavage methods well known in the art. Alternatively, recombinant methods can be used to generate nucleic acid molecules that encode a 24P4C12-related protein. In one embodiment, nucleic acid molecules provide a means to generate defined fragments of a 24P4C12 protein (or variants, homologs or analogs thereof).

III.A.) Motif-Bearing Protein Embodiments

Additional illustrative embodiments of the invention disclosed herein include 24P4C12 polypeptides comprising the amino acid residues of one or more of the biological motifs contained within a 24P4C12 polypeptide sequence set forth in FIG. 1. Various motifs are known in the art, and a protein can be evaluated for the presence of such motifs by a number of publicly available Internet sites such as BIMAS.

Motif bearing subsequences of all 24P4C12 variant proteins have previously been disclosed.

Table IV(h) sets forth several frequently occurring motifs based on pfam searches (see URL address pfam.wustl.edu/). The columns of Table IV(h) list (1) motif name abbreviation, (2) percent identity found amongst the different member of the motif family, (3) motif name or description and (4) most common function; location information is included if the motif is relevant for location.

Polypeptides comprising one or more of the 24P4C12 motifs discussed above are useful in elucidating the specific characteristics of a malignant phenotype in view of the observation that the 24P4C12 motifs discussed above are associated with growth dysregulation and because 24P4C12 is overexpressed in certain cancers (See, e.g., Table I). Casein kinase II, cAMP and camp-dependent protein kinase, and Protein Kinase C, for example, are enzymes known to be associated with the development of the malignant phenotype (see e.g. Chen et al., Lab Invest., 78(2): 165-174 (1998); Gaiddon et al., Endocrinology 136(10): 4331-4338 (1995); Hall et al., Nucleic Acids Research 24(6): 1119-1126 (1996); Peterziel et al., Oncogene 18(46): 6322-6329 (1999) and O'Brian, Oncol. Rep. 5(2): 305-309 (1998)). Moreover, both glycosylation and myristoylation are protein modifications also associated with cancer and cancer progression (see e.g. Dennis et al., Biochem. Biophys. Acta 1473(1):21-34 (1999); Raju et al., Exp. Cell Res. 235(1): 145-154 (1997)). Amidation is another protein modification also associated with cancer and cancer progression (see e.g. Treston et al., J. Natl. Cancer Inst. Monogr. (13): 169-175 (1992)).

In another embodiment, proteins of the invention comprise one or more of the immunoreactive epitopes identified in accordance with art-accepted methods, such as the peptides previously disclosed. CTL epitopes can be determined using specific algorithms to identify peptides within a 24P4C12 protein that are capable of optimally binding to specified HLA alleles (e.g., Table IV; Epimatrix™ and Epimer™, Brown University, URL brown.edu/Research/TB-HIV_Lab/epimatrix/epimatrix.html and BIMAS, URL bimas.dcrt.nih.gov/.) Moreover, processes for identifying peptides that have sufficient binding affinity for HLA molecules and which are correlated with being immunogenic epitopes, are well known in the art, and are carried out without undue experimentation. In addition, processes for identifying peptides that are immunogenic epitopes, are well known in the art, and are carried out without undue experimentation either in vitro or in vivo.

Also known in the art are principles for creating analogs of such epitopes in order to modulate immunogenicity. For example, one begins with an epitope that bears a CTL or HTL motif (see, e.g., the HLA Class I and HLA Class II motifs/supermotifs of Table IV). The epitope is analoged by substituting out an amino acid at one of the specified positions, and replacing it with another amino acid specified for that position. For example, on the basis of residues defined in Table IV, one can substitute out a deleterious residue in favor of any other residue, such as a preferred residue; substitute a less-preferred residue with a preferred residue; or substitute an originally-occurring preferred residue with another preferred residue. Substitutions can occur at primary anchor positions or at other positions in a peptide; see, e.g., Table IV.

A variety of references reflect the art regarding the identification and generation of epitopes in a protein of interest as well as analogs thereof. See, for example, WO 97/33602 to Chesnut et al.; Sette, Immunogenetics 1999 50(3-4): 201-212; Sette et al., J. Immunol. 2001 166(2): 1389-1397; Sidney et al., Hum. Immunol. 1997 58(1): 12-20; Kondo et al., Immunogenetics 1997 45(4): 249-258; Sidney et al., J. Immunol. 1996 157(8): 3480-90; and Falk et al., Nature 351: 290-6 (1991); Hunt et al., Science 255:1261-3 (1992); Parker et al., J. Immunol. 149:3580-7 (1992); Parker et al., J. Immunol. 152:163-75 (1994)); Kast et al., 1994 152(8): 3904-12; Borras-Cuesta et al., Hum. Immunol. 2000 61(3): 266-278; Alexander et al., J. Immunol. 2000 164(3); 164(3): 1625-1633; Alexander et al., PMID: 7895164, UI: 95202582; O'Sullivan et al., J. Immunol. 1991 147(8): 2663-2669; Alexander et al., Immunity 1994 1(9): 751-761 and Alexander et al., Immunol. Res. 1998 18(2): 79-92.

Related embodiments of the invention include polypeptides comprising combinations of the different motifs set forth in Table(s) IV(a), IV(b), IV(c), IV(d), and IV(h), and/or, one or more of the predicted CTL epitopes of previously disclosed, and/or, one or more of the T cell binding motifs known in the art. Preferred embodiments contain no insertions, deletions or substitutions either within the motifs or within the intervening sequences of the polypeptides. In addition, embodiments which include a number of either N-terminal and/or C-terminal amino acid residues on either side of these motifs may be desirable (to, for example, include a greater portion of the polypeptide architecture in which the motif is located). Typically, the number of N-terminal and/or C-terminal amino acid residues on either side of a motif is between about 1 to about 100 amino acid residues, preferably 5 to about 50 amino acid residues.

24P4C12-related proteins are embodied in many forms, preferably in isolated form. A purified 24P4C12 protein molecule will be substantially free of other proteins or molecules that impair the binding of 24P4C12 to antibody, T cell or other ligand. The nature and degree of isolation and purification will depend on the intended use. Embodiments of 24P4C12-related proteins include purified 24P4C12-related proteins and functional, soluble 24P4C12-related proteins. In one embodiment, a functional, soluble 24P4C12 protein or fragment thereof retains the ability to be bound by antibody, T cell or other ligand.

The invention also provides 24P4C12 proteins comprising biologically active fragments of a 24P4C12 amino acid sequence shown in FIG. 1. Such proteins exhibit properties of the starting 24P4C12 protein, such as the ability to elicit the generation of antibodies that specifically bind an epitope associated with the starting 24P4C12 protein; to be bound by such antibodies; to elicit the activation of HTL or CTL; and/or, to be recognized by HTL or CTL that also specifically bind to the starting protein.

24P4C12-related polypeptides that contain particularly interesting structures can be predicted and/or identified using various analytical techniques well known in the art, including, for example, the methods of Chou-Fasman, Garnier-Robson, Kyte-Doolittle, Eisenberg, Karplus-Schultz or Jameson-Wolf analysis, or based on immunogenicity. Fragments that contain such structures are particularly useful in generating subunit-specific anti-24P4C12 antibodies or T cells or in identifying cellular factors that bind to 24P4C12. For example, hydrophilicity profiles can be generated, and immunogenic peptide fragments identified, using the method of Hopp, T. P. and Woods, K. R., 1981, Proc. Natl. Acad. Sci. U.S.A. 78:3824-3828. Hydropathicity profiles can be generated, and immunogenic peptide fragments identified, using the method of Kyte, J. and Doolittle, R. F., 1982, J. Mol. Biol. 157:105-132. Percent (%) Accessible Residues profiles can be generated, and immunogenic peptide fragments identified, using the method of Janin J., 1979, Nature 277:491-492. Average Flexibility profiles can be generated, and immunogenic peptide fragments identified, using the method of Bhaskaran R., Ponnuswamy P. K., 1988, Int. J. Pept. Protein Res. 32:242-255. Beta-turn profiles can be generated, and immunogenic peptide fragments identified, using the method of Deleage, G., Roux B., 1987, Protein Engineering 1:289-294.

CTL epitopes can be determined using specific algorithms to identify peptides within a 24P4C12 protein that are capable of optimally binding to specified HLA alleles such as BIMAS and SYFPEITHI. Illustrating this, peptide epitopes from 24P4C12 that are presented in the context of human MHC Class 1 molecules, e.g., HLA-A1, A2, A3, A11, A24, B7 and B35 were predicted. Specifically, the complete amino acid sequence of the 24P4C12 protein and relevant portions of other variants, i.e., for HLA Class I predictions 9 flanking residues on either side of a point mutation or exon junction, and for HLA Class II predictions 14 flanking residues on either side of a point mutation or exon junction corresponding to that variant, were entered into the HLA Peptide Motif Search algorithm found in the Bioinformatics and Molecular Analysis Section.

The HLA peptide motif search algorithm was developed by Dr. Ken Parker based on binding of specific peptide sequences in the groove of HLA Class 1 molecules, in particular HLA-A2 (see, e.g., Falk et al., Nature 351: 290-6 (1991); Hunt et al., Science 255:1261-3 (1992); Parker et al., J. Immunol. 149:3580-7 (1992); Parker et al., J. Immunol. 152:163-75 (1994)). This algorithm allows location and ranking of 8-mer, 9-mer, and 10-mer peptides from a complete protein sequence for predicted binding to HLA-A2 as well as numerous other HLA Class I molecules. Many HLA class I binding peptides are 8-, 9-, 10 or 11-mers. For example, for Class I HLA-A2, the epitopes preferably contain a leucine (L) or methionine (M) at position 2 and a valine (V) or leucine (L) at the C-terminus (see, e.g., Parker et al., J. Immunol. 149: 3580-7 (1992)). Selected results of 24P4C12 predicted binding peptides have been shown. The binding score corresponds to the estimated half time of dissociation of complexes containing the peptide at 37° C. at pH 6.5. Peptides with the highest binding score are predicted to be the most tightly bound to HLA Class I on the cell surface for the greatest period of time and thus represent the best immunogenic targets for T-cell recognition.

Actual binding of peptides to an HLA allele can be evaluated by stabilization of HLA expression on the antigen-processing defective cell line T2 (see, e.g., Xue et al., Prostate 30:73-8 (1997) and Peshwa et al., Prostate 36:129-38 (1998)). Immunogenicity of specific peptides can be evaluated in vitro by stimulation of CD8+ cytotoxic T lymphocytes (CTL) in the presence of antigen presenting cells such as dendritic cells.

It is to be appreciated that every epitope predicted by the BIMAS site, Epimer™ and Epimatrix™ sites, or specified by the HLA class I or class II motifs available in the art or which become part of the art such as set forth in Table IV are to be "applied" to a 24P4C12 protein in accordance with the invention. As used in this context "applied" means that a 24P4C12 protein is evaluated, e.g., visually or by computer-based patterns finding methods, as appreciated by those of skill in the relevant art. Every subsequence of a 24P4C12 protein of 8, 9, 10, or 11 amino acid residues that bears an HLA Class I motif, or a subsequence of 9 or more amino acid residues that bear an HLA Class II motif are within the scope of the invention.

III.B.) Expression of 24P4C12-Related Proteins

In an embodiment described in the examples that follow, 24P4C12 can be conveniently expressed in cells (such as 293T cells) transfected with a commercially available expression vector such as a CMV-driven expression vector encoding 24P4C12 with a C-terminal 6X His and MYC tag (pcDNA3.1/mycHIS, Invitrogen or Tag5, GenHunter Corporation, Nashville Tenn.). The Tag5 vector provides an IgGK secretion signal that can be used to facilitate the production of a secreted 24P4C12 protein in transfected cells. The secreted HIS-tagged 24P4C12 in the culture media can be purified, e.g., using a nickel column using standard techniques.

III.C.) Modifications of 24P4C12-Related Proteins

Modifications of 24P4C12-related proteins such as covalent modifications are included within the scope of this invention. One type of covalent modification includes reacting targeted amino acid residues of a 24P4C12 polypeptide with an organic derivatizing agent that is capable of reacting with selected side chains or the N- or C-terminal residues of a 24P4C12 protein. Another type of covalent modification of a 24P4C12 polypeptide included within the scope of this invention comprises altering the native glycosylation pattern of a protein of the invention. Another type of covalent modification of 24P4C12 comprises linking a 24P4C12 polypeptide to one of a variety of nonproteinaceous polymers, e.g., polyethylene glycol (PEG), polypropylene glycol, or polyoxyalkylenes, in the manner set forth in U.S. Pat. No. 4,640,835; 4,496,689; 4,301,144; 4,670,417; 4,791,192 or 4,179,337.

The 24P4C12-related proteins of the present invention can also be modified to form a chimeric molecule comprising 24P4C12 fused to another, heterologous polypeptide or amino acid sequence. Such a chimeric molecule can be synthesized chemically or recombinantly. A chimeric molecule can have a protein of the invention fused to another tumor-associated antigen or fragment thereof. Alternatively, a protein in accordance with the invention can comprise a fusion of fragments of a 24P4C12 sequence (amino or nucleic acid) such that a molecule is created that is not, through its length, directly homologous to the amino or nucleic acid sequences shown in FIG. 1. Such a chimeric molecule can comprise multiples of the same subsequence of 24P4C12. A chimeric molecule can comprise a fusion of a 24P4C12-related protein with a polyhistidine epitope tag, which provides an epitope to which immobilized nickel can selectively bind, with cytokines or with growth factors. The epitope tag is generally placed at the amino- or carboxyl-terminus of a 24P4C12 protein. In an alternative embodiment, the chimeric molecule can comprise a fusion of a 24P4C12-related protein with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a 24P4C12 polypeptide in place of at least one variable region within an Ig molecule. In a preferred embodiment, the immunoglobulin fusion includes the hinge, CH2 and CH3, or the hinge, CH1, CH2 and CH3 regions of an IgG1 molecule. For the production of immunoglobulin fusions see, e.g., U.S. Pat. No. 5,428,130 issued Jun. 27, 1995.

III.D.) Uses of 24P4C12-Related Proteins

The proteins of the invention have a number of different specific uses. As 24P4C12 is highly expressed in prostate and other cancers, 24P4C12-related proteins are used in methods that assess the status of 24P4C12 gene products in normal versus cancerous tissues, thereby elucidating the malignant phenotype. Typically, polypeptides from specific regions of a 24P4C12 protein are used to assess the presence of perturbations (such as deletions, insertions, point mutations etc.) in those regions (such as regions containing one or more motifs). Exemplary assays utilize antibodies or T cells targeting 24P4C12-related proteins comprising the amino acid residues of one or more of the biological motifs contained within a 24P4C12 polypeptide sequence in order to evaluate the characteristics of this region in normal versus cancerous tissues or to elicit an immune response to the epitope. Alternatively, 24P4C12-related proteins that contain the amino acid residues of one or more of the biological motifs in a 24P4C12 protein are used to screen for factors that interact with that region of 24P4C12.

24P4C12 protein fragments/subsequences are particularly useful in generating and characterizing domain-specific antibodies (e.g., antibodies recognizing an extracellular or intracellular epitope of a 24P4C12 protein), for identifying agents or cellular factors that bind to 24P4C12 or a particular structural domain thereof, and in various therapeutic and diagnostic contexts, including but not limited to diagnostic assays, cancer vaccines and methods of preparing such vaccines.

Proteins encoded by the 24P4C12 genes, or by analogs, homologs or fragments thereof, have a variety of uses, including but not limited to generating antibodies and in methods for identifying ligands and other agents and cellular constituents that bind to a 24P4C12 gene product. Antibodies raised against a 24P4C12 protein or fragment thereof are useful in diagnostic and prognostic assays, and imaging methodologies in the management of human cancers characterized by expression of 24P4C12 protein, such as those listed in Table I. Such antibodies can be expressed intracellularly and used in methods of treating patients with such cancers. 24P4C12-related nucleic acids or proteins are also used in generating HTL or CTL responses.

Various immunological assays useful for the detection of 24P4C12 proteins are used, including but not limited to various types of radioimmunoassays, enzyme-linked immunosorbent assays (ELISA), enzyme-linked immunofluorescent assays (ELIFA), immunocytochemical methods, and the like. Antibodies can be labeled and used as immunological imaging reagents capable of detecting 24P4C12-expressing cells (e.g., in radioscintigraphic imaging methods). 24P4C12 proteins are also particularly useful in generating cancer vaccines, as further described herein.

IV.) 24P4C12 Antibodies

Another aspect of the invention provides antibodies that bind to 24P4C12-related proteins (See FIG. 1). Preferred antibodies specifically bind to a 24P4C12-related protein and do not bind (or bind weakly) to peptides or proteins that are not 24P4C12-related proteins under physiological conditions. In this context, examples of physiological conditions include: 1) phosphate buffered saline; 2) Tris-buffered saline containing 25 mM Tris and 150 mM NaCl; 3) normal saline (0.9% NaCl); 4) animal serum such as human serum; or, 5) a combination of any of 1) through 4); these reactions preferably taking place at pH 7.5, alternatively in a range of pH 7.0 to 8.0, or alternatively in a range of pH 6.5 to 8.5; also, these reactions taking place at a temperature between 4° C. to 37° C. For example, antibodies that bind 24P4C12 can bind 24P4C12-related proteins such as 24P4C12 variants and the homologs or analogs thereof.

24P4C12 antibodies of the invention are particularly useful in cancer (see, e.g., Table I) diagnostic and prognostic assays, and imaging methodologies. Similarly, such antibodies are useful in the treatment, diagnosis, and/or prognosis of colon and other cancers, to the extent 24P4C12 is also expressed or overexpressed in these other cancers. Moreover, intracellularly expressed antibodies (e.g., single chain antibodies) are therapeutically useful in treating cancers in which the expression of 24P4C12 is involved, such as advanced or metastatic colon cancers or other advanced or metastatic cancers.

The invention also provides various immunological assays useful for the detection and quantification of 24P4C12 and variant 24P4C12-related proteins. Such assays can comprise one or more 24P4C12 antibodies capable of recognizing and binding a 24P4C12-related protein, as appropriate. These assays are performed within various immunological assay formats well known in the art, including but not limited to various types of radioimmunoassays, enzyme-linked immunosorbent assays (ELISA), enzyme-linked immunofluorescent assays (ELIFA), and the like.

Immunological non-antibody assays of the invention also comprise T cell immunogenicity assays (inhibitory or stimulatory) as well as major histocompatibility complex (MHC) binding assays.

In addition, immunological imaging methods capable of detecting prostate or colon cancer and other cancers expressing 24P4C12 are also provided by the invention, including but not limited to radioscintigraphic imaging methods using labeled 24P4C12 MAbs. Such assays are clinically useful in the detection, monitoring, and prognosis of 24P4C12 expressing cancers such as colon cancer.

24P4C12 antibodies are also used in methods for purifying a 24P4C12-related protein and for isolating 24P4C12 homologues and related molecules. For example, a method of purifying a 24P4C12-related protein comprises incubating a 24P4C12 antibody, which has been coupled to a solid matrix, with a lysate or other solution containing a 24P4C12-related protein under conditions that permit the 24P4C12 antibody to bind to the 24P4C12-related protein; washing the solid matrix to eliminate impurities; and eluting the 24P4C12-related protein from the coupled antibody. Other uses of 24P4C12 antibodies in accordance with the invention include generating anti-idiotypic antibodies that mimic a 24P4C12 protein.

Various methods for the preparation of antibodies are well known in the art. For example, antibodies can be prepared by immunizing a suitable mammalian host using a 24P4C12-related protein, peptide, or fragment, in isolated or immunoconjugated form (Antibodies: A Laboratory Manual, CSH Press, Eds., Harlow, and Lane (1988); Harlow, Antibodies, Cold Spring Harbor Press, NY (1989)). In addition, fusion proteins of 24P4C12 can also be used, such as a 24P4C12 GST-fusion protein. In a particular embodiment, a GST fusion protein comprising all or most of the amino acid sequence of FIG. 1 is produced, and then used as an immunogen to generate appropriate antibodies. In another embodiment, a 24P4C12-related protein is synthesized and used as an immunogen.

In addition, naked DNA immunization techniques known in the art are used (with or without purified 24P4C12-related protein or 24P4C12 expressing cells) to generate an immune response to the encoded immunogen (for review, see Donnelly et al., 1997, Ann. Rev. Immunol. 15: 617-648).

The amino acid sequence of a 24P4C12 protein as shown in FIG. 1 can be analyzed to select specific regions of the 24P4C12 protein for generating antibodies. For example, hydrophobicity and hydrophilicity analyses of a 24P4C12 amino acid sequence are used to identify hydrophilic regions in the $24P4C_{1-2}$ structure. Regions of a 24P4C12 protein that show immunogenic structure, as well as other regions and domains, can readily be identified using various other methods known in the art, such as Chou-Fasman, Garnier-Robson, Kyte-Doolittle, Eisenberg, Karplus-Schultz or Jameson-Wolf analysis. Hydrophilicity profiles can be generated using the method of Hopp, T. P. and Woods, K. R., 1981, Proc. Natl. Acad. Sci. U.S.A. 78:3824-3828. Hydropathicity profiles can be generated using the method of Kyte, J. and Doolittle, R. F., 1982, J. Mol. Biol. 157:105-132. Percent (%) Accessible Residues profiles can be generated using the method of Janin J., 1979, Nature 277:491-492. Average Flexibility profiles can be generated using the method of Bhaskaran R., Ponnuswamy P. K., 1988, Int. J. Pept. Protein Res. 32:242-255. Beta-turn profiles can be generated using the method of Deleage, G., Roux B., 1987, Protein Engineering 1:289-294.

Thus, each region identified by any of these programs or methods is within the scope of the present invention. Preferred methods for the generation of 24P4C12 antibodies are further illustrated by way of the examples provided herein. Methods for preparing a protein or polypeptide for use as an immunogen are well known in the art. Also well known in the art are methods for preparing immunogenic conjugates of a protein with a carrier, such as BSA, KLH or other carrier protein. In some circumstances, direct conjugation using, for example, carbodiimide reagents are used; in other instances linking reagents such as those supplied by Pierce Chemical Co., Rockford, Ill., are effective. Administration of a 24P4C12 immunogen is often conducted by injection over a suitable time period and with use of a suitable adjuvant, as is understood in the art. During the immunization schedule, titers of antibodies can be taken to determine adequacy of antibody formation.

24P4C12 monoclonal antibodies can be produced by various means well known in the art. For example, immortalized cell lines that secrete a desired monoclonal antibody are prepared using the standard hybridoma technology of Kohler and Milstein or modifications that immortalize antibody-producing B cells, as is generally known. Immortalized cell lines that secrete the desired antibodies are screened by immunoassay in which the antigen is a 24P4C12-related protein. When the appropriate immortalized cell culture is identified, the cells can be expanded and antibodies produced either from in vitro cultures or from ascites fluid.

The antibodies or fragments of the invention can also be produced, by recombinant means. Regions that bind specifically to the desired regions of a 24P4C12 protein can also be produced in the context of chimeric or complementarity-determining region (CDR) grafted antibodies of multiple species origin. Humanized or human 24P4C12 antibodies can also be produced, and are preferred for use in therapeutic contexts. Methods for humanizing murine and other non-human antibodies, by substituting one or more of the non-human antibody CDRs for corresponding human antibody sequences, are well known (see for example, Jones et al., 1986, Nature 321: 522-525; Riechmann et al., 1988, Nature 332: 323-327; Verhoeyen et al., 1988, Science 239: 1534-1536). See also, Carter et al., 1993, Proc. Natl. Acad. Sci. USA 89: 4285 and Sims et al., 1993, J. Immunol. 151: 2296.

In a preferred embodiment, the antibodies of the present invention comprise fully human 24P4C12 antibodies (24P4C12 MAbs). Various methods in the art provide means for producing fully human 24P4C12 MAbs. For example, a preferred embodiment provides for techniques using transgenic mice, inactivated for antibody production, engineered with human heavy and light chains loci referred to as Xenomouse (Amgen Fremont, Inc.). An exemplary description of preparing transgenic mice that produce human antibodies can be found in U.S. Pat. No. 6,657,103. See, also, U.S. Pat. Nos. 5,569,825; 5,625,126; 5,633,425; 5,661,016; and 5,545,806; and Mendez, et. al. Nature Genetics, 15: 146-156 (1998); Kellerman, S. A. & Green, L. L., Curr. Opin. Biotechnol 13, 593-597 (2002).

In addition, human antibodies of the invention can be generated using the HuMAb mouse (Medarex, Inc.) which contains human immunoglobulin gene miniloci that encode unrearranged human heavy (mu and gamma) and kappa light chain immunoglobulin sequences, together with targeted mutations that inactivate the endogenous mu and kappa chain loci (see e.g., Lonberg, et al. (1994) Nature 368(6474): 856-859).

In another embodiment, fully human antibodies of the invention can be raised using a mouse that carries human immunoglobulin sequences on transgenes and transchromosomes, such as a mouse that carries a human heavy chain transgene and a human light chain transchromosome. Such mice, referred to herein as "KM mice", such mice are described in Tomizuka et al. (2000) Proc. Natl. Acad. Sci. USA 97:722-727 and PCT Publication WO 02/43478 to Tomizuka, et al.

Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

In yet another embodiment, an 24P4C12 MAbs of the invention comprises heavy and light chain variable regions comprising amino acid sequences that are homologous to the amino acid sequences of the preferred antibodies described herein (See, FIG. 3), and wherein the antibodies retain the desired functional properties of the 24P4C12 MAbs of the invention.

For example, the invention provides an isolated monoclonal antibody, or antigen binding portion thereof, comprising a heavy chain variable region and a light chain variable region, wherein:

(a) the heavy chain variable region comprises an amino acid sequence that is at least 80% homologous to an amino acid sequence set forth in FIG. 3;

(b) the light chain variable region comprises an amino acid sequence that is at least 80% homologous to an amino acid sequence set forth in FIG. 3;

In other embodiments, the $V_H$ and/or $V_L$ amino acid sequences may be 85%, 86%, 87%, 88%, 89%, 90%, 91%, 92%, 93%, 94%, 95%, 96%, 97%, 98% or 99% homologous to the sequences set forth in FIG. 3.

Engineered antibodies of the invention include those in which modifications have been made to framework residues within $V_H$ and/or $V_L$ (e.g. to improve the properties of the antibody). Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis (e.g., "backmutated" from leucine to methionine). Such "backmutated" antibodies are also intended to be encompassed by the invention.

Another type of framework modification involves mutating one or more residues within the framework region, or even within one or more CDR regions, to remove T-cell epitopes to thereby reduce the potential immunogenicity of the antibody.

This approach is also referred to as "deimmunization" and is described in further detail in U.S. Patent Publication No. 2003/0153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, a 24P4C12 MAb of the invention may be chemically modified (e.g., one or more chemical moieties can be attached to the antibody) or be modified to alter its glycosylation, again to alter one or more functional properties of the MAb. Each of these embodiments is described in further detail below.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the 24P4C12 MAb.

In another embodiment, the Fc hinge region of an antibody is mutated to decrease the biological half life of the 24P4C12 MAb. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the 24P4C12 MAb is modified to increase its biological half life. Various approaches are possible. For example, mutations can be introduced as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector function(s) of the 24P4C12 MAb. For example, one or more amino acids selected from amino acid specific residues can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

Reactivity of 24P4C12 antibodies with a 24P4C12-related protein can be established by a number of well known means, including Western blot, immunoprecipitation, ELISA, and FACS analyses using, as appropriate, 24P4C12-related proteins, 24P4C12-expressing cells or extracts thereof. A 24P4C12 antibody or fragment thereof can be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. Further, bi-specific antibodies specific for two or more 24P4C12 epitopes are generated using methods generally known in the art. Homodimeric antibodies can also be generated by cross-linking techniques known in the art (e.g., Wolff et al., Cancer Res. 53: 2560-2565).

The antibodies designated Ha5-1(5)1, Ha5-1(5)2.1, Ha5-3(1,4)7.1, Ha5-7acd10.1, Ha5-7acd16.1, and Ha5-11b1.1 were sent (via Federal Express) to the American Type Culture Collection (ATCC), P.O. Box 1549, Manassas, Va. 20108 on 8 Aug. 2007 and assigned Accession numbers PTA-8598, PTA-8602, PTA-8597, PTA-8601, PTA-8600, PTA-8599, respectively.

IV.A.) 24P4C12 Cellular Immune Responses

The mechanism by which T cells recognize antigens has been delineated. Efficacious peptide epitope vaccine compositions of the invention induce therapeutic or prophylactic immune responses in very broad segments of the world-wide population. For an understanding of the value and efficacy of compositions of the invention that induce cellular immune responses, a brief review of immunology-related technology is provided.

A complex of an HLA molecule and a peptidic antigen acts as the ligand recognized by HLA-restricted T cells (Buus, S. et al., Cell 47:1071, 1986; Babbitt, B. P. et al., Nature 317: 359, 1985; Townsend, A. and Bodmer, H., Annu. Rev. Immunol. 7:601, 1989; Germain, R. N., Annu. Rev. Immunol. 11:403, 1993). Through the study of single amino acid substituted antigen analogs and the sequencing of endogenously bound, naturally processed peptides, critical residues that correspond to motifs required for specific binding to HLA antigen molecules have been identified and are set forth in Table IV (see also, e.g., Southwood, et al., J. Immunol. 160: 3363, 1998; Rammensee, et al., Immunogenetics 41:178, 1995; Rammensee et al., SYFPEITHI, access via World Wide Web at URL (134.2.96.221/scripts.hlaserver.dll/home.htm); Sette, A. and Sidney, J. Curr. Opin. Immunol. 10:478, 1998; Engelhard, V. H., Curr. Opin. Immunol. 6:13, 1994; Sette, A. and Grey, H. M., Curr. Opin. Immunol. 4:79, 1992; Sinigaglia, F. and Hammer, J. Curr. Biol. 6:52, 1994; Ruppert et al., Cell 74:929-937, 1993; Kondo et al., J. Immunol. 155: 4307-4312, 1995; Sidney et al., J. Immunol. 157:3480-3490, 1996; Sidney et al., Human Immunol. 45:79-93, 1996; Sette, A. and Sidney, J. Immunogenetics 1999 November; 50(3-4): 201-12, Review).

Furthermore, x-ray crystallographic analyses of HLA-peptide complexes have revealed pockets within the peptide binding cleft/groove of HLA molecules which accommodate, in an allele-specific mode, residues borne by peptide ligands; these residues in turn determine the HLA binding capacity of the peptides in which they are present. (See, e.g., Madden, D. R. Annu. Rev. Immunol. 13:587, 1995; Smith, et al., Immunity 4:203, 1996; Fremont et al., Immunity 8:305, 1998; Stern et al., Structure 2:245, 1994; Jones, E. Y. Curr. Opin. Immunol. 9:75, 1997; Brown, J. H. et al., Nature 364:33, 1993; Guo, H. C. et al., Proc. Natl. Acad. Sci. USA 90:8053, 1993; Guo, H. C. et al., Nature 360:364, 1992; Silver, M. L. et al., Nature 360:367, 1992; Matsumura, M. et al., Science 257:927, 1992; Madden et al., Cell 70:1035, 1992; Fremont, D. H. et al., Science 257:919, 1992; Saper, M. A., Bjorkman, P. J. and Wiley, D. C., J. Mol. Biol. 219:277, 1991.)

Accordingly, the definition of class I and class II allele-specific HLA binding motifs, or class I or class II supermotifs allows identification of regions within a protein that are correlated with binding to particular HLA antigen(s).

Thus, by a process of HLA motif identification, candidates for epitope-based vaccines have been identified; such candidates can be further evaluated by HLA-peptide binding assays to determine binding affinity and/or the time period of association of the epitope and its corresponding HLA molecule. Additional confirmatory work can be performed to select, amongst these vaccine candidates, epitopes with preferred characteristics in terms of population coverage, and/or immunogenicity.

Various strategies can be utilized to evaluate cellular immunogenicity, including:

1) Evaluation of primary T cell cultures from normal individuals (see, e.g., Wentworth, P. A. et al., Mol. Immunol. 32:603, 1995; Celis, E. et al., Proc. Natl. Acad. Sci. USA 91:2105, 1994; Tsai, V. et al., J. Immunol. 158:1796, 1997; Kawashima, I. et al., Human Immunol. 59:1, 1998). This procedure involves the stimulation of peripheral blood lymphocytes (PBL) from normal subjects with a test peptide in the presence of antigen presenting cells in vitro over a period of several weeks. T cells specific for the peptide become activated during this time and are detected using, e.g., a lymphokine- or $^{51}$Cr-release assay involving peptide sensitized target cells.

2) Immunization of HLA transgenic mice (see, e.g., Wentworth, P. A. et al., J. Immunol. 26:97, 1996; Wentworth, P. A. et al., Int. Immunol. 8:651, 1996; Alexander, J. et al., J. Immunol. 159:4753, 1997). For example, in such methods peptides in incomplete Freund's adjuvant are administered subcutaneously to HLA transgenic mice. Several weeks following immunization, splenocytes are removed and cultured in vitro in the presence of test peptide for approximately one week. Peptide-specific T cells are detected using, e.g., a $^{51}$Cr-release assay involving peptide sensitized target cells and target cells expressing endogenously generated antigen.

3) Demonstration of recall T cell responses from immune individuals who have been either effectively vaccinated and/or from chronically ill patients (see, e.g., Rehermann, B. et al., J. Exp. Med. 181:1047, 1995; Doolan, D. L. et al., Immunity 7:97, 1997; Bertoni, R. et al., J. Clin. Invest. 100:503, 1997; Threlkeld, S. C. et al., J. Immunol. 159:1648, 1997; Diepolder, H. M. et al., J. Virol. 71:6011, 1997). Accordingly, recall responses are detected by culturing PBL from subjects that have been exposed to the antigen due to disease and thus have generated an immune response "naturally", or from patients who were vaccinated against the antigen. PBL from subjects are cultured in vitro for 1-2 weeks in the presence of test peptide plus antigen presenting cells (APC) to allow activation of "memory" T cells, as compared to "naive" T cells. At the end of the culture period, T cell activity is detected using assays including $^{51}$Cr release involving peptide-sensitized targets, T cell proliferation, or lymphokine release.

V.) 24P4C12 Transgenic Animals

Nucleic acids that encode a 24P4C12-related protein can also be used to generate either transgenic animals or "knock out" animals that, in turn, are useful in the development and screening of therapeutically useful reagents. In accordance with established techniques, cDNA encoding 24P4C12 can be used to clone genomic DNA that encodes 24P4C12. The cloned genomic sequences can then be used to generate transgenic animals containing cells that express DNA that encode 24P4C12. Methods for generating transgenic animals, particularly animals such as mice or rats, have become conventional in the art and are described, for example, in U.S. Pat. No. 4,736,866 issued 12 Apr. 1988, and U.S. Pat. No. 4,870,009 issued 26 Sep. 1989. Typically, particular cells would be targeted for 24P4C12 transgene incorporation with tissue-specific enhancers.

Transgenic animals that include a copy of a transgene encoding 24P4C12 can be used to examine the effect of increased expression of DNA that encodes 24P4C12. Such animals can be used as tester animals for reagents thought to confer protection from, for example, pathological conditions associated with its overexpression. In accordance with this aspect of the invention, an animal is treated with a reagent and a reduced incidence of a pathological condition, compared to untreated animals that bear the transgene, would indicate a potential therapeutic intervention for the pathological condition.

Alternatively, non-human homologues of 24P4C12 can be used to construct a 24P4C12 "knock out" animal that has a defective or altered gene encoding 24P4C12 as a result of homologous recombination between the endogenous gene encoding 24P4C12 and altered genomic DNA encoding 24P4C12 introduced into an embryonic cell of the animal. For example, cDNA that encodes 24P4C12 can be used to clone genomic DNA encoding 24P4C12 in accordance with established techniques. A portion of the genomic DNA encoding 24P4C12 can be deleted or replaced with another gene, such as a gene encoding a selectable marker that can be used to monitor integration. Typically, several kilobases of unaltered flanking DNA (both at the 5' and 3' ends) are included in the vector (see, e.g., Thomas and Capecchi, Cell, 51:503 (1987) for a description of homologous recombination vectors). The vector is introduced into an embryonic stem cell line (e.g., by electroporation) and cells in which the introduced DNA has homologously recombined with the endogenous DNA are selected (see, e.g., Li et al., Cell, 69:915 (1992)). The selected cells are then injected into a blastocyst of an animal (e.g., a mouse or rat) to form aggregation chimeras (see, e.g., Bradley, in Teratocarcinomas and Embryonic Stem Cells: A Practical Approach, E. J. Robertson, ed. (IRL, Oxford, 1987), pp. 113-152). A chimeric embryo can then be implanted into a suitable pseudopregnant female foster animal, and the embryo brought to term to create a "knock out" animal. Progeny harboring the homologously recombined DNA in their germ cells can be identified by standard techniques and used to breed animals in which all cells of the animal contain the homologously recombined DNA. Knock out animals can be characterized, for example, for their ability to defend against certain pathological conditions or for their development of pathological conditions due to absence of a 24P4C12 polypeptide.

VI.) Methods for the Detection of 24P4C12

Another aspect of the present invention relates to methods for detecting 24P4C12 polynucleotides and 24P4C12-related proteins, as well as methods for identifying a cell that expresses 24P4C12. The expression profile of 24P4C12 makes it a diagnostic marker for metastasized disease. Accordingly, the status of 24P4C12 gene products provides information useful for predicting a variety of factors including susceptibility to advanced stage disease, rate of progression, and/or tumor aggressiveness. As discussed in detail herein, the status of 24P4C12 gene products in patient samples can be analyzed by a variety protocols that are well known in the art including immunohistochemical analysis, the variety of Northern blotting techniques including in situ hybridization, RT-PCR analysis (for example on laser capture micro-dissected samples), Western blot analysis and tissue array analysis.

More particularly, the invention provides assays for the detection of 24P4C12 polynucleotides in a biological sample, such as serum, bone, prostate, and other tissues, urine, semen, cell preparations, and the like. Detectable 24P4C12 polynucleotides include, for example, a 24P4C12 gene or fragment thereof, 24P4C12 mRNA, alternative splice variant 24P4C12 mRNAs, and recombinant DNA or RNA molecules that contain a 24P4C12 polynucleotide. A number of methods for amplifying and/or detecting the presence of 24P4C12 polynucleotides are well known in the art and can be employed in the practice of this aspect of the invention.

In one embodiment, a method for detecting a 24P4C12 mRNA in a biological sample comprises producing cDNA from the sample by reverse transcription using at least one primer; amplifying the cDNA so produced using a 24P4C12 polynucleotides as sense and antisense primers to amplify 24P4C12 cDNAs therein; and detecting the presence of the amplified 24P4C12 cDNA. Optionally, the sequence of the amplified 24P4C12 cDNA can be determined.

In another embodiment, a method of detecting a 24P4C12 gene in a biological sample comprises first isolating genomic DNA from the sample; amplifying the isolated genomic DNA using 24P4C12 polynucleotides as sense and antisense primers; and detecting the presence of the amplified 24P4C12 gene. Any number of appropriate sense and antisense probe combinations can be designed from a 24P4C12 nucleotide sequence (see, e.g., FIG. 1) and used for this purpose.

The invention also provides assays for detecting the presence of a 24P4C12 protein in a tissue or other biological sample such as serum, semen, bone, prostate, urine, cell preparations, and the like. Methods for detecting a 24P4C12-related protein are also well known and include, for example, immunoprecipitation, immunohistochemical analysis, Western blot analysis, molecular binding assays, ELISA, ELIFA and the like. For example, a method of detecting the presence of a 24P4C12-related protein in a biological sample comprises first contacting the sample with a 24P4C12 antibody, a 24P4C12-reactive fragment thereof, or a recombinant protein containing an antigen-binding region of a 24P4C12 antibody; and then detecting the binding of 24P4C12-related protein in the sample.

Methods for identifying a cell that expresses 24P4C12 are also within the scope of the invention. In one embodiment, an assay for identifying a cell that expresses a 24P4C12 gene comprises detecting the presence of 24P4C12 mRNA in the cell. Methods for the detection of particular mRNAs in cells are well known and include, for example, hybridization assays using complementary DNA probes (such as in situ hybridization using labeled 24P4C12 riboprobes, Northern blot and related techniques) and various nucleic acid amplification assays (such as RT-PCR using complementary primers specific for 24P4C12, and other amplification type detection methods, such as, for example, branched DNA, SISBA, TMA and the like). Alternatively, an assay for identifying a cell that expresses a 24P4C12 gene comprises detecting the presence of 24P4C12-related protein in the cell or secreted by the cell. Various methods for the detection of proteins are well known in the art and are employed for the detection of 24P4C12-related proteins and cells that express 24P4C12-related proteins.

24P4C12 expression analysis is also useful as a tool for identifying and evaluating agents that modulate 24P4C12 gene expression. For example, 24P4C12 expression is significantly upregulated in ovarian cancer, and is expressed in cancers of the tissues listed in Table I. Identification of a molecule or biological agent that inhibits 24P4C12 expression or over-expression in cancer cells is of therapeutic value. For example, such an agent can be identified by using a screen that quantifies 24P4C12 expression by RT-PCR, nucleic acid hybridization or antibody binding.

VII.) Methods for Monitoring the Status of 24P4C12-Related Genes and Their Products Oncogenesis is known to be a multistep process where cellular growth becomes progressively dysregulated and cells progress from a normal physiological state to precancerous and then cancerous states (see, e.g., Alers et al., Lab Invest. 77(5): 437-438 (1997) and Isaacs et al., Cancer Surv. 23: 19-32 (1995)). In this context, examining a biological sample for evidence of dysregulated cell growth (such as aberrant 24P4C12 expression in cancers) allows for early detection of such aberrant physiology, before a pathologic state such as cancer has progressed to a stage that therapeutic options are more limited and or the prognosis is worse. In such examinations, the status of 24P4C12 in a biological sample of interest can be compared, for example, to the status of 24P4C12 in a corresponding normal sample (e.g. a sample from that individual or alternatively another individual that is not affected by a pathology). An alteration in the status of 24P4C12 in the biological sample (as compared to the normal sample) provides evidence of dysregulated cellular growth. In addition to using a biological sample that is not affected by a pathology as a normal sample, one can also use a predetermined normative value such as a predetermined normal level of mRNA expression (see, e.g., Grever et al., J. Comp. Neurol. 1996 Dec. 9; 376(2): 306-14 and U.S. Pat. No. 5,837,501) to compare 24P4C12 status in a sample.

The term "status" in this context is used according to its art accepted meaning and refers to the condition or state of a gene and its products. Typically, skilled artisans use a number of parameters to evaluate the condition or state of a gene and its products. These include, but are not limited to the location of expressed gene products (including the location of 24P4C12 expressing cells) as well as the level, and biological activity of expressed gene products (such as 24P4C12 mRNA, polynucleotides and polypeptides). Typically, an alteration in the status of 24P4C12 comprises a change in the location of 24P4C12 and/or 24P4C12 expressing cells and/or an increase in 24P4C12 mRNA and/or protein expression.

24P4C12 status in a sample can be analyzed by a number of means well known in the art, including without limitation, immunohistochemical analysis, in situ hybridization, RT-PCR analysis on laser capture micro-dissected samples, Western blot analysis, and tissue array analysis. Typical protocols for evaluating the status of a 24P4C12 gene and gene products are found, for example in Ausubel et al. eds., 1995, Current Protocols In Molecular Biology, Units 2 (Northern Blotting), 4 (Southern Blotting), 15 (Immunoblotting) and 18 (PCR Analysis). Thus, the status of 24P4C12 in a biological sample is evaluated by various methods utilized by skilled artisans including, but not limited to genomic Southern analysis (to examine, for example perturbations in a 24P4C12 gene), Northern analysis and/or PCR analysis of 24P4C12 mRNA (to examine, for example alterations in the polynucleotide sequences or expression levels of 24P4C12 mRNAs), and, Western and/or immunohistochemical analysis (to examine, for example alterations in polypeptide sequences, alterations in polypeptide localization within a sample, alterations in expression levels of 24P4C12 proteins and/or associations of 24P4C12 proteins with polypeptide binding partners). Detectable 24P4C12 polynucleotides include, for example, a 24P4C12 gene or fragment thereof, 24P4C12 mRNA, alternative splice variants, 24P4C12 mRNAs, and recombinant DNA or RNA molecules containing a 24P4C12 polynucleotide.

The expression profile of 24P4C12 makes it a diagnostic marker for local and/or metastasized disease, and provides information on the growth or oncogenic potential of a biological sample. In particular, the status of 24P4C12 provides information useful for predicting susceptibility to particular disease stages, progression, and/or tumor aggressiveness. The invention provides methods and assays for determining 24P4C12 status and diagnosing cancers that express 24P4C12, such as cancers of the tissues listed in Table I. For example, because 24P4C12 mRNA is so highly expressed in kidney and other cancers relative to normal kidney tissue, assays that evaluate the levels of 24P4C12 mRNA transcripts or proteins in a biological sample can be used to diagnose a disease associated with 24P4C12 dysregulation, and can provide prognostic information useful in defining appropriate therapeutic options.

The expression status of 24P4C12 provides information including the presence, stage and location of dysplastic, precancerous and cancerous cells, predicting susceptibility to various stages of disease, and/or for gauging tumor aggressiveness. Moreover, the expression profile makes it useful as an imaging reagent for metastasized disease. Consequently, an aspect of the invention is directed to the various molecular prognostic and diagnostic methods for examining the status of 24P4C12 in biological samples such as those from individuals suffering from, or suspected of suffering from a pathology characterized by dysregulated cellular growth, such as cancer.

As described above, the status of 24P4C12 in a biological sample can be examined by a number of well-known procedures in the art. For example, the status of 24P4C12 in a biological sample taken from a specific location in the body can be examined by evaluating the sample for the presence or absence of 24P4C12 expressing cells (e.g. those that express 24P4C12 mRNAs or proteins). This examination can provide evidence of dysregulated cellular growth, for example, when 24P4C12-expressing cells are found in a biological sample that does not normally contain such cells (such as a lymph node), because such alterations in the status of 24P4C12 in a biological sample are often associated with dysregulated cellular growth. Specifically, one indicator of dysregulated cellular growth is the metastases of cancer cells from an organ of origin (such as the prostate) to a different area of the body (such as a lymph node). In this context, evidence of dysregulated cellular growth is important for example because occult lymph node metastases can be detected in a substantial proportion of patients with prostate cancer, and such metastases are associated with known predictors of disease progression (see, e.g., Murphy et al., Prostate 42(4): 315-317 (2000); Su et al., Semin. Surg. Oncol. 18(1): 17-28 (2000) and Freeman et al., J Urol 1995 August 154(2 Pt 1):474-8).

In one aspect, the invention provides methods for monitoring 24P4C12 gene products by determining the status of 24P4C12 gene products expressed by cells from an individual suspected of having a disease associated with dysregulated cell growth (such as hyperplasia or cancer) and then comparing the status so determined to the status of 24P4C12 gene products in a corresponding normal sample. The presence of aberrant 24P4C12 gene products in the test sample relative to the normal sample provides an indication of the presence of dysregulated cell growth within the cells of the individual.

In another aspect, the invention provides assays useful in determining the presence of cancer in an individual, comprising detecting a significant increase in 24P4C12 mRNA or protein expression in a test cell or tissue sample relative to expression levels in the corresponding normal cell or tissue. The presence of 24P4C12 mRNA can, for example, be evaluated in tissues including but not limited to those listed in Table I. The presence of significant 24P4C12 expression in any of these tissues is useful to indicate the emergence, presence and/or severity of a cancer, since the corresponding normal tissues do not express 24P4C12 mRNA or express it at lower levels.

In a related embodiment, 24P4C12 status is determined at the protein level rather than at the nucleic acid level. For example, such a method comprises determining the level of 24P4C12 protein expressed by cells in a test tissue sample and comparing the level so determined to the level of 24P4C12 expressed in a corresponding normal sample. In one embodiment, the presence of 24P4C12 protein is evaluated, for example, using immunohistochemical methods. 24P4C12 antibodies or binding partners capable of detecting 24P4C12 protein expression are used in a variety of assay formats well known in the art for this purpose.

In a further embodiment, one can evaluate the status of 24P4C12 nucleotide and amino acid sequences in a biological sample in order to identify perturbations in the structure of these molecules. These perturbations can include insertions, deletions, substitutions and the like. Such evaluations are useful because perturbations in the nucleotide and amino acid sequences are observed in a large number of proteins associated with a growth dysregulated phenotype (see, e.g., Marrogi et al., 1999, J. Cutan. Pathol. 26(8):369-378). For example, a mutation in the sequence of 24P4C12 may be indicative of the presence or promotion of a tumor. Such assays therefore have diagnostic and predictive value where a mutation in 24P4C12 indicates a potential loss of function or increase in tumor growth.

A wide variety of assays for observing perturbations in nucleotide and amino acid sequences are well known in the art. For example, the size and structure of nucleic acid or amino acid sequences of 24P4C12 gene products are observed by the Northern, Southern, Western, PCR and DNA sequencing protocols discussed herein. In addition, other methods for observing perturbations in nucleotide and amino acid sequences such as single strand conformation polymorphism analysis are well known in the art (see, e.g., U.S. Pat. No. 5,382,510 issued 7 Sep. 1999, and U.S. Pat. No. 5,952, 170 issued 17 Jan. 1995).

Additionally, one can examine the methylation status of a 24P4C12 gene in a biological sample. Aberrant demethylation and/or hypermethylation of CpG islands in gene 5' regulatory regions frequently occurs in immortalized and transformed cells, and can result in altered expression of various genes. For example, promoter hypermethylation of the pi-class glutathione S-transferase (a protein expressed in normal prostate but not expressed in >90% of prostate carcinomas) appears to permanently silence transcription of this gene and is the most frequently detected genomic alteration in prostate carcinomas (De Marzo et al., Am. J. Pathol. 155(6): 1985-1992 (1999)). In addition, this alteration is present in at least 70% of cases of high-grade prostatic intraepithelial neoplasia (PIN) (Brooks et al., Cancer Epidemiol. Biomarkers Prev., 1998, 7:531-536). In another example, expression of the LAGE-I tumor specific gene (which is not expressed in normal prostate but is expressed in 25-50% of prostate cancers) is induced by deoxy-azacytidine in lymphoblastoid cells, suggesting that tumoral expression is due to demethylation (Lethe et al., Int. J. Cancer 76(6): 903-908 (1998)). A variety of assays for examining methylation status of a gene are well known in the art. For example, one can utilize, in Southern hybridization approaches, methylation-sensitive restriction enzymes that cannot cleave sequences that contain methylated CpG sites to assess the methylation status of CpG islands. In addition, MSP (methylation specific PCR) can rapidly profile the methylation status of all the CpG sites present in a CpG island of a given gene. This procedure involves initial modification of DNA by sodium bisulfite (which will convert all unmethylated cytosines to uracil) followed by amplification using primers specific for methylated versus unmethylated DNA. Protocols involving methylation interference can also be found for example in Current Protocols In Molecular Biology, Unit 12, Frederick M. Ausubel et al. eds., 1995.

Gene amplification is an additional method for assessing the status of 24P4C12. Gene amplification is measured in a sample directly, for example, by conventional Southern blotting or Northern blotting to quantitate the transcription of mRNA (Thomas, 1980, Proc. Natl. Acad. Sci. USA, 77:5201 5205), dot blotting (DNA analysis), or in situ hybridization, using an appropriately labeled probe, based on the sequences provided herein. Alternatively, antibodies are employed that recognize specific duplexes, including DNA duplexes, RNA duplexes, and DNA RNA hybrid duplexes or DNA protein duplexes. The antibodies in turn are labeled and the assay carried out where the duplex is bound to a surface, so that upon the formation of duplex on the surface, the presence of antibody bound to the duplex can be detected.

Biopsied tissue or peripheral blood can be conveniently assayed for the presence of cancer cells using for example, Northern, dot blot or RT-PCR analysis to detect 24P4C12 expression. The presence of RT-PCR amplifiable 24P4C12 mRNA provides an indication of the presence of cancer. RT-PCR assays are well known in the art. RT-PCR detection assays for tumor cells in peripheral blood are currently being evaluated for use in the diagnosis and management of a number of human solid tumors. In the prostate cancer field, these include RT-PCR assays for the detection of cells expressing PSA and PSM (Verkaik et al., 1997, Urol. Res. 25:373-384; Ghossein et al., 1995, J. Clin. Oncol. 13:1195-2000; Heston et al., 1995, Clin. Chem. 41:1687-1688).

A further aspect of the invention is an assessment of the susceptibility that an individual has for developing cancer. In one embodiment, a method for predicting susceptibility to cancer comprises detecting 24P4C12 mRNA or 24P4C12 protein in a tissue sample, its presence indicating susceptibility to cancer, wherein the degree of 24P4C12 mRNA expression correlates to the degree of susceptibility. In a specific embodiment, the presence of 24P4C12 in prostate or other tissue is examined, with the presence of 24P4C12 in the sample providing an indication of prostate cancer susceptibility (or the emergence or existence of a prostate tumor). Similarly, one can evaluate the integrity 24P4C12 nucleotide and amino acid sequences in a biological sample, in order to identify perturbations in the structure of these molecules such as insertions, deletions, substitutions and the like. The presence of one or more perturbations in 24P4C12 gene products in the sample is an indication of cancer susceptibility (or the emergence or existence of a tumor).

The invention also comprises methods for gauging tumor aggressiveness. In one embodiment, a method for gauging aggressiveness of a tumor comprises determining the level of 24P4C12 mRNA or 24P4C12 protein expressed by tumor cells, comparing the level so determined to the level of 24P4C12 mRNA or 24P4C12 protein expressed in a corresponding normal tissue taken from the same individual or a normal tissue reference sample, wherein the degree of 24P4C12 mRNA or 24P4C12 protein expression in the tumor sample relative to the normal sample indicates the degree of aggressiveness. In a specific embodiment, aggressiveness of a tumor is evaluated by determining the extent to which 24P4C12 is expressed in the tumor cells, with higher expression levels indicating more aggressive tumors. Another embodiment is the evaluation of the integrity of 24P4C12 nucleotide and amino acid sequences in a biological sample, in order to identify perturbations in the structure of these molecules such as insertions, deletions, substitutions and the like. The presence of one or more perturbations indicates more aggressive tumors.

Another embodiment of the invention is directed to methods for observing the progression of a malignancy in an individual over time. In one embodiment, methods for observing the progression of a malignancy in an individual over time comprise determining the level of 24P4C12 mRNA or 24P4C12 protein expressed by cells in a sample of the tumor, comparing the level so determined to the level of 24P4C12 mRNA or 24P4C12 protein expressed in an equivalent tissue sample taken from the same individual at a different time, wherein the degree of 24P4C12 mRNA or 24P4C12 protein expression in the tumor sample over time provides information on the progression of the cancer. In a specific embodiment, the progression of a cancer is evaluated by determining 24P4C12 expression in the tumor cells over time, where increased expression over time indicates a progression of the cancer. Also, one can evaluate the integrity 24P4C12 nucleotide and amino acid sequences in a biological sample in order to identify perturbations in the structure of these molecules such as insertions, deletions, substitutions and the like, where the presence of one or more perturbations indicates a progression of the cancer.

The above diagnostic approaches can be combined with any one of a wide variety of prognostic and diagnostic protocols known in the art. For example, another embodiment of the invention is directed to methods for observing a coincidence between the expression of 24P4C12 gene and 24P4C12 gene products (or perturbations in 24P4C12 gene and 24P4C12 gene products) and a factor that is associated with malignancy, as a means for diagnosing and prognosticating the status of a tissue sample. A wide variety of factors associated with malignancy can be utilized, such as the expression of genes associated with malignancy as well as gross cytological observations (see, e.g., Bocking et al., 1984, Anal. Quant. Cytol. 6(2):74-88; Epstein, 1995, Hum. Pathol. 26(2): 223-9; Thorson et al., 1998, Mod. Pathol. 11(6):543-51; Baisden et al., 1999, Am. J. Surg. Pathol. 23(8):918-24). Methods for observing a coincidence between the expression of 24P4C12 gene and 24P4C12 gene products (or perturbations in 24P4C12 gene and 24P4C12 gene products) and another factor that is associated with malignancy are useful, for example, because the presence of a set of specific factors that coincide with disease provides information crucial for diagnosing and prognosticating the status of a tissue sample.

Methods for detecting and quantifying the expression of 24P4C12 mRNA or protein are described herein, and standard nucleic acid and protein detection and quantification technologies are well known in the art. Standard methods for the detection and quantification of 24P4C12 mRNA include in situ hybridization using labeled 24P4C12 riboprobes, Northern blot and related techniques using 24P4C12 polynucleotide probes, RT-PCR analysis using primers specific for 24P4C12, and other amplification type detection methods, such as, for example, branched DNA, SISBA, TMA and the like. In a specific embodiment, semi-quantitative RT-PCR is used to detect and quantify 24P4C12 mRNA expression. Any number of primers capable of amplifying 24P4C12 can be used for this purpose, including but not limited to the various primer sets specifically described herein. In a specific embodiment, polyclonal or monoclonal antibodies specifically reactive with the wild-type 24P4C12 protein can be used in an immunohistochemical assay of biopsied tissue.

VIII.) Identification of Molecules that Interact with 24P4C12

The 24P4C12 protein and nucleic acid sequences disclosed herein allow a skilled artisan to identify proteins, small molecules and other agents that interact with 24P4C12, as well as pathways activated by 24P4C12 via any one of a variety of art accepted protocols. For example, one can utilize one of the so-called interaction trap systems (also referred to as the "two-hybrid assay"). In such systems, molecules interact and reconstitute a transcription factor which directs expression of a reporter gene, whereupon the expression of the reporter gene is assayed. Other systems identify protein-protein interactions in vivo through reconstitution of a eukaryotic transcriptional activator, see, e.g., U.S. Pat. No. 5,955,280 issued 21 Sep. 1999, U.S. Pat. No. 5,925,523 issued 20 Jul. 1999, 5,846,722 issued 8 Dec. 1998 and U.S. Pat. No. 6,004,746 issued 21 Dec. 1999. Algorithms are also available in the art for genome-based predictions of protein function (see, e.g., Marcotte, et al., Nature 402: 4 Nov. 1999, 83-86).

Alternatively one can screen peptide libraries to identify molecules that interact with 24P4C12 protein sequences. In such methods, peptides that bind to 24P4C12 are identified by screening libraries that encode a random or controlled collection of amino acids. Peptides encoded by the libraries are expressed as fusion proteins of bacteriophage coat proteins, the bacteriophage particles are then screened against the 24P4C12 protein(s).

Accordingly, peptides having a wide variety of uses, such as therapeutic, prognostic or diagnostic reagents, are thus identified without any prior information on the structure of the expected ligand or receptor molecule. Typical peptide libraries and screening methods that can be used to identify molecules that interact with 24P4C12 protein sequences are disclosed for example in U.S. Pat. No. 5,723,286 issued 3 Mar. 1998 and U.S. Pat. No. 5,733,731 issued 31 Mar. 1998.

Alternatively, cell lines that express 24P4C12 are used to identify protein-protein interactions mediated by 24P4C12. Such interactions can be examined using immunoprecipitation techniques (see, e.g., Hamilton B. J., et al. Biochem. Biophys. Res. Commun. 1999, 261:646-51). 24P4C12 protein can be immunoprecipitated from 24P4C12-expressing cell lines using anti-24P4C12 antibodies. Alternatively, antibodies against His-tag can be used in a cell line engineered to express fusions of 24P4C12 and a His-tag (vectors mentioned above). The immunoprecipitated complex can be examined for protein association by procedures such as Western blotting, $^{35}$S-methionine labeling of proteins, protein microsequencing, silver staining and two-dimensional gel electrophoresis.

Small molecules and ligands that interact with 24P4C12 can be identified through related embodiments of such screening assays. For example, small molecules can be identified that interfere with protein function, including molecules that interfere with 24P4C12's ability to mediate phosphorylation and de-phosphorylation, interaction with DNA or RNA molecules as an indication of regulation of cell cycles, second messenger signaling or tumorigenesis. Similarly, small molecules that modulate 24P4C12-related ion channel, transporter, protein pump, or cell communication functions are identified and used to treat patients that have a cancer that expresses 24P4C12 (see, e.g., Hille, B., Ionic Channels of Excitable Membranes 2nd Ed., Sinauer Assoc., Sunderland, Mass., 1992). Moreover, ligands that regulate 24P4C12 function can be identified based on their ability to bind 24P4C12 and activate a reporter construct. Typical methods are discussed for example in U.S. Pat. No. 5,928,868 issued 27 Jul. 1999, and include methods for forming hybrid ligands in which at least one ligand is a small molecule. In an illustrative embodiment, cells engineered to express a fusion protein of 24P4C12 and a DNA-binding protein are used to co-express a fusion protein of a hybrid ligand/small molecule and a cDNA library transcriptional activator protein. The cells further contain a reporter gene, the expression of which is conditioned on the proximity of the first and second fusion proteins to each other, an event that occurs only if the hybrid ligand binds to target sites on both hybrid proteins. Those cells that express the reporter gene are selected and the unknown small molecule or the unknown ligand is identified. This method provides a means of identifying modulators, which activate or inhibit 24P4C12.

An embodiment of this invention comprises a method of screening for a molecule that interacts with a 24P4C12 amino acid sequence shown in FIG. 1, comprising the steps of contacting a population of molecules with a 24P4C12 amino acid sequence, allowing the population of molecules and the 24P4C12 amino acid sequence to interact under conditions that facilitate an interaction, determining the presence of a molecule that interacts with the 24P4C12 amino acid sequence, and then separating molecules that do not interact with the 24P4C12 amino acid sequence from molecules that do. In a specific embodiment, the method further comprises purifying, characterizing and identifying a molecule that interacts with the 24P4C12 amino acid sequence. The identified molecule can be used to modulate a function performed by 24P4C12. In a preferred embodiment, the 24P4C12 amino acid sequence is contacted with a library of peptides.

IX.) Therapeutic Methods and Compositions

The identification of 24P4C12 as a protein that is normally expressed in a restricted set of tissues, but which is also expressed in cancers such as those listed in Table I, opens a number of therapeutic approaches to the treatment of such cancers.

Of note, targeted antitumor therapies have been useful even when the targeted protein is expressed on normal tissues, even vital normal organ tissues. A vital organ is one that is necessary to sustain life, such as the heart or colon. A non-vital organ is one that can be removed whereupon the individual is still able to survive. Examples of non-vital organs are ovary, breast, and prostate.

For example, Herceptin® is an FDA approved pharmaceutical that consists of an antibody which is immunoreactive with the protein variously known as HER2, HER2/neu, and erb-b-2. It is marketed by Genentech and has been a commercially successful antitumor agent. Herceptin® sales reached almost $400 million in 2002. Herceptin® is a treatment for HER2 positive metastatic breast cancer. However, the expression of HER2 is not limited to such tumors. The same protein is expressed in a number of normal tissues. In particular, it is known that HER2/neu is present in normal kidney and heart, thus these tissues are present in all human recipients of Herceptin. The presence of HER2/neu in normal kidney is also confirmed by Latif, Z., et al., B.J.U. International (2002) 89:5-9. As shown in this article (which evaluated whether renal cell carcinoma should be a preferred indication for anti-HER2 antibodies such as Herceptin) both protein and mRNA are produced in benign renal tissues. Notably, HER2/neu protein was strongly overexpressed in benign renal tissue.

Despite the fact that HER2/neu is expressed in such vital tissues as heart and kidney, Herceptin is a very useful, FDA approved, and commercially successful drug. The effect of Herceptin on cardiac tissue, i.e., "cardiotoxicity," has merely been a side effect to treatment. When patients were treated with Herceptin alone, significant cardiotoxicity occurred in a very low percentage of patients. To minimize cariotoxicity there is a more stringent entry requirement for the treatment with HER2/neu. Factors such as predisposition to heart condition are evaluated before treatment can occur.

Of particular note, although kidney tissue is indicated to exhibit normal expression, possibly even higher expression than cardiac tissue, kidney has no appreciable Herceptin side effect whatsoever. Moreover, of the diverse array of normal tissues in which HER2 is expressed, there is very little occurrence of any side effect. Only cardiac tissue has manifested any appreciable side effect at all. A tissue such as kidney, where HER2/neu expression is especially notable, has not been the basis for any side effect.

Furthermore, favorable therapeutic effects have been found for antitumor therapies that target epidermal growth factor receptor (EGFR); Erbitux (InClone). EGFR is also expressed in numerous normal tissues. There have been very limited side effects in normal tissues following use of anti-EGFR therapeutics. A general side effect that occurs with the EGFR treatment is a severe skin rash observed in 100% of the patients undergoing treatment.

Thus, expression of a target protein in normal tissue, even vital normal tissue, does not defeat the utility of a targeting agent for the protein as a therapeutic for certain tumors in which the protein is also overexpressed. For example, expression in vital organs is not in and of itself detrimental. In addition, organs regarded as dispensible, such as the prostate and ovary, can be removed without affecting mortality. Finally, some vital organs are not affected by normal organ expression because of an immunoprivilege. Immunoprivileged organs are organs that are protected from blood by a blood-organ barrier and thus are not accessible to immunotherapy. Examples of immunoprivileged organs are the brain and testis.

Accordingly, therapeutic approaches that inhibit the activity of a 24P4C12 protein are useful for patients suffering from a cancer that expresses 24P4C12. These therapeutic approaches generally fall into three classes. The first class modulates 24P4C12 function as it relates to tumor cell growth leading to inhibition or retardation of tumor cell growth or inducing its killing. The second class comprises various methods for inhibiting the binding or association of a 24P4C12 protein with its binding partner or with other proteins. The third class comprises a variety of methods for inhibiting the transcription of a 24P4C12 gene or translation of 24P4C12 mRNA.

IX.A.) Anti-Cancer Vaccines

The invention provides cancer vaccines comprising a 24P4C12-related protein or 24P4C12-related nucleic acid. In view of the expression of 24P4C12, cancer vaccines prevent and/or treat 24P4C12-expressing cancers with minimal or no effects on non-target tissues. The use of a tumor antigen in a vaccine that generates cell-mediated humoral immune responses as anti-cancer therapy is well known in the art and has been employed in prostate cancer using human PSMA and rodent PAP immunogens (Hodge et al., 1995, Int. J. Cancer 63:231-237; Fong et al., 1997, J. Immunol. 159:3113-3117).

Such methods can be readily practiced by employing a 24P4C12-related protein, or a 24P4C12-encoding nucleic acid molecule and recombinant vectors capable of expressing and presenting the 24P4C12 immunogen (which typically comprises a number of T-cell epitopes or antibody). Skilled artisans understand that a wide variety of vaccine systems for delivery of immunoreactive epitopes are known in the art (see, e.g., Heryln et al., Ann Med 1999 February 31(1):66-78; Maruyama et al., Cancer Immunol Immunother 2000 June 49(3):123-32) Briefly, such methods of generating an immune response (e.g. cell-mediated and/or humoral) in a mammal, comprise the steps of: exposing the mammal's immune system to an immunoreactive epitope (e.g. an epitope present in a 24P4C12 protein shown in FIG. 1 or analog or homolog thereof) so that the mammal generates an immune response that is specific for that epitope (e.g. generates antibodies that specifically recognize that epitope).

The entire 24P4C12 protein, immunogenic regions or epitopes thereof can be combined and delivered by various means. Such vaccine compositions can include, for example, lipopeptides (e.g., Vitiello, A. et al., J. Clin. Invest. 95:341, 1995), peptide compositions encapsulated in poly(DL-lactide-co-glycolide) ("PLG") microspheres (see, e.g., Eldridge, et al., Molec. Immunol. 28:287-294, 1991: Alonso et al., Vaccine 12:299-306, 1994; Jones et al., Vaccine 13:675-681, 1995), peptide compositions contained in immune stimulating complexes (ISCOMS) (see, e.g., Takahashi et al., Nature 344:873-875, 1990; Hu et al., Clin Exp Immunol. 113:235-243, 1998), multiple antigen peptide systems (MAPs) (see e.g., Tam, J. P., Proc. Natl. Acad. Sci. U.S.A. 85:5409-5413, 1988; Tam, J. P., J. Immunol. Methods 196:17-32, 1996), peptides formulated as multivalent peptides; peptides for use in ballistic delivery systems, typically crystallized peptides, viral delivery vectors (Perkus, M. E. et al., In: Concepts in vaccine development, Kaufmann, S. H. E., ed., p. 379, 1996; Chakrabarti, S. et al., Nature 320:535, 1986; Hu, S. L. et al., Nature 320:537, 1986; Kieny, M.-P. et al., AIDS Bio/Technology 4:790, 1986; Top, F. H. et al., J. Infect. Dis. 124:148, 1971; Chanda, P. K. et al., Virology 175:535, 1990), particles of viral or synthetic origin (e.g., Kofler, N. et al., J. Immunol. Methods. 192:25, 1996; Eldridge, J. H. et al., Sem. Hematol. 30:16, 1993; Falo, L. D., Jr. et al., Nature Med. 7:649, 1995), adjuvants (Warren, H. S., Vogel, F. R., and Chedid, L. A. Annu. Rev. Immunol. 4:369, 1986; Gupta, R. K. et al., Vaccine 11:293, 1993), liposomes (Reddy, R. et al., J. Immunol. 148:1585, 1992; Rock, K. L., Immunol. Today 17:131, 1996), or, naked or particle absorbed cDNA (Ulmer, J. B. et al., Science 259:1745, 1993; Robinson, H. L., Hunt, L. A., and Webster, R. G., Vaccine 11:957, 1993; Shiver, J. W. et al., In: Concepts in vaccine development, Kaufmann, S. H. E., ed., p. 423, 1996; Cease, K. B., and Berzofsky, J. A., Annu. Rev. Immunol. 12:923, 1994 and Eldridge, J. H. et al., Sem. Hematol. 30:16, 1993). Toxin-targeted delivery technologies, also known as receptor mediated targeting, such as those of Avant Immunotherapeutics, Inc. (Needham, Mass.) may also be used.

In patients with 24P4C12-associated cancer, the vaccine and antibody compositions of the invention can also be used in conjunction with other treatments used for cancer, e.g., surgery, chemotherapy, drug therapies, radiation therapies, etc. including use in combination with immune adjuvants such as IL-2, IL-12, GM-CSF, and the like.

Cellular Vaccines:

CTL epitopes can be determined using specific algorithms to identify peptides within 24P4C12 protein that bind corresponding HLA alleles (e.g., Brown University, BIMAS, and SYFPEITHI. In a preferred embodiment, a 24P4C12 immunogen contains one or more amino acid sequences identified using techniques well known in the art, such as the sequences shown in Tables previously disclosed or a peptide of 8, 9, 10 or 11 amino acids specified by an HLA Class I motif/supermotif (e.g., Table IV (A), Table IV (D), or Table IV (E)) and/or a peptide of at least 9 amino acids that comprises an HLA Class II motif/supermotif (e.g., Table IV (B) or Table IV (C)). As is appreciated in the art, the HLA Class I binding groove is essentially closed ended so that peptides of only a particular size range can fit into the groove and be bound, generally HLA Class I epitopes are 8, 9, 10, or 11 amino acids long. In contrast, the HLA Class II binding groove is essentially open ended; therefore a peptide of about 9 or more amino acids can be bound by an HLA Class II molecule. Due to the binding groove differences between HLA Class I and II, HLA Class I motifs are length specific, i.e., position two of a Class I motif is the second amino acid in an amino to carboxyl direction of the peptide. The amino acid positions in a Class II motif are relative only to each other, not the overall peptide, i.e., additional amino acids can be attached to the amino and/or carboxyl termini of a motif-bearing sequence. HLA Class II epitopes are often 9, 10, 11, 12, 13, 14, 15, 16, 17, 18, 19, 20, 21, 22, 23, 24, or 25 amino acids long, or longer than 25 amino acids.

A wide variety of methods for generating an immune response in a mammal are known in the art (for example as the first step in the generation of hybridomas). Methods of generating an immune response in a mammal comprise exposing the mammal's immune system to an immunogenic epitope on a protein (e.g. a 24P4C12 protein) so that an immune response is generated. A typical embodiment consists of a method for generating an immune response to 24P4C12 in a host, by contacting the host with a sufficient amount of at least one 24P4C12 B cell or cytotoxic T-cell epitope or analog thereof; and at least one periodic interval thereafter re-contacting the host with the 24P4C12 B cell or cytotoxic T-cell epitope or analog thereof. A specific embodiment consists of a method of generating an immune response against a 24P4C12-related protein or a man-made multiepitopic peptide comprising: administering 24P4C12 immunogen (e.g. a 24P4C12 protein or a peptide fragment thereof, a 24P4C12 fusion protein or analog etc.) in a vaccine preparation to a human or another mammal. Typically, such vaccine preparations further contain a suitable adjuvant (see, e.g., U.S. Pat. No. 6,146,635) or a universal helper epitope such as a PADRE™ peptide (Epimmune Inc., San Diego, Calif.; see, e.g., Alexander et al., J. Immunol. 2000 164(3); 164(3): 1625-1633; Alexander et al., Immunity 1994 1(9): 751-761 and Alexander et al., Immunol. Res. 1998 18(2): 79-92). An alternative method comprises generating an immune response in an individual against a 24P4C12 immunogen by: administering in vivo to muscle or skin of the individual's body a DNA molecule that comprises a DNA sequence that encodes a 24P4C12 immunogen, the DNA sequence operatively linked to regulatory sequences which control the expression of the DNA sequence; wherein the DNA molecule is taken up by cells, the DNA sequence is expressed in the cells and an immune response is generated against the immunogen (see, e.g., U.S. Pat. No. 5,962,428). Optionally a genetic vaccine facilitator such as anionic lipids; saponins; lectins; estrogenic compounds; hydroxylated lower alkyls; dimethyl sulfoxide; and urea is also administered. In addition, an antiidiotypic antibody can be administered that mimics 24P4C12, in order to generate a response to the target antigen.

Nucleic Acid Vaccines:

Vaccine compositions of the invention include nucleic acid-mediated modalities. DNA or RNA that encode protein(s) of the invention can be administered to a patient. Genetic immunization methods can be employed to generate prophylactic or therapeutic humoral and cellular immune responses directed against cancer cells expressing 24P4C12. Constructs comprising DNA encoding a 24P4C12-related protein/immunogen and appropriate regulatory sequences can be injected directly into muscle or skin of an individual, such that the cells of the muscle or skin take-up the construct and express the encoded 24P4C12 protein/immunogen. Alternatively, a vaccine comprises a 24P4C12-related protein. Expression of the 24P4C12-related protein immunogen results in the generation of prophylactic or therapeutic humoral and cellular immunity against cells that bear a 24P4C12 protein. Various prophylactic and therapeutic genetic immunization techniques known in the art can be used. Nucleic acid-based delivery is described, for instance, in Wolff et. al., Science 247:1465 (1990) as well as U.S. Pat. Nos. 5,580,859; 5,589,466; 5,804,566; 5,739,118; 5,736,524; 5,679,647; WO 98/04720. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Pat. No. 5,922,687).

For therapeutic or prophylactic immunization purposes, proteins of the invention can be expressed via viral or bacterial vectors. Various viral gene delivery systems that can be used in the practice of the invention include, but are not limited to, vaccinia, fowlpox, canarypox, adenovirus, influenza, poliovirus, adeno-associated virus, lentivirus, and sindbis virus (see, e.g., Restifo, 1996, Curr. Opin. Immunol. 8:658-663; Tsang et al. J. Natl. Cancer Inst. 87:982-990 (1995)). Non-viral delivery systems can also be employed by introducing naked DNA encoding a 24P4C12-related protein into the patient (e.g., intramuscularly or intradermally) to induce an anti-tumor response.

Vaccinia virus is used, for example, as a vector to express nucleotide sequences that encode the peptides of the invention. Upon introduction into a host, the recombinant vaccinia virus expresses the protein immunogenic peptide, and thereby elicits a host immune response. Vaccinia vectors and methods useful in immunization protocols are described in, e.g., U.S. Pat. No. 4,722,848. Another vector is BCG (Bacille Calmette Guerin). BCG vectors are described in Stover et al., Nature 351:456-460 (1991). A wide variety of other vectors useful for therapeutic administration or immunization of the peptides of the invention, e.g. adeno and adeno-associated virus vectors, retroviral vectors, *Salmonella typhi* vectors, detoxified anthrax toxin vectors, and the like, will be apparent to those skilled in the art from the description herein.

Thus, gene delivery systems are used to deliver a 24P4C12-related nucleic acid molecule. In one embodiment, the full-length human 24P4C12 cDNA is employed. In another embodiment, 24P4C12 nucleic acid molecules encoding specific cytotoxic T lymphocyte (CTL) and/or antibody epitopes are employed.

Ex Vivo Vaccines

Various ex vivo strategies can also be employed to generate an immune response. One approach involves the use of antigen presenting cells (APCs) such as dendritic cells (DC) to present 24P4C12 antigen to a patient's immune system. Dendritic cells express MHC class I and II molecules, B7 costimulator, and IL-12, and are thus highly specialized antigen presenting cells. In prostate cancer, autologous dendritic cells pulsed with peptides of the prostate-specific membrane antigen (PSMA) are being used in a Phase I clinical trial to stimulate prostate cancer patients' immune systems (Tjoa et al., 1996, Prostate 28:65-69; Murphy et al., 1996, Prostate 29:371-380). Thus, dendritic cells can be used to present 24P4C12 peptides to T cells in the context of MHC class I or II molecules. In one embodiment, autologous dendritic cells are pulsed with 24P4C12 peptides capable of binding to MHC class I and/or class II molecules. In another embodiment, dendritic cells are pulsed with the complete 24P4C12 protein. Yet another embodiment involves engineering the overexpression of a 24P4C12 gene in dendritic cells using various implementing vectors known in the art, such as adenovirus (Arthur et al., 1997, Cancer Gene Ther. 4:17-25), retrovirus (Henderson et al., 1996, Cancer Res. 56:3763-3770), lentivirus, adeno-associated virus, DNA transfection (Ribas et al., 1997, Cancer Res. 57:2865-2869), or tumor-derived RNA transfection (Ashley et al., 1997, J. Exp. Med. 186: 1177-1182). Cells that express 24P4C12 can also be engineered to express immune modulators, such as GM-CSF, and used as immunizing agents.

IX.B.) 24P4C12 as a Target for Antibody-Based Therapy

24P4C12 is an attractive target for antibody-based therapeutic strategies. A number of antibody strategies are known in the art for targeting both extracellular and intracellular molecules (see, e.g., complement and ADCC mediated killing as well as the use of intrabodies). Because 24P4C12 is expressed by cancer cells of various lineages relative to corresponding normal cells, systemic administration of 24P4C12-immunoreactive compositions are prepared that exhibit excellent sensitivity without toxic, non-specific and/or non-target effects caused by binding of the immunoreactive composition to non-target organs and tissues. Antibodies specifically reactive with domains of 24P4C12 are useful to treat 24P4C12-expressing cancers systemically, either as conjugates with a toxin or therapeutic agent, or as naked antibodies capable of inhibiting cell proliferation or function.

24P4C12 antibodies can be introduced into a patient such that the antibody binds to 24P4C12 and modulates a function, such as an interaction with a binding partner, and consequently mediates destruction of the tumor cells and/or inhibits the growth of the tumor cells. Mechanisms by which such antibodies exert a therapeutic effect can include complement-mediated cytolysis, antibody-dependent cellular cytotoxicity, modulation of the physiological function of 24P4C12, inhibition of ligand binding or signal transduction pathways, modulation of tumor cell differentiation, alteration of tumor angiogenesis factor profiles, and/or apoptosis.

Those skilled in the art understand that antibodies can be used to specifically target and bind immunogenic molecules such as an immunogenic region of a 24P4C12 sequence shown in FIG. 1. In addition, skilled artisans understand that it is routine to conjugate antibodies to cytotoxic agents (see, e.g., Slevers et al. Blood 93:11 3678-3684 (Jun. 1, 1999)). When cytotoxic and/or therapeutic agents are delivered directly to cells, such as by conjugating them to antibodies specific for a molecule expressed by that cell (e.g. 24P4C12), the cytotoxic agent will exert its known biological effect (i.e. cytotoxicity) on those cells.

A wide variety of compositions and methods for using antibody-cytotoxic agent conjugates to kill cells are known in the art. In the context of cancers, typical methods entail administering to an animal having a tumor a biologically effective amount of a conjugate comprising a selected cytotoxic and/or therapeutic agent linked to a targeting agent (e.g. an anti-24P4C12 antibody) that binds to a marker (e.g. 24P4C12) expressed, accessible to binding or localized on the cell surfaces. A typical embodiment is a method of delivering a cytotoxic and/or therapeutic agent to a cell expressing 24P4C12, comprising conjugating the cytotoxic agent to an antibody that immunospecifically binds to a 24P4C12 epitope, and, exposing the cell to the antibody-agent conjugate. Another illustrative embodiment is a method of treating an individual suspected of suffering from metastasized cancer, comprising a step of administering parenterally to said individual a pharmaceutical composition comprising a therapeutically effective amount of an antibody conjugated to a cytotoxic and/or therapeutic agent.

Cancer immunotherapy using anti-24P4C12 antibodies can be done in accordance with various approaches that have been successfully employed in the treatment of other types of cancer, including but not limited to colon cancer (Arlen et al., 1998, Crit. Rev. Immunol. 18:133-138), multiple myeloma (Ozaki et al., 1997, Blood 90:3179-3186, Tsunenari et al., 1997, Blood 90:2437-2444), gastric cancer (Kasprzyk et al., 1992, Cancer Res. 52:2771-2776), B-cell lymphoma (Funakoshi et al., 1996, J. Immunother. Emphasis Tumor Immunol. 19:93-101), leukemia (Zhong et al., 1996, Leuk. Res. 20:581-589), colorectal cancer (Moun et al., 1994, Cancer Res. 54:6160-6166; Velders et al., 1995, Cancer Res. 55:4398-4403), and breast cancer (Shepard et al., 1991, J. Clin. Immunol. 11:117-127). Some therapeutic approaches involve conjugation of naked antibody to a toxin or radioisotope, such as the conjugation of $Y^{91}$ or $I^{131}$ to anti-CD20 antibodies (e.g., Zevalin™, IDEC Pharmaceuticals Corp. or Bexxar™, Coulter Pharmaceuticals) respectively, while others involve co-administration of antibodies and other therapeutic agents, such as Herceptin™ (trastuzu MAb) with paclitaxel (Genentech, Inc.). The antibodies can be conjugated to a therapeutic agent. To treat prostate cancer, for example, 24P4C12 antibodies can be administered in conjunction with radiation, chemotherapy or hormone ablation. Also, antibodies can be conjugated to a toxin such as calicheamicin (e.g., Mylotarg™, Wyeth-Ayerst, Madison, N.J., a recombinant humanized IgG$_4$ kappa antibody conjugated to antitumor antibiotic calicheamicin) or a maytansinoid (e.g., taxane-based Tumor-Activated Prodrug, TAP, platform, ImmunoGen, Cambridge, Mass., also see e.g., U.S. Pat. No. 5,416,064) or Auristatin E (Nat. Biotechnol. 2003 July; 21(7):778-84. (Seattle Genetics)).

Although 24P4C12 antibody therapy is useful for all stages of cancer, antibody therapy can be particularly appropriate in advanced or metastatic cancers. Treatment with the antibody therapy of the invention is indicated for patients who have received one or more rounds of chemotherapy. Alternatively, antibody therapy of the invention is combined with a chemotherapeutic or radiation regimen for patients who have not received chemotherapeutic treatment. Additionally, antibody therapy can enable the use of reduced dosages of concomitant chemotherapy, particularly for patients who do not tolerate the toxicity of the chemotherapeutic agent very well. Fan et al. (Cancer Res. 53:4637-4642, 1993), Prewett et al. (International J. of Onco. 9:217-224, 1996), and Hancock et al. (Cancer Res. 51:4575-4580, 1991) describe the use of various antibodies together with chemotherapeutic agents.

Although 24P4C12 antibody therapy is useful for all stages of cancer, antibody therapy can be particularly appropriate in advanced or metastatic cancers. Treatment with the antibody therapy of the invention is indicated for patients who have received one or more rounds of chemotherapy. Alternatively, antibody therapy of the invention is combined with a chemotherapeutic or radiation regimen for patients who have not received chemotherapeutic treatment. Additionally, antibody therapy can enable the use of reduced dosages of concomitant chemotherapy, particularly for patients who do not tolerate the toxicity of the chemotherapeutic agent very well.

Cancer patients can be evaluated for the presence and level of 24P4C12 expression, preferably using immunohistochemical assessments of tumor tissue, quantitative 24P4C12 imaging, or other techniques that reliably indicate the presence and degree of 24P4C12 expression. Immunohistochemical analysis of tumor biopsies or surgical specimens is preferred for this purpose. Methods for immunohistochemical analysis of tumor tissues are well known in the art.

Anti-24P4C12 monoclonal antibodies that treat prostate and other cancers include those that initiate a potent immune response against the tumor or those that are directly cytotoxic. In this regard, anti-24P4C12 monoclonal antibodies (MAbs) can elicit tumor cell lysis by either complement-mediated or antibody-dependent cell cytotoxicity (ADCC) mechanisms, both of which require an intact Fc portion of the immunoglobulin molecule for interaction with effector cell Fc receptor sites on complement proteins. In addition, anti-24P4C12 MAbs that exert a direct biological effect on tumor growth are useful to treat cancers that express 24P4C12. Mechanisms by which directly cytotoxic MAbs act include: inhibition of cell growth, modulation of cellular differentiation, modulation of tumor angiogenesis factor profiles, and the induction of apoptosis. The mechanism(s) by which a particular anti-24P4C12 MAb exerts an anti-tumor effect is evaluated using any number of in vitro assays that evaluate cell death such as ADCC, ADMMC, complement-mediated cell lysis, and so forth, as is generally known in the art.

In some patients, the use of murine or other non-human monoclonal antibodies, or human/mouse chimeric MAbs can induce moderate to strong immune responses against the non-human antibody. This can result in clearance of the antibody from circulation and reduced efficacy. In the most severe cases, such an immune response can lead to the extensive formation of immune complexes which, potentially, can cause renal failure. Accordingly, preferred monoclonal antibodies used in the therapeutic methods of the invention are those that are either fully human or humanized and that bind specifically to the target 24P4C12 antigen with high affinity but exhibit low or no antigenicity in the patient.

Therapeutic methods of the invention contemplate the administration of single anti-24P4C12 MAbs as well as combinations, or cocktails, of different MAbs (i.e. 24P4C12 MAbs or Mabs that bind another protein). Such MAb cocktails can have certain advantages inasmuch as they contain MAbs that target different epitopes, exploit different effector mechanisms or combine directly cytotoxic MAbs with MAbs that rely on immune effector functionality. Such MAbs in combination can exhibit synergistic therapeutic effects. In addition, 24P4C12 MAbs can be administered concomitantly with other therapeutic modalities, including but not limited to various chemotherapeutic and biologic agents, androgen-blockers, immune modulators (e.g., IL-2, GM-CSF), surgery or radiation. The 24P4C12 MAbs are administered in their "naked" or unconjugated form, or can have a therapeutic agent(s) conjugated to them.

24P4C12 Mab formulations are administered via any route capable of delivering the antibodies to a tumor cell. Routes of administration include, but are not limited to, intravenous, intraperitoneal, intramuscular, intratumor, intradermal, and the like. Treatment generally involves repeated administration of the 24P4C12 MAb preparation, via an acceptable route of administration such as intravenous injection (IV), typically at a dose in the range, including but not limited to, 0.1, 0.2, 0.3, 0.4, 0.5, 0.6, 0.7, 0.8, 0.9, 1, 2, 3, 4, 5, 6, 7, 8, 9, 10, 15, 20, or 25 mg/kg body weight. In general, doses in the range of 10-1000 mg MAb per week are effective and well tolerated.

Based on clinical experience with the Herceptin® (Trastuzumab) in the treatment of metastatic breast cancer, an initial loading dose of approximately 4 mg/kg patient body weight IV, followed by weekly doses of about 2 mg/kg IV of the MAb preparation represents an acceptable dosing regimen. Preferably, the initial loading dose is administered as a 90-minute or longer infusion. The periodic maintenance dose is administered as a 30 minute or longer infusion, provided the initial dose was well tolerated. As appreciated by those of skill in the art, various factors can influence the ideal dose regimen in a particular case. Such factors include, for example, the binding affinity and half life of the MAbs used, the degree of 24P4C12 expression in the patient, the extent of circulating shed 24P4C12 antigen, the desired steady-state antibody concentration level, frequency of treatment, and the influence of chemotherapeutic or other agents used in combination with the treatment method of the invention, as well as the health status of a particular patient.

Optionally, patients should be evaluated for the levels of 24P4C12 in a given sample (e.g. the levels of circulating 24P4C12 antigen and/or 24P4C12 expressing cells) in order to assist in the determination of the most effective dosing regimen, etc. Such evaluations are also used for monitoring purposes throughout therapy, and are useful to gauge therapeutic success in combination with the evaluation of other parameters (for example, urine cytology and/or ImmunoCyt levels in bladder cancer therapy, or by analogy, serum PSA levels in prostate cancer therapy).

Anti-idiotypic anti-24P4C12 antibodies can also be used in anti-cancer therapy as a vaccine for inducing an immune response to cells expressing a 24P4C12-related protein. In particular, the generation of anti-idiotypic antibodies is well known in the art; this methodology can readily be adapted to generate anti-idiotypic anti-24P4C12 antibodies that mimic an epitope on a 24P4C12-related protein (see, for example, Wagner et al., 1997, Hybridoma 16: 33-40; Foon et al., 1995, J. Clin. Invest. 96:334-342; Herlyn et al., 1996, Cancer Immunol. Immunother. 43:65-76). Such an anti-idiotypic antibody can be used in cancer vaccine strategies.

An object of the present invention is to provide 24P4C12 Mabs, which inhibit or retard the growth of tumor cells expressing 24P4C12. A further object of this invention is to provide methods to inhibit angiogenesis and other biological functions and thereby reduce tumor growth in mammals, preferably humans, using such 24P4C12 MAbs, and in particular using such 24P4C12 MAbs combined with other drugs or immunologically active treatments, including but not limited to: Avastin® (bevacizumab), Sutent® (sunitinib malate), Nexavar® (Sorafinib tosylate), Taxotere® (docetaxel), Interleukin-2 (a.k.a. Proleukin®, IL-2, or Aldesleukin), Interferon Alpha (Interferon-Alpha-2a, or Interferon-Alpha-2b), Paraplatin® (carboplatin) or Gemzar® (gemcitibine) and others in the art known to treat different cancers.

In one embodiment, there is synergy when tumors, including human tumors, are treated with 24P4C12 antibodies in conjunction with chemotherapeutic agents or radiation or combinations thereof. In other words, the inhibition of tumor growth by a 24P4C12 antibody is enhanced more than expected when combined with chemotherapeutic agents or radiation or combinations thereof. Synergy may be shown, for example, by greater inhibition of tumor growth with combined treatment than would be expected from a treatment of only 24P4C12 antibodies or the additive effect of treatment with a 24P4C12 antibody and a chemotherapeutic agent or radiation. Preferably, synergy is demonstrated by remission of the cancer where remission is not expected from treatment either from a naked 24P4C12 antibody or with treatment using an additive combination of a 24P4C12 antibody and a chemotherapeutic agent or radiation.

The method for inhibiting growth of tumor cells using a 24P4C12 antibody and a combination of chemotherapy or radiation or both comprises administering the 24P4C12 antibody before, during, or after commencing chemotherapy or radiation therapy, as well as any combination thereof (i.e. before and during, before and after, during and after, or before, during, and after commencing the chemotherapy and/or radiation therapy). For example, the 24P4C12 antibody is typically administered between 1 and 60 days, preferably between 3 and 40 days, more preferably between 5 and 12 days before commencing radiation therapy and/or chemotherapy. However, depending on the treatment protocol and the specific patient needs, the method is performed in a manner that will provide the most efficacious treatment and ultimately prolong the life of the patient.

The administration of chemotherapeutic agents can be accomplished in a variety of ways including systemically by the parenteral and enteral routes. In one embodiment, the 24P4C12 antibody and the chemotherapeutic agent are administered as separate molecules. In another embodiment, the 24P4C12 antibody is attached, for example, by conjugation, to a chemotherapeutic agent. (See the Example entitled "Human Clinical Trials for the Treatment and Diagnosis of Human Carcinomas through use of 24P4C12 Mabs"). Particular examples of chemotherapeutic agents or chemotherapy include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin, paclitaxel (taxol), docetaxel (taxotere), aldesleukin, asparaginase, busulfan, carboplatin, cladribine, dacarbazine, floxuridine, fludarabine, hydroxyurea, ifosfamide, interferon alpha, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil, taxol and combinations thereof.

The source of radiation, used in combination with a 24P4C12 Mab, can be either external or internal to the patient being treated. When the source is external to the patient, the therapy is known as external beam radiation therapy (EBRT). When the source of radiation is internal to the patient, the treatment is called brachytherapy (BT).

The above described therapeutic regimens may be further combined with additional cancer treating agents and/or regimes, for example additional chemotherapy, cancer vaccines, signal transduction inhibitors, agents useful in treating abnormal cell growth or cancer, antibodies (e.g. Anti-CTLA-4 antibodies as described in WO/2005/092380 (Pfizer)) or other ligands that inhibit tumor growth by binding to IGF-1R, and cytokines.

When the mammal is subjected to additional chemotherapy, chemotherapeutic agents described above may be used. Additionally, growth factor inhibitors, biological response modifiers, anti-hormonal therapy, selective estrogen receptor modulators (SERMs), angiogenesis inhibitors, and anti-androgens may be used. For example, anti-hormones, for example anti-estrogens such as Nolvadex (tamoxifen) or, anti-androgens such as Casodex (4'-cyano-3-(4-fluorophenylsulphonyl)-2-hydroxy-2-methyl-3-'-(trifluoromethyl)propionanilide) may be used.

In certain embodiments of the invention, the above described methods are combined with a cancer vaccine. Useful vaccines may be, without limitation, those comprised of cancer-associated antigens (e.g. BAGE, carcinoembryonic antigen (CEA), EBV, GAGE, gp100 (including gp100:209-217 and gp100:280-288, among others), HBV, HER-2/neu, HPV, HCV, MAGE, mammaglobin, MART-1/Melan-A, Mucin-1, NY-ESO-1, proteinase-3, PSA, RAGE, TRP-1, TRP-2, Tyrosinase (e.g., Tyrosinase: 368-376), WT-1), GM-CSF DNA and cell-based vaccines, dendritic cell vaccines, recombinant viral (e.g. vaccinia virus) vaccines, and heat shock protein (HSP) vaccines. Useful vaccines also include tumor vaccines, such as those formed of melanoma cells, and can be autologous or allogeneic. The vaccines may be, e.g., peptide, DNA or cell-based. These various agents can be combined such that a combination comprising, inter alia, gp100 peptides, Tyrosinase and MART-1 can be administered with the antibody.

Vaccines may be administered prior to, or subsequent to, stem cell transplantation, and when chemotherapy is part of the regimen, a vaccine may be administered prior to chemotherapy. In certain embodiments, the antibody of the invention may also be administered prior to chemotherapy. Vaccine may also be administered after stem cell transplantation and in certain embodiments concomitantly with the antibody.

The above described treatments may also be used with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors, such as VEGF receptors and molecules that can inhibit VEGF; and erbB2 receptor inhibitors, such as organic molecules or antibodies that bind to the erbB2 receptor.

EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein. EGFR-inhibiting agents include, but are not limited to, the monoclonal antibodies ERBITUX (ImClone Systems Incorporated of New York, N.Y.), and VECTIBIX (AMGEN Fremont Inc. of Fremont, Calif.), the compounds ZD-1839 (AstraZeneca), BIBX-1382 (Boehringer Ingelheim), MDX-447 (Medarex Inc. of Annandale, N.J.), and OLX-103 (Merck & Co. of Whitehouse Station, N.J.), VRCTC-310 (Ventech Research) and EGF fusion toxin (Seragen Inc. of Hopkinton, Mass.). These and other EGFR-inhibiting agents can be used in the present invention.

VEGF inhibitors, for example SU-5416 and SU-6668 (Sugen Inc. of South San Francisco, Calif.), can also be employed in combination with the antibody. VEGF inhibitors are described for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998). Other examples of some specific VEGF inhibitors useful in the present invention are IM862 (Cytran Inc. of Kirkland, Wash.); IMC-IC11 Imclone antibody and angiozyme, a synthetic ribozyme from Ribozyme (Boulder, Colo.) and Chiron (Emeryville, Calif.).

ErbB2 receptor inhibitors, such as GW-282974 (Glaxo Wellcome), and the monoclonal antibodies AR-209 (Aronex Pharmaceuticals Inc. of The Woodlands, Tex.) and 2B-1 (Chiron), can furthermore be combined with the antibody, for example those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999). ErbB2 receptor inhibitors useful in the present invention are also described in EP1029853 (published Aug. 23, 2000) and in WO 00/44728, (published Aug. 3, 2000). The erbB2 receptor inhibitor compounds and substance described in the aforementioned PCT applications, U.S. patents, and U.S. provisional applications, as well as other compounds and substances that inhibit the erbB2 receptor, can be used with the antibody in accordance with the present invention.

The present treatment regimens may also be combined with antibodies or other ligands that inhibit tumor growth by binding to IGF-1R (insulin-like growth factor 1 receptor). Specific anti-IGF-1R antibodies that can be used in the present invention include those described in PCT application PCT/US01/51113, filed Dec. 20, 2001 and published as WO02/053596.

The treatment regimens described herein may be combined with anti-angiogenesis agents, such as MMP-2 (matrix-metalloproteinase 2) inhibitors, MMP-9 (matrix-metalloproteinase 9) inhibitors, and COX-II (cyclooxygenase II) inhibitors, can be used in conjunction with the antibody in the method of the invention. Examples of useful COX-II inhibitors include CELEBREX (celecoxib), valdecoxib, and rofecoxib.

IX.C.) 24P4C12 as a Target for Cellular Immune Responses

Vaccines and methods of preparing vaccines that contain an immunogenically effective amount of one or more HLA-binding peptides as described herein are further embodiments of the invention. Furthermore, vaccines in accordance with the invention encompass compositions of one or more of the claimed peptides. A peptide can be present in a vaccine individually. Alternatively, the peptide can exist as a homopolymer comprising multiple copies of the same peptide, or as a heteropolymer of various peptides. Polymers have the advantage of increased immunological reaction and, where different peptide epitopes are used to make up the polymer, the additional ability to induce antibodies and/or CTLs that react with different antigenic determinants of the pathogenic organism or tumor-related peptide targeted for an immune response. The composition can be a naturally occurring region of an antigen or can be prepared, e.g., recombinantly or by chemical synthesis.

Carriers that can be used with vaccines of the invention are well known in the art, and include, e.g., thyroglobulin, albumins such as human serum albumin, tetanus toxoid, polyamino acids such as poly L-lysine, poly L-glutamic acid, influenza, hepatitis B virus core protein, and the like. The vaccines can contain a physiologically tolerable (i.e., acceptable) diluent such as water, or saline, preferably phosphate buffered saline. The vaccines also typically include an adjuvant. Adjuvants such as incomplete Freund's adjuvant, aluminum phosphate, aluminum hydroxide, or alum are examples of materials well known in the art. Additionally, as disclosed herein, CTL responses can be primed by conjugating peptides of the invention to lipids, such as tripalmitoyl-5-glycerylcysteinlyseryl-serine ($P_3CSS$). Moreover, an adjuvant such as synthetic cytosine-phosphorothiolated-guanine-containing (CpG) oligonucleotides has been found to increase CTL responses 10- to 100-fold (see, e.g. Davila and Celis, J. Immunol. 165:539-547 (2000)).

Upon immunization with a peptide composition in accordance with the invention, via injection, aerosol, oral, transdermal, transmucosal, intrapleural, intrathecal, or other suitable routes, the immune system of the host responds to the vaccine by producing large amounts of CTLs and/or helper T-lymphocytes (HTLs) specific for the desired antigen. Consequently, the host becomes at least partially immune to later development of cells that express or overexpress 24P4C12 antigen, or derives at least some therapeutic benefit when the antigen was tumor-associated.

In some embodiments, it may be desirable to combine the class I peptide components with components that induce or facilitate neutralizing antibody and or helper T cell responses directed to the target antigen. A preferred embodiment of such a composition comprises class I and class II epitopes in accordance with the invention. An alternative embodiment of such a composition comprises a class I and/or class II epitope in accordance with the invention, along with a cross reactive HTL epitope such as PADRE™ (Epimmune, San Diego, Calif.) molecule (described e.g., in U.S. Pat. No. 5,736,142).

A vaccine of the invention can also include antigen-presenting cells (APC), such as dendritic cells (DC), as a vehicle to present peptides of the invention. Vaccine compositions can be created in vitro, following dendritic cell mobilization and harvesting, whereby loading of dendritic cells occurs in vitro. For example, dendritic cells are transfected, e.g., with a minigene in accordance with the invention, or are pulsed with peptides. The dendritic cell can then be administered to a patient to elicit immune responses in vivo. Vaccine compositions, either DNA- or peptide-based, can also be administered in vivo in combination with dendritic cell mobilization whereby loading of dendritic cells occurs in vivo.

Preferably, the following principles are utilized when selecting an array of epitopes for inclusion in a polyepitopic composition for use in a vaccine, or for selecting discrete epitopes to be included in a vaccine and/or to be encoded by nucleic acids such as a minigene. It is preferred that each of the following principles be balanced in order to make the selection. The multiple epitopes to be incorporated in a given vaccine composition may be, but need not be, contiguous in sequence in the native antigen from which the epitopes are derived.

1.) Epitopes are selected which, upon administration, mimic immune responses that have been observed to be correlated with tumor clearance. For HLA Class I this includes 3-4 epitopes that come from at least one tumor associated antigen (TAA). For HLA Class II a similar rationale is employed; again 3-4 epitopes are selected from at least one TAA (see, e.g., Rosenberg et al., Science 278:1447-1450). Epitopes from one TAA may be used in combination with epitopes from one or more additional TAAs to produce a vaccine that targets tumors with varying expression patterns of frequently-expressed TAAs.

2.) Epitopes are selected that have the requisite binding affinity established to be correlated with immunogenicity: for HLA Class I an $IC_{50}$ of 500 nM or less, often 200 nM or less; and for Class II an $IC_{50}$ of 1000 nM or less.

3.) Sufficient supermotif bearing-peptides, or a sufficient array of allele-specific motif-bearing peptides, are selected to give broad population coverage. For example, it is preferable to have at least 80% population coverage. A Monte Carlo analysis, a statistical evaluation known in the art, can be employed to assess the breadth, or redundancy of, population coverage.

4.) When selecting epitopes from cancer-related antigens it is often useful to select analogs because the patient may have developed tolerance to the native epitope.

5.) Of particular relevance are epitopes referred to as "nested epitopes." Nested epitopes occur where at least two epitopes overlap in a given peptide sequence. A nested peptide sequence can comprise B cell, HLA class I and/or HLA class II epitopes. When providing nested epitopes, a general objective is to provide the greatest number of epitopes per sequence. Thus, an aspect is to avoid providing a peptide that is any longer than the amino terminus of the amino terminal epitope and the carboxyl terminus of the carboxyl terminal epitope in the peptide. When providing a multi-epitopic sequence, such as a sequence comprising nested epitopes, it is generally important to screen the sequence in order to insure that it does not have pathological or other deleterious biological properties.

6.) If a polyepitopic protein is created, or when creating a minigene, an objective is to generate the smallest peptide that encompasses the epitopes of interest. This principle is similar, if not the same as that employed when selecting a peptide comprising nested epitopes. However, with an artificial polyepitopic peptide, the size minimization objective is balanced against the need to integrate any spacer sequences between epitopes in the polyepitopic protein. Spacer amino acid residues can, for example, be introduced to avoid junctional epitopes (an epitope recognized by the immune system, not present in the target antigen, and only created by the manmade juxtaposition of epitopes), or to facilitate cleavage between epitopes and thereby enhance epitope presentation. Junctional epitopes are generally to be avoided because the recipient may generate an immune response to that nonnative epitope. Of particular concern is a junctional epitope that is a "dominant epitope." A dominant epitope may lead to such a zealous response that immune responses to other epitopes are diminished or suppressed.

7.) Where the sequences of multiple variants of the same target protein are present, potential peptide epitopes can also be selected on the basis of their conservancy. For example, a criterion for conservancy may define that the entire sequence of an HLA class I binding peptide or the entire 9-mer core of a class II binding peptide be conserved in a designated percentage of the sequences evaluated for a specific protein antigen.

IX.C.1. Minigene Vaccines

A number of different approaches are available which allow simultaneous delivery of multiple epitopes. Nucleic acids encoding the peptides of the invention are a particularly useful embodiment of the invention. Epitopes for inclusion in a minigene are preferably selected according to the guidelines set forth in the previous section. A preferred means of administering nucleic acids encoding the peptides of the invention uses minigene constructs encoding a peptide comprising one or multiple epitopes of the invention.

The use of multi-epitope minigenes is described below and in, Ishioka et al., J. Immunol. 162:3915-3925, 1999; An, L. and Whitton, J. L., J. Virol. 71:2292, 1997; Thomson, S. A. et al., J. Immunol. 157:822, 1996; Whitton, J. L. et al., J. Virol. 67:348, 1993; Hanke, R. et al., Vaccine 16:426, 1998. For example, a multi-epitope DNA plasmid encoding supermotif- and/or motif-bearing epitopes derived 24P4C12, the PADRE™ universal helper T cell epitope or multiple HTL epitopes from 24P4C12, and an endoplasmic reticulum-translocating signal sequence can be engineered. A vaccine may also comprise epitopes that are derived from other TAAs.

The immunogenicity of a multi-epitopic minigene can be confirmed in transgenic mice to evaluate the magnitude of CTL induction responses against the epitopes tested. Further, the immunogenicity of DNA-encoded epitopes in vivo can be correlated with the in vitro responses of specific CTL lines against target cells transfected with the DNA plasmid. Thus, these experiments can show that the minigene serves to both: 1.) generate a CTL response and 2.) that the induced CTLs recognized cells expressing the encoded epitopes.

For example, to create a DNA sequence encoding the selected epitopes (minigene) for expression in human cells, the amino acid sequences of the epitopes may be reverse translated. A human codon usage table can be used to guide the codon choice for each amino acid. These epitope-encoding DNA sequences may be directly adjoined, so that when translated, a continuous polypeptide sequence is created. To optimize expression and/or immunogenicity, additional elements can be incorporated into the minigene design. Examples of amino acid sequences that can be reverse translated and included in the minigene sequence include: HLA class I epitopes, HLA class II epitopes, antibody epitopes, a ubiquitination signal sequence, and/or an endoplasmic reticulum targeting signal. In addition, HLA presentation of CTL and HTL epitopes may be improved by including synthetic (e.g. poly-alanine) or naturally-occurring flanking sequences adjacent to the CTL or HTL epitopes; these larger peptides comprising the epitope(s) are within the scope of the invention.

The minigene sequence may be converted to DNA by assembling oligonucleotides that encode the plus and minus strands of the minigene. Overlapping oligonucleotides (30-100 bases long) may be synthesized, phosphorylated, purified and annealed under appropriate conditions using well known techniques. The ends of the oligonucleotides can be joined, for example, using T4 DNA ligase. This synthetic minigene, encoding the epitope polypeptide, can then be cloned into a desired expression vector.

Standard regulatory sequences well known to those of skill in the art are preferably included in the vector to ensure expression in the target cells. Several vector elements are desirable: a promoter with a down-stream cloning site for minigene insertion; a polyadenylation signal for efficient transcription termination; an E. coli origin of replication; and an E. coli selectable marker (e.g., ampicillin or kanamycin resistance). Numerous promoters can be used for this purpose, e.g., the human cytomegalovirus (hCMV) promoter. See, e.g., U.S. Pat. Nos. 5,580,859 and 5,589,466 for other suitable promoter sequences.

Additional vector modifications may be desired to optimize minigene expression and immunogenicity. In some cases, introns are required for efficient gene expression, and one or more synthetic or naturally-occurring introns could be incorporated into the transcribed region of the minigene. The inclusion of mRNA stabilization sequences and sequences for replication in mammalian cells may also be considered for increasing minigene expression.

Once an expression vector is selected, the minigene is cloned into the polylinker region downstream of the promoter. This plasmid is transformed into an appropriate E. coli strain, and DNA is prepared using standard techniques. The orientation and DNA sequence of the minigene, as well as all other elements included in the vector, are confirmed using restriction mapping and DNA sequence analysis. Bacterial cells harboring the correct plasmid can be stored as a master cell bank and a working cell bank.

In addition, immunostimulatory sequences (ISSs or CpGs) appear to play a role in the immunogenicity of DNA vaccines. These sequences may be included in the vector, outside the minigene coding sequence, if desired to enhance immunogenicity.

In some embodiments, a bi-cistronic expression vector which allows production of both the minigene-encoded epitopes and a second protein (included to enhance or decrease immunogenicity) can be used. Examples of proteins or polypeptides that could beneficially enhance the immune response if co-expressed include cytokines (e.g., IL-2, IL-12, GM-CSF), cytokine-inducing molecules (e.g., LeIF), costimulatory molecules, or for HTL responses, pan-DR binding proteins (PADRE™, Epimmune, San Diego, Calif.). Helper (HTL) epitopes can be joined to intracellular targeting signals and expressed separately from expressed CTL epitopes; this allows direction of the HTL epitopes to a cell compartment different than that of the CTL epitopes. If required, this could facilitate more efficient entry of HTL epitopes into the HLA class II pathway, thereby improving HTL induction. In contrast to HTL or CTL induction, specifically decreasing the immune response by co-expression of immunosuppressive molecules (e.g. TGF-β) may be beneficial in certain diseases.

Therapeutic quantities of plasmid DNA can be produced for example, by fermentation in *E. coli*, followed by purification. Aliquots from the working cell bank are used to inoculate growth medium, and grown to saturation in shaker flasks or a bioreactor according to well-known techniques. Plasmid DNA can be purified using standard bioseparation technologies such as solid phase anion-exchange resins supplied by QIAGEN, Inc. (Valencia, Calif.). If required, supercoiled DNA can be isolated from the open circular and linear forms using gel electrophoresis or other methods.

Purified plasmid DNA can be prepared for injection using a variety of formulations. The simplest of these is reconstitution of lyophilized DNA in sterile phosphate-buffer saline (PBS). This approach, known as "naked DNA," is currently being used for intramuscular (IM) administration in clinical trials. To maximize the immunotherapeutic effects of minigene DNA vaccines, an alternative method for formulating purified plasmid DNA may be desirable. A variety of methods have been described, and new techniques may become available. Cationic lipids, glycolipids, and fusogenic liposomes can also be used in the formulation (see, e.g., as described by WO 93/24640; Mannino & Gould-Fogerite, BioTechniques 6(7): 682 (1988); U.S. Pat. No. 5,279,833; WO 91/06309; and Felgner, et al., Proc. Nat'l Acad. Sci. USA 84:7413 (1987). In addition, peptides and compounds referred to collectively as protective, interactive, non-condensing compounds (PINC) could also be complexed to purified plasmid DNA to influence variables such as stability, intramuscular dispersion, or trafficking to specific organs or cell types.

Target cell sensitization can be used as a functional assay for expression and HLA class I presentation of minigene-encoded CTL epitopes. For example, the plasmid DNA is introduced into a mammalian cell line that is suitable as a target for standard CTL chromium release assays. The transfection method used will be dependent on the final formulation. Electroporation can be used for "naked" DNA, whereas cationic lipids allow direct in vitro transfection. A plasmid expressing green fluorescent protein (GFP) can be co-transfected to allow enrichment of transfected cells using fluorescence activated cell sorting (FACS). These cells are then chromium-51 ($^{51}$Cr) labeled and used as target cells for epitope-specific CTL lines; cytolysis, detected by $^{51}$Cr release, indicates both production of, and HLA presentation of, minigene-encoded CTL epitopes. Expression of HTL epitopes may be evaluated in an analogous manner using assays to assess HTL activity.

In vivo immunogenicity is a second approach for functional testing of minigene DNA formulations. Transgenic mice expressing appropriate human HLA proteins are immunized with the DNA product. The dose and route of administration are formulation dependent (e.g., IM for DNA in PBS, intraperitoneal (i.p.) for lipid-complexed DNA). Twenty-one days after immunization, splenocytes are harvested and restimulated for one week in the presence of peptides encoding each epitope being tested. Thereafter, for CTL effector cells, assays are conducted for cytolysis of peptide-loaded, $^{51}$Cr-labeled target cells using standard techniques. Lysis of target cells that were sensitized by HLA loaded with peptide epitopes, corresponding to minigene-encoded epitopes, demonstrates DNA vaccine function for in vivo induction of CTLs. Immunogenicity of HTL epitopes is confirmed in transgenic mice in an analogous manner.

Alternatively, the nucleic acids can be administered using ballistic delivery as described, for instance, in U.S. Pat. No. 5,204,253. Using this technique, particles comprised solely of DNA are administered. In a further alternative embodiment, DNA can be adhered to particles, such as gold particles.

Minigenes can also be delivered using other bacterial or viral delivery systems well known in the art, e.g., an expression construct encoding epitopes of the invention can be incorporated into a viral vector such as vaccinia.

IX.C.2. Combinations of CTL Peptides with Helper Peptides

Vaccine compositions comprising CTL peptides of the invention can be modified, e.g., analoged, to provide desired attributes, such as improved serum half life, broadened population coverage or enhanced immunogenicity.

For instance, the ability of a peptide to induce CTL activity can be enhanced by linking the peptide to a sequence which contains at least one epitope that is capable of inducing a T helper cell response. Although a CTL peptide can be directly linked to a T helper peptide, often CTL epitope/HTL epitope conjugates are linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus may be a hetero- or homo-oligomer. When present, the spacer will usually be at least one or two residues, more usually three to six residues and sometimes 10 or more residues. The CTL peptide epitope can be linked to the T helper peptide epitope either directly or via a spacer either at the amino or carboxy terminus of the CTL peptide. The amino terminus of either the immunogenic peptide or the T helper peptide may be acylated.

HTL peptide epitopes can also be modified to alter their biological properties. For example, they can be modified to include D-amino acids to increase their resistance to proteases and thus extend their serum half life, or they can be conjugated to other molecules such as lipids, proteins, carbohydrates, and the like to increase their biological activity. For example, a T helper peptide can be conjugated to one or more palmitic acid chains at either the amino or carboxyl termini.

IX.C.3. Combinations of CTL Peptides with T Cell Priming Agents

In some embodiments it may be desirable to include in the pharmaceutical compositions of the invention at least one component which primes B lymphocytes or T lymphocytes. Lipids have been identified as agents capable of priming CTL in vivo. For example, palmitic acid residues can be attached to the ε- and α-amino groups of a lysine residue and then linked, e.g., via one or more linking residues such as Gly, Gly-Gly-, Ser, Ser-Ser, or the like, to an immunogenic peptide. The lipidated peptide can then be administered either directly in a micelle or particle, incorporated into a liposome, or emulsified in an adjuvant, e.g., incomplete Freund's adjuvant. In a preferred embodiment, a particularly effective immunogenic composition comprises palmitic acid attached to ε- and α-amino groups of Lys, which is attached via linkage, e.g., Ser-Ser, to the amino terminus of the immunogenic peptide.

As another example of lipid priming of CTL responses, *E. coli* lipoproteins, such as tripalmitoyl-5-glycerylcysteinlyseryl-serine ($P_3CSS$) can be used to prime virus specific CTL when covalently attached to an appropriate peptide (see, e.g., Deres, et al., Nature 342:561, 1989). Peptides of the invention can be coupled to P3CSS, for example, and the lipopeptide administered to an individual to prime specifically an immune response to the target antigen. Moreover, because the induction of neutralizing antibodies can also be primed with P3CSS-conjugated epitopes, two such compositions can be combined to more effectively elicit both humoral and cell-mediated responses.

IX.C.4. Vaccine Compositions Comprising DC Pulsed with CTL and/or HTL Peptides

An embodiment of a vaccine composition in accordance with the invention comprises ex vivo administration of a cocktail of epitope-bearing peptides to PBMC, or isolated DC therefrom, from the patient's blood. A pharmaceutical to facilitate harvesting of DC can be used, such as Progenipoietin™ (Pharmacia-Monsanto, St. Louis, Mo.) or GM-CSF/IL-4. After pulsing the DC with peptides and prior to reinfusion into patients, the DC are washed to remove unbound peptides. In this embodiment, a vaccine comprises peptide-pulsed DCs which present the pulsed peptide epitopes complexed with HLA molecules on their surfaces.

The DC can be pulsed ex vivo with a cocktail of peptides, some of which stimulate CTL responses to 24P4C12. Optionally, a helper T cell (HTL) peptide, such as a natural or artificial loosely restricted HLA Class II peptide, can be included to facilitate the CTL response. Thus, a vaccine in accordance with the invention is used to treat a cancer which expresses or overexpresses 24P4C12.

IX.D.) Adoptive Immunotherapy

Antigenic 24P4C12-related peptides are used to elicit a CTL and/or HTL response ex vivo, as well. The resulting CTL or HTL cells, can be used to treat tumors in patients that do not respond to other conventional forms of therapy, or will not respond to a therapeutic vaccine peptide or nucleic acid in accordance with the invention. Ex vivo CTL or HTL responses to a particular antigen are induced by incubating in tissue culture the patient's, or genetically compatible, CTL or HTL precursor cells together with a source of antigen-presenting cells (APC), such as dendritic cells, and the appropriate immunogenic peptide. After an appropriate incubation time (typically about 7-28 days), in which the precursor cells are activated and expanded into effector cells, the cells are infused back into the patient, where they will destroy (CTL) or facilitate destruction (HTL) of their specific target cell (e.g., a tumor cell). Transfected dendritic cells may also be used as antigen presenting cells.

IX.E.) Administration of Vaccines for Therapeutic or Prophylactic Purposes

Pharmaceutical and vaccine compositions of the invention are typically used to treat and/or prevent a cancer that expresses or overexpresses 24P4C12. In therapeutic applications, peptide and/or nucleic acid compositions are administered to a patient in an amount sufficient to elicit an effective B cell, CTL and/or HTL response to the antigen and to cure or at least partially arrest or slow symptoms and/or complications. An amount adequate to accomplish this is defined as "therapeutically effective dose." Amounts effective for this use will depend on, e.g., the particular composition administered, the manner of administration, the stage and severity of the disease being treated, the weight and general state of health of the patient, and the judgment of the prescribing physician.

For pharmaceutical compositions, the immunogenic peptides of the invention, or DNA encoding them, are generally administered to an individual already bearing a tumor that expresses 24P4C12. The peptides or DNA encoding them can be administered individually or as fusions of one or more peptide sequences. Patients can be treated with the immunogenic peptides separately or in conjunction with other treatments, such as surgery, as appropriate.

For therapeutic use, administration should generally begin at the first diagnosis of 24P4C12-associated cancer. This is followed by boosting doses until at least symptoms are substantially abated and for a period thereafter. The embodiment of the vaccine composition (i.e., including, but not limited to embodiments such as peptide cocktails, polyepitopic polypeptides, minigenes, or TAA-specific CTLs or pulsed dendritic cells) delivered to the patient may vary according to the stage of the disease or the patient's health status. For example, in a patient with a tumor that expresses 24P4C12, a vaccine comprising 24P4C12-specific CTL may be more efficacious in killing tumor cells in patient with advanced disease than alternative embodiments.

It is generally important to provide an amount of the peptide epitope delivered by a mode of administration sufficient to stimulate effectively a cytotoxic T cell response; compositions which stimulate helper T cell responses can also be given in accordance with this embodiment of the invention.

The dosage for an initial therapeutic immunization generally occurs in a unit dosage range where the lower value is about 1, 5, 50, 500, or 1,000 µg and the higher value is about 10,000; 20,000; 30,000; or 50,000 µg. Dosage values for a human typically range from about 500 µg to about 50,000 µg per 70 kilogram patient. Boosting dosages of between about 1.0 µg to about 50,000 µg of peptide pursuant to a boosting regimen over weeks to months may be administered depending upon the patient's response and condition as determined by measuring the specific activity of CTL and HTL obtained from the patient's blood. Administration should continue until at least clinical symptoms or laboratory tests indicate that the neoplasia, has been eliminated or reduced and for a period thereafter. The dosages, routes of administration, and dose schedules are adjusted in accordance with methodologies known in the art.

In certain embodiments, the peptides and compositions of the present invention are employed in serious disease states, that is, life-threatening or potentially life threatening situations. In such cases, as a result of the minimal amounts of extraneous substances and the relative nontoxic nature of the peptides in preferred compositions of the invention, it is possible and may be felt desirable by the treating physician to administer substantial excesses of these peptide compositions relative to these stated dosage amounts.

The vaccine compositions of the invention can also be used purely as prophylactic agents. Generally the dosage for an initial prophylactic immunization generally occurs in a unit dosage range where the lower value is about 1, 5, 50, 500, or 1000 µg and the higher value is about 10,000; 20,000; 30,000; or 50,000 µg. Dosage values for a human typically range from about 500 µg to about 50,000 µg per 70 kilogram patient. This is followed by boosting dosages of between about 1.0 µg to about 50,000 µg of peptide administered at defined intervals from about four weeks to six months after the initial administration of vaccine. The immunogenicity of the vaccine can be assessed by measuring the specific activity of CTL and HTL obtained from a sample of the patient's blood.

The pharmaceutical compositions for therapeutic treatment are intended for parenteral, topical, oral, nasal, intrathecal, or local (e.g. as a cream or topical ointment) administration. Preferably, the pharmaceutical compositions are administered parentally, e.g., intravenously, subcutaneously, intradermally, or intramuscularly. Thus, the invention provides compositions for parenteral administration which comprise a solution of the immunogenic peptides dissolved or suspended in an acceptable carrier, preferably an aqueous carrier.

A variety of aqueous carriers may be used, e.g., water, buffered water, 0.8% saline, 0.3% glycine, hyaluronic acid and the like. These compositions may be sterilized by conventional, well-known sterilization techniques, or may be sterile filtered. The resulting aqueous solutions may be packaged for use as is, or lyophilized, the lyophilized preparation being combined with a sterile solution prior to administration.

The compositions may contain pharmaceutically acceptable auxiliary substances as required to approximate physiological conditions, such as pH-adjusting and buffering agents, tonicity adjusting agents, wetting agents, preservatives, and the like, for example, sodium acetate, sodium lactate, sodium chloride, potassium chloride, calcium chloride, sorbitan monolaurate, triethanolamine oleate, etc.

The concentration of peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

A human unit dose form of a composition is typically included in a pharmaceutical composition that comprises a human unit dose of an acceptable carrier, in one embodiment an aqueous carrier, and is administered in a volume/quantity that is known by those of skill in the art to be used for administration of such compositions to humans (see, e.g., Remington's Pharmaceutical Sciences, 17th Edition, A. Gennaro, Editor, Mack Publishing Co., Easton, Pa., 1985). For example a peptide dose for initial immunization can be from about 1 to about 50,000 µg, generally 100-5,000 µg, for a 70 kg patient. For example, for nucleic acids an initial immunization may be performed using an expression vector in the form of naked nucleic acid administered IM (or SC or ID) in the amounts of 0.5-5 mg at multiple sites. The nucleic acid (0.1 to 1000 µg) can also be administered using a gene gun. Following an incubation period of 3-4 weeks, a booster dose is then administered. The booster can be recombinant fowlpox virus administered at a dose of $5-10^7$ to $5 \times 10^9$ pfu.

For antibodies, a treatment generally involves repeated administration of the anti-24P4C12 antibody preparation, via an acceptable route of administration such as intravenous injection (IV), typically at a dose in the range of about 0.1 to about 10 mg/kg body weight. In general, doses in the range of 10-500 mg MAb per week are effective and well tolerated. Moreover, an initial loading dose of approximately 4 mg/kg patient body weight IV, followed by weekly doses of about 2 mg/kg IV of the anti-24P4C12 MAb preparation represents an acceptable dosing regimen. As appreciated by those of skill in the art, various factors can influence the ideal dose in a particular case. Such factors include, for example, half life of a composition, the binding affinity of an Ab, the immunogenicity of a substance, the degree of 24P4C12 expression in the patient, the extent of circulating shed 24P4C12 antigen, the desired steady-state concentration level, frequency of treatment, and the influence of chemotherapeutic or other agents used in combination with the treatment method of the invention, as well as the health status of a particular patient. Non-limiting preferred human unit doses are, for example, 500 µg-1 mg, 1 mg-50 mg, 50 mg-100 mg, 100 mg-200 mg, 200 mg-300 mg, 400 mg-500 mg, 500 mg-600 mg, 600 mg-700 mg, 700 mg-800 mg, 800 mg-900 mg, 900 mg-1 g, or 1 mg-700 mg. In certain embodiments, the dose is in a range of 2-5 mg/kg body weight, e.g., with follow on weekly doses of 1-3 mg/kg; 0.5 mg, 1, 2, 3, 4, 5, 6, 7, 8, 9, 10 mg/kg body weight followed, e.g., in two, three or four weeks by weekly doses; 0.5-10 mg/kg body weight, e.g., followed in two, three or four weeks by weekly doses; 225, 250, 275, 300, 325, 350, 375, 400 mg m$^2$ of body area weekly; 1-600 mg m$^2$ of body area weekly; 225-400 mg m$^2$ of body area weekly; these does can be followed by weekly doses for 2, 3, 4, 5, 6, 7, 8, 9, 19, 11, 12 or more weeks.

In one embodiment, human unit dose forms of polynucleotides comprise a suitable dosage range or effective amount that provides any therapeutic effect. As appreciated by one of ordinary skill in the art a therapeutic effect depends on a number of factors, including the sequence of the polynucleotide, molecular weight of the polynucleotide and route of administration. Dosages are generally selected by the physician or other health care professional in accordance with a variety of parameters known in the art, such as severity of symptoms, history of the patient and the like. Generally, for a polynucleotide of about 20 bases, a dosage range may be selected from, for example, an independently selected lower limit such as about 0.1, 0.25, 0.5, 1, 2, 5, 10, 20, 30, 40, 50, 60, 70, 80, 90, 100, 200, 300, 400 or 500 mg/kg up to an independently selected upper limit, greater than the lower limit, of about 60, 80, 100, 200, 300, 400, 500, 750, 1000, 1500, 2000, 3000, 4000, 5000, 6000, 7000, 8000, 9000 or 10,000 mg/kg. For example, a dose may be about any of the following: 0.1 to 100 mg/kg, 0.1 to 50 mg/kg, 0.1 to 25 mg/kg, 0.1 to 10 mg/kg, 1 to 500 mg/kg, 100 to 400 mg/kg, 200 to 300 mg/kg, 1 to 100 mg/kg, 100 to 200 mg/kg, 300 to 400 mg/kg, 400 to 500 mg/kg, 500 to 1000 mg/kg, 500 to 5000 mg/kg, or 500 to 10,000 mg/kg. Generally, parenteral routes of administration may require higher doses of polynucleotide compared to more direct application to the nucleotide to diseased tissue, as do polynucleotides of increasing length.

In one embodiment, human unit dose forms of T-cells comprise a suitable dosage range or effective amount that provides any therapeutic effect. As appreciated by one of ordinary skill in the art, a therapeutic effect depends on a number of factors. Dosages are generally selected by the physician or other health care professional in accordance with a variety of parameters known in the art, such as severity of symptoms, history of the patient and the like. A dose may be about $10^4$ cells to about $10^6$ cells, about $10^6$ cells to about $10^8$ cells, about $10^8$ to about $10^{11}$ cells, or about $10^8$ to about $5 \times 10^{10}$ cells. A dose may also about $10^6$ cells/m$^2$ to about $10^{10}$ cells/m$^2$, or about $10^6$ cells/m to about $10^8$ cells/m$^2$.

Proteins(s) of the invention, and/or nucleic acids encoding the protein(s), can also be administered via liposomes, which may also serve to: 1) target the proteins(s) to a particular tissue, such as lymphoid tissue; 2) to target selectively to diseases cells; or, 3) to increase the half-life of the peptide composition. Liposomes include emulsions, foams, micelles, insoluble monolayers, liquid crystals, phospholipid dispersions, lamellar layers and the like. In these preparations, the peptide to be delivered is incorporated as part of a liposome, alone or in conjunction with a molecule which binds to a receptor prevalent among lymphoid cells (such as monoclonal antibodies which bind to the CD45 antigen) or with other therapeutic or immunogenic compositions. Thus, liposomes either filled or decorated with a desired peptide of the invention can be directed to the site of lymphoid cells, where the liposomes then deliver the peptide compositions. Liposomes for use in accordance with the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka, et al., Ann. Rev. Biophys. Bioeng. 9:467 (1980), and U.S. Pat. Nos. 4,235,871, 4,501,728, 4,837,028, and 5,019,369.

For targeting cells of the immune system, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more peptides of the invention, and more preferably at a concentration of 25%-75%.

For aerosol administration, immunogenic peptides are preferably supplied in finely divided form along with a surfactant and propellant. Typical percentages of peptides are about 0.01%-20% by weight, preferably about 1%-10%. The surfactant must, of course, be nontoxic, and preferably soluble in the propellant. Representative of such agents are the esters or partial esters of fatty acids containing from about 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute about 0.1%-20% by weight of the composition, preferably about 0.25-5%. The balance of the composition is ordinarily propellant. A carrier can also be included, as desired, as with, e.g., lecithin for intranasal delivery.

X.) Diagnostic and Prognostic Embodiments of 24P4C12.

As disclosed herein, 24P4C12 polynucleotides, polypeptides, reactive cytotoxic T cells (CTL), reactive helper T cells (HTL) and anti-polypeptide antibodies are used in well known diagnostic, prognostic and therapeutic assays that examine conditions associated with dysregulated cell growth such as cancer, in particular the cancers listed in Table I (see, e.g., both its specific pattern of tissue expression as well as its overexpression in certain cancers as described for example in the Example entitled "Expression analysis of 24P4C12 in normal tissues, and patient specimens").

24P4C12 can be analogized to a prostate associated antigen PSA, the archetypal marker that has been used by medical practitioners for years to identify and monitor the presence of prostate cancer (see, e.g., Merrill et al., J. Urol. 163(2): 503-5120 (2000); Polascik et al., J. Urol. August; 162(2):293-306 (1999) and Fortier et al., J. Nat. Cancer Inst. 91(19): 1635-1640 (1999)). A variety of other diagnostic markers are also used in similar contexts including p53 and K-ras (see, e.g., Tulchinsky et al., Int J Mol Med 1999 July 4(1):99-102 and Minimoto et al., Cancer Detect Prev 2000; 24(1):1-12). Therefore, this disclosure of 24P4C12 polynucleotides and polypeptides (as well as 24P4C12 polynucleotide probes and anti-24P4C12 antibodies used to identify the presence of these molecules) and their properties allows skilled artisans to utilize these molecules in methods that are analogous to those used, for example, in a variety of diagnostic assays directed to examining conditions associated with cancer.

Typical embodiments of diagnostic methods which utilize the 24P4C12 polynucleotides, polypeptides, reactive T cells and antibodies are analogous to those methods from well-established diagnostic assays, which employ, (e.g., PSA polynucleotides, polypeptides, reactive T cells and antibodies.) For example, just as PSA polynucleotides are used as probes (for example in Northern analysis, see, e.g., Sharief et al., Biochem. Mol. Biol. Int. 33(3):567-74 (1994)) and primers (for example in PCR analysis, see, e.g., Okegawa et al., J. Urol. 163(4): 1189-1190 (2000)) to observe the presence and/or the level of PSA mRNAs in methods of monitoring PSA overexpression or the metastasis of prostate cancers, the 24P4C12 polynucleotides described herein can be utilized in the same way to detect 24P4C12 overexpression or the metastasis of prostate and other cancers expressing this gene. Alternatively, just as PSA polypeptides are used to generate antibodies specific for PSA which can then be used to observe the presence and/or the level of PSA proteins in methods to monitor PSA protein overexpression (see, e.g., Stephan et al., Urology 55(4):560-3 (2000)) or the metastasis of prostate cells (see, e.g., Alanen et al., Pathol. Res. Pract. 192(3):233-7 (1996)), the 24P4C12 polypeptides described herein can be utilized to generate antibodies for use in detecting 24P4C12 overexpression or the metastasis of prostate cells and cells of other cancers expressing this gene.

Specifically, because metastases involves the movement of cancer cells from an organ of origin (such as the lung or prostate gland etc.) to a different area of the body (such as a lymph node or bone), assays which examine a biological sample for the presence of cells expressing 24P4C12 polynucleotides and/or polypeptides can be used to provide evidence of metastasis. For example, when a biological sample from tissue that does not normally contain 24P4C12-expressing cells is found to contain 24P4C12-expressing cells this finding is indicative of metastasis.

Alternatively 24P4C12 polynucleotides and/or polypeptides can be used to provide evidence of cancer, for example, when cells in a biological sample that do not normally express 24P4C12 or express 24P4C12 at a different level are found to express 24P4C12 or have an increased expression of 24P4C12 (see, e.g., the 24P4C12 expression in the cancers listed in Table I and in patient samples etc. shown in the accompanying Figures). In such assays, artisans may further wish to generate supplementary evidence of metastasis by testing the biological sample for the presence of a second tissue restricted marker (in addition to 24P4C12).

The use of immunohistochemistry to identify the presence of a 24P4C12 polypeptide within a tissue section can indicate an altered state of certain cells within that tissue. It is well understood in the art that the ability of an antibody to localize to a polypeptide that is expressed in cancer cells is a way of diagnosing presence of disease, disease stage, progression and/or tumor aggressiveness. Such an antibody can also detect an altered distribution of the polypeptide within the cancer cells, as compared to corresponding non-malignant tissue.

The 24P4C12 polypeptide and immunogenic compositions are also useful in view of the phenomena of altered subcellular protein localization in disease states. Alteration of cells from normal to diseased state causes changes in cellular morphology and is often associated with changes in subcellular protein localization/distribution. For example, cell membrane proteins that are expressed in a polarized manner in normal cells can be altered in disease, resulting in distribution of the protein in a non-polar manner over the whole cell surface.

The phenomenon of altered subcellular protein localization in a disease state has been demonstrated with MUC1 and Her2 protein expression by use of immunohistochemical means. Normal epithelial cells have a typical apical distribution of MUC1, in addition to some supranuclear localization of the glycoprotein, whereas malignant lesions often demonstrate an apolar staining pattern (Diaz et al, The Breast Journal, 7; 40-45 (2001); Zhang et al, Clinical Cancer Research, 4; 2669-2676 (1998): Cao, et al, The Journal of Histochemistry and Cytochemistry, 45: 1547-1557 (1997)). In addition, normal breast epithelium is either negative for Her2 protein or exhibits only a basolateral distribution whereas malignant cells can express the protein over the whole cell surface (De Potter, et al, International Journal of Cancer, 44; 969-974 (1989): McCormick, et al, 117; 935-943 (2002)). Alternatively, distribution of the protein may be altered from a surface only localization to include diffuse cytoplasmic expression in the diseased state. Such an example can be seen with MUC1 (Diaz, et al, The Breast Journal, 7: 40-45 (2001)).

Alteration in the localization/distribution of a protein in the cell, as detected by immunohistochemical methods, can also provide valuable information concerning the favorability of certain treatment modalities. This last point is illustrated by a situation where a protein may be intracellular in normal tissue, but cell surface in malignant cells; the cell surface location makes the cells favorably amenable to antibody-based diagnostic and treatment regimens. When such an alteration of protein localization occurs for 24P4C12, the 24P4C12 protein and immune responses related thereto are very useful. Use of the 24P4C12 compositions allows those skilled in the art to make important diagnostic and therapeutic decisions.

Immunohistochemical reagents specific to 24P4C12 are also useful to detect metastases of tumors expressing 24P4C12 when the polypeptide appears in tissues where 24P4C12 is not normally produced.

Thus, 24P4C12 polypeptides and antibodies resulting from immune responses thereto are useful in a variety of important contexts such as diagnostic, prognostic, preventative and/or therapeutic purposes known to those skilled in the art.

Additionally, 24P4C12-related proteins or polynucleotides of the invention can be used to treat a pathologic condition characterized by the over-expression of 24P4C12. For example, the amino acid or nucleic acid sequence of FIG. 1, or fragments of either, can be used to generate an immune response to a 24P4C12 antigen. Antibodies or other molecules that react with 24P4C12 can be used to modulate the function of this molecule, and thereby provide a therapeutic benefit.

X.A.) Inhibition of 24P4C12 Protein Function

The invention includes various methods and compositions for inhibiting the binding of 24P4C12 to its binding partner or its association with other protein(s) as well as methods for inhibiting 24P4C12 function.

X.B.) Inhibition of 24P4C12 with Intracellular Antibodies

In one approach, a recombinant vector that encodes single chain antibodies that specifically bind to 24P4C12 are introduced into 24P4C12 expressing cells via gene transfer technologies. Accordingly, the encoded single chain anti-24P4C12 antibody is expressed intracellularly, binds to 24P4C12 protein, and thereby inhibits its function. Methods for engineering such intracellular single chain antibodies are well known. Such intracellular antibodies, also known as "intrabodies", are specifically targeted to a particular compartment within the cell, providing control over where the inhibitory activity of the treatment is focused. This technology has been successfully applied in the art (for review, see Richardson and Marasco, 1995, TIBTECH vol. 13). Intrabodies have been shown to virtually eliminate the expression of otherwise abundant cell surface receptors (see, e.g., Richardson et al., 1995, Proc. Natl. Acad. Sci. USA 92: 3137-3141; Beerli et al., 1994, J. Biol. Chem. 289: 23931-23936; Deshane et al., 1994, Gene Ther. 1: 332-337).

Single chain antibodies comprise the variable domains of the heavy and light chain joined by a flexible linker polypeptide, and are expressed as a single polypeptide. Optionally, single chain antibodies are expressed as a single chain variable region fragment joined to the light chain constant region or the heavy chain constant region (scFv). Well-known intracellular trafficking signals are engineered into recombinant polynucleotide vectors encoding such single chain antibodies in order to target precisely the intrabody to the desired intracellular compartment. For example, intrabodies targeted to the endoplasmic reticulum (ER) are engineered to incorporate a leader peptide and, optionally, a C-terminal ER retention signal, such as the KDEL amino acid motif. Intrabodies intended to exert activity in the nucleus are engineered to include a nuclear localization signal. Lipid moieties are joined to intrabodies in order to tether the intrabody to the cytosolic side of the plasma membrane. Intrabodies can also be targeted to exert function in the cytosol. For example, cytosolic intrabodies are used to sequester factors within the cytosol, thereby preventing them from being transported to their natural cellular destination.

In one embodiment, intrabodies are used to capture 24P4C12 in the nucleus, thereby preventing its activity within the nucleus. Nuclear targeting signals are engineered into such 24P4C12 intrabodies in order to achieve the desired targeting. Such 24P4C12 intrabodies are designed to bind specifically to a particular 24P4C12 domain. In another embodiment, cytosolic intrabodies that specifically bind to a 24P4C12 protein are used to prevent 24P4C12 from gaining access to the nucleus, thereby preventing it from exerting any biological activity within the nucleus (e.g., preventing 24P4C12 from forming transcription complexes with other factors).

X.C.) Inhibition of 24P4C12 with Recombinant Proteins

In another approach, recombinant molecules bind to 24P4C12 and thereby inhibit 24P4C12 function. For example, these recombinant molecules prevent or inhibit 24P4C12 from accessing/binding to its binding partner(s) or associating with other protein(s). Such recombinant molecules can, for example, contain the reactive part(s) of a 24P4C12 specific antibody molecule. In a particular embodiment, the 24P4C12 binding domain of a 24P4C12 binding partner is engineered into a dimeric fusion protein, whereby the fusion protein comprises two 24P4C12 ligand binding domains linked to the Fc portion of a human IgG, such as human IgG$_1$. Such IgG portion can contain, for example, the $CH_2$ and $CH_3$ domains and the hinge region, but not the $CH_1$ domain. Such dimeric fusion proteins are administered in soluble form to patients suffering from a cancer associated with the expression of 24P4C12, whereby the dimeric fusion protein specifically binds to 24P4C12 and blocks 24P4C12 interaction with a binding partner. Such dimeric fusion proteins are further combined into multimeric proteins using known antibody linking technologies.

X.D.) Inhibition of 24P4C12 Transcription or Translation

The present invention also comprises various methods and compositions for inhibiting the transcription of the 24P4C12 gene. Similarly, the invention also provides methods and compositions for inhibiting the translation of 24P4C12 mRNA into protein.

In one approach, a method of inhibiting the transcription of the 24P4C12 gene comprises contacting the 24P4C12 gene with a 24P4C12 antisense polynucleotide. In another approach, a method of inhibiting 24P4C12 mRNA translation comprises contacting a 24P4C12 mRNA with an antisense polynucleotide. In another approach, a 24P4C12 specific ribozyme is used to cleave a 24P4C12 message, thereby inhibiting translation. Such antisense and ribozyme based methods can also be directed to the regulatory regions of the 24P4C12 gene, such as 24P4C12 promoter and/or enhancer elements. Similarly, proteins capable of inhibiting a 24P4C12 gene transcription factor are used to inhibit 24P4C12 mRNA transcription. The various polynucleotides and compositions useful in the aforementioned methods have been described above. The use of antisense and ribozyme molecules to inhibit transcription and translation is well known in the art.

Other factors that inhibit the transcription of 24P4C12 by interfering with 24P4C12 transcriptional activation are also useful to treat cancers expressing 24P4C12. Similarly, factors that interfere with 24P4C12 processing are useful to treat cancers that express 24P4C12. Cancer treatment methods utilizing such factors are also within the scope of the invention.

X.E.) General Considerations for Therapeutic Strategies

Gene transfer and gene therapy technologies can be used to deliver therapeutic polynucleotide molecules to tumor cells synthesizing 24P4C12 (i.e., antisense, ribozyme, polynucleotides encoding intrabodies and other 24P4C12 inhibitory molecules). A number of gene therapy approaches are known in the art. Recombinant vectors encoding 24P4C12 antisense polynucleotides, ribozymes, factors capable of interfering with 24P4C12 transcription, and so forth, can be delivered to target tumor cells using such gene therapy approaches.

The above therapeutic approaches can be combined with any one of a wide variety of surgical, chemotherapy or radiation therapy regimens. The therapeutic approaches of the invention can enable the use of reduced dosages of chemotherapy (or other therapies) and/or less frequent administration, an advantage for all patients and particularly for those that do not tolerate the toxicity of the chemotherapeutic agent well.

The anti-tumor activity of a particular composition (e.g., antisense, ribozyme, intrabody), or a combination of such compositions, can be evaluated using various in vitro and in vivo assay systems. In vitro assays that evaluate therapeutic activity include cell growth assays, soft agar assays and other assays indicative of tumor promoting activity, binding assays capable of determining the extent to which a therapeutic composition will inhibit the binding of 24P4C12 to a binding partner, etc.

In vivo, the effect of a 24P4C12 therapeutic composition can be evaluated in a suitable animal model. For example, xenogenic kidney cancer models can be used, wherein human prostate cancer explants or passaged xenograft tissues are introduced into immune compromised animals, such as nude or SCID mice (Klein et al., 1997, Nature Medicine 3: 402-408). For example, PCT Patent Application WO98/16628 and U.S. Pat. No. 6,107,540 describe various xenograft models of human prostate cancer capable of recapitulating the development of primary tumors, micrometastasis, and the formation of osteoblastic metastases characteristic of late stage disease. Efficacy can be predicted using assays that measure inhibition of tumor formation, tumor regression or metastasis, and the like.

In vivo assays that evaluate the promotion of apoptosis are useful in evaluating therapeutic compositions. In one embodiment, xenografts from tumor bearing mice treated with the therapeutic composition can be examined for the presence of apoptotic foci and compared to untreated control xenograft-bearing mice. The extent to which apoptotic foci are found in the tumors of the treated mice provides an indication of the therapeutic efficacy of the composition.

The therapeutic compositions used in the practice of the foregoing methods can be formulated into pharmaceutical compositions comprising a carrier suitable for the desired delivery method. Suitable carriers include any material that when combined with the therapeutic composition retains the anti-tumor function of the therapeutic composition and is generally non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences 16th Edition, A. Osal., Ed., 1980).

Therapeutic formulations can be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection comprises the therapeutic composition in a solution of preserved bacteriostatic water, sterile unpreserved water, and/or diluted in polyvinylchloride or polyethylene bags containing 0.9% sterile Sodium Chloride for Injection, USP. Therapeutic protein preparations can be lyophilized and stored as sterile powders, preferably under vacuum, and then reconstituted in bacteriostatic water (containing for example, benzyl alcohol preservative) or in sterile water prior to injection.

Dosages and administration protocols for the treatment of cancers using the foregoing methods will vary with the method and the target cancer, and will generally depend on a number of other factors appreciated in the art.

XI.) Identification, Characterization and Use of Modulators of 24P4C12

Methods to Identify and Use Modulators

In one embodiment, screening is performed to identify modulators that induce or suppress a particular expression profile, suppress or induce specific pathways, preferably generating the associated phenotype thereby. In another embodiment, having identified differentially expressed genes important in a particular state; screens are performed to identify modulators that alter expression of individual genes, either increase or decrease. In another embodiment, screening is performed to identify modulators that alter a biological function of the expression product of a differentially expressed gene. Again, having identified the importance of a gene in a particular state, screens are performed to identify agents that bind and/or modulate the biological activity of the gene product.

In addition, screens are done for genes that are induced in response to a candidate agent. After identifying a modulator (one that suppresses a cancer expression pattern leading to a normal expression pattern, or a modulator of a cancer gene that leads to expression of the gene as in normal tissue) a screen is performed to identify genes that are specifically modulated in response to the agent. Comparing expression profiles between normal tissue and agent-treated cancer tissue reveals genes that are not expressed in normal tissue or cancer tissue, but are expressed in agent treated tissue, and vice versa. These agent-specific sequences are identified and used by methods described herein for cancer genes or proteins. In particular these sequences and the proteins they encode are used in marking or identifying agent-treated cells.

In addition, antibodies are raised against the agent-induced proteins and used to target novel therapeutics to the treated cancer tissue sample.

Modulator-Related Identification and Screening Assays: Gene Expression-Related Assays Proteins, nucleic acids, and antibodies of the invention are used in screening assays. The cancer-associated proteins, antibodies, nucleic acids, modified proteins and cells containing these sequences are used in screening assays, such as evaluating the effect of drug candidates on a "gene expression profile," expression profile of polypeptides or alteration of biological function. In one embodiment, the expression profiles are used, preferably in conjunction with high throughput screening techniques to allow monitoring for expression profile genes after treatment with a candidate agent (e.g., Davis, G F, et al, J Biol Screen 7:69 (2002); Zlokarnik, et al., Science 279:84-8 (1998); Heid, Genome Res 6:986-94, 1996).

The cancer proteins, antibodies, nucleic acids, modified proteins and cells containing the native or modified cancer proteins or genes are used in screening assays. That is, the present invention comprises methods for screening for compositions which modulate the cancer phenotype or a physiological function of a cancer protein of the invention. This is done on a gene itself or by evaluating the effect of drug candidates on a "gene expression profile" or biological function. In one embodiment, expression profiles are used, preferably in conjunction with high throughput screening techniques to allow monitoring after treatment with a candidate agent, see Zlokarnik, supra.

A variety of assays are executed and directed to the genes and proteins of the invention. Assays are run on an individual nucleic acid or protein level. That is, having identified a particular gene as up regulated in cancer, test compounds are screened for the ability to modulate gene expression or for binding to the cancer protein of the invention. "Modulation" in this context includes an increase or a decrease in gene expression. The preferred amount of modulation will depend on the original change of the gene expression in normal versus tissue undergoing cancer, with changes of at least 10%, preferably 50%, more preferably 100-300%, and in some embodiments 300-1000% or greater. Thus, if a gene exhibits a 4-fold increase in cancer tissue compared to normal tissue, a decrease of about four-fold is often desired; similarly, a 10-fold decrease in cancer tissue compared to normal tissue a target value of a 10-fold increase in expression by the test compound is often desired. Modulators that exacerbate the type of gene expression seen in cancer are also useful, e.g., as an upregulated target in further analyses.

The amount of gene expression is monitored using nucleic acid probes and the quantification of gene expression levels, or, alternatively, a gene product itself is monitored, e.g., through the use of antibodies to the cancer protein and standard immunoassays. Proteomics and separation techniques also allow for quantification of expression.

Expression Monitoring to Identify Compounds that Modify Gene Expression

In one embodiment, gene expression monitoring, i.e., an expression profile, is monitored simultaneously for a number of entities. Such profiles will typically involve one or more of the genes of FIG. 1. In this embodiment, e.g., cancer nucleic acid probes are attached to biochips to detect and quantify cancer sequences in a particular cell. Alternatively, PCR can be used. Thus, a series, e.g., wells of a microtiter plate, can be used with dispensed primers in desired wells. A PCR reaction can then be performed and analyzed for each well.

Expression monitoring is performed to identify compounds that modify the expression of one or more cancer-associated sequences, e.g., a polynucleotide sequence set out in FIG. 1. Generally, a test modulator is added to the cells prior to analysis. Moreover, screens are also provided to identify agents that modulate cancer, modulate cancer proteins of the invention, bind to a cancer protein of the invention, or interfere with the binding of a cancer protein of the invention and an antibody or other binding partner.

In one embodiment, high throughput screening methods involve providing a library containing a large number of potential therapeutic compounds (candidate compounds). Such "combinatorial chemical libraries" are then screened in one or more assays to identify those library members (particular chemical species or subclasses) that display a desired characteristic activity. The compounds thus identified can serve as conventional "lead compounds," as compounds for screening, or as therapeutics.

In certain embodiments, combinatorial libraries of potential modulators are screened for an ability to bind to a cancer polypeptide or to modulate activity. Conventionally, new chemical entities with useful properties are generated by identifying a chemical compound (called a "lead compound") with some desirable property or activity, e.g., inhibiting activity, creating variants of the lead compound, and evaluating the property and activity of those variant compounds. Often, high throughput screening (HTS) methods are employed for such an analysis.

As noted above, gene expression monitoring is conveniently used to test candidate modulators (e.g., protein, nucleic acid or small molecule). After the candidate agent has been added and the cells allowed to incubate for a period, the sample containing a target sequence to be analyzed is, e.g., added to a biochip.

If required, the target sequence is prepared using known techniques. For example, a sample is treated to lyse the cells, using known lysis buffers, electroporation, etc., with purification and/or amplification such as PCR performed as appropriate. For example, an in vitro transcription with labels covalently attached to the nucleotides is performed. Generally, the nucleic acids are labeled with biotin-FITC or PE, or with cy3 or cy5.

The target sequence can be labeled with, e.g., a fluorescent, a chemiluminescent, a chemical, or a radioactive signal, to provide a means of detecting the target sequence's specific binding to a probe. The label also can be an enzyme, such as alkaline phosphatase or horseradish peroxidase, which when provided with an appropriate substrate produces a product that is detected. Alternatively, the label is a labeled compound or small molecule, such as an enzyme inhibitor, that binds but is not catalyzed or altered by the enzyme. The label also can be a moiety or compound, such as, an epitope tag or biotin which specifically binds to streptavidin. For the example of biotin, the streptavidin is labeled as described above, thereby, providing a detectable signal for the bound target sequence. Unbound labeled streptavidin is typically removed prior to analysis.

As will be appreciated by those in the art, these assays can be direct hybridization assays or can comprise "sandwich assays", which include the use of multiple probes, as is generally outlined in U.S. Pat. Nos. 5,681,702; 5,597,909; 5,545,730; 5,594,117; 5,591,584; 5,571,670; 5,580,731; 5,571,670; 5,591,584; 5,624,802; 5,635,352; 5,594,118; 5,359,100; 5,124,246; and 5,681,697. In this embodiment, in general, the target nucleic acid is prepared as outlined above, and then added to the biochip comprising a plurality of nucleic acid probes, under conditions that allow the formation of a hybridization complex.

A variety of hybridization conditions are used in the present invention, including high, moderate and low stringency conditions as outlined above. The assays are generally run under stringency conditions which allow formation of the label probe hybridization complex only in the presence of target. Stringency can be controlled by altering a step parameter that is a thermodynamic variable, including, but not limited to, temperature, formamide concentration, salt concentration, chaotropic salt concentration pH, organic solvent concentration, etc. These parameters may also be used to control non-specific binding, as is generally outlined in U.S. Pat. No. 5,681,697. Thus, it can be desirable to perform certain steps at higher stringency conditions to reduce non-specific binding.

The reactions outlined herein can be accomplished in a variety of ways. Components of the reaction can be added simultaneously, or sequentially, in different orders, with preferred embodiments outlined below. In addition, the reaction may include a variety of other reagents. These include salts, buffers, neutral proteins, e.g. albumin, detergents, etc. which can be used to facilitate optimal hybridization and detection, and/or reduce nonspecific or background interactions. Reagents that otherwise improve the efficiency of the assay, such as protease inhibitors, nuclease inhibitors, anti-microbial agents, etc., may also be used as appropriate, depending on the sample preparation methods and purity of the target. The assay data are analyzed to determine the expression levels of individual genes, and changes in expression levels as between states, forming a gene expression profile.

Biological Activity-Related Assays

The invention provides methods to identify or screen for a compound that modulates the activity of a cancer-related gene or protein of the invention. The methods comprise adding a test compound, as defined above, to a cell comprising a cancer protein of the invention. The cells contain a recombinant nucleic acid that encodes a cancer protein of the invention. In another embodiment, a library of candidate agents is tested on a plurality of cells.

In one aspect, the assays are evaluated in the presence or absence or previous or subsequent exposure of physiological signals, e.g. hormones, antibodies, peptides, antigens, cytokines, growth factors, action potentials, pharmacological agents including chemotherapeutics, radiation, carcinogenics, or other cells (i.e., cell-cell contacts). In another example, the determinations are made at different stages of the cell cycle process. In this way, compounds that modulate genes or proteins of the invention are identified. Compounds with pharmacological activity are able to enhance or interfere with the activity of the cancer protein of the invention. Once identified, similar structures are evaluated to identify critical structural features of the compound.

In one embodiment, a method of modulating (e.g., inhibiting) cancer cell division is provided; the method comprises administration of a cancer modulator. In another embodiment, a method of modulating (e.g., inhibiting) cancer is provided; the method comprises administration of a cancer modulator. In a further embodiment, methods of treating cells or individuals with cancer are provided; the method comprises administration of a cancer modulator.

In one embodiment, a method for modulating the status of a cell that expresses a gene of the invention is provided. As used herein status comprises such art-accepted parameters such as growth, proliferation, survival, function, apoptosis, senescence, location, enzymatic activity, signal transduction, etc. of a cell. In one embodiment, a cancer inhibitor is an antibody as discussed above. In another embodiment, the cancer inhibitor is an antisense molecule, siRNA oligomer or shRNA (delivered as DNA or by infection with a virus including, but not limited to, adenovirus, adeno-associated virus, lentivirus or retrovirus). A variety of cell growth, proliferation, and metastasis assays are known to those of skill in the art, as described herein.

High Throughput Screening to Identify Modulators

The assays to identify suitable modulators are amenable to high throughput screening. Preferred assays thus detect enhancement or inhibition of cancer gene transcription, inhibition or enhancement of polypeptide expression, and inhibition or enhancement of polypeptide activity.

In one embodiment, modulators evaluated in high throughput screening methods are proteins, often naturally occurring proteins or fragments of naturally occurring proteins. Thus, e.g., cellular extracts containing proteins, or random or directed digests of proteinaceous cellular extracts, are used. In this way, libraries of proteins are made for screening in the methods of the invention. Particularly preferred in this embodiment are libraries of bacterial, fungal, viral, and mammalian proteins, with the latter being preferred, and human proteins being especially preferred. Particularly useful test compound will be directed to the class of proteins to which the target belongs, e.g., substrates for enzymes, or ligands and receptors.

Use of Soft Agar Growth and Colony Formation to Identify and Characterize Modulators Normal cells require a solid substrate to attach and grow. When cells are transformed, they lose this phenotype and grow detached from the substrate. For example, transformed cells can grow in stirred suspension culture or suspended in semi-solid media, such as semi-solid or soft agar. The transformed cells, when transfected with tumor suppressor genes, can regenerate normal phenotype and once again require a solid substrate to attach to and grow. Soft agar growth or colony formation assays are used to identify modulators of cancer sequences, which when expressed in host cells, inhibit abnormal cellular proliferation and transformation. A modulator reduces or eliminates the host cells' ability to grow suspended in solid or semisolid media, such as agar.

Techniques for soft agar growth or colony formation in suspension assays are described in Freshney, Culture of Animal Cells a Manual of Basic Technique (3rd ed., 1994). See also, the methods section of Garkavtsev et al. (1996), supra.

Evaluation of Contact Inhibition and Growth Density Limitation to Identify and Characterize Modulators Normal cells typically grow in a flat and organized pattern in cell culture until they touch other cells. When the cells touch one another, they are contact inhibited and stop growing. Transformed cells, however, are not contact inhibited and continue to grow to high densities in disorganized foci. Thus, transformed cells grow to a higher saturation density than corresponding normal cells. This is detected morphologically by the formation of a disoriented monolayer of cells or cells in foci. Alternatively, labeling index with ($^3$H)-thymidine at saturation density is used to measure density limitation of growth, similarly an MTT or Alamar blue assay will reveal proliferation capacity of cells and the ability of modulators to affect same. See Freshney (1994), supra. Transformed cells, when transfected with tumor suppressor genes, can regenerate a normal phenotype and become contact inhibited and would grow to a lower density.

In this assay, labeling index with (3H)-thymidine at saturation density is a preferred method of measuring density limitation of growth. Transformed host cells are transfected with a cancer-associated sequence and are grown for 24 hours at saturation density in non-limiting medium conditions. The percentage of cells labeling with (3H)-thymidine is determined by incorporated cpm.

Contact independent growth is used to identify modulators of cancer sequences, which had led to abnormal cellular proliferation and transformation. A modulator reduces or eliminates contact independent growth, and returns the cells to a normal phenotype.

Evaluation of Growth Factor or Serum Dependence to Identify and Characterize Modulators Transformed cells have lower serum dependence than their normal counterparts (see, e.g., Temin, J. Natl. Cancer Inst. 37:167-175 (1966); Eagle et al., J. Exp. Med. 131:836-879 (1970)); Freshney, supra. This is in part due to release of various growth factors by the transformed cells. The degree of growth factor or serum dependence of transformed host cells can be compared with that of control. For example, growth factor or serum dependence of a cell is monitored in methods to identify and characterize compounds that modulate cancer-associated sequences of the invention.

Use of Tumor-Specific Marker Levels to Identify and Characterize Modulators

Tumor cells release an increased amount of certain factors (hereinafter "tumor specific markers") than their normal counterparts. For example, plasminogen activator (PA) is released from human glioma at a higher level than from normal brain cells (see, e.g., Gullino, Angiogenesis, Tumor Vascularization, and Potential Interference with Tumor Growth, in Biological Responses in Cancer, pp. 178-184 (Mihich (ed.) 1985)). Similarly, Tumor Angiogenesis Factor (TAF) is released at a higher level in tumor cells than their normal counterparts. See, e.g., Folkman, Angiogenesis and Cancer, Sem. Cancer Biol. (1992)), while bFGF is released from endothelial tumors (Ensoli, B et al.).

Various techniques which measure the release of these factors are described in Freshney (1994), supra. Also, see, Unkless et al., J. Biol. Chem. 249:4295-4305 (1974); Strickland & Beers, J. Biol. Chem. 251:5694-5702 (1976); Whur et al., Br. J. Cancer 42:305 312 (1980); Gullino, Angiogenesis, Tumor Vascularization, and Potential Interference with Tumor Growth, in Biological Responses in Cancer, pp. 178-184 (Mihich (ed.) 1985); Freshney, Anticancer Res. 5:111-130 (1985). For example, tumor specific marker levels are monitored in methods to identify and characterize compounds that modulate cancer-associated sequences of the invention.

Invasiveness into Matrigel to Identify and Characterize Modulators

The degree of invasiveness into Matrigel or an extracellular matrix constituent can be used as an assay to identify and characterize compounds that modulate cancer associated sequences. Tumor cells exhibit a positive correlation between malignancy and invasiveness of cells into Matrigel or some other extracellular matrix constituent. In this assay, tumorigenic cells are typically used as host cells. Expression of a tumor suppressor gene in these host cells would decrease invasiveness of the host cells. Techniques described in Cancer Res. 1999; 59:6010; Freshney (1994), supra, can be used. Briefly, the level of invasion of host cells is measured by using filters coated with Matrigel or some other extracellular matrix constituent. Penetration into the gel, or through to the distal side of the filter, is rated as invasiveness, and rated histologically by number of cells and distance moved, or by prelabeling the cells with $^{125}$I and counting the radioactivity on the distal side of the filter or bottom of the dish. See, e.g., Freshney (1984), supra.

Evaluation of Tumor Growth In Vivo to Identify and Characterize Modulators

Effects of cancer-associated sequences on cell growth are tested in transgenic or immune-suppressed organisms. Transgenic organisms are prepared in a variety of art-accepted ways. For example, knock-out transgenic organisms, e.g., mammals such as mice, are made, in which a cancer gene is disrupted or in which a cancer gene is inserted. Knock-out transgenic mice are made by insertion of a marker gene or other heterologous gene into the endogenous cancer gene site in the mouse genome via homologous recombination. Such mice can also be made by substituting the endogenous cancer gene with a mutated version of the cancer gene, or by mutating the endogenous cancer gene, e.g., by exposure to carcinogens.

To prepare transgenic chimeric animals, e.g., mice, a DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells some of which are derived from the mutant cell line. Therefore, by breeding the chimeric mice it is possible to obtain a new line of mice containing the introduced genetic lesion (see, e.g., Capecchi et al., Science 244:1288 (1989)). Chimeric mice can be derived according to U.S. Pat. No. 6,365,797, issued 2 Apr. 2002; U.S. Pat. No. 6,107,540 issued 22 Aug. 2000; Hogan et al., Manipulating the Mouse Embryo: A laboratory Manual, Cold Spring Harbor Laboratory (1988) and Teratocarcinomas and Embryonic Stem Cells: A Practical Approach, Robertson, ed., IRL Press, Washington, D.C., (1987).

Alternatively, various immune-suppressed or immune-deficient host animals can be used. For example, a genetically athymic "nude" mouse (see, e.g., Giovanella et al., J. Natl. Cancer Inst. 52:921 (1974)), a SCID mouse, a thymectornized mouse, or an irradiated mouse (see, e.g., Bradley et al., Br. J. Cancer 38:263 (1978); Selby et al., Br. J. Cancer 41:52 (1980)) can be used as a host. Transplantable tumor cells (typically about $10^6$ cells) injected into isogenic hosts produce invasive tumors in a high proportion of cases, while normal cells of similar origin will not. In hosts which developed invasive tumors, cells expressing cancer-associated sequences are injected subcutaneously or orthotopically. Mice are then separated into groups, including control groups and treated experimental groups) e.g. treated with a modulator). After a suitable length of time, preferably 4-8 weeks, tumor growth is measured (e.g., by volume or by its two largest dimensions, or weight) and compared to the control. Tumors that have statistically significant reduction (using, e.g., Student's T test) are said to have inhibited growth.

In Vitro Assays to Identify and Characterize Modulators

Assays to identify compounds with modulating activity can be performed in vitro. For example, a cancer polypeptide is first contacted with a potential modulator and incubated for a suitable amount of time, e.g., from 0.5 to 48 hours. In one embodiment, the cancer polypeptide levels are determined in vitro by measuring the level of protein or mRNA. The level of protein is measured using immunoassays such as Western blotting, ELISA and the like with an antibody that selectively binds to the cancer polypeptide or a fragment thereof. For measurement of mRNA, amplification, e.g., using PCR, LCR, or hybridization assays, e.g., Northern hybridization, RNAse protection, dot blotting, are preferred. The level of protein or mRNA is detected using directly or indirectly labeled detection agents, e.g., fluorescently or radioactively labeled nucleic acids, radioactively or enzymatically labeled antibodies, and the like, as described herein.

Alternatively, a reporter gene system can be devised using a cancer protein promoter operably linked to a reporter gene such as luciferase, green fluorescent protein, CAT, or P-gal. The reporter construct is typically transfected into a cell. After treatment with a potential modulator, the amount of reporter gene transcription, translation, or activity is measured according to standard techniques known to those of skill in the art (Davis G F, supra; Gonzalez, J. & Negulescu, P. Curr. Opin. Biotechnol. 1998: 9:624).

As outlined above, in vitro screens are done on individual genes and gene products. That is, having identified a particular differentially expressed gene as important in a particular state, screening of modulators of the expression of the gene or the gene product itself is performed.

In one embodiment, screening for modulators of expression of specific gene(s) is performed. Typically, the expression of only one or a few genes is evaluated. In another embodiment, screens are designed to first find compounds that bind to differentially expressed proteins. These compounds are then evaluated for the ability to modulate differentially expressed activity. Moreover, once initial candidate compounds are identified, variants can be further screened to better evaluate structure activity relationships.

Binding Assays to Identify and Characterize Modulators

In binding assays in accordance with the invention, a purified or isolated gene product of the invention is generally used. For example, antibodies are generated to a protein of the invention, and immunoassays are run to determine the amount and/or location of protein. Alternatively, cells comprising the cancer proteins are used in the assays.

Thus, the methods comprise combining a cancer protein of the invention and a candidate compound such as a ligand, and determining the binding of the compound to the cancer protein of the invention. Preferred embodiments utilize the human cancer protein; animal models of human disease of can also be developed and used. Also, other analogous mammalian proteins also can be used as appreciated by those of skill in the art. Moreover, in some embodiments variant or derivative cancer proteins are used.

Generally, the cancer protein of the invention, or the ligand, is non-diffusibly bound to an insoluble support. The support can, e.g., be one having isolated sample receiving areas (a microtiter plate, an array, etc.). The insoluble supports can be made of any composition to which the compositions can be bound, is readily separated from soluble material, and is otherwise compatible with the overall method of screening. The surface of such supports can be solid or porous and of any convenient shape.

Examples of suitable insoluble supports include microtiter plates, arrays, membranes and beads. These are typically made of glass, plastic (e.g., polystyrene), polysaccharide, nylon, nitrocellulose, or Teflon™, etc. Microtiter plates and arrays are especially convenient because a large number of assays can be carried out simultaneously, using small amounts of reagents and samples. The particular manner of binding of the composition to the support is not crucial so long as it is compatible with the reagents and overall methods of the invention, maintains the activity of the composition and is nondiffusable. Preferred methods of binding include the use of antibodies which do not sterically block either the ligand binding site or activation sequence when attaching the protein to the support, direct binding to "sticky" or ionic supports, chemical crosslinking, the synthesis of the protein or agent on the surface, etc. Following binding of the protein or ligand/binding agent to the support, excess unbound material is removed by washing. The sample receiving areas may then be blocked through incubation with bovine serum albumin (BSA), casein or other innocuous protein or other moiety.

Once a cancer protein of the invention is bound to the support, and a test compound is added to the assay. Alternatively, the candidate binding agent is bound to the support and the cancer protein of the invention is then added. Binding agents include specific antibodies, non-natural binding agents identified in screens of chemical libraries, peptide analogs, etc.

Of particular interest are assays to identify agents that have a low toxicity for human cells. A wide variety of assays can be used for this purpose, including proliferation assays, cAMP assays, labeled in vitro protein-protein binding assays, electrophoretic mobility shift assays, immunoassays for protein binding, functional assays (phosphorylation assays, etc.) and the like.

A determination of binding of the test compound (ligand, binding agent, modulator, etc.) to a cancer protein of the invention can be done in a number of ways. The test compound can be labeled, and binding determined directly, e.g., by attaching all or a portion of the cancer protein of the invention to a solid support, adding a labeled candidate compound (e.g., a fluorescent label), washing off excess reagent, and determining whether the label is present on the solid support. Various blocking and washing steps can be utilized as appropriate.

In certain embodiments, only one of the components is labeled, e.g., a protein of the invention or ligands labeled. Alternatively, more than one component is labeled with different labels, e.g., $I^{125}$, for the proteins and a fluorophor for the compound. Proximity reagents, e.g., quenching or energy transfer reagents are also useful.

Competitive Binding to Identify and Characterize Modulators

In one embodiment, the binding of the "test compound" is determined by competitive binding assay with a "competitor." The competitor is a binding moiety that binds to the target molecule (e.g., a cancer protein of the invention). Competitors include compounds such as antibodies, peptides, binding partners, ligands, etc. Under certain circumstances, the competitive binding between the test compound and the competitor displaces the test compound. In one embodiment, the test compound is labeled. Either the test compound, the competitor, or both, is added to the protein for a time sufficient to allow binding. Incubations are performed at a temperature that facilitates optimal activity, typically between four and 40° C. Incubation periods are typically optimized, e.g., to facilitate rapid high throughput screening; typically between zero and one hour will be sufficient. Excess reagent is generally removed or washed away. The second component is then added, and the presence or absence of the labeled component is followed, to indicate binding.

In one embodiment, the competitor is added first, followed by the test compound. Displacement of the competitor is an indication that the test compound is binding to the cancer protein and thus is capable of binding to, and potentially modulating, the activity of the cancer protein. In this embodiment, either component can be labeled. Thus, e.g., if the competitor is labeled, the presence of label in the post-test compound wash solution indicates displacement by the test compound. Alternatively, if the test compound is labeled, the presence of the label on the support indicates displacement.

In an alternative embodiment, the test compound is added first, with incubation and washing, followed by the competitor. The absence of binding by the competitor indicates that the test compound binds to the cancer protein with higher affinity than the competitor. Thus, if the test compound is labeled, the presence of the label on the support, coupled with a lack of competitor binding, indicates that the test compound binds to and thus potentially modulates the cancer protein of the invention.

Accordingly, the competitive binding methods comprise differential screening to identity agents that are capable of modulating the activity of the cancer proteins of the invention. In this embodiment, the methods comprise combining a cancer protein and a competitor in a first sample. A second sample comprises a test compound, the cancer protein, and a competitor. The binding of the competitor is determined for both samples, and a change, or difference in binding between the two samples indicates the presence of an agent capable of binding to the cancer protein and potentially modulating its activity. That is, if the binding of the competitor is different in the second sample relative to the first sample, the agent is capable of binding to the cancer protein.

Alternatively, differential screening is used to identify drug candidates that bind to the native cancer protein, but cannot bind to modified cancer proteins. For example the structure of the cancer protein is modeled and used in rational drug design to synthesize agents that interact with that site, agents which generally do not bind to site-modified proteins. Moreover, such drug candidates that affect the activity of a native cancer protein are also identified by screening drugs for the ability to either enhance or reduce the activity of such proteins.

Positive controls and negative controls can be used in the assays. Preferably control and test samples are performed in at least triplicate to obtain statistically significant results. Incubation of all samples occurs for a time sufficient to allow for the binding of the agent to the protein. Following incubation, samples are washed free of non-specifically bound material and the amount of bound, generally labeled agent determined. For example, where a radiolabel is employed, the samples can be counted in a scintillation counter to determine the amount of bound compound.

A variety of other reagents can be included in the screening assays. These include reagents like salts, neutral proteins, e.g. albumin, detergents, etc. which are used to facilitate optimal protein-protein binding and/or reduce non-specific or background interactions. Also reagents that otherwise improve the efficiency of the assay, such as protease inhibitors, nuclease inhibitors, anti-microbial agents, etc., can be used. The mixture of components is added in an order that provides for the requisite binding.

Use of Polynucleotides to Down-Regulate or Inhibit a Protein of the Invention.

Polynucleotide modulators of cancer can be introduced into a cell containing the target nucleotide sequence by formation of a conjugate with a ligand-binding molecule, as described in WO 91/04753. Suitable ligand-binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell. Alternatively, a polynucleotide modulator of cancer can be introduced into a cell containing the target nucleic acid sequence, e.g., by formation of a polynucleotide-lipid complex, as described in WO 90/10448. It is understood that the use of antisense molecules or knock out and knock in models may also be used in screening assays as discussed above, in addition to methods of treatment.

Inhibitory and Antisense Nucleotides

In certain embodiments, the activity of a cancer-associated protein is down-regulated, or entirely inhibited, by the use of antisense polynucleotide or inhibitory small nuclear RNA (snRNA), i.e., a nucleic acid complementary to, and which can preferably hybridize specifically to, a coding mRNA nucleic acid sequence, e.g., a cancer protein of the invention, mRNA, or a subsequence thereof. Binding of the antisense polynucleotide to the mRNA reduces the translation and/or stability of the mRNA.

In the context of this invention, antisense polynucleotides can comprise naturally occurring nucleotides, or synthetic species formed from naturally occurring subunits or their close homologs. Antisense polynucleotides may also have altered sugar moieties or inter-sugar linkages. Exemplary among these are the phosphorothioate and other sulfur containing species which are known for use in the art. Analogs are comprised by this invention so long as they function effectively to hybridize with nucleotides of the invention. See, e.g., Isis Pharmaceuticals, Carlsbad, Calif.; Sequitor, Inc., Natick, Mass.

Such antisense polynucleotides can readily be synthesized using recombinant means, or can be synthesized in vitro. Equipment for such synthesis is sold by several vendors, including Applied Biosystems. The preparation of other oligonucleotides such as phosphorothioates and alkylated derivatives is also well known to those of skill in the art.

Antisense molecules as used herein include antisense or sense oligonucleotides. Sense oligonucleotides can, e.g., be employed to block transcription by binding to the anti-sense strand. The antisense and sense oligonucleotide comprise a single stranded nucleic acid sequence (either RNA or DNA) capable of binding to target mRNA (sense) or DNA (antisense) sequences for cancer molecules. Antisense or sense oligonucleotides, according to the present invention, comprise a fragment generally at least about 12 nucleotides, preferably from about 12 to 30 nucleotides. The ability to derive an antisense or a sense oligonucleotide, based upon a cDNA sequence encoding a given protein is described in, e.g., Stein &Cohen (Cancer Res. 48:2659 (1988 and van der Krol et al. (BioTechniques 6:958 (1988)).

Ribozymes

In addition to antisense polynucleotides, ribozymes can be used to target and inhibit transcription of cancer-associated nucleotide sequences. A ribozyme is an RNA molecule that catalytically cleaves other RNA molecules. Different kinds of ribozymes have been described, including group I ribozymes, hammerhead ribozymes, hairpin ribozymes, RNase P, and axhead ribozymes (see, e.g., Castanotto et al., Adv. in Pharmacology 25: 289-317 (1994) for a general review of the properties of different ribozymes).

The general features of hairpin ribozymes are described, e.g., in Hampel et al., Nucl. Acids Res. 18:299-304 (1990); European Patent Publication No. 0360257; U.S. Pat. No. 5,254,678. Methods of preparing are well known to those of skill in the art (see, e.g., WO 94/26877; Ojwang et al., Proc. Natl. Acad. Sci. USA 90:6340-6344 (1993); Yamada et al., Human Gene Therapy 1:39-45 (1994); Leavitt et al., Proc. Natl. Acad. Sci. USA 92:699-703 (1995); Leavitt et al., Human Gene Therapy 5: 1151-120 (1994); and Yamada et al., Virology 205: 121-126 (1994)).

Use of Modulators in Phenotypic Screening

In one embodiment, a test compound is administered to a population of cancer cells, which have an associated cancer expression profile. By "administration" or "contacting" herein is meant that the modulator is added to the cells in such a manner as to allow the modulator to act upon the cell, whether by uptake and intracellular action, or by action at the cell surface. In some embodiments, a nucleic acid encoding a proteinaceous agent (i.e., a peptide) is put into a viral construct such as an adenoviral or retroviral construct, and added to the cell, such that expression of the peptide agent is accomplished, e.g., PCT US97/01019. Regulatable gene therapy systems can also be used. Once the modulator has been administered to the cells, the cells are washed if desired and are allowed to incubate under preferably physiological conditions for some period. The cells are then harvested and a new gene expression profile is generated. Thus, e.g., cancer tissue is screened for agents that modulate, e.g., induce or suppress, the cancer phenotype. A change in at least one gene, preferably many, of the expression profile indicates that the agent has an effect on cancer activity. Similarly, altering a biological function or a signaling pathway is indicative of modulator activity. By defining such a signature for the cancer phenotype, screens for new drugs that alter the phenotype are devised. With this approach, the drug target need not be known and need not be represented in the original gene/protein expression screening platform, nor does the level of transcript for the target protein need to change. The modulator inhibiting function will serve as a surrogate marker.

As outlined above, screens are done to assess genes or gene products. That is, having identified a particular differentially expressed gene as important in a particular state, screening of modulators of either the expression of the gene or the gene product itself is performed.

Use of Modulators to Affect Peptides of the Invention

Measurements of cancer polypeptide activity, or of the cancer phenotype are performed using a variety of assays. For example, the effects of modulators upon the function of a cancer polypeptide(s) are measured by examining parameters described above. A physiological change that affects activity is used to assess the influence of a test compound on the polypeptides of this invention. When the functional outcomes are determined using intact cells or animals, a variety of effects can be assesses such as, in the case of a cancer associated with solid tumors, tumor growth, tumor metastasis, neovascularization, hormone release, transcriptional changes to both known and uncharacterized genetic markers (e.g., by Northern blots), changes in cell metabolism such as cell growth or pH changes, and changes in intracellular second messengers such as cGNIP.

Methods of Identifying Characterizing Cancer-Associated Sequences

Expression of various gene sequences is correlated with cancer. Accordingly, disorders based on mutant or variant cancer genes are determined. In one embodiment, the invention provides methods for identifying cells containing variant cancer genes, e.g., determining the presence of, all or part, the sequence of at least one endogenous cancer gene in a cell. This is accomplished using any number of sequencing techniques. The invention comprises methods of identifying the cancer genotype of an individual, e.g., determining all or part of the sequence of at least one gene of the invention in the individual. This is generally done in at least one tissue of the individual, e.g., a tissue set forth in Table I, and may include the evaluation of a number of tissues or different samples of the same tissue. The method may include comparing the sequence of the sequenced gene to a known cancer gene, i.e., a wild-type gene to determine the presence of family members, homologies, mutations or variants. The sequence of all or part of the gene can then be compared to the sequence of a known cancer gene to determine if any differences exist. This is done using any number of known homology programs, such as BLAST, Bestfit, etc. The presence of a difference in the sequence between the cancer gene of the patient and the known cancer gene correlates with a disease state or a propensity for a disease state, as outlined herein.

In a preferred embodiment, the cancer genes are used as probes to determine the number of copies of the cancer gene in the genome. The cancer genes are used as probes to determine the chromosomal localization of the cancer genes. Information such as chromosomal localization finds use in providing a diagnosis or prognosis in particular when chromosomal abnormalities such as translocations, and the like are identified in the cancer gene locus.

XII.) RNAi and Therapeutic Use of Small Interfering RNA (siRNAs)

The present invention is also directed towards siRNA oligonucleotides, particularly double stranded RNAs encompassing at least a fragment of the 24P4C12 coding region or 5' UTR regions, or complement, or any antisense oligonucleotide specific to the 24P4C12 sequence. In one embodiment such oligonucleotides are used to elucidate a function of 24P4C12, or are used to screen for or evaluate modulators of 24P4C12 function or expression. In another embodiment, gene expression of 24P4C12 is reduced by using siRNA transfection and results in significantly diminished proliferative capacity of transformed cancer cells that endogenously express the antigen; cells treated with specific 24P4C12 siRNAs show reduced survival as measured, e.g., by a metabolic readout of cell viability, correlating to the reduced proliferative capacity. Thus, 24P4C12 siRNA compositions comprise siRNA (double stranded RNA) that correspond to the nucleic acid ORF sequence of the 24P4C12 protein or subsequences thereof; these subsequences are generally 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more than 35 contiguous RNA nucleotides in length and contain sequences that are complementary and non-complementary to at least a portion of the mRNA coding sequence In a preferred embodiment, the subsequences are 19-25 nucleotides in length, most preferably 21-23 nucleotides in length.

RNA interference is a novel approach to silencing genes in vitro and in vivo, thus small double stranded RNAs (siRNAs) are valuable therapeutic agents. The power of siRNAs to silence specific gene activities has now been brought to animal models of disease and is used in humans as well. For example, hydrodynamic infusion of a solution of siRNA into a mouse with a siRNA against a particular target has been proven to be therapeutically effective.

The pioneering work by Song et al. indicates that one type of entirely natural nucleic acid, small interfering RNAs (siRNAs), served as therapeutic agents even without further chemical modification (Song, E., et al. "RNA interference targeting Fas protects mice from fulminant hepatitis" Nat. Med. 9(3): 347-51 (2003)). This work provided the first in vivo evidence that infusion of siRNAs into an animal could alleviate disease. In that case, the authors gave mice injections of siRNA designed to silence the FAS protein (a cell death receptor that when over-activated during inflammatory response induces hepatocytes and other cells to die). The next day, the animals were given an antibody specific to Fas. Control mice died of acute liver failure within a few days, while over 80% of the siRNA-treated mice remained free from serious disease and survived. About 80% to 90% of their liver cells incorporated the naked siRNA oligonucleotides. Furthermore, the RNA molecules functioned for 10 days before losing effect after 3 weeks.

For use in human therapy, siRNA is delivered by efficient systems that induce long-lasting RNAi activity. A major caveat for clinical use is delivering siRNAs to the appropriate cells. Hepatocytes seem to be particularly receptive to exogenous RNA. Today, targets located in the liver are attractive because liver is an organ that can be readily targeted by nucleic acid molecules and viral vectors. However, other tissue and organs targets are preferred as well.

Formulations of siRNAs with compounds that promote transit across cell membranes are used to improve administration of siRNAs in therapy. Chemically modified synthetic siRNA, that are resistant to nucleases and have serum stability have concomitant enhanced duration of RNAi effects, are an additional embodiment.

Thus, siRNA technology is a therapeutic for human malignancy by delivery of siRNA molecules directed to 24P4C12 to individuals with the cancers, such as those listed in Table 1. Such administration of siRNAs leads to reduced growth of cancer cells expressing 24P4C12, and provides an anti-tumor therapy, lessening the morbidity and/or mortality associated with malignancy. In another embodiment, siRNA is delivered by a virus as shRNA (short hairpin RNA). This enablement allows stable expression of the shRNA in cells both in vitro and in vivo. The shRNA may be delivered by viruses including, but not limited to, adenovirus, adeno-associated virus, lentivirus and retrovirus. Such systems allow for either viral DNA transfection or viral particles to infect cells to achieve stable expression of shRNAs, and stable suppression of cancer-associated genes such as 24P4C12.

The effectiveness of this modality of gene product knockdown is significant when measured in vitro or in vivo. Effectiveness in vitro is readily demonstrable through application of siRNAs or shRNA by DNA plasmid or virus to cells in culture (as described above) or to aliquots of cancer patient biopsies when in vitro methods are used to detect the reduced expression of 24P4C12 protein.

XIII.) Kits/Articles of Manufacture

For use in the laboratory, prognostic, prophylactic, diagnostic and therapeutic applications described herein, kits are within the scope of the invention. Such kits can comprise a carrier, package, or container that is compartmentalized to receive one or more containers such as vials, tubes, and the like, each of the container(s) comprising one of the separate elements to be used in the method, along with a label or insert comprising instructions for use, such as a use described herein. For example, the container(s) can comprise a probe that is or can be detectably labeled. Such probe can be an antibody or polynucleotide specific for a protein or a gene or message of the invention, respectively. Where the method utilizes nucleic acid hybridization to detect the target nucleic acid, the kit can also have containers containing nucleotide(s) for amplification of the target nucleic acid sequence. Kits can comprise a container comprising a reporter, such as a biotin-binding protein, such as avidin or streptavidin, bound to a reporter molecule, such as an enzymatic, fluorescent, or radioisotope label; such a reporter can be used with, e.g., a nucleic acid or antibody. The kit can include all or part of the amino acid sequences in FIG. 1, FIG. 2, or FIG. 3 or analogs thereof, or a nucleic acid molecule that encodes such amino acid sequences.

The kit of the invention will typically comprise the container described above and one or more other containers associated therewith that comprise materials desirable from a commercial and user standpoint, including buffers, diluents, filters, needles, syringes; carrier, package, container, vial and/or tube labels listing contents and/or instructions for use, and package inserts with instructions for use.

A label can be present on or with the container to indicate that the composition is used for a specific therapy or non-therapeutic application, such as a prognostic, prophylactic, diagnostic or laboratory application, and can also indicate directions for either in vivo or in vitro use, such as those described herein. Directions and or other information can also be included on an insert(s) or label(s) which is included with or on the kit. The label can be on or associated with the container. A label a can be on a container when letters, numbers or other characters forming the label are molded or etched into the container itself; a label can be associated with a container when it is present within a receptacle or carrier that also holds the container, e.g., as a package insert. The label can indicate that the composition is used for diagnosing, treating, prophylaxing or prognosing a condition, such as a neoplasia of a tissue set forth in Table I.

The terms "kit" and "article of manufacture" can be used as synonyms.

In another embodiment of the invention, an article(s) of manufacture containing compositions, such as amino acid sequence(s), small molecule(s), nucleic acid sequence(s), and/or antibody(s), e.g., materials useful for the diagnosis, prognosis, prophylaxis and/or treatment of neoplasias of tissues such as those set forth in Table I is provided. The article of manufacture typically comprises at least one container and at least one label. Suitable containers include, for example, bottles, vials, syringes, and test tubes. The containers can be formed from a variety of materials such as glass, metal or plastic. The container can hold amino acid sequence(s), small molecule(s), nucleic acid sequence(s), cell population(s) and/or antibody(s). In one embodiment, the container holds a polynucleotide for use in examining the mRNA expression profile of a cell, together with reagents used for this purpose. In another embodiment a container comprises an antibody, binding fragment thereof or specific binding protein for use in evaluating protein expression of 24P4C12 in cells and tissues, or for relevant laboratory, prognostic, diagnostic, prophylactic and therapeutic purposes; indications and/or directions for such uses can be included on or with such container, as can reagents and other compositions or tools used for these purposes. In another embodiment, a container comprises materials for eliciting a cellular or humoral immune response, together with associated indications and/or directions. In another embodiment, a container comprises materials for adoptive immunotherapy, such as cytotoxic T cells (CTL) or helper T cells (HTL), together with associated indications and/or directions; reagents and other compositions or tools used for such purpose can also be included.

The container can alternatively hold a composition that is effective for treating, diagnosis, prognosing or prophylaxing a condition and can have a sterile access port (for example the container can be an intravenous solution bag or a vial having a stopper pierceable by a hypodermic injection needle). The active agents in the composition can be an antibody capable of specifically binding 24P4C12 and modulating the function of 24P4C12.

The article of manufacture can further comprise a second container comprising a pharmaceutically-acceptable buffer, such as phosphate-buffered saline, Ringer's solution and/or dextrose solution. It can further include other materials desirable from a commercial and user standpoint, including other buffers, diluents, filters, stirrers, needles, syringes, and/or package inserts with indications and/or instructions for use.

EXAMPLES

Various aspects of the invention are further described and illustrated by way of the several examples that follow, none of which is intended to limit the scope of the invention.

Example 1

Expression Analysis of 24P4C12 Variants in Normal Tissues and Patient Specimens Expression of 24P4C12 was tested in ovarian cancer patient specimens (FIG. 5A). Briefly, RNA was extracted from normal ovary, ovary cancer patient tumors and LAPC-9AD prostate cancer xenograft. Northern blots with 10 ug of total RNA were probed with the 24P4C12 cDNA fragment. Size standards in kilobases are on the side. Results show expression of 24P4C12 in 13 of 16 patient cancer specimens tested. No expression was observed in normal ovary.

Expression of 24P4C12 in breast cancer patient specimens is shown in FIG. 5B. RNA was extracted from normal breast, breast cancer patient tumors and cell lines. Northern blots with 10 ug of total RNA were probed with the 24P4C12 cDNA fragment. Size standards in kilobases are on the side. Results show expression of 24P4C12 in the majority of the patient breast cancer specimens tested and in the cell lines.

FIG. 5C displays expression results of 24P4C12 in pancreatic cancer patient specimens. RNA was extracted from normal pancreas, pancreatic cancer cell lines HPAC, CAPAN-1, CFPAC-1 and pancreatic cancer patient tumor specimens. Northern blots with 10 ug of total RNA were probed with the 24P4C12 cDNA fragment. Size standards in kilobases are on the side. Results show expression of 24P4C12 in 6 of 7 patient pancreatic cancer specimens tested, and in 3 of 4 pancreatic cancer xenografts. Low expression relative to the pancreatic cancer specimens was detected in normal pancreas.

Example 2

Splice Variants of 24P4C12

Transcript variants are variants of mature mRNA from the same gene which arise by alternative transcription or alternative splicing. Alternative transcripts are transcripts from the same gene but start transcription at different points. Splice variants are mRNA variants spliced differently from the same transcript. In eukaryotes, when a multi-exon gene is transcribed from genomic DNA, the initial RNA is spliced to produce functional mRNA, which has only exons and is used for translation into an amino acid sequence. Accordingly, a given gene can have zero to many alternative transcripts and each transcript can have zero to many splice variants. Each transcript variant has a unique exon makeup, and can have different coding and/or non-coding (5' or 3' end) portions, from the original transcript. Transcript variants can code for similar or different proteins with the same or a similar function or can encode proteins with different functions, and can be expressed in the same tissue at the same time, or in different tissues at the same time, or in the same tissue at different times, or in different tissues at different times. Proteins encoded by transcript variants can have similar or different cellular or extracellular localizations, e.g., secreted versus intracellular.

Transcript variants are identified by a variety of art-accepted methods. For example, alternative transcripts and splice variants are identified by full-length cloning experiment, or by use of full-length transcript and EST sequences. First, all human ESTs were grouped into clusters which show direct or indirect identity with each other. Second, ESTs in the same cluster were further grouped into sub-clusters and assembled into a consensus sequence. The original gene sequence is compared to the consensus sequence(s) or other full-length sequences. Each consensus sequence is a potential splice variant for that gene. Even when a variant is identified that is not a full-length clone, that portion of the variant is very useful for antigen generation and for further cloning of the full-length splice variant, using techniques known in the art.

Moreover, computer programs are available in the art that identify transcript variants based on genomic sequences. Genomic-based transcript variant identification programs include FgenesH (A. Salamov and V. Solovyev, "Ab initio gene finding in *Drosophila* genomic DNA," Genome Research. 2000 April; 10(4):516-22); Grail (URL at compbio.ornl.gov/Grail-bin/EmptyGrailForm) and GenScan (URL at genes.mit.edu/GENSCAN.html). For a general discussion of splice variant identification protocols see., e.g., Southan, C., A genomic perspective on human proteases, FEBS Lett. 2001 Jun. 8; 498(2-3):214-8; de Souza, S. J., et al., Identification of human chromosome 22 transcribed sequences with ORF expressed sequence tags, Proc. Natl. Acad Sci USA. 2000 Nov. 7; 97(23):12690-3.

To further confirm the parameters of a transcript variant, a variety of techniques are available in the art, such as full-length cloning, proteomic validation, PCR-based validation, and 5' RACE validation, etc. (see e.g., Proteomic Validation: Brennan, S. O., et al., Albumin banks peninsula: a new termination variant characterized by electrospray mass spectrometry, Biochem Biophys Acta. 1999 Aug. 17; 1433(1-2): 321-6; Ferranti P, et al., Differential splicing of pre-messenger RNA produces multiple forms of mature caprine alpha(s1)-casein, Eur J. Biochem. 1997 Oct. 1; 249(1):1-7. For PCR-based Validation: Wellmann S, et al., Specific reverse transcription-PCR quantification of vascular endothelial growth factor (VEGF) splice variants by LightCycler technology, Clin Chem. 2001 April; 47(4):654-60; Jia, H. P., et al., Discovery of new human beta-defensins using a genomics-based approach, Gene. 2001 Jan. 24; 263(1-2): 211-8. For PCR-based and 5' RACE Validation: Brigle, K. E., et al., Organization of the murine reduced folate carrier gene and identification of variant splice forms, Biochem Biophys Acta. 1997 Aug. 7; 1353(2): 191-8).

It is known in the art that genomic regions are modulated in cancers. When the genomic region to which a gene maps is modulated in a particular cancer, the alternative transcripts or splice variants of the gene are modulated as well. Disclosed herein is that 24P4C12 has a particular expression profile related to cancer. Alternative transcripts and splice variants of 24P4C12 may also be involved in cancers in the same or different tissues, thus serving as tumor-associated markers/antigens. Accordingly, the 24P4C12 MAbs disclosed herein also bind to the 24P4C12 variants disclosed in FIG. 1.

Example 3

Single Nucleotide Polymorphisms of 24P4C12

A Single Nucleotide Polymorphism (SNP) is a single base pair variation in a nucleotide sequence at a specific location. At any given point of the genome, there are four possible nucleotide base pairs: A/T, C/G, G/C and T/A. Genotype refers to the specific base pair sequence of one or more locations in the genome of an individual. Haplotype refers to the base pair sequence of more than one location on the same DNA molecule (or the same chromosome in higher organisms), often in the context of one gene or in the context of several tightly linked genes. SNPs that occur on a cDNA are called cSNPs. These cSNPs may change amino acids of the protein encoded by the gene and thus change the functions of the protein. Some SNPs cause inherited diseases; others contribute to quantitative variations in phenotype and reactions to environmental factors including diet and drugs among individuals. Therefore, SNPs and/or combinations of alleles (called haplotypes) have many applications, including diagnosis of inherited diseases, determination of drug reactions and dosage, identification of genes responsible for diseases, and analysis of the genetic relationship between individuals (P. Nowotny, J. M. Kwon and A. M. Goate, "SNP analysis to dissect human traits," Curr. Opin. Neurobiol. 2001 October; 11(5):637-641; M. Pirmohamed and B. K. Park, "Genetic susceptibility to adverse drug reactions," Trends Pharmacol. Sci. 2001 June; 22(6):298-305; J. H. Riley, C. J. Allan, E. Lai and A. Roses, "The use of single nucleotide polymorphisms in the isolation of common disease genes," Pharmacogenomics. 2000 February; 1(1):39-47; R. Judson, J. C. Stephens and A. Windemuth, "The predictive power of haplotypes in clinical response," Pharmacogenomics. 2000 feb; 1(1):15-26).

SNPs are identified by a variety of art-accepted methods (P. Bean, "The promising voyage of SNP target discovery," Am. Clin. Lab. 2001 October-November; 20(9):18-20; K. M. Weiss, "In search of human variation," Genome Res. 1998 July; 8(7):691-697; M. M. She, "Enabling large-scale pharmacogenetic studies by high-throughput mutation detection and genotyping technologies," Clin. Chem. 2001 February; 47(2):164-172). For example, SNPs are identified by sequencing DNA fragments that show polymorphism by gel-based methods such as restriction fragment length polymorphism (RFLP) and denaturing gradient gel electrophoresis (DGGE). They can also be discovered by direct sequencing of DNA samples pooled from different individuals or by comparing sequences from different DNA samples. With the rapid accumulation of sequence data in public and private databases, one can discover SNPs by comparing sequences using computer programs (Z. Gu, L. Hillier and P. Y. Kwok, "Single nucleotide polymorphism hunting in cyberspace," Hum. Mutat. 1998; 12(4):221-225). SNPs can be verified and genotype or haplotype of an individual can be determined by a variety of methods including direct sequencing and high throughput microarrays (P. Y. Kwok, "Methods for genotyping single nucleotide polymorphisms," Annu. Rev. Genomics Hum. Genet. 2001; 2:235-258; M. Kokoris, K. Dix, K. Moynihan, J. Mathis, B. Erwin, P. Grass, B. Hines and A. Duesterhoeft, "High-throughput SNP genotyping with the Masscode system," Mol. Diagn. 2000 December; 5(4):329-340).

Example 4

Production of Recombinant 24P4C12 in Prokaryotic Systems

To express recombinant 24P4C12 and 24P4C12 variants in prokaryotic cells, the full or partial length 24P4C12 and 24P4C12 variant cDNA sequences are cloned into any one of a variety of expression vectors known in the art. The full length cDNA, or any 5, 6, 7, 8, 9, 10, 11, 12, 13, 14, 15, 16, 17, 18, 19, 20, 21, 22, 23, 24, 25, 26, 27, 28, 29, 30 or more contiguous amino acids from 24P4C12, variants, or analogs thereof are used.

A. In Vitro Transcription and Translation Constructs:

pCRII: To generate 24P4C12 sense and anti-sense RNA probes for RNA in situ investigations, pCRII constructs (Invitrogen, Carlsbad Calif.) are generated encoding either all or fragments of the 24P4C12 cDNA. The pCRII vector has Sp6 and T7 promoters flanking the insert to drive the transcription of 24P4C12 RNA for use as probes in RNA in situ hybridization experiments. These probes are used to analyze the cell and tissue expression of 24P4C12 at the RNA level. Transcribed 24P4C12 RNA representing the cDNA amino acid coding region of the 24P4C12 gene is used in in vitro translation systems such as the TnT™ Coupled Reticulolysate System (Promega, Corp., Madison, Wis.) to synthesize 24P4C12 protein.

B. Bacterial Constructs:

pGEX Constructs: To generate recombinant 24P4C12 proteins in bacteria that are fused to the Glutathione S-transferase (GST) protein, all or parts of the 24P4C12 cDNA or variants are cloned into the GST-fusion vector of the pGEX family (Amersham Pharmacia Biotech, Piscataway, N.J.). These constructs allow controlled expression of recombinant 24P4C12 protein sequences with GST fused at the amino-terminus and a six histidine epitope (6X His) at the carboxyl-terminus. The GST and 6X His tags permit purification of the recombinant fusion protein from induced bacteria with the appropriate affinity matrix and allow recognition of the fusion protein with anti-GST and anti-His antibodies. The 6X His tag is generated by adding 6 histidine codons to the cloning primer at the 3' end, e.g., of the open reading frame (ORF). A proteolytic cleavage site, such as the PreScission™ recognition site in pGEX-6P-1, may be employed such that it permits cleavage of the GST tag from 24P4C12-related protein. The ampicillin resistance gene and pBR322 origin permits selection and maintenance of the pGEX plasmids in E. coli.

pMAL Constructs: To generate, in bacteria, recombinant 24P4C12 proteins that are fused to maltose-binding protein (MBP), all or parts of the 24P4C12 cDNA protein coding sequence are fused to the MBP gene by cloning into the pMAL-c2X and pMAL-p2X vectors (New England Biolabs, Beverly, Mass.). These constructs allow controlled expression of recombinant 24P4C12 protein sequences with MBP fused at the amino-terminus and a 6X His epitope tag at the carboxyl-terminus. The MBP and 6X His tags permit purification of the recombinant protein from induced bacteria with the appropriate affinity matrix and allow recognition of the fusion protein with anti-MBP and anti-His antibodies. The 6X His epitope tag is generated by adding 6 histidine codons to the 3' cloning primer. A Factor Xa recognition site permits cleavage of the pMAL tag from 24P4C12. The pMAL-c2X and pMAL-p2X vectors are optimized to express the recombinant protein in the cytoplasm or periplasm respectively. Periplasm expression enhances folding of proteins with disulfide bonds.

C. Yeast Constructs:

pESC Constructs: To express 24P4C12 in the yeast species *Saccharomyces cerevisiae* for generation of recombinant protein and functional studies, all or parts of the 24P4C12 cDNA protein coding sequence are cloned into the pESC family of vectors each of which contain 1 of 4 selectable markers, HIS3, TRP1, LEU2, and URA3 (Stratagene, La Jolla, Calif.). These vectors allow controlled expression from the same plasmid of up to 2 different genes or cloned sequences containing either Flag™ or Myc epitope tags in the same yeast cell. This system is useful to confirm protein-protein interactions of 24P4C12. In addition, expression in yeast yields similar post-translational modifications, such as glycosylations and phosphorylations that are found when expressed in eukaryotic cells.

pESP Constructs: To express 24P4C12 in the yeast species *Saccharomyces pombe*, all or parts of the 24P4C12 cDNA protein coding sequence are cloned into the pESP family of vectors. These vectors allow controlled high level of expression of a 24P4C12 protein sequence that is fused at either the amino terminus or at the carboxyl terminus to GST which aids purification of the recombinant protein. A Flag™ epitope tag allows detection of the recombinant protein with anti-Flag™ antibody.

Example 5

Production of Recombinant 24P4C12 in Higher Eukaryotic Systems

A. Mammalian Constructs:

To express recombinant 24P4C12 in eukaryotic cells, the full or partial length 24P4C12 cDNA sequences can be cloned into any one of a variety of expression vectors known in the art. One or more of the following regions of 24P4C12 are expressed in these constructs, amino acids 1 to 710, or any 8, 9, 10, 11, 12, 13, 14, 15, 16, 17, 18, 19, 20, 21, 22, 23, 24, 25, 26, 27, 28, 29, 30 or more contiguous amino acids from 24P4C12 v.1 through v.6; amino acids 1 to 598, or any 8, 9, 10, 11, 12, 13, 14, 15, 16, 17, 18, 19, 20, 21, 22, 23, 24, 25, 26, 27, 28, 29, 30 or more contiguous amino acids from 24P4C12 v.7, amino acids 1 to 722, or any 8, 9, 10, 11, 12, 13, 14, 15, 16, 17, 18, 19, 20, 21, 22, 23, 24, 25, 26, 27, 28, 29, 30 or more contiguous amino acids from 24P4C12 v.8, amino acids 1 to 712, or any 8, 9, 10, 11, 12, 13, 14, 15, 16, 17, 18, 19, 20, 21, 22, 23, 24, 25, 26, 27, 28, 29, 30 or more contiguous amino acids from 24P4C12 v.9, variants, or analogs thereof.

The constructs can be transfected into any one of a wide variety of mammalian cells such as 293T cells. Transfected 293T cell lysates can be probed with the anti-24P4C12 polyclonal serum, described herein.

pcDNA3.1/MycHis Constructs: To express 24P4C12 in mammalian cells, a 24P4C12 ORF, or portions thereof, of 24P4C12 with a consensus Kozak translation initiation site was cloned into pcDNA3.1/MycHis Version A (Invitrogen, Carlsbad, Calif.). Protein expression is driven from the cytomegalovirus (CMV) promoter. The recombinant proteins have the myc epitope and 6X His epitope fused to the carboxyl-terminus. The pcDNA3.1/MycHis vector also contains the bovine growth hormone (BGH) polyadenylation signal and transcription termination sequence to enhance mRNA stability, along with the SV40 origin for episomal replication and simple vector rescue in cell lines expressing the large T antigen. The Neomycin resistance gene can be used, as it allows for selection of mammalian cells expressing the protein and the ampicillin resistance gene and ColE1 origin permits selection and maintenance of the plasmid in $E.\ coli$.

pcDNA4/HisMax Constructs: To express 24P4C12 in mammalian cells, a 24P4C12 ORF, or portions thereof, of 24P4C12 are cloned into pcDNA4/HisMax Version A (Invitrogen, Carlsbad, Calif.). Protein expression is driven from the cytomegalovirus (CMV) promoter and the SP16 translational enhancer. The recombinant protein has Xpress™ and six histidine (6X His) epitopes fused to the amino-terminus. The pcDNA4/HisMax vector also contains the bovine growth hormone (BGH) polyadenylation signal and transcription termination sequence to enhance mRNA stability along with the SV40 origin for episomal replication and simple vector rescue in cell lines expressing the large T antigen. The Zeocin resistance gene allows for selection of mammalian cells expressing the protein and the ampicillin resistance gene and ColE1 origin permits selection and maintenance of the plasmid in $E.\ coli$.

pcDNA3.1/CT-GFP-TOPO Construct: To express 24P4C12 in mammalian cells and to allow detection of the recombinant proteins using fluorescence, a 24P4C12 ORF, or portions thereof, with a consensus Kozak translation initiation site are cloned into pcDNA3.1/CT-GFP-TOPO (Invitrogen, CA). Protein expression is driven from the cytomegalovirus (CMV) promoter. The recombinant proteins have the Green Fluorescent Protein (GFP) fused to the carboxyl-terminus facilitating non-invasive, in vivo detection and cell biology studies. The pcDNA3.1CT-GFP-TOPO vector also contains the bovine growth hormone (BGH) polyadenylation signal and transcription termination sequence to enhance mRNA stability along with the SV40 origin for episomal replication and simple vector rescue in cell lines expressing the large T antigen. The Neomycin resistance gene allows for selection of mammalian cells that express the protein and the ampicillin resistance gene and ColE1 origin permits selection and maintenance of the plasmid in $E.\ coli$. Additional constructs with an amino-terminal GFP fusion are made in pcDNA3.1/NT-GFP-TOPO spanning the entire length of a 24P4C12 protein.

pTag5: A 24P4C12 ORF, or portions thereof, were cloned into pTag-5. This vector is similar to pAPtag but without the alkaline phosphatase fusion. This construct generates 24P4C12 protein with an amino-terminal IgGκ signal sequence and myc and 6X His epitope tags at the carboxyl-terminus that facilitate detection and affinity purification. The resulting recombinant 24P4C12 protein were optimized for secretion into the media of transfected mammalian cells, and is used as immunogen or ligand to identify proteins such as ligands or receptors that interact with the 24P4C12 proteins. Protein expression is driven from the CMV promoter. The Zeocin resistance gene present in the vector allows for selection of mammalian cells expressing the protein, and the ampicillin resistance gene permits selection of the plasmid in $E.\ coli$.

PAPtag: A 24P4C12 ORF, or portions thereof, is cloned into pAPtag-5 (GenHunter Corp. Nashville, Tenn.). This construct generates an alkaline phosphatase fusion at the carboxyl-terminus of a 24P4C12 protein while fusing the IgGK signal sequence to the amino-terminus. Constructs are also generated in which alkaline phosphatase with an amino-terminal IgGK signal sequence is fused to the amino-terminus of a 24P4C12 protein. The resulting recombinant 24P4C12 proteins are optimized for secretion into the media of transfected mammalian cells and can be used to identify proteins such as ligands or receptors that interact with 24P4C12 proteins. Protein expression is driven from the CMV promoter and the recombinant proteins also contain myc and 6X His epitopes fused at the carboxyl-terminus that facilitates detection and purification. The Zeocin resistance gene present in the vector allows for selection of mammalian cells expressing the recombinant protein and the ampicillin resistance gene permits selection of the plasmid in $E.\ coli$.

PsecFc: A 24P4C12 ORF, or portions thereof, is also cloned into psecFc. The psecFc vector was assembled by cloning the human immunoglobulin GI (IgG) Fc (hinge, $CH_2$, CH3 regions) into pSecTag2 (Invitrogen, California). This construct generates an IgG1 Fc fusion at the carboxyl-terminus of the 24P4C12 proteins, while fusing the IgGK signal sequence to N-terminus. 24P4C12 fusions utilizing the murine IgG1 Fc region are also used. The resulting recombinant 24P4C12 proteins are optimized for secretion into the media of transfected mammalian cells, and can be used as immunogens or to identify proteins such as ligands or receptors that interact with 24P4C12 protein. Protein expression is driven from the CMV promoter. The hygromycin resistance gene present in the vector allows for selection of mammalian cells that express the recombinant protein, and the ampicillin resistance gene permits selection of the plasmid in $E.\ coli$.

pSRα Constructs: To generate mammalian cell lines that express 24P4C12 constitutively, 24P4C12 ORF, or portions thereof, of 24P4C12 were cloned into pSRα constructs. Amphotropic and ecotropic retroviruses were generated by transfection of pSRα constructs into the 293T-10A1 packaging line or co-transfection of pSRα and a helper plasmid (containing deleted packaging sequences) into the 293 cells, respectively. The retrovirus is used to infect a variety of mammalian cell lines, resulting in the integration of the cloned gene, 24P4C12, into the host cell-lines. Protein expression is driven from a long terminal repeat (LTR). The Neomycin resistance gene present in the vector allows for selection of mammalian cells that express the protein, and the ampicillin resistance gene and ColE1 origin permit selection and maintenance of the plasmid in *E. coli*. The retroviral vectors can thereafter be used for infection and generation of various cell lines using, for example, PC3, NIH 3T3, TsuPr1, 293 or rat-1 cells.

Additional pSRα constructs are made that fuse an epitope tag such as the FLAG™ tag to the carboxyl-terminus of 24P4C12 sequences to allow detection using anti-Flag antibodies. For example, the FLAG™ sequence 5' gat tac aag gat gac gac gat aag 3' (SEQ ID NO: 172) is added to cloning primer at the 3' end of the ORF. Additional pSRα constructs are made to produce both amino-terminal and carboxyl-terminal GFP and myc/6X His fusion proteins of the full-length 24P4C12 proteins.

Additional Viral Vectors: Additional constructs are made for viral-mediated delivery and expression of 24P4C12. High virus titer leading to high level expression of 24P4C12 is achieved in viral delivery systems such as adenoviral vectors and herpes amplicon vectors. A 24P4C12 coding sequences or fragments thereof are amplified by PCR and subcloned into the AdEasy shuttle vector (Stratagene). Recombination and virus packaging are performed according to the manufacturer's instructions to generate adenoviral vectors. Alternatively, 24P4C12 coding sequences or fragments thereof are cloned into the HSV-1 vector (Imgenex) to generate herpes viral vectors. The viral vectors are thereafter used for infection of various cell lines such as PC3, NIH 3T3, 293 or rat-1 cells.

Regulated Expression Systems: To control expression of 24P4C12 in mammalian cells, coding sequences of 24P4C12, or portions thereof, are cloned into regulated mammalian expression systems such as the T-Rex System (Invitrogen), the GeneSwitch System (Invitrogen) and the tightly-regulated Ecdysone System (Sratagene). These systems allow the study of the temporal and concentration dependent effects of recombinant 24P4C12. These vectors are thereafter used to control expression of 24P4C12 in various cell lines such as PC3, NIH 3T3, 293 or rat-1 cells.

B. Baculovirus Expression Systems

To generate recombinant 24P4C12 proteins in a baculovirus expression system, 24P4C12 ORF, or portions thereof, are cloned into the baculovirus transfer vector pBlueBac 4.5 (Invitrogen), which provides a His-tag at the N-terminus. Specifically, pBlueBac-24P4C12 is co-transfected with helper plasmid pBac-N-Blue (Invitrogen) into SF9 (*Spodoptera frugiperda*) insect cells to generate recombinant baculovirus (see Invitrogen instruction manual for details). Baculovirus is then collected from cell supernatant and purified by plaque assay.

Recombinant 24P4C12 protein is then generated by infection of HighFive insect cells (Invitrogen) with purified baculovirus. Recombinant 24P4C12 protein can be detected using anti-24P4C12 or anti-His-tag antibody. 24P4C12 protein can be purified and used in various cell-based assays or as immunogen to generate polyclonal and monoclonal antibodies specific for 24P4C12.

Example 6

Antigenicity Profiles and Secondary Structure

24P4C12 antigenicity profiles, Hydrophilicity, (Hopp T. P., Woods K. R., 1981. Proc. Natl. Acad. Sci. U.S.A. 78:3824-3828); Hydropathicity, (Kyte J., Doolittle R. F., 1982. J. Mol. Biol. 157:105-132); Percentage Accessible Residues (Janin J., 1979 Nature 277:491-492); Average Flexibility, (Bhaskaran R., and Ponnuswamy P. K., 1988. Int. J. Pept. Protein Res. 32:242-255); Beta-turn (Deleage, G., Roux B. 1987 Protein Engineering 1:289-294); and optionally others available in the art, such as on the ProtScale website, were used to identify antigenic regions of the 24P4C12 protein. Each of the above amino acid profiles of 24P4C12 were generated using the following ProtScale parameters for analysis: 1) A window size of 9; 2) 100% weight of the window edges compared to the window center; and, 3) amino acid profile values normalized to lie between 0 and 1.

Hydrophilicity, Hydropathicity and Percentage Accessible Residues profiles were used to determine stretches of hydrophilic amino acids (i.e., values greater than 0.5 on the Hydrophilicity and Percentage Accessible Residues profile, and values less than 0.5 on the Hydropathicity profile). Such regions are likely to be exposed to the aqueous environment, be present on the surface of the protein, and thus available for immune recognition, such as by antibodies.

Average Flexibility and Beta-turn profiles determine stretches of amino acids (i.e., values greater than 0.5 on the Beta-turn profile and the Average Flexibility profile) that are not constrained in secondary structures such as beta sheets and alpha helices. Such regions are also more likely to be exposed on the protein and thus accessible to immune recognition, such as by antibodies.

Antigenic sequences of the 24P4C12 protein and of the variant proteins indicated, e.g., by the profiles are used to prepare immunogens, either peptides or nucleic acids that encode them, to generate therapeutic and diagnostic anti-24P4C12 antibodies. The immunogen can be any 5, 6, 7, 8, 9, 10, 11, 12, 13, 14, 15, 16, 17, 18, 19, 20, 21, 22, 23, 24, 25, 30, 35, 40, 45, 50 or more than 50 contiguous amino acids, or the corresponding nucleic acids that encode them, from the 24P4C12 protein variants listed in FIG. 1. In particular, peptide immunogens of the invention can comprise, a peptide region of at least 5 amino acids of FIG. 1 in any whole number increment that includes an amino acid position having a value greater than 0.5 in the Hydrophilicity profile; a peptide region of at least 5 amino acids of FIG. 1 in any whole number increment that includes an amino acid position having a value less than 0.5 in the Hydropathicity profile; a peptide region of at least 5 amino acids of FIG. 1 in any whole number increment that includes an amino acid position having a value greater than 0.5 in the Percent Accessible Residues profile; a peptide region of at least 5 amino acids of FIG. 1 in any whole number increment that includes an amino acid position having a value greater than 0.5 in the Average Flexibility profile; and, a peptide region of at least 5 amino acids of FIG. 1 in any whole number increment that includes an amino acid position having a value greater than 0.5 in the Beta-turn profile. Peptide immunogens of the invention can also comprise nucleic acids that encode any of the forgoing.

All immunogens of the invention, peptide or nucleic acid, can be embodied in human unit dose form, or comprised by a composition that includes a pharmaceutical excipient compatible with human physiology.

Analysis for the potential presence of transmembrane domains in 24P4C12 variants were carried out using a variety of transmembrane prediction algorithms accessed from the ExPasy molecular biology server.

Example 7

Generation of 24P4C12 Polyclonal Antibodies

Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. In addition to immunizing with the full length 24P4C12 protein, computer algorithms are employed in design of immunogens that, based on amino acid sequence analysis contain characteristics of being antigenic and available for recognition by the immune system of the immunized host (see the Example entitled "Antigenicity Profiles and Secondary Structure"). Such regions would be predicted to be hydrophilic, flexible, in beta-turn conformations, and be exposed on the surface of the protein.

For example, 24P4C12 recombinant bacterial fusion proteins or peptides containing hydrophilic, flexible, beta-turn regions of 24P4C12 variant proteins are used as antigens to generate polyclonal antibodies in New Zealand White rabbits. For example, such regions include, but are not limited to, amino acids 1-34, amino acids 118-135, amino acids 194-224, amino acids 280-290, and amino acids 690-710, of 24P4C12 variants 1. It is useful to conjugate the immunizing agent to a protein known to be immunogenic in the mammal being immunized. Examples of such immunogenic proteins include, but are not limited to, keyhole limpet hemocyanin (KLH), serum albumin, bovine thyroglobulin, and soybean trypsin inhibitor. In one embodiment, a peptide encoding amino acids 1-14 of 24P4C12 variant 1 was conjugated to KLH and used to immunize a rabbit. This antiserum exhibited a high titer to the peptide (>10,000) and recognized 24P4C12 in transfected 293T cells by Western blot and flow cytometry (FIG. 24) and in stable recombinant PC3 cells by Western blot and immunohistochemistry (FIG. 25). Alternatively the immunizing agent may include all or portions of the 24P4C12 variant proteins, analogs or fusion proteins thereof. For example, the 24P4C12 variant 1 amino acid sequence can be fused using recombinant DNA techniques to any one of a variety of fusion protein partners that are well known in the art, such as glutathione-5-transferase (GST) and HIS tagged fusion proteins. Such fusion proteins are purified from induced bacteria using the appropriate affinity matrix.

In one embodiment, a GST-fusion protein encoding amino acids 379-453, encompassing the third predicted extracellular loop of variant 1, is produced, purified, and used as immunogen. Other recombinant bacterial fusion proteins that may be employed include maltose binding protein, LacZ, thioredoxin, NusA, or an immunoglobulin constant region (see the section entitled "Production of 24P4C12 in Prokaryotic Systems" and Current Protocols In Molecular Biology, Volume 2, Unit 16, Frederick M. Ausubul et al. eds., 1995; Linsley, P. S., Brady, W., Urnes, M., Grosmaire, L., Damle, N., and Ledbetter, L. (1991) J. Exp. Med. 174, 561-566).

In addition to bacterial derived fusion proteins, mammalian expressed protein antigens are also used. These antigens are expressed from mammalian expression vectors such as the Tag5 and Fc-fusion vectors (see the Example entitled "Production of Recombinant 24P4C12 in Eukaryotic Systems"), and retains post-translational modifications such as glycosylations found in native protein. Each recombinant protein is then purified by metal chelate chromatography from tissue culture supernatants and/or lysates of 293T cells stably expressing the recombinant vector. The purified Tag5 24P4C12 protein is then used as immunogen.

During the immunization protocol, it is useful to mix or emulsify the antigen in adjuvants that enhance the immune response of the host animal. Examples of adjuvants include, but are not limited to, complete Freund's adjuvant (CFA) and MPL-TDM adjuvant (monophosphoryl Lipid A, synthetic trehalose dicorynomycolate).

In a typical protocol, rabbits are initially immunized subcutaneously with up to 200 µg, typically 100-200 µg, of fusion protein or peptide conjugated to KLH mixed in complete Freund's adjuvant (CFA). Rabbits are then injected subcutaneously every two weeks with up to 200 µg, typically 100-200 µg, of the immunogen in incomplete Freund's adjuvant (IFA). Test bleeds are taken approximately 7-10 days following each immunization and used to monitor the titer of the antiserum by ELISA.

Anti-serum from rabbits immunized with 24P4C12 variant fusion proteins, such as GST and MBP fusion proteins, are purified by depletion of antibodies reactive to the fusion partner sequence by passage over an affinity column containing the fusion partner either alone or in the context of an irrelevant fusion protein. For example, antiserum derived from a GST-24P4C12 fusion protein encoding amino acids 379-453 of variant 1 is first purified by passage over a column of GST protein covalently coupled to AffiGel matrix (BioRad, Hercules, Calif.). The antiserum is then affinity purified by passage over a column composed of a MBP-fusion protein also encoding amino acids 379-453 covalently coupled to Affigel matrix. The serum is then further purified by protein G affinity chromatography to isolate the IgG fraction. Sera from other His-tagged antigens and peptide immunized rabbits as well as fusion partner depleted sera are affinity purified by passage over a column matrix composed of the original protein immunogen or free peptide.

Example 8

Generation of 24P4C12 Monoclonal Antibodies (MAbs)

In one embodiment, therapeutic Monoclonal Antibodies ("MAbs") to 24P4C12 and 24P4C12 variants comprise those that react with epitopes specific for each protein or specific to sequences in common between the variants that would bind, internalize, disrupt or modulate the biological function of 24P4C12 or 24P4C12 variants, for example, those that would disrupt the interaction with ligands, substrates, and binding partners. Immunogens for generation of such MAbs include those designed to encode or contain the extracellular domains or the entire 24P4C12 protein sequence, regions predicted to contain functional motifs, and regions of the 24P4C12 protein variants predicted to be antigenic from computer analysis of the amino acid sequence. Immunogens include peptides and recombinant proteins such as tag5-24P4C12, a purified mammalian cell derived His tagged protein. In addition, cells engineered to express high levels of 24P4C12, such as RAT1-24P4C12 or 300.19-24P4C12, are used to immunize mice.

To generate MAbs to 24P4C12, mice are first immunized with 1-50 µg of protein immunogen or between $10^6$ and $10^7$ 24P4C12-expressing cells mixed in a suitable adjuvant. Examples of suitable adjuvants for immunizations are Titer-Max (Sigma) and alum gel. Following an initial injection, mice are immunized twice a week until they are ready to be selected for fusions. When mice are ready for fusions (see below), B cells are harvested either from lymph nodes or spleen. Harvested B cells are mixed with a standard mouse derived fusion partner and cells are fused using electro-cell fusion (ECF).

In the course of the immunizations test bleeds are taken to monitor the titer and specificity of the immune response. In most cases, once appropriate reactivity and specificity are obtained as determined by ELISA, Western blotting, immunoprecipitation, fluorescence microscopy or flow cytometric analyses, fusion and hybridoma generation are then carried out using electrocell fusion (ECF).

In one embodiment, the invention provides for monoclonal antibodies designated: Ha5-1(5)1, Ha5-1(5)2.1, Ha5-3(1,4) 2.1, Ha5-3(1,4)7.1, Ha5-3(3,5)37.1, Ha5-4(2,5)13.1, Ha5-4 (2,5)34.1, Ha5-7acd4.1, Ha5-7acd20.1.1, Ha5-7be31.1, Ha5-7acd10.1, Ha5-7acd13.1, Ha5-7acd19.1, Ha5-7be37.1, Ha5-7acd16.1, Ha5-7acd7.1.1, Ha5-7be20.1, Ha5-7acd5.1.1, Ha5-7be34.1, Ha5-7acd3.1, Ha5-7acd2.1, Ha5-8ac4.1, Ha5-4(2,5)31.1, Ha5-11a1.1.1, Ha5-11b1.1, and Ha5-7be7.1.

MAbs to 24P4C12 were generated using XenoMouse Technology® (Amgem Fremont) wherein the murine heavy and kappa light chain loci have been inactivated and a majority of the human heavy and kappa light chain immunoglobulin loci have been inserted. MAbs designated Ha5-3(1,4)2.1, Ha5-3(1,4)7.1, Ha5-3(3,5)37.1, Ha5-7acd4.1, Ha5-7acd20.1.1, Ha5-7be31.1, Ha5-7acd10.1, Ha5-7acd13.1, Ha5-7acd19.1, Ha5-7be37.1, Ha5-7acd16.1, Ha5-7acd7.1.1, Ha5-7be20.1, Ha5-7acd5.1.1, Ha5-7be34.1, Ha5-7acd3.1, Ha5-7acd2.1, Ha5-8ac4.1, Ha5-4(2,5)31.1, Ha5-11a1.1.1, Ha5-11b1.1, and Ha5-7be7.1 were generated from immunization of human γ1 producing XenoMice with RAT(E)-24P4C12 cells. MAbs designated Ha5-1(5)1 and Ha5-1(5) 2.1 were generated from immunization of human γ2 producing XenoMice with B300.19-24P4C12 cells. MAbs designated Ha5-4(2,5)13.1 and Ha5-4(2,5)34.1 were generated from immunization with human γ1 producing XenoMice with purified tag5-24P4C12 (aa 59-227).

The 24P4C12 MAbs Ha5-1(5)1, Ha5-1(5)2.1, Ha5-3(1,4) 2.1, Ha5-3(1,4)7.1, Ha5-3(3,5)37.1, Ha5-7acd4.1, Ha5-7acd20.1.1, Ha5-7be31.1, Ha5-7acd10.1, Ha5-7acd13.1, Ha5-7acd19.1, Ha5-7be37.1, Ha5-7acd16.1, Ha5-7acd7.1.1, Ha5-7be20.1, Ha5-7acd5.1.1, Ha5-7be34.1, Ha5-7acd3.1, Ha5-7acd2.1, Ha5-8ac4.1, and Ha5-7be7.1 specifically bind to recombinant 24P4C12 expressing cells (PC3-24P4C12) and multiple cancer cell lines expressing 24P4C12 (FIG. 6).

The antibodies designated Ha5-1(5)1, Ha5-1(5)2.1, Ha5-3(1,4)7.1, Ha5-7acd10.1, Ha5-7acd16.1, and Ha5-11b1.1 were sent (via Federal Express) to the American Type Culture Collection (ATCC), P.O. Box 1549, Manassas, Va. 20108 on 8 Aug. 2007 and assigned Accession numbers PTA-8598, PTA-8602, PTA-8597, PTA-8601, PTA-8600, PTA-8599, respectively.

DNA coding sequences for 24P4C12 MAbs Ha5-1(5)1, Ha5-1(5)2.1, Ha5-3(1,4)2.1, Ha5-3(1,4)7.1, Ha5-3(3,5)37.1, Ha5-4(2,5)13.1, Ha5-4(2,5)34.1, Ha5-7acd4.1, Ha5-7acd20.1.1, Ha5-7be31.1, Ha5-7acd10.1, Ha5-7acd13.1, Ha5-7acd19.1, Ha5-7be37.1, Ha5-7acd16.1, Ha5-7acd7.1.1, Ha5-7be20.1, Ha5-7acd5.1.1, Ha5-7be34.1, Ha5-7acd3.1, Ha5-7acd2.1, Ha5-8ac4.1, Ha5-4(2,5)31.1, Ha5-11a1.1.1, Ha5-11b1.1, and Ha5-7be7.1 were determined after isolating mRNA from the respective hybridoma cells with Trizol reagent (Life Technologies, Gibco BRL).

Anti-24P4C12 heavy and light chain variable nucleic acid sequences were sequenced from the hybridoma cells using the following protocol. Anti-24P4C12 secreting hybridoma cells were lysed with Trizol reagent (Life Technologies, Gibco BRL). Total RNA was purified and quantified. First strand cDNAs was generated from total RNA with oligo (dT)12-18 priming using the Gibco-BRL Superscript Preamplification system. First strand cDNA was amplified using human immunoglobulin variable heavy chain primers, and human immunoglobulin variable light chain primers. PCR products were sequenced and the variable heavy and light chain regions determined.

The nucleic acid and amino acid sequences of the variable heavy and light chain regions are listed in FIG. 2 and FIG. 3. Alignment of 24P4C12 antibodies to human Ig germline is set forth in FIG. 4A-4AY.

Example 9

Screening, Identification, and Characterization of 24P4C12 MAbs

Antibodies generated using the procedures set forth in the example entitled "Generation of 24P4C12 Monoclonal Antibodies (MAbs)" were screened, identified, and characterized using a combination of assays including ELISA, FACS, affinity ranking by Surface Plasmon Resonance (BIAcore) ("SPR"), epitope grouping, affinity to recombinant 24P4C12, and 24P4C12 expressed on the cell surface.

24P4C12 Human MAb Screening by FACS.

Primary hybridoma screening for MAbs to 24P4C12 is performed by FACS analysis. The protocol is as follows: 50 μl/well of hybridoma supernatant (neat) or purified antibodies (in serial dilutions) are added to 96-well FACS plates and mixed with 24P4C12-expressing cells (endogenous or recombinant, 50,000 cells/well). The mixture is incubated at 4° C. for two hours. At the end of incubation, the cells are washed with FACS Buffer and incubated with 100 μl of detection antibody (anti-hIgG-PE) for 45 minutes at 4° C. At the end of incubation, the cells are washed with FACS Buffer, fixed with Formaldehyde and analyzed using FACScan. Data are analyzed using CellQuest Pro software.

Positive hybridomas identified from primary screens are transferred to 24-well plates and supernatants collected for confirmatory screens.

B. 24P4C12 Human MAb Screening by ELISA.

24P4C12 MAbs are screened by ELISA to determine antibody isotype. The protocol used is as follows, ELISA plates are coated with Tag5-24P4C12-ECD or anti-hIgG antibody. Several sets of testing antibodies are added on the plates and incubated for 1 hour. After washing the plates to wash out unbound antibodies, bound antibodies are detected by the following HRP conjugated detection antibodies: anti-hIgG1, anti-hIgG2, anti-hIgK, and anti-hIgL.

C. 24P4C12 Human MAb Screening by SPR.

SPR allows identification and real time characterization of the kinetics and affinity of protein-protein interactions and therefore is a useful technique in the selection and characterization of MAbs to target antigens of interest (i.e. 24P4C12). SPR analysis is employed to screen and characterize hybridoma supernatants and purified MAbs to 24P4C12. Hybridoma screening for MAbs to 24P4C12 by SPR biosensor (BIAcore 3000) are performed as follows: 50 μl/well of hybridoma supernatant (neat) diluted to 1.5-2 μg/ml with the running buffer (HBS-P, 10 ug/ml BSA) are added to 96-well plates (BIAcore) and MAbs (20 μl) are captured on goat-anti-human Fcγ pAbs covalently immobilized on the surface of the CM5 sensor chip. Three (3) MAbs containing hybridoma supernatants are tested per run (cycle) on channels 2, 3 and 4 of the flow cell, where channel 1 is reserved as reference for non-specific binding. Prior to measuring antigen binding to captured MAbs in each individual channel, 60 μl of running buffer is injected over the chip surface at the flowrate of 20

μl/min to serve as reference for drift in captured MAb baseline. Sixty microliters (60 μl) of the purified recombinant 161P2F10B at 150 nM is then injected over the chip surface at the same flowrate of 20 μl/min to measure antigen binding. Each cycle of antigen binding to MAbs are followed by surface regeneration with injection of 100 mM phosphoric acid (for 1 min) to strip the surface of any captured MAb.

Data analysis is performed using BiaEvaluation 4.1 and CLAMP software (Myszka and Morton, 1998). After subtracting the references and normalizing the response to the level of captured MAb, data is fit globally using a 1:1 binding model.

The affinities are calculated from the association and dissociation rate constants. As is apparent to one of ordinary skill in the art, slow dissociation rates generally indicate higher overall affinity for MAbs. The preliminary affinity data and dissociation rates are used as a basis of the selection criteria for therapeutic MAbs to 24P4C12.

D. Epitope Grouping by FACS

24P4C12 antibodies were grouped according to epitope by evaluating their binding pattern using Rat1-24P4C12 cells. In brief, a small amount of each of the antibodies were biotinylated; then each of the biotinylated antibodies were incubated with Rat1-24P4C12 in the presence of excess (100×) amount of non-biotinylated antibodies at 4° C. for 1 hour. One of ordinary skill in the art will understand that during the incubation, an excess amount of antibodies will compete with biotinylated antibodies if they bind to the same epitope. At the end of incubation, cells were washed and incubated with Streptavidin-PE for 45 min at 4° C. After washing off the unbound streptavidin-PE, the cells were analyzed using FACS. MFI values were obtained using CellQuest Pro software and were used for data analysis. As described, twenty-eight (28) 24P4C12 MAbs were epitope grouped using Rat1-24P4C12 cells. The results show the antibodies that have the same binding pattern bind to the same epitope among the antibodies and that there are 17 epitope groups within the antibodies tested. The listing of the 24P4C12 MAbs and there respective epitope group are shown in Table VI.

E. Affinity Determination by FACS

A panel of 24 human 24P4C12 MAbs were tested for their binding affinity to 24P4C12 on LNCaP cells. The affinity to LNCaP cells was determined by FACS using saturation equilibrium binding assay. The 24P4C12 MAbs were serially diluted in FACS Buffer and incubated with LNCaP cells with final concentration of 160 to 0.003 nM at 4° C. for 16 hours. At the end of incubation, the cells were washed with FACS Buffer and incubated with 100 ul of detection antibody (anti-hIgG-PE) for 45 minutes at 4° C., the cells were then washed with FACS Buffer, fixed with 2% Formaldehyde and analyzed using FACScan. FACS data were analyzed using CellQuest Pro software to acquire histogram and Mean Fluoresces Intensity (MFI) values of each point. The MFI values were used to calculate the binding affinity using non-linear regression using Prism4 software (Graphpad Software Inc. San Diego Calif.). A summary of affinity values of twenty-four (24) antibodies are set forth in Table VI.

F. Affinity Determination by SPR

Panels of purified anti-human 24P4C12 MAbs are tested for their binding affinity to the purified recombinant 24P4C12 by SPR. Briefly, each purified human MAb is captured onto a CM5 sensor chip surface. On average approximately 150 RUs of each MAb is captured in every cycle. A series of 5-6 dilutions of recombinant 24P4C12 ranging from 1 nM to 100 nM is injected over such surface to generate binding curves (sensograms) that are globally fit to a 1:1 interaction model using CLAMP software (Myszka and Morton, 1998). The affinity of several 24P4C12 MAbs, expressed as $K_D$, defined by dissociation rate constant and association rate constant using the equation $K_D = k_{diss}/k_{assoc}$ is determined.

G. Cross Reactivity with Cynnomolgous Monkey 24P4C12

24P4C12 MAbs are screened and characterized for their ability to react with 24P4C12 of monkey origin. This property is useful to understand the expression of 24P4C12 on tissues from different monkey species for toxicological purposes. The cynomolgous monkey 24P4C12 gene was cloned and sequenced. The homology to human 24P4C12 is 96.8% (FIG. 7). It is shown that 24P4C12 MAbs specifically bind to cynomolgus 24P4C12 protein present on the surface of the cells (FIG. 8).

Example 10

Antibody Immune Mediated Cytotoxicity

ADCC (Antibody-Dependent Cellular Cytotoxicity) is an immune mediated lytic attack on cells bound with an antibody targeted to a specific cell surface antigen. Immune cells recognize the Fc portion of the antibody through binding to Fcã receptors on the surface of leukocytes, monocytes, and NK cells triggering a lytic attack that result in cell death. Briefly, Caki cells engineered to express the target antigen 24P4C12 are incubated in vitro with 51chromium for 1 hr. After washing with fresh medium, the labeled cells are incubated with 2.5 mg/ml human MAbs directed to 24P4C12 and freshly isolated peripheral blood mono nuclear cells at different effector to target cell ratios (E:T Ratio). After 4 hours at 37 C, the cells are gently centrifuged and the supernatant containing 51Cr released from the dead cells is counted in a Beta counter.

The results demonstrate that antibody dependent cell killing increases when the effector to target (E:T) cell ratio increases. The specificity of the assay is determined by showing that an irrelevant IgG1 Control MAb and incubation of target cells and effector cells in the absence of antibody (Cells+PBMCs) do not cause cell killing.

Example 11

Antibody Mediated Secondary Killing

Antibodies to 24P4C12 mediate saporin dependent killing in PC3-24P4C12 cells. Briefly, PC3-24P4C12 or PC3-Neo cells (500 cells/well) were seeded into a 96 well plate on day 1. The following day an equal volume of medium containing 2× concentration of the indicated primary antibody together with a 2 fold excess of anti-human (Hu-Sap) or anti-goat (Gt-Sap) polyclonal antibody conjugated with saporin toxin (Advanced Targeting Systems, San Diego, Calif.) was added to each well. The cells were allowed to incubate for 5 days at 37 degrees C. At the end of the incubation period, Alamar Blue was added to each well and incubation continued for an additional 4 hours. The fluorescence of each well was determined in a plate reader using an excitation wavelength of 530 nm and an emission wavelength of 590 nm.

The results show that 24P4C12 antibodies HA5-1(5)1.1, HA5-1(5)2.1 and HA5-acd16.1 mediated saporin dependent cytotoxicity in PC3 cells expressing 24P4C12 but not in PC3 cells infected with the Neo gene alone. To further demonstrate specificity, the same primary 24P4C12 antibodies were incubated with a 2 fold excess of saporin conjugated goat polyclonal antibody. These results indicate that drugs or cytotoxic proteins can selectively be delivered to cells expressing 24P4C12 using an appropriate anti-24P4C12 MAb.

Example 12

Generation of F(Ab')2 Fragments

Generation of F(Ab')2 fragments of MAbs is useful to study the effects of MAb molecules that retain their bivalent antigen binding site but lack the immune effector Fc domain in in vitro and in vivo therapeutic models. Generally, the protocol is as follows, 20 mgs of MAb in 20 mM sodium acetate buffer pH 4.5 is incubated with and without immobilized pepsin (Pierce. Rockford Ill.) for the indicated times. Intact MAb and digested Fc fragments are removed by protein A chromatography. The reagent can be used to treat animals bearing 24P4C12 expressing tumors. The anti-tumor activity observed with this antibody fragment can distinguish intrinsic biologic activity from activity mediated by immune dependent mechanisms.

Example 13

Expression of Human MAbs Using Recombinant DNA Methods

To express 24P4C12 MAbs recombinantly in transfected cells, 24P4C12 MAb variable heavy and light chain sequences are cloned upstream of the human heavy chain IgG1 and light chain Igκ constant regions respectively. The complete 24P4C12 MAb human heavy chain and light chain cassettes are cloned downstream of the CMV promoter/enhancer in a cloning vector. A polyadenylation site is included downstream of the MAb coding sequence. The recombinant 24P4C12 MAb expressing constructs are transfected into 293T, Cos and CHO cells. The 24P4C12 MAbs secreted from recombinant cells are evaluated for binding to cell surface 24P4C12.

Example 14

In Vivo Assay for 24P4C12 Tumor Growth Promotion

The effect of the 24P4C12 protein on tumor cell growth is evaluated in vivo by evaluating tumor development and growth of cells expressing or lacking 24P4C12. For example, SCID mice are injected subcutaneously on each flank with $1 \times 10^6$ of colon cancer cell lines containing tkNeo empty vector or 24P4C12. At least two strategies may be used: (1) Constitutive 24P4C12 expression under regulation of a promoter such as a constitutive promoter obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), or from heterologous mammalian promoters, e.g., the actin promoter or an immunoglobulin promoter, provided such promoters are compatible with the host cell systems, and (2) Regulated expression under control of an inducible vector system, such as ecdysone, tetracycline, etc., provided such promoters are compatible with the host cell systems. Tumor volume is then monitored by caliper measurement at the appearance of palpable tumors and followed over time to determine if 24P4C12-expressing cells grow at a faster rate and whether tumors produced by 24P4C12-expressing cells demonstrate characteristics of altered aggressiveness (e.g. enhanced metastasis, vascularization, reduced responsiveness to chemotherapeutic drugs).

Additionally, mice can be implanted with $1 \times 10^5$ of the same cells orthotopically to determine if 24P4C12 has an effect on local growth in the colon, and whether 24P4C12 affects the ability of the cells to metastasize (Miki T et al, Oncol Res. 2001; 12:209; Fu X et al, Int J Cancer. 1991; 49:938). The effect of 24P4C12 on tumor formation and growth may be assessed by injecting colon tumor cells intratibially.

The assay is also useful to determine the 24P4C12 inhibitory effect of candidate therapeutic compositions, such as for example, 24P4C12 intrabodies, 24P4C12 antisense molecules, and ribozymes.

Example 15

24P4C12 Monoclonal Antibody-Mediated Inhibition of Tumors In Vivo

The significant expression of 24P4C12 on the cell surface of tumor tissues, together with its restrictive expression in normal tissues makes 24P4C12 a good target for antibody therapy. Similarly, 24P4C12 is a target for T cell-based immunotherapy. Thus, the therapeutic efficacy of 24P4C12 MAbs in human cancer xenograft mouse models is evaluated by using multiple cancer cell lines such as PC3-24P4C12, LNCaP, LAPC9, 22RV1, OVCaR-5, HT29, Calu-1, and CF-PAC.

Antibody efficacy on tumor growth and metastasis formation is studied, e.g., in a mouse orthotopic cancer xenograft model. The antibodies can be unconjugated, as discussed in this Example, or can be conjugated to a therapeutic modality, as appreciated in the art. 24P4C12 MAbs inhibit formation of colon cancer xenografts. 24P4C12 MAbs also retard the growth of established orthotopic tumors and prolonged survival of tumor-bearing mice. These results indicate the utility of 24P4C12 MAbs in the treatment of local and advanced stages of colon cancer and those cancers set forth in Table I.

Administration of the 24P4C12 MAbs led to retardation of established orthotopic tumor growth and inhibition of metastasis to distant sites, resulting in a significant prolongation in the survival of tumor-bearing mice. These studies indicate that 24P4C12 is an attractive target for immunotherapy and demonstrate the therapeutic potential of 24P4C12 MAbs for the treatment of local and metastatic colon cancer. This example demonstrates that unconjugated 24P4C12 MAbs are effective to inhibit the growth of human colon tumor xenografts grown in SCID mice; accordingly a combination of such efficacious MAbs is also effective.

Tumor Inhibition Using Multiple 24P4C12 MAbs
Materials and Methods
24P4C12 Monoclonal Antibodies:

Monoclonal antibodies were raised against 24P4C12 as described in the Example entitled "Generation of 24P4C12 Monoclonal Antibodies (MAbs)." The MAbs are characterized by ELISA, Western blot, FACS, and immunoprecipitation for their capacity to bind 24P4C12. Epitope mapping data for the 24P4C12 MAbs, as determined by ELISA and Western analysis, recognize epitopes on the 24P4C12 protein. Immunohistochemical analysis of normal and cancer tissues and cells with these antibodies is performed.

The MAbs are purified from ascites or hybridoma tissue culture supernatants by Protein-G or Protein-A Sepharose chromatography, dialyzed against PBS, filter sterilized, and stored at −20° C. Protein determinations are performed by a Bradford assay (Bio-Rad, Hercules, Calif.). A therapeutic MAb or a cocktail comprising a mixture of individual MAbs is prepared and used for the treatment of mice receiving subcutaneous or orthotopic injections of UG-K$_3$ and RXF-393 tumor xenografts.

Cell Lines and Xenografts

The cancer cell lines PC3-24P4C12, LNCaP, LAPC9, 22RV1, OVCaR-5, HT29, Calu-1, and CF-PAC are maintained in RPMI and DMEM respectively, supplemented with L-glutamine and 10% FBS.

The xenograft is passaged in 6-8-week-old male ICR-severe combined immunodeficient (SCID) mice (Taconic Farms) by s.c. trocar implant (Craft, N., et al., Nat. Med. 1999, 5:280). Single-cell suspensions of tumor cells are prepared as described in Craft, et al. Other cell lines are used as well.

Xenograft Mouse Models.

Subcutaneous (s.c.) tumors are generated by injection of $1\times10^6$ cancer cells mixed at a 1:1 dilution with Matrigel (Collaborative Research) in the right flank of male SCID mice. To test antibody efficacy on tumor formation, i.e. antibody injections are started on the same day as tumor-cell injections. As a control, mice are injected with either purified mouse IgG (ICN) or PBS; or a purified MAb that recognizes an irrelevant antigen not expressed in human cells. In preliminary studies, no difference is found between mouse IgG or PBS on tumor growth. Tumor sizes are determined by caliper measurements, and the tumor volume is calculated as length× width×height. Mice with subcutaneous tumors greater than 1.5 cm in diameter are sacrificed.

Orthotopic injections are performed under anesthesia by using ketamine/xylazine. To monitor tumor growth, mice are palpated. The mice are segregated into groups for the appropriate treatments, with 24P4C12 MAbs or control MAbs being injected i.p.

24P4C12 MAbs Inhibit Growth of 24P4C12-Expressing Xenograft Tumors

The effect of 24P4C12 MAbs on tumor formation is tested by using orthotopic models. As compared with the s.c. tumor model, the orthotopic model, which requires injection of tumor cells directly in the mouse, results in a local tumor growth, development of metastasis in distal sites, deterioration of mouse health, and subsequent death. These features make the orthotopic model more representative of human disease progression and allowed us to follow the therapeutic effect of 24P4C12 MAbs on clinically relevant end points.

Accordingly, tumor cells are injected into the mouse, and 2 days later, the mice are segregated into two groups and treated with either: a) 250-1000 µg, of 24P4C12 MAb, or b) control antibody three times per week for two to five weeks.

A major advantage of the orthotopic cancer models is the ability to study the development of metastases. Formation of metastasis in mice bearing established orthotopic tumors is studies by IHC analysis on tissue sections.

Another advantage of xenograft cancer models is the ability to study neovascularization and angiogenesis. Tumor growth is partly dependent on new blood vessel development. Although the capillary system and developing blood network is of host origin, the initiation and architecture of the neovasculature is regulated by the xenograft tumor (Davidoff et al., Clin Cancer Res. (2001) 7:2870; Solesvik et al., Eur J Cancer Clin Oncol. (1984) 20:1295). The effect of antibody and small molecule on neovascularization is studied in accordance with procedures known in the art, such as by IHC analysis of tumor tissues and their surrounding microenvironment.

Mice bearing established orthotopic tumors are administered injections of either 24P4C12 MAb or control antibody over a 4-week period. Mice in both groups are allowed to establish a high tumor burden, to ensure a high frequency of metastasis formation in mouse lungs. Mice then are killed and their bladders, livers, bone and lungs are analyzed for the presence of tumor cells by IHC analysis. These studies demonstrate a broad anti-tumor efficacy of anti-24P4C12 antibodies on initiation and progression of cancer in xenograft mouse models. Anti-24P4C12 antibodies inhibit tumor formation of tumors as well as retarding the growth of already established tumors and prolong the survival of treated mice. Moreover, 24P4C12 MAbs demonstrate a dramatic inhibitory effect on the spread of local tumor to distal sites, even in the presence of a large tumor burden. Thus, 24P4C12 MAbs are efficacious on major clinically relevant end points (tumor growth), prolongation of survival, and health.

The results of these experiments show that 24P4C12 MAbs can be used for therapeutic and diagnostic purposes to treat and manage cancers set forth in Table I.

Example 16

Therapeutic and Diagnostic Use of Anti-24P4C12 Antibodies in Humans

Anti-24P4C12 monoclonal antibodies are safely and effectively used for diagnostic, prophylactic, prognostic and/or therapeutic purposes in humans. Western blot and immunohistochemical analysis of cancer tissues and cancer xenografts with anti-24P4C12 MAb show strong extensive staining in carcinoma but significantly lower or undetectable levels in normal tissues. Detection of 24P4C12 in carcinoma and in metastatic disease demonstrates the usefulness of the MAb as a diagnostic and/or prognostic indicator. Anti-24P4C12 antibodies are therefore used in diagnostic applications such as immunohistochemistry of kidney biopsy specimens to detect cancer from suspect patients.

As determined by flow cytometry, anti-24P4C12 MAb specifically binds to carcinoma cells. Thus, anti-24P4C12 antibodies are used in diagnostic whole body imaging applications, such as radioimmunoscintigraphy and radioimmunotherapy, (see, e.g., Potamianos S., et. al. Anticancer Res 20(2A):925-948 (2000)) for the detection of localized and metastatic cancers that exhibit expression of 24P4C12. Shedding or release of an extracellular domain of 24P4C12 into the extracellular milieu, such as that seen for alkaline phosphodiesterase B10 (Meerson, N. R., Hepatology 27:563-568 (1998)), allows diagnostic detection of 24P4C12 by anti-24P4C12 antibodies in serum and/or urine samples from suspect patients.

Anti-24P4C12 antibodies that specifically bind 24P4C12 are used in therapeutic applications for the treatment of cancers that express 24P4C12. Anti-24P4C12 antibodies are used as an unconjugated modality and as conjugated form in which the antibodies are attached to one of various therapeutic or imaging modalities well known in the art, such as a prodrugs, enzymes, toxins, or radioisotopes. In preclinical studies, unconjugated and conjugated anti-24P4C12 antibodies are tested for efficacy of tumor prevention and growth inhibition in the SCID mouse cancer xenograft models, e.g., colon cancer models, (see, e.g., the Example entitled "24P4C12 Monoclonal Antibody-mediated Inhibition of Tumors In Vivo"). Either conjugated and unconjugated anti-24P4C12 antibodies are used as a therapeutic modality in human clinical trials either alone or in combination with other treatments as described in following Examples.

Example 17

Human Clinical Trials for the Treatment and Diagnosis of Human Carcinomas Through Use of 24P4C12 MAbs Antibodies are used in accordance with the present invention which recognize an epitope on 24P4C12, and are used in the treatment of certain tumors, preferably those listed in Table I. In connection with each of these indications, three clinical approaches are successfully pursued.

I.) Adjunctive therapy: In adjunctive therapy, patients are treated with 24P4C12 MAbs (either naked or conjugated to an agent) in combination with a chemotherapeutic or anti-neoplastic agent and/or radiation therapy or a combination thereof. Primary cancer targets, such as those listed in Table I, are treated under standard protocols by the addition of 24P4C12 MAbs to standard first and second line therapy. Protocol designs address effectiveness as assessed by the following examples, including but not limited to, reduction in tumor mass of primary or metastatic lesions, increased progression free survival, overall survival, improvement of patients health, disease stabilization, as well as the ability to reduce usual doses of standard chemotherapy and other biologic agents. These dosage reductions allow additional and/or prolonged therapy by reducing dose-related toxicity of the chemotherapeutic or biologic agent. 24P4C12 MAbs are utilized in several adjunctive clinical trials in combination with the chemotherapeutic or anti-neoplastic agents.

II.) Monotherapy: In connection with the use of the 24P4C12 MAbs (either naked or conjugated) in monotherapy of tumors, the antibodies are administered to patients without a chemotherapeutic or anti-neoplastic agent. In one embodiment, monotherapy is conducted clinically in end-stage cancer patients with extensive metastatic disease. Protocol designs address effectiveness as assessed by the following examples, including but not limited to, reduction in tumor mass of primary or metastatic lesions, increased progression free survival, overall survival, improvement of patients health, disease stabilization, as well as the ability to reduce usual doses of standard chemotherapy and other biologic agents.

III.) Imaging Agent: Through binding a radionuclide (e.g., iodine or yttrium ($I^{131}$, $Y^{90}$) to 24P4C12 MAbs, the radiolabeled antibodies are utilized as a diagnostic and/or imaging agent. In such a role, the labeled antibodies localize to both solid tumors, as well as, metastatic lesions of cells expressing 24P4C12. In connection with the use of the 24P4C12 MAbs as imaging agents, the antibodies are used as an adjunct to surgical treatment of solid tumors, as both a pre-surgical screen as well as a post-operative follow-up to determine what tumor remains and/or returns. In one embodiment, a ($^{111}$In)-24P4C12 antibody is used as an imaging agent in a Phase I human clinical trial in patients having a carcinoma that expresses 24P4C12 (by analogy see, e.g., Divgi et al. J. Natl. Cancer Inst. 83:97-104 (1991)). Patients are followed with standard anterior and posterior gamma camera. The results indicate that primary lesions and metastatic lesions are identified.

Dosage

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the antibody and the particular therapeutic or prophylactic effect to be achieved, and (b) the limitations inherent in the art of compounding such an active compound for the treatment of sensitivity in individuals.

An exemplary, non limiting range for a therapeutically effective amount of an antibody administered in combination according to the invention is at least 1 mg/kg, at least 5 mg/kg, at least 10 mg/kg, more than 10 mg/kg, or at least 15 mg/kg, for example 1-21 mg/kg, or for example 5-21 mg/kg, or for example 5-18 mg/kg, or for example 10-18 mg/kg, or for example 15 mg/kg. The high dose embodiment of the invention relates to a dosage of more than 10 mg/kg. It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Clinical Development Plan (CDP)

The CDP follows and develops treatments of 24P4C12 MAbs in connection with adjunctive therapy, monotherapy, and/or as an imaging agent. Trials initially demonstrate safety and thereafter confirm efficacy in repeat doses. Trials are open label comparing standard chemotherapy with standard therapy plus 24P4C12 MAbs. As will be appreciated, one non-limiting criteria that can be utilized in connection with enrollment of patients is 24P4C12 expression levels in their tumors as determined by biopsy.

As with any protein or antibody infusion-based therapeutic, safety concerns are related primarily to (i) cytokine release syndrome, i.e., hypotension, fever, shaking, chills; (ii) the development of an immunogenic response to the material (i.e., development of human antibodies by the patient to the antibody therapeutic, or HAHA response); and, (iii) toxicity to normal cells that express 24P4C12. Standard tests and follow-up are utilized to monitor each of these safety concerns. 24P4C12 MAbs are found to be safe upon human administration.

Example 18

24P4C12 Functional Studies and 24P4C12 MAb Inhibition Studies

24P4C12, a 10-transmembrane domain protein, is a member of the choline transporter-like (CTL) family of multitransmembrane proteins and is member 4 of the family (CTL4). This family also has been recently named by the HUGO Gene Nomenclature Committee as Solute Carrier family 44 (SLC44) and 24P4C12 as SLC44A4 (solute carrier family 44, member 4). This family was originally identified with the cloning and functional analysis of CTL1. This ubiquitously expressed protein, also known as CDw92, was shown to transport choline in a sodium-independent manner. 24P4C12 is 46% homologous to CTL1 at the amino acid level, thus it is inferred that 24P4C12 also functions as a macromolecule or ion transporter. For reference, the membrane topology of 24P4C12 and CTL1 respectively is shown in FIG. 10 and FIG. 11.

Potential extracellular asparagine linked glycosylation residues are shown in purple, potential extracellular cysteines used in disulfide bonds are shown in green. Charged amino acids within the transmembrane domains are also shown. Basic amino acids residues, arginine, histidine, and lysine are shown in blue and the acidic residue glutamic acid is shown in red. These charged residues are likely to be important for the transport function of the protein through mediating proper tertiary structure of the helices and/or movement of the macromolecule or ion through the channel or pore structure formed by the protein. Although CTL1 has been reported to function as a choline transporter, due to the differences in the transmembrane topology and the number and spacing of the charged amino acids in 24P4C12 compared to CTL1, it is probable that 24P4C12 mediates the transport macromolecules or ions other than choline.

24P4C12 is expressed in the apical membranes of several glandular secretory epithelia, including prostate, colon, small intestine, lung bronchus, pancreas, and the carcinomas that arise from these tissues. 24P4C12 has prominent expression in apical membrane of normal prostate. The major biological function of the prostate is to create and secrete prostatic fluid. It is conceivable that 24P4C12, acting as a transporter, regulates the composition of prostatic fluid. In one embodiment, the substrate of 24P4C12 is present in prostatic fluid. Substrates of 24P4C12 that are present in prostatic fluid are listed in Table VII. Potassium concentration is elevated in prostatic fluid (30-50 mM) compared to serum (3-4 mM), thus in another embodiment 24P4C12 transports potassium or utilizes potassium as a counterion in the transport of another macromolecule.

To confirm 24P4C12 transport activity, MDCK-24P4C12 cells demonstrate a decrease in chloromethylfluorescein diacetate (CMFDA) fluorescence, a pH sensitive fluorescent dye, compared to control neo cells when exposed to high extracellular potassium (K+) concentrations. This result indicates a drop in intracellular pH, suggesting that 24P4C12 transport activity does involve K+ and/or H+ ions. (FIG. 12).

Additionally, prostatic fluid is slightly acidic, exhibiting a pH range of 6.4-6.8, thus 24P4C12 may also regulate the pH homeostasis of prostatic fluid. MDCK-24P4C12 cells exhibit a marked decrease in CMFDA fluorescence compared to control neo cells when exposed to media acidified with sodium propionate. These results suggest 24P4C12 may regulate the intracellular pH homeostasis of cells when exposed to a low pH environment. (FIG. 13).

In another embodiment, 24P4C12 transport activity involves regulating intracellular pH in response to pH changes in the extracellular environment. Many of the macromolecules and ions present in prostatic fluid are also present in the fluids bathing or secreted by apical epithelium of other organs expressing 24P4C12. Such organs include but are not limited to lung bronchus, colon, small intestine, pancreas, and kidney. The transport activity of 24P4C12 may regulate the homeostasis of the fluids and secretions in these organs. Other substrates of 24P4C12 transporter activity based on the composition of fluids present in organs comprising the digestive tract and lung bronchi are listed in Table VIII.

During the oncogenic process of normal tissues, tumor cells may adapt or upregulate transport activities that provide beneficial nutrients, ions, macromolecules, or signaling pathways that promote tumor growth and metastasis. 24P4C12 transport activity may provide such benefits to the tumor. Therefore 24P4C12 MAbs that block or downregulate 24P4C12 transport activity would provide a therapeutic benefit by inhibiting tumor growth or mediating cell death. In one embodiment, 24P4C12 MAbs bind to 24P4C12 protein and sterically block the channel or pore that mediates the transport activity. In another embodiment, 24P4C12 MAbs bind to 24P4C12 causing conformational changes that disrupt the transport activity. In a further embodiment, 24P4C12 MAbs mediate capping, internalization, and downregulation of 24P4C12 from the cell surface.

FIG. 14 shows capping and internalization of 24P4C12 protein on PC3-24P4C12 cells when engaged by 24P4C12 MAbs. Briefly, MAbs Ha5-7acd19, Ha5-7be37, and Ha5-3 (1,4)7 were labeled with Alexa Fluor 488 fluorescent dye as per manufacturer's instructions (Invitrogen, Carlsbad Calif.). PC3-24P4C12 cells were incubated with the labeled MAbs for 2 hours at 4 C. Following washing, the cells were either kept at 4 C or moved to 37 C for 2 hours. Cells were then fixed and examined by fluorescent microscopy. Shown on FIG. 14A are fluorescent pictures of cells incubated with MAb and kept at 4 C demonstrating cell surface staining of 24P4C12 protein. FIG. 14B shows fluorescent pictures of cells stained with MAb and then incubated at 37 C for 2 hours. These cells exhibit a loss of the ring-like cell surface staining and the appearance of bright dots and punctate fluorescence demonstrating MAb-mediated capping and internalization of 24P4C12 protein.

Such capping and internalization removes 24P4C12 transport activity from the cell surface thereby providing an inhibitory effect on the tumor cell.

Example 19

Detection of 24P4C12 Protein in Cancer Patient Specimens by IHC

Expression of 24P4C12 protein by immunohistochemistry was tested in tumor specimens of pancreatic and ovarian cancer. Briefly, formalin fixed, paraffin wax-embedded tissues were cut into 4 micron sections and mounted on glass slides. The sections were de-waxed, rehydrated and treated with trypsin solution (0.05% trypsin (ICN, Aurora, Ohio) in 0.05% calcium chloride, with pH adjusted to 7.8) at 37° C. for 10 minutes. Sections were then treated with 3% hydrogen peroxide solution to inactivate endogenous peroxidase activity. Serum-free protein block (Dako, Carpenteria, Calif.) was used to inhibit non-specific binding prior to incubation with monoclonal mouse anti-24P4C12 antibody. Subsequently, the sections were treated with the Super Sensitive™ Polymer-horseradish peroxidase (HRP) Detection System which consists of an incubation in Super Enhancer™ reagent followed by an incubation with polymer-HRP secondary antibody conjugate (BioGenex, San Ramon, Calif.). The sections were then developed using the DAB kit (BioGenex, San Ramon, Calif.), nuclei were stained using hematoxylin, and analyzed by bright field microscopy. The cells which contain antigen immunoreactive with the 24P4C12 antibody stain brown.

The results show expression of 24P4C12 in the tumor cells of human ovarian cancer tissue and pancreatic cancer tissue. These results indicate that 24P4C12 is expressed in human cancers and that antibodies directed to this antigen are useful for diagnostic and therapeutic purposes. (FIG. 15A and FIG. 15B).

Throughout this application, various website data content, publications, patent applications and patents are referenced. (Websites are referenced by their Uniform Resource Locator, or URL, addresses on the World Wide Web.) The disclosures of each of these references are hereby incorporated by reference herein in their entireties.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

Tables

TABLE I

Tissues that Express 24P4C12 when malignant.

Colon
Pancreas
Ovarian
Breast
Lung
Prostate

TABLE II

Amino Acid Abbreviations

| SINGLE LETTER | THREE LETTER | FULL NAME |
|---|---|---|
| F | Phe | phenylalanine |
| L | Leu | leucine |
| S | Ser | serine |
| Y | Tyr | tyrosine |
| C | Cys | cysteine |
| W | Trp | tryptophan |
| P | Pro | proline |
| H | His | histidine |
| Q | Gln | glutamine |
| R | Arg | arginine |
| I | Ile | isoleucine |
| M | Met | methionine |
| T | Thr | threonine |
| N | Asn | asparagine |
| K | Lys | lysine |
| V | Val | valine |
| A | Ala | alanine |
| D | Asp | aspartic acid |
| E | Glu | glutamic acid |
| G | Gly | glycine |

TABLE III

Amino Acid Substitution Matrix

| A | C | D | E | F | G | H | I | K | L | M | N | P | Q | R | S | T | V | W | Y | |
|---|---|---|---|---|---|---|---|---|---|---|---|---|---|---|---|---|---|---|---|---|
| 4 | 0 | −2 | −1 | −2 | 0 | −2 | −1 | −1 | −1 | −1 | −2 | −1 | −1 | −1 | 1 | 0 | 0 | −3 | −2 | A |
| | 9 | −3 | −4 | −2 | −3 | −3 | −1 | −3 | −1 | −1 | −3 | −3 | −3 | −3 | −1 | −1 | −1 | −2 | −2 | C |
| | | 6 | 2 | −3 | −1 | −1 | −3 | −1 | −4 | −3 | 1 | −1 | 0 | −2 | 0 | −1 | −3 | −4 | −3 | D |
| | | | 5 | −3 | −2 | 0 | −3 | 1 | −3 | −2 | 0 | −1 | 2 | 0 | 0 | −1 | −2 | −3 | −2 | E |
| | | | | 6 | −3 | −1 | 0 | −3 | 0 | 0 | −3 | −4 | −3 | −3 | −2 | −2 | −1 | 1 | 3 | F |
| | | | | | 6 | −2 | −4 | −2 | −4 | −3 | 0 | −2 | −2 | −2 | 0 | −2 | −3 | −2 | −3 | G |
| | | | | | | 8 | −3 | −1 | −3 | −2 | 1 | −2 | 0 | 0 | −1 | −2 | −3 | −2 | 2 | H |
| | | | | | | | 4 | −3 | 2 | 1 | −3 | −3 | −3 | −3 | −2 | −1 | 3 | −3 | −1 | I |
| | | | | | | | | 5 | −2 | −1 | 0 | −1 | 1 | 2 | 0 | −1 | −2 | −3 | −2 | K |
| | | | | | | | | | 4 | 2 | −3 | −3 | −2 | −2 | −2 | −1 | 1 | −2 | −1 | L |
| | | | | | | | | | | 5 | −2 | −2 | 0 | −1 | −1 | −1 | 1 | −1 | −1 | M |
| | | | | | | | | | | | 6 | −2 | 0 | 0 | 1 | 0 | −3 | −4 | −2 | N |
| | | | | | | | | | | | | 7 | −1 | −2 | −1 | −1 | −2 | −4 | −3 | P |
| | | | | | | | | | | | | | 5 | 1 | 0 | −1 | −2 | −2 | −1 | Q |
| | | | | | | | | | | | | | | 5 | −1 | −1 | −3 | −3 | −2 | R |
| | | | | | | | | | | | | | | | 4 | 1 | −2 | −3 | −2 | S |
| | | | | | | | | | | | | | | | | 5 | 0 | −2 | −2 | T |
| | | | | | | | | | | | | | | | | | 4 | −3 | −1 | V |

TABLE III-continued

Amino Acid Substitution Matrix

| A | C | D | E | F | G | H | I | K | L | M | N | P | Q | R | S | T | V | W | Y | . |
|---|---|---|---|---|---|---|---|---|---|---|---|---|---|---|---|---|---|---|---|---|
|   |   |   |   |   |   |   |   |   |   |   |   |   |   |   |   |   |   | 11 | 2 | W |
|   |   |   |   |   |   |   |   |   |   |   |   |   |   |   |   |   |   |    | 7 | Y |

Adapted from the GCG Software 9.0 BLOSUM62 amino acid substitution matrix (block substitution matrix). The higher the value, the more likely a substitution is found in related, natural proteins.

Table IV:

HLA Class I/II Motifs/Supermotifs

TABLE IV (A)

HLA Class I Supermotifs/Motifs

|  | POSITION 2 (Primary Anchor) | POSITION 3 (Primary Anchor) | POSITION C Terminus (Primary Anchor) |
|---|---|---|---|
| SUPERMOTIF |  |  |  |
| A1 | T*ILVMS* |  | FWY |
| A2 | LIVM*ATQ* |  | IV*MATL* |
| A3 | VSM*ATLI* |  | RK |
| A24 | YF*WIVLMT* |  | FI*YWLM* |
| B7 | P |  | VILF*MWYA* |
| B27 | RHK |  | FYL*WMIVA* |
| B44 | E*D* |  | FWYLIMVA |
| B58 | ATS |  | FWY*LIVMA* |
| B62 | QL*IVMP* |  | FWY*MIVLA* |

TABLE IV (A)-continued

HLA Class I Supermotifs/Motifs

|  | POSITION 2 (Primary Anchor) | POSITION 3 (Primary Anchor) | POSITION C Terminus (Primary Anchor) |
|---|---|---|---|
| B*0702 | P |  | LMF*WYAIV* |
| B*3501 | P |  | LMFWY*IVA* |
| B51 | P |  | LIVF*WYAM* |
| B*5301 | P |  | IMFWY*ALV* |
| B*5401 | P |  | ATIV*LMFWY* |

Bolded residues are preferred, italicized residues are less preferred: A peptide is considered motif-bearing if it has primary anchors at each primary anchor position for a motif or supermotif as specified in the above table.

TABLE IV (B)

HLA Class II Supermotif

| 1 | 6 | 9 |
|---|---|---|
| W, F, Y, V, .I, L | A, V, I, L, P, C, S, T | A, V, I, L, C, S, T, M, Y |

TABLE IV (C)

HLA Class II Motifs

| MOTIFS |  | 1° anchor 1 | 2 | 3 | 4 | 5 | 1° anchor 6 | 7 | 8 | 9 |
|---|---|---|---|---|---|---|---|---|---|---|
| DR4 | preferred | FMY*LIVW* | M | T |   | I | VST*CPALIM* | MH | | MH |
|  | deleterious |  |  |  | W |  |  | R | | WDE |
| DR1 | preferred | MF*LIVWY* |  |  | PAMQ |  | CWD VMAT*SPLIC* | M | | AVM |
|  | deleterious |  | C | CH | FD |  |  | GDE | D | |
| DR7 | preferred | MF*LIVWY* | M | W | A |  | IVMSA*CTPL* | M | | IV |
|  | deleterious |  | C |  | G |  |  | GRD | N | G |

| DR3 | MOTIFS | 1° anchor 1 | 2 | 3 | 1° anchor 4 | 5 | 1° anchor 6 |
|---|---|---|---|---|---|---|---|
| Motif a preferred |  | LIVMFY |  |  | D |  |  |
| Motif b preferred |  | LIVMFAY |  |  | DNQEST |  | KRH |
| DR Supermotif |  | MF*LIVWY* |  |  |  |  | VMSTA*CPLI* |

Italicized residues indicate less preferred or "tolerated" residues

TABLE IV (A)-continued

HLA Class I Supermotifs/Motifs

|  | POSITION 2 (Primary Anchor) | POSITION 3 (Primary Anchor) | POSITION C Terminus (Primary Anchor) |
|---|---|---|---|
| MOTIFS |  |  |  |
| A1 | TSM |  | Y |
| A1 |  | DE*AS* | Y |
| A2.1 | LM*VQIAT* |  | V*LIMAT* |
| A3 | LM*VISATFCGD* |  | KYR*HFA* |
| A11 | VTML*ISAGNCDF* |  | KRYH |
| A24 | YF*WM* |  | FLIW |
| A*3101 | MVT*ALIS* |  | RK |
| A*3301 | MVALF*IST* |  | RK |
| A*6801 | AVT*MSLI* |  | RK |

TABLE IV (D)

HLA Class I Supermotifs

| SUPER-MOTIFS | | POSITION: | | | | | | | | |
|---|---|---|---|---|---|---|---|---|---|---|
| | | 1 | 2 | 3 | 4 | 5 | 6 | 7 | 8 | C-terminus |
| A1 | | | 1°Anchor TI*LVMS* | | | | | | | 1°Anchor FW*Y* |
| A2 | | | 1°Anchor LIVM*ATQ* | | | | | | | 1°Anchor LIVMAT |
| A3 | Preferred | | 1°Anchor VSMA*TLI* | YFW (4/5) | | | YFW (3/5) | YFW (4/5) | P (4/5) | 1°Anchor RK |
| | deleterious | DE (3/5); P (5/5) | | DE (4/5) | | | | | | |
| A24 | | | 1°Anchor YF*WIVLMT* | | | | | | | 1°Anchor FIY*WLM* |
| B7 | Preferred | FWY (5/5) LIVM (3/5) | 1°Anchor P | FWY (4/5) | | | | | FWY (3/5) | 1° Anchor VILF*MWYA* |
| | deleterious | DE (3/5); P(5/5); G(4/5); A(3/5); QN(3/5) | | | | DE (3/5) | G (4/5) | QN (4/5) | DE (4/5) | |
| B27 | | | 1°Anchor RHK | | | | | | | 1° Anchor FYL*WMIVA* |
| B44 | | | 1°Anchor E*D* | | | | | | | 1° Anchor FWY*LIMVA* |
| B58 | | | 1°Anchor ATS | | | | | | | 1° Anchor FWY*LIVMA* |
| B62 | | | 1°Anchor QL*IVMP* | | | | | | | 1° Anchor FWY*MIVLA* |

Italicized residues indicate less preferred or "tolerated" residues

TABLE IV (E)

HLA Class I Motifs

| | | POSITION | | | | |
|---|---|---|---|---|---|---|
| | | 1 | 2 | 3 | 4 | 5 |
| A1 9-mer | preferred | GFYW | 1°Anchor STM | DEA | YFW | |
| | deleterious | DE | | RHKLIVMP | A | G |
| A1 9-mer | preferred | GRHK | ASTCLIVM | 1°Anchor DE*AS* | GSTC | |
| | deleterious | A | RHKDEPYFW | | DE | PQN |
| A1 10-mer | preferred | YFW | 1°Anchor STM | DEAQN | A | YFWQN |
| | deleterious | GP | | RHKGLIVM | DE | RHK |
| A1 10-mer | preferred | YFW | STCLIVM | 1°Anchor DE*AS* | A | YFW |
| | deleterious | RHK | RHKDEPYFW | | | P |
| A2.1 9-mer | preferred | YFW | 1°Anchor LM*IVQAT* | YFW | STC | YFW |
| | deleterious | DEP | | DERKH | | |
| A2.1 10-mer | preferred | AYFW | 1°Anchor LM*IVQAT* | LVIM | G | |
| | deleterious | DEP | | DE | RKHA | P |
| A3 | preferred | RHK | 1°Anchor LMVISATFCGD | YFW | PRHKYFW | A |
| | deleterious | DEP | | DE | | |
| A11 | preferred | A | 1°Anchor VTLMISAGN*CDF* | YFW | YFW | A |
| | deleterious | DEP | | | | |
| A24 9-mer | preferred | YFWRHK | 1°Anchor YFW*M* | | STC | |
| | deleterious | DEG | | DE | G | QNP |
| A24 10-mer | Preferred | | 1°Anchor YFW*M* | | P | YFWP |
| | Deleterious | | | GDE | QN | RHK |
| A3101 | Preferred | RHK | 1°Anchor MVT*ALIS* | YFW | P | |
| | Deleterious | DEP | | DE | | ADE |
| A3301 | Preferred | | 1°Anchor MVALF*IST* | YFW | | |
| | Deleterious | GP | | DE | | |

TABLE IV (E)-continued

| HLA Class I Motifs | | | | | | | |
|---|---|---|---|---|---|---|---|
| A6801 | Preferred | YFWSTC | 1°Anchor AVT*MSLI* | | | | YFWLIVM |
|  | deleterious | GP | | | DEG | | RHK |
| B0702 | Preferred | RHKFWY | 1°Anchor P | RHK | | | RHK |
|  | deleterious | DEQNP | | | DEP | DE | DE |
| B3501 | Preferred | FWYLIVM | 1°Anchor P | | FWY | | |
|  | deleterious | AGP | | | | | G |
| B51 | Preferred | LIVMFWY | 1°Anchor P | | FWY | STC | FWY |
|  | deleterious | AGPDER HKSTC | | | | | DE |
| B5301 | preferred | LIVMFWY | 1°Anchor P | | FWY | STC | FWY |
|  | deleterious | AGPQN | | | | | |
| B5401 | preferred | FWY | 1°Anchor P | | FWYLIVM | | LIVM |
|  | deleterious | GPQNDE | | | GDESTC | | RHKDE |

| | | POSITION | | | | |
|---|---|---|---|---|---|---|
| | | 6 | 7 | 8 | 9 or C-terminus | C-terminus |
| A1 9-mer | preferred | P | DEQN | YFW | 1°Anchor Y | |
| | deleterious | A | | | | |
| A1 9-mer | preferred | ASTC | LIVM | DE | 1°Anchor Y | |
| | deleterious | RHK | PG | GP | | |
| A1 10-mer | preferred | | PASTC | GDE | P | 1°Anchor Y |
| | deleterious | QNA | RHKYFW | RHK | A | |
| A1 10-mer | preferred | | PG | G | YFW | 1°Anchor Y |
| | deleterious | G | | PRHK | QN | |
| A2.1 9-mer | preferred | | A | P | 1°Anchor V*LIMAT* | |
| | deleterious | RKH | DERKH | | | |
| A2.1 10-mer | preferred | G | | FYWL VIM | | 1°Anchor V*LIMAT* |
| | deleterious | | RKH | DERKH | RKH | |
| A3 | preferred | YFW | | P | 1°Anchor KYR*HFA* | |
| | deleterious | | | | | |
| A11 | preferred | YFW | YFW | P | 1°Anchor K*RYH* | |
| | deleterious | | A | G | | |
| A24 9-mer | preferred | | YFW | YFW | 1°Anchor FLIW | |
| | deleterious | DERHK | G | AQN | | |
| A24 10-mer | Preferred | | P | | | 1°Anchor FLIW |
| | Deleterious | DE | A | QN | DEA | |
| A3101 | Preferred | YFW | YFW | AP | 1°Anchor R*K* | |
| | Deleterious | DE | DE | DE | | |
| A3301 | Preferred | | AYFW | | 1°Anchor RK | |
| | Deleterious | | | | | |
| A6801 | Preferred | | YFW | P | 1°Anchor RK | |
| | deleterious | | | A | | |
| B0702 | Preferred | RHK | RHK | PA | 1° Anchor LMF*WYAIV* | |
| | deleterious | GDE | QN | DE | | |
| B3501 | Preferred | | FWY | | 1° Anchor LMFWY*IVA* | |
| | deleterious | G | | | | |
| B51 | Preferred | | G | FWY | 1° Anchor LIVF*WYAM* | |
| | deleterious | G | DEQN | GDE | | |
| B5301 | preferred | G | LIVMFWY | FWY | 1° Anchor IMFWY*ALV* | |
| | deleterious | G | RHKQN | DE | | |

TABLE IV (E)-continued

HLA Class I Motifs

| | | | | | |
|---|---|---|---|---|---|
| B5401 | preferred | | ALIVM | FWYA P | 1° Anchor ATIV*LMFWY* |
| | deleterious | DE | QNDGE | DE | |

TABLE IV (F)

Summary of HLA-supertypes
Overall phenotypic frequencies of HLA-supertypes in different ethnic populations

| | Specificity | | Phenotypic frequency | | | | | |
|---|---|---|---|---|---|---|---|---|
| Supertype | Position 2 | C-Terminus | Caucasian | N.A. Black | Japanese | Chinese | Hispanic | Average |
| B7 | P | AILMVFWY | 43.2 | 55.1 | 57.1 | 43.0 | 49.3 | 49.5 |
| A3 | AILMVST | RK | 37.5 | 42.1 | 45.8 | 52.7 | 43.1 | 44.2 |
| A2 | AILMVT | AILMVT | 45.8 | 39.0 | 42.4 | 45.9 | 43.0 | 42.2 |
| A24 | YF (WIVLMT) | FI (YWLM) | 23.9 | 38.9 | 58.6 | 40.1 | 38.3 | 40.0 |
| B44 | E (D) | FWYLIMVA | 43.0 | 21.2 | 42.9 | 39.1 | 39.0 | 37.0 |
| A1 | TI (LVMS) | FWY | 47.1 | 16.1 | 21.8 | 14.7 | 26.3 | 25.2 |
| B27 | RHK | FYL (WMI) | 28.4 | 26.1 | 13.3 | 13.9 | 35.3 | 23.4 |
| B62 | QL (IVMP) | FWY (MIV) | 12.6 | 4.8 | 36.5 | 25.4 | 11.1 | 18.1 |
| B58 | ATS | FWY (LIV) | 10.0 | 25.1 | 1.6 | 9.0 | 5.9 | 10.3 |

TABLE IV (G)

Calculated population coverage afforded by different HLA-supertype combinations

| | Phenotypic frequency | | | | | |
|---|---|---|---|---|---|---|
| HLA-supertypes | Caucasian | N.A Blacks | Japanese | Chinese | Hispanic | Average |
| A2, A3 and B7 | 83.0 | 86.1 | 87.5 | 88.4 | 86.3 | 86.2 |
| A2, A3, B7, A24, B44 and A1 | 99.5 | 98.1 | 100.0 | 99.5 | 99.4 | 99.3 |
| A2, A3, B7, A24, B44, A1, B27, B62, and B58 | 99.9 | 99.6 | 100.0 | 99.8 | 99.9 | 99.8 |

Motifs indicate the residues defining supertype specificites. The motifs incorporate residues determined on the basis of published data to be recognized by multiple alleles within the supertype. Residues within brackets are additional residues also predicted to be tolerated by multiple alleles within the supertype.

TABLE V

Frequently Occurring Motifs

| Name | avrg. % identity | Description | Potential Function |
|---|---|---|---|
| zf-C2H2 | 34% | Zinc finger, C2H2 type | Nucleic acid-binding protein functions as transcription factor, nuclear location probable |
| cytochrome_b_N | 68% | Cytochrome b(N-terminal)/b6/petB | membrane bound oxidase, generate superoxide |
| Ig | 19% | Immunoglobulin domain | domains are one hundred amino acids long and include a conserved intradomain disulfide bond. |
| WD40 | 18% | WD domain, G-beta repeat | tandem repeats of about 40 residues, each containing a Trp-Asp motif. Function in signal transduction and protein interaction |
| PDZ | 23% | PDZ domain | may function in targeting signaling molecules to sub-membranous sites |
| LRR | 28% | Leucine Rich Repeat | short sequence motifs involved in protein-protein interactions |
| Pkinase | 23% | Protein kinase domain | conserved catalytic core common to both serine/threonine and tyrosine protein kinases containing an ATP binding site and a catalytic site |
| PH | 16% | PH domain | pleckstrin homology involved in intracellular signaling or as constituents of the cytoskeleton |

TABLE V-continued

Frequently Occurring Motifs

| Name | avrg. % identity | Description | Potential Function |
|---|---|---|---|
| EGF | 34% | EGF-like domain | 30-40 amino-acid long found in the extracellular domain of membrane-bound proteins or in secreted proteins |
| Rvt | 49% | Reverse transcriptase (RNA-dependent DNA polymerase) | |
| Ank | 25% | Ank repeat | Cytoplasmic protein, associates integral membrane proteins to the cytoskeleton |
| Oxidored_q1 | 32% | NADH-Ubiquinone/plastoquinone (complex I), various chains | membrane associated. Involved in proton translocation across the membrane |
| Efhand | 24% | EF hand | calcium-binding domain, consists of a12 residue loop flanked on both sides by a 12 residue alpha-helical domain |
| Rvp | 79% | Retroviral aspartyl protease | Aspartyl or acid proteases, centered on a catalytic aspartyl residue |
| Collagen | 42% | Collagen triple helix repeat (20 copies) | extracellular structural proteins involved in formation of connective tissue. The sequence consists of the G-X-Y and the polypeptide chains forms a triple helix. |
| Fn3 | 20% | Fibronectin type III domain | Located in the extracellular ligand-binding region of receptors and is about 200 amino acid residues long with two pairs of cysteines involved in disulfide bonds |
| 7tm_1 | 19% | 7 transmembrane receptor (rhodopsin family) | seven hydrophobic transmembrane regions, with the N-terminus located extracellularly while the C-terminus is cytoplasmic. Signal through G proteins |

TABLE VI

24P4C12 MAb Affinity by FACS on LNCaP cells

| Clone | Isotype | Affinity LNCaP (nM)$^x$ | Epitope group$^y$ |
|---|---|---|---|
| Ha5-1(5)1 | γ2 κ | 4.10 | 1 |
| Ha5-1(5)2 | γ2 κ | 2.75 | 1 |
| Ha5-3(1,4)7.1 | γ1 κ | 5.50 | 4 |
| Ha5-3(3,5)37.1 | γ1 κ | 0.45 | 7 |
| Ha5-7be20.1 | γ1 κ | 3.20 | 13 |
| Ha5-7be34.1 | γ1 κ | 1.76 | 13 |
| Ha5-7be37.1 | γ1 κ | 2.80 | 12 |
| Ha5-7be31.1 | γ1 κ | 4.15 | 11 |
| Ha5-7acd2.1 | γ1 κ | 1.95 | 13 |
| Ha5-7acd3.1 | γ1 κ | 4.40 | 10 |
| Ha5-7acd4.1 | γ1 κ | 0.99 | 10 |
| Ha5-7acd10.1 | γ1 κ | 1.26 | 10 |
| Ha5-7acd16.1 | γ1 κ | 0.70 | 13 |
| Ha5-7acd19.1 | γ1 κ | 0.19 | 7 |
| Ha5-7acd7.1.1 | γ1 κ | 1.85 | 13 |
| Ha5-7acd20.1.1 | γ1 κ | 1.10 | 10 |
| Ha5-8ac4.1 | γ1 λ | 0.07 | ND |
| Ha5-11b1.1 | γ1 κ | 3.40 | 14 |

$^x$Affinity determined by FACS equilibrium saturation binding curves
$^y$Epitope group determined by FACS equilibrium competition binding (same numbers share a similar competition pattern against all other MAbs)
ND: Not determined

TABLE VII substrates of 24P4C12 Macromolecules, elements, and ions in prostatic fluid

| | |
|---|---|
| ascorbic acid | magnesium |
| blood-group antigens | nitrogen |
| calcium | phosphorus |
| chlorine | potassium |
| cholesterol | purine |
| choline | pyrimidine |
| citric acid | pyruvic acid |
| creatine | sodium |
| deoxyribonucleic acid | sorbitol |
| nucleotide and nucleoside bases and sugars | spermidine |
| fructose | spermine |
| glutathione | urea |
| hyaluronidase | uric acid |
| inositol | vitamin B12 |
| lactic acid | zinc |
| sodium | pH 6.4-6.8 |

TABLE VIII

Substrates of 24P4C12 macromolecules, elements, and ions present in digestive tract and lung bronchi fluids vitamins A, B1, C, D, E, K, B1, B2, B6, B12
chloride
copper
iodine
biotin
iron
glycerol
short chain fatty acids
monoglycerides
monosaccharides
disaccharides
amino acids
dipeptides
lipids
mucins
bicarbonate

The invention claimed is:

1. An isolated monoclonal antibody or antigen-binding fragment thereof that binds specifically to a 24P4C12 protein comprising the amino acid sequence of SEQ ID NO: 2, wherein the monoclonal antibody comprises the VH region of SEQ ID NO: 123, from residue 1 to 124 and the VL region of SEQ ID NO: 124, from residue 15 to 122.

2. The antibody or fragment of claim 1, wherein the antibody comprises the same amino acid sequence of the VH region and the VL region as those of the antibody produced by the hybridoma assigned A.T.C.C. Accession No.: 8602.

3. The antibody or fragment of claim 1, wherein the fragment is an Fab, F(ab')$_2$, Fv or Sfv fragment.

4. The antibody or fragment of claim 1, wherein the antibody is a fully human antibody.

5. The antibody or fragment of claim 1, which is recombinantly produced.

6. The antibody or fragment of claim 5, which comprises the antigen binding region of said antibody.

7. The antibody or fragment of claim 1, wherein the antibody or fragment is coupled to a detectable marker, a toxin, a therapeutic agent, or a chemotherapeutic agent.

8. The antibody or fragment of claim 7, wherein the detectable marker is a radioisotope, a metal chelator, an enzyme, a fluorescent compound, a bioluminescent compound or a chemiluminescent compound.

9. The antibody or fragment of claim 8, wherein the radioisotope comprises $^{212}$Bi, $^{131}$I, $^{131}$In, $^{90}$Y, $^{186}$Re, $^{211}$At, $^{125}$I, $^{188}$Re, $^{153}$Sm, $^{213}$Bi, $^{32}$P, or Lu.

10. The antibody or fragment of claim 7, wherein the toxin comprises ricin, ricin A chain, doxorubicin, daunorubicin, a maytansinoid, taxol, ethidium bromide, mitomycin, etoposide, tenoposide, vincristine, vinblastine, colchicine, dihydroxy anthracin dione, actinomycin, diphtheria toxin, Pseudomonas exotoxin (PE) A, PE40, abrin, abrin A chain, modeccin A chain, alpha sarcin, gelonin, mitogellin, restrictocin, phenomycin, enomycin, curicin, crotin, calicheamicin, sapaonaria officinalis inhibitor, glucocorticoid, auristatin, auromycin, yttrium, bismuth, combrestatin, duocarmycins, dolastatin, cc1065, or a cisplatin.

11. The antibody or fragment of claim 1, which binds to an epitope within the amino acid sequence of SEQ ID NO:2.

12. A hybridoma that produces the monoclonal antibody of claim 1.

13. A pharmaceutical composition that comprises the antibody or fragment of claim 1 in a human unit dose form.

14. An assay for detecting the presence of a 24P4C12 protein in a biological sample comprising contacting the sample with an antibody of claim 1, and detecting the binding of the protein, which comprises the amino acid sequence of SEQ ID NO:2 in the sample.

15. A method of delivering a cytotoxic agent or a diagnostic agent to a cell that expresses a 24P4C12 protein, comprising: providing a cytotoxic agent or a diagnostic agent conjugated to the antibody or fragment of claim 1, to form an antibody agent or fragment agent conjugate; and, exposing the cell to the antibody agent or fragment agent conjugate.

16. The method of claim 15, wherein the cytotoxic agent or the diagnostic agent is selected from the group consisting of a detectable marker, a toxin, and a therapeutic agent.

17. The method of claim 16, wherein the detectable marker is a radioisotope, a metal chelator, an enzyme, a fluorescent compound, a bioluminescent compound or a chemiluminescent compound.

18. The method of claim 17, wherein the radioisotope comprises $^{212}$Bi, $^{131}$I, $^{131}$In, $^{90}$Y, $^{186}$Re, $^{211}$At, $^{125}$I, $^{188}$Re, $^{153}$Bm, $^{213}$Bi, $^{32}$P, or Lu.

19. The method of claim 16, wherein the toxin comprises ricin, ricin A chain, doxorubicin, daunorubicin, a maytansinoid, taxol, ethidium bromide, mitomycin, etoposide, tenoposide, vincristine, vinblastine, colchicine, dihydroxy anthracin dione, actinomycin, diphtheria toxin, Pseudomonas exotoxin (PE) A, PE40, abrin, abrin A chain, modeccin A chain, alpha sarcin, gelonin, mitogellin, restrictocin, phenomycin, enomycin, curicin, crotin, calicheamicin, sapaonaria officinalis inhibitor, glucocorticoid, auristatins, auromycin, yttrium, bismuth, combrestatin, duocarmycins, dolastatin, cc1065, or a cisplatin.

20. A method for detecting a 24P4C12 protein in a biological sample, comprising steps of: providing the biological sample and a control sample; contacting the biological sample and the control sample with the antibody of claim 1; and determining an amount of a complex of the substance with the 24P4C 12 protein and the antibody present in the biological sample and the control sample, wherein the 24P4C12 protein comprises the amino acid sequence of SEQ ID NO: 2.

21. The method of claim 20 further comprising: taking the biological sample and the control sample from a patient who has or who is suspected of having a cancer listed in Table I.

22. A method for reducing 24P4C12 protein expressing tumor growth in a mammal comprising treating the mammal with an effective amount of a combination of the antibody of claim 1, and radiation.

23. A method for reducing 24P4C12 protein expressing tumor growth in a mammal comprising treating the mammal with an effective amount of a combination of the antibody of claim 1, and a chemotherapeutic agent.

24. A method for reducing 24P4C12 protein expressing tumor growth in a mammal comprising treating the mammal with an effective amount of a combination of the antibody of claim 1, and a drug or biologically active therapy.

* * * * *

SEQUENCE LISTING

<160> NUMBER OF SEQ ID NOS: 173

<210> SEQ ID NO 1
<211> LENGTH: 2587
<212> TYPE: DNA
<213> ORGANISM: Homo sapiens
<220> FEATURE:
<221> NAME/KEY: CDS
<222> LOCATION: (6)...(2138)

<400> SEQUENCE: 1

```
gagcc atg ggg gga aag cag cgg gac gag gat gac gag gcc tac ggg aag     50
      Met Gly Gly Lys Gln Arg Asp Glu Asp Asp Glu Ala Tyr Gly Lys
      1               5                   10                  15 cca gtc aaa tac gac ccc tcc ttt cga ggc ccc atc aag aac aga agc       98
Pro Val Lys Tyr Asp Pro Ser Phe Arg Gly Pro Ile Lys Asn Arg Ser
            20                  25                  30 tgc aca gat gtc atc tgc tgc gtc ctc ttc ctg ctc ttc att cta ggt      146
Cys Thr Asp Val Ile Cys Cys Val Leu Phe Leu Leu Phe Ile Leu Gly
        35                  40                  45 tac atc gtg gtg ggg att gtg gcc tgg ttg tat gga gac ccc cgg caa      194
Tyr Ile Val Val Gly Ile Val Ala Trp Leu Tyr Gly Asp Pro Arg Gln
    50                  55                  60 gtc ctc tac ccc agg aac tct act ggg gcc tac tgt ggc atg ggg gag      242
Val Leu Tyr Pro Arg Asn Ser Thr Gly Ala Tyr Cys Gly Met Gly Glu
65                  70                  75 aac aaa gat aag ccg tat ctc ctg tac ttc aac atc ttc agc tgc atc      290
Asn Lys Asp Lys Pro Tyr Leu Leu Tyr Phe Asn Ile Phe Ser Cys Ile
 80                  85                  90                  95 ctg tcc agc aac atc atc tca gtt gct gag aac ggc cta cag tgc ccc      338
Leu Ser Ser Asn Ile Ile Ser Val Ala Glu Asn Gly Leu Gln Cys Pro
                100                 105                 110 aca ccc cag gtg tgt gtg tcc tcc tgc ccg gag gac cca tgg act gtg      386
Thr Pro Gln Val Cys Val Ser Ser Cys Pro Glu Asp Pro Trp Thr Val
            115                 120                 125 gga aaa aac gag ttc tca cag act gtt ggg gaa gtc ttc tat aca aaa      434
Gly Lys Asn Glu Phe Ser Gln Thr Val Gly Glu Val Phe Tyr Thr Lys
        130                 135                 140 aac agg aac ttt tgt ctg cca ggg gta ccc tgg aat atg acg gtg atc      482
Asn Arg Asn Phe Cys Leu Pro Gly Val Pro Trp Asn Met Thr Val Ile
    145                 150                 155 aca agc ctg caa cag gaa ctc tgc ccc agt ttc ctc ctc ccc tct gct      530
Thr Ser Leu Gln Gln Glu Leu Cys Pro Ser Phe Leu Leu Pro Ser Ala
160                 165                 170                 175 cca gct ctg ggg cgc tgc ttt cca tgg acc aac gtt act cca ccg gcg      578
Pro Ala Leu Gly Arg Cys Phe Pro Trp Thr Asn Val Thr Pro Pro Ala
                180                 185                 190 ctc cca ggg atc acc aat gac acc acc ata cag cag ggg atc agc ggt      626
Leu Pro Gly Ile Thr Asn Asp Thr Thr Ile Gln Gln Gly Ile Ser Gly
            195                 200                 205 ctt att gac agc ctc aat gcc cga gac atc agt gtt aag atc ttt gaa      674
Leu Ile Asp Ser Leu Asn Ala Arg Asp Ile Ser Val Lys Ile Phe Glu
        210                 215                 220 gat ttt gcc cag tcc tgg tat tgg att ctt gtt gcc ctg ggg gtg gct      722
Asp Phe Ala Gln Ser Trp Tyr Trp Ile Leu Val Ala Leu Gly Val Ala
    225                 230                 235 ctg gtc ttg agc cta ctg ttt atc ttg ctt cgc ctg gtg gct ggg          770
Leu Val Leu Ser Leu Leu Phe Ile Leu Leu Arg Leu Val Ala Gly
240                 245                 250                 255 ccc ctg gtg ctg gtg ctg atc ctg gga gtg ctg ggc gtg ctg gca tac      818
```

-continued

```
            Pro Leu Val Leu Val Leu Ile Leu Gly Val Leu Gly Val Leu Ala Tyr
                        260                 265                 270 ggc atc tac tac tgc tgg gag gag tac cga gtg ctg cgg gac aag ggc        866
Gly Ile Tyr Tyr Cys Trp Glu Glu Tyr Arg Val Leu Arg Asp Lys Gly
            275                 280                 285 gcc tcc atc tcc cag ctg ggt ttc acc acc aac ctc agt gcc tac cag        914
Ala Ser Ile Ser Gln Leu Gly Phe Thr Thr Asn Leu Ser Ala Tyr Gln
            290                 295                 300 agc gtg cag gag acc tgg ctg gcc gcc ctg atc gtg ttg gcg gtg ctt        962
Ser Val Gln Glu Thr Trp Leu Ala Ala Leu Ile Val Leu Ala Val Leu
305                 310                 315 gaa gcc atc ctg ctg ctg atg ctc atc ttc ctg cgg cag cgg att cgt       1010
Glu Ala Ile Leu Leu Leu Met Leu Ile Phe Leu Arg Gln Arg Ile Arg
320                 325                 330                 335 att gcc atc gcc ctc ctg aag gag gcc agc aag gct gtg gga cag atg       1058
Ile Ala Ile Ala Leu Leu Lys Glu Ala Ser Lys Ala Val Gly Gln Met
                340                 345                 350 atg tct acc atg ttc tac cca ctg gtc acc ttt gtc ctc ctc ctc atc       1106
Met Ser Thr Met Phe Tyr Pro Leu Val Thr Phe Val Leu Leu Leu Ile
            355                 360                 365 tgc att gcc tac tgg gcc atg act gct ctg tac ctg gct aca tcg ggg       1154
Cys Ile Ala Tyr Trp Ala Met Thr Ala Leu Tyr Leu Ala Thr Ser Gly
            370                 375                 380 caa ccc cag tat gtg ctc tgg gca tcc aac atc agc tcc ccc ggc tgt       1202
Gln Pro Gln Tyr Val Leu Trp Ala Ser Asn Ile Ser Ser Pro Gly Cys
385                 390                 395 gag aaa gtg cca ata aat aca tca tgc aac ccc acg gcc cac ctt gtg       1250
Glu Lys Val Pro Ile Asn Thr Ser Cys Asn Pro Thr Ala His Leu Val
400                 405                 410                 415 aac tcc tcg tgc cca ggg ctg atg tgc gtc ttc cag ggc tac tca tcc       1298
Asn Ser Ser Cys Pro Gly Leu Met Cys Val Phe Gln Gly Tyr Ser Ser
                420                 425                 430 aaa ggc cta atc caa cgt tct gtc ttc aat ctg caa atc tat ggg gtc       1346
Lys Gly Leu Ile Gln Arg Ser Val Phe Asn Leu Gln Ile Tyr Gly Val
            435                 440                 445 ctg ggg ctc ttc tgg acc ctt aac tgg gta ctg gcc ctg ggc caa tgc       1394
Leu Gly Leu Phe Trp Thr Leu Asn Trp Val Leu Ala Leu Gly Gln Cys
            450                 455                 460 gtc ctc gct gga gcc ttt gcc tcc ttc tac tgg gcc ttc cac aag ccc       1442
Val Leu Ala Gly Ala Phe Ala Ser Phe Tyr Trp Ala Phe His Lys Pro
465                 470                 475 cag gac atc cct acc ttc ccc tta atc tct gcc ttc atc cgc aca ctc       1490
Gln Asp Ile Pro Thr Phe Pro Leu Ile Ser Ala Phe Ile Arg Thr Leu
480                 485                 490                 495 cgt tac cac act ggg tca ttg gca ttt gga gcc ctc atc ctg acc ctt       1538
Arg Tyr His Thr Gly Ser Leu Ala Phe Gly Ala Leu Ile Leu Thr Leu
                500                 505                 510 gtg cag ata gcc cgg gtc atc ttg gag tat att gac cac aag ctc aga       1586
Val Gln Ile Ala Arg Val Ile Leu Glu Tyr Ile Asp His Lys Leu Arg
            515                 520                 525 gga gtg cag aac cct gta gcc cgc tgc atc atg tgc tgt ttc aag tgc       1634
Gly Val Gln Asn Pro Val Ala Arg Cys Ile Met Cys Cys Phe Lys Cys
            530                 535                 540 tgc ctc tgg tgt ctg gaa aaa ttt atc aag ttc cta aac cgc aat gca       1682
Cys Leu Trp Cys Leu Glu Lys Phe Ile Lys Phe Leu Asn Arg Asn Ala
545                 550                 555 tac atc atg atc gcc atc tac ggg aag aat ttc tgt gtc tca gcc aaa       1730
Tyr Ile Met Ile Ala Ile Tyr Gly Lys Asn Phe Cys Val Ser Ala Lys
560                 565                 570                 575 aat gcg ttc atg cta ctc atg cga aac att gtc agg gtg gtc gtc ctg       1778
```

| | | | | | | | | | | | | |
|---|---|---|---|---|---|---|---|---|---|---|---|---|
| Asn | Ala | Phe | Met | Leu | Leu | Met | Arg | Asn | Ile | Val | Arg | Val Val Leu |
| | | | | 580 | | | | 585 | | | | 590 | gac aaa gtc aca gac ctg ctg ctg ttc ttt ggg aag ctg ctg gtg gtc    1826
Asp Lys Val Thr Asp Leu Leu Leu Phe Phe Gly Lys Leu Leu Val Val
            595                 600                 605 gga ggc gtg ggg gtc ctg tcc ttc ttt ttt ttc tcc ggt cgc atc ccg    1874
Gly Gly Val Gly Val Leu Ser Phe Phe Phe Phe Ser Gly Arg Ile Pro
            610                 615                 620 ggg ctg ggt aaa gac ttt aag agc ccc cac ctc aac tat tac tgg ctg    1922
Gly Leu Gly Lys Asp Phe Lys Ser Pro His Leu Asn Tyr Tyr Trp Leu
    625                 630                 635 ccc atc atg acc tcc atc ctg ggg gcc tat gtc atc gcc agc ggc ttc    1970
Pro Ile Met Thr Ser Ile Leu Gly Ala Tyr Val Ile Ala Ser Gly Phe
640                 645                 650                 655 ttc agc gtt ttc ggc atg tgt gtg gac acg ctc ttc ctc tgc ttc ctg    2018
Phe Ser Val Phe Gly Met Cys Val Asp Thr Leu Phe Leu Cys Phe Leu
                660                 665                 670 gaa gac ctg gag cgg aac aac ggc tcc ctg gac cgg ccc tac tac atg    2066
Glu Asp Leu Glu Arg Asn Asn Gly Ser Leu Asp Arg Pro Tyr Tyr Met
            675                 680                 685 tcc aag agc ctt cta aag att ctg ggc aag aag aac gag gcg ccc ccg    2114
Ser Lys Ser Leu Leu Lys Ile Leu Gly Lys Lys Asn Glu Ala Pro Pro
        690                 695                 700 gac aac aag aag agg aag aag tga cagctccggc cctgatccag gactgcaccc   2168
Asp Asn Lys Lys Arg Lys Lys
    705                 710 caccccacc gtccagccat ccaacctcac ttcgccttac aggtctccat tttgtggtaa   2228
aaaaaggttt taggccaggc gccgtggctc acgcctgtaa tccaacactt tgagaggctg   2288
aggcgggcgg atcacctgag tcaggagttc gagaccagcc tggccaacat ggtgaaacct   2348
ccgtctctat aaaaatacaa aaattagcc gagagtggtg gcatgcacct gtcatcccag    2408
ctactcggga ggctgaggca ggagaatcgc ttgaacccgg gaggcagagg ttgcagtgag   2468
ccgagatcgc gccactgcac tccaacctgg gtgacagact ctgtctccaa acaaaacaa    2528 acaaacaaaa agattttatt aaagatattt tgttaactca gtaaaaaaaa aaaaaaaaa    2587

<210> SEQ ID NO 2
<211> LENGTH: 710
<212> TYPE: PRT
<213> ORGANISM: Homo sapiens

<400> SEQUENCE: 2

Met Gly Gly Lys Gln Arg Asp Glu Asp Glu Ala Tyr Gly Lys Pro
1               5                   10                  15

Val Lys Tyr Asp Pro Ser Phe Arg Gly Pro Ile Lys Asn Arg Ser Cys
            20                  25                  30

Thr Asp Val Ile Cys Cys Val Leu Phe Leu Leu Phe Ile Leu Gly Tyr
        35                  40                  45

Ile Val Val Gly Ile Val Ala Trp Leu Tyr Gly Asp Pro Arg Gln Val
    50                  55                  60

Leu Tyr Pro Arg Asn Ser Thr Gly Ala Tyr Cys Gly Met Gly Glu Asn
65                  70                  75                  80

Lys Asp Lys Pro Tyr Leu Leu Tyr Phe Asn Ile Phe Ser Cys Ile Leu
                85                  90                  95

Ser Ser Asn Ile Ile Ser Val Ala Glu Asn Gly Leu Gln Cys Pro Thr
            100                 105                 110

Pro Gln Val Cys Val Ser Ser Cys Pro Glu Asp Pro Trp Thr Val Gly
        115                 120                 125

```
Lys Asn Glu Phe Ser Gln Thr Val Gly Glu Val Phe Tyr Thr Lys Asn
        130                 135                 140
Arg Asn Phe Cys Leu Pro Gly Val Pro Trp Asn Met Thr Val Ile Thr
145                 150                 155                 160
Ser Leu Gln Gln Glu Leu Cys Pro Ser Phe Leu Leu Pro Ser Ala Pro
                    165                 170                 175
Ala Leu Gly Arg Cys Phe Pro Trp Thr Asn Val Thr Pro Pro Ala Leu
            180                 185                 190
Pro Gly Ile Thr Asn Asp Thr Thr Ile Gln Gln Gly Ile Ser Gly Leu
        195                 200                 205
Ile Asp Ser Leu Asn Ala Arg Asp Ile Ser Val Lys Ile Phe Glu Asp
        210                 215                 220
Phe Ala Gln Ser Trp Tyr Trp Ile Leu Val Ala Leu Gly Val Ala Leu
225                 230                 235                 240
Val Leu Ser Leu Leu Phe Ile Leu Leu Arg Leu Val Ala Gly Pro
                    245                 250                 255
Leu Val Leu Val Leu Ile Leu Gly Val Leu Gly Val Leu Ala Tyr Gly
            260                 265                 270
Ile Tyr Tyr Cys Trp Glu Glu Tyr Arg Val Leu Arg Asp Lys Gly Ala
        275                 280                 285
Ser Ile Ser Gln Leu Gly Phe Thr Thr Asn Leu Ser Ala Tyr Gln Ser
        290                 295                 300
Val Gln Glu Thr Trp Leu Ala Ala Leu Ile Val Leu Ala Val Leu Glu
305                 310                 315                 320
Ala Ile Leu Leu Leu Met Leu Ile Phe Leu Arg Gln Arg Ile Arg Ile
                    325                 330                 335
Ala Ile Ala Leu Leu Lys Glu Ala Ser Lys Ala Val Gly Gln Met Met
            340                 345                 350
Ser Thr Met Phe Tyr Pro Leu Val Thr Phe Val Leu Leu Leu Ile Cys
        355                 360                 365
Ile Ala Tyr Trp Ala Met Thr Ala Leu Tyr Leu Ala Thr Ser Gly Gln
        370                 375                 380
Pro Gln Tyr Val Leu Trp Ala Ser Asn Ile Ser Ser Pro Gly Cys Glu
385                 390                 395                 400
Lys Val Pro Ile Asn Thr Ser Cys Asn Pro Thr Ala His Leu Val Asn
                    405                 410                 415
Ser Ser Cys Pro Gly Leu Met Cys Val Phe Gln Gly Tyr Ser Ser Lys
            420                 425                 430
Gly Leu Ile Gln Arg Ser Val Phe Asn Leu Gln Ile Tyr Gly Val Leu
        435                 440                 445
Gly Leu Phe Trp Thr Leu Asn Trp Val Leu Ala Leu Gly Gln Cys Val
        450                 455                 460
Leu Ala Gly Ala Phe Ala Ser Phe Tyr Trp Ala Phe His Lys Pro Gln
465                 470                 475                 480
Asp Ile Pro Thr Phe Pro Leu Ile Ser Ala Phe Ile Arg Thr Leu Arg
                    485                 490                 495
Tyr His Thr Gly Ser Leu Ala Phe Gly Ala Leu Ile Leu Thr Leu Val
            500                 505                 510
Gln Ile Ala Arg Val Ile Leu Glu Tyr Ile Asp His Lys Leu Arg Gly
        515                 520                 525
Val Gln Asn Pro Val Ala Arg Cys Ile Met Cys Cys Phe Lys Cys Cys
        530                 535                 540
Leu Trp Cys Leu Glu Lys Phe Ile Lys Phe Leu Asn Arg Asn Ala Tyr
```

```
                545                 550                 555                 560
Ile Met Ile Ala Ile Tyr Gly Lys Asn Phe Cys Val Ser Ala Lys Asn
                    565                 570                 575

Ala Phe Met Leu Leu Met Arg Asn Ile Val Arg Val Val Leu Asp
                580                 585                 590

Lys Val Thr Asp Leu Leu Leu Phe Phe Gly Lys Leu Val Val Gly
                595                 600                 605

Gly Val Gly Val Leu Ser Phe Phe Phe Ser Gly Arg Ile Pro Gly
    610                 615                 620

Leu Gly Lys Asp Phe Lys Ser Pro His Leu Asn Tyr Tyr Trp Leu Pro
625                 630                 635                 640

Ile Met Thr Ser Ile Leu Gly Ala Tyr Val Ile Ala Ser Gly Phe Phe
                645                 650                 655

Ser Val Phe Gly Met Cys Val Asp Thr Leu Phe Leu Cys Phe Leu Glu
                660                 665                 670

Asp Leu Glu Arg Asn Asn Gly Ser Leu Asp Arg Pro Tyr Tyr Met Ser
                675                 680                 685

Lys Ser Leu Leu Lys Ile Leu Gly Lys Asn Glu Ala Pro Pro Asp
    690                 695                 700

Asn Lys Lys Arg Lys Lys
705                 710

<210> SEQ ID NO 3
<211> LENGTH: 2587
<212> TYPE: DNA
<213> ORGANISM: Homo sapiens
<220> FEATURE:
<221> NAME/KEY: CDS
<222> LOCATION: (6)...(2138)

<400> SEQUENCE: 3 gagcc atg ggg gga aag cag cgg gac gag gat gac gag gcc tac ggg aag      50
      Met Gly Gly Lys Gln Arg Asp Glu Asp Asp Glu Ala Tyr Gly Lys
      1               5                   10                  15 cca gtc aaa tac gac ccc tcc ttt cga ggc ccc atc aag aac aga agc      98
Pro Val Lys Tyr Asp Pro Ser Phe Arg Gly Pro Ile Lys Asn Arg Ser
            20                  25                  30 tgc aca gat gtc atc tgc tgc gtc ctc ttc ctg ctc ttc att cta ggt     146
Cys Thr Asp Val Ile Cys Cys Val Leu Phe Leu Leu Phe Ile Leu Gly
        35                  40                  45 tac atc gtg gtg ggg att gtg gcc tgg ttg tat gga gac ccc cgg caa     194
Tyr Ile Val Val Gly Ile Val Ala Trp Leu Tyr Gly Asp Pro Arg Gln
    50                  55                  60 gtc ctc tac ccc agg aac tct act ggg gcc tac tgt ggc atg ggg gag     242
Val Leu Tyr Pro Arg Asn Ser Thr Gly Ala Tyr Cys Gly Met Gly Glu
65                  70                  75 aac aaa gat aag ccg tat ctc ctg tac ttc aac atc ttc agc tgc atc     290
Asn Lys Asp Lys Pro Tyr Leu Leu Tyr Phe Asn Ile Phe Ser Cys Ile
80                  85                  90                  95 ctg tcc agc aac atc atc tca gtt gct gag aac ggc tta cag tgc ccc     338
Leu Ser Ser Asn Ile Ile Ser Val Ala Glu Asn Gly Leu Gln Cys Pro
                100                 105                 110 aca ccc cag gtg tgt gtg tcc tcc tgc ccg gag gac cca tgg act gtg     386
Thr Pro Gln Val Cys Val Ser Ser Cys Pro Glu Asp Pro Trp Thr Val
            115                 120                 125 gga aaa aac gag ttc tca cag act gtt ggg gaa gtc ttc tat aca aaa     434
Gly Lys Asn Glu Phe Ser Gln Thr Val Gly Glu Val Phe Tyr Thr Lys
        130                 135                 140 aac agg aac ttt tgt ctg cca ggg gta ccc tgg aat atg acg gtg atc     482
```

-continued

| | | |
|---|---|---|
| Asn Arg Asn Phe Cys Leu Pro Gly Val Pro Trp Asn Met Thr Val Ile<br>145                    150                    155 | | |
| aca agc ctg caa cag gaa ctc tgc ccc agt ttc ctc ctc ccc tct gct<br>Thr Ser Leu Gln Gln Glu Leu Cys Pro Ser Phe Leu Leu Pro Ser Ala<br>160                    165                    170                    175 | 530 |
| cca gct ctg gga cgc tgc ttt cca tgg acc aac gtt act cca ccg gcg<br>Pro Ala Leu Gly Arg Cys Phe Pro Trp Thr Asn Val Thr Pro Pro Ala<br>                    180                    185                    190 | 578 |
| ctc cca ggg atc acc aat gac acc acc ata cag cag ggg atc agc ggt<br>Leu Pro Gly Ile Thr Asn Asp Thr Thr Ile Gln Gln Gly Ile Ser Gly<br>              195                    200                    205 | 626 |
| ctt att gac agc ctc aat gcc cga gac atc agt gtt aag atc ttt gaa<br>Leu Ile Asp Ser Leu Asn Ala Arg Asp Ile Ser Val Lys Ile Phe Glu<br>        210                    215                    220 | 674 |
| gat ttt gcc cag tcc tgg tat tgg att ctt gtt gcc ctg ggg gtg gct<br>Asp Phe Ala Gln Ser Trp Tyr Trp Ile Leu Val Ala Leu Gly Val Ala<br>225                    230                    235 | 722 |
| ctg gtc ttg agc cta ctg ttt atc ttg ctt ctg cgc ctg gtg gct ggg<br>Leu Val Leu Ser Leu Leu Phe Ile Leu Leu Leu Arg Leu Val Ala Gly<br>240                    245                    250                    255 | 770 |
| ccc ctg gtg ctg gtg ctg atc ctg gga gtg ctg ggc gtg ctg gca tac<br>Pro Leu Val Leu Val Leu Ile Leu Gly Val Leu Gly Val Leu Ala Tyr<br>                        260                    265                    270 | 818 |
| ggc atc tac tac tgc tgg gag gag tac cga gtg ctg cgg gac aag ggc<br>Gly Ile Tyr Tyr Cys Trp Glu Glu Tyr Arg Val Leu Arg Asp Lys Gly<br>              275                    280                    285 | 866 |
| gcc tcc atc tcc cag ctg ggt ttc acc acc aac ctc agt gcc tac cag<br>Ala Ser Ile Ser Gln Leu Gly Phe Thr Thr Asn Leu Ser Ala Tyr Gln<br>        290                    295                    300 | 914 |
| agc gtg cag gag acc tgg ctg gcc gcc ctg atc gtg ttg gcg gtg ctt<br>Ser Val Gln Glu Thr Trp Leu Ala Ala Leu Ile Val Leu Ala Val Leu<br>305                    310                    315 | 962 |
| gaa gcc atc ctg ctg ctg atg ctc atc ttc ctg cgg cag cgg att cgt<br>Glu Ala Ile Leu Leu Leu Met Leu Ile Phe Leu Arg Gln Arg Ile Arg<br>320                    325                    330                    335 | 1010 |
| att gcc atc gcc ctc ctg aag gag gcc agc aag gct gtg gga cag atg<br>Ile Ala Ile Ala Leu Leu Lys Glu Ala Ser Lys Ala Val Gly Gln Met<br>                    340                    345                    350 | 1058 |
| atg tct acc atg ttc tac cca ctg gtc acc ttt gtc ctc ctc atc<br>Met Ser Thr Met Phe Tyr Pro Leu Val Thr Phe Val Leu Leu Leu Ile<br>              355                    360                    365 | 1106 |
| tgc att gcc tac tgg gcc atg act gct ctg tac ctg gct aca tcg ggg<br>Cys Ile Ala Tyr Trp Ala Met Thr Ala Leu Tyr Leu Ala Thr Ser Gly<br>        370                    375                    380 | 1154 |
| caa ccc cag tat gtg ctc tgg gca tcc aac atc agc tcc ccc ggc tgt<br>Gln Pro Gln Tyr Val Leu Trp Ala Ser Asn Ile Ser Ser Pro Gly Cys<br>385                    390                    395 | 1202 |
| gag aaa gtg cca ata aat aca tca tgc aac ccc acg gcc cac ctt gtg<br>Glu Lys Val Pro Ile Asn Thr Ser Cys Asn Pro Thr Ala His Leu Val<br>400                    405                    410                    415 | 1250 |
| aac tcc tcg tgc cca ggg ctg atg tgc gtc ttc cag ggc tac tca tcc<br>Asn Ser Ser Cys Pro Gly Leu Met Cys Val Phe Gln Gly Tyr Ser Ser<br>                    420                    425                    430 | 1298 |
| aaa ggc cta atc caa cgt tct gtc ttc aat ctg caa atc tat ggg gtc<br>Lys Gly Leu Ile Gln Arg Ser Val Phe Asn Leu Gln Ile Tyr Gly Val<br>              435                    440                    445 | 1346 |
| ctg ggg ctc ttc tgg acc ctt aac tgg gta ctg gcc ctg ggc caa tgc<br>Leu Gly Leu Phe Trp Thr Leu Asn Trp Val Leu Ala Leu Gly Gln Cys<br>        450                    455                    460 | 1394 |
| gtc ctc gct gga gcc ttt gcc tcc ttc tac tgg gcc ttc cac aag ccc | 1442 |

```
Val Leu Ala Gly Ala Phe Ala Ser Phe Tyr Trp Ala Phe His Lys Pro
            465                 470                 475 cag gac atc cct acc ttc ccc tta atc tct gcc ttc atc cgc aca ctc     1490
Gln Asp Ile Pro Thr Phe Pro Leu Ile Ser Ala Phe Ile Arg Thr Leu
480                 485                 490                 495 cgt tac cac act ggg tca ttg gca ttt gga gcc ctc atc ctg acc ctt     1538
Arg Tyr His Thr Gly Ser Leu Ala Phe Gly Ala Leu Ile Leu Thr Leu
                500                 505                 510 gtg cag ata gcc cgg gtc atc ttg gag tat att gac cac aag ctc aga     1586
Val Gln Ile Ala Arg Val Ile Leu Glu Tyr Ile Asp His Lys Leu Arg
            515                 520                 525 gga gtg cag aac cct gta gcc cgc tgc atc atg tgc tgt ttc aag tgc     1634
Gly Val Gln Asn Pro Val Ala Arg Cys Ile Met Cys Cys Phe Lys Cys
        530                 535                 540 tgc ctc tgg tgt ctg gaa aaa ttt atc aag ttc cta aac cgc aat gca     1682
Cys Leu Trp Cys Leu Glu Lys Phe Ile Lys Phe Leu Asn Arg Asn Ala
545                 550                 555 tac atc atg atc gcc atc tac ggg aag aat ttc tgt gtc tca gcc aaa     1730
Tyr Ile Met Ile Ala Ile Tyr Gly Lys Asn Phe Cys Val Ser Ala Lys
560                 565                 570                 575 aat gcg ttc atg cta ctc atg cga aac att gtc agg gtg gtc gtc ctg     1778
Asn Ala Phe Met Leu Leu Met Arg Asn Ile Val Arg Val Val Val Leu
                580                 585                 590 gac aaa gtc aca gac ctg ctg ctg ttc ttt ggg aag ctg ctg gtg gtc     1826
Asp Lys Val Thr Asp Leu Leu Leu Phe Phe Gly Lys Leu Leu Val Val
            595                 600                 605 gga ggc gtg ggg gtc ctg tcc ttc ttt ttt ttc tcc ggt cgc atc ccg     1874
Gly Gly Val Gly Val Leu Ser Phe Phe Phe Phe Ser Gly Arg Ile Pro
        610                 615                 620 ggg ctg ggt aaa gac ttt aag agc ccc cac ctc aac tat tac tgg ctg     1922
Gly Leu Gly Lys Asp Phe Lys Ser Pro His Leu Asn Tyr Tyr Trp Leu
625                 630                 635 ccc atc atg acc tcc atc ctg ggg gcc tat gtc atc gcc agc ggc ttc     1970
Pro Ile Met Thr Ser Ile Leu Gly Ala Tyr Val Ile Ala Ser Gly Phe
640                 645                 650                 655 ttc agc gtt ttc ggc atg tgt gtg gac acg ctc ttc ctc tgc ttc ctg     2018
Phe Ser Val Phe Gly Met Cys Val Asp Thr Leu Phe Leu Cys Phe Leu
                660                 665                 670 gaa gac ctg gag cgg aac aac ggc tcc ctg gac cgg ccc tac tac atg     2066
Glu Asp Leu Glu Arg Asn Asn Gly Ser Leu Asp Arg Pro Tyr Tyr Met
            675                 680                 685 tcc aag agc ctt cta aag att ctg ggc aag aag aac gag gcg ccc ccg     2114
Ser Lys Ser Leu Leu Lys Ile Leu Gly Lys Lys Asn Glu Ala Pro Pro
        690                 695                 700 gac aac aag aag agg aag aag tga cagctccggc cctgatccag gactgcaccc   2168
Asp Asn Lys Lys Arg Lys Lys
        705                 710 cacccccacc gtccagccat ccaacctcac ttcgccttac aggtctccat tttgtggtaa   2228
aaaaaggttt taggccaggc gccgtggctc acgcctgtaa tccaacactt tgagaggctg   2288
aggcgggcgg atcacctgag tcaggagttc gagaccagcc tggccaacat ggtgaaacct   2348
ccgtctctat taaaaataca aaaattagcc gagagtggtg gcatgcacct gtcatcccag   2408
ctactcggga ggctgaggca ggagaatcgc ttgaacccgg gaggcagagg ttgcagtgag   2468
ccgagatcgc gccactgcac tccaacctgg gtgacagact ctgtctccaa acaaaacaa    2528 acaaacaaaa agattttatt aaagatattt tgttaactca gtaaaaaaaa aaaaaaaa     2587

<210> SEQ ID NO 4
<211> LENGTH: 710
```

<212> TYPE: PRT
<213> ORGANISM: Homo sapiens

<400> SEQUENCE: 4

```
Met Gly Gly Lys Gln Arg Asp Glu Asp Glu Ala Tyr Gly Lys Pro
1               5                   10                  15

Val Lys Tyr Asp Pro Ser Phe Arg Gly Pro Ile Lys Asn Arg Ser Cys
            20                  25                  30

Thr Asp Val Ile Cys Cys Val Leu Phe Leu Leu Phe Ile Leu Gly Tyr
            35                  40                  45

Ile Val Val Gly Ile Val Ala Trp Leu Tyr Gly Asp Pro Arg Gln Val
        50                  55                  60

Leu Tyr Pro Arg Asn Ser Thr Gly Ala Tyr Cys Gly Met Gly Glu Asn
65              70                  75                  80

Lys Asp Lys Pro Tyr Leu Leu Tyr Phe Asn Ile Phe Ser Cys Ile Leu
                85                  90                  95

Ser Ser Asn Ile Ile Ser Val Ala Glu Asn Gly Leu Gln Cys Pro Thr
            100                 105                 110

Pro Gln Val Cys Val Ser Ser Cys Pro Glu Asp Pro Trp Thr Val Gly
        115                 120                 125

Lys Asn Glu Phe Ser Gln Thr Val Gly Glu Val Phe Tyr Thr Lys Asn
130             135                 140

Arg Asn Phe Cys Leu Pro Gly Val Pro Trp Asn Met Thr Val Ile Thr
145                 150                 155                 160

Ser Leu Gln Gln Glu Leu Cys Pro Ser Phe Leu Leu Pro Ser Ala Pro
                165                 170                 175

Ala Leu Gly Arg Cys Phe Pro Trp Thr Asn Val Thr Pro Pro Ala Leu
            180                 185                 190

Pro Gly Ile Thr Asn Asp Thr Thr Ile Gln Gln Gly Ile Ser Gly Leu
        195                 200                 205

Ile Asp Ser Leu Asn Ala Arg Asp Ile Ser Val Lys Ile Phe Glu Asp
210                 215                 220

Phe Ala Gln Ser Trp Tyr Trp Ile Leu Val Ala Leu Gly Val Ala Leu
225                 230                 235                 240

Val Leu Ser Leu Leu Phe Ile Leu Leu Leu Arg Leu Val Ala Gly Pro
                245                 250                 255

Leu Val Leu Val Leu Ile Leu Gly Val Leu Gly Val Leu Ala Tyr Gly
            260                 265                 270

Ile Tyr Tyr Cys Trp Glu Glu Tyr Arg Val Leu Arg Asp Lys Gly Ala
        275                 280                 285

Ser Ile Ser Gln Leu Gly Phe Thr Thr Asn Leu Ser Ala Tyr Gln Ser
290                 295                 300

Val Gln Glu Thr Trp Leu Ala Ala Leu Ile Val Leu Ala Val Leu Glu
305                 310                 315                 320

Ala Ile Leu Leu Leu Met Leu Ile Phe Leu Arg Gln Arg Ile Arg Ile
                325                 330                 335

Ala Ile Ala Leu Leu Lys Glu Ala Ser Lys Ala Val Gly Gln Met Met
            340                 345                 350

Ser Thr Met Phe Tyr Pro Leu Val Thr Phe Val Leu Leu Leu Ile Cys
        355                 360                 365

Ile Ala Tyr Trp Ala Met Thr Ala Leu Tyr Leu Ala Thr Ser Gly Gln
370                 375                 380

Pro Gln Tyr Val Leu Trp Ala Ser Asn Ile Ser Ser Pro Gly Cys Glu
385                 390                 395                 400
```

```
Lys Val Pro Ile Asn Thr Ser Cys Asn Pro Thr Ala His Leu Val Asn
                405                 410                 415

Ser Ser Cys Pro Gly Leu Met Cys Val Phe Gln Gly Tyr Ser Ser Lys
            420                 425                 430

Gly Leu Ile Gln Arg Ser Val Phe Asn Leu Gln Ile Tyr Gly Val Leu
        435                 440                 445

Gly Leu Phe Trp Thr Leu Asn Trp Val Leu Ala Leu Gly Gln Cys Val
    450                 455                 460

Leu Ala Gly Ala Phe Ala Ser Phe Tyr Trp Ala Phe His Lys Pro Gln
465                 470                 475                 480

Asp Ile Pro Thr Phe Pro Leu Ile Ser Ala Phe Ile Arg Thr Leu Arg
                485                 490                 495

Tyr His Thr Gly Ser Leu Ala Phe Gly Ala Leu Ile Leu Thr Leu Val
            500                 505                 510

Gln Ile Ala Arg Val Ile Leu Glu Tyr Ile Asp His Lys Leu Arg Gly
        515                 520                 525

Val Gln Asn Pro Val Ala Arg Cys Ile Met Cys Cys Phe Lys Cys Cys
    530                 535                 540

Leu Trp Cys Leu Glu Lys Phe Ile Lys Phe Leu Asn Arg Asn Ala Tyr
545                 550                 555                 560

Ile Met Ile Ala Ile Tyr Gly Lys Asn Phe Cys Val Ser Ala Lys Asn
                565                 570                 575

Ala Phe Met Leu Leu Met Arg Asn Ile Val Arg Val Val Leu Asp
            580                 585                 590

Lys Val Thr Asp Leu Leu Leu Phe Phe Gly Lys Leu Val Val Gly
        595                 600                 605

Gly Val Gly Val Leu Ser Phe Phe Phe Ser Gly Arg Ile Pro Gly
    610                 615                 620

Leu Gly Lys Asp Phe Lys Ser Pro His Leu Asn Tyr Tyr Trp Leu Pro
625                 630                 635                 640

Ile Met Thr Ser Ile Leu Gly Ala Tyr Val Ile Ala Ser Gly Phe Phe
                645                 650                 655

Ser Val Phe Gly Met Cys Val Asp Thr Leu Phe Leu Cys Phe Leu Glu
            660                 665                 670

Asp Leu Glu Arg Asn Asn Gly Ser Leu Asp Arg Pro Tyr Tyr Met Ser
        675                 680                 685

Lys Ser Leu Leu Lys Ile Leu Gly Lys Asn Glu Ala Pro Pro Asp
    690                 695                 700

Asn Lys Lys Arg Lys Lys
705                 710

<210> SEQ ID NO 5
<211> LENGTH: 2587
<212> TYPE: DNA
<213> ORGANISM: Homo sapiens
<220> FEATURE:
<221> NAME/KEY: CDS
<222> LOCATION: (6)...(2138)

<400> SEQUENCE: 5 gagcc atg ggg gga aag cag cgg gac gag gat gac gag gcc tac ggg aag      50
      Met Gly Gly Lys Gln Arg Asp Glu Asp Asp Glu Ala Tyr Gly Lys
      1               5                   10                  15 cca gtc aaa tac gac ccc tcc ttt cga ggc ccc atc aag aac aga agc       98
Pro Val Lys Tyr Asp Pro Ser Phe Arg Gly Pro Ile Lys Asn Arg Ser
            20                  25                  30 tgc aca gat gtc atc tgc tgc gtc ctc ttc ctg ctc ttc att cta ggt      146
```

```
                Cys Thr Asp Val Ile Cys Cys Val Leu Phe Leu Leu Phe Ile Leu Gly
                            35                  40                  45 tac atc gtg gtg ggg att gtg gcc tgg ttg tat gga gac ccc cgg caa         194
Tyr Ile Val Val Gly Ile Val Ala Trp Leu Tyr Gly Asp Pro Arg Gln
        50                  55                  60 gtc ctc tac ccc agg aac tct act ggg gcc tac tgt ggc atg ggg gag         242
Val Leu Tyr Pro Arg Asn Ser Thr Gly Ala Tyr Cys Gly Met Gly Glu
65                  70                  75 aac aaa gat aag ccg tat ctc ctg tac ttc aac atc ttc agc tgc atc         290
Asn Lys Asp Lys Pro Tyr Leu Leu Tyr Phe Asn Ile Phe Ser Cys Ile
80                  85                  90                  95 ctg tcc agc aac atc atc tca gtt gct gag aac ggc cta cag tgc ccc         338
Leu Ser Ser Asn Ile Ile Ser Val Ala Glu Asn Gly Leu Gln Cys Pro
                100                 105                 110 aca ccc cag gtg tgt gtg tcc tcc tgc ccg gag gac cca tgg act gtg         386
Thr Pro Gln Val Cys Val Ser Ser Cys Pro Glu Asp Pro Trp Thr Val
            115                 120                 125 gga aaa aac gag ttc tca cag act gtt ggg gaa gtc ttc tat aca aaa         434
Gly Lys Asn Glu Phe Ser Gln Thr Val Gly Glu Val Phe Tyr Thr Lys
        130                 135                 140 aac agg aac ttt tgt ctg cca ggg gta ccc tgg aat atg acg gtg atc         482
Asn Arg Asn Phe Cys Leu Pro Gly Val Pro Trp Asn Met Thr Val Ile
145                 150                 155 aca agc ctg caa cag gaa ctc tgc ccc agt ttc ctc ctc ccc tct gct         530
Thr Ser Leu Gln Gln Glu Leu Cys Pro Ser Phe Leu Leu Pro Ser Ala
160                 165                 170                 175 cca gct ctg ggg cgc tgc ttt cca tgg acc aac att act cca ccg gcg         578
Pro Ala Leu Gly Arg Cys Phe Pro Trp Thr Asn Ile Thr Pro Pro Ala
            180                 185                 190 ctc cca ggg atc acc aat gac acc acc ata cag cag ggg atc agc ggt         626
Leu Pro Gly Ile Thr Asn Asp Thr Thr Ile Gln Gln Gly Ile Ser Gly
        195                 200                 205 ctt att gac agc ctc aat gcc cga gac atc agt gtt aag atc ttt gaa         674
Leu Ile Asp Ser Leu Asn Ala Arg Asp Ile Ser Val Lys Ile Phe Glu
210                 215                 220 gat ttt gcc cag tcc tgg tat tgg att ctt gtt gcc ctg ggg gtg gct         722
Asp Phe Ala Gln Ser Trp Tyr Trp Ile Leu Val Ala Leu Gly Val Ala
225                 230                 235 ctg gtc ttg agc cta ctg ttt atc ttg ctt ctg cgc ctg gtg gct ggg         770
Leu Val Leu Ser Leu Leu Phe Ile Leu Leu Leu Arg Leu Val Ala Gly
240                 245                 250                 255 ccc ctg gtg ctg gtg ctg atc ctg gga gtg ctg ggc gtg ctg gca tac         818
Pro Leu Val Leu Val Leu Ile Leu Gly Val Leu Gly Val Leu Ala Tyr
            260                 265                 270 ggc atc tac tac tgc tgg gag gag tac cga gtg ctg cgg gac aag ggc         866
Gly Ile Tyr Tyr Cys Trp Glu Glu Tyr Arg Val Leu Arg Asp Lys Gly
        275                 280                 285 gcc tcc atc tcc cag ctg ggt ttc acc acc aac ctc agt gcc tac cag         914
Ala Ser Ile Ser Gln Leu Gly Phe Thr Thr Asn Leu Ser Ala Tyr Gln
290                 295                 300 agc gtg cag gag acc tgg ctg gcc gcc ctg atc gtg ttg gcg gtg ctt         962
Ser Val Gln Glu Thr Trp Leu Ala Ala Leu Ile Val Leu Ala Val Leu
305                 310                 315 gaa gcc atc ctg ctg ctg atg ctc atc ttc ctg cgg cag cgg att cgt         1010
Glu Ala Ile Leu Leu Leu Met Leu Ile Phe Leu Arg Gln Arg Ile Arg
320                 325                 330                 335 att gcc atc gcc ctc ctg aag gag gcc agc aag gct gtg gga cag atg         1058
Ile Ala Ile Ala Leu Leu Lys Glu Ala Ser Lys Ala Val Gly Gln Met
            340                 345                 350 atg tct acc atg ttc tac cca ctg gtc acc ttt gtc ctc ctc ctc atc         1106
```

```
                Met Ser Thr Met Phe Tyr Pro Leu Val Thr Phe Val Leu Leu Leu Ile
                            355                 360                 365 tgc att gcc tac tgg gcc atg act gct ctg tac ctg gct aca tcg ggg         1154
Cys Ile Ala Tyr Trp Ala Met Thr Ala Leu Tyr Leu Ala Thr Ser Gly
            370                 375                 380 caa ccc cag tat gtg ctc tgg gca tcc aac atc agc tcc ccc ggc tgt         1202
Gln Pro Gln Tyr Val Leu Trp Ala Ser Asn Ile Ser Ser Pro Gly Cys
            385                 390                 395 gag aaa gtg cca ata aat aca tca tgc aac ccc acg gcc cac ctt gtg         1250
Glu Lys Val Pro Ile Asn Thr Ser Cys Asn Pro Thr Ala His Leu Val
400                 405                 410                 415 aac tcc tcg tgc cca ggg ctg atg tgc gtc ttc cag ggc tac tca tcc         1298
Asn Ser Ser Cys Pro Gly Leu Met Cys Val Phe Gln Gly Tyr Ser Ser
                420                 425                 430 aaa ggc cta atc caa cgt tct gtc ttc aat ctg caa atc tat ggg gtc         1346
Lys Gly Leu Ile Gln Arg Ser Val Phe Asn Leu Gln Ile Tyr Gly Val
            435                 440                 445 ctg ggg ctc ttc tgg acc ctt aac tgg gta ctg gcc ctg gga caa tgc         1394
Leu Gly Leu Phe Trp Thr Leu Asn Trp Val Leu Ala Leu Gly Gln Cys
            450                 455                 460 gtc ctc gct gga gcc ttt gcc tcc ttc tac tgg gcc ttc cac aag ccc         1442
Val Leu Ala Gly Ala Phe Ala Ser Phe Tyr Trp Ala Phe His Lys Pro
        465                 470                 475 cag gac atc cct acc ttc ccc tta atc tct gcc ttc atc cgc aca ctc         1490
Gln Asp Ile Pro Thr Phe Pro Leu Ile Ser Ala Phe Ile Arg Thr Leu
480                 485                 490                 495 cgt tac cac act ggg tca ttg gca ttt gga gcc ctc atc ctg acc ctt         1538
Arg Tyr His Thr Gly Ser Leu Ala Phe Gly Ala Leu Ile Leu Thr Leu
                500                 505                 510 gtg cag ata gcc cgg gtc atc ttg gag tat att gac cac aag ctc aga         1586
Val Gln Ile Ala Arg Val Ile Leu Glu Tyr Ile Asp His Lys Leu Arg
            515                 520                 525 gga gtg cag aac cct gta gcc cgc tgc atc atg tgc tgt ttc aag tgc         1634
Gly Val Gln Asn Pro Val Ala Arg Cys Ile Met Cys Cys Phe Lys Cys
            530                 535                 540 tgc ctc tgg tgt ctg gaa aaa ttt atc aag ttc cta aac cgc aat gca         1682
Cys Leu Trp Cys Leu Glu Lys Phe Ile Lys Phe Leu Asn Arg Asn Ala
545                 550                 555 tac atc atg atc gcc atc tac ggg aag aat ttc tgt gtc tca gcc aaa         1730
Tyr Ile Met Ile Ala Ile Tyr Gly Lys Asn Phe Cys Val Ser Ala Lys
            560                 565                 570                 575 aat gcg ttc atg cta ctc atg cga aac att gtc agg gtg gtc gtc ctg         1778
Asn Ala Phe Met Leu Leu Met Arg Asn Ile Val Arg Val Val Val Leu
                580                 585                 590 gac aaa gtc aca gac ctg ctg ctg ttc ttt ggg aag ctg ctg gtg gtc         1826
Asp Lys Val Thr Asp Leu Leu Leu Phe Phe Gly Lys Leu Leu Val Val
            595                 600                 605 gga ggc gtg ggg gtc ctg tcc ttc ttt ttt ttc tcc ggt cgc atc ccg         1874
Gly Gly Val Gly Val Leu Ser Phe Phe Phe Phe Ser Gly Arg Ile Pro
            610                 615                 620 ggg ctg ggt aaa gac ttt aag agc ccc cac ctc aac tat tac tgg ctg         1922
Gly Leu Gly Lys Asp Phe Lys Ser Pro His Leu Asn Tyr Tyr Trp Leu
625                 630                 635 ccc atc atg acc tcc atc ctg ggg gcc tat gtc atc gcc agc ggc ttc         1970
Pro Ile Met Thr Ser Ile Leu Gly Ala Tyr Val Ile Ala Ser Gly Phe
640                 645                 650                 655 ttc agc gtt ttc ggc atg tgt gtg gac acg ctc ttc ctc tgc ttc ctg         2018
Phe Ser Val Phe Gly Met Cys Val Asp Thr Leu Phe Leu Cys Phe Leu
                660                 665                 670 gaa gac ctg gag cgg aac aac ggc tcc ctg gac cgg ccc tac tac atg         2066
```

-continued

```
Glu Asp Leu Glu Arg Asn Asn Gly Ser Leu Asp Arg Pro Tyr Tyr Met
                675                 680                 685 tcc aag agc ctt cta aag att ctg ggc aag aag aac gag gcg ccc ccg      2114
Ser Lys Ser Leu Leu Lys Ile Leu Gly Lys Lys Asn Glu Ala Pro Pro
            690                 695                 700 gac aac aag aag agg aag aag tga cagctccggc cctgatccag gactgcaccc     2168
Asp Asn Lys Lys Arg Lys Lys
705                 710 cacccccacc gtccagccat ccaacctcac ttcgccttac aggtctccat tttgtggtaa    2228
aaaaaggttt taggccaggc gccgtggctc acgcctgtaa tccaacactt tgagaggctg    2288
aggcgggcgg atcacctgag tcaggagttc gagaccagcc tggccaacat ggtgaaacct    2348
ccgtctctat aaaaataca aaaattagcc gagagtggtg gcatgcacct gtcatcccag     2408
ctactcggga ggctgaggca ggagaatcgc ttgaacccgg gaggcagagg ttgcagtgag    2468
ccgagatcgc gccactgcac tccaacctgg gtgacagact ctgtctccaa aacaaaacaa    2528
acaaacaaaa agattttatt aaagatattt tgttaactca gtaaaaaaaa aaaaaaaa     2587

<210> SEQ ID NO 6
<211> LENGTH: 710
<212> TYPE: PRT
<213> ORGANISM: Homo sapiens

<400> SEQUENCE: 6

Met Gly Gly Lys Gln Arg Asp Glu Asp Asp Glu Ala Tyr Gly Lys Pro
1               5                  10                  15

Val Lys Tyr Asp Pro Ser Phe Arg Gly Pro Ile Lys Asn Arg Ser Cys
            20                  25                  30

Thr Asp Val Ile Cys Cys Val Leu Phe Leu Leu Phe Ile Leu Gly Tyr
        35                  40                  45

Ile Val Val Gly Ile Val Ala Trp Leu Tyr Gly Asp Pro Arg Gln Val
    50                  55                  60

Leu Tyr Pro Arg Asn Ser Thr Gly Ala Tyr Cys Gly Met Gly Glu Asn
65                  70                  75                  80

Lys Asp Lys Pro Tyr Leu Leu Tyr Phe Asn Ile Phe Ser Cys Ile Leu
                85                  90                  95

Ser Ser Asn Ile Ile Ser Val Ala Glu Asn Gly Leu Gln Cys Pro Thr
            100                 105                 110

Pro Gln Val Cys Val Ser Ser Cys Pro Glu Asp Pro Trp Thr Val Gly
        115                 120                 125

Lys Asn Glu Phe Ser Gln Thr Val Gly Glu Val Phe Tyr Thr Lys Asn
    130                 135                 140

Arg Asn Phe Cys Leu Pro Gly Val Pro Trp Asn Met Thr Val Ile Thr
145                 150                 155                 160

Ser Leu Gln Gln Glu Leu Cys Pro Ser Phe Leu Leu Pro Ser Ala Pro
                165                 170                 175

Ala Leu Gly Arg Cys Phe Pro Trp Thr Asn Ile Thr Pro Pro Ala Leu
            180                 185                 190

Pro Gly Ile Thr Asn Asp Thr Thr Ile Gln Gln Gly Ile Ser Gly Leu
        195                 200                 205

Ile Asp Ser Leu Asn Ala Arg Asp Ile Ser Val Lys Ile Phe Glu Asp
    210                 215                 220

Phe Ala Gln Ser Trp Tyr Trp Ile Leu Val Ala Leu Gly Val Ala Leu
225                 230                 235                 240

Val Leu Ser Leu Leu Phe Ile Leu Leu Leu Arg Leu Val Ala Gly Pro
                245                 250                 255
```

```
Leu Val Leu Val Leu Ile Leu Gly Val Leu Gly Val Leu Ala Tyr Gly
            260                 265                 270

Ile Tyr Tyr Cys Trp Glu Glu Tyr Arg Val Leu Arg Asp Lys Gly Ala
            275                 280                 285

Ser Ile Ser Gln Leu Gly Phe Thr Thr Asn Leu Ser Ala Tyr Gln Ser
290                 295                 300

Val Gln Glu Thr Trp Leu Ala Ala Leu Ile Val Leu Ala Val Leu Glu
305                 310                 315                 320

Ala Ile Leu Leu Leu Met Leu Ile Phe Leu Arg Gln Arg Ile Arg Ile
                325                 330                 335

Ala Ile Ala Leu Leu Lys Glu Ala Ser Lys Ala Val Gly Gln Met Met
                340                 345                 350

Ser Thr Met Phe Tyr Pro Leu Val Thr Phe Val Leu Leu Ile Cys
            355                 360                 365

Ile Ala Tyr Trp Ala Met Thr Ala Leu Tyr Leu Ala Thr Ser Gly Gln
            370                 375                 380

Pro Gln Tyr Val Leu Trp Ala Ser Asn Ile Ser Ser Pro Gly Cys Glu
385                 390                 395                 400

Lys Val Pro Ile Asn Thr Ser Cys Asn Pro Thr Ala His Leu Val Asn
                405                 410                 415

Ser Ser Cys Pro Gly Leu Met Cys Val Phe Gln Gly Tyr Ser Ser Lys
                420                 425                 430

Gly Leu Ile Gln Arg Ser Val Phe Asn Leu Gln Ile Tyr Gly Val Leu
            435                 440                 445

Gly Leu Phe Trp Thr Leu Asn Trp Val Leu Ala Leu Gly Gln Cys Val
            450                 455                 460

Leu Ala Gly Ala Phe Ala Ser Phe Tyr Trp Ala Phe His Lys Pro Gln
465                 470                 475                 480

Asp Ile Pro Thr Phe Pro Leu Ile Ser Ala Phe Ile Arg Thr Leu Arg
                485                 490                 495

Tyr His Thr Gly Ser Leu Ala Phe Gly Ala Leu Ile Leu Thr Leu Val
            500                 505                 510

Gln Ile Ala Arg Val Ile Leu Glu Tyr Ile Asp His Lys Leu Arg Gly
            515                 520                 525

Val Gln Asn Pro Val Ala Arg Cys Ile Met Cys Cys Phe Lys Cys Cys
            530                 535                 540

Leu Trp Cys Leu Glu Lys Phe Ile Lys Phe Leu Asn Arg Asn Ala Tyr
545                 550                 555                 560

Ile Met Ile Ala Ile Tyr Gly Lys Asn Phe Cys Val Ser Ala Lys Asn
                565                 570                 575

Ala Phe Met Leu Leu Met Arg Asn Ile Val Arg Val Val Val Leu Asp
                580                 585                 590

Lys Val Thr Asp Leu Leu Leu Phe Phe Gly Lys Leu Leu Val Val Gly
                595                 600                 605

Gly Val Gly Val Leu Ser Phe Phe Phe Ser Gly Arg Ile Pro Gly
610                 615                 620

Leu Gly Lys Asp Phe Lys Ser Pro His Leu Asn Tyr Tyr Trp Leu Pro
625                 630                 635                 640

Ile Met Thr Ser Ile Leu Gly Ala Tyr Val Ile Ala Ser Gly Phe Phe
                645                 650                 655

Ser Val Phe Gly Met Cys Val Asp Thr Leu Phe Leu Cys Phe Leu Glu
                660                 665                 670

Asp Leu Glu Arg Asn Asn Gly Ser Leu Asp Arg Pro Tyr Tyr Met Ser
```

```
                    675                 680                 685
Lys Ser Leu Leu Lys Ile Leu Gly Lys Lys Asn Glu Ala Pro Pro Asp
            690                 695                 700

Asn Lys Lys Arg Lys Lys
705             710

<210> SEQ ID NO 7
<211> LENGTH: 2587
<212> TYPE: DNA
<213> ORGANISM: Homo sapiens
<220> FEATURE:
<221> NAME/KEY: CDS
<222> LOCATION: (6)...(2138)

<400> SEQUENCE: 7 gagcc atg ggg gga aag cag cgg gac gag gat gac gag gcc tac ggg aag     50
      Met Gly Gly Lys Gln Arg Asp Glu Asp Asp Glu Ala Tyr Gly Lys
      1               5                   10                  15 cca gtc aaa tac gac ccc tcc ttt cga ggc ccc atc aag aac aga agc      98
Pro Val Lys Tyr Asp Pro Ser Phe Arg Gly Pro Ile Lys Asn Arg Ser
            20                  25                  30 tgc aca gat gtc atc tgc tgc gtc ctc ttc ctg ctc ttc att cta ggt     146
Cys Thr Asp Val Ile Cys Cys Val Leu Phe Leu Leu Phe Ile Leu Gly
        35                  40                  45 tac atc gtg gtg ggg att gtg gcc tgg ttg tat gga gac ccc cgg caa     194
Tyr Ile Val Val Gly Ile Val Ala Trp Leu Tyr Gly Asp Pro Arg Gln
    50                  55                  60 gtc ctc tac ccc agg aac tct act ggg gcc tac tgt ggc atg ggg gag     242
Val Leu Tyr Pro Arg Asn Ser Thr Gly Ala Tyr Cys Gly Met Gly Glu
65                  70                  75 aac aaa gat aag ccg tat ctc ctg tac ttc aac atc ttc agc tgc atc     290
Asn Lys Asp Lys Pro Tyr Leu Leu Tyr Phe Asn Ile Phe Ser Cys Ile
80                  85                  90                  95 ctg tcc agc aac atc atc tca gtt gct gag aac ggc cta cag tgc ccc     338
Leu Ser Ser Asn Ile Ile Ser Val Ala Glu Asn Gly Leu Gln Cys Pro
                100                 105                 110 aca ccc cag gtg tgt gtg tcc tcc tgc ccg gag gac cca tgg act gtg     386
Thr Pro Gln Val Cys Val Ser Ser Cys Pro Glu Asp Pro Trp Thr Val
            115                 120                 125 gga aaa aac gag ttc tca cag act gtt ggg gaa gtc ttc tat aca aaa     434
Gly Lys Asn Glu Phe Ser Gln Thr Val Gly Glu Val Phe Tyr Thr Lys
        130                 135                 140 aac agg aac ttt tgt ctg cca ggg gta ccc tgg aat atg acg gtg atc     482
Asn Arg Asn Phe Cys Leu Pro Gly Val Pro Trp Asn Met Thr Val Ile
    145                 150                 155 aca agc ctg caa cag gaa ctc tgc ccc agt ttc ctc ctc ccc tct gct     530
Thr Ser Leu Gln Gln Glu Leu Cys Pro Ser Phe Leu Leu Pro Ser Ala
160                 165                 170                 175 cca gct ctg ggg cgc tgc ttt cca tgg acc aac gtt act cca ccg gcg     578
Pro Ala Leu Gly Arg Cys Phe Pro Trp Thr Asn Val Thr Pro Pro Ala
                180                 185                 190 ctc cca ggg atc acc aat gac acc acc ata cag cag ggg atc agc ggt     626
Leu Pro Gly Ile Thr Asn Asp Thr Thr Ile Gln Gln Gly Ile Ser Gly
            195                 200                 205 ctt att gac agc ctc aat gcc gga gac atc agt gtt aag atc ttt gaa     674
Leu Ile Asp Ser Leu Asn Ala Arg Asp Ile Ser Val Lys Ile Phe Glu
        210                 215                 220 gat ttt gcc cag tcc tgg tat tgg att ctt gtt gcc ctg ggg gtg gct     722
Asp Phe Ala Gln Ser Trp Tyr Trp Ile Leu Val Ala Leu Gly Val Ala
    225                 230                 235 ctg gtc ttg agc cta ctg ttt atc ttg ctt ctg cgc ctg gtg gct ggg     770
Leu Val Leu Ser Leu Leu Phe Ile Leu Leu Leu Arg Leu Val Ala Gly
```

```
                -continued

Leu Val Leu Ser Leu Leu Phe Ile Leu Leu Arg Leu Val Ala Gly
240             245                 250             255 ccc ctg gtg ctg gtg ctg atc ctg gga gtg ctg ggc gtg ctg gca tat       818
Pro Leu Val Leu Val Leu Ile Leu Gly Val Leu Gly Val Leu Ala Tyr
                260             265             270 ggc atc tac tac tgc tgg gag gag tac cga gtg ctg cgg gac aag ggc       866
Gly Ile Tyr Tyr Cys Trp Glu Glu Tyr Arg Val Leu Arg Asp Lys Gly
            275             280             285 gcc tcc atc tcc cag ctg ggt ttc acc acc aac ctc agt gcc tac cag       914
Ala Ser Ile Ser Gln Leu Gly Phe Thr Thr Asn Leu Ser Ala Tyr Gln
        290             295             300 agc gtg cag gag acc tgg ctg gcc gcc ctg atc gtg ttg gcg gtg ctt       962
Ser Val Gln Glu Thr Trp Leu Ala Ala Leu Ile Val Leu Ala Val Leu
    305             310             315 gaa gcc atc ctg ctg ctg atg ctc atc ttc ctg cgg cag cgg att cgt      1010
Glu Ala Ile Leu Leu Leu Met Leu Ile Phe Leu Arg Gln Arg Ile Arg
320             325             330             335 att gcc atc gcc ctc ctg aag gag gcc agc aag gct gtg gga cag atg      1058
Ile Ala Ile Ala Leu Leu Lys Glu Ala Ser Lys Ala Val Gly Gln Met
            340             345             350 atg tct acc atg ttc tac cca ctg gtc acc ttt gtc ctc ctc ctc atc      1106
Met Ser Thr Met Phe Tyr Pro Leu Val Thr Phe Val Leu Leu Leu Ile
        355             360             365 tgc att gcc tac tgg gcc atg act gct ctg tac ctg gct aca tcg ggg      1154
Cys Ile Ala Tyr Trp Ala Met Thr Ala Leu Tyr Leu Ala Thr Ser Gly
    370             375             380 caa ccc cag tat gtg ctc tgg gca tcc aac atc agc tcc ccc ggc tgt      1202
Gln Pro Gln Tyr Val Leu Trp Ala Ser Asn Ile Ser Ser Pro Gly Cys
385             390             395 gag aaa gtg cca ata aat aca tca tgc aac ccc acg gcc cac ctt gtg      1250
Glu Lys Val Pro Ile Asn Thr Ser Cys Asn Pro Thr Ala His Leu Val
400             405             410             415 aac tcc tcg tgc cca ggg ctg atg tgc gtc ttc cag ggc tac tca tcc      1298
Asn Ser Ser Cys Pro Gly Leu Met Cys Val Phe Gln Gly Tyr Ser Ser
            420             425             430 aaa ggc cta atc caa cgt tct gtc ttc aat ctg caa atc tat ggg gtc      1346
Lys Gly Leu Ile Gln Arg Ser Val Phe Asn Leu Gln Ile Tyr Gly Val
        435             440             445 ctg ggg ctc ttc tgg acc ctt aac tgg gta ctg gcc ctg ggc caa tgc      1394
Leu Gly Leu Phe Trp Thr Leu Asn Trp Val Leu Ala Leu Gly Gln Cys
    450             455             460 gtc ctc gct gga gcc ttt gcc tcc ttc tac tgg gcc ttc cac aag ccc      1442
Val Leu Ala Gly Ala Phe Ala Ser Phe Tyr Trp Ala Phe His Lys Pro
465             470             475 cag gac atc cct acc ttc ccc tta atc tct gcc ttc atc cgc aca ctc      1490
Gln Asp Ile Pro Thr Phe Pro Leu Ile Ser Ala Phe Ile Arg Thr Leu
480             485             490             495 cgt tac cac act ggg tca ttg gca ttt gga gcc ctc atc ctg acc ctt      1538
Arg Tyr His Thr Gly Ser Leu Ala Phe Gly Ala Leu Ile Leu Thr Leu
            500             505             510 gtg cag ata gcc cgg gtc atc ttg gag tat att gac cac aag ctc aga      1586
Val Gln Ile Ala Arg Val Ile Leu Glu Tyr Ile Asp His Lys Leu Arg
        515             520             525 gga gtg cag aac cct gta gcc cgc tgc atc atg tgt tgt ttc aag tgc      1634
Gly Val Gln Asn Pro Val Ala Arg Cys Ile Met Cys Cys Phe Lys Cys
    530             535             540 tgc ctc tgg tgt ctg gaa aaa ttt atc aag ttc cta aac cgc aat gca      1682
Cys Leu Trp Cys Leu Glu Lys Phe Ile Lys Phe Leu Asn Arg Asn Ala
545             550             555 tac atc atg atc gcc atc tac ggg aag aat ttc tgt gtc tca gcc aaa      1730
```

-continued

```
Tyr Ile Met Ile Ala Ile Tyr Gly Lys Asn Phe Cys Val Ser Ala Lys
560                 565                 570                 575 aat gcg ttc atg cta ctc atg cga aac att gtc agg gtg gtc gtc ctg      1778
Asn Ala Phe Met Leu Leu Met Arg Asn Ile Val Arg Val Val Val Leu
                580                 585                 590 gac aaa gtc aca gac ctg ctg ctg ttc ttt ggg aag ctg ctg gtg gtc      1826
Asp Lys Val Thr Asp Leu Leu Leu Phe Phe Gly Lys Leu Leu Val Val
            595                 600                 605 gga ggc gtg ggg gtc ctg tcc ttc ttt ttt ttc tcc ggt cgc atc ccg      1874
Gly Gly Val Gly Val Leu Ser Phe Phe Phe Phe Ser Gly Arg Ile Pro
        610                 615                 620 ggg ctg ggt aaa gac ttt aag agc ccc cac ctc aac tat tac tgg ctg      1922
Gly Leu Gly Lys Asp Phe Lys Ser Pro His Leu Asn Tyr Tyr Trp Leu
    625                 630                 635 ccc atc atg acc tcc atc ctg ggg gcc tat gtc atc gcc agc ggc ttc      1970
Pro Ile Met Thr Ser Ile Leu Gly Ala Tyr Val Ile Ala Ser Gly Phe
640                 645                 650                 655 ttc agc gtt ttc ggc atg tgt gtg gac acg ctc ttc ctc tgc ttc ctg      2018
Phe Ser Val Phe Gly Met Cys Val Asp Thr Leu Phe Leu Cys Phe Leu
                660                 665                 670 gaa gac ctg gag cgg aac aac ggc tcc ctg gac cgg ccc tac tac atg      2066
Glu Asp Leu Glu Arg Asn Asn Gly Ser Leu Asp Arg Pro Tyr Tyr Met
            675                 680                 685 tcc aag agc ctt cta aag att ctg ggc aag aag aac gag gcg ccc ccg      2114
Ser Lys Ser Leu Leu Lys Ile Leu Gly Lys Lys Asn Glu Ala Pro Pro
        690                 695                 700 gac aac aag aag agg aag aag tga cagctccggc cctgatccag gactgcaccc     2168
Asp Asn Lys Lys Arg Lys Lys
        705                 710 cacccccacc gtccagccat ccaacctcac ttcgccttac aggtctccat tttgtggtaa    2228
aaaaaggttt taggccaggc gccgtggctc acgcctgtaa tccaacactt tgagaggctg    2288
aggcgggcgg atcacctgag tcaggagttc gagaccagcc tggccaacat ggtgaaacct    2348
ccgtctctat taaaaataca aaaattagcc gagagtggtg gcatgcacct gtcatcccag    2408
ctactcggga ggctgaggca ggagaatcgc ttgaacccgg gaggcagagg ttgcagtgag    2468
ccgagatcgc gccactgcac tccaacctgg gtgacagact ctgtctccaa acaaaaacaa    2528
acaaacaaaa agattttatt aaagatattt tgttaactca gtaaaaaaaa aaaaaaaa     2587

<210> SEQ ID NO 8
<211> LENGTH: 710
<212> TYPE: PRT
<213> ORGANISM: Homo sapiens

<400> SEQUENCE: 8

Met Gly Gly Lys Gln Arg Asp Glu Asp Glu Ala Tyr Gly Lys Pro
1               5                   10                  15

Val Lys Tyr Asp Pro Ser Phe Arg Gly Pro Ile Lys Asn Arg Ser Cys
                20                  25                  30

Thr Asp Val Ile Cys Cys Val Leu Phe Leu Leu Phe Ile Leu Gly Tyr
            35                  40                  45

Ile Val Val Gly Ile Val Ala Trp Leu Tyr Gly Asp Pro Arg Gln Val
        50                  55                  60

Leu Tyr Pro Arg Asn Ser Thr Gly Ala Tyr Cys Gly Met Gly Glu Asn
65                  70                  75                  80

Lys Asp Lys Pro Tyr Leu Leu Tyr Phe Asn Ile Phe Ser Cys Ile Leu
                85                  90                  95

Ser Ser Asn Ile Ile Ser Val Ala Glu Asn Gly Leu Gln Cys Pro Thr
```

```
                100             105             110
Pro Gln Val Cys Val Ser Ser Cys Pro Glu Asp Pro Trp Thr Val Gly
            115                 120             125
Lys Asn Glu Phe Ser Gln Thr Val Gly Glu Val Phe Tyr Thr Lys Asn
    130                 135                 140
Arg Asn Phe Cys Leu Pro Gly Val Pro Trp Asn Met Thr Val Ile Thr
145                 150                 155                 160
Ser Leu Gln Gln Glu Leu Cys Pro Ser Phe Leu Leu Pro Ser Ala Pro
                165                 170                 175
Ala Leu Gly Arg Cys Phe Pro Trp Thr Asn Val Thr Pro Pro Ala Leu
            180                 185                 190
Pro Gly Ile Thr Asn Asp Thr Thr Ile Gln Gln Gly Ile Ser Gly Leu
            195                 200                 205
Ile Asp Ser Leu Asn Ala Arg Asp Ile Ser Val Lys Ile Phe Glu Asp
        210                 215                 220
Phe Ala Gln Ser Trp Tyr Trp Ile Leu Val Ala Leu Gly Val Ala Leu
225                 230                 235                 240
Val Leu Ser Leu Leu Phe Ile Leu Leu Arg Leu Val Ala Gly Pro
                245                 250                 255
Leu Val Leu Val Leu Ile Leu Gly Val Leu Gly Val Leu Ala Tyr Gly
                260                 265                 270
Ile Tyr Tyr Cys Trp Glu Glu Tyr Arg Val Leu Arg Asp Lys Gly Ala
            275                 280                 285
Ser Ile Ser Gln Leu Gly Phe Thr Thr Asn Leu Ser Ala Tyr Gln Ser
        290                 295                 300
Val Gln Glu Thr Trp Leu Ala Ala Leu Ile Val Leu Ala Val Leu Glu
305                 310                 315                 320
Ala Ile Leu Leu Leu Met Leu Ile Phe Leu Arg Gln Arg Ile Arg Ile
                325                 330                 335
Ala Ile Ala Leu Leu Lys Glu Ala Ser Lys Ala Val Gly Gln Met Met
            340                 345                 350
Ser Thr Met Phe Tyr Pro Leu Val Thr Phe Val Leu Leu Leu Ile Cys
            355                 360                 365
Ile Ala Tyr Trp Ala Met Thr Ala Leu Tyr Leu Ala Thr Ser Gly Gln
        370                 375                 380
Pro Gln Tyr Val Leu Trp Ala Ser Asn Ile Ser Ser Pro Gly Cys Glu
385                 390                 395                 400
Lys Val Pro Ile Asn Thr Ser Cys Asn Pro Thr Ala His Leu Val Asn
                405                 410                 415
Ser Ser Cys Pro Gly Leu Met Cys Val Phe Gln Gly Tyr Ser Ser Lys
            420                 425                 430
Gly Leu Ile Gln Arg Ser Val Phe Asn Leu Gln Ile Tyr Gly Val Leu
        435                 440                 445
Gly Leu Phe Trp Thr Leu Asn Trp Val Leu Ala Leu Gly Gln Cys Val
            450                 455                 460
Leu Ala Gly Ala Phe Ala Ser Phe Tyr Trp Ala Phe His Lys Pro Gln
465                 470                 475                 480
Asp Ile Pro Thr Phe Pro Leu Ile Ser Ala Phe Ile Arg Thr Leu Arg
                485                 490                 495
Tyr His Thr Gly Ser Leu Ala Phe Gly Ala Leu Ile Leu Thr Leu Val
            500                 505                 510
Gln Ile Ala Arg Val Ile Leu Glu Tyr Ile Asp His Lys Leu Arg Gly
            515                 520                 525
```

```
Val Gln Asn Pro Val Ala Arg Cys Ile Met Cys Cys Phe Lys Cys Cys
        530                 535                 540

Leu Trp Cys Leu Glu Lys Phe Ile Lys Phe Leu Asn Arg Asn Ala Tyr
545                 550                 555                 560

Ile Met Ile Ala Ile Tyr Gly Lys Asn Phe Cys Val Ser Ala Lys Asn
                565                 570                 575

Ala Phe Met Leu Leu Met Arg Asn Ile Val Arg Val Val Leu Asp
            580                 585                 590

Lys Val Thr Asp Leu Leu Leu Phe Gly Lys Leu Leu Val Val Gly
            595                 600                 605

Gly Val Gly Val Leu Ser Phe Phe Phe Ser Gly Arg Ile Pro Gly
    610                 615                 620

Leu Gly Lys Asp Phe Lys Ser Pro His Leu Asn Tyr Tyr Trp Leu Pro
625                 630                 635                 640

Ile Met Thr Ser Ile Leu Gly Ala Tyr Val Ile Ala Ser Gly Phe Phe
                645                 650                 655

Ser Val Phe Gly Met Cys Val Asp Thr Leu Phe Leu Cys Phe Leu Glu
                660                 665                 670

Asp Leu Glu Arg Asn Asn Gly Ser Leu Asp Arg Pro Tyr Tyr Met Ser
            675                 680                 685

Lys Ser Leu Leu Lys Ile Leu Gly Lys Asn Glu Ala Pro Pro Asp
            690                 695                 700

Asn Lys Lys Arg Lys Lys
705                 710

<210> SEQ ID NO 9
<211> LENGTH: 2587
<212> TYPE: DNA
<213> ORGANISM: Homo sapiens
<220> FEATURE:
<221> NAME/KEY: CDS
<222> LOCATION: (6)...(2138)

<400> SEQUENCE: 9 gagcc atg ggg gga aag cag cgg gac gag gat gac gag gcc tac ggg aag       50
      Met Gly Gly Lys Gln Arg Asp Glu Asp Asp Glu Ala Tyr Gly Lys
      1               5                   10                  15 cca gtc aaa tac gac ccc tcc ttt cga ggc ccc atc aag aac aga agc        98
Pro Val Lys Tyr Asp Pro Ser Phe Arg Gly Pro Ile Lys Asn Arg Ser
            20                  25                  30 tgc aca gat gtc atc tgc tgc gtc ctc ttc ctg ctc ttc att cta ggt       146
Cys Thr Asp Val Ile Cys Cys Val Leu Phe Leu Leu Phe Ile Leu Gly
                35                  40                  45 tac atc gtg gtg ggg att gtg gcc tgg ttg tat gga gac ccc cgg caa       194
Tyr Ile Val Val Gly Ile Val Ala Trp Leu Tyr Gly Asp Pro Arg Gln
        50                  55                  60 gtc ctc tac ccc agg aac tct act ggg gcc tac tgt ggc atg ggg gag       242
Val Leu Tyr Pro Arg Asn Ser Thr Gly Ala Tyr Cys Gly Met Gly Glu
    65                  70                  75 aac aaa gat aag ccg tat ctc ctg tac ttc aac atc ttc agc tgc atc       290
Asn Lys Asp Lys Pro Tyr Leu Leu Tyr Phe Asn Ile Phe Ser Cys Ile
80                  85                  90                  95 ctg tcc agc aac atc atc tca gtt gct gag aac gga cta cag tgc ccc       338
Leu Ser Ser Asn Ile Ile Ser Val Ala Glu Asn Gly Leu Gln Cys Pro
                100                 105                 110 aca ccc cag gtg tgt gtc tcc tgc ccg gag gac cca tgg act gtg             386
Thr Pro Gln Val Cys Val Ser Cys Pro Glu Asp Pro Trp Thr Val
            115                 120                 125 gga aaa aac gag ttc tca cag act gtt ggg gaa gtc ttc tat aca aaa       434
```

-continued

```
            Gly Lys Asn Glu Phe Ser Gln Thr Val Gly Glu Val Phe Tyr Thr Lys
                    130                 135                 140 aac agg aac ttt tgt ctg cca ggg gta ccc tgg aat atg acg gtg atc       482
Asn Arg Asn Phe Cys Leu Pro Gly Val Pro Trp Asn Met Thr Val Ile
        145                 150                 155 aca agc ctg caa cag gaa ctc tgc ccc agt ttc ctc ctc ccc tct gct       530
Thr Ser Leu Gln Gln Glu Leu Cys Pro Ser Phe Leu Leu Pro Ser Ala
160                 165                 170                 175 cca gct ctg ggg cgc tgc ttt cca tgg acc aac gtt act cca ccg gcg       578
Pro Ala Leu Gly Arg Cys Phe Pro Trp Thr Asn Val Thr Pro Pro Ala
                180                 185                 190 ctc cca ggg atc acc aat gac acc acc ata cag cag ggg atc agc ggt       626
Leu Pro Gly Ile Thr Asn Asp Thr Thr Ile Gln Gln Gly Ile Ser Gly
                195                 200                 205 ctt att gac agc ctc aat gcc cga gac atc agt gtt aag atc ttt gaa       674
Leu Ile Asp Ser Leu Asn Ala Arg Asp Ile Ser Val Lys Ile Phe Glu
                210                 215                 220 gat ttt gcc cag tcc tgg tat tgg att ctt gtt gcc ctg ggg gtg gct       722
Asp Phe Ala Gln Ser Trp Tyr Trp Ile Leu Val Ala Leu Gly Val Ala
        225                 230                 235 ctg gtc ttg agc cta ctg ttt atc ttg ctt ctg cgc ctg gtg gct ggg       770
Leu Val Leu Ser Leu Leu Phe Ile Leu Leu Leu Arg Leu Val Ala Gly
240                 245                 250                 255 ccc ctg gtg ctg gtg ctg atc ctg gga gtg ctg ggc gtg ctg gca tac       818
Pro Leu Val Leu Val Leu Ile Leu Gly Val Leu Gly Val Leu Ala Tyr
                260                 265                 270 ggc atc tac tac tgc tgg gag gag tac cga gtg ctg cgg gac aag ggc       866
Gly Ile Tyr Tyr Cys Trp Glu Glu Tyr Arg Val Leu Arg Asp Lys Gly
                275                 280                 285 gcc tcc atc tcc cag ctg ggt ttc acc acc aac ctc agt gcc tac cag       914
Ala Ser Ile Ser Gln Leu Gly Phe Thr Thr Asn Leu Ser Ala Tyr Gln
        290                 295                 300 agc gtg cag gag acc tgg ctg gcc gcc ctg atc gtg ttg gcg gtg ctt       962
Ser Val Gln Glu Thr Trp Leu Ala Ala Leu Ile Val Leu Ala Val Leu
305                 310                 315 gaa gcc atc ctg ctg ctg gtg ctc atc ttc ctg cgg cag cgg att cgt      1010
Glu Ala Ile Leu Leu Leu Val Leu Ile Phe Leu Arg Gln Arg Ile Arg
320                 325                 330                 335 att gcc atc gcc ctc ctg aag gag gcc agc aag gct gtg gga cag atg      1058
Ile Ala Ile Ala Leu Leu Lys Glu Ala Ser Lys Ala Val Gly Gln Met
                340                 345                 350 atg tct acc atg ttc tac cca ctg gtc acc ttt gtc ctc ctc ctc atc      1106
Met Ser Thr Met Phe Tyr Pro Leu Val Thr Phe Val Leu Leu Leu Ile
                355                 360                 365 tgc att gcc tac tgg gcc atg act gct ctg tac ctg gct aca tcg ggg      1154
Cys Ile Ala Tyr Trp Ala Met Thr Ala Leu Tyr Leu Ala Thr Ser Gly
                370                 375                 380 caa ccc cag tat gtg ctc tgg gca tcc aac atc agc tcc ccc ggc tgt      1202
Gln Pro Gln Tyr Val Leu Trp Ala Ser Asn Ile Ser Ser Pro Gly Cys
385                 390                 395 gag aaa gtg cca ata aat aca tca tgc aac ccc acg gcc cac ctt gtg      1250
Glu Lys Val Pro Ile Asn Thr Ser Cys Asn Pro Thr Ala His Leu Val
400                 405                 410                 415 aac tcc tcg tgc cca ggg ctg atg tgc gtc ttc cag ggc tac tca tcc      1298
Asn Ser Ser Cys Pro Gly Leu Met Cys Val Phe Gln Gly Tyr Ser Ser
                420                 425                 430 aaa ggc cta atc caa cgt tct gtc ttc aat ctg caa atc tat ggg gtc      1346
Lys Gly Leu Ile Gln Arg Ser Val Phe Asn Leu Gln Ile Tyr Gly Val
                435                 440                 445 ctg ggg ctc ttc tgg acc ctt aac tgg gta ctg gcc ctg ggc caa tgc      1394
```

-continued

```
Leu Gly Leu Phe Trp Thr Leu Asn Trp Val Leu Ala Leu Gly Gln Cys
        450                 455                 460 gtc ctc gct gga gcc ttt gcc tcc ttc tac tgg gcc ttc cac aag ccc      1442
Val Leu Ala Gly Ala Phe Ala Ser Phe Tyr Trp Ala Phe His Lys Pro
465                 470                 475 cag gac atc cct acc ttc ccc tta atc tct gcc ttc atc cgc aca ctc      1490
Gln Asp Ile Pro Thr Phe Pro Leu Ile Ser Ala Phe Ile Arg Thr Leu
480                 485                 490                 495 cgt tac cac act ggg tca ttg gca ttt gga gcc ctc atc ctg acc ctt      1538
Arg Tyr His Thr Gly Ser Leu Ala Phe Gly Ala Leu Ile Leu Thr Leu
                500                 505                 510 gtg cag ata gcc cgg gtc atc ttg gag tat att gac cac aag ctc aga      1586
Val Gln Ile Ala Arg Val Ile Leu Glu Tyr Ile Asp His Lys Leu Arg
            515                 520                 525 gga gtg cag aac cct gta gcc cgc tgc atc atg tgc tgt ttc aag tgc      1634
Gly Val Gln Asn Pro Val Ala Arg Cys Ile Met Cys Cys Phe Lys Cys
        530                 535                 540 tgc ctc tgg tgt ctg gaa aaa ttt atc aag ttc cta aac cgc aat gca      1682
Cys Leu Trp Cys Leu Glu Lys Phe Ile Lys Phe Leu Asn Arg Asn Ala
545                 550                 555 tac atc atg atc gcc atc tac ggg aag aat ttc tgt gtc tca gcc aaa      1730
Tyr Ile Met Ile Ala Ile Tyr Gly Lys Asn Phe Cys Val Ser Ala Lys
560                 565                 570                 575 aat gcg ttc atg cta ctc atg cga aac att gtc agg gtg gtc gtc ctg      1778
Asn Ala Phe Met Leu Leu Met Arg Asn Ile Val Arg Val Val Val Leu
                580                 585                 590 gac aaa gtc aca gac ctg ctg ctg ttc ttt ggg aag ctg ctg gtg gtc      1826
Asp Lys Val Thr Asp Leu Leu Leu Phe Phe Gly Lys Leu Leu Val Val
            595                 600                 605 gga ggc gtg ggg gtc ctg tcc ttc ttt ttt ttc tcc ggt cgc atc ccg      1874
Gly Gly Val Gly Val Leu Ser Phe Phe Phe Ser Gly Arg Ile Pro
        610                 615                 620 ggg ctg ggt aaa gac ttt aag agc ccc cac ctc aac tat tac tgg ctg      1922
Gly Leu Gly Lys Asp Phe Lys Ser Pro His Leu Asn Tyr Tyr Trp Leu
625                 630                 635 ccc atc atg acc tcc atc ctg ggg gcc tat gtc atc gcc agc ggc ttc      1970
Pro Ile Met Thr Ser Ile Leu Gly Ala Tyr Val Ile Ala Ser Gly Phe
640                 645                 650                 655 ttc agc gtt ttc ggc atg tgt gtg gac acg ctc ttc ctc tgc ttc ctg      2018
Phe Ser Val Phe Gly Met Cys Val Asp Thr Leu Phe Leu Cys Phe Leu
                660                 665                 670 gaa gac ctg gag cgg aac aac ggc tcc ctg gac cgg ccc tac tac atg      2066
Glu Asp Leu Glu Arg Asn Asn Gly Ser Leu Asp Arg Pro Tyr Tyr Met
            675                 680                 685 tcc aag agc ctt cta aag att ctg ggc aag aag aac gag gcg ccc ccg      2114
Ser Lys Ser Leu Leu Lys Ile Leu Gly Lys Lys Asn Glu Ala Pro Pro
        690                 695                 700 gac aac aag aag agg aag aag tga cagctccggc cctgatccag gactgcaccc    2168
Asp Asn Lys Lys Arg Lys Lys
705                 710 cacccccacc gtccagccat ccaacctcac ttcgccttac aggtctccat tttgtggtaa    2228
aaaaaggttt taggccaggc gccgtggctc acgcctgtaa tccaacactt tgagaggctg    2288
aggcgggcgg atcacctgag tcaggagttc gagaccagcc tggccaacat ggtgaaacct    2348
ccgtctctat taaaaataca aaattagcc gagagtggtg gcatgcacct gtcatcccag     2408
ctactcggga ggctgaggca ggagaatcgc ttgaacccgg gaggcagagg ttgcagtgag    2468
ccgagatcgc gccactgcac tccaacctgg gtgacagact ctgtctccaa acaaaacaa    2528 acaaacaaaa agatttttatt aaagatattt tgttaactca gtaaaaaaaa aaaaaaaaa   2587
```

<210> SEQ ID NO 10
<211> LENGTH: 710
<212> TYPE: PRT
<213> ORGANISM: Homo sapiens

<400> SEQUENCE: 10

```
Met Gly Gly Lys Gln Arg Asp Glu Asp Asp Glu Ala Tyr Gly Lys Pro
1               5                   10                  15

Val Lys Tyr Asp Pro Ser Phe Arg Gly Pro Ile Lys Asn Arg Ser Cys
            20                  25                  30

Thr Asp Val Ile Cys Cys Val Leu Phe Leu Phe Ile Leu Gly Tyr
        35                  40                  45

Ile Val Val Gly Ile Val Ala Trp Leu Tyr Gly Asp Pro Arg Gln Val
    50                  55                  60

Leu Tyr Pro Arg Asn Ser Thr Gly Ala Tyr Cys Gly Met Gly Glu Asn
65              70                  75                  80

Lys Asp Lys Pro Tyr Leu Leu Tyr Phe Asn Ile Phe Ser Cys Ile Leu
            85                  90                  95

Ser Ser Asn Ile Ile Ser Val Ala Glu Asn Gly Leu Gln Cys Pro Thr
            100                 105                 110

Pro Gln Val Cys Val Ser Ser Cys Pro Glu Asp Pro Trp Thr Val Gly
        115                 120                 125

Lys Asn Glu Phe Ser Gln Thr Val Gly Glu Val Phe Tyr Thr Lys Asn
130             135                 140

Arg Asn Phe Cys Leu Pro Gly Val Pro Trp Asn Met Thr Val Ile Thr
145             150                 155                 160

Ser Leu Gln Gln Glu Leu Cys Pro Ser Phe Leu Leu Pro Ser Ala Pro
                165                 170                 175

Ala Leu Gly Arg Cys Phe Pro Trp Thr Asn Val Thr Pro Pro Ala Leu
            180                 185                 190

Pro Gly Ile Thr Asn Asp Thr Thr Ile Gln Gln Gly Ile Ser Gly Leu
        195                 200                 205

Ile Asp Ser Leu Asn Ala Arg Asp Ile Ser Val Lys Ile Phe Glu Asp
    210                 215                 220

Phe Ala Gln Ser Trp Tyr Trp Ile Leu Val Ala Leu Gly Val Ala Leu
225             230                 235                 240

Val Leu Ser Leu Leu Phe Ile Leu Leu Leu Arg Leu Ala Gly Pro
                245                 250                 255

Leu Val Leu Val Leu Ile Leu Gly Leu Gly Val Leu Ala Tyr Gly
            260                 265                 270

Ile Tyr Tyr Cys Trp Glu Glu Tyr Arg Val Leu Arg Asp Lys Gly Ala
    275                 280                 285

Ser Ile Ser Gln Leu Gly Phe Thr Thr Asn Leu Ser Ala Tyr Gln Ser
    290                 295                 300

Val Gln Glu Thr Trp Leu Ala Ala Leu Ile Val Leu Ala Val Leu Glu
305             310                 315                 320

Ala Ile Leu Leu Leu Val Leu Ile Phe Leu Arg Gln Arg Ile Arg Ile
            325                 330                 335

Ala Ile Ala Leu Leu Lys Glu Ala Ser Lys Ala Val Gly Gln Met Met
            340                 345                 350

Ser Thr Met Phe Tyr Pro Leu Val Thr Phe Val Leu Leu Ile Cys
        355                 360                 365

Ile Ala Tyr Trp Ala Met Thr Ala Leu Tyr Leu Ala Thr Ser Gly Gln
    370                 375                 380
```

```
Pro Gln Tyr Val Leu Trp Ala Ser Asn Ile Ser Ser Pro Gly Cys Glu
385                 390                 395                 400

Lys Val Pro Ile Asn Thr Ser Cys Asn Pro Thr Ala His Leu Val Asn
            405                 410                 415

Ser Ser Cys Pro Gly Leu Met Cys Val Phe Gln Gly Tyr Ser Ser Lys
        420                 425                 430

Gly Leu Ile Gln Arg Ser Val Phe Asn Leu Gln Ile Tyr Gly Val Leu
            435                 440                 445

Gly Leu Phe Trp Thr Leu Asn Trp Val Leu Ala Leu Gly Gln Cys Val
        450                 455                 460

Leu Ala Gly Ala Phe Ala Ser Phe Tyr Trp Ala Phe His Lys Pro Gln
465                 470                 475                 480

Asp Ile Pro Thr Phe Pro Leu Ile Ser Ala Phe Ile Arg Thr Leu Arg
            485                 490                 495

Tyr His Thr Gly Ser Leu Ala Phe Gly Ala Leu Ile Leu Thr Leu Val
        500                 505                 510

Gln Ile Ala Arg Val Ile Leu Glu Tyr Ile Asp His Lys Leu Arg Gly
        515                 520                 525

Val Gln Asn Pro Val Ala Arg Cys Ile Met Cys Cys Phe Lys Cys Cys
530                 535                 540

Leu Trp Cys Leu Glu Lys Phe Ile Lys Phe Leu Asn Arg Asn Ala Tyr
545                 550                 555                 560

Ile Met Ile Ala Ile Tyr Gly Lys Asn Phe Cys Val Ser Ala Lys Asn
            565                 570                 575

Ala Phe Met Leu Leu Met Arg Asn Ile Val Arg Val Val Leu Asp
        580                 585                 590

Lys Val Thr Asp Leu Leu Leu Phe Phe Gly Lys Leu Leu Val Val Gly
        595                 600                 605

Gly Val Gly Val Leu Ser Phe Phe Phe Ser Gly Arg Ile Pro Gly
610                 615                 620

Leu Gly Lys Asp Phe Lys Ser Pro His Leu Asn Tyr Tyr Trp Leu Pro
625                 630                 635                 640

Ile Met Thr Ser Ile Leu Gly Ala Tyr Val Ile Ala Ser Gly Phe Phe
            645                 650                 655

Ser Val Phe Gly Met Cys Val Asp Thr Leu Phe Leu Cys Phe Leu Glu
        660                 665                 670

Asp Leu Glu Arg Asn Asn Gly Ser Leu Asp Arg Pro Tyr Tyr Met Ser
        675                 680                 685

Lys Ser Leu Leu Lys Ile Leu Gly Lys Lys Asn Glu Ala Pro Pro Asp
690                 695                 700

Asn Lys Lys Arg Lys Lys
705                 710

<210> SEQ ID NO 11
<211> LENGTH: 2587
<212> TYPE: DNA
<213> ORGANISM: Homo sapiens
<220> FEATURE:
<221> NAME/KEY: CDS
<222> LOCATION: (6)...(2138)

<400> SEQUENCE: 11 gagcc atg ggg gga aag cag cgg gac gag gat gac gag gcc tac ggg aag      50
      Met Gly Gly Lys Gln Arg Asp Glu Asp Asp Glu Ala Tyr Gly Lys
      1               5                   10                  15 cca gtc aaa tac gac ccc tcc ttt cga ggc ccc atc aag aac aga agc       98
```

```
            Pro Val Lys Tyr Asp Pro Ser Phe Arg Gly Pro Ile Lys Asn Arg Ser
                         20                  25                  30 tgc aca gat gtc atc tgc tgc gtc ctc ttc ctg ctc ttc att cta ggt        146
Cys Thr Asp Val Ile Cys Cys Val Leu Phe Leu Leu Phe Ile Leu Gly
                    35                  40                  45 tac atc gtg gtg ggg att gtg gcc tgg ttg tat gga gac ccc cgg caa        194
Tyr Ile Val Val Gly Ile Val Ala Trp Leu Tyr Gly Asp Pro Arg Gln
                50                  55                  60 gtc ctc tac ccc agg aac tct act ggg gcc tac tgt ggc atg ggg gag        242
Val Leu Tyr Pro Arg Asn Ser Thr Gly Ala Tyr Cys Gly Met Gly Glu
            65                  70                  75 aac aaa gat aag ccg tat ctc ctg tac ttc aac atc ttc agc tgc atc        290
Asn Lys Asp Lys Pro Tyr Leu Leu Tyr Phe Asn Ile Phe Ser Cys Ile
80                  85                  90                  95 ctg tcc agc aac atc atc tca gtt gct gag aac ggc cta cag tgc ccc        338
Leu Ser Ser Asn Ile Ile Ser Val Ala Glu Asn Gly Leu Gln Cys Pro
                    100                 105                 110 aca ccc cag gtg tgt gtg tcc tcc tgc ccg gag gac cca tgg act gtg        386
Thr Pro Gln Val Cys Val Ser Ser Cys Pro Glu Asp Pro Trp Thr Val
                115                 120                 125 gga aaa aac gag ttc tca cag act gtt ggg gaa gtc ttc tat aca aaa        434
Gly Lys Asn Glu Phe Ser Gln Thr Val Gly Glu Val Phe Tyr Thr Lys
            130                 135                 140 aac agg aac ttt tgt ctg cca ggg gta ccc tgg aat atg acg gtg atc        482
Asn Arg Asn Phe Cys Leu Pro Gly Val Pro Trp Asn Met Thr Val Ile
        145                 150                 155 aca agc ctg caa cag gaa ctc tgc ccc agt ttc ctc ctc ccc tct gct        530
Thr Ser Leu Gln Gln Glu Leu Cys Pro Ser Phe Leu Leu Pro Ser Ala
160                 165                 170                 175 cca gct ctg ggg cgc tgc ttt cca tgg acc aac gtt act cca ccg gcg        578
Pro Ala Leu Gly Arg Cys Phe Pro Trp Thr Asn Val Thr Pro Pro Ala
                    180                 185                 190 ctc cca ggg atc acc aat gac acc acc ata cag cag ggg atc agc ggt        626
Leu Pro Gly Ile Thr Asn Asp Thr Thr Ile Gln Gln Gly Ile Ser Gly
                195                 200                 205 ctt att gac agc ctc aat gcc cga gac atc agt gtt aag atc ttt gaa        674
Leu Ile Asp Ser Leu Asn Ala Arg Asp Ile Ser Val Lys Ile Phe Glu
            210                 215                 220 gat ttt gcc cag tcc tgg tat tgg att ctt gtt gcc ctg ggg gtg gct        722
Asp Phe Ala Gln Ser Trp Tyr Trp Ile Leu Val Ala Leu Gly Val Ala
        225                 230                 235 ctg gtc ttg agc cta ctg ttt atc ttg ctt ctg cgc ctg gtg gct ggg        770
Leu Val Leu Ser Leu Leu Phe Ile Leu Leu Leu Arg Leu Val Ala Gly
240                 245                 250                 255 ccc ctg gtg ctg gtg ctg atc ctg gga gtg ctg ggc gtg ctg gca tac        818
Pro Leu Val Leu Val Leu Ile Leu Gly Val Leu Gly Val Leu Ala Tyr
                    260                 265                 270 ggc atc tac tac tgc tgg gag gag tac cga gtg ctg cgg gac aag ggc        866
Gly Ile Tyr Tyr Cys Trp Glu Glu Tyr Arg Val Leu Arg Asp Lys Gly
                275                 280                 285 gcc tcc atc tcc cag ctg ggt ttc acc acc aac ctc agt gcc tac cag        914
Ala Ser Ile Ser Gln Leu Gly Phe Thr Thr Asn Leu Ser Ala Tyr Gln
            290                 295                 300 agc gtg cag gag acc tgg ctg gcc gcc ctg atc gtg ttg gcg gtg ctt        962
Ser Val Gln Glu Thr Trp Leu Ala Ala Leu Ile Val Leu Ala Val Leu
        305                 310                 315 gaa gcc atc ctg ctg ctg atg ctc atc ttc ctg cgg cag cgg att cgt        1010
Glu Ala Ile Leu Leu Leu Met Leu Ile Phe Leu Arg Gln Arg Ile Arg
320                 325                 330                 335 att gcc atc gcc ctc ctg aag gag gcc agc aag gct gtg gga cag atg        1058
```

-continued

| | | |
|---|---|---|
| Ile Ala Ile Ala Leu Leu Lys Glu Ala Ser Lys Ala Val Gly Gln Met<br>340 345 350 | | |
| atg tct acc atg ttc tac cca ctg gtc acc ttt gtc ctc ctc ctc atc<br>Met Ser Thr Met Phe Tyr Pro Leu Val Thr Phe Val Leu Leu Leu Ile<br>355 360 365 | 1106 | |
| tgc att gcc tac tgg gcc atg act gct ctg tac ctg gct aca tcg ggg<br>Cys Ile Ala Tyr Trp Ala Met Thr Ala Leu Tyr Leu Ala Thr Ser Gly<br>370 375 380 | 1154 | |
| caa ccc cag tat gtg ctc tgg gca tcc aac atc agc tcc ccc ggc tgt<br>Gln Pro Gln Tyr Val Leu Trp Ala Ser Asn Ile Ser Ser Pro Gly Cys<br>385 390 395 | 1202 | |
| gag aaa gtg cca ata aat aca tca tgc aac ccc acg gcc cac ctt gtg<br>Glu Lys Val Pro Ile Asn Thr Ser Cys Asn Pro Thr Ala His Leu Val<br>400 405 410 415 | 1250 | |
| aac tcc tcg tgc cca ggg ctg atg tgc gtc ttc cag ggc tac tca tcc<br>Asn Ser Ser Cys Pro Gly Leu Met Cys Val Phe Gln Gly Tyr Ser Ser<br>420 425 430 | 1298 | |
| aaa ggc cta atc cca cgt tct gtc ttc aat ctg caa atc tat ggg gtc<br>Lys Gly Leu Ile Pro Arg Ser Val Phe Asn Leu Gln Ile Tyr Gly Val<br>435 440 445 | 1346 | |
| ctg ggg ctc ttc tgg acc ctt aac tgg gta ctg gcc ctg gga caa tgc<br>Leu Gly Leu Phe Trp Thr Leu Asn Trp Val Leu Ala Leu Gly Gln Cys<br>450 455 460 | 1394 | |
| gtc ctc gct gga gcc ttt gcc tcc ttc tac tgg gcc ttc cac aag ccc<br>Val Leu Ala Gly Ala Phe Ala Ser Phe Tyr Trp Ala Phe His Lys Pro<br>465 470 475 | 1442 | |
| cag gac atc cct acc ttc ccc tta atc tct gcc ttc atc cgc aca ctc<br>Gln Asp Ile Pro Thr Phe Pro Leu Ile Ser Ala Phe Ile Arg Thr Leu<br>480 485 490 495 | 1490 | |
| cgt tac cac act ggg tca ttg gca ttt gga gcc ctc atc ctg acc ctt<br>Arg Tyr His Thr Gly Ser Leu Ala Phe Gly Ala Leu Ile Leu Thr Leu<br>500 505 510 | 1538 | |
| gtg cag ata gcc cgg gtc atc ttg gag tat att gac cac aag ctc aga<br>Val Gln Ile Ala Arg Val Ile Leu Glu Tyr Ile Asp His Lys Leu Arg<br>515 520 525 | 1586 | |
| gga gtg cag aac cct gta gcc cgc tgc atc atg tgc tgt ttc aag tgc<br>Gly Val Gln Asn Pro Val Ala Arg Cys Ile Met Cys Cys Phe Lys Cys<br>530 535 540 | 1634 | |
| tgc ctc tgg tgt ctg gaa aaa ttt atc aag ttc cta aac cgc aat gca<br>Cys Leu Trp Cys Leu Glu Lys Phe Ile Lys Phe Leu Asn Arg Asn Ala<br>545 550 555 | 1682 | |
| tac atc atg atc gcc atc tac ggg aag aat ttc tgt gtc tca gcc aaa<br>Tyr Ile Met Ile Ala Ile Tyr Gly Lys Asn Phe Cys Val Ser Ala Lys<br>560 565 570 575 | 1730 | |
| aat gcg ttc atg cta ctc atg cga aac att gtc agg gtg gtc gtc ctg<br>Asn Ala Phe Met Leu Leu Met Arg Asn Ile Val Arg Val Val Val Leu<br>580 585 590 | 1778 | |
| gac aaa gtc aca gac ctg ctg ctg ttc ttt ggg aag ctg ctg gtg gtc<br>Asp Lys Val Thr Asp Leu Leu Leu Phe Phe Gly Lys Leu Leu Val Val<br>595 600 605 | 1826 | |
| gga ggc gtg ggg gtc ctg tcc ttc ttt ttc tcc ggt cgc atc ccg<br>Gly Gly Val Gly Val Leu Ser Phe Phe Phe Ser Gly Arg Ile Pro<br>610 615 620 | 1874 | |
| ggg ctg ggt aaa gac ttt aag agc ccc cac ctc aac tat tac tgg ctg<br>Gly Leu Gly Lys Asp Phe Lys Ser Pro His Leu Asn Tyr Tyr Trp Leu<br>625 630 635 | 1922 | |
| ccc atc atg acc tcc atc ctg ggg gcc tat gtc atc gcc agc ggc ttc<br>Pro Ile Met Thr Ser Ile Leu Gly Ala Tyr Val Ile Ala Ser Gly Phe<br>640 645 650 655 | 1970 | |
| ttc agc gtt ttc ggc atg tgt gtg gac acg ctc ttc ctc tgc ttc ctg | 2018 | |

```
                Phe Ser Val Phe Gly Met Cys Val Asp Thr Leu Phe Leu Cys Phe Leu
                                660                 665                 670 gaa gac ctg gag cgg aac aac ggc tcc ctg gac cgg ccc tac tac atg                2066
Glu Asp Leu Glu Arg Asn Asn Gly Ser Leu Asp Arg Pro Tyr Tyr Met
            675                 680                 685 tcc aag agc ctt cta aag att ctg ggc aag aag aac gag gcg ccc ccg                2114
Ser Lys Ser Leu Leu Lys Ile Leu Gly Lys Lys Asn Glu Ala Pro Pro
            690                 695                 700 gac aac aag aag agg aag aag tga cagctccggc cctgatccag gactgcaccc               2168
Asp Asn Lys Lys Arg Lys Lys
            705                 710 cacccccacc gtccagccat ccaacctcac ttcgccttac aggtctccat tttgtggtaa              2228
aaaaaggttt taggccaggc gccgtggctc acgcctgtaa tccaacactt tgagaggctg              2288
aggcgggcgg atcacctgag tcaggagttc gagaccagcc tggccaacat ggtgaaacct              2348
ccgtctctat aaaaataca aaaattagcc gagagtggtg gcatgcacct gtcatcccag               2408
ctactcggga ggctgaggca ggagaatcgc ttgaacccgg gaggcagagg ttgcagtgag              2468
ccgagatcgc gccactgcac tccaacctgg gtgacagact ctgtctccaa acaaaacaa               2528 acaaacaaaa agattttatt aaagatattt tgttaactca gtaaaaaaaa aaaaaaaaa               2587

<210> SEQ ID NO 12
<211> LENGTH: 710
<212> TYPE: PRT
<213> ORGANISM: Homo sapiens

<400> SEQUENCE: 12

Met Gly Gly Lys Gln Arg Asp Glu Asp Glu Ala Tyr Gly Lys Pro
1               5                   10                  15

Val Lys Tyr Asp Pro Ser Phe Arg Gly Pro Ile Lys Asn Arg Ser Cys
            20                  25                  30

Thr Asp Val Ile Cys Cys Val Leu Phe Leu Leu Phe Ile Leu Gly Tyr
            35                  40                  45

Ile Val Val Gly Ile Val Ala Trp Leu Tyr Gly Asp Pro Arg Gln Val
        50                  55                  60

Leu Tyr Pro Arg Asn Ser Thr Gly Ala Tyr Cys Gly Met Gly Glu Asn
65                  70                  75                  80

Lys Asp Lys Pro Tyr Leu Leu Tyr Phe Asn Ile Phe Ser Cys Ile Leu
                85                  90                  95

Ser Ser Asn Ile Ile Ser Val Ala Glu Asn Gly Leu Gln Cys Pro Thr
            100                 105                 110

Pro Gln Val Cys Val Ser Ser Cys Pro Glu Asp Pro Trp Thr Val Gly
            115                 120                 125

Lys Asn Glu Phe Ser Gln Thr Val Gly Glu Val Phe Tyr Thr Lys Asn
        130                 135                 140

Arg Asn Phe Cys Leu Pro Gly Val Pro Trp Asn Met Thr Val Ile Thr
145                 150                 155                 160

Ser Leu Gln Gln Glu Leu Cys Pro Ser Phe Leu Leu Pro Ser Ala Pro
                165                 170                 175

Ala Leu Gly Arg Cys Phe Pro Trp Thr Asn Val Thr Pro Pro Ala Leu
            180                 185                 190

Pro Gly Ile Thr Asn Asp Thr Thr Ile Gln Gln Gly Ile Ser Gly Leu
            195                 200                 205

Ile Asp Ser Leu Asn Ala Arg Asp Ile Ser Val Lys Ile Phe Glu Asp
        210                 215                 220

Phe Ala Gln Ser Trp Tyr Trp Ile Leu Val Ala Leu Gly Val Ala Leu
```

```
                225                 230                 235                 240
        Val Leu Ser Leu Leu Phe Ile Leu Leu Arg Leu Val Ala Gly Pro
                        245                 250                 255

Leu Val Leu Val Leu Ile Leu Gly Val Leu Gly Val Leu Ala Tyr Gly
                        260                 265                 270

Ile Tyr Tyr Cys Trp Glu Glu Tyr Arg Val Leu Arg Asp Lys Gly Ala
                        275                 280                 285

Ser Ile Ser Gln Leu Gly Phe Thr Thr Asn Leu Ser Ala Tyr Gln Ser
                        290                 295                 300

Val Gln Glu Thr Trp Leu Ala Ala Leu Ile Val Leu Ala Val Leu Glu
        305                 310                 315                 320

Ala Ile Leu Leu Leu Met Leu Ile Phe Leu Arg Gln Arg Ile Arg Ile
                        325                 330                 335

Ala Ile Ala Leu Leu Lys Glu Ala Ser Lys Ala Val Gly Gln Met Met
                        340                 345                 350

Ser Thr Met Phe Tyr Pro Leu Val Thr Phe Val Leu Leu Ile Cys
                        355                 360                 365

Ile Ala Tyr Trp Ala Met Thr Ala Leu Tyr Leu Ala Thr Ser Gly Gln
                        370                 375                 380

Pro Gln Tyr Val Leu Trp Ala Ser Asn Ile Ser Ser Pro Gly Cys Glu
        385                 390                 395                 400

Lys Val Pro Ile Asn Thr Ser Cys Asn Pro Thr Ala His Leu Val Asn
                        405                 410                 415

Ser Ser Cys Pro Gly Leu Met Cys Val Phe Gln Gly Tyr Ser Ser Lys
                        420                 425                 430

Gly Leu Ile Pro Arg Ser Val Phe Asn Leu Gln Ile Tyr Gly Val Leu
                        435                 440                 445

Gly Leu Phe Trp Thr Leu Asn Trp Val Leu Ala Leu Gly Gln Cys Val
                        450                 455                 460

Leu Ala Gly Ala Phe Ala Ser Phe Tyr Trp Ala Phe His Lys Pro Gln
        465                 470                 475                 480

Asp Ile Pro Thr Phe Pro Leu Ile Ser Ala Phe Ile Arg Thr Leu Arg
                        485                 490                 495

Tyr His Thr Gly Ser Leu Ala Phe Gly Ala Leu Ile Leu Thr Leu Val
                        500                 505                 510

Gln Ile Ala Arg Val Ile Leu Glu Tyr Ile Asp His Lys Leu Arg Gly
                        515                 520                 525

Val Gln Asn Pro Val Ala Arg Cys Ile Met Cys Cys Phe Lys Cys Cys
        530                 535                 540

Leu Trp Cys Leu Glu Lys Phe Ile Lys Phe Leu Asn Arg Asn Ala Tyr
        545                 550                 555                 560

Ile Met Ile Ala Ile Tyr Gly Lys Asn Phe Cys Val Ser Ala Lys Asn
                        565                 570                 575

Ala Phe Met Leu Leu Met Arg Asn Ile Val Arg Val Val Leu Asp
                        580                 585                 590

Lys Val Thr Asp Leu Leu Leu Phe Phe Gly Lys Leu Leu Val Val Gly
                        595                 600                 605

Gly Val Gly Val Leu Ser Phe Phe Phe Ser Gly Arg Ile Pro Gly
                        610                 615                 620

Leu Gly Lys Asp Phe Lys Ser Pro His Leu Asn Tyr Tyr Trp Leu Pro
        625                 630                 635                 640

Ile Met Thr Ser Ile Leu Gly Ala Tyr Val Ile Ala Ser Gly Phe Phe
                        645                 650                 655
```

```
                Ser Val Phe Gly Met Cys Val Asp Thr Leu Phe Leu Cys Phe Leu Glu
                                660                 665                 670

Asp Leu Glu Arg Asn Asn Gly Ser Leu Asp Arg Pro Tyr Tyr Met Ser
                            675                 680                 685

Lys Ser Leu Leu Lys Ile Leu Gly Lys Lys Asn Glu Ala Pro Pro Asp
                690                 695                 700

Asn Lys Lys Arg Lys Lys
                705                 710

<210> SEQ ID NO 13
<211> LENGTH: 2251
<212> TYPE: DNA
<213> ORGANISM: Homo sapiens
<220> FEATURE:
<221> NAME/KEY: CDS
<222> LOCATION: (6)...(1802)

<400> SEQUENCE: 13 gagcc atg ggg gga aag cag cgg gac gag gat gac gag gcc tac ggg aag       50
      Met Gly Gly Lys Gln Arg Asp Glu Asp Asp Glu Ala Tyr Gly Lys
      1               5                   10                  15 cca gtc aaa tac gac ccc tcc ttt cga ggc ccc atc aag aac aga agc        98
Pro Val Lys Tyr Asp Pro Ser Phe Arg Gly Pro Ile Lys Asn Arg Ser
            20                  25                  30 tgc aca gat gtc atc tgc tgc gtc ctc ttc ctg ctc ttc att cta ggt       146
Cys Thr Asp Val Ile Cys Cys Val Leu Phe Leu Leu Phe Ile Leu Gly
        35                  40                  45 tac atc gtg gtg ggg att gtg gcc tgg ttg tat gga gac ccc cgg caa       194
Tyr Ile Val Val Gly Ile Val Ala Trp Leu Tyr Gly Asp Pro Arg Gln
    50                  55                  60 gtc ctc tac ccc agg aac tct act ggg gcc tac tgt ggc atg ggg gag       242
Val Leu Tyr Pro Arg Asn Ser Thr Gly Ala Tyr Cys Gly Met Gly Glu
65                  70                  75 aac aaa gat aag ccg tat ctc ctg tac ttc aac atc ttc agc tgc atc       290
Asn Lys Asp Lys Pro Tyr Leu Leu Tyr Phe Asn Ile Phe Ser Cys Ile
 80                 85                  90                  95 ctg tcc agc aac atc atc tca gtt gct gag aac ggc cta cag tgc ccc       338
Leu Ser Ser Asn Ile Ile Ser Val Ala Glu Asn Gly Leu Gln Cys Pro
                100                 105                 110 aca ccc cag gtg tgt gtg tcc tcc tgc ccg gag gac cca tgg act gtg       386
Thr Pro Gln Val Cys Val Ser Ser Cys Pro Glu Asp Pro Trp Thr Val
            115                 120                 125 gga aaa aac gag ttc tca cag act gtt ggg gaa gtc ttc tat aca aaa       434
Gly Lys Asn Glu Phe Ser Gln Thr Val Gly Glu Val Phe Tyr Thr Lys
        130                 135                 140 aac agg aac ttt tgt ctg cca ggg gta ccc tgg aat atg acg gtg atc       482
Asn Arg Asn Phe Cys Leu Pro Gly Val Pro Trp Asn Met Thr Val Ile
    145                 150                 155 aca agc ctg caa cag gaa ctc tgc ccc agt ttc ctc ctc ccc tct gct       530
Thr Ser Leu Gln Gln Glu Leu Cys Pro Ser Phe Leu Leu Pro Ser Ala
160                 165                 170                 175 cca gct ctg ggg cgc tgc ttt cca tgg acc aac gtt act ccg gcg            578
Pro Ala Leu Gly Arg Cys Phe Pro Trp Thr Asn Val Thr Pro Ala
            180                 185                 190 ctc cca ggg atc acc aat gac acc acc ata cag cag ggg atc agc ggt       626
Leu Pro Gly Ile Thr Asn Asp Thr Thr Ile Gln Gln Gly Ile Ser Gly
        195                 200                 205 ctt att gac agc ctc aat gcc cga gac atc agt gtt aag atc ttt gaa       674
Leu Ile Asp Ser Leu Asn Ala Arg Asp Ile Ser Val Lys Ile Phe Glu
    210                 215                 220 gat ttt gcc cag tcc tgg tat tgg att ctt gtg gct gtg gga cag atg       722
```

-continued

```
                Asp Phe Ala Gln Ser Trp Tyr Trp Ile Leu Val Ala Val Gly Gln Met
                    225                 230                 235 atg tct acc atg ttc tac cca ctg gtc acc ttt gtc ctc ctc ctc atc          770
Met Ser Thr Met Phe Tyr Pro Leu Val Thr Phe Val Leu Leu Leu Ile
240                 245                 250                 255 tgc att gcc tac tgg gcc atg act gct ctg tac ctg gct aca tcg ggg          818
Cys Ile Ala Tyr Trp Ala Met Thr Ala Leu Tyr Leu Ala Thr Ser Gly
                260                 265                 270 caa ccc cag tat gtg ctc tgg gca tcc aac atc agc tcc ccc ggc tgt          866
Gln Pro Gln Tyr Val Leu Trp Ala Ser Asn Ile Ser Ser Pro Gly Cys
            275                 280                 285 gag aaa gtg cca ata aat aca tca tgc aac ccc acg gcc cac ctt gtg          914
Glu Lys Val Pro Ile Asn Thr Ser Cys Asn Pro Thr Ala His Leu Val
        290                 295                 300 aac tcc tcg tgc cca ggg ctg atg tgc gtc ttc cag ggc tac tca tcc          962
Asn Ser Ser Cys Pro Gly Leu Met Cys Val Phe Gln Gly Tyr Ser Ser
    305                 310                 315 aaa ggc cta atc caa cgt tct gtc ttc aat ctg caa atc tat ggg gtc         1010
Lys Gly Leu Ile Gln Arg Ser Val Phe Asn Leu Gln Ile Tyr Gly Val
320                 325                 330                 335 ctg ggg ctc ttc tgg acc ctt aac tgg gta ctg gcc ctg gga caa tgc         1058
Leu Gly Leu Phe Trp Thr Leu Asn Trp Val Leu Ala Leu Gly Gln Cys
                340                 345                 350 gtc ctc gct gga gcc ttt gcc tcc ttc tac tgg gcc ttc cac aag ccc         1106
Val Leu Ala Gly Ala Phe Ala Ser Phe Tyr Trp Ala Phe His Lys Pro
            355                 360                 365 cag gac atc cct acc ttc ccc tta atc tct gcc ttc atc cgc aca ctc         1154
Gln Asp Ile Pro Thr Phe Pro Leu Ile Ser Ala Phe Ile Arg Thr Leu
        370                 375                 380 cgt tac cac act ggg tca ttg gca ttt gga gcc ctc atc ctg acc ctt         1202
Arg Tyr His Thr Gly Ser Leu Ala Phe Gly Ala Leu Ile Leu Thr Leu
    385                 390                 395 gtg cag ata gcc cgg gtc atc ttg gag tat att gac cac aag ctc aga         1250
Val Gln Ile Ala Arg Val Ile Leu Glu Tyr Ile Asp His Lys Leu Arg
400                 405                 410                 415 gga gtg cag aac cct gta gcc cgc tgc atc atg tgc tgt ttc aag tgc         1298
Gly Val Gln Asn Pro Val Ala Arg Cys Ile Met Cys Cys Phe Lys Cys
                420                 425                 430 tgc ctc tgg tgt ctg gaa aaa ttt atc aag ttc cta aac cgc aat gca         1346
Cys Leu Trp Cys Leu Glu Lys Phe Ile Lys Phe Leu Asn Arg Asn Ala
            435                 440                 445 tac atc atg atc gcc atc tac ggg aag aat ttc tgt gtc tca gcc aaa         1394
Tyr Ile Met Ile Ala Ile Tyr Gly Lys Asn Phe Cys Val Ser Ala Lys
        450                 455                 460 aat gcg ttc atg cta ctc atg cga aac att gtc agg gtg gtc gtc ctg         1442
Asn Ala Phe Met Leu Leu Met Arg Asn Ile Val Arg Val Val Val Leu
    465                 470                 475 gac aaa gtc aca gac ctg ctg ctg ttc ttt ggg aag ctg ctg gtg gtc         1490
Asp Lys Val Thr Asp Leu Leu Leu Phe Phe Gly Lys Leu Leu Val Val
480                 485                 490                 495 gga ggc gtg ggg gtc ctg tcc ttc ttt ttt ttc tcc ggt cgc atc ccg         1538
Gly Gly Val Gly Val Leu Ser Phe Phe Phe Phe Ser Gly Arg Ile Pro
                500                 505                 510 ggg ctg ggt aaa gac ttt aag agc ccc cac ctc aac tat tac tgg ctg         1586
Gly Leu Gly Lys Asp Phe Lys Ser Pro His Leu Asn Tyr Tyr Trp Leu
            515                 520                 525 ccc atc atg acc tcc atc ctg ggg gcc tat gtc atc gcc agc ggc ttc         1634
Pro Ile Met Thr Ser Ile Leu Gly Ala Tyr Val Ile Ala Ser Gly Phe
        530                 535                 540 ttc agc gtt ttc ggc atg tgt gtg gac acg ctc ttc ctc tgc ttc ctg         1682
```

```
Phe Ser Val Phe Gly Met Cys Val Asp Thr Leu Phe Leu Cys Phe Leu
    545                 550                 555 gaa gac ctg gag cgg aac aac ggc tcc ctg gac cgg ccc tac tac atg    1730
Glu Asp Leu Glu Arg Asn Asn Gly Ser Leu Asp Arg Pro Tyr Tyr Met
560                 565                 570                 575 tcc aag agc ctt cta aag att ctg ggc aag aag aac gag gcg ccc ccg    1778
Ser Lys Ser Leu Leu Lys Ile Leu Gly Lys Lys Asn Glu Ala Pro Pro
                580                 585                 590 gac aac aag aag agg aag aag tga cagctccggc cctgatccag gactgcaccc   1832
Asp Asn Lys Lys Arg Lys Lys
                595 cacccccacc gtccagccat ccaacctcac ttcgccttac aggtctccat tttgtggtaa   1892 aaaaaggttt taggccaggc gccgtggctc acgcctgtaa tccaacactt tgagaggctg   1952 aggcgggcgg atcacctgag tcaggagttc gagaccagcc tggccaacat ggtgaaacct   2012 ccgtctctat aaaaatacaa aaattagcc gagagtggtg gcatgcacct gtcatcccag    2072 ctactcggga ggctgaggca ggagaatcgc ttgaacccgg gaggcagagg ttgcagtgag   2132 ccgagatcgc gccactgcac tccaacctgg gtgacagact ctgtctccaa acaaaacaa    2192 acaaacaaaa agatttatt aaagatattt tgttaactca gtaaaaaaaa aaaaaaaaa     2251

<210> SEQ ID NO 14
<211> LENGTH: 598
<212> TYPE: PRT
<213> ORGANISM: Homo sapiens

<400> SEQUENCE: 14

Met Gly Gly Lys Gln Arg Asp Glu Asp Asp Glu Ala Tyr Gly Lys Pro
1               5                   10                  15

Val Lys Tyr Asp Pro Ser Phe Arg Gly Pro Ile Lys Asn Arg Ser Cys
            20                  25                  30

Thr Asp Val Ile Cys Cys Val Leu Phe Leu Leu Phe Ile Leu Gly Tyr
        35                  40                  45

Ile Val Val Gly Ile Val Ala Trp Leu Tyr Gly Asp Pro Arg Gln Val
    50                  55                  60

Leu Tyr Pro Arg Asn Ser Thr Gly Ala Tyr Cys Gly Met Gly Glu Asn
65                  70                  75                  80

Lys Asp Lys Pro Tyr Leu Leu Tyr Phe Asn Ile Phe Ser Cys Ile Leu
                85                  90                  95

Ser Ser Asn Ile Ile Ser Val Ala Glu Asn Gly Leu Gln Cys Pro Thr
            100                 105                 110

Pro Gln Val Cys Val Ser Ser Cys Pro Glu Asp Pro Trp Thr Val Gly
        115                 120                 125

Lys Asn Glu Phe Ser Gln Thr Val Gly Glu Val Phe Tyr Thr Lys Asn
    130                 135                 140

Arg Asn Phe Cys Leu Pro Gly Val Pro Trp Asn Met Thr Val Ile Thr
145                 150                 155                 160

Ser Leu Gln Gln Glu Leu Cys Pro Ser Phe Leu Leu Pro Ser Ala Pro
                165                 170                 175

Ala Leu Gly Arg Cys Phe Pro Trp Thr Asn Val Thr Pro Pro Ala Leu
            180                 185                 190

Pro Gly Ile Thr Asn Asp Thr Thr Ile Gln Gly Ile Ser Gly Leu
        195                 200                 205

Ile Asp Ser Leu Asn Ala Arg Asp Ile Ser Val Lys Ile Phe Glu Asp
    210                 215                 220

Phe Ala Gln Ser Trp Tyr Trp Ile Leu Val Ala Val Gly Gln Met Met
```

```
                    225                 230                 235                 240

Ser Thr Met Phe Tyr Pro Leu Val Thr Phe Val Leu Leu Ile Cys
                245                 250                 255

Ile Ala Tyr Trp Ala Met Thr Ala Leu Tyr Leu Ala Thr Ser Gly Gln
            260                 265                 270

Pro Gln Tyr Val Leu Trp Ala Ser Asn Ile Ser Ser Pro Gly Cys Glu
            275                 280                 285

Lys Val Pro Ile Asn Thr Ser Cys Asn Pro Thr Ala His Leu Val Asn
        290                 295                 300

Ser Ser Cys Pro Gly Leu Met Cys Val Phe Gln Gly Tyr Ser Ser Lys
305                 310                 315                 320

Gly Leu Ile Gln Arg Ser Val Phe Asn Leu Gln Ile Tyr Gly Val Leu
                325                 330                 335

Gly Leu Phe Trp Thr Leu Asn Trp Val Leu Ala Leu Gly Gln Cys Val
                340                 345                 350

Leu Ala Gly Ala Phe Ala Ser Phe Tyr Trp Ala Phe His Lys Pro Gln
            355                 360                 365

Asp Ile Pro Thr Phe Pro Leu Ile Ser Ala Phe Ile Arg Thr Leu Arg
        370                 375                 380

Tyr His Thr Gly Ser Leu Ala Phe Gly Ala Leu Ile Leu Thr Leu Val
385                 390                 395                 400

Gln Ile Ala Arg Val Ile Leu Glu Tyr Ile Asp His Lys Leu Arg Gly
                405                 410                 415

Val Gln Asn Pro Val Ala Arg Cys Ile Met Cys Cys Phe Lys Cys Cys
                420                 425                 430

Leu Trp Cys Leu Glu Lys Phe Ile Lys Phe Leu Asn Arg Asn Ala Tyr
            435                 440                 445

Ile Met Ile Ala Ile Tyr Gly Lys Asn Phe Cys Val Ser Ala Lys Asn
        450                 455                 460

Ala Phe Met Leu Leu Met Arg Asn Ile Val Arg Val Val Leu Asp
465                 470                 475                 480

Lys Val Thr Asp Leu Leu Leu Phe Phe Gly Lys Leu Leu Val Val Gly
                485                 490                 495

Gly Val Gly Val Leu Ser Phe Phe Phe Ser Gly Arg Ile Pro Gly
            500                 505                 510

Leu Gly Lys Asp Phe Lys Ser Pro His Leu Asn Tyr Tyr Trp Leu Pro
            515                 520                 525

Ile Met Thr Ser Ile Leu Gly Ala Tyr Val Ile Ala Ser Gly Phe Phe
        530                 535                 540

Ser Val Phe Gly Met Cys Val Asp Thr Leu Phe Leu Cys Phe Leu Glu
545                 550                 555                 560

Asp Leu Glu Arg Asn Asn Gly Ser Leu Asp Arg Pro Tyr Tyr Met Ser
                565                 570                 575

Lys Ser Leu Leu Lys Ile Leu Gly Lys Lys Asn Glu Ala Pro Pro Asp
            580                 585                 590

Asn Lys Lys Arg Lys Lys
        595

<210> SEQ ID NO 15
<211> LENGTH: 2623
<212> TYPE: DNA
<213> ORGANISM: Homo sapiens
<220> FEATURE:
<221> NAME/KEY: CDS
<222> LOCATION: (6)...(2174)
```

<400> SEQUENCE: 15

```
gagcc atg ggg gga aag cag cgg gac gag gat gac gag gcc tac ggg aag      50
      Met Gly Gly Lys Gln Arg Asp Glu Asp Asp Glu Ala Tyr Gly Lys
      1               5                   10                  15 cca gtc aaa tac gac ccc tcc ttt cga ggc ccc atc aag aac aga agc        98
Pro Val Lys Tyr Asp Pro Ser Phe Arg Gly Pro Ile Lys Asn Arg Ser
                20                  25                  30 tgc aca gat gtc atc tgc tgc gtc ctc ttc ctg ctc ttc att cta ggt       146
Cys Thr Asp Val Ile Cys Cys Val Leu Phe Leu Leu Phe Ile Leu Gly
            35                  40                  45 tac atc gtg gtg ggg att gtg gcc tgg ttg tat gga gac ccc cgg caa       194
Tyr Ile Val Val Gly Ile Val Ala Trp Leu Tyr Gly Asp Pro Arg Gln
        50                  55                  60 gtc ctc tac ccc agg aac tct act ggg gcc tac tgt ggc atg ggg gag       242
Val Leu Tyr Pro Arg Asn Ser Thr Gly Ala Tyr Cys Gly Met Gly Glu
    65                  70                  75 aac aaa gat aag ccg tat ctc ctg tac ttc aac atc ttc agc tgc atc       290
Asn Lys Asp Lys Pro Tyr Leu Leu Tyr Phe Asn Ile Phe Ser Cys Ile
80                  85                  90                  95 ctg tcc agc aac atc atc tca gtt gct gag aac ggc cta cag tgc ccc       338
Leu Ser Ser Asn Ile Ile Ser Val Ala Glu Asn Gly Leu Gln Cys Pro
                100                 105                 110 aca ccc cag gtg tgt gtg tcc tcc tgc ccg gag gac cca tgg act gtg       386
Thr Pro Gln Val Cys Val Ser Ser Cys Pro Glu Asp Pro Trp Thr Val
            115                 120                 125 gga aaa aac gag ttc tca cag act gtt ggg gaa gtc ttc tat aca aaa       434
Gly Lys Asn Glu Phe Ser Gln Thr Val Gly Glu Val Phe Tyr Thr Lys
        130                 135                 140 aac agg aac ttt tgt ctg cca ggg gta ccc tgg aat atg acg gtg atc       482
Asn Arg Asn Phe Cys Leu Pro Gly Val Pro Trp Asn Met Thr Val Ile
145                 150                 155 aca agc ctg caa cag gaa ctc tgc ccc agt ttc ctc ctc ccc tct gct       530
Thr Ser Leu Gln Gln Glu Leu Cys Pro Ser Phe Leu Leu Pro Ser Ala
160                 165                 170                 175 cca gct ctg ggg cgc tgc ttt cca tgg acc aac gtt act cca ccg gcg       578
Pro Ala Leu Gly Arg Cys Phe Pro Trp Thr Asn Val Thr Pro Pro Ala
                180                 185                 190 ctc cca ggg atc acc aat gac acc acc ata cag cag ggg atc agc ggt       626
Leu Pro Gly Ile Thr Asn Asp Thr Thr Ile Gln Gln Gly Ile Ser Gly
            195                 200                 205 ctt att gac agc ctc aat gcc cga gac atc agt gtt aag atc ttt gaa       674
Leu Ile Asp Ser Leu Asn Ala Arg Asp Ile Ser Val Lys Ile Phe Glu
        210                 215                 220 gat ttt gcc cag tcc tgg tat tgg att ctt gtt gcc ctg ggg gtg gct       722
Asp Phe Ala Gln Ser Trp Tyr Trp Ile Leu Val Ala Leu Gly Val Ala
225                 230                 235 ctg gtc ttg agc cta ctg ttt atc ttg ctt ctg cgc ctg gtg gct ggg       770
Leu Val Leu Ser Leu Leu Phe Ile Leu Leu Leu Arg Leu Val Ala Gly
240                 245                 250                 255 ccc ctg gtg ctg gtg ctg atc ctg gga gtg ctg ggc gtg ctg gca tac       818
Pro Leu Val Leu Val Leu Ile Leu Gly Val Leu Gly Val Leu Ala Tyr
                260                 265                 270 ggc atc tac tac tgc tgg gag gag tac cga gtg ctg cgg gac aag ggc       866
Gly Ile Tyr Tyr Cys Trp Glu Glu Tyr Arg Val Leu Arg Asp Lys Gly
            275                 280                 285 gcc tcc atc tcc cag ctg ggt ttc acc acc aac ctc agt gcc tac cag       914
Ala Ser Ile Ser Gln Leu Gly Phe Thr Thr Asn Leu Ser Ala Tyr Gln
        290                 295                 300 agc gtg cag gag acc tgg ctg gcc gcc ctg atc gtg ttg gcg gtg ctt       962
Ser Val Gln Glu Thr Trp Leu Ala Ala Leu Ile Val Leu Ala Val Leu
```

```
                305                310                315
gaa gcc atc ctg ctg ctg atg ctc atc ttc ctg cgg cag cgg att cgt      1010
Glu Ala Ile Leu Leu Leu Met Leu Ile Phe Leu Arg Gln Arg Ile Arg
320                 325                330                335 att gcc atc gcc ctc ctg aag gag gcc agc aag gct gtg gga cag atg      1058
Ile Ala Ile Ala Leu Leu Lys Glu Ala Ser Lys Ala Val Gly Gln Met
                340                 345                350 atg tct acc atg ttc tac cca ctg gtc acc ttt gtc ctc ctc ctc atc      1106
Met Ser Thr Met Phe Tyr Pro Leu Val Thr Phe Val Leu Leu Leu Ile
        355                 360                 365 tgc att gcc tac tgg gcc atg act gct ctg tac ctg gct aca tcg ggg      1154
Cys Ile Ala Tyr Trp Ala Met Thr Ala Leu Tyr Leu Ala Thr Ser Gly
            370                 375                 380 caa ccc cag tat gtg ctc tgg gca tcc aac atc agc tcc ccc ggc tgt      1202
Gln Pro Gln Tyr Val Leu Trp Ala Ser Asn Ile Ser Ser Pro Gly Cys
385                 390                 395 gag aaa gtg cca ata aat aca tca tgc aac ccc acg gcc cac ctt gtg      1250
Glu Lys Val Pro Ile Asn Thr Ser Cys Asn Pro Thr Ala His Leu Val
400                 405                 410                 415 aac tcc tcg tgc cca ggg ctg atg tgc gtc ttc cag ggc tac tca tcc      1298
Asn Ser Ser Cys Pro Gly Leu Met Cys Val Phe Gln Gly Tyr Ser Ser
                420                 425                 430 aaa ggc cta atc caa cgt tct gtc ttc aat ctg caa atc tat ggg gtc      1346
Lys Gly Leu Ile Gln Arg Ser Val Phe Asn Leu Gln Ile Tyr Gly Val
        435                 440                 445 ctg ggg ctc ttc tgg acc ctt aac tgg gta ctg gcc ctg ggc caa tgc      1394
Leu Gly Leu Phe Trp Thr Leu Asn Trp Val Leu Ala Leu Gly Gln Cys
            450                 455                 460 gtc ctc gct gga gcc ttt gcc tcc ttc tac tgg gcc ttc cac aag ccc      1442
Val Leu Ala Gly Ala Phe Ala Ser Phe Tyr Trp Ala Phe His Lys Pro
465                 470                 475 cag gac atc cct acc ttc ccc tta atc tct gcc ttc atc cgc aca ctc      1490
Gln Asp Ile Pro Thr Phe Pro Leu Ile Ser Ala Phe Ile Arg Thr Leu
480                 485                 490                 495 cgt tac cac act ggg tca ttg gca ttt gga gcc ctc atc ctg acc ctt      1538
Arg Tyr His Thr Gly Ser Leu Ala Phe Gly Ala Leu Ile Leu Thr Leu
                500                 505                 510 gtg cag ata gcc cgg gtc atc ttg gag tat att gac cac aag ctc aga      1586
Val Gln Ile Ala Arg Val Ile Leu Glu Tyr Ile Asp His Lys Leu Arg
        515                 520                 525 gga gtg cag aac cct gta gcc cgc tgc atc atg tgc tgt ttc aag tgc      1634
Gly Val Gln Asn Pro Val Ala Arg Cys Ile Met Cys Cys Phe Lys Cys
            530                 535                 540 tgc ctc tgg tgt ctg gaa aaa ttt atc aag ttc cta aac cgc aat gca      1682
Cys Leu Trp Cys Leu Glu Lys Phe Ile Lys Phe Leu Asn Arg Asn Ala
545                 550                 555 tac atc atg atc gcc atc tac ggg aag aat ttc tgt gtc tca gcc aaa      1730
Tyr Ile Met Ile Ala Ile Tyr Gly Lys Asn Phe Cys Val Ser Ala Lys
560                 565                 570                 575 aat gcg ttc atg cta ctc atg cga aac att gtc agg gtg gtc gtc ctg      1778
Asn Ala Phe Met Leu Leu Met Arg Asn Ile Val Arg Val Val Val Leu
                580                 585                 590 gac aaa gtc aca gac ctg ctg ctg ttc ttt ggg aag ctg ctg gtg gtc      1826
Asp Lys Val Thr Asp Leu Leu Leu Phe Phe Gly Lys Leu Leu Val Val
        595                 600                 605 gga ggc gtg ggg gtc ctg tcc ttc ttt ttc tcc ggt cgc atc ccg         1874
Gly Gly Val Gly Val Leu Ser Phe Phe Phe Ser Gly Arg Ile Pro
            610                 615                 620 ggg ctg ggt aaa gac ttt aag agc ccc cac ctc aac tat tac tgg ctg      1922
Gly Leu Gly Lys Asp Phe Lys Ser Pro His Leu Asn Tyr Tyr Trp Leu
```

-continued

```
                  625                 630                 635
ccc atc atg agg aac cca ata acc cca acg ggt cat gtc ttc cag acc    1970
Pro Ile Met Arg Asn Pro Ile Thr Pro Thr Gly His Val Phe Gln Thr
640                 645                 650                 655 tcc atc ctg ggg gcc tat gtc atc gcc agc ggc ttc ttc agc gtt ttc    2018
Ser Ile Leu Gly Ala Tyr Val Ile Ala Ser Gly Phe Phe Ser Val Phe
                660                 665                 670 ggc atg tgt gtg gac acg ctc ttc ctc tgc ttc ctg gaa gac ctg gag    2066
Gly Met Cys Val Asp Thr Leu Phe Leu Cys Phe Leu Glu Asp Leu Glu
            675                 680                 685 cgg aac aac ggc tcc ctg gac cgg ccc tac tac atg tcc aag agc ctt    2114
Arg Asn Asn Gly Ser Leu Asp Arg Pro Tyr Tyr Met Ser Lys Ser Leu
        690                 695                 700 cta aag att ctg ggc aag aag aac gag gcg ccc ccg gac aac aag aag    2162
Leu Lys Ile Leu Gly Lys Lys Asn Glu Ala Pro Pro Asp Asn Lys Lys
    705                 710                 715 agg aag aag tga cagctccggc cctgatccag gactgcaccc cacccccacc        2214
Arg Lys Lys
720 gtccagccat ccaacctcac ttcgccttac aggtctccat tttgtggtaa aaaaaggttt   2274 taggccaggc gccgtggctc acgcctgtaa tccaacactt tgagaggctg aggcgggcgg   2334 atcacctgag tcaggagttc gagaccagcc tggccaacat ggtgaaacct ccgtctctat   2394 taaaaataca aaaattagcc gagagtggtg gcatgcacct gtcatcccag ctactcggga   2454 ggctgaggca ggagaatcgc ttgaacccgg gaggcagagg ttgcagtgag ccgagatcgc   2514 gccactgcac tccaacctgg gtgacagact ctgtctccaa acaaaacaa acaaacaaaa    2574 agattttatt aaagatattt tgttaactca gtaaaaaaaa aaaaaaaaa              2623

<210> SEQ ID NO 16
<211> LENGTH: 722
<212> TYPE: PRT
<213> ORGANISM: Homo sapiens

<400> SEQUENCE: 16

Met Gly Gly Lys Gln Arg Asp Glu Asp Glu Ala Tyr Gly Lys Pro
1               5                   10                  15

Val Lys Tyr Asp Pro Ser Phe Arg Gly Pro Ile Lys Asn Arg Ser Cys
            20                  25                  30

Thr Asp Val Ile Cys Cys Val Leu Phe Leu Leu Phe Ile Leu Gly Tyr
        35                  40                  45

Ile Val Val Gly Ile Val Ala Trp Leu Tyr Gly Asp Pro Arg Gln Val
    50                  55                  60

Leu Tyr Pro Arg Asn Ser Thr Gly Ala Tyr Cys Gly Met Gly Glu Asn
65                  70                  75                  80

Lys Asp Lys Pro Tyr Leu Leu Tyr Phe Asn Ile Phe Ser Cys Ile Leu
                85                  90                  95

Ser Ser Asn Ile Ile Ser Val Ala Glu Asn Gly Leu Gln Cys Pro Thr
            100                 105                 110

Pro Gln Val Cys Val Ser Ser Cys Pro Glu Asp Pro Trp Thr Val Gly
        115                 120                 125

Lys Asn Glu Phe Ser Gln Thr Val Gly Glu Val Phe Tyr Thr Lys Asn
    130                 135                 140

Arg Asn Phe Cys Leu Pro Gly Val Pro Trp Asn Met Thr Val Ile Thr
145                 150                 155                 160

Ser Leu Gln Gln Glu Leu Cys Pro Ser Phe Leu Leu Pro Ser Ala Pro
                165                 170                 175
```

```
Ala Leu Gly Arg Cys Phe Pro Trp Thr Asn Val Thr Pro Ala Leu
            180                 185                 190

Pro Gly Ile Thr Asn Asp Thr Thr Ile Gln Gln Gly Ile Ser Gly Leu
        195                 200                 205

Ile Asp Ser Leu Asn Ala Arg Asp Ile Ser Val Lys Ile Phe Glu Asp
    210                 215                 220

Phe Ala Gln Ser Trp Tyr Trp Ile Leu Val Ala Leu Gly Val Ala Leu
225                 230                 235                 240

Val Leu Ser Leu Leu Phe Ile Leu Leu Arg Leu Val Ala Gly Pro
                245                 250                 255

Leu Val Leu Val Leu Ile Leu Gly Val Leu Gly Val Leu Ala Tyr Gly
                260                 265                 270

Ile Tyr Tyr Cys Trp Glu Glu Tyr Arg Val Leu Arg Asp Lys Gly Ala
                275                 280                 285

Ser Ile Ser Gln Leu Gly Phe Thr Thr Asn Leu Ser Ala Tyr Gln Ser
    290                 295                 300

Val Gln Glu Thr Trp Leu Ala Ala Leu Ile Val Leu Ala Val Leu Glu
305                 310                 315                 320

Ala Ile Leu Leu Leu Met Leu Ile Phe Leu Arg Gln Arg Ile Arg Ile
                325                 330                 335

Ala Ile Ala Leu Leu Lys Glu Ala Ser Lys Ala Val Gly Gln Met Met
                340                 345                 350

Ser Thr Met Phe Tyr Pro Leu Val Thr Phe Val Leu Leu Leu Ile Cys
                355                 360                 365

Ile Ala Tyr Trp Ala Met Thr Ala Leu Tyr Leu Ala Thr Ser Gly Gln
    370                 375                 380

Pro Gln Tyr Val Leu Trp Ala Ser Asn Ile Ser Ser Pro Gly Cys Glu
385                 390                 395                 400

Lys Val Pro Ile Asn Thr Ser Cys Asn Pro Thr Ala His Leu Val Asn
                405                 410                 415

Ser Ser Cys Pro Gly Leu Met Cys Val Phe Gln Gly Tyr Ser Ser Lys
                420                 425                 430

Gly Leu Ile Gln Arg Ser Val Phe Asn Leu Gln Ile Tyr Gly Val Leu
                435                 440                 445

Gly Leu Phe Trp Thr Leu Asn Trp Val Leu Ala Leu Gly Gln Cys Val
                450                 455                 460

Leu Ala Gly Ala Phe Ala Ser Phe Tyr Trp Ala Phe His Lys Pro Gln
465                 470                 475                 480

Asp Ile Pro Thr Phe Pro Leu Ile Ser Ala Phe Ile Arg Thr Leu Arg
                485                 490                 495

Tyr His Thr Gly Ser Leu Ala Phe Gly Ala Leu Ile Leu Thr Leu Val
                500                 505                 510

Gln Ile Ala Arg Val Ile Leu Glu Tyr Ile Asp His Lys Leu Arg Gly
                515                 520                 525

Val Gln Asn Pro Val Ala Arg Cys Ile Met Cys Cys Phe Lys Cys Cys
                530                 535                 540

Leu Trp Cys Leu Glu Lys Phe Ile Lys Phe Leu Asn Arg Asn Ala Tyr
545                 550                 555                 560

Ile Met Ile Ala Ile Tyr Gly Lys Asn Phe Cys Val Ser Ala Lys Asn
                565                 570                 575

Ala Phe Met Leu Leu Met Arg Asn Ile Val Arg Val Val Leu Asp
                580                 585                 590

Lys Val Thr Asp Leu Leu Leu Phe Phe Gly Lys Leu Leu Val Val Gly
```

```
                595                 600                 605
Gly Val Gly Val Leu Ser Phe Phe Phe Ser Gly Arg Ile Pro Gly
            610                 615                 620

Leu Gly Lys Asp Phe Lys Ser Pro His Leu Asn Tyr Tyr Trp Leu Pro
625                 630                 635                 640

Ile Met Arg Asn Pro Ile Thr Pro Thr Gly His Val Phe Gln Thr Ser
                645                 650                 655

Ile Leu Gly Ala Tyr Val Ile Ala Ser Gly Phe Phe Ser Val Phe Gly
            660                 665                 670

Met Cys Val Asp Thr Leu Phe Leu Cys Phe Leu Glu Asp Leu Glu Arg
        675                 680                 685

Asn Asn Gly Ser Leu Asp Arg Pro Tyr Tyr Met Ser Lys Ser Leu Leu
690                 695                 700

Lys Ile Leu Gly Lys Lys Asn Glu Ala Pro Pro Asp Asn Lys Lys Arg
705                 710                 715                 720

Lys Lys

<210> SEQ ID NO 17
<211> LENGTH: 2593
<212> TYPE: DNA
<213> ORGANISM: Homo sapiens
<220> FEATURE:
<221> NAME/KEY: CDS
<222> LOCATION: (6)...(2144)

<400> SEQUENCE: 17 gagcc atg ggg gga aag cag cgg gac gag gat gac gag gcc tac ggg aag    50
      Met Gly Gly Lys Gln Arg Asp Glu Asp Asp Glu Ala Tyr Gly Lys
      1               5                   10                  15 cca gtc aaa tac gac ccc tcc ttt cga ggc ccc atc aag aac aga agc       98
Pro Val Lys Tyr Asp Pro Ser Phe Arg Gly Pro Ile Lys Asn Arg Ser
                20                  25                  30 tgc aca gat gtc atc tgc tgc gtc ctc ttc ctg ctc ttc att cta ggt      146
Cys Thr Asp Val Ile Cys Cys Val Leu Phe Leu Leu Phe Ile Leu Gly
            35                  40                  45 tac atc gtg gtg ggg att gtg gcc tgg ttg tat gga gac ccc cgg caa      194
Tyr Ile Val Val Gly Ile Val Ala Trp Leu Tyr Gly Asp Pro Arg Gln
        50                  55                  60 gtc ctc tac ccc agg aac tct act ggg gcc tac tgt ggc atg ggg gag      242
Val Leu Tyr Pro Arg Asn Ser Thr Gly Ala Tyr Cys Gly Met Gly Glu
65                  70                  75 aac aaa gat aag ccg tat ctc ctg tac ttc aac atc ttc agc tgc atc      290
Asn Lys Asp Lys Pro Tyr Leu Leu Tyr Phe Asn Ile Phe Ser Cys Ile
80                  85                  90                  95 ctg tcc agc aac atc atc tca gtt gct gag aac ggc cta cag tgc ccc      338
Leu Ser Ser Asn Ile Ile Ser Val Ala Glu Asn Gly Leu Gln Cys Pro
                100                 105                 110 aca ccc cag gtg tgt gtg tcc tcc tgc ccg gag gac cca tgg act gtg      386
Thr Pro Gln Val Cys Val Ser Ser Cys Pro Glu Asp Pro Trp Thr Val
            115                 120                 125 gga aaa aac gag ttc tca cag act gtt ggg gaa gtc ttc tat aca aaa      434
Gly Lys Asn Glu Phe Ser Gln Thr Val Gly Glu Val Phe Tyr Thr Lys
        130                 135                 140 aac agg aac ttt tgt ctg cca ggg gta ccc tgg aat atg acg gtg atc      482
Asn Arg Asn Phe Cys Leu Pro Gly Val Pro Trp Asn Met Thr Val Ile
145                 150                 155 aca agc ctg caa cag gaa ctc tgc ccc agt ttc ctc ctc ccc tct gct      530
Thr Ser Leu Gln Gln Glu Leu Cys Pro Ser Phe Leu Leu Pro Ser Ala
160                 165                 170                 175
```

```
cca gct ctg ggg cgc tgc ttt cca tgg acc aac gtt act cca ccg gcg    578
Pro Ala Leu Gly Arg Cys Phe Pro Trp Thr Asn Val Thr Pro Pro Ala
            180                 185                 190 ctc cca ggg atc acc aat gac acc acc ata cag cag ggg atc agc ggt    626
Leu Pro Gly Ile Thr Asn Asp Thr Thr Ile Gln Gln Gly Ile Ser Gly
        195                 200                 205 ctt att gac agc ctc aat gcc cga gac atc agt gtt aag atc ttt gaa    674
Leu Ile Asp Ser Leu Asn Ala Arg Asp Ile Ser Val Lys Ile Phe Glu
    210                 215                 220 gat ttt gcc cag tcc tgg tat tgg att ctt gtt gcc ctg ggg gtg gct    722
Asp Phe Ala Gln Ser Trp Tyr Trp Ile Leu Val Ala Leu Gly Val Ala
225                 230                 235 ctg gtc ttg agc cta ctg ttt atc ttg ctt ctg cgc ctg gtg gct ggg    770
Leu Val Leu Ser Leu Leu Phe Ile Leu Leu Leu Arg Leu Val Ala Gly
240                 245                 250                 255 ccc ctg gtg ctg gtg ctg atc ctg gga gtg ctg ggc gtg ctg gca tac    818
Pro Leu Val Leu Val Leu Ile Leu Gly Val Leu Gly Val Leu Ala Tyr
            260                 265                 270 ggc atc tac tac tgc tgg gag gag tac cga gtg ctg cgg gac aag ggc    866
Gly Ile Tyr Tyr Cys Trp Glu Glu Tyr Arg Val Leu Arg Asp Lys Gly
        275                 280                 285 gcc tcc atc tcc cag ctg ggt ttc acc acc aac ctc agt gcc tac cag    914
Ala Ser Ile Ser Gln Leu Gly Phe Thr Thr Asn Leu Ser Ala Tyr Gln
    290                 295                 300 agc gtg cag gag acc tgg ctg gcc gcc ctg atc gtg ttg gcg gtg ctt    962
Ser Val Gln Glu Thr Trp Leu Ala Ala Leu Ile Val Leu Ala Val Leu
305                 310                 315 gaa gcc atc ctg ctg ctg atg ctc atc ttc ctg cgg cag cgg att cgt   1010
Glu Ala Ile Leu Leu Leu Met Leu Ile Phe Leu Arg Gln Arg Ile Arg
320                 325                 330                 335 att gcc atc gcc ctc ctg aag gag gcc agc aag gct gtg gga cag atg   1058
Ile Ala Ile Ala Leu Leu Lys Glu Ala Ser Lys Ala Val Gly Gln Met
            340                 345                 350 atg tct acc atg ttc tac cca ctg gtc acc ttt gtc ctc ctc ctc atc   1106
Met Ser Thr Met Phe Tyr Pro Leu Val Thr Phe Val Leu Leu Leu Ile
        355                 360                 365 tgc att gcc tac tgg gcc atg act gct ctg tat cct ctg ccc acg cag   1154
Cys Ile Ala Tyr Trp Ala Met Thr Ala Leu Tyr Pro Leu Pro Thr Gln
    370                 375                 380 cca gcc act ctt gga tat gtg ctc tgg gca tcc aac atc agc tcc ccc   1202
Pro Ala Thr Leu Gly Tyr Val Leu Trp Ala Ser Asn Ile Ser Ser Pro
385                 390                 395 ggc tgt gag aaa gtg cca ata aat aca tca tgc aac ccc acg gcc cac   1250
Gly Cys Glu Lys Val Pro Ile Asn Thr Ser Cys Asn Pro Thr Ala His
400                 405                 410                 415 ctt gtg aac tcc tcg tgc cca ggg ctg atg tgc gtc ttc cag ggc tac   1298
Leu Val Asn Ser Ser Cys Pro Gly Leu Met Cys Val Phe Gln Gly Tyr
            420                 425                 430 tca tcc aaa ggc cta atc caa cgt tct gtc ttc aat ctg caa atc tat   1346
Ser Ser Lys Gly Leu Ile Gln Arg Ser Val Phe Asn Leu Gln Ile Tyr
        435                 440                 445 ggg gtc ctg ggg ctc ttc tgg acc ctt aac tgg gta ctg gcc ctg ggc   1394
Gly Val Leu Gly Leu Phe Trp Thr Leu Asn Trp Val Leu Ala Leu Gly
    450                 455                 460 caa tgc gtc ctc gct gga gcc ttt gcc tcc ttc tac tgg gcc ttc cac   1442
Gln Cys Val Leu Ala Gly Ala Phe Ala Ser Phe Tyr Trp Ala Phe His
465                 470                 475 aag ccc cag gac atc cct acc ttc ccc tta atc tct gcc ttc atc cgc   1490
Lys Pro Gln Asp Ile Pro Thr Phe Pro Leu Ile Ser Ala Phe Ile Arg
480                 485                 490                 495
```

-continued

| | |
|---|---|
| aca ctc cgt tac cac act ggg tca ttg gca ttt gga gcc ctc atc ctg<br>Thr Leu Arg Tyr His Thr Gly Ser Leu Ala Phe Gly Ala Leu Ile Leu<br>              500                          505                         510 | 1538 |
| acc ctt gtg cag ata gcc cgg gtc atc ttg gag tat att gac cac aag<br>Thr Leu Val Gln Ile Ala Arg Val Ile Leu Glu Tyr Ile Asp His Lys<br>              515                          520                         525 | 1586 |
| ctc aga gga gtg cag aac cct gta gcc cgc tgc atc atg tgc tgt ttc<br>Leu Arg Gly Val Gln Asn Pro Val Ala Arg Cys Ile Met Cys Cys Phe<br>              530                          535                         540 | 1634 |
| aag tgc tgc ctc tgg tgt ctg gaa aaa ttt atc aag ttc cta aac cgc<br>Lys Cys Cys Leu Trp Cys Leu Glu Lys Phe Ile Lys Phe Leu Asn Arg<br>545                          550                         555 | 1682 |
| aat gca tac atc atg atc gcc atc tac ggg aag aat ttc tgt gtc tca<br>Asn Ala Tyr Ile Met Ile Ala Ile Tyr Gly Lys Asn Phe Cys Val Ser<br>560                          565                         570                         575 | 1730 |
| gcc aaa aat gcg ttc atg cta ctc atg cga aac att gtc agg gtg gtc<br>Ala Lys Asn Ala Phe Met Leu Leu Met Arg Asn Ile Val Arg Val Val<br>                        580                          585                         590 | 1778 |
| gtc ctg gac aaa gtc aca gac ctg ctg ctg ttc ttt ggg aag ctg ctg<br>Val Leu Asp Lys Val Thr Asp Leu Leu Leu Phe Phe Gly Lys Leu Leu<br>              595                          600                         605 | 1826 |
| gtg gtc gga ggc gtg ggg gtc ctg tcc ttc ttt ttc tcc ggt cgc<br>Val Val Gly Gly Val Gly Val Leu Ser Phe Phe Phe Ser Gly Arg<br>              610                          615                         620 | 1874 |
| atc ccg ggg ctg ggt aaa gac ttt aag agc ccc cac ctc aac tat tac<br>Ile Pro Gly Leu Gly Lys Asp Phe Lys Ser Pro His Leu Asn Tyr Tyr<br>              625                          630                         635 | 1922 |
| tgg ctg ccc atc atg acc tcc atc ctg ggg gcc tat gtc atc gcc agc<br>Trp Leu Pro Ile Met Thr Ser Ile Leu Gly Ala Tyr Val Ile Ala Ser<br>640                          645                         650                         655 | 1970 |
| ggc ttc ttc agc gtt ttc ggc atg tgt gtg gac acg ctc ttc ctc tgc<br>Gly Phe Phe Ser Val Phe Gly Met Cys Val Asp Thr Leu Phe Leu Cys<br>                        660                          665                         670 | 2018 |
| ttc ctg gaa gac ctg gag cgg aac aac ggc tcc ctg gac cgg ccc tac<br>Phe Leu Glu Asp Leu Glu Arg Asn Asn Gly Ser Leu Asp Arg Pro Tyr<br>              675                          680                         685 | 2066 |
| tac atg tcc aag agc ctt cta aag att ctg ggc aag aag aac gag gcg<br>Tyr Met Ser Lys Ser Leu Leu Lys Ile Leu Gly Lys Lys Asn Glu Ala<br>                        690                          695                         700 | 2114 |
| ccc ccg gac aac aag aag agg aag aag tga cagctccggc cctgatccag<br>Pro Pro Asp Asn Lys Lys Arg Lys Lys<br>              705                          710 | 2164 |
| gactgcaccc cacccccacc gtccagccat ccaacctcac ttcgccttac aggtctccat | 2224 |
| tttgtggtaa aaaaaggttt taggccaggc gccgtggctc acgcctgtaa tccaacactt | 2284 |
| tgagaggctg aggcgggcgg atcacctgag tcaggagttc gagaccagcc tggccaacat | 2344 |
| ggtgaaaacct ccgtctctat taaaaataca aaaattagcc gagagtggtg gcatgcacct | 2404 |
| gtcatcccag ctactcggga ggctgaggca ggagaatcgc ttgaacccgg gaggcagagg | 2464 |
| ttgcagtgag ccgagatcgc gccactgcac tccaacctgg gtgacagact ctgtctccaa | 2524 |
| aacaaaacaa acaaacaaaa agattttatt aaagatattt tgttaactca gtaaaaaaaa | 2584 |
| aaaaaaaaa | 2593 |

```
<210> SEQ ID NO 18
<211> LENGTH: 712
<212> TYPE: PRT
<213> ORGANISM: Homo sapiens

<400> SEQUENCE: 18
```

```
Met Gly Gly Lys Gln Arg Asp Glu Asp Glu Ala Tyr Gly Lys Pro
1               5                   10                  15
Val Lys Tyr Asp Pro Ser Phe Arg Gly Pro Ile Lys Asn Arg Ser Cys
            20                  25                  30
Thr Asp Val Ile Cys Cys Val Leu Phe Leu Leu Phe Ile Leu Gly Tyr
        35                  40                  45
Ile Val Val Gly Ile Val Ala Trp Leu Tyr Gly Asp Pro Arg Gln Val
        50                  55                  60
Leu Tyr Pro Arg Asn Ser Thr Gly Ala Tyr Cys Gly Met Gly Glu Asn
65                  70                  75                  80
Lys Asp Lys Pro Tyr Leu Leu Tyr Phe Asn Ile Phe Ser Cys Ile Leu
                85                  90                  95
Ser Ser Asn Ile Ile Ser Val Ala Glu Asn Gly Leu Gln Cys Pro Thr
            100                 105                 110
Pro Gln Val Cys Val Ser Ser Cys Pro Glu Asp Pro Trp Thr Val Gly
            115                 120                 125
Lys Asn Glu Phe Ser Gln Thr Val Gly Val Phe Tyr Thr Lys Asn
        130                 135                 140
Arg Asn Phe Cys Leu Pro Gly Val Pro Trp Asn Met Thr Val Ile Thr
145                 150                 155                 160
Ser Leu Gln Gln Glu Leu Cys Pro Ser Phe Leu Leu Pro Ser Ala Pro
                165                 170                 175
Ala Leu Gly Arg Cys Phe Pro Trp Thr Asn Val Thr Pro Pro Ala Leu
            180                 185                 190
Pro Gly Ile Thr Asn Asp Thr Thr Ile Gln Gly Ile Ser Gly Leu
            195                 200                 205
Ile Asp Ser Leu Asn Ala Arg Asp Ile Ser Val Lys Ile Phe Glu Asp
210                 215                 220
Phe Ala Gln Ser Trp Tyr Trp Ile Leu Val Ala Leu Gly Val Ala Leu
225                 230                 235                 240
Val Leu Ser Leu Leu Phe Ile Leu Leu Leu Arg Leu Val Ala Gly Pro
                245                 250                 255
Leu Val Leu Val Leu Ile Leu Gly Val Leu Gly Val Leu Ala Tyr Gly
            260                 265                 270
Ile Tyr Tyr Cys Trp Glu Glu Tyr Arg Val Leu Arg Asp Lys Gly Ala
            275                 280                 285
Ser Ile Ser Gln Leu Gly Phe Thr Thr Asn Leu Ser Ala Tyr Gln Ser
            290                 295                 300
Val Gln Glu Thr Trp Leu Ala Ala Leu Ile Val Leu Ala Val Leu Glu
305                 310                 315                 320
Ala Ile Leu Leu Leu Met Leu Ile Phe Leu Arg Gln Arg Ile Arg Ile
                325                 330                 335
Ala Ile Ala Leu Leu Lys Glu Ala Ser Lys Ala Val Gly Gln Met Met
            340                 345                 350
Ser Thr Met Phe Tyr Pro Leu Val Thr Phe Val Leu Leu Ile Cys
        355                 360                 365
Ile Ala Tyr Trp Ala Met Thr Ala Leu Tyr Pro Leu Pro Thr Gln Pro
        370                 375                 380
Ala Thr Leu Gly Tyr Val Leu Trp Ala Ser Asn Ile Ser Ser Pro Gly
385                 390                 395                 400
Cys Glu Lys Val Pro Ile Asn Thr Ser Cys Asn Pro Thr Ala His Leu
                405                 410                 415
Val Asn Ser Ser Cys Pro Gly Leu Met Cys Val Phe Gln Gly Tyr Ser
            420                 425                 430
```

Ser Lys Gly Leu Ile Gln Arg Ser Val Phe Asn Leu Gln Ile Tyr Gly
    435                 440                 445

Val Leu Gly Leu Phe Trp Thr Leu Asn Trp Val Leu Ala Leu Gly Gln
450                 455                 460

Cys Val Leu Ala Gly Ala Phe Ala Ser Phe Tyr Trp Ala Phe His Lys
465                 470                 475                 480

Pro Gln Asp Ile Pro Thr Phe Pro Leu Ile Ser Ala Phe Ile Arg Thr
                485                 490                 495

Leu Arg Tyr His Thr Gly Ser Leu Ala Phe Gly Ala Leu Ile Leu Thr
            500                 505                 510

Leu Val Gln Ile Ala Arg Val Ile Leu Glu Tyr Ile Asp His Lys Leu
        515                 520                 525

Arg Gly Val Gln Asn Pro Val Ala Arg Cys Ile Met Cys Cys Phe Lys
    530                 535                 540

Cys Cys Leu Trp Cys Leu Glu Lys Phe Ile Lys Phe Leu Asn Arg Asn
545                 550                 555                 560

Ala Tyr Ile Met Ile Ala Ile Tyr Gly Lys Asn Phe Cys Val Ser Ala
                565                 570                 575

Lys Asn Ala Phe Met Leu Leu Met Arg Asn Ile Val Arg Val Val Val
            580                 585                 590

Leu Asp Lys Val Thr Asp Leu Leu Leu Phe Phe Gly Lys Leu Leu Val
        595                 600                 605

Val Gly Val Gly Val Leu Ser Phe Phe Phe Ser Gly Arg Ile
    610                 615                 620

Pro Gly Leu Gly Lys Asp Phe Lys Ser Pro His Leu Asn Tyr Tyr Trp
625                 630                 635                 640

Leu Pro Ile Met Thr Ser Ile Leu Gly Ala Tyr Val Ile Ala Ser Gly
                645                 650                 655

Phe Phe Ser Val Phe Gly Met Cys Val Asp Thr Leu Phe Leu Cys Phe
            660                 665                 670

Leu Glu Asp Leu Glu Arg Asn Asn Gly Ser Leu Asp Arg Pro Tyr Tyr
        675                 680                 685

Met Ser Lys Ser Leu Leu Lys Ile Leu Gly Lys Lys Asn Glu Ala Pro
    690                 695                 700

Pro Asp Asn Lys Lys Arg Lys Lys
705                 710

<210> SEQ ID NO 19
<211> LENGTH: 576
<212> TYPE: DNA
<213> ORGANISM: Homo sapiens

<400> SEQUENCE: 19
caggtgcagc tggtggagtc tgggggaggc gtggtccagc ctggagggtc cctgagactc      60
tcctgtggag cctctggatt caccttcagt agttatggca tgcactgggt ccgccaggct     120
ccaggcaagg ggctggagtg ggtggcagtt atgtcatatg atggaagtaa aaaatactat     180
acagactccg tgaagggccg attcaccatc tccagagaca attccaagaa cacgctgtat     240
ctgcaaatga acagcctgag agttgaggac acggctgtgt attactgtgc gagagatggg     300
ggtgactacg tccgctacta ctactacggt atggacgtct ggggccaagg gaccacggtc     360
accgtctcct cagcctccac caagggccca tcggtcttcc ccctggcgcc ctgctccagg     420
agcacctccg agagcacagc ggccctgggc tgcctggtca aggactactt ccccgaaccg     480
gtgacggtgt cgtggaactc aggcgctctg accagcggcg tgcacacctt cccagctgtc     540

```
ctacagtcct caggactcta ctccctcagc agcgtg                            576
```

<210> SEQ ID NO 20
<211> LENGTH: 192
<212> TYPE: PRT
<213> ORGANISM: Homo sapiens

<400> SEQUENCE: 20

```
Gln Val Gln Leu Val Glu Ser Gly Gly Val Gln Pro Gly Arg
 1               5                  10                  15

Ser Leu Arg Leu Ser Cys Gly Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Met Ser Tyr Asp Gly Ser Lys Lys Tyr Tyr Thr Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Val Glu Asp Thr Ala Val Tyr Tyr Cys
                85                  90                  95

Ala Arg Asp Gly Gly Asp Tyr Val Arg Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190
```

<210> SEQ ID NO 21
<211> LENGTH: 625
<212> TYPE: DNA
<213> ORGANISM: Homo sapiens

<400> SEQUENCE: 21

```
ctcccagata ccagatgtga catccagatg acccagtctc catcctccct gtctgcatct     60
gtaggagaca gagtcaccat cacttgccgg gcgcgtcagg gcattaccta tcatttagcc    120
tggtatcagc agagaccggg gaaagttcct aaactcctga tctatgatac atcctctttg    180
caatcagggg tcccatctcg gttcagtggc agtggatctg ggacagattt cactctcacc    240
atcagcagcc tgcagcctga agatgttgca acttattact gtcaaaggtt taacagtgcc    300
ccgctcactt tcggcggagg gaccaaggtg gagatcaaac gaactgtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaagt ctacgcctgc    600 gaagtcaccc atcagggcct gagct                                         625
```

<210> SEQ ID NO 22
<211> LENGTH: 208

<212> TYPE: PRT
<213> ORGANISM: Homo sapiens

<400> SEQUENCE: 22

Leu Pro Asp Thr Arg Cys Asp Ile Gln Met Thr Gln Ser Pro Ser Ser
1               5                   10                  15

Leu Ser Ala Ser Val Gly Asp Arg Val Thr Ile Thr Cys Arg Ala Arg
            20                  25                  30

Gln Gly Ile Thr Tyr His Leu Ala Trp Tyr Gln Gln Arg Pro Gly Lys
        35                  40                  45

Val Pro Lys Leu Leu Ile Tyr Asp Thr Ser Ser Leu Gln Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Val Ala Thr Tyr Tyr Cys Gln Arg
                85                  90                  95

Phe Asn Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

<210> SEQ ID NO 23
<211> LENGTH: 571
<212> TYPE: DNA
<213> ORGANISM: Homo sapiens

<400> SEQUENCE: 23
caggtgcagc tggtggagtc tgggggaggc gtggtccagc ctggggaggtc cctgagactc    60
tcctgtgcag cctctggatt caccttcagt agttatggca tgcactgggt ccgccaggct   120
ccaggcaagg ggctggagtg ggtggcagtt atgtcatatg atggaagtaa aaaattctat   180
acagactccg tgaagggccg attcaccatc tccagagaca attccaagaa cacgctgtat   240
ctgcaaatga acagcctgag agctgaggac acggctgtgt attactgtgc gagagatggg   300
ggtgactatg tccgctacca ctactacggt atggacgtct ggggccaagg gaccacggtc   360
accgtctcct cagcctccac caagggccca tcggtcttcc ccctggcgcc ctgctccagg   420
agcacctccg agagcacagc ggccctgggc tgcctggtca aggactactt ccccgaaccg   480
gtgacggtgt cgtggaactc aggcgctctg accagcggcg tgcacacctt cccagctgtc   540
ctacagtcct caggactcta ctccctcagc a                                 571

<210> SEQ ID NO 24
<211> LENGTH: 190
<212> TYPE: PRT
<213> ORGANISM: Homo sapiens

<400> SEQUENCE: 24

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Met Ser Tyr Asp Gly Ser Lys Lys Phe Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gly Asp Tyr Val Arg Tyr His Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser
            180                 185                 190

<210> SEQ ID NO 25
<211> LENGTH: 678
<212> TYPE: DNA
<213> ORGANISM: Homo sapiens

<400> SEQUENCE: 25
ctcctgggac tcctgctgct ctggctccca gataccagat gtgacatcca gatgacccag    60
tctccatcca ccctgtctgc atctatagga gacagagtca ccatcacttg ccgggcgagt   120
cagggcatta gctattattt agcctggtat cagcagaaac cggggaaaat tcctaagctc   180
ctgatctatg atacatcctc tttgcaatca ggggtcccat ctcgattcag tggcagtaga   240
tctgggacag atctctctct caccatcagc agcctgcagc tgaagatgtt gcaacttat   300 tactgtcaaa ggtatgacag tgccccgctc actttcggcg agggaccaa ggtggagatc   360 aaacgaactg tggctgcacc atctgtcttc atcttcccgc catctgatga gcagttgaaa   420
tctggaactg cctctgttgt gtgcctgctg aataacttct atcccagaga ggccaaagta   480
cagtggaagg tggataacgc cctccaatcg ggtaactccc aggagagtgt cacagagcag   540
gacagcaagg acagcaccta cagcctcagc agcaccctga cgctgagcaa agcagactac   600
gagaaacaca agtctacgc ctgcgaagtc acccatcagg gcctgagctc gcccgtcaca   660
aagagcttca acagggga                                                 678

<210> SEQ ID NO 26
<211> LENGTH: 226
<212> TYPE: PRT
<213> ORGANISM: Homo sapiens

<400> SEQUENCE: 26

Leu Leu Gly Leu Leu Leu Leu Trp Leu Pro Asp Thr Arg Cys Asp Ile
1               5                   10                  15

Gln Met Thr Gln Ser Pro Ser Thr Leu Ser Ala Ser Ile Gly Asp Arg
```

```
            20                  25                  30
Val Thr Ile Thr Cys Arg Ala Ser Gln Gly Ile Ser Tyr Tyr Leu Ala
         35                  40                  45

Trp Tyr Gln Gln Lys Pro Gly Lys Ile Pro Lys Leu Leu Ile Tyr Asp
 50                  55                  60

Thr Ser Ser Leu Gln Ser Gly Val Pro Ser Arg Phe Ser Gly Ser Arg
 65                  70                  75                  80

Ser Gly Thr Asp Leu Ser Leu Thr Ile Ser Ser Leu Gln Pro Glu Asp
             85                  90                  95

Val Ala Thr Tyr Tyr Cys Gln Arg Tyr Asp Ser Ala Pro Leu Thr Phe
         100                 105                 110

Gly Gly Gly Thr Lys Val Glu Ile Lys Arg Thr Val Ala Ala Pro Ser
         115                 120                 125

Val Phe Ile Phe Pro Pro Ser Asp Glu Gln Leu Lys Ser Gly Thr Ala
         130                 135                 140

Ser Val Val Cys Leu Leu Asn Asn Phe Tyr Pro Arg Glu Ala Lys Val
145                 150                 155                 160

Gln Trp Lys Val Asp Asn Ala Leu Gln Ser Gly Asn Ser Gln Glu Ser
                 165                 170                 175

Val Thr Glu Gln Asp Ser Lys Asp Ser Thr Tyr Ser Leu Ser Ser Thr
             180                 185                 190

Leu Thr Leu Ser Lys Ala Asp Tyr Glu Lys His Lys Val Tyr Ala Cys
         195                 200                 205

Glu Val Thr His Gln Gly Leu Ser Ser Pro Val Thr Lys Ser Phe Asn
         210                 215                 220

Arg Gly
225

<210> SEQ ID NO 27
<211> LENGTH: 410
<212> TYPE: DNA
<213> ORGANISM: Homo sapiens

<400> SEQUENCE: 27
caggtgcagc tggtggagtc tgggggaggc gtggtccagc ctggggaggtc cctgagactc      60 tcctgtgcag cgtctggatt caccttcagt agctatggca tgcactgggt ccgccaggct     120
ccaggcaagg ggctggagtg ggtggcagtt atatggtatg atggaagaaa taaattctat     180
gcagactccg tgaagggccg attcaccgtc tccagagaca attccaagaa cacgctgtat     240
ctgcaaatga acagcctgag agccgaggac acggctgtgt attactgtgc gagagattgg     300
ggagctacta tggcttttga tatctggggc caagggacaa tggtcaccgt ctcttcagcc     360
tccaccaagg gcccatcggt cttccccctg gcaccctcct ccaagagcac                410

<210> SEQ ID NO 28
<211> LENGTH: 136
<212> TYPE: PRT
<213> ORGANISM: Homo sapiens

<400> SEQUENCE: 28

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45
```

```
Ala Val Ile Trp Tyr Asp Gly Arg Asn Lys Phe Tyr Ala Asp Ser Val
             50                  55                  60

Lys Gly Arg Phe Thr Val Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Trp Gly Ala Thr Met Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser
    130                 135
```

<210> SEQ ID NO 29
<211> LENGTH: 646
<212> TYPE: DNA
<213> ORGANISM: Homo sapiens

<400> SEQUENCE: 29

```
ctcctcaccc tcctcactca ctgtgcaggg tcctgggccc agtctgtgct gactcagcca    60
ccctcagcgt ctaagacccc cgggcagagg gtcaccatct cttgttctgg aagcagctcc   120
aacatcggaa gtaatactgt caactggtac aacagctcc caggaacggc cccaaaactc   180
ctcatctttg gtaataatca gcggccctca ggggtcctg accgattctc tggctccaag   240
tctggcacct cagcctccct ggccatcagt ggtctccagt ctgaggatga ggctgattat   300
tactgtgcag catgggatga cagcctgaat tatgtcttcg gaactgggac caaggtcacc   360
gtcctaggtc agcccaaggc aaccccact gtcactctgt tcccgccctc ctctgaggag   420
ctccaagcca acaaggccac actagtgtgt ctgatcagtg acttctaccc gggagctgtg   480
acagtggcct ggaaggcaga tgcagcccc gtcaaggcgg gagtggagac caccaaaccc   540
tccaaacaga gcaacaacaa gtacgcggcc agcagctacc tgagcctgac gcccgagcag   600
tggaagtccc acagaagcta cagctgccag gtcacgcatg aaggag               646
```

<210> SEQ ID NO 30
<211> LENGTH: 215
<212> TYPE: PRT
<213> ORGANISM: Homo sapiens

<400> SEQUENCE: 30

```
Leu Leu Thr Leu Leu Thr His Cys Ala Gly Ser Trp Ala Gln Ser Val
  1               5                  10                  15

Leu Thr Gln Pro Pro Ser Ala Ser Lys Thr Pro Gly Gln Arg Val Thr
                 20                  25                  30

Ile Ser Cys Ser Gly Ser Ser Ser Asn Ile Gly Ser Asn Thr Val Asn
             35                  40                  45

Trp Tyr Gln Gln Leu Pro Gly Thr Ala Pro Lys Leu Leu Ile Phe Gly
         50                  55                  60

Asn Asn Gln Arg Pro Ser Gly Val Pro Asp Arg Phe Ser Gly Ser Lys
 65                  70                  75                  80

Ser Gly Thr Ser Ala Ser Leu Ala Ile Ser Gly Leu Gln Ser Glu Asp
                 85                  90                  95

Glu Ala Asp Tyr Tyr Cys Ala Ala Trp Asp Asp Ser Leu Asn Tyr Val
            100                 105                 110

Phe Gly Thr Gly Thr Lys Val Thr Val Leu Gly Gln Pro Lys Ala Asn
        115                 120                 125
```

```
Pro Thr Val Thr Leu Phe Pro Pro Ser Ser Glu Glu Leu Gln Ala Asn
    130                 135                 140

Lys Ala Thr Leu Val Cys Leu Ile Ser Asp Phe Tyr Pro Gly Ala Val
145                 150                 155                 160

Thr Val Ala Trp Lys Ala Asp Gly Ser Pro Val Lys Ala Gly Val Glu
                165                 170                 175

Thr Thr Lys Pro Ser Lys Gln Ser Asn Asn Lys Tyr Ala Ala Ser Ser
            180                 185                 190

Tyr Leu Ser Leu Thr Pro Glu Gln Trp Lys Ser His Arg Ser Tyr Ser
        195                 200                 205

Cys Gln Val Thr His Glu Gly
    210                 215

<210> SEQ ID NO 31
<211> LENGTH: 416
<212> TYPE: DNA
<213> ORGANISM: Homo sapiens

<400> SEQUENCE: 31
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg gctggagtg gtggcagtt atatggtatg atggaagtaa taaatactat       180
gcagactccg tgaagggccg attcaccatc tccagagaca attccaagaa cacgctgtat     240
ctgcaaatga acagcctgag agccgaagac acggctgtct attactgtgc gagagatcga     300
tatagtggct acggttacta ctactactac ggtatggacg tctggggcca agggaccacg     360
gtcaccgtct cctcagcctc caccaagggc ccatcggtct tccccctggc accctc         416

<210> SEQ ID NO 32
<211> LENGTH: 138
<212> TYPE: PRT
<213> ORGANISM: Homo sapiens

<400> SEQUENCE: 32

Gln Val Gln Leu Val Glu Ser Gly Gly Gly Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Tyr Ser Gly Tyr Gly Tyr Tyr Tyr Tyr Gly Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro
    130                 135

<210> SEQ ID NO 33
<211> LENGTH: 651
<212> TYPE: DNA
<213> ORGANISM: Homo sapiens
```

<400> SEQUENCE: 33

```
ggtgccagat gtgacatcca gatgacccag tctccatcct cactgtctgc atctgtagga      60
gacagagtca ccatcacttg tcgggcgagt caggacatta gcaattattt agcctggttt     120
cagcagaaac cagggaaagc ccctaagtcc ctgatctatg ctgcatccag tttgcacagt     180
ggggtcccat caaagttcag cggcagtgga tctgggacag atttcactct caccatcagc     240
agcctgcagc ctgaagattt tgcaacttat tactgccaac agtatactat ttacccattc     300
actttcggcc ctgggaccaa agtggatatc aaacgaactg tggctgcacc atctgtcttc     360
atcttcccgc catctgatga gcagttgaaa tctggaactg cctctgttgt gtgcctgctg     420
aataacttct atcccagaga ggccaaagta cagtggaagg tggataacgc cctccaatcg     480
ggtaactccc aggagagtgt cacagagcag gacagcaagg acagcaccta cagcctcagc     540
agcaccctga cgctgagcaa agcagactac gagaaacaca agtctacgc ctgcgaagtc      600
acccatcagg gcctgagctc gcccgtcaca aagagcttca caggggaga g               651
```

<210> SEQ ID NO 34
<211> LENGTH: 217
<212> TYPE: PRT
<213> ORGANISM: Homo sapiens

<400> SEQUENCE: 34

```
Gly Ala Arg Cys Asp Ile Gln Met Thr Gln Ser Pro Ser Ser Leu Ser
1               5                   10                  15
Ala Ser Val Gly Asp Arg Val Thr Ile Thr Cys Arg Ala Ser Gln Asp
            20                  25                  30
Ile Ser Asn Tyr Leu Ala Trp Phe Gln Gln Lys Pro Gly Lys Ala Pro
        35                  40                  45
Lys Ser Leu Ile Tyr Ala Ala Ser Ser Leu His Ser Gly Val Pro Ser
    50                  55                  60
Lys Phe Ser Gly Ser Gly Ser Gly Thr Asp Phe Thr Leu Thr Ile Ser
65                  70                  75                  80
Ser Leu Gln Pro Glu Asp Phe Ala Thr Tyr Tyr Cys Gln Gln Tyr Thr
                85                  90                  95
Ile Tyr Pro Phe Thr Phe Gly Pro Gly Thr Lys Val Asp Ile Lys Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu
    210                 215
```

<210> SEQ ID NO 35
<211> LENGTH: 532
<212> TYPE: DNA
<213> ORGANISM: Homo sapiens

<400> SEQUENCE: 35

```
caggtgcagc tgcaggagtc tggcccagga ctggtgaagc cttcggagac cctgtccctc      60
acctgcactg tctctggtgg ctccatcagt agttactact ggagctggat ccggcagccc     120
ccagggaagg gactggagtg gattgggtat atctattaca gtgggagcac caactacaac     180
ccctccctca agagtcgagt caccatatca gtagacacgt ccaagaacca gttctccctg     240
aagctgaact ctgtgaccgc tgcggacacg gccgtgtatt actgtgcgag agggtattac     300
tatggttcgg agagtccata cggtatggac gtctggggcc aagggaccac ggtcaccgtc     360
tcctcagcct ccaccaaggg cccatcggtc ttccccctgg cacccctcct caagagcacc     420
tctgggggca gcgcggccct gggctgcctg gtcaaggact acttccccga accggtgacg     480
gtgtcgtgga actcaggcgc cctgaccagc ggcgtgcaca ccttcccagc tg             532
```

<210> SEQ ID NO 36
<211> LENGTH: 177
<212> TYPE: PRT
<213> ORGANISM: Homo sapiens

<400> SEQUENCE: 36

```
Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Ser Ser Tyr
            20                  25                  30
Tyr Trp Ser Trp Ile Arg Gln Pro Pro Gly Lys Gly Leu Glu Trp Ile
        35                  40                  45
Gly Tyr Ile Tyr Tyr Ser Gly Ser Thr Asn Tyr Asn Pro Ser Leu Lys
    50                  55                  60
Ser Arg Val Thr Ile Ser Val Asp Thr Ser Lys Asn Gln Phe Ser Leu
65                  70                  75                  80
Lys Leu Asn Ser Val Thr Ala Ala Asp Thr Ala Val Tyr Tyr Cys Ala
                85                  90                  95
Arg Gly Tyr Tyr Tyr Gly Ser Glu Ser Pro Tyr Gly Met Asp Val Trp
            100                 105                 110
Gly Gln Gly Thr Thr Val Thr Val Ser Ser Ala Ser Thr Lys Gly Pro
        115                 120                 125
Ser Val Phe Pro Leu Ala Pro Ser Ser Lys Ser Thr Ser Gly Gly Thr
    130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala
```

<210> SEQ ID NO 37
<211> LENGTH: 649
<212> TYPE: DNA
<213> ORGANISM: Homo sapiens

<400> SEQUENCE: 37

```
gatattgtga tgactcagtc tccactctcc ctgcccgtca cccctggaga gccggcctcc      60
atctcctgca ggtctagtca gagcctcctg catagtaatg gacacaacta tttggattgg     120
tacctgcaga agccagggca gtctccacac ctcctgatct atttgggttc taatcgggac     180
tccggggtcc ctgacaggtt cagtggcagt ggatcaggca cagattttac actgaaaatc     240
```

-continued

```
agcagagtgg aggctgagga tgttggggtt tattactgca tgcaagctct acaaattccg    300
tgcagttttg gccaggggac caagctggag atcaaacgaa ctgtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacaggg              649
```

<210> SEQ ID NO 38
<211> LENGTH: 216
<212> TYPE: PRT
<213> ORGANISM: Homo sapiens

<400> SEQUENCE: 38

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly His Asn Tyr Leu Asp Trp Tyr Leu Gln Lys Pro Gly Gln Ser
        35                  40                  45

Pro His Leu Leu Ile Tyr Leu Gly Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Ile Pro Cys Ser Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg
    210                 215

<210> SEQ ID NO 39
<211> LENGTH: 524
<212> TYPE: DNA
<213> ORGANISM: Homo sapiens

<400> SEQUENCE: 39

```
caggtgcagc tggtggagtt tgggggaggc gtggtccagc ctgggaggtc cctgagactc     60
tcctgtgcag cgtctggatt caccttcaga agctatggca tgcactgggt ccgccaggct    120
ccaggcaagg ggctggagtg ggtggcagtt atatggtatg atggaagtaa taaatactat    180
gcagactccg tgaagggccg atccaccatc tccagagaca actccaagaa cacgctgtat    240
```

```
ctgcaaatga acagcctgag agccgaggac acggctgtgt attactgtgc gagagatggg    300
gtagcagtgg ctggtacaga ctactttgac tactggggcc agggaaccct ggtcaccgtc    360
tcctcagcct ccaccaaggg cccatcggtc ttccccctgg caccctcctc caagagcacc    420
tctgggggca gcggccct gggctgcctg gtcaaggact acttccccga accggtgacg      480
gtgtcgtgga actcaggcgc cctgaccagc ggcgtgcaca cctt                     524
```

<210> SEQ ID NO 40
<211> LENGTH: 174
<212> TYPE: PRT
<213> ORGANISM: Homo sapiens

<400> SEQUENCE: 40

```
Gln Val Gln Leu Val Glu Phe Gly Gly Gly Val Val Gln Pro Gly Arg
 1               5                  10                  15

Ser Leu Arg Leu Ser Cys Ala Ala Ser Gly Phe Thr Phe Arg Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Ser Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Val Ala Val Ala Gly Thr Asp Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr
                165                 170
```

<210> SEQ ID NO 41
<211> LENGTH: 639
<212> TYPE: DNA
<213> ORGANISM: Homo sapiens

<400> SEQUENCE: 41

```
tctggctccg aggtgccaga tgtgacatcc agatgaccca gtctccatcc tccctgtctg     60
catctgtagg agacagagtc accatcactt gccgggcaag tcagagcatt agcagccatt    120
taaattggta tcagcagaaa ccagggaaag cccctaagct cctgatctat gttgcatcca    180
gtttgcaaag tggggtccca tcaaggttca gtggcagtgg atctgggaca gatttcactc    240
tcaccatcag cagtctgcaa cctgaagatt ttgcaactta ctactgtcaa cagagttaca    300
gtaccccgct cattttcggc ggagggacca aggtggagat caaacgaact gtggctgcac    360
catctgtctt catcttcccg ccatctgatg agcagttgaa atctggaact gcctctgttg    420
tgtgcctgct gaataacttc tatcccagag aggccaaagt acagtggaag gtggataacg    480
ccctccaatc gggtaactcc caggagagtg tcacagagca ggacagcaag gacagcacct    540
acagcctcag cagcaccctg acgctgagca agcagacta cgagaaacac aaagtctacg    600
cctgcgaagt cacccatcag ggcctgagct cgcccgtca                          639
```

<210> SEQ ID NO 42
<211> LENGTH: 212
<212> TYPE: PRT
<213> ORGANISM: Homo sapiens

<400> SEQUENCE: 42

```
Trp Leu Arg Gly Ala Arg Cys Asp Ile Gln Met Thr Gln Ser Pro Ser
1               5                   10                  15

Ser Leu Ser Ala Ser Val Gly Asp Arg Val Thr Ile Thr Cys Arg Ala
            20                  25                  30

Ser Gln Ser Ile Ser Ser His Leu Asn Trp Tyr Gln Gln Lys Pro Gly
        35                  40                  45

Lys Ala Pro Lys Leu Leu Ile Tyr Val Ala Ser Ser Leu Gln Ser Gly
    50                  55                  60

Val Pro Ser Arg Phe Ser Gly Ser Gly Ser Gly Thr Asp Phe Thr Leu
65                  70                  75                  80

Thr Ile Ser Ser Leu Gln Pro Glu Asp Phe Ala Thr Tyr Tyr Cys Gln
                85                  90                  95

Gln Ser Tyr Ser Thr Pro Leu Ile Phe Gly Gly Gly Thr Lys Val Glu
            100                 105                 110

Ile Lys Arg Thr Val Ala Ala Pro Ser Val Phe Ile Phe Pro Pro Ser
        115                 120                 125

Asp Glu Gln Leu Lys Ser Gly Thr Ala Ser Val Val Cys Leu Leu Asn
    130                 135                 140

Asn Phe Tyr Pro Arg Glu Ala Lys Val Gln Trp Lys Val Asp Asn Ala
145                 150                 155                 160

Leu Gln Ser Gly Asn Ser Gln Glu Ser Val Thr Glu Gln Asp Ser Lys
                165                 170                 175

Asp Ser Thr Tyr Ser Leu Ser Ser Thr Leu Thr Leu Ser Lys Ala Asp
            180                 185                 190

Tyr Glu Lys His Lys Val Tyr Ala Cys Glu Val Thr His Gln Gly Leu
        195                 200                 205

Ser Ser Pro Val
    210
```

<210> SEQ ID NO 43
<211> LENGTH: 478
<212> TYPE: DNA
<213> ORGANISM: Homo sapiens

<400> SEQUENCE: 43

```
gaggtgcagc tgttggagtc tgggggaggc ttggtacagc ctgggggtc cctgagactc      60
tcctgtgcag cctctacatt caccttagc agctatgcca tgagctgggt ccgccaggct    120
ccagggaagg ggctggagtg ggtctcagct tttagtggtc gtggtggtag cacatactac   180
gcagactccg tgaagggccg gttcaccatc tccagaaaga cacgctgtt tctgcaaatg    240
aacagcctga gagccgagga cacggccgta tattactgtg cgaaagatag cagtggcccc   300
ctgctgggct acggtatgga cgtctggggc caagggacca cggtcaccgt ctcctcagcc   360
tccaccaagg gcccatcggt cttccccctg gcaccctcct ccaagagcac ctctggggc    420
acagcggccc tgggctgcct ggtcaaggac tacttccccg aaccggtgac ggtgtcgt     478
```

<210> SEQ ID NO 44
<211> LENGTH: 162
<212> TYPE: PRT
<213> ORGANISM: Homo sapiens

<400> SEQUENCE: 44

Glu Val Gln Leu Leu Glu Ser Gly Gly Gly Leu Val Gln Pro Gly Gly
1               5                   10                  15

Ser Leu Arg Leu Ser Cys Ala Ala Ser Thr Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Phe Ser Gly Arg Gly Gly Ser Thr Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Lys Asp Ser Ser Gly Pro Leu Leu Gly Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser

<210> SEQ ID NO 45
<211> LENGTH: 620
<212> TYPE: DNA
<213> ORGANISM: Homo sapiens

<400> SEQUENCE: 45
tcctatgagc tgactcagcc accctcagtg tccgtgtccc caggacagac agccagcatc      60
acctgctctg gagataaagt gggggataaa tatgcttgtt ggtatcagca aaagccaggc     120
cagtcccctg tactggtcat ctatcaagat agcaagcggc cctcagggat ccctgagcga     180
ttctctggct ccaattctgg aaacacagcc actctgacca tcagcgggac ccaggctatg     240
gatgaggctg actattactg tcaggcgtgg gacagcagca cttatgtggt attcggcgga     300
gggaccaaac tgaccgtcct aggtcagccc aaggctgccc cctcggtcac tctgttcccg     360
ccctcctctg aggagcttca agccaacaag gccacactgg tgtgtctcat aagtgacttc     420
tacccgggag ccgtgacagt ggcctggaag gcagatagca gccccgtcaa ggcgggagtg     480
gagaccacca cacctccaa acaaagcaac aacaagtacg cggccagcag ctatctgagc     540
ctgacgcctg agcagtggaa gtcccacaga agctacagct gccaggtcac gcatgaaggg     600
agcaccgtgg agaagacagt                                                 620

<210> SEQ ID NO 46
<211> LENGTH: 206
<212> TYPE: PRT
<213> ORGANISM: Homo sapiens

<400> SEQUENCE: 46

Ser Tyr Glu Leu Thr Gln Pro Pro Ser Val Ser Val Pro Gly Gln
1               5                   10                  15

Thr Ala Ser Ile Thr Cys Ser Gly Asp Lys Val Gly Asp Lys Tyr Ala
            20                  25                  30

Cys Trp Tyr Gln Gln Lys Pro Gly Gln Ser Pro Val Leu Val Ile Tyr

```
               35                  40                  45
Gln Asp Ser Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Asp Ser Ser Thr Tyr Val
                 85                  90                  95

Val Phe Gly Gly Gly Thr Lys Leu Thr Val Leu Gly Gln Pro Lys Ala
                100                 105                 110

Ala Pro Ser Val Thr Leu Phe Pro Pro Ser Ser Glu Glu Leu Gln Ala
            115                 120                 125

Asn Lys Ala Thr Leu Val Cys Leu Ile Ser Asp Phe Tyr Pro Gly Ala
            130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr
            195                 200                 205

<210> SEQ ID NO 47
<211> LENGTH: 417
<212> TYPE: DNA
<213> ORGANISM: Homo sapiens

<400> SEQUENCE: 47
caggtgcagc tggtggagtc tgggggaggc gtggtccagc ctggagggtc cctgagactc      60
tcctgtgcag cgtctggatt caccttcagt agctatggca tgcactgggt ccgccaggct     120
ccaggcaagg ggctggagtg ggtggcagtt atatggtatg atggaagtaa taaatactat     180
gcagactccg tgaagggccg attcaccatc tccagagaca attccaagaa cacgctgtat     240
ctgcaaatga acagcctgag agccgaggac acggctgtgt attactgtgc gagagatcga     300
tatagtggct acgattacta ctactactac ggtatggacg tctggggcca agggaccacg     360
gtcaccgtct cctcagcctc caccaagggc ccatcggtct tccccctggc accctcc       417

<210> SEQ ID NO 48
<211> LENGTH: 139
<212> TYPE: PRT
<213> ORGANISM: Homo sapiens

<400> SEQUENCE: 48

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Trp Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95
```

Ala Arg Asp Arg Tyr Ser Gly Tyr Asp Tyr Tyr Tyr Tyr Gly Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Ser
    130                 135

<210> SEQ ID NO 49
<211> LENGTH: 640
<212> TYPE: DNA
<213> ORGANISM: Homo sapiens

<400> SEQUENCE: 49

```
ctctgtttcc caggtgccag atgtgacatc cagatgaccc agtctccatc ctcactgtct    60
gcatctgtgg gagacagagt caccatcact tgtcgggcga gtcaggtcat ttacaattat   120
ttagcctggt ttcagcagaa accagggaaa gcccctaagt ccctgatcta tggtgcatcc   180
agtttgcaca gtgggtccc atcaaagttc agcggcagtg gatctgggac agaattcact   240
ctcaccatca gcagcctgca gcctgaagat tttgcaactt attactgcca acaatatact   300
atttacccct tctctttcgg ccctgggacc aaagtggata tcaaacgaac tgtggctgca   360
ccatctgtct tcatcttccc gccatctgat gagcagttga aatctggaac tgcctctgtt   420
gtgtgcctgc tgaataactt ctatcccaga gaggccaaag tacagtggaa ggtggataac   480
gccctccaat cgggtaactc ccaggagagt gtcacagagc aggacagcaa ggacagcacc   540
tacagcctca gcagcaccct gacgctgagc aaagcagact acgagaaaca caaagtctac   600
gcctgcgaag tcacccatca gggcctgagc tcgcccgtca                         640
```

<210> SEQ ID NO 50
<211> LENGTH: 213
<212> TYPE: PRT
<213> ORGANISM: Homo sapiens

<400> SEQUENCE: 50

Leu Cys Phe Pro Gly Ala Arg Cys Asp Ile Gln Met Thr Gln Ser Pro
1               5                   10                  15

Ser Ser Leu Ser Ala Ser Val Gly Asp Arg Val Thr Ile Thr Cys Arg
            20                  25                  30

Ala Ser Gln Val Ile Tyr Asn Tyr Leu Ala Trp Phe Gln Gln Lys Pro
        35                  40                  45

Gly Lys Ala Pro Lys Ser Leu Ile Tyr Gly Ala Ser Ser Leu His Ser
    50                  55                  60

Gly Val Pro Ser Lys Phe Ser Gly Ser Gly Ser Gly Thr Glu Phe Thr
65                  70                  75                  80

Leu Thr Ile Ser Ser Leu Gln Pro Glu Asp Phe Ala Thr Tyr Tyr Cys
                85                  90                  95

Gln Gln Tyr Thr Ile Tyr Pro Phe Ser Phe Gly Pro Gly Thr Lys Val
            100                 105                 110

Asp Ile Lys Arg Thr Val Ala Ala Pro Ser Val Phe Ile Phe Pro Pro
        115                 120                 125

Ser Asp Glu Gln Leu Lys Ser Gly Thr Ala Ser Val Val Cys Leu Leu
    130                 135                 140

Asn Asn Phe Tyr Pro Arg Glu Ala Lys Val Gln Trp Lys Val Asp Asn
145                 150                 155                 160

Ala Leu Gln Ser Gly Asn Ser Gln Glu Ser Val Thr Glu Gln Asp Ser
                165                 170                 175

```
Lys Asp Ser Thr Tyr Ser Leu Ser Ser Thr Leu Thr Leu Ser Lys Ala
            180                 185                 190

Asp Tyr Glu Lys His Lys Val Tyr Ala Cys Glu Val Thr His Gln Gly
        195                 200                 205

Leu Ser Ser Pro Val
    210

<210> SEQ ID NO 51
<211> LENGTH: 410
<212> TYPE: DNA
<213> ORGANISM: Homo sapiens

<400> SEQUENCE: 51
caggtgcagc tggtggagtc tgggggaggc gtggtccagc ctgggaggtc cctgagactc    60
tcctgtgcag cgtctggatt caccttcagc agctatggca tgcactgggt ccgccaggct   120
ccaggcaagg ggctggagtg ggtggcagtt atatggtatg atggaagaaa taaatattat   180
gtagactccg tgaagggccg attcaccatc tccagagaca attccaagaa tacgctgtat   240
ctgcaaatga acagcctgag agccgaggac acggctgtgt attactgtgc gagagatcgg   300
tatagtggct ccgattacta ctactactac ggtatggacg tctggggcca agggaccacg   360
gtcaccgtct cctcagcctc caccaagggc ccatcggtct tccccctggc               410

<210> SEQ ID NO 52
<211> LENGTH: 136
<212> TYPE: PRT
<213> ORGANISM: Homo sapiens

<400> SEQUENCE: 52

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Arg Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asp Arg Tyr Ser Gly Ser Asp Tyr Tyr Tyr Tyr Gly Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu
    130                 135

<210> SEQ ID NO 53
<211> LENGTH: 659
<212> TYPE: DNA
<213> ORGANISM: Homo sapiens

<400> SEQUENCE: 53
tgctctgttt cccaggtgcc agatgtgaca ttcagatgac ccagtctcca tcctcactgt    60
ctgcatctgt aggagacaga gtcaccatca cttgtcgggc gagtcagggc atttacaatt   120
atttagcctg gtttcagcag aaaccaggga agcccctaa gtccctgatc tatgctgcat    180
```

```
ccagtttgca aagtggggtc ccatcaaagt tcagcggcag tggatctggg acagttttca      240
ctctcaccat cagcagcctg cagcctgaag atttttgcaac ttattactgc caacagtata     300
```
(Note: line 300 as printed: ctctcaccat cagcagcctg cagcctgaag attttgcaac ttattactgc caacagtata)

```
ctctcaccat cagcagcctg cagcctgaag attttgcaac ttattactgc caacagtata      300
ctgtttaccc attcactttc ggccctggga ccaaagtgga tttcaaacga actgtggctg      360
caccatctgt cttcatcttc ccgccatctg atgagcagtt gaaatctgga actgcctctg      420
ttgtgtgcct gctgaataac ttctatccca gagaggccaa agtacagtgg aaggtggata      480
acgccctcca atcgggtaac tcccaggaga gtgtcacaga gcaggacagc aaggacagca      540
cctacagcct cagcagcacc ctgacgctga gcaaagcaga ctacgagaaa cacaaagtct      600
acgcctgcga agtcacccat cagggcctga gctcgcccgt cacaaagagc ttcaacagg       659
```

<210> SEQ ID NO 54
<211> LENGTH: 219
<212> TYPE: PRT
<213> ORGANISM: Homo sapiens

<400> SEQUENCE: 54

```
Leu Cys Phe Pro Gly Ala Arg Cys Asp Ile Gln Met Thr Gln Ser Pro
  1               5                  10                  15

Ser Ser Leu Ser Ala Ser Val Gly Asp Arg Val Thr Ile Thr Cys Arg
             20                  25                  30

Ala Ser Gln Gly Ile Tyr Asn Tyr Leu Ala Trp Phe Gln Gln Lys Pro
         35                  40                  45

Gly Lys Ala Pro Lys Ser Leu Ile Tyr Ala Ala Ser Ser Leu Gln Ser
     50                  55                  60

Gly Val Pro Ser Lys Phe Ser Gly Ser Gly Ser Gly Thr Val Phe Thr
 65                  70                  75                  80

Leu Thr Ile Ser Ser Leu Gln Pro Glu Asp Phe Ala Thr Tyr Tyr Cys
                 85                  90                  95

Gln Gln Tyr Thr Val Tyr Pro Phe Thr Phe Gly Pro Gly Thr Lys Val
            100                 105                 110

Asp Phe Lys Arg Thr Val Ala Ala Pro Ser Val Phe Ile Phe Pro Pro
        115                 120                 125

Ser Asp Glu Gln Leu Lys Ser Gly Thr Ala Ser Val Val Cys Leu Leu
    130                 135                 140

Asn Asn Phe Tyr Pro Arg Glu Ala Lys Val Gln Trp Lys Val Asp Asn
145                 150                 155                 160

Ala Leu Gln Ser Gly Asn Ser Gln Glu Ser Val Thr Glu Gln Asp Ser
                165                 170                 175

Lys Asp Ser Thr Tyr Ser Leu Ser Ser Thr Leu Thr Leu Ser Lys Ala
            180                 185                 190

Asp Tyr Glu Lys His Lys Val Tyr Ala Cys Glu Val Thr His Gln Gly
        195                 200                 205

Leu Ser Ser Pro Val Thr Lys Ser Phe Asn Arg
    210                 215
```

<210> SEQ ID NO 55
<211> LENGTH: 402
<212> TYPE: DNA
<213> ORGANISM: Homo sapiens

<400> SEQUENCE: 55

```
caggtgcagc tgcaggagtc gggcccagga ctggtgaagc cttcggagac cctgtccctc       60
acctgcactg tctctggtgg ctccatcagt agttactact ggagctggat ccggcagccc      120
ccagggaagg gactggagtg gattgggtat atctattaca gtgggagcac caactacaac      180
```

```
cctcccctca agagtcgagt caccatatca gtagacacgt ccaagaacca gttctccctg    240
aagctgagct ctgtgaccgc tgcggacacg gccgtgtatt actgtgcgag aggctattac    300
tatggtgcgg ggagttacgg tatggacgtc tggggccaag gaccacggt caccgtctcc     360 tcagcctcca ccaagggccc atcggtcttc cccctggcac cc                        402
```

<210> SEQ ID NO 56
<211> LENGTH: 134
<212> TYPE: PRT
<213> ORGANISM: Homo sapiens

<400> SEQUENCE: 56

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Tyr Tyr Tyr Gly Ala Gly Ser Tyr Gly Met Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro
    130
```

<210> SEQ ID NO 57
<211> LENGTH: 677
<212> TYPE: DNA
<213> ORGANISM: Homo sapiens

<400> SEQUENCE: 57

```
ttctctgggt ctctggatcc agtggggata ttgtgatgac tcagtctcca ctctccctgc    60
ccgtcacccc tggagagccg gcctccatct cctgcaggtc tagtcagagc ctcctgcata   120
gtactggatt caactatttg gattggtacc tgcagaagcc agggcagtct ccacagctcc   180
tgatctattt gggttctatt cgggcctccg gggtccctga caggttcagt ggcagtggtt   240
caggcacaga ttttacactg aaaatcagca gagtggagac tgaggatgtt ggggtttatt   300
actgcatgca aactctacaa actcccatca ccttcggcca aggacacga ctggagatta    360 aacgaactgt ggctgcacca tctgtcttca tcttcccgcc atctgatgag cagttgaaat   420
ctggaactgc ctctgttgtg tgcctgctga ataacttcta tcccagagag gccaaagtac   480
agtggaaggt ggataacgcc ctccaatcgg gtaactccca ggagagtgtc acagagcagg   540
acagcaagga cagcacctac agcctcagca gcaccctgac gctgagcaaa gcagactacg   600
agaaacacaa agtctacgcc tgcgaagtca cccatcaggg cctgagctcg cccgtcacaa   660
agagcttcaa caggggga                                                  677
```

<210> SEQ ID NO 58
<211> LENGTH: 226
<212> TYPE: PRT
<213> ORGANISM: Homo sapiens

<400> SEQUENCE: 58

```
Leu Trp Val Ser Gly Ser Ser Gly Asp Ile Val Met Thr Gln Ser Pro
1               5                   10                  15
Leu Ser Leu Pro Val Thr Pro Gly Glu Pro Ala Ser Ile Ser Cys Arg
            20                  25                  30
Ser Ser Gln Ser Leu Leu His Ser Thr Gly Phe Asn Tyr Leu Asp Trp
        35                  40                  45
Tyr Leu Gln Lys Pro Gly Gln Ser Pro Gln Leu Leu Ile Tyr Leu Gly
    50                  55                  60
Ser Ile Arg Ala Ser Gly Val Pro Asp Arg Phe Ser Gly Ser Gly Ser
65                  70                  75                  80
Gly Thr Asp Phe Thr Leu Lys Ile Ser Arg Val Glu Thr Glu Asp Val
                85                  90                  95
Gly Val Tyr Tyr Cys Met Gln Thr Leu Gln Thr Pro Ile Thr Phe Gly
            100                 105                 110
Gln Gly Thr Arg Leu Glu Ile Lys Arg Thr Val Ala Ala Pro Ser Val
        115                 120                 125
Phe Ile Phe Pro Pro Ser Asp Glu Gln Leu Lys Ser Gly Thr Ala Ser
130                 135                 140
Val Val Cys Leu Leu Asn Asn Phe Tyr Pro Arg Glu Ala Lys Val Gln
145                 150                 155                 160
Trp Lys Val Asp Asn Ala Leu Gln Ser Gly Asn Ser Gln Glu Ser Val
                165                 170                 175
Thr Glu Gln Asp Ser Lys Asp Ser Thr Tyr Ser Leu Ser Ser Thr Leu
            180                 185                 190
Thr Leu Ser Lys Ala Asp Tyr Glu Lys His Lys Val Tyr Ala Cys Glu
        195                 200                 205
Val Thr His Gln Gly Leu Ser Ser Pro Val Thr Lys Ser Phe Asn Arg
    210                 215                 220
Gly Gly
225
```

<210> SEQ ID NO 59
<211> LENGTH: 420
<212> TYPE: DNA
<213> ORGANISM: Homo sapiens

<400> SEQUENCE: 59

```
caggtgcagc tggtggagtc tgggggaggc gtggtccagc ctggggaggtc cctgagactc      60
tcctgtgcag cgtctggatt caccttcagt agctatggca tgcactgggt ccgccaggct     120
ccaggcaagg ggctggagtg gtggcagtt atatggtatg atggaagtaa taaatactat     180
gcagactccg tgaagggccg attcaccatc tccagagaca attccaagaa cacgctgtat     240
ctgcaaatga acagcctgag agccgaggac acggctgtgt attactgtgc gagagatcgg     300
tatagtggct acgattacta ctactactac ggtatggacg tctggggcca agggaccacg     360
gtcaccgtct cctcagcctc caccaagggc ccatcggtct tccccctggc accctcctcc     420
```

<210> SEQ ID NO 60
<211> LENGTH: 140
<212> TYPE: PRT
<213> ORGANISM: Homo sapiens

<400> SEQUENCE: 60

```
Gln Val Gln Leu Val Glu Ser Gly Gly Gly Val Val Gln Pro Gly Arg
1               5                   10                  15
```

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Tyr Ser Gly Tyr Tyr Tyr Tyr Tyr Gly Met
            100                 105                 110

Asp Val Trp Gly Gln Gly Thr Thr Val Thr Val Ser Ser Ala Ser Thr
            115                 120                 125

Lys Gly Pro Ser Val Phe Pro Leu Ala Pro Ser Ser
        130                 135                 140

<210> SEQ ID NO 61
<211> LENGTH: 660
<212> TYPE: DNA
<213> ORGANISM: Homo sapiens

<400> SEQUENCE: 61
tgctctgttt cccaggtgcc agatgtgaca tccagatgac ccagtctcca tcctcactgt     60
ctgcatctgt cggagacaga gtcaccatca cttgtcgggc gagtcagggc atttataatt    120
atttggcctg gtttcagcag aaaccaggga agcccctaa gtccctgatc tatgctgcat    180
ccagtttgca cagtggggtc ccatcaaagt tcagcggcgg tggttctggg acagatttca    240
ctctcaccat cagcagcctg cagcctgaag attttgcaac ttattactgc caacagtata    300
ctatttaccc attcactttc ggccctggga ccaaagtgga tatcaaacga actgtggctg    360
caccatctgt cttcatcttc ccgccatctg atgagcagtt gaaatctgga actgcctctg    420
ttgtgtgcct gctgaataac ttctatccca gagaggccaa agtacagtgg aaggtggata    480
acgccctcca atcgggtaac tcccaggaga gtgtcacaga gcaggacagc aaggacagca    540
cctacagcct cagcagcacc ctgacgctga gcaaagcaga ctacgagaaa cacaaagtct    600
acgcctgcga agtcacccat cagggcctga gctcgcccgt cacaaagagc ttcaacaggg    660

<210> SEQ ID NO 62
<211> LENGTH: 219
<212> TYPE: PRT
<213> ORGANISM: Homo sapiens

<400> SEQUENCE: 62

Leu Cys Phe Pro Gly Ala Arg Cys Asp Ile Gln Met Thr Gln Ser Pro
1               5                   10                  15

Ser Ser Leu Ser Ala Ser Val Gly Asp Arg Val Thr Ile Thr Cys Arg
            20                  25                  30

Ala Ser Gln Gly Ile Tyr Asn Tyr Leu Ala Trp Phe Gln Gln Lys Pro
        35                  40                  45

Gly Lys Ala Pro Lys Ser Leu Ile Tyr Ala Ala Ser Ser Leu His Ser
50                  55                  60

Gly Val Pro Ser Lys Phe Ser Gly Gly Gly Ser Gly Thr Asp Phe Thr
65                  70                  75                  80

Leu Thr Ile Ser Ser Leu Gln Pro Glu Asp Phe Ala Thr Tyr Tyr Cys
                85                  90                  95

Gln Gln Tyr Thr Ile Tyr Pro Phe Thr Phe Gly Pro Gly Thr Lys Val
            100                 105                 110

Asp Ile Lys Arg Thr Val Ala Ala Pro Ser Val Phe Ile Phe Pro Pro
        115                 120                 125

Ser Asp Glu Gln Leu Lys Ser Gly Thr Ala Ser Val Val Cys Leu Leu
    130                 135                 140

Asn Asn Phe Tyr Pro Arg Glu Ala Lys Val Gln Trp Lys Val Asp Asn
145                 150                 155                 160

Ala Leu Gln Ser Gly Asn Ser Gln Glu Ser Val Thr Glu Gln Asp Ser
                165                 170                 175

Lys Asp Ser Thr Tyr Ser Leu Ser Ser Thr Leu Thr Leu Ser Lys Ala
            180                 185                 190

Asp Tyr Glu Lys His Lys Val Tyr Ala Cys Glu Val Thr His Gln Gly
        195                 200                 205

Leu Ser Ser Pro Val Thr Lys Ser Phe Asn Arg
    210                 215

<210> SEQ ID NO 63
<211> LENGTH: 400
<212> TYPE: DNA
<213> ORGANISM: Homo sapiens

<400> SEQUENCE: 63
caggtgcagc tgcaggagtc tggcccagga ctggtgaagc cttcggagac cctgtccctc      60
acctgcactg tctctggtgg ctccatcagt agttactact ggagctggat ccggcagccc     120
ccagggaagg gactggagtg gattgggtat atctattaca gtgggagcac caactacaac     180
ccctccctca gagtcgagt caccatatca gtagacacgt ccaagaacca gttctccctg     240
aagctgagct ctgtgaccgc tgcggacacg gccgtgtatt actgtgcgaa cacgtattac     300
tatggttcgg ggtacggtat ggacgtctgg ggccaaggga ccacggtcac cgtctcctca     360
gcctccacca agggcccatc ggtcttcccc ctggcaccct                           400

<210> SEQ ID NO 64
<211> LENGTH: 133
<212> TYPE: PRT
<213> ORGANISM: Homo sapiens

<400> SEQUENCE: 64

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Asn Thr Tyr Tyr Tyr Gly Ser Gly Tyr Gly Met Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro

-continued

130

<210> SEQ ID NO 65
<211> LENGTH: 658
<212> TYPE: DNA
<213> ORGANISM: Homo sapiens

<400> SEQUENCE: 65

```
tgctctgggt ctctggatcc agtggggata ttgtgatgac tcagtctcca ctctccctgc      60
ccgtcacccc tggagagccg gcctccatct cctgcaggtc tagtcagagc ctcctgcata     120
gtactggaca caactatttg gattggtacc tgcagaagcc agggcagtct ccacagctcc     180
tgatctattt gggttctatt cgggcctccg ggtccctga caggttcagt ggcagtggat     240
caggcacaga ttttcactg aaaatcagca gagtggaggc tgaggatgtt ggggtttatt     300
actgcatgca agctctacaa actatcacct tcggccaagg gacacgactg gagattaaac     360
gaactgtggc tgcaccatct gtcttcatct tcccgccatc tgatgagcag ttgaaatctg     420
gaactgcctc tgttgtgtgc ctgctgaata acttctatcc cagagaggcc aaagtacagt     480
ggaaggtgga taacgccctc caatcgggta actcccagga gagtgtcaca gagcaggaca     540
gcaaggacag cacctacagc ctcagcagca ccctgacgct gagcaaagca gactacgaga     600
aacacaaagt ctacgcctgc gaagtcaccc atcagggcct gagctcgccc gtcacaaa      658
```

<210> SEQ ID NO 66
<211> LENGTH: 218
<212> TYPE: PRT
<213> ORGANISM: Homo sapiens

<400> SEQUENCE: 66

Leu Trp Val Ser Gly Ser Ser Gly Asp Ile Val Met Thr Gln Ser Pro
1               5                   10                  15

Leu Ser Leu Pro Val Thr Pro Gly Glu Pro Ala Ser Ile Ser Cys Arg
            20                  25                  30

Ser Ser Gln Ser Leu Leu His Ser Thr Gly His Asn Tyr Leu Asp Trp
        35                  40                  45

Tyr Leu Gln Lys Pro Gly Gln Ser Pro Gln Leu Leu Ile Tyr Leu Gly
    50                  55                  60

Ser Ile Arg Ala Ser Gly Val Pro Asp Arg Phe Ser Gly Ser Gly Ser
65                  70                  75                  80

Gly Thr Asp Phe Thr Leu Lys Ile Ser Arg Val Glu Ala Glu Asp Val
                85                  90                  95

Gly Val Tyr Tyr Cys Met Gln Ala Leu Gln Thr Ile Thr Phe Gly Gln
            100                 105                 110

Gly Thr Arg Leu Glu Ile Lys Arg Thr Val Ala Ala Pro Ser Val Phe
        115                 120                 125

Ile Phe Pro Pro Ser Asp Glu Gln Leu Lys Ser Gly Thr Ala Ser Val
    130                 135                 140

Val Cys Leu Leu Asn Asn Phe Tyr Pro Arg Glu Ala Lys Val Gln Trp
145                 150                 155                 160

Lys Val Asp Asn Ala Leu Gln Ser Gly Asn Ser Gln Glu Ser Val Thr
                165                 170                 175

Glu Gln Asp Ser Lys Asp Ser Thr Tyr Ser Leu Ser Ser Thr Leu Thr
            180                 185                 190

Leu Ser Lys Ala Asp Tyr Glu Lys His Lys Val Tyr Ala Cys Glu Val
        195                 200                 205

Thr His Gln Gly Leu Ser Ser Pro Val Thr

<210> SEQ ID NO 67
<211> LENGTH: 407
<212> TYPE: DNA
<213> ORGANISM: Homo sapiens

<400> SEQUENCE: 67

```
caggtgcagc tgcaggagtc tggccccgga ctggtgaagc cttcggagac cctgtccctc      60
acctgcactg tctctggtgg ctccatcagt agttactact ggagctggat ccggcagccc     120
ccagggaagg gactggagtg gattggattt atctattaca ctgggagcac caactacaac     180
ccctccctca agagtcgagt caccatatca gtagacacgt ccaagaacca gttctccctg     240
aagctgagct ctgtgaccgc tgcggacacg gccgtgtatt actgtgcgaa cacgtattac     300
tatggttcgg ggtacggtat ggacgtctgg ggccaaggga ccacggtcac cgtctcctca     360
gcctccacca agggcccatc ggtcttcccc ctggcaccct cctccaa                   407
```

<210> SEQ ID NO 68
<211> LENGTH: 135
<212> TYPE: PRT
<213> ORGANISM: Homo sapiens

<400> SEQUENCE: 68

```
Gln Val Gln Leu Gln Glu Ser Gly Pro Gly Leu Val Lys Pro Ser Glu
  1               5                  10                  15
Thr Leu Ser Leu Thr Cys Thr Val Ser Gly Gly Ser Ile Ser Ser Tyr
             20                  25                  30
Tyr Trp Ser Trp Ile Arg Gln Pro Pro Gly Lys Gly Leu Glu Trp Ile
         35                  40                  45
Gly Phe Ile Tyr Tyr Thr Gly Ser Thr Asn Tyr Asn Pro Ser Leu Lys
     50                  55                  60
Ser Arg Val Thr Ile Ser Val Asp Thr Ser Lys Asn Gln Phe Ser Leu
 65                  70                  75                  80
Lys Leu Ser Ser Val Thr Ala Ala Asp Thr Ala Val Tyr Tyr Cys Ala
                 85                  90                  95
Asn Thr Tyr Tyr Tyr Gly Ser Gly Tyr Gly Met Asp Val Trp Gly Gln
                100                 105                 110
Gly Thr Thr Val Thr Val Ser Ser Ala Ser Thr Lys Gly Pro Ser Val
            115                 120                 125
Phe Pro Leu Ala Pro Ser Ser
        130                 135
```

<210> SEQ ID NO 69
<211> LENGTH: 690
<212> TYPE: DNA
<213> ORGANISM: Homo sapiens

<400> SEQUENCE: 69

```
agctcctggg gctgctaatg ctctgggtct ctggatccag cggggatatt gtgatgactc      60
agtctccact ctccctgccc gtcacccctg gagagccggc ctccatctcc tgcaggtcta     120
gtcagagcct cctgcatagt aatggattca actatttgga ttggtacctg cagaagccag     180
ggcagtctcc acagctcctg atctatttgg gttctagacg gcctccgggg tccctgaca      240
ggttcagtgg cagtggatca ggcacagatt ttacactgaa aatcagcaga gtggaggctg     300
aggatgttgg ggtttattac tgcatgcaag ctctagaaac tatcaccttc ggccaaggga     360
cacgactgga gattaaacga actgtggctg caccatctgt cttcatcttc ccgccatctg     420
```

```
atgagcagtt gaaatctgga actgcctctg ttgtgtgcct gctgaataac ttctatccca    480
gagaggccaa agtacagtgg aaggtggata acgccctcca atcgggtaac tcccaggaga    540
gtgtcacaga gcaggacagc aaggacagca cctacagcct cagcagcacc ctgacgctga    600
gcaaagcaga ctacgagaaa cacaaagtct acgcctgcga agtcacccat cagggcctga    660
gctcgcccgt cacaaagagc ttcaacaggg                                     690
```

<210> SEQ ID NO 70
<211> LENGTH: 229
<212> TYPE: PRT
<213> ORGANISM: Homo sapiens

<400> SEQUENCE: 70

```
Leu Leu Gly Leu Leu Met Leu Trp Val Ser Gly Ser Ser Gly Asp Ile
1               5                   10                  15

Val Met Thr Gln Ser Pro Leu Ser Leu Pro Val Thr Pro Gly Glu Pro
            20                  25                  30

Ala Ser Ile Ser Cys Arg Ser Ser Gln Ser Leu Leu His Ser Asn Gly
        35                  40                  45

Phe Asn Tyr Leu Asp Trp Tyr Leu Gln Lys Pro Gly Gln Ser Pro Gln
    50                  55                  60

Leu Leu Ile Tyr Leu Gly Ser Arg Arg Ala Ser Gly Val Pro Asp Arg
65                  70                  75                  80

Phe Ser Gly Ser Gly Ser Gly Thr Asp Phe Thr Leu Lys Ile Ser Arg
                85                  90                  95

Val Glu Ala Glu Asp Val Gly Val Tyr Tyr Cys Met Gln Ala Leu Glu
            100                 105                 110

Thr Ile Thr Phe Gly Gln Gly Thr Arg Leu Glu Ile Lys Arg Thr Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg
225
```

<210> SEQ ID NO 71
<211> LENGTH: 410
<212> TYPE: DNA
<213> ORGANISM: Homo sapiens

<400> SEQUENCE: 71

```
caggtgcagc tgcaggagtc tgggcccagga ctggtgaagc cttcggagac cctgtccctc     60
acctgcactg tctctggtgg ctccatcagt agttactact ggagctggat ccggcagccc    120
ccagggaagg gactggagtg gattgggtat atctattaca gtgggagcac caactacaac    180
ccctccctca agagtcgagt caccatatca gtagacacgt ccaagaacca gttctccctg    240
```

```
aagctgagct ctgtgaccgc tgcggacacg gccgtgtatt actgtgcgag aggctattac      300
tatggttcgg ggagttacgg tatggacgtc tggggccaag ggaccacggt caccgtctcc      360
tcagcctcca ccaagggccc atcggtcttc cccctggcac cctcctccaa                 410
```

<210> SEQ ID NO 72
<211> LENGTH: 136
<212> TYPE: PRT
<213> ORGANISM: Homo sapiens

<400> SEQUENCE: 72

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Tyr Tyr Tyr Gly Ser Gly Ser Tyr Gly Met Asp Val Trp Gly
           100                 105                 110

Gln Gly Thr Thr Val Thr Val Ser Ser Ala Ser Thr Lys Gly Pro Ser
       115                 120                 125

Val Phe Pro Leu Ala Pro Ser Ser
   130                 135
```

<210> SEQ ID NO 73
<211> LENGTH: 647
<212> TYPE: DNA
<213> ORGANISM: Homo sapiens

<400> SEQUENCE: 73

```
ggatccagtg gggatattgt gatgactcag tctccactct ccctgcccgt caccoctgga      60 gagccggcct ccatctcctg caggtctagt cagagcctcc tgcatagtac tggatacaac     120
tatttggatt ggtacctgca gaagccaggg cagtctccac agctcctgat ctatttgggt     180
tctaatcggg cctccggggt ccctgacagg ttcagtggca gtggatcagg cacagatttt     240
acactgaaga tcagcagagt ggaggctgag gatgttgggg tttgttactg catgcaagct     300
ctacaaactc ccatcacctt cggccaaggg acacgactgg agattaaacg aactgtggct     360
gcaccatctg tcttcatctt cccgccatct gatgagcagt tgaaatctgg aactgcctct     420
gttgtgtgcc tgctgaataa cttctatccc agagaggcca agtacagtg gaaggtggat      480 aacgccctcc aatcgggtaa ctcccaggag agtgtcacag agcaggacag caaggacagc     540
acctacagcc tcagcagcac cctgacgctg agcaaagcag actacgagaa acacaaagtc     600
tacgcctgcg aagtcaccca tcagggcctg agctcgcccg tcacaaa                   647
```

<210> SEQ ID NO 74
<211> LENGTH: 215
<212> TYPE: PRT
<213> ORGANISM: Homo sapiens

<400> SEQUENCE: 74

```
Gly Ser Ser Gly Asp Ile Val Met Thr Gln Ser Pro Leu Ser Leu Pro
```

```
                1               5                   10                  15
Val Thr Pro Gly Glu Pro Ala Ser Ile Ser Cys Arg Ser Ser Gln Ser
                    20                  25                  30

Leu Leu His Ser Thr Gly Tyr Asn Tyr Leu Asp Trp Tyr Leu Gln Lys
                35                  40                  45

Pro Gly Gln Ser Pro Gln Leu Leu Ile Tyr Leu Gly Ser Asn Arg Ala
            50                  55                  60

Ser Gly Val Pro Asp Arg Phe Ser Gly Ser Gly Ser Gly Thr Asp Phe
65                  70                  75                  80

Thr Leu Lys Ile Ser Arg Val Glu Ala Glu Asp Val Gly Val Cys Tyr
                    85                  90                  95

Cys Met Gln Ala Leu Gln Thr Pro Ile Thr Phe Gly Gln Gly Thr Arg
                100                 105                 110

Leu Glu Ile Lys Arg Thr Val Ala Ala Pro Ser Val Phe Ile Phe Pro
            115                 120                 125

Pro Ser Asp Glu Gln Leu Lys Ser Gly Thr Ala Ser Val Val Cys Leu
        130                 135                 140

Leu Asn Asn Phe Tyr Pro Arg Glu Ala Lys Val Gln Trp Lys Val Asp
145                 150                 155                 160

Asn Ala Leu Gln Ser Gly Asn Ser Gln Glu Ser Val Thr Glu Gln Asp
                    165                 170                 175

Ser Lys Asp Ser Thr Tyr Ser Leu Ser Ser Thr Leu Thr Leu Ser Lys
                180                 185                 190

Ala Asp Tyr Glu Lys His Lys Val Tyr Ala Cys Glu Val Thr His Gln
            195                 200                 205

Gly Leu Ser Ser Pro Val Thr
        210                 215

<210> SEQ ID NO 75
<211> LENGTH: 410
<212> TYPE: DNA
<213> ORGANISM: Homo sapiens

<400> SEQUENCE: 75
caggtgcagc tggtggagtc tgggggaggc gtggtccagc ctggggaggtc cctgagactc      60 tcctgtgcag cgtctggatt caccttcagt agccatggca tgcactgggt ccgccaggct     120
ccaggcaagg ggctggagtg ggtggcagtt atatggtatg atggaagtaa taaatactat     180
gcagactccg tgaagggccg attcaccatc tccagagaca attccaagaa cacgctgtat     240
ctgcaaatga acagcctgag agccgaggac acggctgtgt attactgtgc gagagatgca     300
tatagtggct acgattacta ctactactac ggtatggacg tctggggcca agggaccacg     360
gtcaccgtct cctcagcctc caccaagggc ccatcggtct tccccctggc              410

<210> SEQ ID NO 76
<211> LENGTH: 136
<212> TYPE: PRT
<213> ORGANISM: Homo sapiens

<400> SEQUENCE: 76

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser His
                    20                  25                  30

Gly Met His Trp Val Arg Gln Ala Pro Gly Lys Gly Leu Glu Trp Val
                35                  40                  45
```

```
Ala Val Ile Trp Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Ala Tyr Ser Gly Tyr Asp Tyr Tyr Tyr Tyr Gly Met
                100                 105                 110

Asp Val Trp Gly Gln Gly Thr Thr Val Thr Val Ser Ser Ala Ser Thr
            115                 120                 125

Lys Gly Pro Ser Val Phe Pro Leu
    130                 135

<210> SEQ ID NO 77
<211> LENGTH: 671
<212> TYPE: DNA
<213> ORGANISM: Homo sapiens

<400> SEQUENCE: 77
ggggctcctg ctgctctgtt tcccaggtgc cagatgtgac atccagatga cccagtctcc     60
atcctcactg tctgcatctg taggagacag agtcaccatc acttgtcggg cgagtcaggg    120
catttacact tatttagcct ggtttcagca gaaaccaggg aaagcccta agtccctgat     180 ctatggtgca tccagtctgc aaagtggggt cccatcaaag ttcagcggca gtggatctgg    240
gacagatttc actctcacca tcaccagcct gcagcctgaa gattttgcaa cttattactg    300
ccaacagtat actatttacc cattcagttt cggccctggg accaaagtgg atatcaaacg    360
aactgtggct gcaccatctg tcttcatctt cccgccatct gatgagcagt tgaaatctgg    420
aactgcctct gttgtgtgcc tgctgaataa cttctatccc agagaggcca agtacagtg     480 gaaggtggat aacgcctcc aatcgggtaa ctcccaggag agtgtcacag agcaggacag    540
caaggacagc acctacagcc tcagcagcac cctgacgctg agcaaagcag actacgagaa    600
acacaaagtc tacgcctgcg aagtcaccca tcagggcctg agctcgcccg tcacaaagag    660
cttcaacagg g                                                        671

<210> SEQ ID NO 78
<211> LENGTH: 223
<212> TYPE: PRT
<213> ORGANISM: Homo sapiens

<400> SEQUENCE: 78

Gly Leu Leu Leu Leu Cys Phe Pro Gly Ala Arg Cys Asp Ile Gln Met
 1               5                  10                  15

Thr Gln Ser Pro Ser Ser Leu Ser Ala Ser Val Gly Asp Arg Val Thr
                 20                  25                  30

Ile Thr Cys Arg Ala Ser Gln Gly Ile Tyr Thr Tyr Leu Ala Trp Phe
             35                  40                  45

Gln Gln Lys Pro Gly Lys Ala Pro Lys Ser Leu Ile Tyr Gly Ala Ser
         50                  55                  60

Ser Leu Gln Ser Gly Val Pro Ser Lys Phe Ser Gly Ser Gly Ser Gly
 65                  70                  75                  80

Thr Asp Phe Thr Leu Thr Ile Ser Leu Gln Pro Glu Asp Phe Ala
                 85                  90                  95

Thr Tyr Tyr Cys Gln Gln Tyr Thr Ile Tyr Pro Phe Ser Phe Gly Pro
            100                 105                 110

Gly Thr Lys Val Asp Ile Lys Arg Thr Val Ala Ala Pro Ser Val Phe
```

```
              115                 120                 125
Ile Phe Pro Pro Ser Asp Glu Gln Leu Lys Ser Gly Thr Ala Ser Val
130                 135                 140

Val Cys Leu Leu Asn Asn Phe Tyr Pro Arg Glu Ala Lys Val Gln Trp
145                 150                 155                 160

Lys Val Asp Asn Ala Leu Gln Ser Gly Asn Ser Gln Glu Ser Val Thr
                165                 170                 175

Glu Gln Asp Ser Lys Asp Ser Thr Tyr Ser Leu Ser Ser Thr Leu Thr
            180                 185                 190

Leu Ser Lys Ala Asp Tyr Glu Lys His Lys Val Tyr Ala Cys Glu Val
        195                 200                 205

Thr His Gln Gly Leu Ser Ser Pro Val Thr Lys Ser Phe Asn Arg
    210                 215                 220
```

<210> SEQ ID NO 79
<211> LENGTH: 424
<212> TYPE: DNA
<213> ORGANISM: Homo sapiens

<400> SEQUENCE: 79

```
caggtgcagc tgcaggagtc tgggcccagga ctggtgaagc cttcggagac cctgtccctc    60
acctgcactg tctctggtgg ctccgtcagc agtggtggtt actactggag ctggatccgg   120
cagcccccag ggaagggact ggagtggatt gggtatatct attacagtgg gggcaccaac   180
tacaacccct ccctcaagag tcgagtcacc atatcagtag acacgtccaa gaaccagttc   240
tccctgaagc tgacctctgt gaccgctgcg gacacggccg tgtattactg tgcgagagag   300
tcgggatatt gtactaatgt tgcatgcttc cctgatgctt ttgatatctg gggccaaggg   360
acaatggtca ccgtgtcttc agcctccacc aagggcccat cggtcttccc cctggcaccc   420
tcct                                                                 424
```

<210> SEQ ID NO 80
<211> LENGTH: 141
<212> TYPE: PRT
<213> ORGANISM: Homo sapiens

<400> SEQUENCE: 80

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Gly Tyr Tyr Trp Ser Trp Ile Arg Gln Pro Pro Gly Lys Gly Leu Glu
        35                  40                  45

Trp Ile Gly Tyr Ile Tyr Tyr Ser Gly Gly Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Thr Ser Val Thr Ala Ala Asp Thr Ala Val Tyr Tyr
                85                  90                  95

Cys Ala Arg Glu Ser Gly Tyr Cys Thr Asn Val Ala Cys Phe Pro Asp
            100                 105                 110

Ala Phe Asp Ile Trp Gly Gln Gly Thr Met Val Thr Val Ser Ser Ala
        115                 120                 125

Ser Thr Lys Gly Pro Ser Val Phe Pro Leu Ala Pro Ser
    130                 135                 140
```

-continued

```
<210> SEQ ID NO 81
<211> LENGTH: 677
<212> TYPE: DNA
<213> ORGANISM: Homo sapiens

<400> SEQUENCE: 81
ctcctggggc tgctaatgct ctgggtctct ggatccagtg gggatgttgt gatgactcag      60
tctccattct ccctgcccgt cacccctgga gagccggcct ccatctcctg caggtctagt     120
cagagcctcc tgcatagtaa tggattcaac tttttggatt ggtacctgca gaagccaggg     180
cagtctccac agctcctgat ctatttgggt tctattcggg cctccggggt ccctgacagg     240
ttcagtggca gtggatcagg cacagatttt acactgaaaa tcagcagagt ggaggctgag     300
gatgttggag tttattactg catgcaagct ctacaaactc cactcacttt cggcggcggg     360
accagggtgg agatcaaacg aactgtggct gcaccatctg tcttcatctt cccgccatct     420
gatgagcagt tgaaatctgg aactgcctct gttgtgtgcc tgctgaataa cttctatccc     480
agagaggcca aagtacagtg gaaggtggat aacgccctcc aatcgggtaa ctcccaggag     540
agtgtcacag agcaggacag caaggacagc acctacagcc tcagcagcac cctgacgctg     600
agcaaagcag actacgagaa acacaaagtc tacgcctgcg aagtcacccc tcagggcctg     660
agctcgcccg tcacaaa                                                    677

<210> SEQ ID NO 82
<211> LENGTH: 225
<212> TYPE: PRT
<213> ORGANISM: Homo sapiens

<400> SEQUENCE: 82
```

Leu Leu Gly Leu Leu Met Leu Trp Val Ser Gly Ser Ser Gly Asp Val
1               5                   10                  15

Val Met Thr Gln Ser Pro Phe Ser Leu Pro Val Thr Pro Gly Glu Pro
            20                  25                  30

Ala Ser Ile Ser Cys Arg Ser Ser Gln Ser Leu Leu His Ser Asn Gly
        35                  40                  45

Phe Asn Phe Leu Asp Trp Tyr Leu Gln Lys Pro Gly Gln Ser Pro Gln
    50                  55                  60

Leu Leu Ile Tyr Leu Gly Ser Ile Arg Ala Ser Gly Val Pro Asp Arg
65                  70                  75                  80

Phe Ser Gly Ser Gly Ser Gly Thr Asp Phe Thr Leu Lys Ile Ser Arg
                85                  90                  95

Val Glu Ala Glu Asp Val Gly Val Tyr Tyr Cys Met Gln Ala Leu Gln
            100                 105                 110

Thr Pro Leu Thr Phe Gly Gly Gly Thr Arg Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr
225

<210> SEQ ID NO 83
<211> LENGTH: 409
<212> TYPE: DNA
<213> ORGANISM: Homo sapiens

<400> SEQUENCE: 83

```
caggtgcagc tgcaggagtc tggcccagga ctggtgaagc cttcggagac cctgtccctc      60
acctgcactg tctctggtgg ctccatcagt agttactact ggagctggat ccggcagccc     120
ccagggaagg gactggagtg gattgggtat atctattaca gtgggagcac caactacaat     180
ccctccctca gagtcgagt caccatatca gtagacacgt ccaagaacca gttctccctg     240
aagctgagct ctgtgaccgc tgcggacacg gccgtgtatt attgtgcgag aggctattac     300
tatggttcgg ggagttacgg cttggacgtc tggggccaag ggaccacggt caccgtctcc     360
tcagcctcca ccaagggccc atcggtcttc cccctggcac cctcctcca                409
```

<210> SEQ ID NO 84
<211> LENGTH: 136
<212> TYPE: PRT
<213> ORGANISM: Homo sapiens

<400> SEQUENCE: 84

```
Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Ser Ser Tyr
            20                  25                  30
Tyr Trp Ser Trp Ile Arg Gln Pro Pro Gly Lys Gly Leu Glu Trp Ile
        35                  40                  45
Gly Tyr Ile Tyr Tyr Ser Gly Ser Thr Asn Tyr Asn Pro Ser Leu Lys
    50                  55                  60
Ser Arg Val Thr Ile Ser Val Asp Thr Ser Lys Asn Gln Phe Ser Leu
65                  70                  75                  80
Lys Leu Ser Ser Val Thr Ala Ala Asp Thr Ala Val Tyr Tyr Cys Ala
                85                  90                  95
Arg Gly Tyr Tyr Tyr Gly Ser Gly Ser Tyr Gly Leu Asp Val Trp Gly
            100                 105                 110
Gln Gly Thr Thr Val Thr Val Ser Ser Ala Ser Thr Lys Gly Pro Ser
        115                 120                 125
Val Phe Pro Leu Ala Pro Ser Ser
    130                 135
```

<210> SEQ ID NO 85
<211> LENGTH: 693
<212> TYPE: DNA
<213> ORGANISM: Homo sapiens

<400> SEQUENCE: 85

```
agctcctggg gctgctaatg ctctgggtct ctggatccag tggggatatt gtgatgactc      60
agtctccact ctccctgccc gtcaccctg gagagccggc ctccatctcc tgcaggtcta     120
gtcagagcct cctgcatagt actggataca actatttgga ttggtacctg cagaagccag     180
ggcagtctcc acaactcctg atctatttgg ttctattcg gcctccgggg tccctgaca     240
ggttcagtgg cagtggatca ggcacagatt ttacactgaa aatcagcaga gtggaggctg     300
aggatgttgg ggtttattac tgcatgcaag ctctacagac tcccatcacc ttcggccaag     360
```

```
ggacacgact ggagattaaa cgaactgtgg ctgcaccatc tgtcttcatc ttcccgccat    420
ctgatgagca gttgaaatct ggaactgcct ctgttgtgtg cctgctgaat aacttctatc    480
ccagagaggc caaagtacag tggaaggtgg ataacgccct ccaatcgggt aactcccagg    540
agagtgtcac agagcaggac agcaaggaca gcacctacag cctcagcagc accctgacgc    600
tgagcaaagc agactacgag aaacacaaag tctacgcctg cgaagtcacc catcagggcc    660
tgagctcgcc cgtcacaaag agcttcaaca ggg                                 693
```

<210> SEQ ID NO 86
<211> LENGTH: 230
<212> TYPE: PRT
<213> ORGANISM: Homo sapiens

<400> SEQUENCE: 86

```
Leu Leu Gly Leu Leu Met Leu Trp Val Ser Gly Ser Ser Gly Asp Ile
1               5                   10                  15

Val Met Thr Gln Ser Pro Leu Ser Leu Pro Val Thr Pro Gly Glu Pro
            20                  25                  30

Ala Ser Ile Ser Cys Arg Ser Ser Gln Ser Leu Leu His Ser Thr Gly
        35                  40                  45

Tyr Asn Tyr Leu Asp Trp Tyr Leu Gln Lys Pro Gly Gln Ser Pro Gln
    50                  55                  60

Leu Leu Ile Tyr Leu Gly Ser Ile Arg Ala Ser Gly Val Pro Asp Arg
65                  70                  75                  80

Phe Ser Gly Ser Gly Ser Gly Thr Asp Phe Thr Leu Lys Ile Ser Arg
                85                  90                  95

Val Glu Ala Glu Asp Val Gly Val Tyr Tyr Cys Met Gln Ala Leu Gln
            100                 105                 110

Thr Pro Ile Thr Phe Gly Gln Gly Thr Arg Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg
225                 230
```

<210> SEQ ID NO 87
<211> LENGTH: 366
<212> TYPE: DNA
<213> ORGANISM: Homo sapiens

<400> SEQUENCE: 87

```
caggtgcagc tgcaggagtc gggcccagga ctggtgaagc cttcggagac cctgtccctc     60
acctgcactg tctctggtgg ctccatcagt agttactact ggagctggat ccggcagccc    120
ccagggaagg gactggagtg gattgggtat atctattaca gtgggagcac caactacaac    180
```

```
cctcccctca agagtcgagt caccatatca gtagacacgt ccaagaacca gttctccctg    240
aagctgagct ctgtgaccgc tgcggacacg gccgtgtatt actgtgcgaa cacgtattac    300
tatggttcgg ggtacggtat ggacgtctgg ggccaaggga ccacggtcac cgtctcctca    360
gcctcc                                                               366
```

```
<210> SEQ ID NO 88
<211> LENGTH: 122
<212> TYPE: PRT
<213> ORGANISM: Homo sapiens

<400> SEQUENCE: 88
```

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Asn Thr Tyr Tyr Tyr Gly Ser Gly Tyr Gly Met Asp Val Trp Gly Gln
            100                 105                 110

Gly Thr Thr Val Thr Val Ser Ser Ala Ser
        115                 120

```
<210> SEQ ID NO 89
<211> LENGTH: 661
<212> TYPE: DNA
<213> ORGANISM: Homo sapiens
<400> SEQUENCE: 89
tctggatcca gtggggatat tgtgatgact cagtctccac tctccctgcc cgtcacccct     60
ggagagccgg cctccatctc ctgcaggtct agtcagagcc tcctgcatag tactggacac    120
aactatttgg attggtacct gcagaagcca gggcagtctc cacagctcct gatctatttg    180
ggttctattc gggcctccgg ggtccctgac aggttcagtg gcagtggatc aggcacagat    240
tttacactga aaatcagcag agtggaggct gaggatgttg gggtttatta ctgcatgcaa    300
gctctacaaa ctatcacctt cggccaaggg acacgactgg agattaaacg aactgtggct    360
gcaccatctg tcttcatctt cccgccatct gatgagcagt tgaaatctgg aactgcctct    420
gttgtgtgcc tgctgaataa cttctatccc agagaggcca agtacagtg gaaggtggat    480 aacgccctcc aatcgggtaa ctcccaggag agtgtcacag agcaggacag caaggacagc    540
acctacagcc tcagcagcac cctgacgctg agcaaagcag actacgagaa acacaaagtc    600
tacgcctgcg aagtcaccca tcagggcctg agctcgcccg tcacaaagag cttcaacagg    660
g                                                                    661
```

```
<210> SEQ ID NO 90
<211> LENGTH: 220
<212> TYPE: PRT
<213> ORGANISM: Homo sapiens

<400> SEQUENCE: 90
```

Ser Gly Ser Ser Gly Asp Ile Val Met Thr Gln Ser Pro Leu Ser Leu
1               5                   10                  15

Pro Val Thr Pro Gly Glu Pro Ala Ser Ile Ser Cys Arg Ser Ser Gln
            20                  25                  30

Ser Leu Leu His Ser Thr Gly His Asn Tyr Leu Asp Trp Tyr Leu Gln
        35                  40                  45

Lys Pro Gly Gln Ser Pro Gln Leu Leu Ile Tyr Leu Gly Ser Ile Arg
    50                  55                  60

Ala Ser Gly Val Pro Asp Arg Phe Ser Gly Ser Gly Ser Gly Thr Asp
65                  70                  75                  80

Phe Thr Leu Lys Ile Ser Arg Val Glu Ala Glu Asp Val Gly Val Tyr
                85                  90                  95

Tyr Cys Met Gln Ala Leu Gln Thr Ile Thr Phe Gly Gln Gly Thr Arg
            100                 105                 110

Leu Glu Ile Lys Arg Thr Val Ala Ala Pro Ser Val Phe Ile Phe Pro
        115                 120                 125

Pro Ser Asp Glu Gln Leu Lys Ser Gly Thr Ala Ser Val Val Cys Leu
    130                 135                 140

Leu Asn Asn Phe Tyr Pro Arg Glu Ala Lys Val Gln Trp Lys Val Asp
145                 150                 155                 160

Asn Ala Leu Gln Ser Gly Asn Ser Gln Glu Ser Val Thr Glu Gln Asp
                165                 170                 175

Ser Lys Asp Ser Thr Tyr Ser Leu Ser Ser Thr Leu Thr Leu Ser Lys
            180                 185                 190

Ala Asp Tyr Glu Lys His Lys Val Tyr Ala Cys Glu Val Thr His Gln
        195                 200                 205

Gly Leu Ser Ser Pro Val Thr Lys Ser Phe Asn Arg
210                 215                 220

<210> SEQ ID NO 91
<211> LENGTH: 409
<212> TYPE: DNA
<213> ORGANISM: Homo sapiens

<400> SEQUENCE: 91
caggtgcagc tgcaggagtc tggcccagga ctggtgaagc cttcggagac cctgtccctc        60
acctgcactg tctctggtgg ctccatcagt agttactact ggagctggat ccggcagccc       120
ccagggaagg gactggagtg gattgggtat atctattaca gtgggagcac caactacaaa       180
ccctccctca gagtcgagt caccatatca gtagacacgt ccaagaacca gttctccctg       240
aagctgagct ctgtgaccgc tgcggacacg gccgtgtatt actgtgcgag aggctattac       300
tatggttcgg ggagttacgg tatggacgtc tggggccaag gaccacggt caccgtctcc       360 tcagcctcca ccaagggccc atcggtcttc cccctggcac cctcctcca                   409

<210> SEQ ID NO 92
<211> LENGTH: 136
<212> TYPE: PRT
<213> ORGANISM: Homo sapiens

<400> SEQUENCE: 92

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Lys Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Tyr Tyr Tyr Gly Ser Gly Ser Tyr Gly Met Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser
    130                 135

<210> SEQ ID NO 93
<211> LENGTH: 694
<212> TYPE: DNA
<213> ORGANISM: Homo sapiens

<400> SEQUENCE: 93
gctcctgggg ctgctaatgc tctgggtctc tggatccagt ggggatattg tgatgactca      60
gtctccactc tccctgcccg tcacccctgg agagccggcc tccatctcct gcaggtctag     120
tcagagcctc ctgcatagta ctggatacaa ctatttggat tggtacctgc agaagccagg     180
gcagtctcca cagctcctca tctatttggg ttctattcgg gcctccgggg tccctgacag     240
gttcagtggc agtggatcag gcacagattt tacactgaaa atcagcagag tggaggctga     300
ggatgttgga atttattact gcatgcaagc tctacaaact cccatccct tcggccaagg      360 gacacgactg gagattaaac gaactgtggc tgcaccatct gtcttcatct tcccgccatc     420
tgatgagcag ttgaaatctg gaactgcctc tgttgtgtgc ctgctgaata acttctatcc     480
cagagaggcc aaagtacagt ggaaggtgga taacgccctc caatcgggta actcccagga     540
gagtgtcaca gagcaggaca gcaaggacag cacctacagc ctcagcagca ccctgacgct     600
gagcaaagca gactacgaga aacacaaagt ctacgcctgc gaagtcaccc atcagggcct     660
gagctcgccc gtcacaaaga gcttcaacag ggga                                 694

<210> SEQ ID NO 94
<211> LENGTH: 231
<212> TYPE: PRT
<213> ORGANISM: Homo sapiens

<400> SEQUENCE: 94

Leu Leu Gly Leu Leu Met Leu Trp Val Ser Gly Ser Ser Gly Asp Ile
1               5                   10                  15

Val Met Thr Gln Ser Pro Leu Ser Leu Pro Val Thr Pro Gly Glu Pro
            20                  25                  30

Ala Ser Ile Ser Cys Arg Ser Ser Gln Ser Leu Leu His Ser Thr Gly
        35                  40                  45

Tyr Asn Tyr Leu Asp Trp Tyr Leu Gln Lys Pro Gly Gln Ser Pro Gln
    50                  55                  60

Leu Leu Ile Tyr Leu Gly Ser Ile Arg Ala Ser Gly Val Pro Asp Arg
65                  70                  75                  80

Phe Ser Gly Ser Gly Ser Gly Thr Asp Phe Thr Leu Lys Ile Ser Arg
                85                  90                  95

Val Glu Ala Glu Asp Val Gly Ile Tyr Tyr Cys Met Gln Ala Leu Gln
            100                 105                 110

```
Thr Pro Ile Thr Phe Gly Gln Gly Thr Arg Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly
225                 230
```

<210> SEQ ID NO 95
<211> LENGTH: 415
<212> TYPE: DNA
<213> ORGANISM: Homo sapiens

<400> SEQUENCE: 95

```
caggtgcagc tggtggagtc tgggggaggc gtggtccagc ctggagggtc cctgagactc    60
tcctgtgcag cgtctggatt caccttcagt agctatggca tgcactgggt ccgccaggct   120
ccaggcaagg ggctggagtg ggtggcagtt atttggtatg atggaagtaa taaatactat   180
acagactccg tgaagggccg attcaccatc tccagagaca attccaagaa cacgctgtat   240
ctgcaaatga acagcctgag agccgaggac acggctgtgt attactgtgc gcgagatcgg   300
tatagtggct acgattactt ctactactac ggtatggacg tctggggcca agggaccacg   360
gtcaccgtct cctcagcctc caccaagggc ccatcggtct tccccctggc accct        415
```

<210> SEQ ID NO 96
<211> LENGTH: 138
<212> TYPE: PRT
<213> ORGANISM: Homo sapiens

<400> SEQUENCE: 96

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Tyr Ser Gly Tyr Asp Tyr Phe Tyr Tyr Tyr Gly Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro
    130                 135
```

<210> SEQ ID NO 97
<211> LENGTH: 636
<212> TYPE: DNA
<213> ORGANISM: Homo sapiens

<400> SEQUENCE: 97

```
tgtttcccag gtgccagatg tgacatccag atgacccagt ctccatcctc actgtctgca      60
tctgtaggag acagagtcac catcacttgt cgggcgagtc agggcattta caattattta     120
gcctggtttc agcagaaacc cgggaaagcc cctaggtccc tgatctatgc tgcatccagt     180
ttgcacagtg gggtcccatc taagttcagc ggcagtggat ctgggacaga tttcactctc     240
accatcagca gcctgcagcc tgaagatttt gcaacttatt actgccaaca atatactatt     300
tacccattca ctttcggccc tgggaccaaa gtggatatca aacgaactgt ggctgcacca     360
tctgtcttca tcttcccgcc atctgatgag cagttgaaat ctggaactgc ctctgttgtg     420
tgcctgctga ataacttcta tcccagagag gccaaagtac agtggaaggt ggataacgcc     480
ctccaatcgg gtaactccca ggagagtgtc acagagcagg acagcaagga cagcacctac     540
agcctcagca gcaccctgac gctgagcaaa gcagactacg agaaacacaa agtctacgcc     600
tgcgaagtca cccatcaggg cctgagctcg cccgtc                               636
```

<210> SEQ ID NO 98
<211> LENGTH: 212
<212> TYPE: PRT
<213> ORGANISM: Homo sapiens

<400> SEQUENCE: 98

```
Cys Phe Pro Gly Ala Arg Cys Asp Ile Gln Met Thr Gln Ser Pro Ser
1               5                   10                  15

Ser Leu Ser Ala Ser Val Gly Asp Arg Val Thr Ile Thr Cys Arg Ala
            20                  25                  30

Ser Gln Gly Ile Tyr Asn Tyr Leu Ala Trp Phe Gln Gln Lys Pro Gly
        35                  40                  45

Lys Ala Pro Arg Ser Leu Ile Tyr Ala Ala Ser Ser Leu His Ser Gly
    50                  55                  60

Val Pro Ser Lys Phe Ser Gly Ser Gly Ser Gly Thr Asp Phe Thr Leu
65                  70                  75                  80

Thr Ile Ser Ser Leu Gln Pro Glu Asp Phe Ala Thr Tyr Tyr Cys Gln
                85                  90                  95

Gln Tyr Thr Ile Tyr Pro Phe Thr Phe Gly Pro Gly Thr Lys Val Asp
            100                 105                 110

Ile Lys Arg Thr Val Ala Ala Pro Ser Val Phe Ile Phe Pro Pro Ser
        115                 120                 125

Asp Glu Gln Leu Lys Ser Gly Thr Ala Ser Val Val Cys Leu Leu Asn
    130                 135                 140

Asn Phe Tyr Pro Arg Glu Ala Lys Val Gln Trp Lys Val Asp Asn Ala
145                 150                 155                 160

Leu Gln Ser Gly Asn Ser Gln Glu Ser Val Thr Glu Gln Asp Ser Lys
                165                 170                 175

Asp Ser Thr Tyr Ser Leu Ser Ser Thr Leu Thr Leu Ser Lys Ala Asp
            180                 185                 190

Tyr Glu Lys His Lys Val Tyr Ala Cys Glu Val Thr His Gln Gly Leu
        195                 200                 205

Ser Ser Pro Val
    210
```

<210> SEQ ID NO 99
<211> LENGTH: 399
<212> TYPE: DNA
<213> ORGANISM: Homo sapiens

<400> SEQUENCE: 99

```
caggtgcagc tgcaggagtc tgggcccagga ctggtgaagc cttcggagac cctgtccctc    60
acctgcactg tctctggtgg ctccatcagt agttactact ggagctggat ccggcagccc   120
ccagggaagg gactggagtg gattgggtat atctattaca gtgggagcac caactacaac   180
ccctccctca gagtcgagt caccatatca gtagacacgt ccaagaacca gttctccctg   240
aagctgagct ctgtgaccgc tgcggacacg gccgtgtatt actgtgcgaa cacgtattac   300
tatggttcgg ggtacggtat ggacgtctgg ggccaaggga ccacggtcac cgtctcctca   360
gcctccacca agggcccatc ggtcttcccc ctggcaccc                          399
```

<210> SEQ ID NO 100
<211> LENGTH: 133
<212> TYPE: PRT
<213> ORGANISM: Homo sapiens

<400> SEQUENCE: 100

```
Gln Val Gln Leu Gln Glu Ser Gly Pro Gly Leu Val Lys Pro Ser Glu
  1               5                  10                  15
Thr Leu Ser Leu Thr Cys Thr Val Ser Gly Gly Ser Ile Ser Ser Tyr
             20                  25                  30
Tyr Trp Ser Trp Ile Arg Gln Pro Pro Gly Lys Gly Leu Glu Trp Ile
         35                  40                  45
Gly Tyr Ile Tyr Tyr Ser Gly Ser Thr Asn Tyr Asn Pro Ser Leu Lys
     50                  55                  60
Ser Arg Val Thr Ile Ser Val Asp Thr Ser Lys Asn Gln Phe Ser Leu
 65                  70                  75                  80
Lys Leu Ser Ser Val Thr Ala Ala Asp Thr Ala Val Tyr Tyr Cys Ala
                 85                  90                  95
Asn Thr Tyr Tyr Tyr Gly Ser Gly Tyr Gly Met Asp Val Trp Gly Gln
            100                 105                 110
Gly Thr Thr Val Thr Val Ser Ser Ala Ser Thr Lys Gly Pro Ser Val
        115                 120                 125
Phe Pro Leu Ala Pro
    130
```

<210> SEQ ID NO 101
<211> LENGTH: 672
<212> TYPE: DNA
<213> ORGANISM: Homo sapiens

<400> SEQUENCE: 101

```
ctctgggtct ctggatccag tggggatatt gtgatgactc agtctccact ctccctgccc    60
gtcacccctg gagagccggc ctccatctcc tgcaggtcta gtcagagcct cctgcatagt   120
actggacaca actatttgga ttggtacctg cagaagccag ggcagtctcc acagctcctg   180
atctatttgg gttctattcg ggcctccggg gtccctgaca ggttcagtgg cagtggatca   240
ggcacagatt ttacactgaa aatcagcaga gtggaggctg aggatgttgg ggtttattac   300
tgcatgcaag ctctacaaac tatcaccttc ggccaaggga cacgactgga gattaaacga   360
actgtggctg caccatctgt cttcatcttc ccgccatctg atgagcagtt gaaatctgga   420
```

```
actgcctctg ttgtgtgcct gctgaataac ttctatccca gagaggccaa agtacagtgg      480
aaggtggata acgccctcca atcgggtaac tcccaggaga gtgtcacaga gcaggacagc      540
aaggacagca cctacagcct cagcagcacc ctgacgctga gcaaagcaga ctacgagaaa      600
cacaaagtct acgcctgcga agtcacccat cagggcctga gctcgcccgt cacaaagagc      660
ttcaacaggg ga                                                          672
```

<210> SEQ ID NO 102
<211> LENGTH: 224
<212> TYPE: PRT
<213> ORGANISM: Homo sapiens

<400> SEQUENCE: 102

```
Leu Trp Val Ser Gly Ser Ser Gly Asp Ile Val Met Thr Gln Ser Pro
1               5                   10                  15

Leu Ser Leu Pro Val Thr Pro Gly Glu Pro Ala Ser Ile Ser Cys Arg
            20                  25                  30

Ser Ser Gln Ser Leu Leu His Ser Thr Gly His Asn Tyr Leu Asp Trp
        35                  40                  45

Tyr Leu Gln Lys Pro Gly Gln Ser Pro Gln Leu Leu Ile Tyr Leu Gly
    50                  55                  60

Ser Ile Arg Ala Ser Gly Val Pro Asp Arg Phe Ser Gly Ser Gly Ser
65                  70                  75                  80

Gly Thr Asp Phe Thr Leu Lys Ile Ser Arg Val Glu Ala Glu Asp Val
                85                  90                  95

Gly Val Tyr Tyr Cys Met Gln Ala Leu Gln Thr Ile Thr Phe Gly Gln
            100                 105                 110

Gly Thr Arg Leu Glu Ile Lys Arg Thr Val Ala Ala Pro Ser Val Phe
        115                 120                 125

Ile Phe Pro Pro Ser Asp Glu Gln Leu Lys Ser Gly Thr Ala Ser Val
    130                 135                 140

Val Cys Leu Leu Asn Asn Phe Tyr Pro Arg Glu Ala Lys Val Gln Trp
145                 150                 155                 160

Lys Val Asp Asn Ala Leu Gln Ser Gly Asn Ser Gln Glu Ser Val Thr
                165                 170                 175

Glu Gln Asp Ser Lys Asp Ser Thr Tyr Ser Leu Ser Ser Thr Leu Thr
            180                 185                 190

Leu Ser Lys Ala Asp Tyr Glu Lys His Lys Val Tyr Ala Cys Glu Val
        195                 200                 205

Thr His Gln Gly Leu Ser Ser Pro Val Thr Lys Ser Phe Asn Arg Gly
    210                 215                 220
```

<210> SEQ ID NO 103
<211> LENGTH: 398
<212> TYPE: DNA
<213> ORGANISM: Homo sapiens

<400> SEQUENCE: 103

```
caggtgcagc tgcaggagtc tgggcccagga ctggtgaagc cttcggagac cctgtccctc      60
acctgcactg tctctggtgg ctccatcagt cgttactact ggagctggat ccggcagccc     120
gccgggaagg gactggagag gattgggcgg atctatacca gtgggagcac cgactacaac     180
ccctctctca agagtcgagt caccatgtca gtagacacgt ccaagaacca gttctccctg     240
aagctgaggt ctgtgaccgc cgcggacacg gccgtgtatt actgtgcgag agatttgtat     300
agcaatggct actggtactt cgatctctgg ggccgtggca cctggtcac tgtctcctca     360
```
gcctccacca agggcccatc ggtcttcccc ctggcacc                                398

<210> SEQ ID NO 104
<211> LENGTH: 132
<212> TYPE: PRT
<213> ORGANISM: Homo sapiens

<400> SEQUENCE: 104

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Arg Tyr
            20                  25                  30

Tyr Trp Ser Trp Ile Arg Gln Pro Ala Gly Lys Gly Leu Glu Arg Ile
        35                  40                  45

Gly Arg Ile Tyr Thr Ser Gly Ser Thr Asp Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Arg Asp Leu Tyr Ser Asn Gly Tyr Trp Tyr Phe Asp Leu Trp Gly Arg
            100                 105                 110

Gly Thr Leu Val Thr Val Ser Ser Ala Ser Thr Lys Gly Pro Ser Val
        115                 120                 125

Phe Pro Leu Ala
    130

<210> SEQ ID NO 105
<211> LENGTH: 584
<212> TYPE: DNA
<213> ORGANISM: Homo sapiens

<400> SEQUENCE: 105
tgcccagtct gtgctgacgc agccgccctc agtgtctggg gccccagggc agagggtcac      60
catctcctgc actgggagca gctccaacat cggggcaggt tatgatgtac actggtacca     120
gcagcttcca ggaacagccc ccaaactcct catctatggt aacagcaatc ggccctcagg     180
ggtccctgac cgattctctg gctccaagtc tggcacctca gcctcctggg ccatcactgg     240
gctccaggct gaggatgagg ctgattatta ctgccagtcc tatgacagca gcctgagtgg     300
tgtggtattc ggcggaggga ccaagctgac cgtcctaggt cagcccaagg ctgcccctc      360 ggtcactctg ttcccgccct cctctgagga gcttcaagcc aacaaggcca cactggtgtg     420
tctcataagt gacttctacc cgggagccgt caacaagtac gcggccagca gctatctgag     480
cctgacgcct gagcagtgga agtcccacag aagctacagc tgccaggtca cgcatgaagg     540
gagcaccgtg gagaagacag tggccccctac agaatgttca taga                     584

<210> SEQ ID NO 106
<211> LENGTH: 217
<212> TYPE: PRT
<213> ORGANISM: Homo sapiens

<400> SEQUENCE: 106

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu

```
                35                  40                  45
Leu Ile Tyr Gly Asn Ser Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                 85                  90                  95

Leu Ser Gly Val Val Phe Gly Gly Gly Thr Lys Leu Thr Val Leu Gly
                100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 107
<211> LENGTH: 406
<212> TYPE: DNA
<213> ORGANISM: Homo sapiens

<400> SEQUENCE: 107
caggtgcagc tggtggagtc tgggggaggc gtggtccagc ctggggaggtc cctgagactc      60
tcctgtgcag cgtctggatt caccttcaga agctatggca tgcactgggt ccgccaggct     120
ccaggcaagg ggctggagtg ggtggcagtt atatggtatg atggaagtaa taaatactat     180
gcagactccg tgaagggccg atccaccatc tccagagaca actccaagaa cacgctgtat     240
ctgcaaatga acagcctgag agccgaggac acggctgtgt attactgtgc gagagatggg     300
gtagcagtgg ctggtacaga ctactttgac tactggggcc agggaaccct ggtcaccgtc     360
tcctcagcct ccaccaaggg cccatcggtc ttccccctgg caccct                    406

<210> SEQ ID NO 108
<211> LENGTH: 135
<212> TYPE: PRT
<213> ORGANISM: Homo sapiens

<400> SEQUENCE: 108

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Arg Ser Tyr
             20                  25                  30

Gly Met His Trp Val Arg Gln Ala Pro Gly Lys Gly Leu Glu Trp Val
         35                  40                  45

Ala Val Ile Trp Tyr Asp Gly Ser Asn Lys Tyr Tyr Ala Asp Ser Val
 50                  55                  60

Lys Gly Arg Ser Thr Ile Ser Arg Asp Asn Ser Lys Asn Thr Leu Tyr
 65                  70                  75                  80
```

```
Leu Gln Met Asn Ser Leu Arg Ala Glu Asp Thr Ala Val Tyr Tyr Cys
                85                  90                  95
Ala Arg Asp Gly Val Ala Val Ala Gly Thr Asp Tyr Phe Asp Tyr Trp
            100                 105                 110
Gly Gln Gly Thr Leu Val Thr Val Ser Ser Ala Ser Thr Lys Gly Pro
        115                 120                 125
Ser Val Phe Pro Leu Ala Pro
    130                 135

<210> SEQ ID NO 109
<211> LENGTH: 638
<212> TYPE: DNA
<213> ORGANISM: Homo sapiens

<400> SEQUENCE: 109
ctggctccga ggtgccagat gtgacatcca gatgacccag tctccatcct ccctgtctac      60
atctgtagga gacagagtca ccatcacttg ccgggcaact cagagcatta gcagccattt     120
aaattggtat cagcagaaac cagggaaagc ccctaagctc ctgatctatg ttgcatccag     180
tttgcaaagt ggggtcccat caaggttcag tggcagtgga tctgggacag atttcactct     240
caccatcagc agtctgcaac tgaagatttt gcaacttac tactgtcaac agagttacag     300
taccccgctc actttcggcg agggaccaa ggtggagatc aaacgaactg tggctgcacc     360
atctgtcttc atcttcccgc catctgatga gcagttgaaa tctggaactg cctctgttgt     420
gtgcctgctg aataacttct atcccagaga ggccaaagta cagtggaagg tggataacgc     480
cctccaatcg ggtaactccc aggagagtgt cacagagcag gacagcaagg acagcaccta     540
cagcctcagc agcaccctga cgctgagcaa agcagactac gagaaacaca agtctacgc      600 ctgcgaagtc acccatcagg gcctgagctc gcccgtca                              638

<210> SEQ ID NO 110
<211> LENGTH: 212
<212> TYPE: PRT
<213> ORGANISM: Homo sapiens

<400> SEQUENCE: 110

Trp Leu Arg Gly Ala Arg Cys Asp Ile Gln Met Thr Gln Ser Pro Ser
1               5                   10                  15
Ser Leu Ser Thr Ser Val Gly Asp Arg Val Thr Ile Thr Cys Arg Ala
            20                  25                  30
Thr Gln Ser Ile Ser Ser His Leu Asn Trp Tyr Gln Gln Lys Pro Gly
        35                  40                  45
Lys Ala Pro Lys Leu Leu Ile Tyr Val Ala Ser Ser Leu Gln Ser Gly
    50                  55                  60
Val Pro Ser Arg Phe Ser Gly Ser Gly Ser Gly Thr Asp Phe Thr Leu
65                  70                  75                  80
Thr Ile Ser Ser Leu Gln Pro Glu Asp Phe Ala Thr Tyr Tyr Cys Gln
                85                  90                  95
Gln Ser Tyr Ser Thr Pro Leu Thr Phe Gly Gly Gly Thr Lys Val Glu
            100                 105                 110
Ile Lys Arg Thr Val Ala Ala Pro Ser Val Phe Ile Phe Pro Pro Ser
        115                 120                 125
Asp Glu Gln Leu Lys Ser Gly Thr Ala Ser Val Val Cys Leu Leu Asn
    130                 135                 140
Asn Phe Tyr Pro Arg Glu Ala Lys Val Gln Trp Lys Val Asp Asn Ala
145                 150                 155                 160
```

Leu Gln Ser Gly Asn Ser Gln Glu Ser Val Thr Glu Gln Asp Ser Lys
            165                 170                 175

Asp Ser Thr Tyr Ser Leu Ser Ser Thr Leu Thr Leu Ser Lys Ala Asp
        180                 185                 190

Tyr Glu Lys His Lys Val Tyr Ala Cys Glu Val Thr His Gln Gly Leu
        195                 200                 205

Ser Ser Pro Val
    210

<210> SEQ ID NO 111
<211> LENGTH: 411
<212> TYPE: DNA
<213> ORGANISM: Homo sapiens

<400> SEQUENCE: 111
caggtgcagc tgcaggagtc tggcccagga ctggtgaagc cttcacagac cctgtccctc      60
accagcactg tctctggtgg ctccatcagc agtggtggtt actactggag ctggatccgc     120
cagctcccag ggaagggcct ggagtgggtt gggtacatcc ataacagtgg gagcacctac     180
tacaacccgt ccctcaagag tcgagttacc atatcagtag acacgtctaa gaaccagttc     240
tccctgaagc tgagatctgt gactgccgcg gacacggccg tgtattactg tgcgagaggg     300
tattactatg gttcggggag cccctacggt atggacgtct ggggccaagg gaccacggtc     360
accgtctcct cagcctccac caagggccca tcggtcttcc cctggcacc c               411

<210> SEQ ID NO 112
<211> LENGTH: 137
<212> TYPE: PRT
<213> ORGANISM: Homo sapiens

<400> SEQUENCE: 112

Gln Val Gln Leu Gln Glu Ser Gly Pro Gly Leu Val Lys Pro Ser Gln
1               5                   10                  15

Thr Leu Ser Leu Thr Ser Thr Val Ser Gly Gly Ser Ile Ser Ser Gly
            20                  25                  30

Gly Tyr Tyr Trp Ser Trp Ile Arg Gln Leu Pro Gly Lys Gly Leu Glu
        35                  40                  45

Trp Val Gly Tyr Ile His Asn Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Arg Ser Val Thr Ala Ala Asp Thr Ala Val Tyr Tyr
                85                  90                  95

Cys Ala Arg Gly Tyr Tyr Tyr Gly Ser Gly Ser Pro Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro
    130                 135

<210> SEQ ID NO 113
<211> LENGTH: 660
<212> TYPE: DNA
<213> ORGANISM: Homo sapiens

<400> SEQUENCE: 113
gctctgggtc tctggatcca gtggggatat tgtgatgact cagtctccac tctccctgcc      60
cgtcacccct ggagagacgg cctccatctc ctgcaggtct agtcagagcc tcctgcaaag     120

```
taatggacac aactatttgg attggtacct gcagaagcca gggcagtccc cacagctcct    180
gatctatttg ggttcttatc gggactccgg ggtccctgac aggttcagtg gcagtggatc    240
aggcacggat tttaccctga aaatcagcag agtggaggct gaggatgttg gggtctatta    300
ctgcatgcaa gctcttcaaa ctcctcctac tttcggcgga gggaccaagt ggagatcaa     360 acgaactgtg gctgcaccat ctgtcttcat cttcccgcca tctgatgagc agttgaaatc    420
tggaactgcc tctgttgtgt gcctgctgaa taacttctat cccagagagg ccaaagtaca    480
gtggaaggtg gataacgccc tccaatcggg taactcccag gagagtgtca cagagcagga    540
cagcaaggac agcacctaca gcctcagcag caccctgacg ctgagcaaag cagactacga    600
gaaacacaaa gtctacgcct gcgaagtcac ccatcagggc ctgagctcgc cgtcacaaa     660
```

<210> SEQ ID NO 114
<211> LENGTH: 219
<212> TYPE: PRT
<213> ORGANISM: Homo sapiens

<400> SEQUENCE: 114

```
Leu Trp Val Ser Gly Ser Ser Gly Asp Ile Val Met Thr Gln Ser Pro
1               5                   10                  15

Leu Ser Leu Pro Val Thr Pro Gly Glu Thr Ala Ser Ile Ser Cys Arg
                20                  25                  30

Ser Ser Gln Ser Leu Leu Gln Ser Asn Gly His Asn Tyr Leu Asp Trp
            35                  40                  45

Tyr Leu Gln Lys Pro Gly Gln Ser Pro Gln Leu Leu Ile Tyr Leu Gly
        50                  55                  60

Ser Tyr Arg Asp Ser Gly Val Pro Asp Arg Phe Ser Gly Ser Gly Ser
65                  70                  75                  80

Gly Thr Asp Phe Thr Leu Lys Ile Ser Arg Val Glu Ala Glu Asp Val
                85                  90                  95

Gly Val Tyr Tyr Cys Met Gln Ala Leu Gln Thr Pro Pro Thr Phe Gly
            100                 105                 110

Gly Gly Thr Lys Leu Glu Ile Lys Arg Thr Val Ala Ala Pro Ser Val
        115                 120                 125

Phe Ile Phe Pro Pro Ser Asp Glu Gln Leu Lys Ser Gly Thr Ala Ser
130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr
    210                 215
```

<210> SEQ ID NO 115
<211> LENGTH: 416
<212> TYPE: DNA
<213> ORGANISM: Homo sapiens

<400> SEQUENCE: 115

```
caggtgcagc tggtggagtc tgggggaggc gtggtccagc ctgggaggtc cctgagactc    60
tcctgtgcag cgtctggatt caccttcagt agtcatggca tgcactgggt ccgccaggct   120
```

```
ccaggcaagg ggctggagtg ggtggcagtt atatggtatg atggaagtaa taaatactat    180
gcagactccg tgaagggccg attcaccatc tccagagaca attccaagaa cacgctgtat    240
ctgcaaatga acagcctgag agccgaggac acggctgtgt attactgtgc gagagatcaa    300
tatagtggct acgatctcta ctactactac ggtatggacg tctggggcca agggaccacg    360
gtcaccgtct cctcagcctc caccaagggc ccatcggtct tccccctggc accctc        416
```

<210> SEQ ID NO 116
<211> LENGTH: 138
<212> TYPE: PRT
<213> ORGANISM: Homo sapiens

<400> SEQUENCE: 116

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser His
             20                  25                  30

Gly Met His Trp Val Arg Gln Ala Pro Gly Lys Gly Leu Glu Trp Val
         35                  40                  45

Ala Val Ile Trp Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gln Tyr Ser Gly Tyr Asp Leu Tyr Tyr Tyr Tyr Gly Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro
    130                 135
```

<210> SEQ ID NO 117
<211> LENGTH: 690
<212> TYPE: DNA
<213> ORGANISM: Homo sapiens

<400> SEQUENCE: 117

```
tctgttgctc tggatctctg gtgcctacgg ggacatcgtg atgacccagt ctccagactc    60
cctggctgtg tctctgggcg agagggccac catcaactgc aagtccagcc agagtgtttt   120
atacagctcc aacaataaga actacttagc ttggtaccag cagaaaccag gacagcctcc   180
taagctgctc atttactggg catctacccg ggaatccggg gtccctgacc gattcagtgg   240
cagcgggtct gggacagatt tcactctcac catcagcagc ctgcaggctg aagatgtggc   300
agtttattac tgtcagcaat attatagtac ccctcggacg ttcggccaag ggaccaaggt   360
ggaaatcaaa cgaactgtgg ctgcaccatc tgtcttcatc ttcccgccat ctgatgagca   420
gttgaaatct ggaactgcct ctgttgtgtg cctgctgaat aacttctatc ccagagaggc   480
caaagtacag tggaaggtgg ataacgccct ccaatcgggt aactcccagg agagtgtcac   540
agagcaggac agcaaggaca gcacctacag cctcagcagc accctgacgc tgagcaaagc   600
agactacgag aaacacaaag tctacgcctg cgaagtcacc catcagggcc tgagctcgcc   660
cgtcacaaag agcttcaaca ggggagagtg                                    690
```

<210> SEQ ID NO 118

<211> LENGTH: 229
<212> TYPE: PRT
<213> ORGANISM: Homo sapiens

<400> SEQUENCE: 118

```
Leu Leu Leu Trp Ile Ser Gly Ala Tyr Gly Asp Ile Val Met Thr Gln
1               5                   10                  15

Ser Pro Asp Ser Leu Ala Val Ser Leu Gly Glu Arg Ala Thr Ile Asn
            20                  25                  30

Cys Lys Ser Ser Gln Ser Val Leu Tyr Ser Ser Asn Asn Lys Asn Tyr
        35                  40                  45

Leu Ala Trp Tyr Gln Gln Lys Pro Gly Gln Pro Lys Leu Leu Ile
    50                  55                  60

Tyr Trp Ala Ser Thr Arg Glu Ser Gly Val Pro Asp Arg Phe Ser Gly
65                  70                  75                  80

Ser Gly Ser Gly Thr Asp Phe Thr Leu Thr Ile Ser Ser Leu Gln Ala
                85                  90                  95

Glu Asp Val Ala Val Tyr Tyr Cys Gln Gln Tyr Tyr Ser Thr Pro Arg
            100                 105                 110

Thr Phe Gly Gln Gly Thr Lys Val Glu Ile Lys Arg Thr Val Ala Ala
        115                 120                 125

Pro Ser Val Phe Ile Phe Pro Pro Ser Asp Glu Gln Leu Lys Ser Gly
    130                 135                 140

Thr Ala Ser Val Val Cys Leu Leu Asn Asn Phe Tyr Pro Arg Glu Ala
145                 150                 155                 160

Lys Val Gln Trp Lys Val Asp Asn Ala Leu Gln Ser Gly Asn Ser Gln
                165                 170                 175

Glu Ser Val Thr Glu Gln Asp Ser Lys Asp Ser Thr Tyr Ser Leu Ser
            180                 185                 190

Ser Thr Leu Thr Leu Ser Lys Ala Asp Tyr Glu Lys His Lys Val Tyr
        195                 200                 205

Ala Cys Glu Val Thr His Gln Gly Leu Ser Ser Pro Val Thr Lys Ser
    210                 215                 220

Phe Asn Arg Gly Glu
225
```

<210> SEQ ID NO 119
<211> LENGTH: 399
<212> TYPE: DNA
<213> ORGANISM: Homo sapiens

<400> SEQUENCE: 119

```
gaggtgcagc tgttggagtc tgggggaggc ttggtacagc ctgggggtc cctgagactc      60
tcctgtgcag cctctggatt cacctttagc agcaatgcca tgaactgggt ccgccaggct     120
ccagggaagg ggctggagtg gtctcagct attagtggta gtggtggtag cacatgctac     180
gcagactccg tgaagggccg gttcaccatc tccagagaca attccaagaa cacgctgtat    240
ctgcaaatga acagcctgag agccgaggac acggccgtat attactgtgc gaaagccccg    300
taccagctgc tgccatacta ttttgactac tggggccagg gaaccctggt caccgtctcc    360
tcagcctcca ccaagggccc atcggtcttc cccctggca                           399
```

<210> SEQ ID NO 120
<211> LENGTH: 133
<212> TYPE: PRT
<213> ORGANISM: Homo sapiens

<400> SEQUENCE: 120

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Ala Met Asn Trp Val Arg Gln Ala Pro Gly Lys Gly Leu Glu Trp Val
        35                  40                  45

Ser Ala Ile Ser Gly Ser Gly Gly Ser Thr Cys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Pro Tyr Gln Leu Leu Pro Tyr Tyr Phe Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala
            130
```

<210> SEQ ID NO 121
<211> LENGTH: 192
<212> TYPE: PRT
<213> ORGANISM: Homo sapiens

<400> SEQUENCE: 121

```
Gln Val Gln Leu Val Glu Ser Gly Gly Gly Val Val Gln Pro Gly Arg
1               5                   10                  15

Ser Leu Arg Leu Ser Cys Gly Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Met Ser Tyr Asp Gly Ser Lys Lys Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Asp Gly Gly Asp Tyr Val Arg Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190
```

<210> SEQ ID NO 122
<211> LENGTH: 208
<212> TYPE: PRT
<213> ORGANISM: Homo sapiens

<400> SEQUENCE: 122

```
Leu Pro Asp Thr Arg Cys Asp Ile Gln Met Thr Gln Ser Pro Ser Ser
1               5                   10                  15

Leu Ser Ala Ser Val Gly Asp Arg Val Thr Ile Thr Cys Arg Ala Arg
            20                  25                  30

Gln Gly Ile Thr Tyr His Leu Ala Trp Tyr Gln Gln Arg Pro Gly Lys
        35                  40                  45

Val Pro Lys Leu Leu Ile Tyr Asp Thr Ser Ser Leu Gln Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Val Ala Thr Tyr Tyr Cys Gln Arg
                85                  90                  95

Phe Asn Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

<210> SEQ ID NO 123
<211> LENGTH: 190
<212> TYPE: PRT
<213> ORGANISM: Homo sapiens

<400> SEQUENCE: 123

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Met Ser Tyr Asp Gly Ser Lys Lys Phe Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gly Asp Tyr Val Arg Tyr His Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175
```

Phe Pro Ala Val Leu Gln Ser Ser Gly Leu Tyr Ser Leu Ser
            180                 185                 190

<210> SEQ ID NO 124
<211> LENGTH: 226
<212> TYPE: PRT
<213> ORGANISM: Homo sapiens

<400> SEQUENCE: 124

Leu Leu Gly Leu Leu Leu Leu Trp Leu Pro Asp Thr Arg Cys Asp Ile
1               5                   10                  15

Gln Met Thr Gln Ser Pro Ser Thr Leu Ser Ala Ser Ile Gly Asp Arg
            20                  25                  30

Val Thr Ile Thr Cys Arg Ala Ser Gln Gly Ile Ser Tyr Tyr Leu Ala
        35                  40                  45

Trp Tyr Gln Gln Lys Pro Gly Lys Ile Pro Lys Leu Leu Ile Tyr Asp
    50                  55                  60

Thr Ser Ser Leu Gln Ser Gly Val Pro Ser Arg Phe Ser Gly Ser Arg
65                  70                  75                  80

Ser Gly Thr Asp Leu Ser Leu Thr Ile Ser Ser Leu Gln Pro Glu Asp
                85                  90                  95

Val Ala Thr Tyr Tyr Cys Gln Arg Tyr Asp Ser Ala Pro Leu Thr Phe
            100                 105                 110

Gly Gly Gly Thr Lys Val Glu Ile Lys Arg Thr Val Ala Ala Pro Ser
        115                 120                 125

Val Phe Ile Phe Pro Pro Ser Asp Glu Gln Leu Lys Ser Gly Thr Ala
    130                 135                 140

Ser Val Val Cys Leu Leu Asn Asn Phe Tyr Pro Arg Glu Ala Lys Val
145                 150                 155                 160

Gln Trp Lys Val Asp Asn Ala Leu Gln Ser Gly Asn Ser Gln Glu Ser
                165                 170                 175

Val Thr Glu Gln Asp Ser Lys Asp Ser Thr Tyr Ser Leu Ser Ser Thr
            180                 185                 190

Leu Thr Leu Ser Lys Ala Asp Tyr Glu Lys His Lys Val Tyr Ala Cys
        195                 200                 205

Glu Val Thr His Gln Gly Leu Ser Ser Pro Val Thr Lys Ser Phe Asn
    210                 215                 220

Arg Gly
225

<210> SEQ ID NO 125
<211> LENGTH: 136
<212> TYPE: PRT
<213> ORGANISM: Homo sapiens

<400> SEQUENCE: 125

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Arg Asn Lys Phe Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

```
                    85                  90                  95
Ala Arg Asp Trp Gly Ala Thr Met Ala Phe Asp Ile Trp Gly Gln Gly
            100                 105                 110

Thr Met Val Thr Val Ser Ser Ala Ser Thr Lys Gly Pro Ser Val Phe
            115                 120                 125

Pro Leu Ala Pro Ser Ser Lys Ser
            130                 135
```

```
<210> SEQ ID NO 126
<211> LENGTH: 215
<212> TYPE: PRT
<213> ORGANISM: Homo sapiens

<400> SEQUENCE: 126

Leu Leu Thr Leu Thr His Cys Ala Gly Ser Trp Ala Gln Ser Val
1               5                   10                  15

Leu Thr Gln Pro Pro Ser Ala Ser Lys Thr Pro Gly Gln Arg Val Thr
            20                  25                  30

Ile Ser Cys Ser Gly Ser Ser Asn Ile Gly Ser Asn Thr Val Asn
            35                  40                  45

Trp Tyr Gln Gln Leu Pro Gly Thr Ala Pro Lys Leu Leu Ile Phe Gly
50                  55                  60

Asn Asn Gln Arg Pro Ser Gly Val Pro Asp Arg Phe Ser Gly Ser Lys
65                  70                  75                  80

Ser Gly Thr Ser Ala Ser Leu Ala Ile Ser Gly Leu Gln Ser Glu Asp
            85                  90                  95

Glu Ala Asp Tyr Tyr Cys Ala Ala Trp Asp Asp Ser Leu Asn Tyr Val
            100                 105                 110

Phe Gly Thr Gly Thr Lys Val Thr Val Leu Gly Gln Pro Lys Ala Asn
            115                 120                 125

Pro Thr Val Thr Leu Phe Pro Pro Ser Glu Glu Leu Gln Ala Asn
            130                 135                 140

Lys Ala Thr Leu Val Cys Leu Ile Ser Asp Phe Tyr Pro Gly Ala Val
145                 150                 155                 160

Thr Val Ala Trp Lys Ala Asp Gly Ser Pro Val Lys Ala Gly Val Glu
            165                 170                 175

Thr Thr Lys Pro Ser Lys Gln Ser Asn Asn Lys Tyr Ala Ala Ser Ser
            180                 185                 190

Tyr Leu Ser Leu Thr Pro Glu Gln Trp Lys Ser His Arg Ser Tyr Ser
            195                 200                 205

Cys Gln Val Thr His Glu Gly
            210                 215
```

```
<210> SEQ ID NO 127
<211> LENGTH: 138
<212> TYPE: PRT
<213> ORGANISM: Homo sapiens

<400> SEQUENCE: 127

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Tyr Ser Gly Tyr Gly Tyr Tyr Tyr Tyr Gly Met
            100                 105                 110

Asp Val Trp Gly Gln Gly Thr Thr Val Thr Val Ser Ser Ala Ser Thr
            115                 120                 125

Lys Gly Pro Ser Val Phe Pro Leu Ala Pro
            130                 135
```

```
<210> SEQ ID NO 128
<211> LENGTH: 217
<212> TYPE: PRT
<213> ORGANISM: Homo sapiens

<400> SEQUENCE: 128

Gly Ala Arg Cys Asp Ile Gln Met Thr Gln Ser Pro Ser Ser Leu Ser
 1               5                  10                  15

Ala Ser Val Gly Asp Arg Val Thr Ile Thr Cys Arg Ala Ser Gln Asp
            20                  25                  30

Ile Ser Asn Tyr Leu Ala Trp Phe Gln Gln Lys Pro Gly Lys Ala Pro
        35                  40                  45

Lys Ser Leu Ile Tyr Ala Ala Ser Ser Leu His Ser Gly Val Pro Ser
 50                  55                  60

Lys Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Tyr Thr
                 85                  90                  95

Ile Tyr Pro Phe Thr Phe Gly Pro Gly Thr Lys Val Asp Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu
    210                 215
```

```
<210> SEQ ID NO 129
<211> LENGTH: 177
<212> TYPE: PRT
<213> ORGANISM: Homo sapiens

<400> SEQUENCE: 129

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
            20                  25                  30
```

```
Tyr Trp Ser Trp Ile Arg Gln Pro Pro Gly Lys Gly Leu Glu Trp Ile
             35                  40                  45

Gly Tyr Ile Tyr Tyr Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Asn Ser Val Thr Ala Ala Asp Thr Ala Val Tyr Tyr Cys Ala
                 85                  90                  95

Arg Gly Tyr Tyr Tyr Gly Ser Glu Ser Pro Tyr Gly Met Asp Val Trp
                100                 105                 110

Gly Gln Gly Thr Thr Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala

<210> SEQ ID NO 130
<211> LENGTH: 216
<212> TYPE: PRT
<213> ORGANISM: Homo sapiens

<400> SEQUENCE: 130

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
             20                  25                  30

Asn Gly His Asn Tyr Leu Asp Trp Tyr Leu Gln Lys Pro Gly Gln Ser
         35                  40                  45

Pro His Leu Leu Ile Tyr Leu Gly Ser Asn Arg Asp Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Ile Pro Cys Ser Phe Gly Gln Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg
    210                 215
```

```
<210> SEQ ID NO 131
<211> LENGTH: 174
<212> TYPE: PRT
<213> ORGANISM: Homo sapiens

<400> SEQUENCE: 131

Gln Val Gln Leu Val Glu Phe Gly Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Ser Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Val Ala Val Ala Gly Thr Asp Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr
                165                 170

<210> SEQ ID NO 132
<211> LENGTH: 212
<212> TYPE: PRT
<213> ORGANISM: Homo sapiens

<400> SEQUENCE: 132

Trp Leu Arg Gly Ala Arg Cys Asp Ile Gln Met Thr Gln Ser Pro Ser
1               5                   10                  15

Ser Leu Ser Ala Ser Val Gly Asp Arg Val Thr Ile Thr Cys Arg Ala
            20                  25                  30

Ser Gln Ser Ile Ser Ser His Leu Asn Trp Tyr Gln Gln Lys Pro Gly
        35                  40                  45

Lys Ala Pro Lys Leu Leu Ile Tyr Val Ala Ser Leu Gln Ser Gly
    50                  55                  60

Val Pro Ser Arg Phe Ser Gly Ser Gly Ser Gly Thr Asp Phe Thr Leu
65                  70                  75                  80

Thr Ile Ser Ser Leu Gln Pro Glu Asp Phe Ala Thr Tyr Tyr Cys Gln
                85                  90                  95

Gln Ser Tyr Ser Thr Pro Leu Ile Phe Gly Gly Thr Lys Val Glu
            100                 105                 110

Ile Lys Arg Thr Val Ala Ala Pro Ser Val Phe Ile Phe Pro Pro Ser
        115                 120                 125

Asp Glu Gln Leu Lys Ser Gly Thr Ala Ser Val Val Cys Leu Leu Asn
    130                 135                 140

Asn Phe Tyr Pro Arg Glu Ala Lys Val Gln Trp Lys Val Asp Asn Ala
145                 150                 155                 160

Leu Gln Ser Gly Asn Ser Gln Glu Ser Val Thr Glu Gln Asp Ser Lys
                165                 170                 175
```

```
Asp Ser Thr Tyr Ser Leu Ser Ser Thr Leu Thr Leu Ser Lys Ala Asp
            180                 185                 190

Tyr Glu Lys His Lys Val Tyr Ala Cys Glu Val Thr His Gln Gly Leu
        195                 200                 205

Ser Ser Pro Val
    210

<210> SEQ ID NO 133
<211> LENGTH: 162
<212> TYPE: PRT
<213> ORGANISM: Homo sapiens

<400> SEQUENCE: 133

Glu Val Gln Leu Leu Glu Ser Gly Gly Gly Leu Val Gln Pro Gly Gly
1               5                   10                  15

Ser Leu Arg Leu Ser Cys Ala Ala Ser Thr Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Phe Ser Gly Arg Gly Gly Ser Thr Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Lys Asp Ser Ser Gly Pro Leu Leu Gly Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser

<210> SEQ ID NO 134
<211> LENGTH: 206
<212> TYPE: PRT
<213> ORGANISM: Homo sapiens

<400> SEQUENCE: 134

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Val Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Tyr Val
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
```

```
                115                 120                     125
Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr
        195                 200                 205

<210> SEQ ID NO 135
<211> LENGTH: 139
<212> TYPE: PRT
<213> ORGANISM: Homo sapiens

<400> SEQUENCE: 135

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Tyr Ser Gly Tyr Asp Tyr Tyr Tyr Tyr Gly Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Ser
    130                 135

<210> SEQ ID NO 136
<211> LENGTH: 213
<212> TYPE: PRT
<213> ORGANISM: Homo sapiens

<400> SEQUENCE: 136

Leu Cys Phe Pro Gly Ala Arg Cys Asp Ile Gln Met Thr Gln Ser Pro
1               5                   10                  15

Ser Ser Leu Ser Ala Ser Val Gly Asp Arg Val Thr Ile Thr Cys Arg
            20                  25                  30

Ala Ser Gln Val Ile Tyr Asn Tyr Leu Ala Trp Phe Gln Gln Lys Pro
        35                  40                  45

Gly Lys Ala Pro Lys Ser Leu Ile Tyr Gly Ala Ser Ser Leu His Ser
    50                  55                  60

Gly Val Pro Ser Lys Phe Ser Gly Ser Gly Ser Gly Thr Glu Phe Thr
65                  70                  75                  80

Leu Thr Ile Ser Ser Leu Gln Pro Glu Asp Phe Ala Thr Tyr Tyr Cys
                85                  90                  95

Gln Gln Tyr Thr Ile Tyr Pro Phe Ser Phe Gly Pro Gly Thr Lys Val
            100                 105                 110
```

```
Asp Ile Lys Arg Thr Val Ala Ala Pro Ser Val Phe Ile Phe Pro Pro
            115                 120                 125

Ser Asp Glu Gln Leu Lys Ser Gly Thr Ala Ser Val Val Cys Leu Leu
130                 135                 140

Asn Asn Phe Tyr Pro Arg Glu Ala Lys Val Gln Trp Lys Val Asp Asn
145                 150                 155                 160

Ala Leu Gln Ser Gly Asn Ser Gln Glu Ser Val Thr Glu Gln Asp Ser
                165                 170                 175

Lys Asp Ser Thr Tyr Ser Leu Ser Ser Thr Leu Thr Leu Ser Lys Ala
            180                 185                 190

Asp Tyr Glu Lys His Lys Val Tyr Ala Cys Glu Val Thr His Gln Gly
        195                 200                 205

Leu Ser Ser Pro Val
    210
```

<210> SEQ ID NO 137
<211> LENGTH: 136
<212> TYPE: PRT
<213> ORGANISM: Homo sapiens

<400> SEQUENCE: 137

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Arg Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Tyr Ser Gly Ser Asp Tyr Tyr Tyr Tyr Tyr Gly Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu
    130                 135
```

<210> SEQ ID NO 138
<211> LENGTH: 219
<212> TYPE: PRT
<213> ORGANISM: Homo sapiens

<400> SEQUENCE: 138

```
Leu Cys Phe Pro Gly Ala Arg Cys Asp Ile Gln Met Thr Gln Ser Pro
1               5                   10                  15

Ser Ser Leu Ser Ala Ser Val Gly Asp Arg Val Thr Ile Thr Cys Arg
            20                  25                  30

Ala Ser Gln Gly Ile Tyr Asn Tyr Leu Ala Trp Phe Gln Gln Lys Pro
        35                  40                  45

Gly Lys Ala Pro Lys Ser Leu Ile Tyr Ala Ala Ser Ser Leu Gln Ser
    50                  55                  60

Gly Val Pro Ser Lys Phe Ser Gly Ser Gly Ser Gly Thr Val Phe Thr
65                  70                  75                  80
```

```
Leu Thr Ile Ser Ser Leu Gln Pro Glu Asp Phe Ala Thr Tyr Tyr Cys
                85                  90                  95

Gln Gln Tyr Thr Val Tyr Pro Phe Thr Phe Gly Pro Gly Thr Lys Val
            100                 105                 110

Asp Phe Lys Arg Thr Val Ala Ala Pro Ser Val Phe Ile Phe Pro Pro
        115                 120                 125

Ser Asp Glu Gln Leu Lys Ser Gly Thr Ala Ser Val Val Cys Leu Leu
130                 135                 140

Asn Asn Phe Tyr Pro Arg Glu Ala Lys Val Gln Trp Lys Val Asp Asn
145                 150                 155                 160

Ala Leu Gln Ser Gly Asn Ser Gln Glu Ser Val Thr Glu Gln Asp Ser
                165                 170                 175

Lys Asp Ser Thr Tyr Ser Leu Ser Ser Thr Leu Thr Leu Ser Lys Ala
            180                 185                 190

Asp Tyr Glu Lys His Lys Val Tyr Ala Cys Glu Val Thr His Gln Gly
        195                 200                 205

Leu Ser Ser Pro Val Thr Lys Ser Phe Asn Arg
    210                 215
```

<210> SEQ ID NO 139
<211> LENGTH: 134
<212> TYPE: PRT
<213> ORGANISM: Homo sapiens

<400> SEQUENCE: 139

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Tyr Tyr Tyr Gly Ala Gly Ser Tyr Gly Met Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro
    130
```

<210> SEQ ID NO 140
<211> LENGTH: 225
<212> TYPE: PRT
<213> ORGANISM: Homo sapiens

<400> SEQUENCE: 140

```
Leu Trp Val Ser Gly Ser Ser Gly Asp Ile Val Met Thr Gln Ser Pro
1               5                   10                  15

Leu Ser Leu Pro Val Thr Pro Gly Glu Pro Ala Ser Ile Ser Cys Arg
            20                  25                  30

Ser Ser Gln Ser Leu Leu His Ser Thr Gly Phe Asn Tyr Leu Asp Trp
        35                  40                  45

Tyr Leu Gln Lys Pro Gly Gln Ser Pro Gln Leu Leu Ile Tyr Leu Gly
```

```
                 50                 55                  60
Ser Ile Arg Ala Ser Gly Val Pro Asp Arg Phe Ser Gly Ser Gly Ser
 65                  70                  75                  80

Gly Thr Asp Phe Thr Leu Lys Ile Ser Arg Val Glu Thr Glu Asp Val
                     85                  90                  95

Gly Val Tyr Tyr Cys Met Gln Thr Leu Gln Thr Pro Ile Thr Phe Gly
                100                 105                 110

Gln Gly Thr Arg Leu Glu Ile Lys Arg Thr Val Ala Ala Pro Ser Val
            115                 120                 125

Phe Ile Phe Pro Pro Ser Asp Glu Gln Leu Lys Ser Gly Thr Ala Ser
        130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                    165                 170                 175

Thr Glu Gln Asp Ser Lys Asp Ser Thr Tyr Ser Leu Ser Ser Thr Leu
                180                 185                 190

Thr Leu Ser Lys Ala Asp Tyr Glu Lys His Lys Val Tyr Ala Cys Glu
            195                 200                 205

Val Thr His Gln Gly Leu Ser Ser Pro Val Thr Lys Ser Phe Asn Arg
        210                 215                 220

Gly
225

<210> SEQ ID NO 141
<211> LENGTH: 140
<212> TYPE: PRT
<213> ORGANISM: Homo sapiens

<400> SEQUENCE: 141

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Tyr Ser Gly Tyr Asp Tyr Tyr Tyr Tyr Gly Met
                100                 105                 110

Asp Val Trp Gly Gln Gly Thr Thr Val Thr Val Ser Ser Ala Ser Thr
            115                 120                 125

Lys Gly Pro Ser Val Phe Pro Leu Ala Pro Ser Ser
        130                 135                 140

<210> SEQ ID NO 142
<211> LENGTH: 219
<212> TYPE: PRT
<213> ORGANISM: Homo sapiens

<400> SEQUENCE: 142

Leu Cys Phe Pro Gly Ala Arg Cys Asp Ile Gln Met Thr Gln Ser Pro
 1               5                  10                  15
```

```
Ser Ser Leu Ser Ala Ser Val Gly Asp Arg Val Thr Ile Thr Cys Arg
            20                  25                  30

Ala Ser Gln Gly Ile Tyr Asn Tyr Leu Ala Trp Phe Gln Gln Lys Pro
        35                  40                  45

Gly Lys Ala Pro Lys Ser Leu Ile Tyr Ala Ala Ser Ser Leu His Ser
    50                  55                  60

Gly Val Pro Ser Lys Phe Ser Gly Gly Ser Gly Thr Asp Phe Thr
65                  70                  75                  80

Leu Thr Ile Ser Ser Leu Gln Pro Glu Asp Phe Ala Thr Tyr Tyr Cys
                85                  90                  95

Gln Gln Tyr Thr Ile Tyr Pro Phe Thr Phe Gly Pro Gly Thr Lys Val
            100                 105                 110

Asp Ile Lys Arg Thr Val Ala Ala Pro Ser Val Phe Ile Phe Pro Pro
        115                 120                 125

Ser Asp Glu Gln Leu Lys Ser Gly Thr Ala Ser Val Val Cys Leu Leu
    130                 135                 140

Asn Asn Phe Tyr Pro Arg Glu Ala Lys Val Gln Trp Lys Val Asp Asn
145                 150                 155                 160

Ala Leu Gln Ser Gly Asn Ser Gln Glu Ser Val Thr Glu Gln Asp Ser
                165                 170                 175

Lys Asp Ser Thr Tyr Ser Leu Ser Ser Thr Leu Thr Leu Ser Lys Ala
            180                 185                 190

Asp Tyr Glu Lys His Lys Val Tyr Ala Cys Glu Val Thr His Gln Gly
        195                 200                 205

Leu Ser Ser Pro Val Thr Lys Ser Phe Asn Arg
    210                 215

<210> SEQ ID NO 143
<211> LENGTH: 133
<212> TYPE: PRT
<213> ORGANISM: Homo sapiens

<400> SEQUENCE: 143

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Asn Thr Tyr Tyr Tyr Gly Ser Gly Tyr Gly Met Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro
    130

<210> SEQ ID NO 144
<211> LENGTH: 218
<212> TYPE: PRT
<213> ORGANISM: Homo sapiens
```

<400> SEQUENCE: 144

Leu Trp Val Ser Gly Ser Ser Gly Asp Ile Val Met Thr Gln Ser Pro
1               5                   10                  15

Leu Ser Leu Pro Val Thr Pro Gly Glu Pro Ala Ser Ile Ser Cys Arg
            20                  25                  30

Ser Ser Gln Ser Leu Leu His Ser Thr Gly His Asn Tyr Leu Asp Trp
        35                  40                  45

Tyr Leu Gln Lys Pro Gly Gln Ser Pro Gln Leu Leu Ile Tyr Leu Gly
    50                  55                  60

Ser Ile Arg Ala Ser Gly Val Pro Asp Arg Phe Ser Gly Ser Gly Ser
65                  70                  75                  80

Gly Thr Asp Phe Thr Leu Lys Ile Ser Arg Val Glu Ala Glu Asp Val
            85                  90                  95

Gly Val Tyr Tyr Cys Met Gln Ala Leu Gln Thr Ile Thr Phe Gly Gln
            100                 105                 110

Gly Thr Arg Leu Glu Ile Lys Arg Thr Val Ala Ala Pro Ser Val Phe
        115                 120                 125

Ile Phe Pro Pro Ser Asp Glu Gln Leu Lys Ser Gly Thr Ala Ser Val
130                 135                 140

Val Cys Leu Leu Asn Asn Phe Tyr Pro Arg Glu Ala Lys Val Gln Trp
145                 150                 155                 160

Lys Val Asp Asn Ala Leu Gln Ser Gly Asn Ser Gln Glu Ser Val Thr
            165                 170                 175

Glu Gln Asp Ser Lys Asp Ser Thr Tyr Ser Leu Ser Ser Thr Leu Thr
        180                 185                 190

Leu Ser Lys Ala Asp Tyr Glu Lys His Lys Val Tyr Ala Cys Glu Val
    195                 200                 205

Thr His Gln Gly Leu Ser Ser Pro Val Thr
210                 215

<210> SEQ ID NO 145
<211> LENGTH: 135
<212> TYPE: PRT
<213> ORGANISM: Homo sapiens

<400> SEQUENCE: 145

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Phe Ile Tyr Tyr Thr Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
            85                  90                  95

Asn Thr Tyr Tyr Tyr Gly Ser Gly Tyr Gly Met Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser
130                 135

<210> SEQ ID NO 146
<211> LENGTH: 229
<212> TYPE: PRT
<213> ORGANISM: Homo sapiens

<400> SEQUENCE: 146

```
Leu Leu Gly Leu Leu Met Leu Trp Val Ser Gly Ser Gly Asp Ile
1               5                   10                  15

Val Met Thr Gln Ser Pro Leu Ser Leu Pro Val Thr Pro Gly Glu Pro
            20                  25                  30

Ala Ser Ile Ser Cys Arg Ser Ser Gln Ser Leu Leu His Ser Asn Gly
            35                  40                  45

Phe Asn Tyr Leu Asp Trp Tyr Leu Gln Lys Pro Gly Gln Ser Pro Gln
    50                  55                  60

Leu Leu Ile Tyr Leu Gly Ser Arg Arg Ala Ser Gly Val Pro Asp Arg
65                  70                  75                  80

Phe Ser Gly Ser Gly Ser Gly Thr Asp Phe Thr Leu Lys Ile Ser Arg
                85                  90                  95

Val Glu Ala Glu Asp Val Gly Val Tyr Tyr Cys Met Gln Ala Leu Glu
            100                 105                 110

Thr Ile Thr Phe Gly Gln Gly Thr Arg Leu Glu Ile Lys Arg Thr Val
            115                 120                 125

Ala Ala Pro Ser Val Phe Ile Phe Pro Pro Ser Asp Glu Gln Leu Lys
130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
            195                 200                 205

Val Tyr Ala Cys Glu Val Thr His Gln Gly Leu Ser Ser Pro Val Thr
210                 215                 220

Lys Ser Phe Asn Arg
225
```

<210> SEQ ID NO 147
<211> LENGTH: 136
<212> TYPE: PRT
<213> ORGANISM: Homo sapiens

<400> SEQUENCE: 147

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
            35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Tyr Tyr Tyr Gly Ser Gly Ser Tyr Gly Met Asp Val Trp Gly
```

-continued

```
                100                 105                 110
Gln Gly Thr Thr Val Thr Val Ser Ser Ala Ser Thr Lys Gly Pro Ser
            115                 120                 125
Val Phe Pro Leu Ala Pro Ser Ser
            130                 135

<210> SEQ ID NO 148
<211> LENGTH: 215
<212> TYPE: PRT
<213> ORGANISM: Homo sapiens

<400> SEQUENCE: 148

Gly Ser Ser Gly Asp Ile Val Met Thr Gln Ser Pro Leu Ser Leu Pro
1               5                   10                  15
Val Thr Pro Gly Glu Pro Ala Ser Ile Ser Cys Arg Ser Ser Gln Ser
            20                  25                  30
Leu Leu His Ser Thr Gly Tyr Asn Tyr Leu Asp Trp Tyr Leu Gln Lys
        35                  40                  45
Pro Gly Gln Ser Pro Gln Leu Leu Ile Tyr Leu Gly Ser Asn Arg Ala
    50                  55                  60
Ser Gly Val Pro Asp Arg Phe Ser Gly Ser Gly Ser Gly Thr Asp Phe
65                  70                  75                  80
Thr Leu Lys Ile Ser Arg Val Glu Ala Glu Asp Val Gly Val Cys Tyr
                85                  90                  95
Cys Met Gln Ala Leu Gln Thr Pro Ile Thr Phe Gly Gln Gly Thr Arg
            100                 105                 110
Leu Glu Ile Lys Arg Thr Val Ala Ala Pro Ser Val Phe Ile Phe Pro
        115                 120                 125
Pro Ser Asp Glu Gln Leu Lys Ser Gly Thr Ala Ser Val Val Cys Leu
    130                 135                 140
Leu Asn Asn Phe Tyr Pro Arg Glu Ala Lys Val Gln Trp Lys Val Asp
145                 150                 155                 160
Asn Ala Leu Gln Ser Gly Asn Ser Gln Glu Ser Val Thr Glu Gln Asp
                165                 170                 175
Ser Lys Asp Ser Thr Tyr Ser Leu Ser Ser Thr Leu Thr Leu Ser Lys
            180                 185                 190
Ala Asp Tyr Glu Lys His Lys Val Tyr Ala Cys Glu Val Thr His Gln
        195                 200                 205
Gly Leu Ser Ser Pro Val Thr
    210                 215

<210> SEQ ID NO 149
<211> LENGTH: 136
<212> TYPE: PRT
<213> ORGANISM: Homo sapiens

<400> SEQUENCE: 149

Gln Val Gln Leu Val Glu Ser Gly Gly Val Val Gln Pro Gly Arg
1               5                   10                  15
Ser Leu Arg Leu Ser Cys Ala Ala Ser Gly Phe Thr Phe Ser Ser His
            20                  25                  30
Gly Met His Trp Val Arg Gln Ala Pro Gly Lys Gly Leu Glu Trp Val
        35                  40                  45
Ala Val Ile Trp Tyr Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                 85                  90                  95

Ala Arg Asp Ala Tyr Ser Gly Tyr Asp Tyr Tyr Tyr Tyr Gly Met
            100                 105                 110

Asp Val Trp Gly Gln Gly Thr Thr Val Thr Val Ser Ser Ala Ser Thr
            115                 120                 125

Lys Gly Pro Ser Val Phe Pro Leu
        130                 135

<210> SEQ ID NO 150
<211> LENGTH: 223
<212> TYPE: PRT
<213> ORGANISM: Homo sapiens

<400> SEQUENCE: 150

Gly Leu Leu Leu Cys Phe Pro Gly Ala Arg Cys Asp Ile Gln Met
1               5                   10                  15

Thr Gln Ser Pro Ser Ser Leu Ser Ala Ser Val Gly Asp Arg Val Thr
            20                  25                  30

Ile Thr Cys Arg Ala Ser Gln Gly Ile Tyr Thr Tyr Leu Ala Trp Phe
        35                  40                  45

Gln Gln Lys Pro Gly Lys Ala Pro Lys Ser Leu Ile Tyr Gly Ala Ser
50                  55                  60

Ser Leu Gln Ser Gly Val Pro Ser Lys Phe Ser Gly Ser Gly Ser Gly
65                  70                  75                  80

Thr Asp Phe Thr Leu Thr Ile Thr Ser Leu Gln Pro Glu Asp Phe Ala
                85                  90                  95

Thr Tyr Tyr Cys Gln Gln Tyr Thr Ile Tyr Pro Phe Ser Phe Gly Pro
            100                 105                 110

Gly Thr Lys Val Asp Ile Lys Arg Thr Val Ala Ala Pro Ser Val Phe
            115                 120                 125

Ile Phe Pro Pro Ser Asp Glu Gln Leu Lys Ser Gly Thr Ala Ser Val
        130                 135                 140

Val Cys Leu Leu Asn Asn Phe Tyr Pro Arg Glu Ala Lys Val Gln Trp
145                 150                 155                 160

Lys Val Asp Asn Ala Leu Gln Ser Gly Asn Ser Gln Glu Ser Val Thr
                165                 170                 175

Glu Gln Asp Ser Lys Asp Ser Thr Tyr Ser Leu Ser Ser Thr Leu Thr
            180                 185                 190

Leu Ser Lys Ala Asp Tyr Glu Lys His Lys Val Tyr Ala Cys Glu Val
        195                 200                 205

Thr His Gln Gly Leu Ser Ser Pro Val Thr Lys Ser Phe Asn Arg
    210                 215                 220

<210> SEQ ID NO 151
<211> LENGTH: 141
<212> TYPE: PRT
<213> ORGANISM: Homo sapiens

<400> SEQUENCE: 151

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Gly Tyr Tyr Trp Ser Trp Ile Arg Gln Pro Pro Gly Lys Gly Leu Glu
        35                  40                  45
```

```
Trp Ile Gly Tyr Ile Tyr Tyr Ser Gly Gly Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Thr Ser Val Thr Ala Ala Asp Thr Ala Val Tyr Tyr
                85                  90                  95

Cys Ala Arg Glu Ser Gly Tyr Cys Thr Asn Val Ala Cys Phe Pro Asp
            100                 105                 110

Ala Phe Asp Ile Trp Gly Gln Gly Thr Met Val Thr Val Ser Ser Ala
            115                 120                 125

Ser Thr Lys Gly Pro Ser Val Phe Pro Leu Ala Pro Ser
            130                 135                 140

<210> SEQ ID NO 152
<211> LENGTH: 225
<212> TYPE: PRT
<213> ORGANISM: Homo sapiens

<400> SEQUENCE: 152

Leu Leu Gly Leu Leu Met Leu Trp Val Ser Gly Ser Ser Gly Asp Val
1               5                   10                  15

Val Met Thr Gln Ser Pro Phe Ser Leu Pro Val Thr Pro Gly Glu Pro
                20                  25                  30

Ala Ser Ile Ser Cys Arg Ser Ser Gln Ser Leu Leu His Ser Asn Gly
            35                  40                  45

Phe Asn Phe Leu Asp Trp Tyr Leu Gln Lys Pro Gly Gln Ser Pro Gln
        50                  55                  60

Leu Leu Ile Tyr Leu Gly Ser Ile Arg Ala Ser Gly Val Pro Asp Arg
65                  70                  75                  80

Phe Ser Gly Ser Gly Ser Gly Thr Asp Phe Thr Leu Lys Ile Ser Arg
                85                  90                  95

Val Glu Ala Glu Asp Val Gly Val Tyr Tyr Cys Met Gln Ala Leu Gln
            100                 105                 110

Thr Pro Leu Thr Phe Gly Gly Gly Thr Arg Val Glu Ile Lys Arg Thr
            115                 120                 125

Val Ala Ala Pro Ser Val Phe Ile Phe Pro Pro Ser Asp Glu Gln Leu
130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
            165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
            195                 200                 205

Lys Val Tyr Ala Cys Glu Val Thr His Gln Gly Leu Ser Ser Pro Val
            210                 215                 220

Thr
225

<210> SEQ ID NO 153
<211> LENGTH: 136
<212> TYPE: PRT
<213> ORGANISM: Homo sapiens

<400> SEQUENCE: 153

Gln Val Gln Leu Gln Glu Ser Gly Pro Gly Leu Val Lys Pro Ser Glu
```

-continued

```
                    1               5                  10                 15
            Thr Leu Ser Leu Thr Cys Thr Val Ser Gly Gly Ser Ile Ser Ser Tyr
                            20                 25                 30

Tyr Trp Ser Trp Ile Arg Gln Pro Pro Gly Lys Gly Leu Glu Trp Ile
                        35                 40                 45

Gly Tyr Ile Tyr Tyr Ser Gly Ser Thr Asn Tyr Asn Pro Ser Leu Lys
                    50                 55                 60

Ser Arg Val Thr Ile Ser Val Asp Thr Ser Lys Asn Gln Phe Ser Leu
            65                 70                 75                 80

Lys Leu Ser Ser Val Thr Ala Ala Asp Thr Ala Val Tyr Tyr Cys Ala
                            85                 90                 95

Arg Gly Tyr Tyr Tyr Gly Ser Gly Ser Tyr Gly Leu Asp Val Trp Gly
                            100                105                110

Gln Gly Thr Thr Val Thr Val Ser Ser Ala Ser Thr Lys Gly Pro Ser
                            115                120                125

Val Phe Pro Leu Ala Pro Ser Ser
                            130                135

<210> SEQ ID NO 154
<211> LENGTH: 230
<212> TYPE: PRT
<213> ORGANISM: Homo sapiens

<400> SEQUENCE: 154

Leu Leu Gly Leu Leu Met Leu Trp Val Ser Gly Ser Ser Gly Asp Ile
            1               5                  10                 15

Val Met Thr Gln Ser Pro Leu Ser Leu Pro Val Thr Pro Gly Glu Pro
                            20                 25                 30

Ala Ser Ile Ser Cys Arg Ser Ser Gln Ser Leu Leu His Ser Thr Gly
                        35                 40                 45

Tyr Asn Tyr Leu Asp Trp Tyr Leu Gln Lys Pro Gly Gln Ser Pro Gln
                    50                 55                 60

Leu Leu Ile Tyr Leu Gly Ser Ile Arg Ala Ser Gly Val Pro Asp Arg
            65                 70                 75                 80

Phe Ser Gly Ser Gly Ser Gly Thr Asp Phe Thr Leu Lys Ile Ser Arg
                            85                 90                 95

Val Glu Ala Glu Asp Val Gly Val Tyr Tyr Cys Met Gln Ala Leu Gln
                            100                105                110

Thr Pro Ile Thr Phe Gly Gln Gly Thr Arg Leu Glu Ile Lys Arg Thr
                            115                120                125

Val Ala Ala Pro Ser Val Phe Ile Phe Pro Pro Ser Asp Glu Gln Leu
                            130                135                140

Lys Ser Gly Thr Ala Ser Val Val Cys Leu Leu Asn Asn Phe Tyr Pro
            145                150                155                160

Arg Glu Ala Lys Val Gln Trp Lys Val Asp Asn Ala Leu Gln Ser Gly
                            165                170                175

Asn Ser Gln Glu Ser Val Thr Glu Gln Asp Ser Lys Asp Ser Thr Tyr
                            180                185                190

Ser Leu Ser Ser Thr Leu Thr Leu Ser Lys Ala Asp Tyr Glu Lys His
                            195                200                205

Lys Val Tyr Ala Cys Glu Val Thr His Gln Gly Leu Ser Ser Pro Val
                            210                215                220

Thr Lys Ser Phe Asn Arg
            225                230
```

```
<210> SEQ ID NO 155
<211> LENGTH: 122
<212> TYPE: PRT
<213> ORGANISM: Homo sapiens

<400> SEQUENCE: 155

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Asn Thr Tyr Tyr Tyr Gly Ser Gly Tyr Gly Met Asp Val Trp Gly Gln
            100                 105                 110

Gly Thr Thr Val Thr Val Ser Ser Ala Ser
        115                 120

<210> SEQ ID NO 156
<211> LENGTH: 220
<212> TYPE: PRT
<213> ORGANISM: Homo sapiens

<400> SEQUENCE: 156

Ser Gly Ser Ser Gly Asp Ile Val Met Thr Gln Ser Pro Leu Ser Leu
1               5                   10                  15

Pro Val Thr Pro Gly Glu Pro Ala Ser Ile Ser Cys Arg Ser Ser Gln
            20                  25                  30

Ser Leu Leu His Ser Thr Gly His Asn Tyr Leu Asp Trp Tyr Leu Gln
        35                  40                  45

Lys Pro Gly Gln Ser Pro Gln Leu Leu Ile Tyr Leu Gly Ser Ile Arg
    50                  55                  60

Ala Ser Gly Val Pro Asp Arg Phe Ser Gly Ser Gly Ser Gly Thr Asp
65                  70                  75                  80

Phe Thr Leu Lys Ile Ser Arg Val Glu Ala Glu Asp Val Gly Val Tyr
                85                  90                  95

Tyr Cys Met Gln Ala Leu Gln Thr Ile Thr Phe Gly Gly Gly Thr Arg
            100                 105                 110

Leu Glu Ile Lys Arg Thr Val Ala Ala Pro Ser Val Phe Ile Phe Pro
        115                 120                 125

Pro Ser Asp Glu Gln Leu Lys Ser Gly Thr Ala Ser Val Val Cys Leu
    130                 135                 140

Leu Asn Asn Phe Tyr Pro Arg Glu Ala Lys Val Gln Trp Lys Val Asp
145                 150                 155                 160

Asn Ala Leu Gln Ser Gly Asn Ser Gln Glu Ser Val Thr Glu Gln Asp
                165                 170                 175

Ser Lys Asp Ser Thr Tyr Ser Leu Ser Ser Thr Leu Thr Leu Ser Lys
            180                 185                 190

Ala Asp Tyr Glu Lys His Lys Val Tyr Ala Cys Glu Val Thr His Gln
        195                 200                 205

Gly Leu Ser Ser Pro Val Thr Lys Ser Phe Asn Arg
    210                 215                 220
```

<210> SEQ ID NO 157
<211> LENGTH: 136
<212> TYPE: PRT
<213> ORGANISM: Homo sapiens

<400> SEQUENCE: 157

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Lys Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Tyr Tyr Tyr Gly Ser Gly Ser Tyr Gly Met Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser
    130                 135

<210> SEQ ID NO 158
<211> LENGTH: 231
<212> TYPE: PRT
<213> ORGANISM: Homo sapiens

<400> SEQUENCE: 158

Leu Leu Gly Leu Leu Met Leu Trp Val Ser Gly Ser Ser Gly Asp Ile
1               5                   10                  15

Val Met Thr Gln Ser Pro Leu Ser Leu Pro Val Thr Pro Gly Glu Pro
            20                  25                  30

Ala Ser Ile Ser Cys Arg Ser Ser Gln Ser Leu Leu His Ser Thr Gly
        35                  40                  45

Tyr Asn Tyr Leu Asp Trp Tyr Leu Gln Lys Pro Gly Gln Ser Pro Gln
    50                  55                  60

Leu Leu Ile Tyr Leu Gly Ser Ile Arg Ala Ser Gly Val Pro Asp Arg
65                  70                  75                  80

Phe Ser Gly Ser Gly Ser Gly Thr Asp Phe Thr Leu Lys Ile Ser Arg
                85                  90                  95

Val Glu Ala Glu Asp Val Gly Ile Tyr Tyr Cys Met Gln Ala Leu Gln
            100                 105                 110

Thr Pro Ile Thr Phe Gly Gln Gly Thr Arg Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

```
Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
        210                 215                 220

Thr Lys Ser Phe Asn Arg Gly
225                 230

<210> SEQ ID NO 159
<211> LENGTH: 138
<212> TYPE: PRT
<213> ORGANISM: Homo sapiens

<400> SEQUENCE: 159

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Tyr Ser Gly Tyr Asp Tyr Phe Tyr Tyr Tyr Gly Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro
    130                 135

<210> SEQ ID NO 160
<211> LENGTH: 212
<212> TYPE: PRT
<213> ORGANISM: Homo sapiens

<400> SEQUENCE: 160

Cys Phe Pro Gly Ala Arg Cys Asp Ile Gln Met Thr Gln Ser Pro Ser
1               5                   10                  15

Ser Leu Ser Ala Ser Val Gly Asp Arg Val Thr Ile Thr Cys Arg Ala
            20                  25                  30

Ser Gln Gly Ile Tyr Asn Tyr Leu Ala Trp Phe Gln Gln Lys Pro Gly
        35                  40                  45

Lys Ala Pro Arg Ser Leu Ile Tyr Ala Ala Ser Ser Leu His Ser Gly
    50                  55                  60

Val Pro Ser Lys Phe Ser Gly Ser Gly Ser Gly Thr Asp Phe Thr Leu
65                  70                  75                  80

Thr Ile Ser Ser Leu Gln Pro Glu Asp Phe Ala Thr Tyr Tyr Cys Gln
                85                  90                  95

Gln Tyr Thr Ile Tyr Pro Phe Thr Phe Gly Pro Gly Thr Lys Val Asp
            100                 105                 110

Ile Lys Arg Thr Val Ala Ala Pro Ser Val Phe Ile Phe Pro Pro Ser
        115                 120                 125

Asp Glu Gln Leu Lys Ser Gly Thr Ala Ser Val Val Cys Leu Leu Asn
    130                 135                 140

Asn Phe Tyr Pro Arg Glu Ala Lys Val Gln Trp Lys Val Asp Asn Ala
```

```
            145                 150                 155                 160
Leu Gln Ser Gly Asn Ser Gln Glu Ser Val Thr Glu Gln Asp Ser Lys
                165                 170                 175

Asp Ser Thr Tyr Ser Leu Ser Ser Thr Leu Thr Leu Ser Lys Ala Asp
            180                 185                 190

Tyr Glu Lys His Lys Val Tyr Ala Cys Glu Val Thr His Gln Gly Leu
        195                 200                 205

Ser Ser Pro Val
        210

<210> SEQ ID NO 161
<211> LENGTH: 133
<212> TYPE: PRT
<213> ORGANISM: Homo sapiens

<400> SEQUENCE: 161

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Asn Thr Tyr Tyr Tyr Gly Ser Gly Tyr Gly Met Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro
    130

<210> SEQ ID NO 162
<211> LENGTH: 224
<212> TYPE: PRT
<213> ORGANISM: Homo sapiens

<400> SEQUENCE: 162

Leu Trp Val Ser Gly Ser Ser Gly Asp Ile Val Met Thr Gln Ser Pro
1               5                   10                  15

Leu Ser Leu Pro Val Thr Pro Gly Glu Pro Ala Ser Ile Ser Cys Arg
            20                  25                  30

Ser Ser Gln Ser Leu Leu His Ser Thr Gly His Asn Tyr Leu Asp Trp
        35                  40                  45

Tyr Leu Gln Lys Pro Gly Gln Ser Pro Gln Leu Leu Ile Tyr Leu Gly
    50                  55                  60

Ser Ile Arg Ala Ser Gly Val Pro Asp Arg Phe Ser Gly Ser Gly Ser
65                  70                  75                  80

Gly Thr Asp Phe Thr Leu Lys Ile Ser Arg Val Glu Ala Glu Asp Val
                85                  90                  95

Gly Val Tyr Tyr Cys Met Gln Ala Leu Gln Thr Ile Thr Phe Gly Gln
            100                 105                 110

Gly Thr Arg Leu Glu Ile Lys Arg Thr Val Ala Ala Pro Ser Val Phe
        115                 120                 125
```

Ile Phe Pro Pro Ser Asp Glu Gln Leu Lys Ser Gly Thr Ala Ser Val
    130                 135                 140

Val Cys Leu Leu Asn Asn Phe Tyr Pro Arg Glu Ala Lys Val Gln Trp
145                 150                 155                 160

Lys Val Asp Asn Ala Leu Gln Ser Gly Asn Ser Gln Glu Ser Val Thr
                165                 170                 175

Glu Gln Asp Ser Lys Asp Ser Thr Tyr Ser Leu Ser Ser Thr Leu Thr
            180                 185                 190

Leu Ser Lys Ala Asp Tyr Glu Lys His Lys Val Tyr Ala Cys Glu Val
        195                 200                 205

Thr His Gln Gly Leu Ser Ser Pro Val Thr Lys Ser Phe Asn Arg Gly
    210                 215                 220

<210> SEQ ID NO 163
<211> LENGTH: 132
<212> TYPE: PRT
<213> ORGANISM: Homo sapiens

<400> SEQUENCE: 163

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Arg Tyr
            20                  25                  30

Tyr Trp Ser Trp Ile Arg Gln Pro Ala Gly Lys Gly Leu Glu Arg Ile
        35                  40                  45

Gly Arg Ile Tyr Thr Ser Gly Ser Thr Asp Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Arg Asp Leu Tyr Ser Asn Gly Tyr Trp Tyr Phe Asp Leu Trp Gly Arg
            100                 105                 110

Gly Thr Leu Val Thr Val Ser Ser Ala Ser Thr Lys Gly Pro Ser Val
        115                 120                 125

Phe Pro Leu Ala
    130

<210> SEQ ID NO 164
<211> LENGTH: 217
<212> TYPE: PRT
<213> ORGANISM: Homo sapiens

<400> SEQUENCE: 164

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Val Val Phe Gly Gly Thr Lys Leu Thr Val Leu Gly
            100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
            165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
            195                 200                 205

Lys Thr Val Ala Pro Thr Glu Cys Ser
            210                 215

<210> SEQ ID NO 165
<211> LENGTH: 135
<212> TYPE: PRT
<213> ORGANISM: Homo sapiens

<400> SEQUENCE: 165

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
50                  55                  60

Lys Gly Arg Ser Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asp Gly Val Ala Val Ala Gly Thr Asp Tyr Phe Asp Tyr Trp
            100                 105                 110

Gly Gln Gly Thr Leu Val Thr Val Ser Ser Ala Ser Thr Lys Gly Pro
            115                 120                 125

Ser Val Phe Pro Leu Ala Pro
            130                 135

<210> SEQ ID NO 166
<211> LENGTH: 212
<212> TYPE: PRT
<213> ORGANISM: Homo sapiens

<400> SEQUENCE: 166

Trp Leu Arg Gly Ala Arg Cys Asp Ile Gln Met Thr Gln Ser Pro Ser
1               5                   10                  15

Ser Leu Ser Thr Ser Val Gly Asp Arg Val Thr Ile Thr Cys Arg Ala
            20                  25                  30

Thr Gln Ser Ile Ser Ser His Leu Asn Trp Tyr Gln Gln Lys Pro Gly
            35                  40                  45

Lys Ala Pro Lys Leu Leu Ile Tyr Val Ala Ser Ser Leu Gln Ser Gly
50                  55                  60

Val Pro Ser Arg Phe Ser Gly Ser Gly Ser Gly Thr Asp Phe Thr Leu

```
                65                  70                  75                  80
Thr Ile Ser Ser Leu Gln Pro Glu Asp Phe Ala Thr Tyr Tyr Cys Gln
                    85                  90                  95

Gln Ser Tyr Ser Thr Pro Leu Thr Phe Gly Gly Gly Thr Lys Val Glu
                100                 105                 110

Ile Lys Arg Thr Val Ala Ala Pro Ser Val Phe Ile Phe Pro Pro Ser
            115                 120                 125

Asp Glu Gln Leu Lys Ser Gly Thr Ala Ser Val Val Cys Leu Leu Asn
        130                 135                 140

Asn Phe Tyr Pro Arg Glu Ala Lys Val Gln Trp Lys Val Asp Asn Ala
145                 150                 155                 160

Leu Gln Ser Gly Asn Ser Gln Glu Ser Val Thr Glu Gln Asp Ser Lys
                165                 170                 175

Asp Ser Thr Tyr Ser Leu Ser Ser Thr Leu Thr Leu Ser Lys Ala Asp
            180                 185                 190

Tyr Glu Lys His Lys Val Tyr Ala Cys Glu Val Thr His Gln Gly Leu
        195                 200                 205

Ser Ser Pro Val
    210

<210> SEQ ID NO 167
<211> LENGTH: 137
<212> TYPE: PRT
<213> ORGANISM: Homo sapiens

<400> SEQUENCE: 167

Gln Val Gln Leu Gln Glu Ser Gly Pro Gly Leu Val Lys Pro Ser Gln
1               5                   10                  15

Thr Leu Ser Leu Thr Ser Thr Val Ser Gly Gly Ser Ile Ser Ser Gly
                20                  25                  30

Gly Tyr Tyr Trp Ser Trp Ile Arg Gln Leu Pro Gly Lys Gly Leu Glu
            35                  40                  45

Trp Val Gly Tyr Ile His Asn Ser Gly Ser Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Arg Ser Val Thr Ala Ala Asp Thr Ala Val Tyr Tyr
                85                  90                  95

Cys Ala Arg Gly Tyr Tyr Tyr Gly Ser Gly Ser Pro Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro
    130                 135

<210> SEQ ID NO 168
<211> LENGTH: 219
<212> TYPE: PRT
<213> ORGANISM: Homo sapiens

<400> SEQUENCE: 168

Leu Trp Val Ser Gly Ser Ser Gly Asp Ile Val Met Thr Gln Ser Pro
1               5                   10                  15

Leu Ser Leu Pro Val Thr Pro Gly Glu Thr Ala Ser Ile Ser Cys Arg
                20                  25                  30

Ser Ser Gln Ser Leu Leu Gln Ser Asn Gly His Asn Tyr Leu Asp Trp
            35                  40                  45
```

```
Tyr Leu Gln Lys Pro Gly Gln Ser Pro Gln Leu Leu Ile Tyr Leu Gly
    50                  55                  60

Ser Tyr Arg Asp Ser Gly Val Pro Asp Arg Phe Ser Gly Ser Gly Ser
 65                  70                  75                  80

Gly Thr Asp Phe Thr Leu Lys Ile Ser Arg Val Glu Ala Glu Asp Val
                 85                  90                  95

Gly Val Tyr Tyr Cys Met Gln Ala Leu Gln Thr Pro Pro Thr Phe Gly
             100                 105                 110

Gly Gly Thr Lys Leu Glu Ile Lys Arg Thr Val Ala Ala Pro Ser Val
         115                 120                 125

Phe Ile Phe Pro Pro Ser Asp Glu Gln Leu Lys Ser Gly Thr Ala Ser
     130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr
    210                 215

<210> SEQ ID NO 169
<211> LENGTH: 138
<212> TYPE: PRT
<213> ORGANISM: Homo sapiens

<400> SEQUENCE: 169

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser His
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Arg Asp Gln Tyr Ser Gly Tyr Asp Leu Tyr Tyr Tyr Gly Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro
    130                 135

<210> SEQ ID NO 170
<211> LENGTH: 229
<212> TYPE: PRT
<213> ORGANISM: Homo sapiens

<400> SEQUENCE: 170

Leu Leu Leu Trp Ile Ser Gly Ala Tyr Gly Asp Ile Val Met Thr Gln
1               5                   10                  15
```

```
Ser Pro Asp Ser Leu Ala Val Ser Leu Gly Glu Arg Ala Thr Ile Asn
            20                  25                  30

Cys Lys Ser Ser Gln Ser Val Leu Tyr Ser Ser Asn Asn Lys Asn Tyr
                35                  40                  45

Leu Ala Trp Tyr Gln Gln Lys Pro Gly Gln Pro Pro Lys Leu Leu Ile
 50                  55                  60

Tyr Trp Ala Ser Thr Arg Glu Ser Gly Val Pro Asp Arg Phe Ser Gly
 65                  70                  75                  80

Ser Gly Ser Gly Thr Asp Phe Thr Leu Thr Ile Ser Ser Leu Gln Ala
                85                  90                  95

Glu Asp Val Ala Val Tyr Tyr Cys Gln Gln Tyr Tyr Ser Thr Pro Arg
                100                 105                 110

Thr Phe Gly Gln Gly Thr Lys Val Glu Ile Lys Arg Thr Val Ala Ala
                115                 120                 125

Pro Ser Val Phe Ile Phe Pro Pro Ser Asp Glu Gln Leu Lys Ser Gly
                130                 135                 140

Thr Ala Ser Val Val Cys Leu Leu Asn Asn Phe Tyr Pro Arg Glu Ala
145                 150                 155                 160

Lys Val Gln Trp Lys Val Asp Asn Ala Leu Gln Ser Gly Asn Ser Gln
                165                 170                 175

Glu Ser Val Thr Glu Gln Asp Ser Lys Asp Ser Thr Tyr Ser Leu Ser
                180                 185                 190

Ser Thr Leu Thr Leu Ser Lys Ala Asp Tyr Glu Lys His Lys Val Tyr
                195                 200                 205

Ala Cys Glu Val Thr His Gln Gly Leu Ser Ser Pro Val Thr Lys Ser
                210                 215                 220

Phe Asn Arg Gly Glu
225

<210> SEQ ID NO 171
<211> LENGTH: 133
<212> TYPE: PRT
<213> ORGANISM: Homo sapiens

<400> SEQUENCE: 171

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Asn
                20                  25                  30

Ala Met Asn Trp Val Arg Gln Ala Pro Gly Lys Gly Leu Glu Trp Val
                35                  40                  45

Ser Ala Ile Ser Gly Ser Gly Gly Ser Thr Cys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Ala Pro Tyr Gln Leu Leu Pro Tyr Tyr Phe Asp Tyr Trp Gly
                100                 105                 110

Gln Gly Thr Leu Val Thr Val Ser Ser Ala Ser Thr Lys Gly Pro Ser
                115                 120                 125

Val Phe Pro Leu Ala
    130

<210> SEQ ID NO 172
<211> LENGTH: 24
```

-continued

```
<212> TYPE: DNA
<213> ORGANISM: Homo sapiens
<220> FEATURE:
<223> OTHER INFORMATION: Flag Tag

<400> SEQUENCE: 172
gattacaagg atgacgacga taag                                              24

<210> SEQ ID NO 173
<211> LENGTH: 710
<212> TYPE: PRT
<213> ORGANISM: Macaca fascicularis

<400> SEQUENCE: 173
```

Met Gly Gly Lys Gln Arg Asp Lys Asp Glu Ala Tyr Gly Lys Pro
1               5                   10                  15

Val Lys Tyr Asp Pro Ser Phe Arg Gly Pro Ile Lys Asn Arg Ser Cys
            20                  25                  30

Thr Asp Val Ile Cys Cys Val Leu Phe Leu Leu Phe Ile Leu Gly Tyr
                35                  40                  45

Ile Val Val Gly Ile Val Ala Trp Leu Tyr Gly Asp Pro Arg Gln Val
    50                  55                  60

Leu Tyr Pro Arg Asn Ser Thr Gly Ala Tyr Cys Gly Met Gly Glu Asn
65                  70                  75                  80

Lys Asp Lys Pro Tyr Leu Leu Tyr Phe Asn Ile Phe Ser Cys Ile Leu
                85                  90                  95

Ser Thr Asn Ile Ile Ser Val Ala Glu Asn Gly Leu Gln Cys Pro Thr
            100                 105                 110

Pro Gln Val Cys Val Ser Ser Cys Pro Glu Ala Pro Trp Thr Val Gly
        115                 120                 125

Lys Asn Gln Phe Ser Gln Thr Val Gly Glu Val Phe Tyr Thr Lys Asn
    130                 135                 140

Arg Asn Phe Cys Leu Pro Gly Val Pro Trp Asn Met Met Val Ile Thr
145                 150                 155                 160

Ser Leu Gln Gln Glu Leu Cys Pro Ser Phe Leu Leu Pro Ser Ala Pro
                165                 170                 175

Ala Leu Gly Arg Cys Phe Pro Trp Thr Asn Val Thr Leu Pro Glu Leu
            180                 185                 190

Pro Gly Ile Thr Asn Asp Thr Thr Ile Ala Gln Gly Ile Ser Gly Leu
        195                 200                 205

Ile Asp Ser Leu Asn Ala Arg Asp Ile Ser Val Lys Ile Phe Glu Asp
    210                 215                 220

Phe Ala His Ser Trp Tyr Trp Ile Leu Val Ala Leu Gly Val Ala Leu
225                 230                 235                 240

Leu Leu Ser Leu Leu Phe Ile Leu Leu Leu Arg Leu Val Ala Gly Pro
                245                 250                 255

Leu Val Leu Val Leu Ile Leu Gly Val Leu Gly Val Leu Ala Tyr Gly
            260                 265                 270

Ile Tyr Tyr Cys Trp Glu Glu Tyr Arg Val Leu Arg Asp Lys Gly Ala
        275                 280                 285

Ser Ile Ser Gln Leu Gly Phe Thr Thr Asn Leu Ser Ala Tyr Gln Ser
    290                 295                 300

Val Gln Glu Thr Trp Leu Ala Ala Leu Ile Val Leu Ala Val Leu Glu
305                 310                 315                 320

Ala Ile Leu Leu Leu Val Leu Ile Phe Leu Arg Gln Arg Ile Arg Ile
                325                 330                 335

```
Ala Ile Ala Leu Leu Lys Glu Ala Ser Lys Ala Val Gly Gln Met Met
            340                 345                 350

Ser Thr Met Phe Tyr Pro Leu Val Thr Phe Val Leu Leu Leu Ile Cys
        355                 360                 365

Ile Ala Tyr Trp Ala Met Thr Ala Leu Tyr Leu Ala Thr Ser Gly Gln
    370                 375                 380

Pro Gln Tyr Val Leu Trp Ala Ser Asn Ile Ser Ser Pro Gly Cys Glu
385                 390                 395                 400

Lys Val Ser Ile Asn Thr Ser Cys Asn Pro Met Asp Gln Pro Val Asn
                405                 410                 415

Ser Ser Cys Pro Gly Leu Met Cys Val Phe Gln Gly Tyr Ser Ser Lys
            420                 425                 430

Gly Leu Val Gln Arg Ser Leu Phe Asn Leu Gln Ile Tyr Gly Val Leu
        435                 440                 445

Gly Leu Phe Trp Thr Leu Asn Trp Val Leu Ala Leu Gly Gln Cys Val
    450                 455                 460

Leu Ala Gly Ala Phe Ala Ser Phe Tyr Trp Ala Phe His Lys Pro Gln
465                 470                 475                 480

Asp Ile Pro Thr Phe Pro Leu Ile Ser Ala Phe Ile Arg Thr Leu Arg
                485                 490                 495

Tyr His Thr Gly Ser Leu Ala Phe Gly Ala Leu Ile Leu Thr Leu Val
            500                 505                 510

Gln Ile Ala Arg Val Ile Leu Glu Tyr Ile Asp His Lys Leu Arg Gly
        515                 520                 525

Val Gln Asn Pro Val Ala Arg Cys Ile Met Cys Cys Phe Lys Cys Cys
    530                 535                 540

Leu Trp Cys Leu Glu Lys Phe Ile Lys Phe Leu Asn Arg Asn Ala Tyr
545                 550                 555                 560

Ile Met Ile Ala Ile Tyr Gly Lys Asn Phe Cys Val Ser Ala Lys Asn
                565                 570                 575

Ala Phe Met Leu Leu Met Arg Asn Ile Val Arg Val Val Val Leu Asp
            580                 585                 590

Lys Val Thr Asp Leu Leu Leu Phe Phe Gly Lys Leu Leu Val Val Gly
        595                 600                 605

Gly Val Gly Val Leu Ser Phe Phe Phe Ser Gly Arg Ile Pro Gly
    610                 615                 620

Leu Gly Arg Asp Phe Lys Ser Pro His Leu Asn Tyr Tyr Trp Leu Pro
625                 630                 635                 640

Ile Met Thr Ser Ile Met Gly Ala Tyr Val Ile Ala Ser Gly Phe Phe
                645                 650                 655

Ser Val Phe Gly Met Cys Val Asp Thr Leu Phe Leu Cys Phe Leu Glu
            660                 665                 670

Asp Leu Glu Arg Asn Asn Gly Ser Leu Asp Arg Pro Tyr Tyr Met Ser
        675                 680                 685

Lys Ser Leu Leu Lys Ile Leu Gly Lys Lys Asn Glu Ala Pro Pro Asp
    690                 695                 700

Asn Lys Lys Arg Lys Lys
705                 710
```